(12) United States Patent
Nara et al.

(10) Patent No.: US 9,371,320 B2
(45) Date of Patent: Jun. 21, 2016

(54) HETEROCYCLIC COMPOUND

(71) Applicant: TAKEDA PHARMACEUTICAL COMPANY LIMITED, Osaka (JP)

(72) Inventors: Hiroshi Nara, Kanagawa (JP); Masaki Daini, Kanagawa (JP); Akira Kaieda, Kanagawa (JP); Toshihiro Imaeda, Kanagawa (JP); Fumiaki Kikuchi, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 14/404,126

(22) PCT Filed: May 31, 2013

(86) PCT No.: PCT/JP2013/065183
§ 371 (c)(1),
(2) Date: Nov. 26, 2014

(87) PCT Pub. No.: WO2013/180265
PCT Pub. Date: Dec. 5, 2013

(65) Prior Publication Data
US 2015/0141406 A1 May 21, 2015

(30) Foreign Application Priority Data
Jun. 1, 2012 (JP) .................................. 2012-126462

(51) Int. Cl.
C07D 401/14 (2006.01)
A61K 31/437 (2006.01)
C07D 471/04 (2006.01)

(52) U.S. Cl.
CPC .................................... *C07D 471/04* (2013.01)

(58) Field of Classification Search
CPC .......................... C07D 401/14; A61K 31/437
USPC .......................................... 546/119; 514/303
See application file for complete search history.

(56) References Cited

U.S. PATENT DOCUMENTS

| | | | |
|---|---|---|---|
| 3,663,559 A | 5/1972 | Derijckere et al. | |
| 7,049,312 B1 | 5/2006 | Rafferty et al. | |
| 7,429,609 B2 * | 9/2008 | Ohi et al. | 514/406 |
| 2005/0137201 A1 | 6/2005 | Aronov et al. | |
| 2005/0208582 A1 | 9/2005 | Ohi et al. | |
| 2005/0261339 A1 | 11/2005 | Ohi et al. | |
| 2007/0275965 A1 | 11/2007 | Thomas et al. | |
| 2009/0054397 A1 | 2/2009 | Ohi et al. | |
| 2010/0197678 A1 | 8/2010 | Kuzmich et al. | |
| 2013/0303533 A1 | 11/2013 | Chao et al. | |
| 2015/0045349 A1 | 2/2015 | Nagamiya et al. | |

FOREIGN PATENT DOCUMENTS

| | | |
|---|---|---|
| CN | 1636005 A | 7/2005 |
| EP | 2 108 642 | 10/2009 |
| JP | 52078895 | * 12/1975 |
| JP | 52083394 | * 12/1975 |
| JP | 52-78895 | 7/1977 |
| JP | 52-83394 | 7/1977 |
| JP | 4-139185 | 5/1992 |
| JP | 2003-501429 | 1/2003 |
| WO | 03/101968 | 12/2003 |
| WO | 2005/028475 | 3/2005 |
| WO | 2007/115231 | 10/2007 |
| WO | 2008/047831 | 4/2008 |
| WO | 2008/070507 | 6/2008 |
| WO | 2012/030924 | 3/2012 |
| WO | 2013/125543 | 8/2013 |
| WO | 2014146246 | * 9/2014 |

OTHER PUBLICATIONS

Keller et al., Science of Synthesis (2005), 15, 285-387.*
Liu et al., Tetrahedron Letters (2005), 46(46), 8009-8012.*
Singh et al., ACS Medicinal Chemistry Letters (2012), 3(10), 814-817.*
International Search Report issued Jun. 25, 2013 in International (PCT) Application No. PCT/JP2013/065183.
L. A. Smyth et al., "Design and Evaluation of 3-Aminopyrazolopyridinone Kinase Inhibitors Inspired by the Natural Product Indirubin", Bioorganic & Medicinal Chemistry, vol. 19, No. 11, pp. 3569-3578, 2011.
L.A. Smyth et al., "Synthesis and Reactivity of 3-amino-1*H*-pyrazolo[4,3-c]pyridine-4(5*H*)-ones: Development of a Novel Kinase-Focussed Library", Tetrahedron, vol. 66, No. 15, pp. 2843-2854, 2010.

(Continued)

*Primary Examiner* — Niloofar Rahmani
(74) *Attorney, Agent, or Firm* — Wenderoth, Lind & Ponack, LLP.

(57) ABSTRACT

The present invention provides a compound having a superior JAK inhibitory action, which is useful as an agent for the prophylaxis or treatment of autoimmune diseases (rheumatoid arthritis, psoriasis, inflammatory bowel disease, Sjogren's syndrome, Behcet's disease, multiple sclerosis, systemic lupus erythematosus, etc.), cancer (leukemia, uterine leiomyosarcoma, prostate cancer, multiple myeloma, cachexia, myelofibrosis, etc.) and the like, or a salt thereof. The present invention relates to a compound represented by the formula

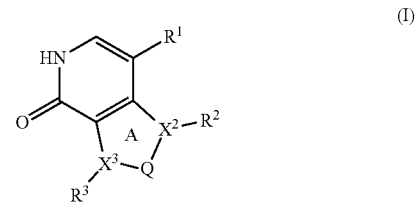

(I)

wherein each symbol is as defined in the specification, or a salt thereof.

8 Claims, No Drawings

(56) References Cited

OTHER PUBLICATIONS

D. Donati et al., "On the Reactivity of Isoxazoles with Mo(CO)$_6$", Journal of Heterocyclic Chemistry, vol. 41, No. 5, pp. 761-766, 2004.
STN Search Results including Registry Numbers: 30081-66-4; 30081-67-5; 143035-29-4-; 143035-23-8;13945-10-3; 143035-24-9; 143035-25-0; 143035-26-1; 143035-27-2; 143035-30-7; 143035-31-8; 143035-32-9; 143035-33-0; 143035-34-1;143035-28-3; 143035-35-2; 143035-36-3; 30081-66-4; 30081-67-5; 32460-25-6; 30081-66-4; 30081-67-5; 13945-10-3; 13945-11-4; 13945-12-5; 13945-13-6; 14033-34-2; 14633-09-1 and 958795-03-4.

Extended European Search Report mailed Nov. 5, 2015 in corresponding European Patent Application No. 13797604.9.
F. Eloy et al., "Sur une synthèse nouvelle des pyrazolo [4,3-c]pyridines comme analogues structuraux des antagonistes des bases puriques", Chime Therapeutique, Editions Dimeo, Arcueil, FR, vol. 6, No. 1, Jan. 1, 1971, pp. 1-5.
Office Action issued Oct. 12, 2015 in corresponding Chinese Patent Application No. 201380040684.1.

* cited by examiner

HETEROCYCLIC COMPOUND

TECHNICAL FIELD

The present invention relates to a heterocyclic compound having a janus kinase (In the present specification, sometimes to be abbreviated as "JAK") inhibitory action, which is useful as an agent for the treatment of autoimmune diseases (rheumatoid arthritis, psoriasis, inflammatory bowel disease, Sjogren's syndrome, Behcet's disease, multiple sclerosis, systemic lupus erythematosus, etc.), cancer (leukemia, uterine leiomyosarcoma, prostate cancer, multiple myeloma, cachexia, myelofibrosis, etc.) and the like, a pharmaceutical composition containing thereof, and the like.

BACKGROUND OF THE INVENTION

Cytokines are proteins secreted by a cell of the immune system and transduce a signal to a specific cell. Cytokines have various kinds, and many of them are especially associated with immunity and inflammation and also associated with cell growth, cell differentiation, cell death, wound healing and the like (Curr Opin Cell Biol. 1991 April; 3(2):171-5).

The janus kinase (JAK) family plays a role in cytokine-dependent regulation of the function of cells associated with growth and immune response. JAK family consists of four kinds of janus kinases (JAK1 (janus kinase 1), JAK2 (janus kinase 2), JAK3 (janus kinase 3) and TYK2 (tyrosine kinase 2)). Among them, JAK1 is known to be involved in signal transduction of cytokines such as IL(interleukin)-2, IL-4, IL-7, IL-15, IL-21, IL-6, OSM (oncostatin M), IL-10 family, IFN(interferon)-α, IFN-β, IFN-γ and the like (Nature Immunology 10, 356-360 (2009)). TYK2 is known to be involved in signal transduction of cytokines such as IFN-α, IFN-β, IL-6, IL-10 family (IL-10, IL-19, IL-20, IL-22, IL-28, IL-29), IL-12, IL-23 and the like (Nature Immunology 10, 356-360 (2009), New York Academy of Science 1246, 34-40 (2011)). In addition, these cytokines play an important role in immune response when exist in an appropriate amount. However, excessive production of them is involved in many autoimmune diseases such as rheumatoid arthritis, psoriasis, inflammatory bowel disease, Sjogren's syndrome, Behcet's disease, multiple sclerosis, systemic lupus erythematosus and the like (Journal of Allergy and Clinical Immunology 127, 3, 701-721.e70 (2011), Cytokine & Growth Factor Reviews 19, 41-52 (2008), Invest Ophthalmol Vis Sci. 2008 July; 49(7): 3058-3064, Ann Rheum Dis. 2010 July; 69(7):1325-1328).

Tocilizumab, which is an anti-IL-6 receptor monoclonal antibody, has been approved as a therapeutic drug for rheumatoid arthritis in Japan and Europe, and furthermore, clinical trials for various diseases in which the IL-6 signaling pathway is suggested to be involved are performed. From the foregoing, a JAK1 inhibitor can be a therapeutic drug for various autoimmune diseases such as rheumatoid arthritis, psoriasis, inflammatory bowel disease, Sjogren's syndrome, Behcet's disease, multiple sclerosis, systemic lupus erythematosus and the like (Clinical Science 122, 143-159 (2012)).

Moreover, JAK signal is also associated with differentiation and growth of various cancer cell (Trends Biochem. Sci. 33, 122-131 (2008)). Particularly, JAK1 is associated with leukemia and uterine leiomyosarcoma due to the constant activation therein (J Exp Med 205, 751-758 (2008), Oncogene 25, 4016-4026, (2006)). In addition, clinical trials of antibody and low molecule compound which target at IL-6 are performed for cancer diseases such as prostate cancer, multiple myeloma, cachexia, myelofibrosis and the like (Clinical Science 122, 143-159 (2012), The New England Journal of Medicine 363, 1117-1127 (2010)). From the foregoing, a JAK1 inhibitor can be a therapeutic drug for cancer diseases such as leukemia, uterine leiomyosarcoma, prostate cancer, multiple myeloma, cachexia, myelofibrosis and the like.

Ustekinumab, which is an anti-IL-12/23 monoclonal antibody, has been approved as a therapeutic drug for moderate to severe psoriasis patient in Europe, and furthermore, clinical trials for various diseases in which the IL-12/23 signaling pathway is suggested to be involved are performed. From the foregoing, a TYK2 inhibitor can be a therapeutic drug for various autoimmune diseases such as rheumatoid arthritis, psoriasis, inflammatory bowel disease, Sjogren's syndrome, Behcet's disease, multiple sclerosis, systemic lupus erythematosus and the like (Front Biosci. 2011 Jun. 1; 17:3214-32).

Examples of the compound having a structure similar to the compound described in the present specification include the following compounds.

(1) A compound represented by the following formula:

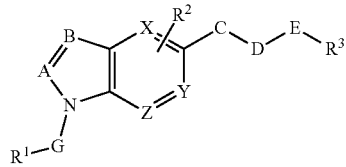

wherein
$R^1$ is H, aryl or the like;
G is H or halogen;
X, Y and Z are each independently C or N;
A and B are each independently C or N;
E is a bond, —$CH_2$— or the like;
D is —$CR^5R^6$—;
$R^5$ is trifluoromethyl;
$R^6$ is hydroxy or H; and
$R^3$ is an optionally substituted heteroaryl or the like,
which is a glucocorticoid receptor modulator, and is useful for the treatment of sex hormone-dependent disease (prostatic hyperplasia, uterus myopathy, etc.) and the like (Patent Document 1).

(2) A compound represented by the following formula:

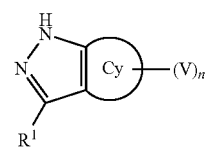

wherein
$R^1$ is a formula —$(CO)_h$—$(NR^a)$—$(CR^b$=$CR^c)_k$—Ar
  wherein
  $R^a$, $R^b$ and $R^e$ are each independently H, —OH or the like; and
  h, j and k are each independently 0-1;
Cy is an optionally substituted 5-6-membered aromatic heterocyclic group; and
V is -L-X—Y
  wherein
  L is a bond, $C_{1-6}$ alkylene or the like;
  X is a bond, —O—, —CO— or the like; and
  Y is H, NO or the like, which is a JNK inhibitor, and is useful for the treatment of Alzheimer's disease and the like, and

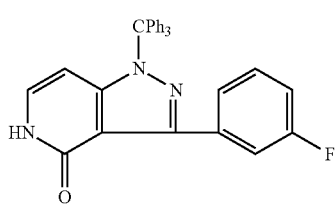

3-(3-fluorophenyl)-1-trityl-1,5-dihydro-4H-pyrazolo[4,3-c]pyridin-4-one (Patent Document 2).

(3) A compound represented by the following formula:

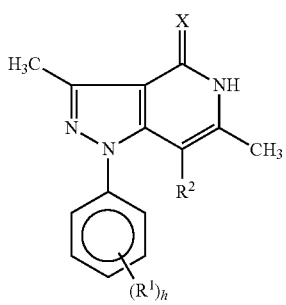

wherein
R$^1$ is H, —OH or the like;
l is 1-2;
R$^2$ is H, nitro or acetylamino; and
X is O or S,
which is a cardiac stimulant (Patent Document 3).

(4) A production method represented by the following formula:

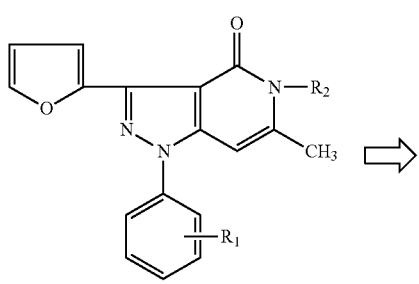

wherein
R$^1$ is H, halogen or the like; and
R$^2$ is H, alkyl or phenyl,
(Patent Document 4).

(5) A compound represented by the following formula:

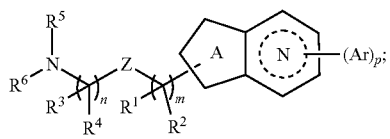

wherein
R$^1$, R$^2$, R$^3$ and R$^4$ are each independently C$_{1-8}$ alkyl, C$_{1-8}$ hetero alkyl or the like;
R$^5$ and R$^6$ are each independently C$_{1-8}$ alkyl, C$_{1-8}$ hetero alkyl or the like;
R$^1$, R$^2$, R$^3$, R$^4$, R$^5$ and R$^6$ optionally form a 5-10-membered ring;
Ring A is an optionally substituted 5-membered aromatic heterocycle or the like;
Ring N is an optionally substituted 6-membered aromatic heterocycle or the like;
Ar is an optionally substituted 5-10-membered aryl or an optionally substituted 5-10-membered heteroaryl;
m and n are each independently 1-6; and
p is 0-1,
which is a CXCR4 inhibitor, and is useful for the treatment of rheumatoid arthritis and the like (Patent Document 5).

(6) A compound represented by the following formula:

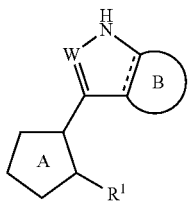

wherein
W is CH or N;
Ring B is an optionally substituted 5-6-membered aromatic heterocycle;
R$^1$ is an optionally substituted aryl or the like; and Ring A is an optionally substituted 5-membered nitrogen-containing aromatic heterocycle,
which is a JAK (JAK1, JAK2, JAK3, TYK2) inhibitor, and is useful for the treatment of rheumatism, psoriasis and the like (Patent Document 6).

(7) A compound represented by the following formula:

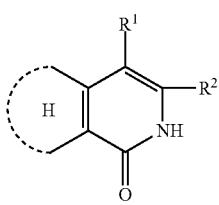

wherein
R$^2$ and R$^3$ are each independently H or C$_{1-6}$ alkyl, (Patent Document 7).

(8) A compound represented by the following formula:

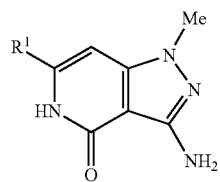

R¹
26 methyl
27 phenyl
28 2-pyridyl
29 4-methoxyphenyl
30 3-methoxyphenyl
31 4-(4-methylpiperazin-1-yl)-phenyl
32 piperidin-4-yl.

which is an inhibitor of kinase such as CDK, GSK3β and the like, and is useful for the treatment of cancer and the like (Non-Patent Document 1).

(9) A compound represented by the following formula:

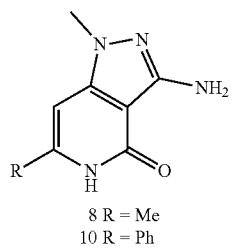

8 R = Me
10 R = Ph (Non-Patent Document 2).

(10) A compound represented by the following formula:

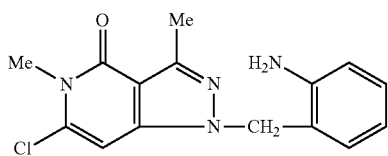

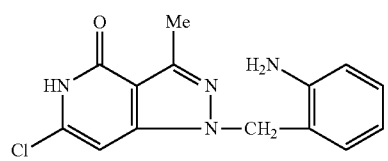

(Non-Patent Document 3).

(11) The following compounds are disclosed in Chemical Abstract.

1) Registry Number: 30081-66-4

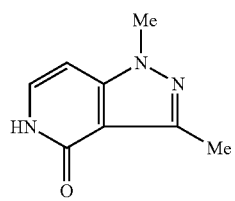

2) Registry Number: 30081-67-5

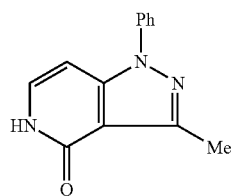 [SMILES: Cc1nn(-c2ccccc2)c2cc[nH]c(=O)c12]

3) Registry Number: 143035-29-4

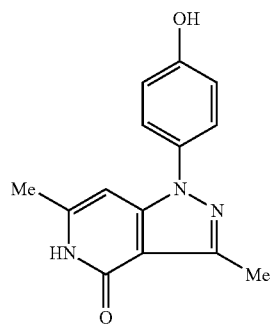

4) Registry Number: 143035-23-8

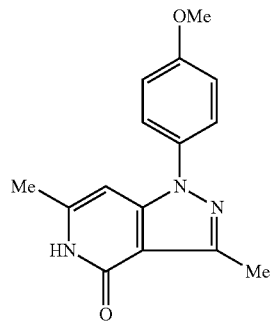

5) Registry Number: 13945-10-3
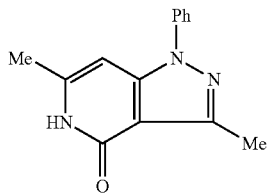 [SMILES: Cc1cc2c(c(C)nn2-c2ccccc2)c(=O)[nH]1]
6) Registry Number: 143035-24-9
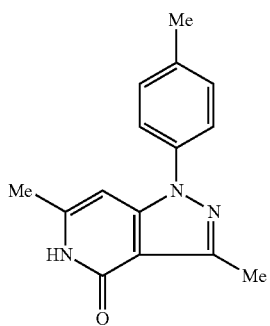 [SMILES: Cc1ccc(-n2nc(C)c3c(=O)[nH]c(C)cc32)cc1]
7) Registry Number: 143035-25-0
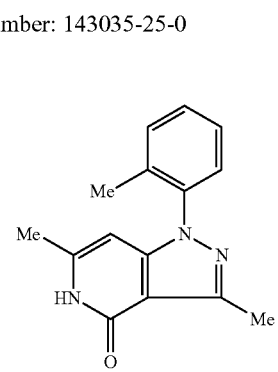
8) Registry Number: 143035-26-1
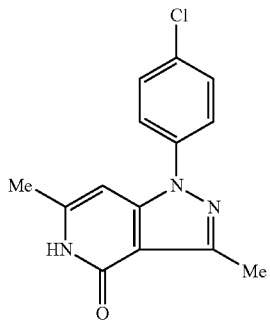 [SMILES: Cc1cc2c(c(C)nn2-c2ccc(Cl)cc2)c(=O)[nH]1]
9) Registry Number: 143035-27-2
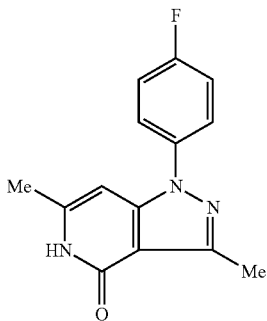
10) Registry Number: 143035-30-7
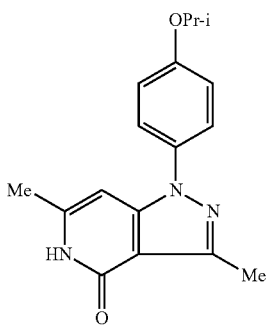
11) Registry Number: 143035-31-8
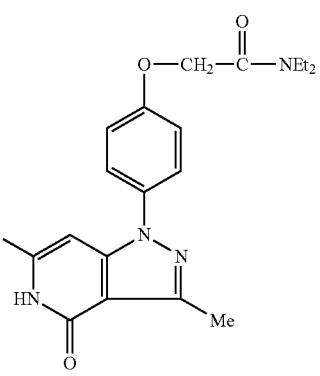

12) Registry Number: 143035-32-9
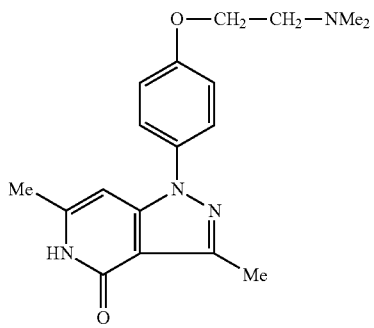 [SMILES: Cc1cc2c(c(C)nn2-c2ccc(OCCN(C)C)cc2)c(=O)[nH]1]
13) Registry Number: 143035-33-0
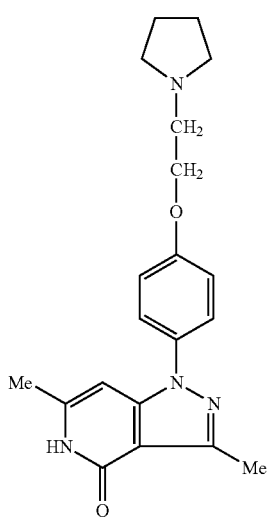 [SMILES: Cc1cc2c(c(C)nn2-c2ccc(OCCN3CCCC3)cc2)c(=O)[nH]1]
14) Registry Number: 143035-34-1
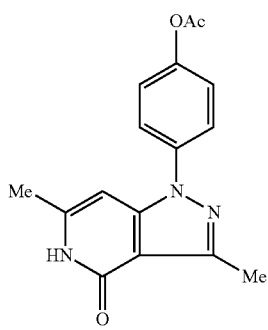 [SMILES: CC(=O)Oc1ccc(-n2nc(C)c3c(=O)[nH]c(C)cc32)cc1]
15) Registry Number: 143035-28-3
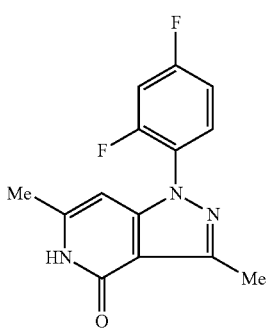 [SMILES: Cc1cc2c(c(C)nn2-c2ccc(F)cc2F)c(=O)[nH]1]
16) Registry Number: 143035-35-2
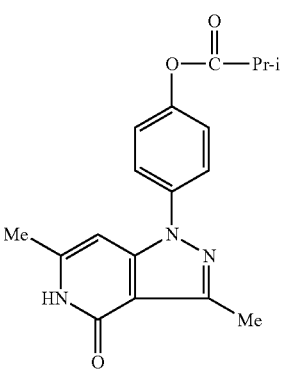
17) Registry Number: 143035-36-3
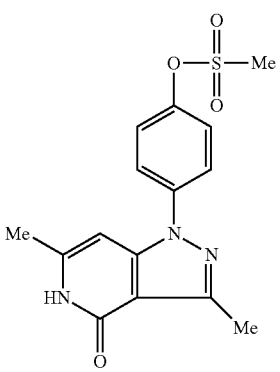 [SMILES: Cc1cc2c(c(C)nn2-c2ccc(OS(C)(=O)=O)cc2)c(=O)[nH]1]
18) Registry Number: 30081-66-4
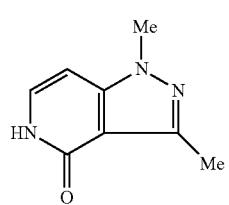 [SMILES: Cc1nn(C)c2cc[nH]c(=O)c12]

19) Registry Number: 30081-67-5
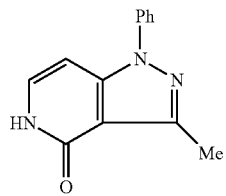 [SMILES: Cc1nn(-c2ccccc2)c2cc[nH]c(=O)c12]
20) Registry Number: 32460-25-6
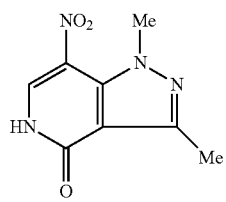 [SMILES: Cc1nn(C)c2c([N+](=O)[O-])c[nH]c(=O)c12]
21) Registry Number: 30081-66-4
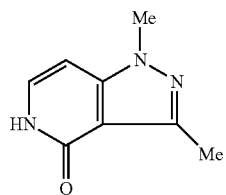 [SMILES: Cc1nn(C)c2cc[nH]c(=O)c12]
22) Registry Number: 30081-67-5
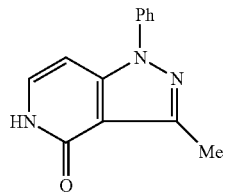 [SMILES: Cc1nn(-c2ccccc2)c2cc[nH]c(=O)c12]
23) Registry Number: 13945-10-3
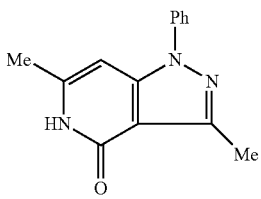
24) Registry Number: 13945-11-4
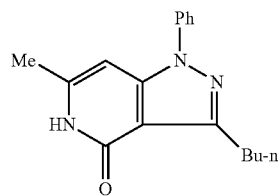
25) Registry Number: 13945-12-5
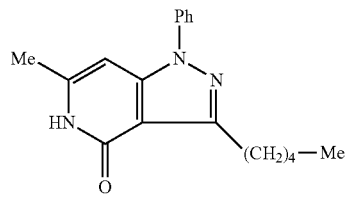
26) Registry Number: 13945-13-6
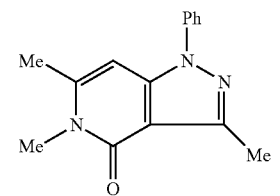 [SMILES: Cc1nn(-c2ccccc2)c2cc(C)n(C)c(=O)c12]
27) Registry Number: 14033-34-2
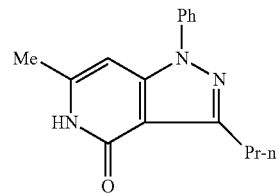
28) Registry Number: 14633-09-1
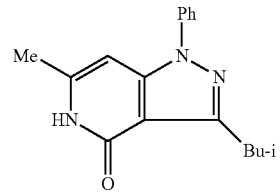

29) Registry Number: 958795-03-4

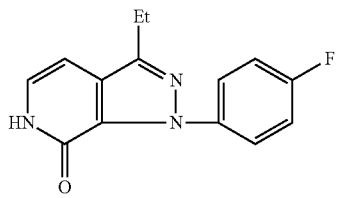 [SMILES: CCc1nn(-c2ccc(F)cc2)c2c(=O)[nH]ccc12]

DOCUMENT LIST

Patent Document

[Patent Document 1] WO 2008/070507
[Patent Document 2] WO 2003/101968
[Patent Document 3] JP-A-H4-139185
[Patent Document 4] JP-A-S52-078895
[Patent Document 5] WO 2007/115231
[Patent Document 6] WO 2005/028475
[Patent Document 7] U.S. Pat. No. 3,663,559

Non-Patent Document

[Non-Patent Document 1] Bioorganic & Medicinal Chemistry (2011), 19(11), 3569-3578
[Non-Patent Document 2] Tetrahedron (2010), 66(15), 2843-2854
[Non-Patent Document 3] Journal of Heterocyclic Chemistry (2004), 41(5), 761-766

SUMMARY OF THE INVENTION

Problems to be Solved by the Invention

An object of the present invention is to provide a compound having a superior JAK inhibitory action, which is useful as an agent for the prophylaxis or treatment of autoimmune disease (rheumatoid arthritis, psoriasis, inflammatory bowel disease, Sjogren's syndrome, Behcet's disease, multiple sclerosis, systemic lupus erythematosus, etc.), cancer (leukemia, uterine leiomyosarcoma, prostate cancer, multiple myeloma, cachexia, myelofibrosis, etc.) and the like.

Means of Solving the Problems

The present inventors have conducted intensive studies in an attempt to solve the above-mentioned problem and found that a compound represented by the following formula (I) has a superior JAK inhibitory action, which resulted in the completion of the present invention.

Accordingly, the present invention provides the following.
[1] A compound represented by the formula (I):

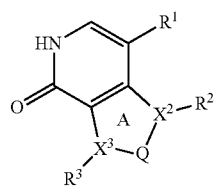

(I)

wherein
Ring A moiety is a nitrogen-containing aromatic heterocycle
wherein
Q is a carbon atom or a nitrogen atom, and
$X^2$ and $X^3$ are each independently a carbon atom or a nitrogen atom, and any one of them is a nitrogen atom;
$R^1$ is a hydrogen atom, a halogen atom, a cyano group, an acyl group, an optionally substituted $C_{1-6}$ alkyl group, an optionally substituted $C_{3-6}$ cycloalkyl group or an optionally substituted hydroxy group;
$R^2$ is a substituted $C_{1-2}$ alkyl group, an optionally substituted $C_{3-6}$ alkyl group, an acyl group, an optionally substituted hydroxy group, an optionally substituted amino group, an optionally substituted carbocyclic group or an optionally substituted heterocyclic group; and
$R^3$ is a substituted $C_{1-2}$ alkyl group, an optionally substituted $C_{3-6}$ alkyl group, an acyl group, an optionally substituted hydroxy group, an optionally substituted amino group, an optionally substituted carbocyclic group or an optionally substituted heterocyclic group,
provided that 3-(3-fluorophenyl)-1-trityl-1,5-dihydro-4H-pyrazolo[4,3-c]pyridin-4-one is excluded,
or a salt thereof.
[2] The compound or salt of the above-mentioned [1], wherein
$R^1$ is
(1) a hydrogen atom,
(2) a halogen atom,
(3) a cyano group,
(4) a carboxy group,
(5) a $C_{1-6}$ alkyl-carbonyl group,
(6) a $C_{1-6}$ alkoxy-carbonyl group,
(7) a carbamoyl group optionally mono- or di-substituted by $C_{1-6}$ alkyl group(s),
(8) a $C_{1-6}$ alkyl group optionally substituted by 1 to 3 hydroxy groups, or
(9) a $C_{3-6}$ cycloalkyl group;
$R^2$ is
(1) a $C_{1-2}$ alkyl group substituted by 1 to 3 substituents selected from
   (a) a $C_{6-14}$ aryl group optionally substituted by 1 to 3 $C_{1-6}$ alkoxy groups, and
   (b) a 3- to 8-membered monocyclic non-aromatic heterocyclic group optionally substituted by 1 to 3 $C_{1-6}$ alkyl groups,
(2) a $C_{3-6}$ alkyl group optionally substituted by 1 to 3 substituents selected from
   (a) a hydroxy group, and
   (b) a $C_{1-6}$ alkoxy group,
(3) a $C_{3-10}$ cycloalkyl group optionally substituted by 1 to 3 substituents selected from
   (a) a hydroxy group,
   (b) a $C_{1-6}$ alkyl group,
   (c) an oxo group,
   (d) a $C_{1-6}$ alkylenedioxy group,
   (e) a $C_{6-14}$ aryl group,
   (f) a halogen atom, and
   (g) an amino group,
(4) a $C_{6-14}$ aryl group optionally substituted by 1 to 3 substituents selected from
   (a) a halogen atom,
   (b) a $C_{1-6}$ alkyl group optionally substituted by 1 to 3 halogen atoms,
   (c) a cyano group,
   (d) a carbamoyl group,
   (e) an amino group, and
   (f) a $C_{1-6}$ alkoxy group, (5) a 3- to 8-membered monocyclic non-aromatic heterocyclic group, or
(6) a 5- to 7-membered monocyclic aromatic heterocyclic group; and
$R^3$ is
(1) a $C_{1-2}$ alkyl group substituted by 1 to 3 substituents selected from a $C_{6-14}$ aryl group optionally substituted by 1 to 3 sulfamoyl groups,
(2) a $C_{3-10}$ cycloalkyl group,
(3) a $C_{3-10}$ cycloalkenyl group,
(4) a $C_{6-14}$ aryl group optionally substituted by 1 to 3 substituents selected from
    (a) a halogen atom,
    (b) a nitro group,
    (c) a cyano group,
    (d) a carbamoyl group optionally mono- or di-substituted by $C_{1-6}$ alkyl group(s) optionally substituted by 1 to 3 substituents selected from
        (i) a $C_{1-6}$ alkoxy group,
        (ii) a hydroxy group, and
        (iii) an amino group optionally mono- or di-substituted by $C_{1-6}$ alkyl group(s),
    (e) a sulfamoyl group optionally mono- or di-substituted by $C_{1-6}$ alkyl group(s),
    (f) a $C_{1-6}$ alkyl group optionally substituted by 1 to 3 substituents selected from
        (i) a halogen atom,
        (ii) a cyano group,
        (iii) a hydroxy group,
        (iv) a carbamoyl group optionally mono- or di-substituted by substituent(s) selected from a $C_{1-6}$ alkyl group and a $C_{3-10}$ cycloalkyl group,
        (v) an amino group optionally mono- or di-substituted by $C_{1-6}$ alkyl group(s), and
        (vi) a 3- to 8-membered monocyclic non-aromatic heterocyclic group optionally substituted by 1 to 3 substituents selected from an oxo group and a halogen atom,
    (g) a $C_{1-6}$ alkoxy group optionally substituted by 1 to 3 substituents selected from
        (i) a halogen atom,
        (ii) a cyano group,
        (iii) a hydroxy group, and
        (iv) a carbamoyl group optionally mono- or di-substituted by substituent(s) selected from a $C_{1-6}$ alkyl group optionally substituted by 1 to 3 $C_{1-6}$ alkoxy groups,
    (h) a $C_{1-6}$ alkoxy-carbonyl group,
    (i) an amino group optionally mono- or di-substituted by substituent(s) selected from
        (i) a $C_{1-6}$ alkyl-carbonyl group, and
        (ii) a $C_{1-6}$ alkyl group optionally substituted by 1 to 3 $C_{1-6}$ alkoxy groups,
    (j) a 3- to 8-membered monocyclic non-aromatic heterocyclic group optionally substituted by 1 to 3 substituents selected from
        (i) an oxo group,
        (ii) a $C_{1-6}$ alkyl group,
        (iii) a $C_{1-6}$ alkyl-carbonyl group optionally substituted by 1 to 3 substituents selected from a hydroxy group and a alkoxy group,
        (iv) a carbamoyl group optionally mono- or di-substituted by alkyl group(s),
        (v) a $C_{1-6}$ alkylsulfonyl group, and
        (vi) a halogen atom, and
    (k) a alkylenedioxy group,
(5) a 5- to 7-membered monocyclic aromatic heterocyclic group optionally substituted by 1 to 3 substituents selected from
    (a) a carboxy group,
    (b) a cyano group,
    (c) a $C_{1-6}$ alkoxy-carbonyl group,
    (d) a carbamoyl group optionally mono- or di-substituted by substituent(s) selected from
        (i) a $C_{1-6}$ alkyl group optionally substituted by 1 to 3 substituents selected from a hydroxy group and a cyano group,
        (ii) a $C_{3-10}$ cycloalkyl group optionally substituted by 1 to 3 cyano groups,
        (iii) a 5- to 7-membered monocyclic aromatic heterocyclic group optionally substituted by 1 to 3 $C_{1-6}$ alkyl groups, and
        (iv) a 3- to 8-membered monocyclic non-aromatic heterocyclic group,
    (e) a 3- to 8-membered monocyclic non-aromatic heterocyclic group optionally substituted by 1 to 3 oxo groups,
    (f) a $C_{1-6}$ alkyl group optionally substituted by 1 to 3 substituents selected from
        (i) a cyano group,
        (ii) a carbamoyl group, and
        (iii) a 3- to 8-membered monocyclic non-aromatic heterocyclic group optionally substituted by 1 to 3 oxo groups,
    (g) a $C_{3-10}$ cycloalkyl group,
    (h) a 3- to 8-membered monocyclic non-aromatic heterocyclylcarbonyl group, and
    (i) an amino group,
(6) a 8- to 12-membered fused aromatic heterocyclic group optionally substituted by 1 to 3 $C_{1-6}$ alkyl groups,
(7) a 3- to 8-membered monocyclic non-aromatic heterocyclic group optionally substituted by 1 to 3 substituents selected from
    (a) an oxo group, and
    (b) a $C_{1-6}$ alkyl group,
(8) a 8- to 12-membered fused non-aromatic heterocyclic group optionally substituted by 1 to 3 oxo groups, or
(9) an amino group optionally mono- or di-substituted by substituent(s) selected from
    (a) a $C_{6-14}$ aryl group optionally substituted by 1 to 3 substituents selected from
        (i) a carbamoyl group, and
        (ii) a sulfamoyl group,
    (b) a $C_{1-6}$ alkyl group optionally substituted by 1 to 3 substituents selected from a $C_{6-14}$ aryl group optionally substituted by 1 to 3 $C_{1-6}$ alkoxy groups, and
    (c) a $C_{6-14}$ aryl-carbonyl group.

[3] The compound or salt of the above-mentioned [1], which is 4-(1-cyclopentyl-4-oxo-4,5-dihydro-1H-pyrrolo[3,2-c]pyridin-3-yl)thiophene-2-carboxamide.

[4] The compound or salt of the above-mentioned [1], which is 2-(4-(1-(2,6-difluorophenyl)-4-oxo-4,5-dihydro-1H-pyrazolo[4,3-c]pyridin-3-yl)phenyl)acetamide.

[5] The compound or salt of the above-mentioned [1], which is 3-((1-cyclopentyl-4-oxo-4,5-dihydro-1H-pyrazolo[4,3-c]pyridin-3-yl)amino)benzenesulfonamide.

[6] A medicament comprising the compound or salt of the above-mentioned [1].

[7] The medicament of the above-mentioned [6], which is a Janus kinase inhibitor.

[8] The medicament of the above-mentioned [6], which is an agent for the prophylaxis or treatment of autoimmune disease.

[9] The compound or salt of the above-mentioned [1] for use in the prophylaxis or treatment of autoimmune diseases.

[10] A method of inhibiting janus kinase in a mammal, which comprises administering an effective amount of the compound or salt of the above-mentioned [1] to the mammal.

[11] A method for the prophylaxis or treatment of autoimmune diseases, which comprises administering an effective amount of the compound or salt of the above-mentioned [1] to the mammal.

[12] Use of the compound or salt of the above-mentioned [1] for the production of an agent for the prophylaxis or treatment of autoimmune diseases.

[13] The medicament of the above-mentioned [8], wherein the autoimmune disease is rheumatoid arthritis (rheumatoid arthritis), psoriasis (psoriasis), inflammatory bowel disease (inflammatory bowel disease), Sjogren's syndrome (Sjogren's syndrome), Behcet's disease (Behcet's syndrome), multiple sclerosis (multiple sclerosis) or systemic lupus erythematosus (systemic lupus erythematosus).

[14] The compound or salt of the above-mentioned [9], wherein autoimmune disease is rheumatoid arthritis, psoriasis, inflammatory bowel disease, Sjogren's syndrome, Behcet's disease, multiple sclerosis or systemic lupus erythematosus.

[15] The method of the above-mentioned [11], wherein autoimmune disease is rheumatoid arthritis, psoriasis, inflammatory bowel disease, Sjogren's syndrome, Behcet's disease, multiple sclerosis or systemic lupus erythematosus.

[16] The use of the above-mentioned [12], wherein autoimmune disease is rheumatoid arthritis, psoriasis, inflammatory bowel disease, Sjogren's syndrome, Behcet's disease, multiple sclerosis or systemic lupus erythematosus.

[17] A compound represented by the formula (I'):

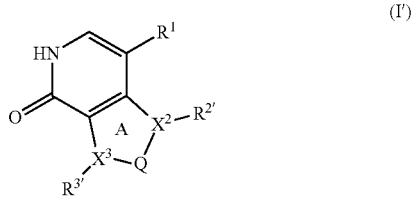

(I')

wherein

Ring A, Q, $X^2$, $X^3$ and $R^1$ are as defined above;

$R^{2'}$ and $R^{3'}$ are each independently a halogen atom, a substituted $C_{1-2}$ alkyl group, an optionally substituted $C_{3-6}$ alkyl group, an acyl group, an optionally substituted hydroxy group, an optionally substituted amino group, an optionally substituted carbocyclic group or an optionally substituted heterocyclic group, or a salt thereof.

Effect of the Invention

Compound (I) has a superior JAK inhibitory action, and is useful as an agent for the treatment of autoimmune disease (rheumatoid arthritis, psoriasis, inflammatory bowel disease (Crohn's disease, ulcerative colitis, etc.), Sjogren's syndrome, Behcet's disease, multiple sclerosis, systemic lupus erythematosus, etc.), cancer (leukemia, uterine leiomyosarcoma, prostate cancer, multiple myeloma, cachexia, myelofibrosis, etc.) and the like.

DETAILED DESCRIPTION OF THE INVENTION

In the present specification, the "halogen atom" means a fluorine atom, a chlorine atom, a bromine atom or an iodine atom.

In the present specification, the "$C_{1-2}$ alkyl group" means, for example, methyl or ethyl.

In the present specification, the "$C_{3-6}$ alkyl group" means, for example, propyl, isopropyl, butyl, 2-methylpropyl, 1-methylpropyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl or the like.

In the present specification, the "$C_{1-6}$ alkyl (group)" means, for example, methyl, ethyl, propyl, isopropyl, butyl, 2-methylpropyl, 1-methylpropyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl or the like.

In the present specification, the "$C_{1-10}$ alkyl (group)" means, for example, methyl, ethyl, propyl, isopropyl, butyl, 2-methylpropyl, 1-methylpropyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl or the like. Among them, a $C_{1-6}$ alkyl group is preferable.

In the present specification, the "$C_{2-6}$ alkenyl (group)" means, for example, vinyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl or the like.

In the present specification, the "$C_{2-10}$ alkenyl (group)" means, for example, vinyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-1-hexenyl, 3-hexenyl, 5-hexenyl, 1-heptenyl, 1-octenyl or the like. Among them, a $C_{2-6}$ alkenyl group is preferable.

In the present specification, the "$C_{2-6}$ alkynyl (group)" means, for example, ethynyl, 1-propynyl, 2-propynyl, 1-butynyl, 2-butynyl, 3-butynyl, 1-pentynyl, 2-pentynyl, 3-pentynyl, 4-pentynyl, 1,1-dimethylprop-2-yn-1-yl, 1-hexynyl, 2-hexynyl, 3-hexynyl, 4-hexynyl, 5-hexynyl or the like.

In the present specification, the "$C_{2-10}$ alkynyl (group)" means, for example, ethynyl, 1-propynyl, 2-propynyl, 1-butynyl, 2-butynyl, 3-butynyl, 1-pentynyl, 2-pentynyl, 3-pentynyl, 4-pentynyl, 1,1-dimethylprop-2-yn-1-yl, 1-hexynyl, 2-hexynyl, 3-hexynyl, 4-hexynyl, 5-hexynyl, 1-heptynyl, 1-octynyl or the like. Among them, a $C_{2-6}$ alkynyl group is preferable.

In the present specification, the "$C_{1-6}$ alkoxy (group)" means, for example, methoxy, ethoxy, propoxy, isopropoxy, butoxy, isobutoxy, sec-butoxy, tert-butoxy, pentyloxy, isopentyloxy, hexyloxy or the like.

In the present specification, the "$C_{2-6}$ alkenyloxy (group)" means, for example, vinyloxy, 1-propenyloxy, 2-propenyloxy, 2-methyl-1-propenyloxy, 1-butenyloxy, 2-butenyloxy, 3-butenyloxy, 3-methyl-2-butenyloxy, 1-pentenyloxy, 2-pentenyloxy, 3-pentenyloxy, 4-pentenyloxy, 4-methyl-3-pentenyloxy, 1-hexenyl, 3-hexenyloxy, 5-hexenyloxy or the like.

In the present specification, the "$C_{2-6}$ alkynyloxy (group)" means, for example, ethynyloxy, 1-propynyloxy, 2-propynyloxy, 1-butynyloxy, 2-butynyloxy, 3-butynyloxy, 1-pentynyloxy, 2-pentynyloxy, 3-pentynyloxy, 4-pentynyloxy, 1,1-dimethylprop-2-yn-1-yloxy, 1-hexynyloxy, 2-hexynyloxy, 3-hexynyloxy, 4-hexynyloxy, 5-hexynyloxy or the like.

In the present specification, the "$C_{1-6}$ alkylenedioxy (group)" means, for example, methylenedioxy, ethylenedioxy or the like.

In the present specification, the "$C_{1-6}$ alkoxy-carbonyl (group)" means, for example, methoxycarbonyl, ethoxycarbonyl, propoxycarbonyl, isopropoxycarbonyl, butoxycarbonyl, isobutoxycarbonyl, tert-butoxycarbonyl or the like.

In the present specification, the "$C_{1-6}$ alkyl-carbonyl (group)" means, for example, acetyl, propanoyl, butanoyl, 2-methylpropanoyl or the like.

In the present specification, the "$C_{3-6}$ cycloalkyl (group)" means, for example, cyclopropyl, cyclobutyl, cyclopentyl and cyclohexyl or the like.

In the present specification, the "$C_{3-10}$ cycloalkyl (group)" means, for example, cyclopropyl, cyclobutyl, cyclopentyl, cyclohexyl, cycloheptyl, cyclooctyl, cyclononyl, cyclodecyl or the like. Among them, a $C_{3-6}$ cycloalkyl group is preferable.

In the present specification, the "$C_{3-8}$ cycloalkyl (group)" means, for example, cyclopropyl, cyclobutyl, cyclopentyl, cyclohexyl, cycloheptyl, cyclooctyl or the like. Among them, a $C_{3-6}$ cycloalkyl group is preferable.

In the present specification, the "$C_{3-8}$ cycloalkenyl (group)" means, for example, cyclopropenyl (e.g., 2-cyclopropen-1-yl), cyclobutenyl (e.g., 2-cyclobuten-1-yl), cyclopentenyl 1-cyclopenten-1-yl, 2-cyclopenten-1-yl, 3-cyclopenten-1-yl), cyclohexenyl (e.g., 1-cyclohexen-1-yl, 2-cyclohexen-1-yl, 3-cyclohexen-1-yl) or the like.

In the present specification, the "$C_{3-10}$ cycloalkenyl (group)" means, for example, cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 1-cyclohexen-1-yl, 2-cyclohexen-1-yl, 3-cyclohexen-1-yl), cycloheptenyl (e.g., 1-cyclopenten-1-yl, 2-cyclohepten-1-yl, 2-cyclohepten-1-yl), cyclooctenyl (e.g., 1-cyclohepten-1-yl, 2-cyclohepten-1-yl, 3-cyclohepten-1-yl), cyclononenyl (e.g., 1-cyclononen-1-yl, 2-cyclononen-1-yl, 3-cyclononen-1-yl) or the like. Among them, a $C_{3-8}$ cycloalkenyl group is preferable.

In the present specification, the "$C_{4-6}$ cycloalkadienyl (group)" means, for example, 1,3-cyclobutadien-1-yl, 1,3-cyclopentadien-1-yl, 1,4-cyclopentadien-1-yl, 2,4-cyclopentadien-1-yl, 1,3-cyclohexadien-1-yl, 1,4-cyclohexadien-1-yl, 1,5-cyclohexadien-1-yl, 2,4-cyclohexadien-1-yl, 2,5-cyclohexadien-1-yl or the like.

In the present specification, the "$C_{4-10}$ cycloalkadienyl (group)" means, for example, 1,3-cyclobutadien-1-yl, 1,3-cyclopentadien-1-yl, 1,4-cyclopentadien-1-yl, 2,4-cyclopentadien-1-yl, 1,3-cyclohexadien-1-yl, 1,4-cyclohexadien-1-yl, 1,5-cyclohexadien-1-yl, 2,4-cyclohexadien-1-yl, 2,5-cyclohexadien-1-yl, 1,3-cyclooctadien-1-yl, 1,4-cyclooctadien-1-yl, 1,5-cyclooctadien-1-yl, 1,6-cyclooctadien-1-yl, 1,7-cyclooctadien-1-yl, 2,4-cyclooctadien-1-yl, 2,5-cyclooctadien-1-yl, 2,6-cyclooctadien-1-yl, 2,7-cyclooctadien-1-yl, 3,5-cyclooctadien-1-yl, 3,6-cyclooctadien-1-yl or the like. Among them, a $C_{4-6}$ cycloalkadienyl group is preferable.

The above-mentioned $C_{3-10}$ cycloalkyl group, $C_{3-10}$ cycloalkenyl group and $C_{4-10}$ cycloalkadienyl group are each optionally fused with a benzene ring to form a fused ring group, and examples of the fused ring group include indanyl, dihydronaphthyl, tetrahydronaphthyl, fluorenyl and the like.

The above-mentioned $C_{3-10}$ cycloalkyl group, $C_{3-10}$ cycloalkenyl group and $C_{4-10}$ cycloalkadienyl group may be a $C_{7-10}$ bridged hydrocarbon group. Examples of the $C_{7-10}$ bridged hydrocarbon group include bicyclo[2.2.1]heptyl (norbornyl), bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

In addition, the above-mentioned $C_{3-10}$ cycloalkyl group, $C_{3-10}$ cycloalkenyl group and $C_{4-10}$ cycloalkadienyl group may each form a spiro ring group with a $C_{3-10}$ cycloalkane, a $C_{3-10}$ cycloalkene or a $C_{4-10}$ cycloalkadiene. Examples of the $C_{3-10}$ cycloalkane, $C_{3-10}$ cycloalkene and $C_{4-10}$ cycloalkadiene include rings corresponding to the above-mentioned $C_{3-10}$ cycloalkyl group, $C_{3-10}$ cycloalkenyl group and $C_{4-10}$ cycloalkadienyl group. Examples of the Spiro ring group include spiro[4.5]decan-8-yl and the like.

In the present specification, the "$C_{3-6}$ cycloalkyloxy (group)" means, for example, cyclopropyloxy, cyclobutyloxy, cyclopentyloxy, cyclohexyloxy or the like.

In the present specification, the "$C_{3-8}$ cycloalkyloxy (group)" means, for example, cyclopropyloxy, cyclobutyloxy, cyclopentyloxy, cyclohexyloxy, cycloheptyloxy, cyclooctyloxy or the like. Among them, a $C_{3-6}$ cycloalkyloxy group is preferable.

In the present specification, the "$C_{3-8}$ cycloalkenyloxy (group)" means, for example, cyclopropenyloxy (e.g., 2-cyclopropen-1-yloxy), cyclobutenyloxy (e.g., 2-cyclobuten-1-yloxy), cyclopentenyloxy (e.g., 2-cyclopenten-1-yloxy, 3-cyclopenten-1-yloxy), cyclohexenyloxy (e.g., 2-cyclohexen-1-yloxy, 3-cyclohexen-1-yloxy) or the like.

In the present specification, the "$C_{6-14}$ aryl (group)" means, for example, phenyl, 1-naphthyl, 2-naphthyl or the like.

In the present specification, the "$C_{6-14}$ aryloxy (group)" means, for example, phenoxy, 1-naphthyloxy, 2-naphthyloxy or the like.

In the present specification, the "$C_{7-14}$ aralkyl (group)" means, for example, benzyl, phenethyl or the like.

In the present specification, the "$C_{7-14}$ aralkyloxy (group)" means, for example, benzyloxy, phenethyloxy or the like.

In the present specification, the "$C_{8-13}$ arylalkenyl (group)" means, for example, styryl or the like.

In the present specification, the "heterocyclic group" means an aromatic heterocyclic group or a non-aromatic heterocyclic group.

In the present specification, the "aromatic heterocyclic group" means a monocyclic aromatic heterocyclic group or a fused aromatic heterocyclic group.

In the present specification, examples of the "monocyclic aromatic heterocyclic group" include a 5- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom (optionally oxidized) and a nitrogen atom (optionally oxidized), for example, furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like.

In the present specification, examples of the "fused aromatic heterocyclic group" include an 8- to 12-membered fused aromatic heterocyclic group, specifically, a group derived from a fused ring wherein a ring corresponding to the above-mentioned 5- to 7-membered monocyclic aromatic heterocyclic group is fused with a $C_{6-14}$ aromatic hydrocarbon; and a group derived from a fused ring wherein rings corresponding to the above-mentioned 5- to 7-membered monocyclic aromatic heterocyclic groups are fused, for example, quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl, 2H-imidazo[1,2-a]pyridin-3-yl), thienopyridyl (e.g., thieno[2,3-b]pyridin-3-yl), imidazopyrazinyl (e.g., 1H-imidazo[4,5-b]pyrazin-2-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

In the present specification, the "non-aromatic heterocyclic group" means a monocyclic non-aromatic heterocyclic group or a non-aromatic heterocyclic group.

In the present specification, examples of the "monocyclic non-aromatic heterocyclic group" include a 3- to 8-membered (preferably 5- or 6-membered) monocyclic non-aromatic heterocyclic group containing, as a ring-constituting atom besides carbon atoms, 1 to 4 hetero atoms selected from an oxygen atom, a sulfur atom (optionally oxidized) and a nitrogen atom (optionally oxidized), for example, azetidinyl (e.g., 1-azetidinyl, 2-azetidinyl), pyrrolidinyl (e.g., 1-pyrrolidinyl, 2-pyrrolidinyl), piperidyl (e.g., piperidino, 2-piperidyl, 3-piperidyl, 4-piperidyl), morpholinyl (e.g., morpholino), thiomorpholinyl (e.g., thiomorpholino), piperazinyl (e.g., 1-piperazinyl, 2-piperazinyl, 3-piperazinyl), oxazolidinyl (e.g., oxazolidin-2-yl), thiazolidinyl (e.g., thiazolidin-2-yl), dihydrothiopyranyl (e.g., dihydrothiopyran-3-yl, dihydrothiopyran-4-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-31), pyranyl (e.g., 2-pyranyl, 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidetetrahydrothiopyranyl (e.g., 1-oxidetetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), oxetanyl (e.g., oxetan-2-yl, oxetan-3-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl), azepanyl (e.g., 1-azepanyl, 2-azepanyl, 3-azepanyl, 4-azepanyl), dihydropyridyl (e.g., dihydropyridin-1-yl, dihydropyridin-2-yl, dihydropyridin-3-yl, dihydropyridin-4-yl), tetrahydropyridyl (e.g., 1,2,3,4-tetrahydropyridin-1-yl, 1,2,3,4-tetrahydropyridin-2-yl, 1,2,3,4-tetrahydropyridin-3-yl, 1,2,3,4-tetrahydropyridin-4-yl), benzoxadiazolyl (e.g., 2,1,3-benzoxadiazol-5-yl) and the like.

In the present specification, examples of the "fused non-aromatic heterocyclic group" include an 8- to 12-membered fused non-aromatic heterocyclic group, specifically, a group derived from a fused ring wherein a ring corresponding to the above-mentioned 3- to 8-membered monocyclic non-aromatic heterocyclic group is fused with a $C_{6-14}$ aromatic hydrocarbon; a group derived from a fused ring wherein rings corresponding to the above-mentioned 3- to 8-membered monocyclic non-aromatic heterocyclic groups are fused; a group derived from a fused ring wherein a ring corresponding to the above-mentioned 3- to 8-membered monocyclic non-aromatic heterocyclic group is fused with a ring corresponding to the above-mentioned 5- to 7-membered monocyclic aromatic heterocyclic group; and a group wherein the above-mentioned group is partially saturated, for example, dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), tetrahydrobenzofuranyl (e.g., 4,5,6,7-tetrahydro-1-benzofuran-3-yl), dihydrobenzodioxinyl (e.g., 2,3-dihydro-1,4-benzodioxin-2-yl), dihydrobenzodioxepinyl (e.g., 3,4-dihydro-2H-1,5-benzodioxepin-2-yl), chromenyl (e.g., 4H-chromen-2-yl, 2H-chromen-3-yl), dihydrochromenyl (e.g., 3,4-dihydro-2H-chromen-2-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like.

In the present specification, examples of the "$C_{6-14}$ aromatic hydrocarbon" include benzene and naphthalene.

In the present specification, examples of the "carbocyclic group" include a $C_{6-14}$ aryl group, a $C_{3-10}$ cycloalkyl group, a $C_{3-10}$ cycloalkenyl group and a $C_{4-10}$ cycloalkadienyl group.

Each symbol of the formula (I) is explained below.

In the formula (I), $R^1$ is a hydrogen atom, a halogen atom, a cyano group, an acyl group, an optionally substituted $C_{1-6}$ alkyl group, an optionally substituted $C_{3-6}$ cycloalkyl group or an optionally substituted hydroxy group.

The "$C_{1-6}$ alkyl group" of the "optionally substituted $C_{1-6}$ alkyl group" for $R^1$ optionally has 1 to 5 (preferably 1 to 3) substituents at substitutable position(s). Examples of the substituent include substituents selected from the following Substituent Group A. When the number of the substituents is plural, the respective substituents may be the same or different.

Substituent Group A:
(1) a halogen atom;
(2) a cyano group;
(3) a nitro group;
(4) a hydroxy group;
(5) a $C_{3-8}$ cycloalkyl group optionally substituted by 1 to 3 substituents selected from
    (a) a halogen atom,
    (b) a cyano group,
    (c) a $C_{1-6}$ alkyl group optionally substituted by 1 to 3 halogen atoms, and
    (d) a $C_{1-6}$ alkoxy group optionally substituted by 1 to 3 halogen atoms;
(6) a $C_{6-14}$ aryl group optionally substituted by 1 to 3 substituents selected from (a) a halogen atom,
(b) a cyano group,
(c) a $C_{1-6}$ alkyl group optionally substituted by 1 to 3 halogen atoms,
(d) a $C_{1-6}$ alkoxy group optionally substituted by 1 to 3 halogen atoms, and
(e) a carbamoyl group;
(7) a $C_{1-6}$ alkoxy group optionally substituted by 1 to 3 substituents selected from
 (a) a halogen atom,
 (b) a cyano group,
 (c) a $C_{3-8}$ cycloalkyl group optionally having 1 to 3 halogen atoms,
 (d) a $C_{3-8}$ cycloalkenyl group optionally having 1 to 3 halogen atoms,
 (e) a $C_{6-14}$ aryl group optionally having 1 to 3 halogen atoms,
 (f) a 5- or 6-membered monocyclic aromatic heterocyclic group, and
 (g) a silyl group optionally having 1 to 3 $C_{1-6}$ alkyl groups;
(8) a $C_{2-6}$ alkenyloxy group (e.g., vinyloxy, propenyloxy, butenyloxy, pentenyloxy, hexenyloxy) optionally having 1 to 3 halogen atoms;
(9) a $C_{2-6}$ alkynyloxy group (e.g., ethynyloxy, propynyloxy, butynyloxy, pentynyloxy, hexynyloxy) optionally having 1 to 3 halogen atoms;
(10) a $C_{3-8}$ cycloalkyloxy group (e.g., cyclopropyloxy, cyclobutyloxy, cyclopentyloxy, cyclohexyloxy) optionally having 1 to 3 halogen atoms;
(11) a $C_{3-8}$ cycloalkenyloxy group (e.g., cyclopropenyloxy, cyclobutenyloxy, cyclopentenyloxy, cyclohexenyloxy) optionally having 1 to 3 halogen atoms;
(12) a $C_{6-14}$ aryloxy group optionally having 1 to 3 halogen atoms;
(13) a $C_{7-14}$ aralkyloxy group optionally substituted by 1 to 3 substituents selected from
 (a) a halogen atom, and
 (b) a $C_{1-6}$ alkoxy group;
(14) a carbamoyl group optionally mono- or di-substituted by substituent(s) selected from
 (a) a $C_{1-6}$ alkyl group,
 (b) a $C_{3-8}$ cycloalkyl group,
 (c) a $C_{6-14}$ aryl group,
 (d) a $C_{1-6}$ alkoxy group,
 (e) a 5- or 6-membered monocyclic aromatic heterocyclic group,
 (f) a 8- to 12-membered fused aromatic heterocyclic group,
 (g) a 3- to 8-membered monocyclic non-aromatic heterocyclic group, and
 (h) a 8- to 12-membered fused non-aromatic heterocyclic group;
(15) a sulfamoyl group optionally mono- or di-substituted by substituent(s) selected from
 (a) a $C_{1-6}$ alkyl group,
 (b) a $C_{3-8}$ cycloalkyl group,
 (c) a $C_{6-14}$ aryl group,
 (d) a $C_{1-6}$ alkoxy group,
 (e) a 5- or 6-membered monocyclic aromatic heterocyclic group,
 (f) a 8- to 12-membered fused aromatic heterocyclic group,
 (g) a 3- to 8-membered monocyclic non-aromatic heterocyclic, group, and
 (h) a 8- to 12-membered fused non-aromatic heterocyclic group;
(16) formyl;
(17) a $C_{1-6}$ alkyl-carbonyl group;
(18) a $C_{2-6}$ alkenyl-carbonyl group (e.g., acryloyl, butenoyl, pentenoyl, hexenoyl, heptenoyl);
(19) a $C_{2-6}$ alkynyl-carbonyl group (e.g., propioloyl, propynylcarbonyl, butynylcarbonyl, pentynylcarbonyl, hexynylcarbonyl);
(20) a $C_{3-8}$ cycloalkyl-carbonyl group (e.g., cyclopropylcarbonyl, cyclobutylcarbonyl, cyclopentylcarbonyl, cyclohexylcarbonyl);
(21) a $C_{3-8}$ cycloalkenyl-carbonyl group (e.g., cyclopropenylcarbonyl, cyclobutenylcarbonyl, cyclopentenylcarbonyl, cyclohexenylcarbonyl);
(22) a $C_{6-14}$ aryl-carbonyl group (e.g., benzoyl, 1-naphthylcarbonyl, 2-naphthylcarbonyl);
(23) a $C_{3-8}$ cycloalkyl-$C_{1-6}$ alkyl-carbonyl group (e.g., cyclopropylacetyl, 3-cyclopropylpropionyl, cyclobutylacetyl, cyclopentylacetyl, cyclohexyl acetyl, cyclohexyl propionyl);
(24) a $C_{3-8}$ cycloalkenyl-$C_{1-6}$ alkyl-carbonyl group (e.g., cyclopentenylacetyl, cyclohexenylacetyl, 3-cyclohexenylpropionyl, 3-cyclohexenylpropionyl);
(25) a $C_{7-14}$ aralkyl-carbonyl group (e.g., phenylacetyl, 3-phenylpropionyl);
(26) a 5- or 6-membered monocyclic aromatic heterocyclylcarbonyl group (e.g., furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyridylcarbonyl, pyrazolylcarbonyl);
(27) a 8- to 12-membered fused aromatic heterocyclylcarbonyl group (e.g., benzofuranylcarbonyl, isobenzofuranylcarbonyl, benzothienylcarbonyl, isobenzothienylcarbonyl, indolylcarbonyl, isoindolylcarbonyl, indazolylcarbonyl, benzimidazolylcarbonyl, benzoxazolylcarbonyl);
(28) a 3- to 8-membered monocyclic non-aromatic heterocyclylcarbonyl group (e.g., oxiranylcarbonyl, azetidinylcarbohyl, oxetanylcarbonyl, thietanylcarbonyl, pyrrolidinylcarbonyl, tetrahydrofurylcarbonyl, thiolanylcarbonyl, piperidylcarbonyl);
(29) a 8- to 12-membered fused non-aromatic heterocyclylcarbonyl group (e.g., dihydrobenzofuranyl);
(30) an amino group optionally mono- or di-substituted by substituent(s) selected from
 (a) a $C_{1-5}$ alkyl group optionally having 1 to 3 halogen atoms,
 (b) a $C_{1-5}$ alkyl-carbonyl group optionally having 1 to 3 halogen atoms,
 (c) a $C_{3-8}$ cycloalkyl-carbonyl group,
 (d) a $C_{6-14}$ aryl-carbonyl group optionally having 1 to 3 halogen atoms,
 (e) a 5- or 6-membered monocyclic aromatic heterocyclylcarbonyl group,
 (f) a 8- to 12-membered fused aromatic heterocyclylcarbonyl group,
 (g) a 3- to 8-membered monocyclic non-aromatic heterocyclylcarbonyl group, and
 (h) a 8- to 12-membered fused non-aromatic heterocyclylcarbonyl group;
(31) a sulfanyl group;
(32) a $C_{1-6}$ alkylsulfanyl group (e.g., methylsulfanyl, ethylsulfanyl);
(33) a $C_{2-6}$ alkenylsulfinyl group (e.g., vinylsulfanyl, propenylsulfinyl);
(34) a $C_{2-6}$ alkynylsulfanyl group (e.g., ethynylsulfanyl, propynylsulfinyl);
(35) a $C_{3-8}$ cycloalkylsulfanyl group (e.g., cyclopropylsulfanyl, cyclobutylsulfanyl);
(36) a $C_{3-8}$ cycloalkenylsulfinyl group (e.g., cyclopropenylsulfanyl, cyclobutenylsulfinyl);
(37) a $C_{6-14}$ arylsulfanyl group (e.g., phenylsulfanyl);

(38) a $C_{3-8}$ cycloalkyl-$C_{1-6}$ alkylsulfanyl group (e.g., cyclopropylmethylsulfanyl);
(39) a $C_{3-8}$ cycloalkenyl-$C_{1-6}$ alkylsulfanyl group (e.g., cyclopentenylmethylsulfanyl);
(40) a $C_{1-6}$ alkylsulfinyl group (e.g., methylsulfinyl, ethylsulfinyl);
(41) a $C_{2-6}$ alkenylsulfinyl group (e.g., vinylsulfinyl, propenylsulfinyl);
(42) a $C_{2-6}$ alkynylsulfinyl group (e.g., ethynylsulfinyl, propynylsulfinyl);
(43) a $C_{3-8}$ cycloalkylsulfinyl group (e.g., cyclopropylsulfinyl, cyclobutylsulfinyl);
(44) a $C_{3-8}$ cycloalkenylsulfinyl group (e.g., cyclopropenylsulfinyl, cyclobutenylsulfinyl);
(45) a $C_{6-14}$ arylsulfinyl group (e.g., phenylsulfinyl);
(46) a $C_{3-8}$ cycloalkyl-$C_{1-6}$ alkylsulfinyl group (e.g., cyclopropylmethylsulfinyl);
(47) a $C_{3-8}$ cycloalkenyl-$C_{1-6}$ alkylsulfinyl group (e.g., cyclopentenylmethylsulfinyl);
(48) a $C_{1-6}$ alkylsulfonyl group (e.g., methylsulfonyl, ethylsulfonyl);
(49) a $C_{2-6}$ alkenylsulfonyl group (e.g., vinylsulfonyl, propenylsulfonyl);
(50) a $C_{2-6}$ alkynylsulfonyl group (e.g., ethynylsulfonyl, propynylsulfonyl);
(51) a $C_{3-8}$ cycloalkylsulfonyl group (e.g., cyclopropylsulfonyl, cyclobutylsulfonyl);
(52) a $C_{3-8}$ cycloalkenylsulfonyl group (e.g., cyclopropenylsulfonyl, cyclobutenylsulfonyl);
(53) a $C_{6-14}$ arylsulfonyl group (e.g., phenylsulfonyl);
(54) a $C_{3-8}$ cycloalkyl-$C_{1-6}$ alkylsulfonyl group (e.g., cyclopropylmethylsulfonyl);
(55) a $C_{3-8}$ cycloalkenyl-$C_{1-6}$ alkylsulfonyl group (e.g., cyclopentenylmethylsulfonyl);
(56) a $C_{6-14}$ aryl-$C_{1-6}$ alkylsulfonyl group (e.g., benzylsulfonyl);
(57) a 5- or 6-membered monocyclic aromatic heterocyclylsulfonyl group (e.g., furylsulfonyl, thienylsulfonyl, pyridylsulfonyl);
(58) a 8- to 12-membered fused aromatic heterocyclylsulfonyl group (e.g., benzofuranylsulfonyl, isobenzofuranylsulfonyl);
(59) a 3- to 8-membered monocyclic non-aromatic heterocyclylsulfonyl group (e.g., oxiranylsulfonyl, azetidinylsulfonyl);
(60) a 8- to 12-membered fused non-aromatic heterocyclylsulfonyl group (e.g., dihydrobenzofuranylsulfonyl);
(61) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl) optionally substituted by 1 to 3 substituents selected from
   (a) a halogen atom,
   (b) a $C_{1-6}$ alkyl group optionally substituted by 1 to 3 halogen atoms, and
   (c) a $C_{1-6}$ alkoxy group optionally substituted by 1 to 3 halogen atoms;
(62) a 8- to 12-membered fused aromatic heterocyclic group (e.g., benzofuranyl, isobenzofuranyl, benzothienyl, isobenzothienyl, indolyl, isoindolyl, indazolyl, benzimidazolyl, benzoxazolyl) optionally substituted by 1 to 3 substituents selected from
   (a) a halogen atom,
   (b) a $C_{1-6}$ alkyl group optionally substituted by 1 to 3 halogen atoms, and
   (c) a $C_{1-6}$ alkoxy group optionally substituted by 1 to 3 halogen atoms;
(63) a 3- to 8-membered monocyclic non-aromatic heterocyclic group (e.g., oxiranyl, azetidinyl, oxetanyl, thietanyl, pyrrolidinyl, tetrahydrofuryl, thiolanyl, piperidyl, piperazinyl, dihydrooxadiazolyl, thiazolinyl, dioxolanyl, morpholinyl) optionally substituted by 1 to 3 substituents selected from
   (a) a halogen atom,
   (b) a $C_{1-6}$ alkyl group optionally substituted by 1 to 3 halogen atoms,
   (c) a $C_{1-6}$ alkoxy group optionally substituted by 1 to 3 halogen atoms, and
   (d) an oxo group;
(64) a 8- to 12-membered fused non-aromatic heterocyclic group (e.g., dihydrobenzofuranyl) optionally substituted by 1 to 3 substituents selected from
   (a) a halogen atom,
   (b) a $C_{1-6}$ alkyl group optionally substituted by 1 to 3 halogen atoms,
   (c) a $C_{1-6}$ alkoxy group optionally substituted by 1 to 3 halogen atoms, and
   (d) an oxo group;
(65) a 5- or 6-membered monocyclic aromatic heterocyclyloxy group (e.g., furyloxy, thienyloxy, pyrrolyloxy, oxazolyloxy, isoxazolyloxy, thiazolyloxy, isothiazolyloxy, imidazolyloxy, pyridyloxy, pyrazolyloxy);
(66) a 8- to 12-membered fused aromatic heterocyclyloxy group (e.g., benzofuranyloxy, isobenzofuranyloxy, benzothienyloxy, isobenzothienyloxy, indolyloxy, isoindolyloxy, indazolyloxy, benzimidazolyloxy, benzoxazolyloxy);
(67) a 3- to 8-membered monocyclic non-aromatic heterocyclyloxy group (e.g., oxetanyloxy, azetidinyloxy, oxetanyloxy, thietanyloxy, pyrrolidinyloxy, tetrahydrofuryloxy, thiolanyloxy, piperidyloxy);
(68) a 8- to 12-membered fused non-aromatic heterocyclyloxy group (e.g., dihydrobenzofuranyloxy);
(69) a carboxy group;
(70) a $C_{1-6}$ alkoxy-carbonyl group;
(71) a $C_{2-6}$ alkenyloxy-carbonyl group (e.g., vinyloxycarbonyl, propenyloxycarbonyl, butenyloxycarbonyl, pentenyloxycarbonyl, hexenyloxycarbonyl);
(72) a $C_{2-6}$ alkynyloxy-carbonyl group (e.g., ethynyloxycarbonyl, propynyloxycarbonyl, butynyloxycarbonyl, pentynyloxycarbonyl, hexynyloxycarbonyl);
(73) a $C_{3-8}$ cycloalkyloxy-carbonyl group (e.g., cyclopropyloxycarbonyl, cyclobutyloxycarbonyl, cyclopentyloxycarbonyl, cyclohexyloxycarbonyl);
(74) a $C_{3-8}$ cycloalkenyloxy-carbonyl group (e.g., cyclopropenyloxycarbonyl, cyclobutenyloxycarbonyl, cyclopentenyloxycarbonyl, cyclohexenyloxycarbonyl);
(75) a $C_{6-14}$ aryloxy-carbonyl group (e.g., phenoxycarbonyl, 1-naphthyloxycarbonyl, 2-naphthyloxycarbonyl);
(76) a $C_{3-8}$ cycloalkyl-$C_{1-6}$ alkoxy-carbonyl group (e.g., cyclopropylmethyloxycarbonyl, cyclopropylethyloxycarbonyl, cyclobutylmethyloxycarbonyl, cyclopentylmethyloxycarbonyl, cyclohexyl methyloxycarbonyl, cyclohexyl ethyloxycarbonyl);
(77) a $C_{3-8}$ cycloalkenyl-$C_{1-6}$ alkoxy-carbonyl group (e.g., cyclopentenylmethyloxycarbonyl, cyclohexenylmethyloxycarbonyl, cyclohexenylethyloxycarbonyl, cyclohexenylpropyloxycarbonyl);
(78) a $C_{7-14}$ aralkyloxy-carbonyl group (e.g., benzyloxycarbonyl, phenethyloxycarbonyl);
(79) a mono-$C_{1-6}$ alkylthio-carbamoyl group (e.g., methylthiocarbamoyl, ethylthiocarbamoyl, propylthiocarbamoyl);
(80) a di-$C_{1-6}$ alkylthio-carbamoyl group (e.g., dimethylthiocarbamoyl, diethylthiocarbamoyl, dipropylthiocarbamoyl);
(81) a $C_{1-6}$ alkyl-carbonyloxy group (e.g., acetyloxy, propanoyloxy, butanoyloxy, 2-methylpropanoyloxy);

(82) an imino group optionally substituted by a hydroxy group; and
(83) a $C_{1-6}$ alkylenedioxy group (e.g., methylenedioxy, ethylenedioxy).

The "$C_{3-6}$ cycloalkyl group" of the "optionally substituted $C_{3-6}$ cycloalkyl group" for $R^1$ optionally has 1 to 5 (preferably 1 to 3) substituents at substitutable position(s). Examples of the substituent include substituents selected from the following Substituent Group B. When the number of the substituents is plural, the respective substituents may be the same or different.

Substituent Group B:
(1) the aforementioned Substituent Group A;
(2) a $C_{1-6}$ alkyl group optionally substituted by 1 to 3 substituents selected from
   (a) a halogen atom,
   (b) a cyano group,
   (c) a hydroxy group,
   (d) a $C_{3-8}$ cycloalkyl group optionally substituted by 1 to 3 substituents selected from
      (i) a halogen atom,
      (ii) a cyano group, and
      (iii) a $C_{1-6}$ alkyl group optionally substituted by 1 to 3 halogen atoms;
   (e) a $C_{6-14}$ aryl group optionally substituted by 1 to 3 substituents selected from
      (i) a halogen atom,
      (ii) a cyano group, and
      (iii) a $C_{1-6}$ alkyl group optionally substituted by 1 to 3 halogen atoms,
   (f) a $C_{1-6}$ alkoxy group optionally substituted by 1 to 3 halogen atoms,
   (g) an amino group optionally mono- or di-substituted by $C_{1-6}$ alkyl,
   (h) a 5- or 6-membered monocyclic aromatic heterocyclic group,
   (i) a 8- to 12-membered fused aromatic heterocyclic group,
   (j) a 3- to 8-membered monocyclic non-aromatic heterocyclic group,
   (k) a 8- to 12-membered fused non-aromatic heterocyclic group,
   (l) a carboxy group,
   (m) a $C_{1-6}$ alkoxy-carbonyl group optionally substituted by 1 to 3 halogen atoms, and
   (n) a carbamoyl group;
(3) a $C_{2-6}$ alkenyl group optionally substituted by 1 to 3 substituents selected from
   (a) a halogen atom,
   (b) a hydroxy group,
   (c) a $C_{1-6}$ alkoxy group,
   (d) an amino group optionally mono- or di-substituted by $C_{1-6}$ alkyl,
   (e) a carboxy group, and
   (f) a $C_{1-6}$ alkoxy-carbonyl group;
(4) a $C_{7-14}$ aralkyl group optionally substituted by 1 to 3 substituents selected from
   (a) a halogen atom,
   (b) a hydroxy group,
   (c) a $C_{1-6}$ alkoxy group, and
   (d) a $C_{1-6}$ alkyl group optionally substituted by 1 to 3 halogen atoms; and
(5) an oxo group.

Examples of the "optionally substituted hydroxy group" for $R^1$ include a hydroxy group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-14}$ aralkyl group, a $C_{8-13}$ arylalkenyl group, a $C_{1-6}$ alkyl-carbonyl group, a heterocyclic group and the like, each of which is optionally substituted.

The $C_{1-10}$ alkyl group, $C_{2-10}$ alkenyl group and $C_{1-6}$ alkyl-carbonyl group optionally have 1 to 5 (preferably 1 to 3) substituents at substitutable position(s). Examples of the substituent include substituents selected from the above-mentioned Substituent Group A. When the number of the substituents is plural, the respective substituents may be the same or different.

The $C_{3-10}$ cycloalkyl group, $C_{3-10}$ cycloalkenyl group, $C_{6-14}$ aryl group, $C_{7-14}$ aralkyl group, $C_{8-13}$ arylalkenyl group and heterocyclic group optionally have 1 to 5 (preferably 1 to 3) substituents at substitutable position(s). Examples of the substituent include substituents selected from the above-mentioned Substituent Group B. When the number of the substituents is plural, the respective substituents may be the same or different.

Examples of the "acyl group" for $R^1$ include a group represented by the formula: —$COR^A$, —CO—$OR^A$, —$SO_3R^A$, —$S(O)_2R^A$, —$SOR^A$, —CO—$NR^{A'}R^{B'}$, —CS—$NR^{A'}R^{B'}$ or —$S(O)_2NR^{A'}R^{B'}$ wherein $R^A$ is a hydrogen atom, an optionally substituted hydrocarbon group or an optionally substituted heterocyclic group, and $R^{A'}$ and $R^{B'}$ are the same or different and each is a hydrogen atom, an optionally substituted hydrocarbon group or an optionally substituted heterocyclic group, or $R^{A'}$ and $R^{B'}$ in combination optionally form, together with the adjacent nitrogen atom, an optionally substituted nitrogen-containing heterocycle, and the like.

Examples of the "hydrocarbon group" of the "optionally substituted hydrocarbon group" for $R^A$, $R^{A'}$ or $R^{B'}$ include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-14}$ aralkyl group, a $C_{8-13}$ arylalkenyl group and the like.

The $C_{1-10}$ alkyl group, $C_{2-10}$ alkenyl group and $C_{2-10}$ alkynyl group, which are exemplified as the above-mentioned "hydrocarbon group", optionally have 1 to 5 (preferably 1 to 3) substituents at substitutable position(s). Examples of the substituent include substituents selected from the above-mentioned Substituent Group A. When the number of the substituents is plural, the respective substituents may be the same or different.

The $C_{3-10}$ cycloalkyl group, $C_{3-10}$ cycloalkenyl group, $C_{4-10}$ cycloalkadienyl group, $C_{6-14}$ aryl group, $C_{7-14}$ aralkyl group and $C_{8-13}$ arylalkenyl group, which are exemplified as the above-mentioned "hydrocarbon group", optionally have 1 to 5 (preferably 1 to 3) substituents at substitutable position(s). Examples of the substituent include substituents selected from the above-mentioned Substituent Group B. When the number of the substituents is plural, the respective substituents may be the same or different.

The "heterocyclic group" of the "optionally substituted heterocyclic group" for $R^A$, $R^{A'}$ or $R^{B'}$ optionally has 1 to 5 (preferably 1 to 3) substituents at substitutable position(s). Examples of the substituent include substituents selected from the above-mentioned Substituent Group B. When the number of the substituents is plural, the respective substituents may be the same or different.

Examples of the "nitrogen-containing heterocycle" of the "optionally substituted nitrogen-containing heterocycle" formed by $R^{A'}$ and $R^{B'}$ together with the adjacent nitrogen atom include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

The nitrogen-containing heterocycle optionally has 1 to 5 (preferably 1 to 3) substituents at substitutable position(s). Examples of the substituent include substituents selected from the above-mentioned Substituent Group B. When the number of the substituents is plural, the respective substituents may be the same or different.

Preferable examples of the "acyl group" include
(1) a formyl group;
(2) a carboxy group;
(3) a $C_{1-6}$ alkyl-carbonyl group (e.g., acetyl) optionally substituted by 1 to 3 halogen atoms;
(4) a $C_{1-6}$ alkoxy-carbonyl group (e.g., methoxycarbonyl, ethoxycarbonyl, propoxycarbonyl, tert-butoxycarbonyl) optionally substituted by 1 to 3 halogen atoms;
(5) a $C_{3-10}$ cycloalkyl-carbonyl group (e.g., cyclopropylcarbonyl, cyclopentylcarbonyl, cyclohexylcarbonyl);
(6) a $C_{6-14}$ aryl-carbonyl group (e.g., benzoyl, 1-naphthoyl, 2-naphthoyl) optionally substituted by 1 to 3 halogen atoms;
(7) a carbamoyl group optionally mono- or di-substituted by substituent(s) selected from
  (a) a $C_{1-6}$ alkyl group optionally substituted by 1 to 3 substituents selected from a halogen atom, a $C_{1-6}$ alkoxy group, a $C_{1-6}$ alkoxy-carbonyl group and a carboxy group, and
  (b) an amino group optionally mono- or di-substituted by $C_{1-6}$ alkoxy-carbonyl group(s);
(8) a $C_{1-6}$ alkylsulfonyl group (e.g., methylsulfonyl, ethylsulfonyl, isopropylsulfonyl) optionally substituted by 1 to 3 halogen atoms;
(9) a $C_{6-14}$ arylsulfonyl group (e.g., benzenesulfonyl);
(10) a sulfamoyl group;
(11) a thiocarbamoyl group;
(12) an aromatic heterocyclylcarbonyl group (e.g., furylcarbonyl, thienylcarbonyl) optionally substituted by 1 to 3 substituents selected from a $C_{1-6}$ alkyl group optionally substituted by 1 to 3 halogen atoms;
(13) a non-aromatic heterocyclylcarbonyl group (e.g., tetrahydrofurylcarbonyl, pyrrolidinocarbonyl) optionally substituted by 1 to 3 substituents selected from a $C_{1-6}$ alkyl group optionally substituted by 1 to 3 halogen atoms;
and the like.

$R^1$ is preferably a hydrogen atom, a halogen atom, a cyano group, an acyl group (preferably a carboxy group, a $C_{1-6}$ alkyl-carbonyl group, a $C_{1-6}$ alkoxy-carbonyl group, a carbamoyl group optionally mono- or di-substituted by $C_{1-6}$ alkyl group(s)), or an optionally substituted $C_{1-6}$ alkyl group.

$R^1$ is more preferably
(1) a hydrogen atom,
(2) a halogen atom (e.g., a chlorine atom, a bromine atom),
(3) a cyano group,
(4) a carboxy group,
(5) a $C_{1-6}$ alkyl-carbonyl group (e.g., acetyl),
(6) a $C_{1-6}$ alkoxy-carbonyl group (e.g., methoxycarbonyl),
(7) a carbamoyl group optionally mono- or di-substituted by $C_{1-6}$ alkyl group(s) (e.g., methyl), or
(8) a $C_{1-6}$ alkyl group (e.g., methyl) optionally substituted by 1 to 3 hydroxy groups.

In another embodiment, $R^1$ is preferably a hydrogen atom, a halogen atom, a cyano group, an acyl group (preferably a carboxy group, a $C_{1-6}$ alkyl-carbonyl group, a $C_{1-6}$ alkoxy-carbonyl group, a carbamoyl group optionally mono- or di-substituted by $C_{1-6}$ alkyl group(s)), an optionally substituted $C_{1-6}$ alkyl group or an optionally substituted $C_{3-6}$ cycloalkyl group.

$R^1$ is more preferably
(1) a hydrogen atom,
(2) a halogen atom (e.g., a chlorine atom, a bromine atom),
(3) a cyano group,
(4) a carboxy group,
(5) a $C_{1-6}$ alkyl-carbonyl group (e.g., acetyl),
(6) a $C_{1-6}$ alkoxy-carbonyl group (e.g., methoxycarbonyl),
(7) a carbamoyl group optionally mono- or di-substituted by $C_{1-6}$ alkyl group(s) (e.g., methyl),
(8) a $C_{1-6}$ alkyl group (e.g., methyl) optionally substituted by 1 to 3 hydroxy groups, or
(9) a $C_{3-6}$ cycloalkyl group (e.g., cyclopropyl).

In the formula (I), $R^2$ is a substituted $C_{1-2}$ alkyl group, an optionally substituted $C_{3-6}$ alkyl group, an acyl group, an optionally substituted hydroxy group, an optionally substituted amino group, an optionally substituted carbocyclic group or an optionally substituted heterocyclic group.

The "$C_{1-2}$ alkyl group" of the "substituted $C_{1-2}$ alkyl group" for $R^2$ has 1 to 5 (preferably 1 to 3) substituents at substitutable position(s). Examples of the substituent include substituents selected from the above-mentioned Substituent Group A. When the number of the substituents is plural, the respective substituents may be the same or different.

The "$C_{3-6}$ alkyl group" of the "optionally substituted $C_{3-6}$ alkyl group" for $R^2$ optionally has 1 to 5 (preferably 1 to 3) substituents at substitutable position(s). Examples of the substituent include substituents selected from the above-mentioned Substituent Group A. When the number of the substituents is plural, the respective substituents may be the same or different.

Examples of the "acyl group" for $R^2$ include those similar to the "acyl group" for $R^1$.

Examples of the "optionally substituted hydroxy group" for $R^2$ include those similar to the "optionally substituted hydroxy group" for $R^1$.

Examples of the "optionally substituted amino group" for $R^2$ include an amino group optionally mono- or di-substituted by substituent(s) selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-14}$ aralkyl group, a $C_{8-13}$ arylalkenyl group and a heterocyclic group, each of which is optionally substituted; an acyl group and the like.

The $C_{1-10}$ alkyl group and $C_{2-10}$ alkenyl group optionally have 1 to 5 (preferably 1 to 3) substituents at substitutable position(s). Examples of the substituent include substituents selected from the above-mentioned Substituent Group A. When the number of the substituents is plural, the respective substituents may be the same or different.

The $C_{3-10}$ cycloalkyl group, $C_{3-10}$ cycloalkenyl group, $C_{6-14}$ aryl group, $C_{7-14}$ aralkyl group, $C_{8-13}$ arylalkenyl group and heterocyclic group optionally have 1 to 5 (preferably 1 to 3) substituents at substitutable position(s). Examples of the substituent include substituents selected from the above-mentioned Substituent Group B. When the number of the substituents is plural, the respective substituents may be the same or different.

Examples of the "acyl group" exemplified as a substituent for the "optionally substituted amino group" include those similar to the "acyl group" for $R^1$.

The "carbocyclic group" of the "optionally substituted carbocyclic group" for $R^2$ optionally has 1 to 5 (preferably 1 to 3) substituents at substitutable position(s). Examples of the substituent include substituents selected from the above-mentioned Substituent Group B. When the number of the substituents is plural, the respective substituents may be the same or different.

The "heterocyclic group" of the "optionally substituted heterocyclic group" for $R^2$ optionally has 1 to 5 (preferably 1 to 3) substituents at substitutable position(s). Examples of the substituent include substituents selected from the above-mentioned Substituent Group B. When the number of the substituents is plural, the respective substituents may be the same or different.

$R^2$ is preferably a substituted $C_{1-2}$ alkyl group, an optionally substituted $C_{3-6}$ alkyl group, an optionally substituted carbocyclic group (preferably a $C_{3-10}$ cycloalkyl group, a $C_{6-14}$ aryl group) or an optionally substituted heterocyclic group (preferably a 3- to 8-membered (preferably 5- or 6-membered) monocyclic non-aromatic heterocyclic group).

$R^2$ is more preferably (1) a $C_{1-2}$ alkyl group (e.g., methyl) substituted by 1 to 3 substituents selected from
  (a) a $C_{6-14}$ aryl group (e.g., phenyl) optionally substituted by 1 to 3 $C_{1-6}$ alkoxy groups (e.g., methoxy), and
  (b) a 3- to 8-membered monocyclic non-aromatic heterocyclic group (e.g., dioxolanyl, oxetanyl, tetrahydrofuryl) optionally substituted by 1 to 3 $C_{1-6}$ alkyl groups (e.g., methyl),
(2) a $C_{3-6}$ alkyl group (e.g., propyl, tert-butyl, 1-methylpropyl, 1-ethylpropyl) optionally substituted by 1 to 3 substituents selected from
  (a) a hydroxy group, and
  (b) a $C_{1-6}$ alkoxy group (e.g., methoxy),
(3) a $C_{3-10}$ cycloalkyl group (e.g., cyclopentyl, cyclohexyl) optionally substituted by 1 to 3 substituents selected from
  (a) a hydroxy group,
  (b) a $C_{1-6}$ alkyl group (e.g., methyl),
  (c) an oxo group,
  (d) a $C_{1-6}$ alkylenedioxy group (e.g., ethylenedioxy), and
  (e) a $C_{6-14}$ aryl group (e.g., phenyl),
(4) a $C_{6-14}$ aryl group (e.g., phenyl) optionally substituted by 1 to 3 substituents selected from
  (a) a halogen atom (e.g., a fluorine atom), and
  (b) a $C_{1-6}$ alkyl group (e.g., methyl), or
(5) a 3- to 8-membered (preferably 5- or 6-membered) monocyclic non-aromatic heterocyclic group (e.g., tetrahydropyranyl, tetrahydrofuryl).

In another embodiment, $R^2$ is preferably a substituted $C_{1-2}$ alkyl group, an optionally substituted $C_{3-6}$ alkyl group, an optionally substituted carbocyclic group (preferably a $C_{3-10}$ cycloalkyl group, a $C_{6-14}$ aryl group) or an optionally substituted heterocyclic group (preferably a 3- to 8-membered (preferably 5- or 6-membered) monocyclic non-aromatic heterocyclic group, a 5- to 7-membered (preferably 5- or 6-membered) monocyclic aromatic heterocyclic group).

$R^2$ is more preferably (1) a $C_{1-2}$ alkyl group (e.g., methyl) substituted by 1 to 3 substituents selected from
  (a) a $C_{6-14}$ aryl group (e.g., phenyl) optionally substituted by 1 to 3 $C_{1-6}$ alkoxy groups (e.g., methoxy), and
  (b) a 3- to 8-membered monocyclic non-aromatic heterocyclic group (e.g., dioxolanyl, oxetanyl, tetrahydrofuryl) optionally substituted by 1 to 3 $C_{1-6}$ alkyl groups (e.g., methyl),
(2) a $C_{3-6}$ alkyl group (e.g., propyl, tert-butyl, 1-methylpropyl, 1-ethylpropyl) optionally substituted by 1 to 3 substituents selected from
  (a) a hydroxy group, and
  (b) a $C_{1-6}$ alkoxy group (e.g., methoxy),
(3) a $C_{3-10}$ cycloalkyl group (e.g., cyclopentyl, cyclohexyl) optionally substituted by 1 to 3 substituents selected from
  (a) a hydroxy group,
  (b) a $C_{1-6}$ alkyl group (e.g., methyl, ethyl),
  (c) an oxo group,
  (d) a $C_{1-6}$ alkylenedioxy group (e.g., ethylenedioxy),
  (e) a $C_{6-14}$ aryl group (e.g., phenyl),
  (f) a halogen atom (e.g., a fluorine atom), and
  (g) an amino group,
(4) a $C_{6-14}$ aryl group (e.g., phenyl) optionally substituted by 1 to 3 substituents selected from
  (a) a halogen atom (e.g., a fluorine atom, a chlorine atom),
  (b) a $C_{1-6}$ alkyl group (e.g., methyl) optionally substituted by 1 to 3 halogen atoms (e.g., a fluorine atom),
  (c) a cyano group,
  (d) a carbamoyl group,
  (e) an amino group, and
  (f) a $C_{1-6}$ alkoxy group (e.g., methoxy),
(5) a 3- to 8-membered (preferably 5- or 6-membered) monocyclic non-aromatic heterocyclic group (e.g., tetrahydropyranyl, tetrahydrofuryl), or
(6) a 5- to 7-membered (preferably 5- or 6-membered) monocyclic aromatic heterocyclic group (e.g., pyridyl).

In the formula (I'), $R^{2'}$ is a halogen atom, a substituted $C_{1-2}$ alkyl group, an optionally substituted $C_{3-6}$ alkyl group, an acyl group, an optionally substituted hydroxy group, an optionally substituted amino group, an optionally substituted carbocyclic group or an optionally substituted heterocyclic group.

Examples of the "substituted $C_{1-2}$ alkyl group" for $R^{2'}$ include those similar to the "substituted $C_{1-2}$ alkyl group" for $R^2$.

Examples of "optionally substituted $C_{3-6}$ alkyl group" for $R^{2'}$ include those similar to the "optionally substituted $C_{3-6}$ alkyl group" for $R^2$.

Examples of "acyl group" for $R^{2'}$ include those similar to the "acyl group" for $R^1$.

Examples of "optionally substituted hydroxy group" for $R^{2'}$ include those similar to the "optionally substituted hydroxy group" for $R^1$.

Examples of "optionally substituted amino group" for $R^{2'}$ include those similar to the "optionally substituted amino group" for $R^2$.

Examples of "optionally substituted carbocyclic group" for $R^{2'}$ include those similar to the "optionally substituted carbocyclic group" for $R^2$.

Examples of "optionally substituted heterocyclic group" for $R^{2'}$ include those similar to the "optionally substituted heterocyclic group" for $R^2$.

$R^{2'}$ is preferably a substituted $C_{1-2}$ alkyl group, an optionally substituted $C_{3-6}$ alkyl group, an optionally substituted carbocyclic group (preferably a $C_{3-10}$ cycloalkyl group, a $C_{6-14}$ aryl group) or an optionally substituted heterocyclic group (preferably a 3- to 8-membered (preferably 5- or 6-membered) monocyclic non-aromatic heterocyclic group).

$R^{2'}$ is more preferably (1) a $C_{1-2}$ alkyl group (e.g., methyl) substituted by 1 to 3 substituents selected from
  (a) a $C_{6-14}$ aryl group (e.g., phenyl) optionally substituted by 1 to 3 $C_{1-6}$ alkoxy groups (e.g., methoxy), and
  (b) a 3- to 8-membered monocyclic non-aromatic heterocyclic group (e.g., dioxolanyl, oxetanyl, tetrahydrofuryl) optionally substituted by 1 to 3 $C_{1-6}$ alkyl groups (e.g., methyl),
(2) a $C_{3-6}$ alkyl group (e.g., propyl, tert-butyl, 1-methylpropyl, 1-ethylpropyl) optionally substituted by 1 to 3 substituents selected from
  (a) a hydroxy group, and
  (b) a $C_{1-6}$ alkoxy group (e.g., methoxy),
(3) a $C_{3-10}$ cycloalkyl group (e.g., cyclopentyl, cyclohexyl) optionally substituted by 1 to 3 substituents selected from (a) a hydroxy group,
(b) a $C_{1-6}$ alkyl group (e.g., methyl),
(c) an oxo group,
(d) a $C_{1-6}$ alkylenedioxy group (e.g., ethylenedioxy), and
(e) a $C_{6-14}$ aryl group (e.g., phenyl), (4) a $C_{6-14}$ aryl group (e.g., phenyl) optionally substituted by 1 to 3 substituents selected from
(a) a halogen atom (e.g., a fluorine atom), and
(b) a $C_{1-6}$ alkyl group (e.g., methyl), or (5) a 3- to 8-membered (preferably 5- or 6-membered) monocyclic non-aromatic heterocyclic group (e.g., tetrahydropyranyl, tetrahydrofuryl).

In another embodiment, $R^{2'}$ is preferably a substituted $C_{1-2}$ alkyl group, an optionally substituted $C_{3-6}$ alkyl group, an optionally substituted carbocyclic group (preferably a $C_{3-10}$ cycloalkyl group, a $C_{6-14}$ aryl group) or an optionally substituted heterocyclic group (preferably a 3- to 8-membered (preferably 5- or 6-membered) monocyclic non-aromatic heterocyclic group, a 5- to 7-membered (preferably 5- or 6-membered) monocyclic aromatic heterocyclic group).

$R^{2'}$ is more preferably
(1) a $C_{1-2}$ alkyl group (e.g., methyl) substituted by 1 to 3 substituents selected from
(a) a $C_{6-14}$ aryl group (e.g., phenyl) optionally substituted by 1 to 3 $C_{1-6}$ alkoxy groups (e.g., methoxy), and
(b) a 3- to 8-membered monocyclic non-aromatic heterocyclic group (e.g., dioxolanyl, oxetanyl, tetrahydrofuryl) optionally substituted by 1 to 3 $C_{1-6}$ alkyl groups (e.g., methyl), (2) a $C_{3-6}$ alkyl group (e.g., propyl, tert-butyl, 1-methylpropyl, 1-ethylpropyl) optionally substituted by 1 to 3 substituents selected from
(a) a hydroxy group, and
(b) a $C_{1-6}$ alkoxy group (e.g., methoxy), (3) a $C_{3-10}$ cycloalkyl group (e.g., cyclopentyl, cyclohexyl) optionally substituted by 1 to 3 substituents selected from
(a) a hydroxy group,
(b) a $C_{1-6}$ alkyl group (e.g., methyl, ethyl),
(c) an oxo group,
(d) a $C_{1-6}$ alkylenedioxy group (e.g., ethylenedioxy),
(e) a $C_{6-14}$ aryl group (e.g., phenyl),
(f) a halogen atom (e.g., a fluorine atom), and
(g) an amino group, (4) a $C_{6-14}$ aryl group (e.g., phenyl) optionally substituted by 1 to 3 substituents selected from
(a) a halogen, atom (e.g., a fluorine atom, a chlorine atom),
(b) a $C_{1-6}$ alkyl group (e.g., methyl) optionally substituted by 1 to 3 halogen atoms (e.g., a fluorine atom),
(c) a cyano group,
(d) a carbamoyl group,
(e) an amino group, and
(f) a $C_{1-6}$ alkoxy group (e.g., methoxy), (5) a 3- to 8-membered (preferably 5- or 6-membered) monocyclic non-aromatic heterocyclic group (e.g., tetrahydropyranyl, tetrahydrofuryl), or (6) a 5- to 7-membered (preferably 5- or 6-membered) monocyclic aromatic heterocyclic group (e.g., pyridyl).

In the formula (I), $R^3$ is a substituted $C_{1-2}$ alkyl group, an optionally substituted $C_{3-6}$ alkyl group, an acyl group, an optionally substituted hydroxy group, an optionally substituted amino group, an optionally substituted carbocyclic group or an optionally substituted heterocyclic group.

The "$C_{1-2}$ alkyl group" of the "substituted $C_{1-2}$ alkyl group" for $R^3$ has 1 to 5 (preferably 1 to 3) substituents at substitutable position(s). Examples of the substituent include substituents selected from the above-mentioned Substituent Group A. When the number of the substituents is plural, the respective substituents may be the same or different.

The "$C_{3-6}$ alkyl group" of the "optionally substituted $C_{3-6}$ alkyl group" for $R^3$ optionally has 1 to 5 (preferably 1 to 3) substituents at substitutable position(s). Examples of the substituent include substituents selected from the above-mentioned Substituent Group A. When the number of the substituents is plural, the respective substituents may be the same or different.

Examples of the "acyl group" for $R^3$ include those similar to the "acyl group" for $R^1$.

Examples of the "optionally substituted hydroxy group" for $R^3$ include those similar to the "optionally substituted hydroxy group" for $R^1$.

Examples of the "optionally substituted amino group" for $R^3$ include those similar to the "optionally substituted amino group" for $R^2$.

The "carbocyclic group" of the "optionally substituted carbocyclic group" for $R^3$ optionally has 1 to 5 (preferably 1 to 3) substituents at substitutable position(s). Examples of the substituent include substituents selected from the above-mentioned Substituent Group B. When the number of the substituents is plural, the respective substituents may be the same or different.

The "heterocyclic group" of the "optionally substituted heterocyclic group" for $R^3$ optionally has 1 to 5 (preferably 1 to 3) substituents at substitutable position(s). Examples of the substituent include substituents selected from the above-mentioned Substituent Group B. When the number of the substituents is plural, the respective substituents may be the same or different.

$R^3$ is preferably a substituted $C_{1-2}$ alkyl group, an optionally substituted carbocyclic group (preferably a $C_{3-10}$ cycloalkenyl group, a $C_{6-14}$ aryl group), an optionally substituted heterocyclic group (preferably a 5- to 7-membered (preferably 5- or 6-membered) monocyclic aromatic heterocyclic group, a 8- to 12-membered fused aromatic heterocyclic group, a 3- to 8-membered (preferably 5- or 6-membered) monocyclic non-aromatic heterocyclic group, a 8- to 12-membered fused non-aromatic heterocyclic group) or an optionally substituted amino group.

$R^3$ is more preferably
(1) a $C_{1-2}$ alkyl group (e.g., methyl) substituted by 1 to 3 substituents selected from a $C_{6-14}$ aryl group (e.g., phenyl) optionally substituted by 1 to 3 sulfamoyl groups,
(2) a $C_{3-10}$ cycloalkenyl group (e.g., cyclohexenyl),
(3) a $C_{6-14}$ aryl group (e.g., phenyl) optionally substituted by 1 to 3 substituents selected from
(a) a halogen atom (e.g., a fluorine atom),
(b) a nitro group,
(c) a cyano group,
(d) a carbamoyl group optionally substituted by 1 to 3 $C_{1-6}$ alkyl groups (e.g., methyl),
(e) a sulfamoyl group,
(f) a $C_{1-6}$ alkyl group (e.g., methyl, isopropyl) optionally substituted by 1 to 3 substituents selected from
  (i) a halogen atom (e.g., a fluorine atom),
  (ii) a cyano group, and
  (iii) a carbamoyl group optionally mono- or di-substituted by substituent(s) selected from a $C_{1-6}$ alkyl group (e.g., methyl) and a $C_{3-10}$ cycloalkyl group (e.g., cyclopropyl),
(g) a $C_{1-6}$ alkoxy group (e.g., methoxy, ethoxy) optionally substituted by 1 to 3 substituents selected from a halogen atom (e.g., a fluorine atom), a cyano group, a hydroxy group and a carbamoyl group, (h) an amino group optionally mono- or di-substituted by $C_{1-6}$ alkyl-carbonyl group(s) (e.g., acetyl),
(i) a 3- to 8-membered (preferably 5- or 6-membered) monocyclic non-aromatic heterocyclic group (e.g., morpholinyl), and
(j) a $C_{1-6}$ alkylenedioxy group (e.g., methylenedioxy), (4) a 5- to 7-membered (preferably 5- or 6-membered) monocyclic aromatic heterocyclic group (e.g., thienyl, pyridyl, pyrazolyl) optionally substituted by 1 to 3 substituents selected from
- (a) a carboxy group,
- (b) a cyano group,
- (c) a $C_{1-6}$ alkoxy-carbonyl group (e.g., methoxycarbonyl),
- (d) a carbamoyl group optionally mono- or di-substituted by substituent(s) selected from
  - (i) a $C_{1-6}$ alkyl group (e.g., methyl, ethyl, tert-butyl) optionally substituted by 1 to 3 hydroxy groups
  - (ii) a $C_{3-10}$ cycloalkyl group (e.g., cyclopropyl) optionally substituted by 1 to 3 cyano groups, and
  - (iii) a 5- to 7-membered (preferably 5- or 6-membered) monocyclic aromatic heterocyclic group (e.g., pyrazolyl) optionally substituted by 1 to 3 $C_{1-6}$ alkyl groups (e.g., methyl),
- (e) a 3- to 8-membered (preferably 5- or 6-membered) monocyclic non-aromatic heterocyclic group (e.g., dihydrooxadiazolyl, morpholinyl) optionally substituted by 1 to 3 oxo groups,
- (f) a $C_{1-6}$ alkyl group (e.g., methyl, 2-methylpropyl) optionally substituted by 1 to 3 substituents selected from a cyano group and a carbamoyl group, and
- (g) a $C_{3-10}$ cycloalkyl group (e.g., cyclopropyl, cyclopentyl), (5) a 8- to 12-membered fused aromatic heterocyclic group (e.g., benzoxadiazolyl),
(6) a 3- to 8-membered (preferably 5- or 6-membered) monocyclic non-aromatic heterocyclic group (e.g., dihydropyranyl),
(7) a 8- to 12-membered fused non-aromatic heterocyclic group (e.g., indolinyl) optionally substituted by 1 to 3 oxo groups, or
(8) an amino group optionally mono- or di-substituted by $C_{6-14}$ aryl group(s) (e.g., phenyl) optionally substituted by 1 to 3 carbamoyl groups.

In another embodiment, $R^3$ is preferably a substituted $C_{1-2}$ alkyl group, an optionally substituted carbocyclic group (preferably a $C_{3-10}$ cycloalkyl group, a $C_{3-10}$ cycloalkenyl group, a $C_{6-14}$ aryl group), an optionally substituted heterocyclic group (preferably a 5- to 7-membered (preferably 5- or 6-membered) monocyclic aromatic heterocyclic group, a 8- to 12-membered fused aromatic heterocyclic group, a 3- to 8-membered (preferably 5- or 6-membered) monocyclic non-aromatic heterocyclic group, a 8- to 12-membered fused non-aromatic heterocyclic group) or an optionally substituted amino group.

$R^3$ is more preferably
(1) a $C_{1-2}$ alkyl group (e.g., methyl) substituted by 1 to 3 substituents selected from a $C_{6-14}$ aryl group (e.g., phenyl) optionally substituted by 1 to 3 sulfamoyl groups,
(2) a $C_{3-10}$ cycloalkyl group (e.g., cyclopropyl),
(3) a $C_{3-10}$ cycloalkenyl group (e.g., cyclohexenyl),
(4) a $C_{6-14}$ aryl group (e.g., phenyl) optionally substituted by 1 to 3 substituents selected from
- (a) a halogen atom (e.g., a fluorine atom, a chlorine atom),
- (b) a nitro group,
- (c) a cyano group,
- (d) a carbamoyl group optionally mono- or di-substituted by $C_{1-6}$ alkyl group(s) (e.g., methyl, ethyl) optionally substituted by 1 to 3 substituents selected from
  - (i) a $C_{1-6}$ alkoxy group (e.g., methoxy),
  - (ii) a hydroxy group, and
  - (iii) an amino group optionally mono- or di-substituted by $C_{1-6}$ alkyl group(s) (e.g., methyl),
- (e) a sulfamoyl group optionally mono- or di-substituted by alkyl group(s) (e.g., methyl),
- (f) a $C_{1-6}$ alkyl group (e.g., methyl, isopropyl) optionally substituted by 1 to 3 substituents selected from
  - (i) a halogen atom (e.g., a fluorine atom),
  - (ii) a cyano group,
  - (iii) a hydroxy group,
  - (iv) a carbamoyl group optionally mono- or di-substituted by substituent(s) selected from a $C_{1-6}$ alkyl group (e.g., methyl) and a $C_{3-10}$ cycloalkyl group (e.g., cyclopropyl),
  - (v) an amino group optionally mono- or di-substituted by $C_{1-6}$ alkyl group(s) (e.g., methyl), and
  - (vi) a 3- to 8-membered (preferably 5- or 6-membered) monocyclic non-aromatic heterocyclic group (e.g., oxazolidinyl, morpholinyl, pyrrolidinyl) optionally substituted by 1 to 3 substituents selected from an oxo group and a halogen atom (e.g., a fluorine atom),
- (g) a $C_{1-6}$ alkoxy group (e.g., methoxy, ethoxy) optionally substituted by 1 to 3 substituents selected from
  - (i) a halogen atom (e.g., a fluorine atom),
  - (ii) a cyano group,
  - (iii) a hydroxy group, and
  - (iv) a carbamoyl group optionally mono- or di-substituted by substituent(s) selected from a $C_{1-6}$ alkyl group (e.g., methyl, ethyl) optionally substituted by 1 to 3 $C_{1-6}$ alkoxy groups (e.g., methoxy),
- (h) a $C_{1-6}$ alkoxy-carbonyl group (e.g., ethoxycarbonyl),
- (i) an amino group optionally mono- or di-substituted by substituent(s) selected from
  - (i) a $C_{1-6}$ alkyl-carbonyl group (e.g., acetyl), and
  - (ii) a $C_{1-6}$ alkyl group (e.g., methyl, ethyl) optionally substituted by 1 to 3 $C_{1-6}$ alkoxy groups (e.g., methoxy),
- (j) a 3- to 8-membered (preferably 5- or 6-membered) monocyclic non-aromatic heterocyclic group (e.g., morpholinyl, pyrrolidinyl, tetrahydrooxazepinyl, thiomorpholinyl, 1,1-dioxidothiomorpholinyl, dihydropyranyl, tetrahydropyranyl, imidazolidinyl, piperazinyl, piperidyl) optionally substituted by 1 to 3 substituents selected from
  - (i) an oxo group,
  - (ii) a $C_{1-6}$ alkyl group (e.g., methyl),
  - (iii) a $C_{1-6}$ alkyl-carbonyl group (e.g., acetyl) optionally substituted by 1 to 3 substituents selected from a hydroxy group and a $C_{1-6}$ alkoxy group (e.g., methoxy),
  - (iv) a carbamoyl group optionally mono- or di-substituted by $C_{1-6}$ alkyl group(s) (e.g., methyl),
  - (v) a $C_{1-6}$ alkylsulfonyl group (e.g., methylsulfonyl), and
  - (vi) a halogen atom (e.g., a fluorine atom), and
- (k) a $C_{1-6}$ alkylenedioxy group (e.g., methylenedioxy), (5) a 5- to 7-membered (preferably 5- or 6-membered) monocyclic aromatic heterocyclic group (e.g., thienyl, pyridyl, pyrazolyl, pyrimidinyl) optionally substituted by 1 to 3 substituents selected from
- (a) a carboxy group,
- (b) a cyano group,
- (c) a $C_{1-6}$ alkoxy-carbonyl group (e.g., methoxycarbonyl, ethoxycarbonyl), (d) a carbamoyl group optionally mono- or di-substituted by substituent(s) selected from
   (i) a $C_{1-6}$ alkyl group (e.g., methyl, ethyl, tert-butyl) optionally substituted by 1 to 3 substituents selected from a hydroxy group and a cyano group,
   (ii) a $C_{3-10}$ cycloalkyl group (e.g., cyclopropyl) optionally substituted by 1 to 3 cyano groups,
   (iii) a 5- to 7-membered (preferably 5- or 6-membered) monocyclic aromatic heterocyclic group (e.g., pyrazolyl) optionally substituted by 1 to 3 $C_{1-6}$ alkyl groups (e.g., methyl), and
   (iv) a 3- to 8-membered (preferably 5- or 6-membered) monocyclic non-aromatic heterocyclic group (e.g., morpholinyl),
(e) a 3- to 8-membered (preferably 5- or 6-membered) monocyclic non-aromatic heterocyclic group (e.g., dihydrooxadiazolyl, morpholinyl, tetrahydropyranyl) optionally substituted by 1 to 3 oxo groups,
(f) a $C_{1-6}$ alkyl group (e.g., methyl, 2-methylpropyl) optionally substituted by 1 to 3 substituents selected from
   (i) a cyano group,
   (ii) a carbamoyl group, and
   (iii) a 3- to 8-membered (preferably 5- or 6-membered) monocyclic non-aromatic heterocyclic group (e.g., morpholinyl, pyrrolidinyl) optionally substituted by 1 to 3 oxo groups,
(g) a $C_{3-10}$ cycloalkyl-group (e.g., cyclopropyl, cyclopentyl),
(h) a 3- to 8-membered (preferably 5- or 6-membered) monocyclic non-aromatic heterocyclylcarbonyl group (e.g., morpholinylcarbonyl), and
(i) an amino group,
(6) a 8- to 12-membered fused aromatic heterocyclic group (e.g., benzoxadiazolyl, benzimidazolyl) optionally substituted by 1 to 3 $C_{1-6}$ alkyl groups (e.g., methyl),
(7) a 3- to 8-membered (preferably 5- or 6-membered) monocyclic non-aromatic heterocyclic group (e.g., dihydropyranyl, dihydropyridyl) optionally substituted by 1 to 3 substituents selected from
   (a) an oxo group, and
   (b) a $C_{1-6}$ alkyl group (e.g., methyl),
(8) a 8- to 12-membered fused non-aromatic heterocyclic group (e.g., indolinyl) optionally substituted by 1 to 3 oxo groups, or
(9) an amino group optionally mono- or di-substituted by substituent(s) selected from
   (a) a $C_{6-14}$ aryl group (e.g., phenyl) optionally substituted by 1 to 3 substituents selected from
      (i) a carbamoyl group, and
      (ii) a sulfamoyl group,
   (b) a $C_{1-6}$ alkyl group (e.g., methyl) optionally substituted by 1 to 3 substituents selected from a $C_{6-14}$ aryl group (e.g., phenyl) optionally substituted by 1 to 3 $C_{1-6}$ alkoxy groups (e.g., methoxy), and
   (c) a $C_{6-14}$ aryl-carbonyl group (e.g., benzoyl).

In the formula (I'), $R^{3'}$ is a halogen atom, a substituted $C_{1-2}$ alkyl group, an optionally substituted $C_{3-6}$ alkyl group, an acyl group, an optionally substituted hydroxy group, an optionally substituted amino group, an optionally substituted carbocyclic group or an optionally substituted heterocyclic group.

Examples of the "substituted $C_{1-2}$ alkyl group" for $R^{3'}$ include those similar to the "substituted $C_{1-2}$ alkyl group" for $R^2$.

Examples of the "optionally substituted $C_{3-6}$ alkyl group" for $R^{3'}$ include those similar to the "optionally substituted $C_{3-6}$ alkyl group" for $R^2$.

Examples of the "acyl group" for $R^{3'}$ include those similar to the "acyl group" for $R^1$.

Examples of the "optionally substituted hydroxy group" for $R^{3'}$ include those similar to the "optionally substituted hydroxy group" for $R^1$.

Examples of the "optionally substituted amino group" for $R^{3'}$ include those similar to the "optionally substituted amino group" for $R^2$.

Examples of the "optionally substituted carbocyclic group" for $R^{3'}$ include those similar to the "optionally substituted carbocyclic group" for $R^2$.

Examples of the "optionally substituted heterocyclic group" for $R^{3'}$ include those similar to the "optionally substituted heterocyclic group" for $R^2$.

$R^{3'}$ is preferably a halogen atom, a substituted $C_{1-2}$ alkyl group, an optionally substituted carbocyclic group (preferably a $C_{3-10}$ cycloalkenyl group, a $C_{6-14}$ aryl group), an optionally substituted heterocyclic group (preferably a 5- to 7-membered (preferably 5- or 6-membered) monocyclic aromatic heterocyclic group, a 8- to 12-membered fused aromatic heterocyclic group, a 3- to 8-membered (preferably 5- or 6-membered) monocyclic non-aromatic heterocyclic group, a 8- to 12-membered fused non-aromatic heterocyclic group) or an optionally substituted amino group.

$R^{3'}$ is more preferably
(1) a halogen atom (e.g., a bromine atom),
(2) a $C_{1-2}$ alkyl group (e.g., methyl) substituted by 1 to 3 substituents selected from a $C_{6-14}$ aryl group (e.g., phenyl) optionally substituted by 1 to 3 sulfamoyl groups,
(3) a $C_{3-10}$ cycloalkenyl group (e.g., cyclohexenyl),
(4) a $C_{6-14}$ aryl group (e.g., phenyl) optionally substituted by 1 to 3 substituents selected from
   (a) a halogen atom (e.g., a fluorine atom),
   (b) a nitro group,
   (c) a cyano group,
   (d) a carbamoyl group optionally substituted by 1 to 3 $C_{1-6}$ alkyl groups (e.g., methyl),
   (e) a sulfamoyl group,
   (f) a $C_{1-5}$ alkyl group (e.g., methyl, isopropyl) optionally substituted by 1 to 3 substituents selected from
      (i) a halogen atom (e.g., a fluorine atom),
      (ii) a cyano group, and
      (iii) a carbamoyl group optionally mono- or di-substituted by substituent(s) selected from a $C_{1-6}$ alkyl group (e.g., methyl) and a $C_{3-10}$ cycloalkyl group (e.g., cyclopropyl),
   (g) a $C_{1-6}$ alkoxy group (e.g., methoxy, ethoxy) optionally substituted by 1 to 3 substituents selected from a halogen atom (e.g., a fluorine atom), a cyano group, a hydroxy group and a carbamoyl group,
   (h) an amino group optionally mono- or di-substituted by $C_{1-6}$ alkyl-carbonyl group(s) (e.g., acetyl),
   (i) a 3- to 8-membered (preferably 5- or 6-membered) monocyclic non-aromatic heterocyclic group (e.g., morpholinyl), and
   (j) a $C_{1-6}$ alkylenedioxy group (e.g., methylenedioxy),
(5) a 5- to 7-membered (preferably 5- or 6-membered) monocyclic aromatic heterocyclic group (e.g., thienyl, pyridyl, pyrazolyl) optionally substituted by 1 to 3 substituents selected from
   (a) a carboxy group,
   (b) a cyano group,
   (c) a $C_{1-6}$ alkoxy-carbonyl group (e.g., methoxycarbonyl), (d) a carbamoyl group optionally mono- or di-substituted by substituent(s) selected from
  (i) a $C_{1-6}$ alkyl group (e.g., methyl, ethyl, tert-butyl) optionally substituted by 1 to 3 hydroxy groups
  (ii) a $C_{3-10}$ cycloalkyl group (e.g., cyclopropyl) optionally substituted by 1 to 3 cyano groups, and
  (iii) a 5- to 7-membered (preferably 5- or 6-membered) monocyclic aromatic heterocyclic group (e.g., pyrazolyl) optionally substituted by 1 to 3 $C_{1-6}$ alkyl groups (e.g., methyl),
(e) a 3- to 8-membered (preferably 5- or 6-membered) monocyclic non-aromatic heterocyclic group (e.g., dihydrooxadiazolyl, morpholinyl) optionally substituted by 1 to 3 oxo groups,
(f) a $C_{1-6}$ alkyl group (e.g., methyl, 2-methylpropyl) optionally substituted by 1 to 3 substituents selected from a cyano group and a carbamoyl group, and
(g) a $C_{3-10}$ cycloalkyl group (e.g., cyclopropyl, cyclopentyl),
(6) a 8- to 12-membered fused aromatic heterocyclic group (e.g., benzoxadiazolyl),
(7) a 3- to 8-membered (preferably 5- or 6-membered) monocyclic non-aromatic heterocyclic group (e.g., dihydropyranyl),
(8) a 8- to 12-membered fused non-aromatic heterocyclic group (e.g., indolinyl) optionally substituted by 1 to 3 oxo groups, or
(9) an amino group optionally mono- or di-substituted by $C_{6-14}$ aryl group(s) (e.g., phenyl) optionally substituted by 1 to 3 carbamoyl groups.

In another embodiment, $R^{3'}$ is preferably a halogen atom, a substituted $C_{1-2}$ alkyl group, an optionally substituted carbocyclic group (preferably a $C_{3-10}$ cycloalkyl group, a $C_{3-10}$ cycloalkenyl group, a $C_{6-14}$ aryl group), an optionally substituted heterocyclic group (preferably a 5- to 7-membered (preferably 5- or 6-membered) monocyclic aromatic heterocyclic group, a 8- to 12-membered fused aromatic heterocyclic group, a 3- to 8-membered (preferably 5- or 6-membered) monocyclic non-aromatic heterocyclic group, a 8- to 12-membered fused non-aromatic heterocyclic group) or an optionally substituted amino group.

$R^{3'}$ is more preferably
(1) a halogen atom (e.g., a bromine atom),
(2) a $C_{1-2}$ alkyl group (e.g., methyl) substituted by 1 to 3 substituents selected from a $C_{6-14}$ aryl group (e.g., phenyl) optionally substituted by 1 to 3 sulfamoyl groups,
(3) a $C_{3-10}$ cycloalkyl group (e.g., cyclopropyl),
(4) a $C_{3-10}$ cycloalkenyl group (e.g., cyclohexenyl),
(5) a $C_{6-14}$ aryl group (e.g., phenyl) optionally substituted by 1 to 3 substituents selected from
  (a) a halogen atom (e.g., a fluorine atom, a chlorine atom),
  (b) a nitro group,
  (c) a cyano group,
  (d) a carbamoyl group optionally mono- or di-substituted by $C_{1-6}$ alkyl group(s) (e.g., methyl, ethyl) optionally substituted by 1 to 3 substituents selected from
    (i) a $C_{1-6}$ alkoxy group (e.g., methoxy),
    (ii) a hydroxy group, and
    (iii) an amino group optionally mono- or di-substituted by $C_{1-6}$ alkyl group(s) (e.g., methyl),
  (e) a sulfamoyl group optionally mono- or di-substituted by $C_{1-6}$ alkyl group(s) (e.g., methyl),
  (f) a $C_{1-6}$ alkyl group (e.g., methyl, isopropyl) optionally substituted by 1 to 3 substituents selected from
    (i) a halogen atom (e.g., a fluorine atom),
    (ii) a cyano group,
    (iii) a hydroxy group,
    (iv) a carbamoyl group optionally mono- or di-substituted by substituent(s) selected from a $C_{1-6}$ alkyl group (e.g., methyl) and a $C_{3-10}$ cycloalkyl group (e.g., cyclopropyl),
    (v) an amino group optionally mono- or di-substituted by $C_{1-6}$ alkyl group(s) (e.g., methyl), and
    (vi) a 3- to 8-membered (preferably 5- or 6-membered) monocyclic non-aromatic heterocyclic group (e.g., oxazolidinyl, morpholinyl, pyrrolidinyl) optionally substituted by 1 to 3 substituents selected from an oxo group and a halogen atom (e.g., a fluorine atom),
  (g) a $C_{1-6}$ alkoxy group (e.g., methoxy, ethoxy) optionally substituted by 1 to 3 substituents selected from
    (i) a halogen atom (e.g., a fluorine atom),
    (ii) a cyano group,
    (iii) a hydroxy group, and
    (iv) a carbamoyl group optionally mono- or di-m substituted by substituent(s) selected from a $C_{1-6}$ alkyl group (e.g., methyl, ethyl) optionally substituted by 1 to 3 $C_{1-6}$ alkoxy groups (e.g., methoxy),
  (h) a $C_{1-6}$ alkoxy-carbonyl group (e.g., ethoxycarbonyl),
  (i) an amino group optionally mono- or di-substituted by substituent(s) selected from
    (i) a $C_{1-6}$ alkyl-carbonyl group (e.g., acetyl), and
    (ii) a $C_{1-6}$ alkyl group (e.g., methyl(ethyl) optionally substituted by 1 to 3 $C_{1-6}$ alkoxy groups (e.g., methoxy),
  (j) a 3- to 8-membered (preferably 5- or 6-membered) monocyclic non-aromatic heterocyclic group (e.g., morpholinyl, pyrrolidinyl, tetrahydrooxazepinyl, thiomorpholinyl, 1,1-dioxidothiomorpholinyl, dihydropyranyl, tetrahydropyranyl, imidazolidinyl, piperazinyl, piperidyl) optionally substituted by 1 to 3 substituents selected from
    (i) an oxo group,
    (ii) a $C_{1-6}$ alkyl group (e.g., methyl),
    (iii) a $C_{1-6}$ alkyl-carbonyl group (e.g., acetyl) optionally substituted by 1 to 3 substituents selected from a hydroxy group and a $C_{1-6}$ alkoxy group (e.g., methoxy),
    (iv) a carbamoyl group optionally mono- or di-substituted by $C_{1-6}$ alkyl group(s) (e.g., methyl),
    (v) a $C_{1-6}$ alkylsulfonyl group (e.g., methylsulfonyl), and
    (vi) a halogen atom (e.g., a fluorine atom), and
  (k) a $C_{1-6}$ alkylenedioxy group (e.g., methylenedioxy),
(6) a 5- to 7-membered (preferably 5- or 6-membered) monocyclic aromatic heterocyclic group (e.g., thienyl, pyridyl, pyrazolyl, pyrimidinyl) optionally substituted by 1 to 3 substituents selected from
  (a) a carboxy group,
  (b) a cyano group,
  (c) a $C_{1-6}$ alkoxy-carbonyl group (e.g., methoxycarbonyl, ethoxycarbonyl),
  (d) a carbamoyl group optionally mono- or di-substituted by substituent(s) selected from
    (i) a $C_{1-6}$ alkyl group (e.g., methyl, ethyl, tert-butyl) optionally substituted by 1 to 3 substituents selected from a hydroxy group and a cyano group,
    (ii) a $C_{3-10}$ cycloalkyl group (e.g., cyclopropyl) optionally substituted by 1 to 3 cyano groups,
    (iii) a 5- to 7-membered (preferably 5- or 6-membered) monocyclic aromatic heterocyclic group (e.g., pyrazolyl) optionally substituted by 1 to 3 $C_{1-6}$ alkyl groups (e.g., methyl), and
    (iv) a 3- to 8-membered (preferably 5- or 6-membered) monocyclic non-aromatic heterocyclic group (e.g., morpholinyl), (e) a 3- to 8-membered (preferably 5- or 6-membered) monocyclic non-aromatic heterocyclic group (e.g., dihydrooxadiazolyl, morpholinyl, tetrahydropyranyl) optionally substituted by 1 to 3 oxo groups,
(f) a $C_{1-6}$ alkyl group (e.g., methyl, 2-methylpropyl) optionally substituted by 1 to 3 substituents selected from
  (i) a cyano group,
  (ii) a carbamoyl group, and
  (iii) a 3- to 8-membered (preferably 5- or 6-membered) monocyclic non-aromatic heterocyclic group (e.g., morpholinyl, pyrrolidinyl) optionally substituted by 1 to 3 oxo groups,
(g) a $C_{3-10}$ cycloalkyl group (e.g., cyclopropyl, cyclopentyl),
(h) a 3- to 8-membered (preferably 5- or 6-membered) monocyclic non-aromatic heterocyclylcarbonyl group (e.g., morpholinylcarbonyl), and
(i) an amino group,
(7) a 8- to 12-membered fused aromatic heterocyclic group (e.g., benzoxadiazolyl, benzimidazolyl) optionally substituted by 1 to 3 $C_{1-6}$ alkyl groups (e.g., methyl),
(8) a 3- to 8-membered (preferably 5- or 6-membered) monocyclic non-aromatic heterocyclic group (e.g., dihydropyranyl, dihydropyridyl) optionally substituted by 1 to 3 substituents selected from
  (a) an oxo group, and
  (b) a $C_{1-6}$ alkyl group (e.g., methyl),
(9) a 8- to 12-membered fused non-aromatic heterocyclic group (e.g., indolinyl) optionally substituted by 1 to 3 oxo groups, or
(10) an amino group optionally mono- or di-substituted by substituent(s) selected from
  (a) a $C_{6-14}$ aryl group (e.g., phenyl) optionally substituted by 1 to 3 substituents selected from
    (i) a carbamoyl group, and
    (ii) a sulfamoyl group,
  (b) a $C_{1-6}$ alkyl group (e.g., methyl) optionally substituted by 1 to 3 substituents selected from a $C_{6-14}$ aryl group (e.g., phenyl) optionally substituted by 1 to 3 $C_{1-6}$ alkoxy groups (e.g., methoxy), and
  (c) a $C_{6-14}$ aryl-carbonyl group (e.g., benzoyl).

Ring A moiety is a nitrogen-containing aromatic heterocycle wherein Q is a carbon atom or a nitrogen atom, $X^2$ and $X^3$ are each independently a carbon atom or a nitrogen atom, and any one of them is a nitrogen atom.

Examples of the "nitrogen-containing aromatic heterocycle" for Ring A include pyrrole, imidazole, pyrazole and triazole (e.g., 1,2,3-triazole).

Preferably, one of $X^2$ and $X^3$ is a carbon atom (CH), and the other is a nitrogen atom.

Ring A moiety is preferably pyrrole or pyrazole.

Ring A moiety is more preferably pyrrole wherein Q is a carbon atom (CH), and one of $X^2$ and $X^3$ is a carbon atom, and the other is a nitrogen atom, or pyrazole wherein Q is a nitrogen atom, and one of $X^2$ and $X^3$ is a carbon atom, and the other is a nitrogen atom.

Preferable examples of compound (I) include the following compounds:

[Compound A-1]
Compound (I) wherein
Ring A moiety is a nitrogen-containing aromatic heterocycle, wherein
  Q is a carbon atom (CH) or a nitrogen atom, and
  $X^2$ and $X^3$ are each independently a carbon atom or a nitrogen atom, and any one of them is a nitrogen atom;
$R^1$ is a hydrogen atom, a halogen atom, a cyano group, an acyl group (preferably a carboxy group, a $C_{1-6}$ alkyl-carbonyl group, a $C_{1-6}$ alkoxy-carbonyl group, a carbamoyl group optionally mono- or di-substituted by $C_{1-6}$ alkyl group(s)) or an optionally substituted $C_{1-6}$ alkyl group;
$R^2$ is a substituted $C_{1-2}$ alkyl group, an optionally substituted $C_{3-6}$ alkyl group, an optionally substituted carbocyclic group (preferably a $C_{3-10}$ cycloalkyl group, a $C_{6-14}$ aryl group) or an optionally substituted heterocyclic group (preferably a 3- to 8-membered (preferably 5- or 6-membered) monocyclic non-aromatic heterocyclic group); and
$R^3$ is a substituted $C_{1-2}$ alkyl group, an optionally substituted carbocyclic group (preferably a $C_{3-10}$ cycloalkenyl group, a $C_{6-14}$ aryl group), an optionally substituted heterocyclic group (preferably a 5- to 7-membered (preferably 5- or 6-membered) monocyclic aromatic heterocyclic group, a 8- to 12-membered fused aromatic heterocyclic group, a 3- to 8-membered (preferably 5- or 6-membered) monocyclic non-aromatic heterocyclic group, a 8- to 12-membered fused non-aromatic heterocyclic group) or an optionally substituted amino group.

[Compound A-2]
Compound (I) wherein
Ring A moiety is a nitrogen-containing aromatic heterocycle, wherein
  Q is a carbon atom (CH) or a nitrogen atom, and
  $X^2$ and $X^3$ are each independently a carbon atom or a nitrogen atom, and any one of them is a nitrogen atom;
$R^1$ is a hydrogen atom, a halogen atom, a cyano group, an acyl group (preferably a carboxy group, a $C_{1-6}$ alkyl-carbonyl group, a $C_{1-6}$ alkoxy-carbonyl group, a carbamoyl group optionally mono- or di-substituted by $C_{1-6}$ alkyl group(s)), an optionally substituted $C_{1-6}$ alkyl group or an optionally substituted $C_{3-6}$ cycloalkyl group;
$R^2$ is a substituted $C_{1-2}$ alkyl group, an optionally substituted $C_{3-6}$ alkyl group, an optionally substituted carbocyclic group (preferably a $C_{3-10}$ cycloalkyl group, a $C_{6-14}$ aryl group) or an optionally substituted heterocyclic group (preferably a 3- to 8-membered (preferably 5- or 6-membered) monocyclic non-aromatic heterocyclic group, a 5- to 7-membered (preferably 5- or 6-membered) monocyclic aromatic heterocyclic group); and
$R^3$ is a substituted $C_{1-2}$ alkyl group, an optionally substituted carbocyclic group (preferably a $C_{3-10}$ cycloalkyl group, a $C_{3-10}$ cycloalkenyl group, a $C_{6-14}$ aryl group), an optionally substituted heterocyclic group (preferably a 5- to 7-membered (preferably 5- or 6-membered) monocyclic aromatic heterocyclic group, a 8- to 12-membered fused aromatic heterocyclic group, a 3- to 8-membered (preferably 5- or 6-membered) monocyclic non-aromatic heterocyclic group, a 8- to 12-membered fused non-aromatic heterocyclic group) or an optionally substituted amino group.

[Compound B-1]
Compound (I) wherein
Ring A moiety is pyrrole wherein Q is a carbon atom (CH), and one of $X^2$ and $X^3$ is a carbon atom, and the other is a nitrogen atom, or pyrazole wherein Q is a nitrogen atom, and one of $X^2$ m and $X^3$ is a carbon atom, and the other is a nitrogen atom);
$R^1$ is
(1) a hydrogen atom,
(2) a halogen atom (e.g., a chlorine atom, a bromine atom),
(3) a cyano group,
(4) a carboxy group,
(5) a $C_{1-6}$ alkyl-carbonyl group (e.g., acetyl),
(6) a $C_{1-6}$ alkoxy-carbonyl group (e.g., methoxycarbonyl), (7) a carbamoyl group optionally mono- or di-substituted by $C_{1-6}$ alkyl group(s) (e.g., methyl), or
(8) a $C_{1-6}$ alkyl group (e.g., methyl) optionally substituted by 1 to 3 hydroxy groups;
$R^2$ is
(1) a $C_{1-2}$ alkyl group (e.g., methyl) substituted by 1 to 3 substituents selected from
   (a) a $C_{6-14}$ aryl group (e.g., phenyl) optionally substituted by 1 to 3 $C_{1-6}$ alkoxy groups (e.g., methoxy), and
   (b) a 3- to 8-membered monocyclic non-aromatic heterocyclic group (e.g., dioxolanyl, oxetanyl, tetrahydrofuryl) optionally substituted by 1 to 3 $C_{1-6}$ alkyl groups (e.g., methyl),
(2) a $C_{3-6}$ alkyl group (e.g., propyl, tert-butyl, 1-methylpropyl, 1-ethylpropyl) optionally substituted by 1 to 3 substituents selected from
   (a) a hydroxy group, and
   (b) a $C_{1-6}$ alkoxy group (e.g., methoxy),
(3) a $C_{3-10}$ cycloalkyl group (e.g., cyclopentyl, cyclohexyl) optionally substituted by 1 to 3 substituents selected from
   (a) a hydroxy group,
   (b) a $C_{1-6}$ alkyl group (e.g., methyl),
   (c) an oxo group,
   (d) a $C_{1-6}$ alkylenedioxy group (e.g., ethylenedioxy), and
   (e) a $C_{6-14}$ aryl group (e.g., phenyl),
(4) a $C_{6-14}$ aryl group (e.g., phenyl) optionally substituted by 1 to 3 substituents selected from
   (a) a halogen atom (e.g., a fluorine atom), and
   (b) a $C_{1-6}$ alkyl group (e.g., methyl), or
(5) a 3- to 8-membered (preferably 5- or 6-membered) monocyclic non-aromatic heterocyclic group (e.g., tetrahydropyranyl, tetrahydrofuryl); and
$R^3$ is
(1) a $C_{1-2}$ alkyl group (e.g., methyl) substituted by 1 to 3 substituents selected from a $C_{6-14}$ aryl group (e.g., phenyl) optionally substituted by 1 to 3 sulfamoyl groups,
(2) a $C_{3-10}$ cycloalkenyl group (e.g., cyclohexenyl),
(3) a $C_{6-14}$ aryl group (e.g., phenyl) optionally substituted by 1 to 3 substituents selected from
   (a) a halogen atom (e.g., a fluorine atom),
   (b) a nitro group,
   (c) a cyano group,
   (d) a carbamoyl group optionally substituted by 1 to 3 $C_{1-6}$ alkyl groups (e.g., methyl),
   (e) a sulfamoyl group,
   (f) a $C_{1-6}$ alkyl group (e.g., methyl, isopropyl) optionally substituted by 1 to 3 substituents selected from
      (i) a halogen atom (e.g., a fluorine atom),
      (ii) a cyano group, and
      (iii) a carbamoyl group optionally mono- or di-substituted by substituent(s) selected from a $C_{1-6}$ alkyl group (e.g., methyl) and a $C_{3-10}$ cycloalkyl group (e.g., cyclopropyl),
   (g) a $C_{1-6}$ alkoxy group (e.g., methoxy, ethoxy) optionally substituted by 1 to 3 substituents selected from a halogen atom (e.g., a fluorine atom), a cyano group, a hydroxy group and a carbamoyl group,
   (h) an amino group optionally mono- or di-substituted by $C_{1-6}$ alkyl-carbonyl group(s) (e.g., acetyl),
   (i) a 3- to 8-membered (preferably 5- or 6-membered) monocyclic non-aromatic heterocyclic group (e.g., morpholinyl), and
   (j) a $C_{1-6}$ alkylenedioxy group (e.g., methylenedioxy),
(4) a 5- to 7-membered (preferably 5- or 6-membered) monocyclic aromatic heterocyclic group (e.g., thienyl, pyridyl, pyrazolyl) optionally substituted by 1 to 3 substituents selected from
   (a) a carboxy group,
   (b) a cyano group,
   (c) a $C_{1-6}$ alkoxy-carbonyl group (e.g., methoxycarbonyl),
   (d) a carbamoyl group optionally mono- or di-substituted by substituent(s) selected from
      (i) a $C_{1-6}$ alkyl group (e.g., methyl, ethyl, tert-butyl) optionally substituted by 1 to 3 hydroxy groups
      (ii) a $C_{3-10}$ cycloalkyl group (e.g., cyclopropyl) optionally substituted by 1 to 3 cyano groups, and
      (iii) a 5- to 7-membered (preferably 5- or 6-membered) monocyclic aromatic heterocyclic group (e.g., pyrazolyl) optionally substituted by 1 to 3 $C_{1-6}$ alkyl groups (e.g., methyl),
   (e) a 3- to 8-membered (preferably 5- or 6-membered) monocyclic non-aromatic heterocyclic group (e.g., dihydrooxadiazolyl, morpholinyl) optionally substituted by 1 to 3 oxo groups,
   (f) a $C_{1-6}$ alkyl group (e.g., methyl, 2-methylpropyl) optionally substituted by 1 to 3 substituents selected from a cyano group and a carbamoyl group, and
   (g) a $C_{3-10}$ cycloalkyl group (e.g., cyclopropyl, cyclopentyl),
(5) a 8- to 12-membered fused aromatic heterocyclic group (e.g., benzoxadiazolyl),
(6) a 3- to 8-membered (preferably 5- or 6-membered) monocyclic non-aromatic heterocyclic group (e.g., dihydropyranyl),
(7) a 8- to 12-membered fused non-aromatic heterocyclic group (e.g., indolinyl) optionally substituted by 1 to 3 oxo groups, or
(8) an amino group optionally mono- or di-substituted by $C_{6-14}$ aryl group(s) (e.g., phenyl) optionally substituted by 1 to 3 carbamoyl groups.
[Compound B-2]
Compound (I) wherein
Ring A moiety is pyrrole wherein Q is a carbon atom (CH), and one of $X^2$ and $X^3$ is a carbon atom, and the other is a nitrogen atom, or pyrazole wherein Q is a nitrogen atom, and one of $X^2$ and $X^3$ is a carbon atom, and the other is a nitrogen atom); $R^1$ is
(1) a hydrogen atom,
(2) a halogen atom (e.g., a chlorine atom, a bromine atom),
(3) a cyano group,
(4) a carboxy group,
(5) a $C_{1-6}$ alkyl-carbonyl group (e.g., acetyl),
(6) a $C_{1-6}$ alkoxy-carbonyl group (e.g., methoxycarbonyl),
(7) a carbamoyl group optionally mono- or di-substituted by $C_{1-6}$ alkyl group(s) (e.g., methyl),
(8) a $C_{1-6}$ alkyl group (e.g., methyl) optionally substituted by 1 to 3 hydroxy groups, or
(9) a $C_{3-6}$ cycloalkyl group (e.g., cyclopropyl);
$R^2$ is
(1) a $C_{1-2}$ alkyl group (e.g., methyl) substituted by 1 to 3 substituents selected from
   (a) a $C_{6-14}$ aryl group (e.g., phenyl) optionally substituted by 1 to 3 $C_{1-6}$ alkoxy groups (e.g., methoxy), and
   (b) a 3- to 8-membered monocyclic non-aromatic heterocyclic group (e.g., dioxolanyl, oxetanyl, tetrahydrofuryl) optionally substituted by 1 to 3 $C_{1-6}$ alkyl groups (e.g., methyl),
(2) a $C_{3-6}$ alkyl group (e.g., propyl, tert-butyl, 1-methylpropyl, 1-ethylpropyl) optionally substituted by 1 to 3 substituents selected from
   (a) a hydroxy group, and
   (b) a $C_{1-6}$ alkoxy group (e.g., methoxy),
(3) a $C_{3-10}$ cycloalkyl group (e.g., cyclopentyl, cyclohexyl) optionally substituted by 1 to 3 substituents selected from (a) a hydroxy group,
(b) a $C_{1-6}$ alkyl group (e.g., methyl, ethyl),
(c) an oxo group,
(d) a $C_{1-6}$ alkylenedioxy group (e.g., ethylenedioxy),
(e) a $C_{6-14}$ aryl group (e.g., phenyl),
(f) a halogen atom (e.g., a fluorine atom), and
(g) an amino group,
(4) a $C_{6-14}$ aryl group (e.g., phenyl) optionally substituted by 1 to 3 substituents selected from
  (a) a halogen atom (e.g., a fluorine atom, a chlorine atom),
  (b) a $C_{1-6}$ alkyl group (e.g., methyl) optionally substituted by 1 to 3 halogen atoms (e.g., a fluorine atom),
  (c) a cyano group,
  (d) a carbamoyl group,
  (e) an amino group, and
  (f) a $C_{1-6}$ alkoxy group (e.g., methoxy),
(5) a 3- to 8-membered (preferably 5- or 6-membered) monocyclic non-aromatic heterocyclic group (e.g., tetrahydropyranyl, tetrahydrofuryl), or
(6) a 5- to 7-membered (preferably 5- or 6-membered) monocyclic aromatic heterocyclic group (e.g., pyridyl); and
$R^3$ is
(1) a $C_{1-2}$ alkyl group (e.g., methyl) substituted by 1 to 3 substituents selected from a $C_{6-14}$ aryl group (e.g., phenyl) optionally substituted by 1 to 3 sulfamoyl groups,
(2) a $C_{3-10}$ cycloalkyl group (e.g., cyclopropyl),
(3) a $C_{3-10}$ cycloalkenyl group (e.g., cyclohexenyl),
(4) a $C_{6-14}$ aryl group (e.g., phenyl) optionally substituted by 1 to 3 substituents selected from
  (a) a halogen atom (e.g., a fluorine atom, a chlorine atom),
  (b) a nitro group,
  (c) a cyano group,
  (d) a carbamoyl group optionally mono- or di-substituted by $C_1$-6 alkyl group(s) (e.g., methyl, ethyl) optionally substituted by 1 to 3 substituents selected from
    (i) a $C_{1-6}$ alkoxy group (e.g., methoxy),
    (ii) a hydroxy group, and
    (iii) an amino group optionally mono- or di-substituted by $C_{1-6}$ alkyl group (s) (e.g., methyl),
  (e) a sulfamoyl group optionally mono- or di-substituted by $C_{1-6}$ alkyl group(s) (e.g., methyl),
  (f) a $C_{1-6}$ alkyl group (e.g., methyl, isopropyl) optionally substituted by 1 to 3 substituents selected from
    (i) a halogen atom (e.g., a fluorine atom),
    (ii) a cyano group,
    (iii) a hydroxy group,
    (iv) a carbamoyl group optionally mono- or di-substituted by substituent(s) selected from a $C_{1-6}$ alkyl group (e.g., methyl) and a $C_{3-10}$ cycloalkyl group (e.g., cyclopropyl),
    (v) an amino group optionally mono- or di-substituted by $C_{1-6}$ alkyl group(s) (e.g., methyl), and
    (vi) a 3- to 8-membered (preferably 5- or 6-membered) monocyclic non-aromatic heterocyclic group (e.g., oxazolidinyl, morpholinyl, pyrrolidinyl) optionally substituted by 1 to 3 substituents selected from an oxo group and a halogen atom (e.g., a fluorine atom),
  (g) a $C_{1-6}$ alkoxy group (e.g., methoxy, ethoxy) optionally substituted by 1 to 3 substituents selected from
    (i) a halogen atom (e.g., a fluorine atom),
    (ii) a cyano group,
    (iii) a hydroxy group, and
    (iv) a carbamoyl group optionally mono- or di-substituted by substituent(s) selected from a $C_{1-6}$ alkyl group (e.g., methyl, ethyl) optionally substituted by 1 to 3 $C_{1-6}$ alkoxy groups (e.g., methoxy),
  (h) a $C_{1-6}$ alkoxy-carbonyl group (e.g., ethoxycarbonyl),
  (i) an amino group optionally mono- or di-substituted by substituent(s) selected from
    (i) a $C_{1-6}$ alkyl-carbonyl group (e.g., acetyl), and
    (ii) a $C_{1-6}$ alkyl group (e.g., methyl, ethyl) optionally substituted by 1 to 3 $C_{1-6}$ alkoxy groups (e.g., methoxy),
  (j) a 3- to 8-membered (preferably 5- or 6-membered) monocyclic non-aromatic heterocyclic group (e.g., morpholinyl, pyrrolidinyl, tetrahydrooxazepinyl, thiomorpholinyl, 1,1-dioxidothiomorpholinyl, dihydropyranyl, tetrahydropyranyl, imidazolidinyl, piperazinyl, piperidyl) optionally substituted by 1 to 3 substituents selected from
    (i) an oxo group,
    (ii) a $C_{1-6}$ alkyl group (e.g., methyl),
    (iii) a $C_{1-6}$ alkyl-carbonyl group (e.g., acetyl) optionally substituted by 1 to 3 substituents selected from a hydroxy group and a $C_{1-6}$ alkoxy group (e.g., methoxy),
    (iv) a carbamoyl group optionally mono- or di-substituted by $C_{1-6}$ alkyl group(s) (e.g., methyl),
    (v) a $C_{1-6}$ alkylsulfonyl group (e.g., methylsulfonyl), and
    (vi) a halogen atom (e.g., a fluorine atom), and
  (k) a $C_{1-6}$ alkylenedioxy group (e.g., methylenedioxy),
(5) a 5- to 7-membered (preferably 5- or 6-membered) monocyclic aromatic heterocyclic group (e.g., thienyl, pyridyl, pyrazolyl, pyrimidinyl) optionally substituted by 1 to 3 substituents selected from
  (a) a carboxy group,
  (b) a cyano group,
  (c) a $C_{1-6}$ alkoxy-carbonyl group (e.g., methoxycarbonyl, ethoxycarbonyl),
  (d) a carbamoyl group optionally mono- or di-substituted by substituent(s) selected from
    (i) a $C_{1-6}$ alkyl group (e.g., methyl, ethyl, tert-butyl) optionally substituted by 1 to 3 substituents selected from a hydroxy group and a cyano group,
    (ii) a $C_{3-10}$ cycloalkyl group (e.g., cyclopropyl) optionally substituted by 1 to 3 cyano groups,
    (iii) a 5- to 7-membered (preferably 5- or 6-membered) monocyclic aromatic heterocyclic group (e.g., pyrazolyl) optionally substituted by 1 to 3 $C_{1-6}$ alkyl groups (e.g., methyl), and
    (iv) a 3- to 8-membered (preferably 5- or 6-membered) monocyclic non-aromatic heterocyclic group (e.g., morpholinyl),
  (e) a 3- to 8-membered (preferably 5- or 6-membered) monocyclic non-aromatic heterocyclic group (e.g., dihydrooxadiazolyl, morpholinyl, tetrahydropyranyl) optionally substituted by 1 to 3 oxo groups,
  (f) a $C_{1-6}$ alkyl group (e.g., methyl, 2-methylpropyl) optionally substituted by 1 to 3 substituents selected from
    (i) a cyano group,
    (ii) a carbamoyl group, and
    (iii) a 3- to 8-membered (preferably 5- or 6-membered) monocyclic non-aromatic heterocyclic group (e.g., morpholinyl, pyrrolidinyl) optionally substituted by 1 to 3 oxo groups,
  (g) a $C_{3-10}$ cycloalkyl group (e.g., cyclopropyl, cyclopentyl),
  (h) a 3- to 8-membered (preferably 5- or 6-membered) monocyclic non-aromatic heterocyclylcarbonyl group (e.g., morpholinylcarbonyl), and
  (i) an amino group, (6) a 8- to 12-membered fused aromatic heterocyclic group (e.g., benzoxadiazolyl, benzimidazolyl) optionally substituted by 1 to 3 $C_{1-6}$ alkyl groups (e.g., methyl),
(7) a 3- to 8-membered (preferably 5- or 6-membered) monocyclic non-aromatic heterocyclic group (e.g., dihydropyranyl, dihydropyridyl) optionally substituted by 1 to 3 substituents selected from
  (a) an oxo group, and
  (b) a $C_{1-6}$ alkyl group (e.g., methyl),
(8) a 8- to 12-membered fused non-aromatic heterocyclic group (e.g., indolinyl) optionally substituted by 1 to 3 oxo groups, or
(9) an amino group optionally mono- or di-substituted by substituent(s) selected from
  (a) a $C_{6-14}$ aryl group (e.g., phenyl) optionally substituted by 1 to 3 substituents selected from
    (i) a carbamoyl group, and
    (ii) a sulfamoyl group,
  (b) a $C_{1-6}$ alkyl group (e.g., methyl) optionally substituted by 1 to 3 substituents selected from a $C_{6-14}$ aryl group (e.g., phenyl) optionally substituted by 1 to 3 $C_{1-6}$ alkoxy groups (e.g., methoxy), and
  (c) a $C_{6-14}$ aryl-carbonyl group (e.g., benzoyl).

[Compound C]
4-(1-cyclopentyl-4-oxo-4,5-dihydro-1H-pyrrolo[3,2-c]pyridin-3-yl)thiophene-2-carboxamide or a salt thereof;
2-(4-(1-(2,6-difluorophenyl)-4-oxo-4,5-dihydro-1H-pyrazolo[4,3-c]pyridin-3-yl)phenyl)acetamide or a salt thereof; or
3-((1-cyclopentyl-4-oxo-4,5-dihydro-1H-pyrazolo[4,3-c]pyridin-3-yl)amino)benzenesulfonamide or a salt thereof.

When compound (I) is in a form of a salt, examples thereof include metal salts, an ammonium salt, salts with organic base, salts with inorganic acid, salts with organic acid, salts with basic or acidic amino acid, and the like. Preferable examples of the metal salt include alkali metal salts such as sodium salt, potassium salt and the like; alkaline earth metal salts such as calcium salt, magnesium salt, barium salt and the like; an aluminum salt, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like.

Among them, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

[Production Method]
The production method of compound (I) is explained in the followings by referring to typical production methods, which are not to be construed as limitative. Compound (I) can also be produced according to the method shown in the following Schemes 1 to 15 or method analogous thereto, the methods described in Examples, or the like.

Unless otherwise specified, the symbols in Schemes 1 to 15 are as defined above.

The compounds in Schemes 1 to 15 may be in the form of a salt, and examples thereof include those similar to the salts of compound (I) and the like. The salt may be a commercially available product, or can also be produced according to the method shown in the following Schemes 1 to 15 or method analogous thereto, or the methods described in Examples.

Unless otherwise specified, the solvent in each reaction is not particularly limited as long as the reaction proceeds, and the reaction can be carried out in a solvent inert to the reaction or without solvent. These solvents are used alone or in a combination of two or more at a suitable ratio. Examples of the solvent include the following ones. Specifically, the solvents described in Examples can be used.

Examples of the solvent include the followings. alcohols: methanol, ethanol, 1-propanol, 2-propanol, tert-butyl alcohol, 2-methoxyethanol, 2,2,2-trifluoroethanol and the like; ethers: diethyl ether, diisopropyl ether, diphenyl ether, tert-butyl methyl ether, tetrahydrofuran, 1,4-dioxane, 1,2-dimethoxyethane and the like; aromatic hydrocarbons: benzene, chlorobenzene, toluene, xylene and the like; saturated hydrocarbons: cyclohexane, hexane, heptane and the like; amides: N,N-dimethylformamide, N,N-dimethylacetamide, N-methylpyrrolidone, hexamethylphosphoric triamide and the like; halogenated hydrocarbons: dichloromethane, chloroform, carbon tetrachloride, 1,2-dichloroethane and the like; nitriles: acetonitrile, propionitrile and the like; sulfoxides: dimethyl sulfoxide and the like; aromatic organic bases: pyridine, lutidine and the like; anhydrides: acetic anhydride and the like; organic acids: formic acid, acetic acid, propionic acid, trifluoroacetic acid, methanesulfonic acid and the like; inorganic acids: hydrochloric acid, sulfuric acid and the like; esters: methyl acetate, ethyl acetate, isopropyl acetate, butyl acetate and the like; ketones: acetone, methyl ethyl ketone and the like; water.

Unless otherwise specified, the reaction time in each reaction is generally 1 min-200 hr.

Unless otherwise specified, the reaction temperature in each reaction is −100 to 300° C. Specifically, the reaction can be carried out at the reaction temperature in described in Examples. In addition, the reaction can also be carried out under microwave irradiation in order to promote the reaction.

The reagent and reactant to be used in each reaction may be a commercially available product, or can also be produced according to a method known per se or a method analogous thereto, or the method described in Examples. Examples thereof include the following ones. Specifically, the reagent and reactant described in Examples can be used.

Examples of the base or acid scavenger include the followings.
inorganic bases: lithium hydroxide, sodium hydroxide, potassium hydroxide, calcium hydroxide, magnesium hydroxide, barium hydroxide and the like; basic salts: sodium carbonate, potassium carbonate, lithium carbonate, cesium carbonate, calcium carbonate, sodium hydrogencarbonate, potassium hydrogencarbonate, lithium hydrogencarbonate, calcium hydrogencarbonate, sodium phosphate, potassium phosphate, sodium acetate, potassium acetate, cesium acetate and the like; organic bases: triethylamine, diisopropylethylamine, tributylamine, cyclohexyldimethylamine, pyridine, picoline, lutidine, collidine, 4-dimethylaminopyridine, N,N-dimethylaniline, piperidine, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, tetramethylethylene diamine, imidazole and the like; metal alkoxides: sodium methoxide, sodium ethoxide, potassium tert-butoxide and the like; alkali metal hydrides: sodium hydride, potassium hydride and the like; metal amides: sodium amide, lithium diisopropylamide, lithiumhexamethyldisilazide and the like; organic lithium reagents: methyllithium, n-butyllithium, sec-butyllithium, tert-butyllithium and the like.

Unless otherwise specified, the equivalent of the reagent and reactant to be used in each reaction is 0.001 mol equivalent-100 mol equivalent relative to the substrate in each reaction.

The product in each reaction can be used directly as the reaction mixture or as a crude product for the next reaction, or can be isolated from a reaction mixture according to a method known per se, and easily purified by a separation means such as recrystallization, distillation, column chromatography and the like.

When the raw material compound mentioned below has amino, carboxy, hydroxy or a heterocyclic group, these groups may be protected by a protecting group generally used in peptide chemistry and the like. By removing the protecting group as necessary after the reaction, the objective compound can be obtained. The introduction and removal of the protecting group can be carried out according to a method known per se, for example, the method described in "Protective Groups in Organic Synthesis, 4th Ed", Wiley-Interscience, Inc. (2006) (Theodora W. Greene, Peter G. M. Wuts), the method described in Examples and the like.

Compound (1-2) can be produced according to the method shown in the following Scheme 1.

(Scheme 1)

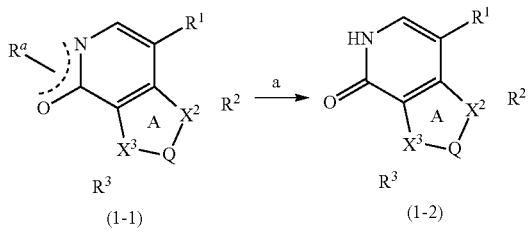

wherein $R^a$ is an optionally substituted $C_{1-6}$ alkyl group, and the other symbols are as defined above.

The "$C_{1-6}$ alkyl group" of the "optionally substituted $C_{1-6}$ alkyl group" for $R^a$ optionally has 1 to 5 (preferably 1 to 3) substituents at substitutable position(s). Examples of the substituent include substituents selected from the above-mentioned Substituent Group A. When the number of the substituents is plural, the respective substituents may be the same or different.

Preferable examples of the "optionally substituted $C_{1-6}$ alkyl group" for $R^a$ include a methyl group, an ethyl group, a (2-(trimethylsilyl)ethoxy)methyl group, a methoxymethyl group, an ethoxymethyl group, a benzyloxymethyl group, a benzyl group, a 4-methoxybenzyl group, a 2,4-methoxybenzyl group, a tert-butyl group, a trityl group and the like.

Compound (1-1) can be produced according to the method shown in Scheme 2, 6 or 11, or a method known per se or a method analogous thereto.

Compound (1-2) can be produced by removing the protecting group $R^a$ of compound (1-1). The removal of the protecting group $R^a$ can be carried out according to a method known per se, for example, the method described in "Protective Groups in Organic Synthesis, 4th Ed", Wiley-Interscience, Inc. (2006) (Theodora W. Greene, Peter G. M. Wuts) and the like.

(Scheme 2)

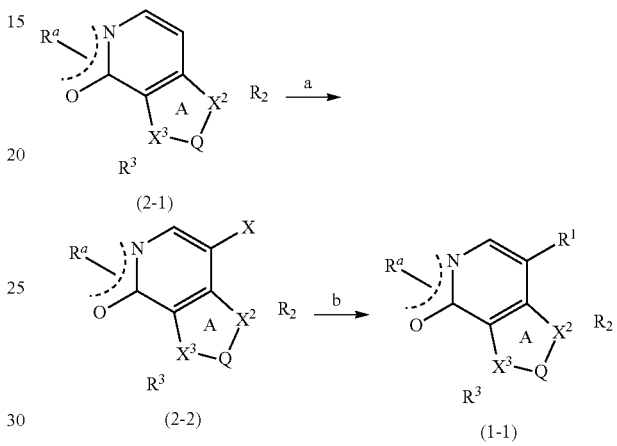

wherein X is a halogen atom, and the other symbols are as defined above.

Preferable examples of the halogen atom for X include chlorine, bromine, iodine and the like.

Compound (2-1) and (2-2) can be produced according to the method shown in Scheme 3, 4, 5, 7, 12, 13 or 14 or a method known per se, or a method analogous thereto.

Compound (2-2) can be obtained by halogenating compound (2-1) with the corresponding halogenating agent. This reaction is carried out in the presence of a base if desired.

Examples of the halogenating agent include N-bromosuccinimide, N-chlorosuccinimide, N-iodosuccinimide, bromine and the like.

Examples of the base include inorganic bases, basic salts, organic bases and the like.

This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, sulfoxides, aromatic organic bases, esters, mixed solvent thereof and the like.

Compound (1-1) can be obtained by reacting compound (2-2) with an organic metal reagent (e.g., a boronic acid, a zinc cyanide etc.) corresponding to $R^1$ or an amine corresponding to $R^1$, in the presence of an organic metal catalyst and a base if desired. When a metal catalyst unstable to oxygen is used, the reaction is preferably carried out under an inert gas atmosphere (e.g., argon gas, nitrogen gas etc.).

Examples of the organic metal catalyst include palladium catalysts (e.g., palladium(II) acetate, palladium(II) chloride, tetrakis(triphenylphosphine)palladium(0), dichlorobis(triphenylphosphine)palladium(II), dichlorobis(triethylphosphine)palladium(II), tris(dibenzylideneacetone)dipalladium (0), (1,1'-bis(diphenylphosphino)ferrocene)

dichloropalladium(II), etc.), and nickel catalysts (e.g., nickel (II) chloride, (1,1'-bis(diphenylphosphino)ferrocene)dichloronickel(II), etc.). In addition, a metal oxide (e.g., copper oxide, silver oxide, etc.) can also be used as a co-catalyst.

The organic metal catalyst can be used together with a phosphine ligand if desired. Examples of the phosphine ligand include triphenylphosphine, 2,2'-bis(diphenylphosphino)-1,1'-binaphthyl, 2,2'-bis(di-p-tolylphosphino)-1,1'-binaphthyl, 4,5-bis(diphenylphosphino)-9,9-dimethylxanthene, tri-tert-butylphosphine, 2-dicyclohexyl phosphino-2',4',6'-triisopropylbiphenyl, 2-dicyclohexyl phosphino-2',6'-dimethoxybiphenyl, 2-dicyclohexyl phosphino-2',6'-diisopropoxybiphenyl and the like. In addition, a salt such as tri-tert-butylphosphine tetrafluoroborate can also be used.

Examples of the base include inorganic bases, basic salts, organic bases and the like.

This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, sulfoxides, aromatic organic bases, esters, ketones, water, mixed solvent thereof and the like.

Compound (3-1) may be a commercially available product, or can also be produced according to a method known per se or a method analogous thereto.

Compound (3-2) can be obtained by reacting compound (3-1) with an aldehyde corresponding to $R^2$ in the presence of a base.

Examples of the base include metal amides, organic lithium reagents and the like.

This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, sulfoxides, aromatic organic bases, esters, mixed solvent thereof and the like.

Compound (3-3) can be obtained by reacting compound (3-2) with an oxidizing agent.

Examples of the oxidizing agent include Jones reagent (chromium(VI) oxide-sulfuric acid-acetone), pyridinium chlorochromate, pyridinium dichromate, pyridinium fluorochromate, Kiliani reagent (dichromate-sulfuric acid), chromic acid-acetic acid-water, chromium(VI) oxide-pyridine complex, hypervalent iodine compounds (Dess-Martin reagent, etc.), Swern reagents (DMSO-oxalyl chloride, DMSO-trifluoroacetic anhydride) and the like.

This reaction is advantageously carried out in a solvent inert to the reaction. The solvent is not particularly limited as long as the reaction proceeds. Preferable examples thereof include aromatic hydrocarbons, saturated hydrocarbons, amides, halogenated hydrocarbons, nitriles, sulfoxides, aromatic organic bases, esters, organic acids, water, mixed solvent thereof and the like.

Compound (3-4) can be obtained by reacting compound (3-3) with hydrazine or hydrazine hydrate.

This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, sulfoxides, aromatic organic bases, water, mixed solvent thereof and the like.

Compound (3-5) can be obtained by reacting compound (3-4) with an organic metal reagent (e.g., a boronic acid etc.) or a halide, both of which correspond to $R^3$, in the presence of an organic metal reagent or a copper halide and a base, if desired.

Examples of the organic metal reagent include copper(II) acetate and the like.

Examples of the copper halide include copper(I) iodide, copper(I) bromide and the like.

Examples of the base include basic salts, organic bases and the like.

This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, sulfoxides, aromatic organic bases, esters, mixed solvent thereof and the like.

Compound (3-6) can be obtained by subjecting compound (3-5) to a hydrogenation reaction in the presence of a metal catalyst. The reaction can also be carried out in the presence of a base if desired. The reaction is preferably carried out under 1-100 atm of hydrogen gas atmosphere if desired.

Examples of the metal catalyst include palladium on carbon, palladium-barium sulfate, palladium-alumina, rhodium

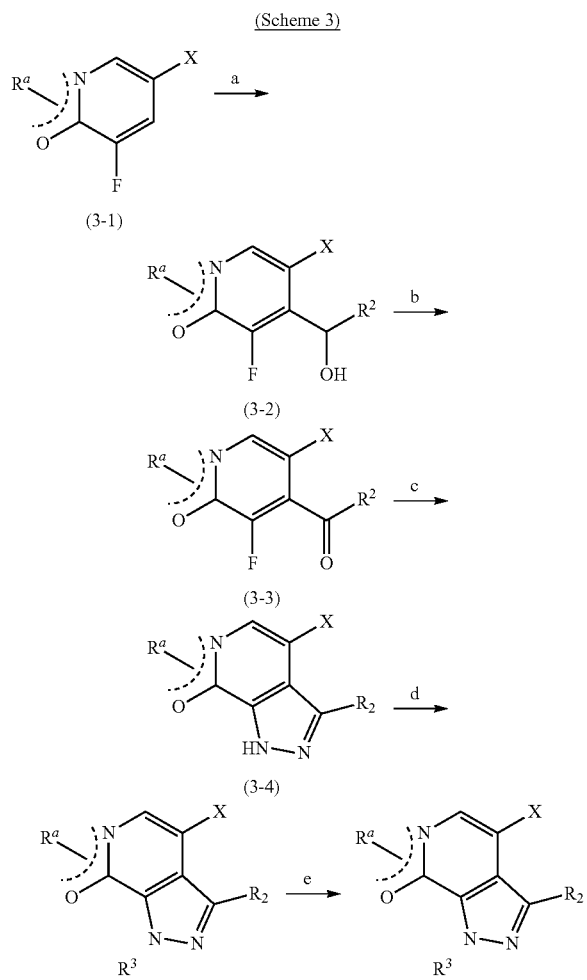

(Scheme 3)

wherein each symbol is as defined above.

on carbon, ruthenium carbon, ruthenium-silica, ruthenium-alumina, Raney nickel, Raney cobalt, platinum oxide and the like.

Examples of the base include inorganic bases, basic salts, organic bases and the like.

This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, sulfoxides, aromatic organic bases, organic acids, esters, water, mixed solvent thereof and the like.

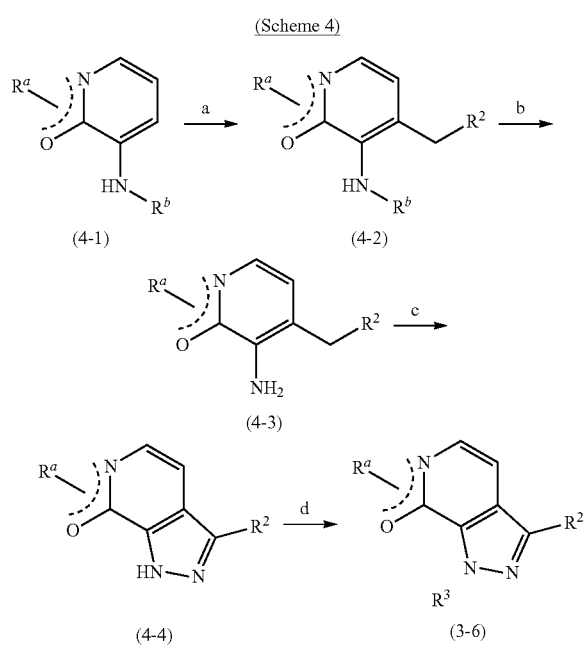

(Scheme 4)

wherein $R^b$ is an amino-protecting group, and the other symbols are as defined above.

Examples of the amino-protecting group for $R^b$ include a formyl group, and a $C_{1-6}$ alkyl group (e.g., methyl, ethyl, propyl, isopropyl, butyl, tert-butyl, etc.), a $C_{1-6}$ alkyl-carbonyl group (e.g., acetyl, propionyl, etc.), a phenylcarbonyl group, a $C_{1-6}$ alkoxy-carbonyl group (e.g., methoxycarbonyl, ethoxycarbonyl, tert-butoxycarbonyl, etc.), a $C_{1-6}$ alkoxy-$C_{1-6}$ alkyl group (e.g., methoxymethyl, ethoxymethyl, etc.), a phenyloxy-$C_{1-6}$ alkyl group (e.g., benzyloxymethyl, etc.), a phenyloxycarbonyl group, a $C_{7-10}$ aralkyl group (e.g., benzyl, etc.), a $C_{7-10}$ aralkyloxy-carbonyl group (e.g., benzyloxycarbonyl, etc.), a trityl group, a phthaloyl group, and a silyl group, each of which is optionally substituted, and the like. Examples of the substituent include a halogen atom (e.g., fluorine, chlorine, bromine, iodine, etc.), a $C_{1-6}$ alkyl group (e.g., methyl, ethyl, propyl, isopropyl, tert-butyl, butyl, tert-butyl, etc.), a $C_{1-6}$ alkoxy group (e.g., methoxy, ethoxy, etc.), a $C_{1-6}$ alkyl-carbonyl group (e.g., acetyl, propionyl, valeryl, etc.), a nitro group, a 9-fluorenylmethyl group, a trimethylsilyl group, a phenyl group and the like. The number of the substituent is, for example, 1 to 3.

Preferable examples of the amino-protecting group for $R^b$ include a formyl group, a tert-butylcarbonyl group, a tert-butoxycarbonyl group (Boc group), a benzyloxycarbonyl group (Z group), a 9-fluorenylmethyloxycarbonyl group (Fmoc group), a (2-(trimethylsilyl)ethoxy)methyl group, a methoxymethyl group, an ethoxymethyl group, a benzyloxymethyl group, a benzyl group, a 4-methoxybenzyl group, a 2,4-methoxybenzyl group, a trityl group, a trimethylsilyl group, a triethylsilyl group, a tert-butyldimethylsilyl group and the like.

Compound (4-1) may be a commercially available product, or can also be produced according to a method known per se or a method analogous thereto.

Compound (4-2) can be obtained by reacting compound (4-1) with a base in the presence of an organic base if desired, and then reacting the resulting compound with a halide corresponding to $R^2$—$CH_2$—.

Examples of the base include metal amides, organic lithium reagents and the like.

This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, sulfoxides, aromatic organic bases, mixed solvent thereof and the like.

Compound (4-3) can be produced by removing the protecting group $R^b$ of compound (4-2). The removal of the protecting group $R^b$ can be carried out according to a method known per se, for example, the method described in "Protective Groups in Organic Synthesis, 4th Ed", Wiley-Interscience, Inc. (2006) (Theodora W. Greene, Peter G. M. Wuts) and the like.

Compound (4-4) can be obtained by reacting compound (4-3) with sodium nitrite or a nitrite in the presence of an acid.

Examples of the acid include sulfuric acid, hydrochloric acid, nitric acid, organic acids and the like.

This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, sulfoxides, aromatic organic bases, organic acids, water, mixed solvent thereof and the like.

Compound (3-6) can be obtained using compound (4-4) in the same manner as in Step d of Scheme 3.

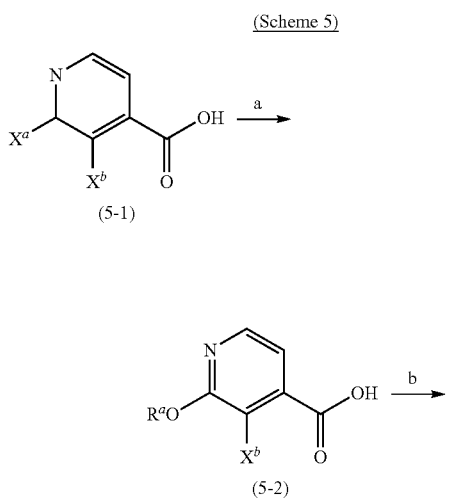

(Scheme 5)

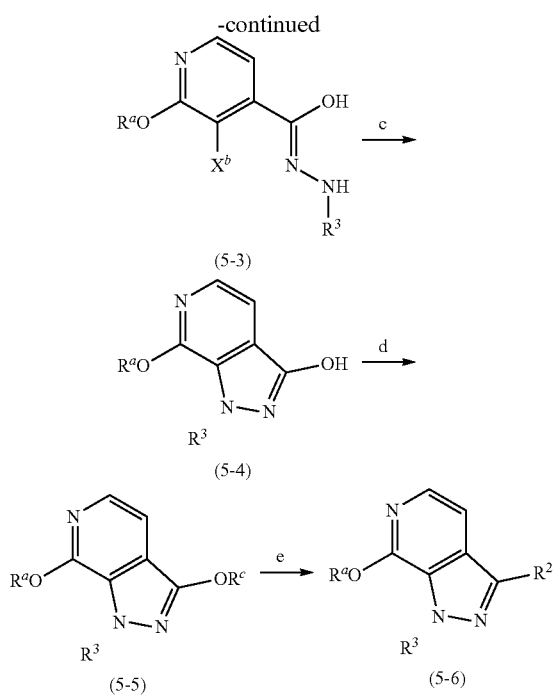

wherein $X^a$ and $X^b$ are each independently a halogen atom, $R^c$ is an optionally substituted sulfonyl group, and the other symbols are as defined above.

Preferable examples of the halogen atom for $X^a$ or $X^b$ include chlorine, bromine, iodine and the like.

The "sulfonyl group" of the "optionally substituted sulfonyl group" for $R^c$ optionally has 1 to 5 (preferably 1 to 3) substituents at substitutable position(s). Examples of the substituent include substituents selected from the above-mentioned Substituent Group A. When the number of the substituents is plural, the respective substituents may be the same or different.

Preferable examples of the optionally substituted sulfonyl group for $R^c$ include a trifluoromethanesulfonyl group, a benzenesulfonyl group, a 4-methylbenzenesulfonyl group, a 4-fluorobenzenesulfonyl group and the like.

Compound (5-1) may be a commercially available product, or can also be produced according to a method known per se or a method analogous thereto.

Compound (5-2) can be obtained by reacting compound (5-1) with a metal alkoxide corresponding to $R^a$.

This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, sulfoxides, aromatic organic bases, mixed solvent thereof and the like.

Compound (5-3) can be obtained by reacting compound (5-2) with a hydrazine compound corresponding to $R^3$ in the presence of a dehydration condensing agent. The reaction can also be carried out using a base if desired. The hydrazine compound may be a commercially available product, or can also be produced according to a method known per se or a method analogous thereto.

Examples of the dehydration condensing agent include N,N'-di-substituted carbodiimides (e.g., N,N'-dicyclohexyl carbodiimide, 1-ethyl-3-(3-dimethylaminopropyl)carbodiimide (WSC) hydrochloride etc.), azolides (e.g., N,N'-carbonyldiimidazole etc.), phosphorylcyanides (e.g., diethylphosphorylcyanide etc.), 2-halogeno pyridinium salts (e.g., 2-chloromethylpyridinium iodide, 2-fluoro-1-methylpyridinium iodide etc.), 1-hydroxybenzotriazole (HOBt), 2-(7-azabenzotriazol-1-yl)-1,1,3,3-hexafluorophosphate (HATU), O-(7-azabenzotriazol-1-yl)-N,N,N',N'-tetramethyluronium tetrafluoroborate (TATU), N-ethoxycarbonyl-2-ethoxy-1,2-dihydroquinoline, phosphorus oxychloride, alkoxy acetylenes and the like.

Examples of the base include basic salts, organic bases and the like.

This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, sulfoxides, aromatic organic bases, mixed solvent thereof and the like.

Compound (5-3) can also be obtained by reacting a reactive derivative of compound (5-2) with a hydrazine compound corresponding to $R^3$.

Examples of the reactive derivative include acid halides (e.g., acid chlorides, acid bromides etc.), acid amides (e.g., acid amides with pyrazole, imidazole, benzotriazole etc.), mixed anhydrides (e.g., anhydrides with acetic acid, propionic acid, butyric acid etc.), acid azides, activated esters (e.g., diethoxyphosphorate ester, diphenoxyphosphorate ester, p-nitrophenyl ester, 2,4-dinitrophenyl ester, cyanomethyl ester, pentachlorophenyl ester, ester with N-hydroxysuccinimide, ester with N-hydroxyphthalimide, ester with 1-hydroxybenzotriazole, ester with 6-chloro-1-hydroxybenzotriazole, ester with 1-hydroxy-1H-2-pyridone, etc.), activated thio esters (e.g., 2-pyridylthio ester, 2-benzothiazolylthio ester etc.) and the like.

This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, sulfoxides, aromatic organic bases, mixed solvent thereof and the like.

Compound (5-4) can be obtained by reacting compound (5-3) in the presence of copper or a copper halide and a base. The reaction can also be carried out using a ligand if desired.

Examples of the copper halides include copper(I) iodide, copper(I) bromide and the like.

Examples of the base include basic salts, organic bases and the like.

Examples of the ligand include L-proline, D-proline, trans-1,2-cyclohexyl diamine, phenanthroline and the like.

This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, sulfoxides, aromatic organic bases, esters, mixed solvent thereof and the like.

Compound (5-5) can be obtained by reacting compound (5-4) with a sulfonic anhydride or a sulfonyl halide compound, both of which correspond to $R^c$, in the presence of a base if desired.

Examples of the base include basic salts, organic bases, alkali metal hydrides and the like.

This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, sulfoxides, aromatic organic bases, mixed solvent thereof and the like.

Compound (5-6) can be obtained by reacting compound (5-5) with an organic metal reagent (e.g., boronic acid etc.) corresponding to R² in the presence of an organic metal catalyst and a base. When a metal catalyst unstable to oxygen is used, the reaction is preferably carried out under an inert gas atmosphere (e.g., argon gas, nitrogen gas etc.).

Examples of the organic metal catalyst include palladium catalysts (e.g., palladium(II) acetate, palladium(II) chloride, tetrakis(triphenylphosphine)palladium(0), dichlorobis(triphenylphosphine)palladium(II), dichlorobis(triethylphosphine)palladium(II), tris(dibenzylideneacetone)dipalladium (0), (1,1'-bis(diphenylphosphino)ferrocene) dichloropalladium(II), etc.), and nickel catalysts (e.g., nickel (II) chloride, (1,1'-bis(diphenylphosphino)ferrocene) dichloronickel(II), etc.). In addition, a metal oxide (e.g., copper oxide, silver oxide, etc.) can also be used as a co-catalyst.

The organic metal catalyst can be used together with a phosphine ligand if desired. Examples of the phosphine ligand include triphenylphosphine, 2,2'-bis(diphenylphosphino)-1,1'-binaphthyl, 2,2'-bis(di-p-tolylphosphino)-1,1'-binaphthyl, 4,5-bis(diphenylphosphino)-9,9-dimethylxanthene, tri-tert-butylphosphine, 2-dicyclohexyl phosphino-2',4',6'-triisopropylbiphenyl, 2-dicyclohexyl phosphino-2',6'-dimethoxybiphenyl, 2-dicyclohexyl phosphino-2',6'-diisopropoxybiphenyl and the like. In addition, a salt such as tri-tert-butylphosphine tetrafluoroborate can also be used.

Examples of the base include inorganic bases, basic salts, organic bases and the like.

This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, sulfoxides, aromatic organic bases, esters, ketones, water, mixed solvent thereof and the like.

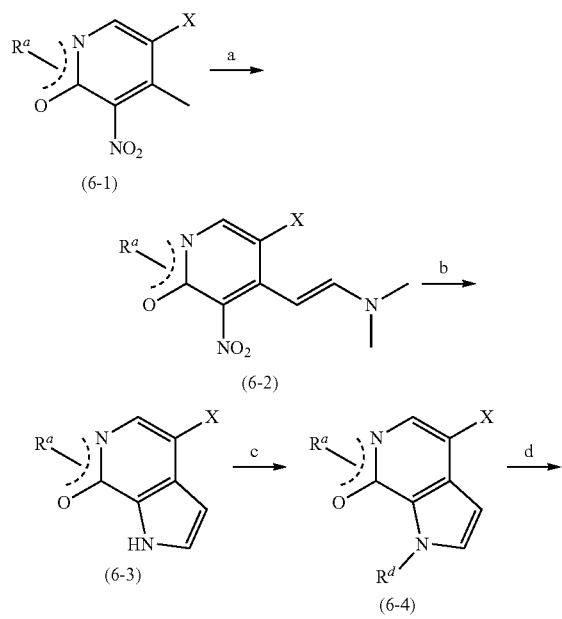

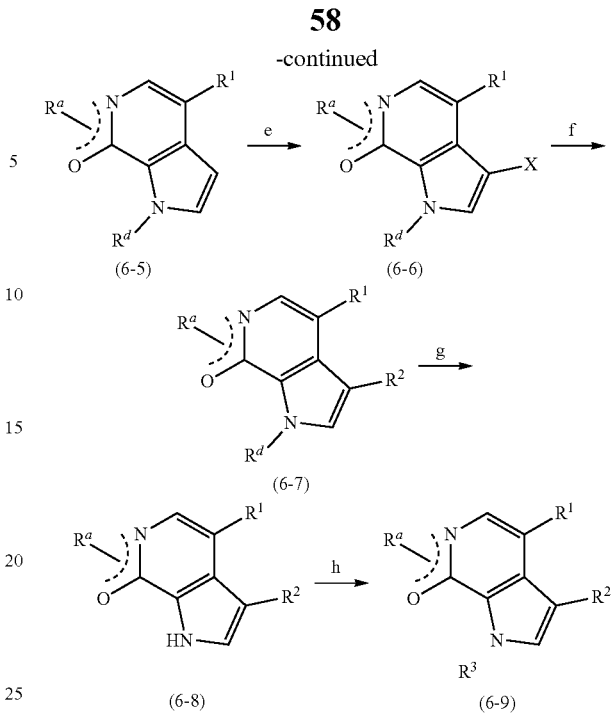

wherein $R^d$ is an amino-protecting group, and the other symbols are as defined above.

Examples of the amino-protecting group for $R^d$ include a formyl group, and a $C_{1-6}$ alkyl group (e.g., methyl, ethyl, propyl, isopropyl, butyl, tert-butyl, etc.), a $C_{1-6}$ alkyl-carbonyl group (e.g., acetyl, propionyl, etc.), a phenylcarbonyl group, a $C_{1-6}$ alkoxy-carbonyl group (e.g., methoxycarbonyl, ethoxycarbonyl, tert-butoxycarbonyl, etc.), a $C_{1-6}$ alkoxy-$C_{1-6}$ alkyl group (e.g., methoxymethyl, ethoxymethyl, etc.), a phenyloxy-$C_{1-6}$ alkyl group (e.g., benzyloxymethyl, etc.), a phenyloxycarbonyl group, a $C_{7-10}$ aralkyl group (e.g., benzyl, etc.), a $C_{7-10}$ aralkyloxy-carbonyl group (e.g., benzyloxycarbonyl, etc.), a trityl group, a phthaloyl group and a silyl group, each of which is optionally substituted, and the like. Examples of the substituent include a halogen atom (e.g., fluorine, chlorine, bromine, iodine, etc.), a $C_{1-6}$ alkyl group (e.g., methyl, ethyl, propyl, isopropyl, tert-butyl, butyl, tert-butyl, etc.), a $C_{1-6}$ alkoxy group (e.g., methoxy, ethoxy, etc.), a $C_{1-6}$ alkyl-carbonyl group (e.g., acetyl, propionyl, valeryl, etc.), a nitro group, a 9-fluorenylmethyl group, a trimethylsilyl group, a phenyl group and the like. The number of the substituent is, for example, 1 to 3.

Preferable examples of the amino-protecting group for $R^d$ include a tert-butoxycarbonyl group (Boc group), a benzyloxycarbonyl group (Z group), a 9-fluorenylmethyloxycarbonyl group (Fmoc group), a (2-(trimethylsilyl)ethoxy)methyl group, a methoxymethyl group, an ethoxymethyl group, a benzyloxymethyl group, a benzyl group, a 4-methoxybenzyl group, a 2,4-methoxybenzyl group, a tert-butyl group, a trityl group, a trimethylsilyl group, a triethylsilyl group, a tert-butyldimethylsilyl group and the like.

Compound (6-1) and (6-3) may be a commercially available product, or can also be produced according to a method known per se or a method analogous thereto.

Compound (6-2) can be obtained by reacting compound (6-1) with dimethylformamide dimethyl acetal.

This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, sulfoxides, aromatic organic bases, esters, ketones, water, mixed solvent thereof and the like.

Compound (6-3) can be obtained by reacting compound (6-2) in the presence of a metal, in an acidic solvent.

Examples of the metal include zinc and iron.

Examples of the acidic solvent include formic acid, acetic acid, propionic acid, trifluomacetic acid, methanesulfonic acid and the like.

This reaction can also be carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, sulfoxides, aromatic organic bases, organic acids, esters, ketones, water, mixed solvent thereof and the like.

Compound (6-4) can be produced by introducing the protecting group $R^d$ into compound (6-3). The introduction of the protecting group $R^d$ can be carried out according to a method known per se, for example, the method described in "Protective Groups in Organic Synthesis, 4th Ed", Wiley-Interscience, Inc. (2006) (Theodora W. Greene, Peter G. M. Wuts) and the like.

Compound (6-5) can be obtained using compound (6-4) in the same manner as in Step b of Scheme 2.

Compound (6-6) can be obtained using compound (6-5) in the same manner as in Step a of Scheme 2.

Compound (6-7) can be obtained using compound (6-6) in the same manner as in Step e of Scheme 5.

Compound (6-8) can be produced by removing the protecting group $R^d$ of compound (6-7). The removal of the protecting group $R^d$ can be carried out according to a method known per se, for example, the method described in "Protective Groups in Organic Synthesis, 4th Ed", Wiley-Interscience, Inc. (2006) (Theodora W. Greene, Peter G. M. Wuts) and the like.

Compound (6-9) can be obtained using compound (6-8) in the same manner as in Step d of Scheme 3.

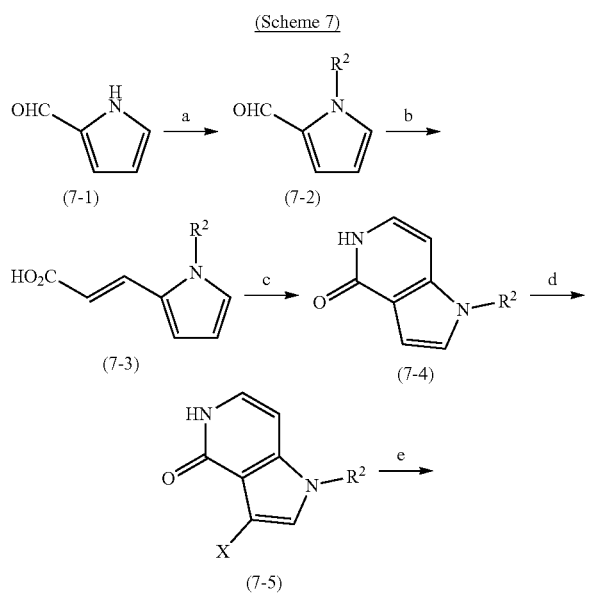

(Scheme 7)

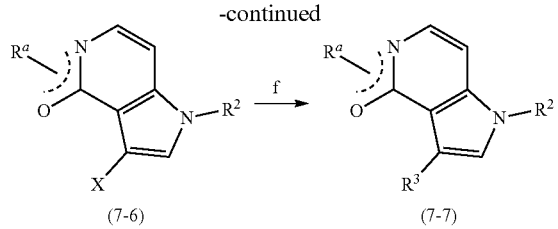

wherein each symbol is as defined above.

Compound (7-1) may be a commercially available product, or can also be produced according to a method known per se or a method analogous thereto.

Compound (7-2) can be obtained by reacting compound (7-1) with a halide corresponding to $R^2$ in the presence of a base. Alternatively, Compound (7-2) can be obtained by the method employing Mitsunobu reaction (described in Tetrahedron Letters, pages 769-770, 1980, and the like) or a method analogous thereto.

Examples of the base include inorganic bases, basic salts, organic bases, metal alkoxides, alkali metal hydrides, metal amides, organic lithium reagents and the like.

This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, sulfoxides, aromatic organic bases, esters, ketones, mixed solvent thereof and the like.

Compound (7-3) can be obtained by reacting compound (7-2) with an activated methylene compound, in the presence of a base. The reaction can be carried out by subjecting compound (7-2) to an acid or alkali hydrolysis reaction if desired. The hydrolysis reaction can be carried out according to a method known per se, for example, the method described in "Protective Groups in Organic Synthesis, 4th Ed", Wiley-Interscience, Inc. (2006) (Theodora W. Greene, Peter G. M. Wuts) and the like.

Examples of the base include inorganic bases, basic salts, organic bases, metal alkoxides, alkali metal hydrides, metal amides, organic lithium reagents and the like.

Examples of the activated methylene compound include malonic acid, dimethyl malonate, diethyl malonate, ethyl 2-(diethoxyphosphoryl)acetate and the like.

This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, sulfoxides, aromatic organic bases, esters, ketones, mixed solvent thereof and the like.

Compound (7-4) can be obtained by reacting compound (7-3) with an electrophile in the presence of a base, and then reacting the resulting compound with an azide compound, and then heating the resulting compound in the presence of a base, at 150-250° C.

Examples of the base include inorganic bases, basic salts, organic bases, metal alkoxides, alkali metal hydrides, metal amides, organic lithium reagents and the like.

Examples of the electrophile include ethyl chloroformate and the like.

Examples of the azide compound include sodium azide, diphenylphosphorylazide and the like.

This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, sulfoxides, aromatic organic bases, esters, ketones, mixed solvent thereof and the like.

Compound (7-5) can be obtained using compound (7-4) in the same manner as in Step a of Scheme 2. Alternatively, compound (7-5) can be obtained according to the method shown in Scheme 8 or 10.

Compound (7-6) can be produced by introducing the protecting group $R^a$ into compound (7-5). The introduction of the protecting group $R^a$ can be carried out according to a method known per se, for example, the method described in "Protective Groups in Organic Synthesis, 4th Ed", Wiley-Interscience, Inc. (2006) (Theodora W. Greene, Peter G. M. Wuts) and the like. Alternatively, compound (7-6) can be obtained according to the method shown in Scheme 9.

Compound (7-7) can be obtained using compound (7-6) in the same manner as in Step e of Scheme 5.

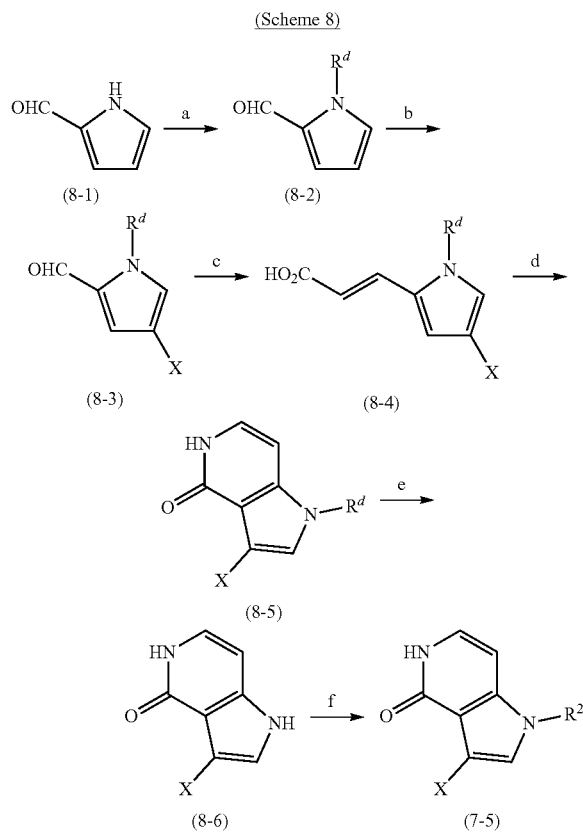

wherein each symbol is as defined above.

Compound (8-1) may be a commercially available product, or can also be produced according to a method known per se or a method analogous thereto.

Compound (8-2) can be produced by introducing the protecting group $R^d$ into compound (8-1). The introduction of the protecting group $R^d$ can be carried out according to a method known per se, for example, the method described in "Protective Groups in Organic Synthesis, 4th Ed", Wiley-Interscience, Inc. (2006) (Theodora W. Greene, Peter G. M. Wuts) and the like.

Compound (8-3) can be obtained using compound (8-2) in the same manner as in Step a of Scheme 2.

Compound (8-4) can be obtained using compound (8-3) in the same manner as in Step b of Scheme 7.

Compound (8-5) can be obtained using compound (8-4) in the same manner as in Step c of Scheme V.

Compound (8-6) can be produced by removing the protecting group of compound (8-5). The removal of the protecting group can be carried out according to a method known per se, for example, the method described in "Protective Groups in Organic Synthesis, 4th Ed", Wiley-Interscience, Inc. (2006) (Theodora W. Greene, Peter G. M. Wuts) and the like.

Compound (7-5) can be obtained using compound (8-6) in the same manner as in Step a of Scheme 7.

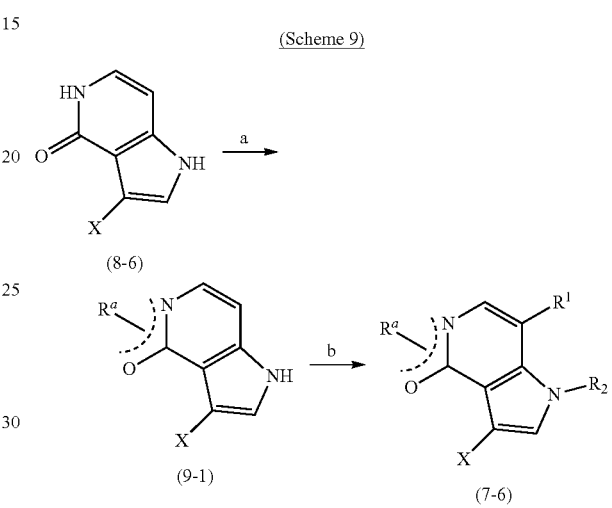

wherein each symbol is as defined above.

Compound (8-6) and (9-1) may be a commercially available product, or can also be produced according to a method known per se or a method analogous thereto.

Compound (9-1) can be produced by introducing the protecting group $R^a$ into compound (8-6). The introduction of the protecting group $R^a$ can be carried out according to a method known per se, for example, the method described in "Protective Groups in Organic Synthesis, 4th Ed", Wiley-Interscience, Inc. (2006) (Theodora W. Greene, Peter G. M. Wuts) and the like.

Compound (7-6) can be obtained using compound (9-1) in the same manner as in Step a of Scheme 7.

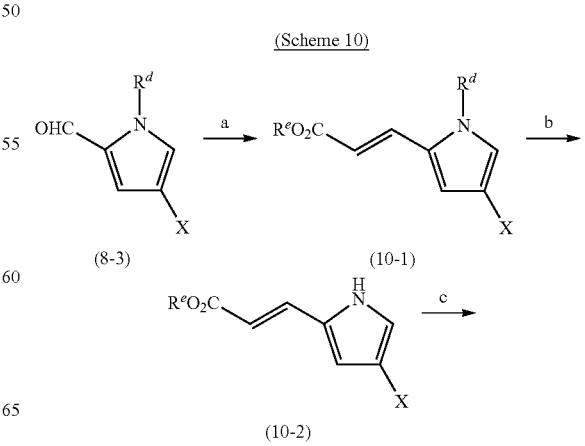

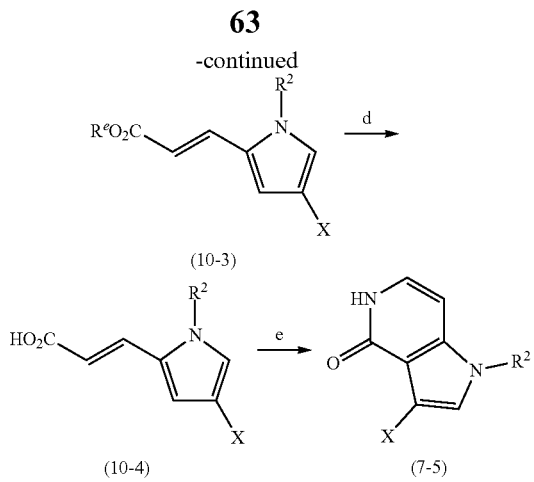

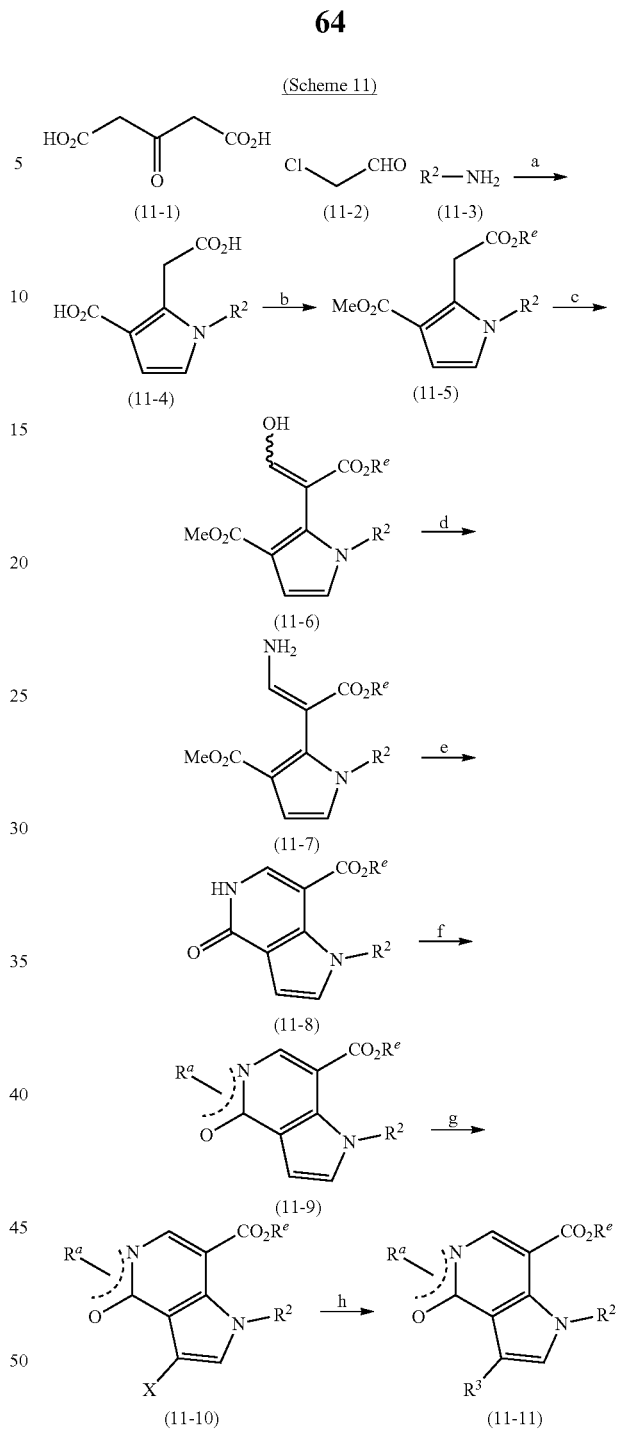

(Scheme 11)

wherein $R^e$ is an optionally substituted $C_{1-6}$ alkyl group, and the other symbols are as defined above.

The "$C_{1-6}$ alkyl group" of the "optionally substituted $C_{1-6}$ alkyl group" for $R^e$ optionally has 1 to 5 (preferably 1 to 3) substituents at substitutable position(s). Examples of the substituent include substituents selected from the above-mentioned Substituent Group A. When the number of the substituents is plural, the respective substituents may be the same or different.

Preferable examples of the "optionally substituted $C_{1-6}$ alkyl group" for $R^e$ include a methyl group, an ethyl group, a benzyl group, a trityl group and the like.

Compound (10-1) can be obtained by reacting compound (8-3) with an activated methylene compound in the presence of a base.

Examples of the base include inorganic bases, basic salts, organic bases, metal alkoxides, alkali metal hydrides, metal amides, organic lithium reagents and the like.

Examples of the activated methylene compound include dimethyl malonate, diethyl malonate, ethyl 2-(diethoxyphosphoryl)acetate and the like.

This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, sulfoxides, aromatic organic bases, esters, ketones, mixed solvent thereof and the like.

Compound (10-2) can be produced by removing the protecting group $R^d$ of compound (10-1). The removal of the protecting group $R^d$ can be carried out according to a method known per se, for example, the method described in "Protective Groups in Organic Synthesis, 4th Ed", Wiley-Interscience, Inc. (2006) (Theodora W. Greene, Peter G. M. Wuts) and the like.

Compound (10-3) can be obtained using compound (10-2) in the same manner as in Step a of Scheme V.

Compound (10-4) can be obtained by subjecting compound, (10-3) to an acid or alkali hydrolysis reaction. The hydrolysis reaction can be carried out according to a method known per se, for example, the method described in "Protective Groups in Organic Synthesis, 4th Ed", Wiley-Interscience, Inc. (2006) (Theodora W. Greene, Peter G. M. Wuts) and the like.

Compound (7-5) can be obtained using compound (10-4) in the same manner as in Step c of Scheme 7.

wherein each symbol is as defined above.

Compound (11-1), (11-2) and (11-3) may be a commercially available product, or can also be produced according to a method known per se or a method analogous thereto.

Compound (11-4) can be obtained by reacting compounds (11-1), (11-2) and (11-3).

This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, sulfoxides, aromatic organic bases, esters, ketones, water, mixed solvent thereof and the like.

Compound (11-5) can be produced by introducing the protecting group $R^e$ into compound (11-4). The introduction of the protecting group $R^e$ can be carried out according to a method known per se, for example, the method described in "Protective Groups in Organic Synthesis, 4th Ed", Wiley-Interscience, Inc. (2006) (Theodora W. Greene, Peter G. M. Wuts) and the like.

Compound (11-6) can be obtained by reacting compound (11-5) with methyl formate, dimethylformamide or the like in the presence of a base.

Examples of the base include inorganic bases, basic salts, organic bases, metal alkoxides, alkali metal hydrides, metal amides, organic lithium reagents and the like.

This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, sulfoxides, aromatic organic bases, esters, ketones, water, mixed solvent thereof and the like.

Compound (11-7) can be obtained by reacting compound (11-6) with ammonia or an ammonium salts (e.g., ammonium acetate, ammonium formate etc.).

This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, sulfoxides, aromatic organic bases, esters, ketones, water, mixed solvent thereof and the like.

Compound (11-8) can be obtained by reacting compound (11-7) in the presence of a base.

Examples of the base include inorganic bases, basic salts, organic bases, metal alkoxides, alkali metal hydrides, metal amides, organic lithium reagents and the like.

This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, sulfoxides, aromatic organic bases, esters, ketones, water, mixed solvent thereof and the like.

Compound (11-9) can be produced by introducing the protecting group $R^a$ into compound (11-8). The introduction of the protecting group $R^a$ can be carried out according to a method known per se, for example, the method described in "Protective Groups in Organic Synthesis, 4th Ed", Wiley-Interscience, Inc. (2006) (Theodora W. Greene, Peter G. M. Wuts) and the like. Alternatively, compound (11-9) can be obtained by reacting compound (11-8) with oxy phosphorus chloride, and then reacting the resulting compound with a metal alkoxide (e.g., sodium methoxide, etc.) corresponding to $R^a$.

This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, sulfoxides, aromatic organic bases, esters, ketones, water, mixed solvent thereof and the like.

Compound (11-10) can be obtained using compound (11-9) in the same manner as in Step a of Scheme 2.

Compound (11-11) can be obtained using compound (11-10) in the same manner as in Step e of Scheme 5.

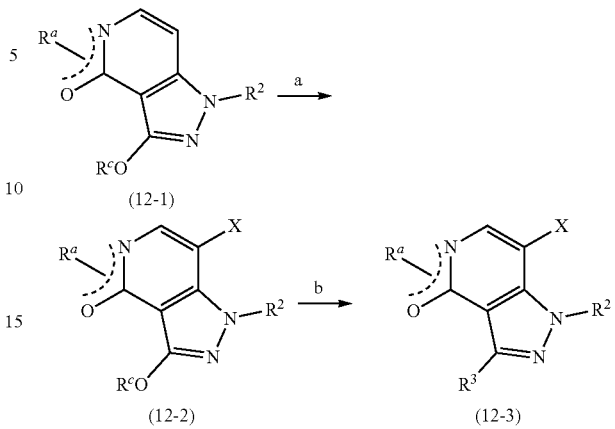

(Scheme 12)

wherein each symbol is as defined above.

Compound (12-1) and (12-2) may be a commercially available product, or can also be produced according to the method shown in Scheme 15 or a method known per se, or a method analogous thereto.

Compound (12-2) can be obtained using compound (12-1) in the same manner as in Step a of Scheme 2.

Compound (12-3) can be obtained using compound (12-2) in the same manner as in Step e of Scheme 5.

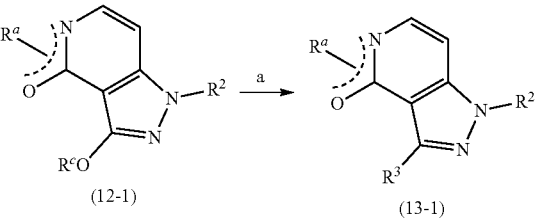

(Scheme 13)

wherein each symbol is as defined above.

Compound (13-1) can be obtained using compound (12-1) in the same manner as in Step e of Scheme 5.

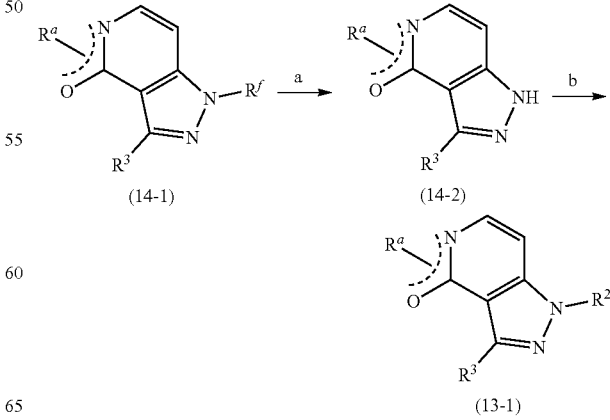

(Scheme 14)

wherein R$^f$ is an amino-protecting group, and the other symbols are as defined above.

Examples of the amino-protecting group for R$^f$ include a formyl group, and a C$_{1-6}$ alkyl-carbonyl group (e.g., acetyl, propionyl, etc.), a phenylcarbonyl group, a C$_{1-6}$ alkoxy-carbonyl group (e.g., methoxycarbonyl, ethoxycarbonyl, etc.), a phenyloxycarbonyl, a C$_{7-10}$ aralkyloxy-carbonyl group (e.g., benzyloxycarbonyl, etc.), a trityl group and a phthaloyl group, each of which is optionally substituted, and the like. Examples of the substituent include a halogen atom (e.g., fluorine, chlorine, bromine, iodine, etc.), a C$_{1-6}$ alkyl-carbonyl group (e.g., acetyl, propionyl, valeryl, etc.), a nitro group and the like. The number of the substituent is, for example, 1 to 3.

Preferable examples of the amino-protecting group for R$^f$ include a (2-(trimethylsilyl)ethoxy)methyl group, a methoxymethyl group, an ethoxymethyl group, a benzyloxymethyl group, a benzyl group, a 4-methoxybenzyl group, a 2,4-methoxybenzyl group, a tert-butyl group, a trityl group, a trimethylsilyl group, a triethylsilyl group, a tert-butyldimethylsilyl group and the like.

Compound (14-1) can be produced according to the method shown in Scheme 13 or 15, or a method known per se or a method analogous thereto.

Compound (14-2) can be produced by removing the protecting group R$^f$ of compound (14-1). The removal of the protecting group R$^f$ can be carried out according to a method known per se, for example, the method described in "Protective Groups in Organic Synthesis, 4th Ed", Wiley-Interscience, Inc. (2006) (Theodora W. Greene, Peter G. M. Wuts) and the like.

Compound (13-1) can be obtained using compound (14-2) in the same manner as in Step a of Scheme 7.

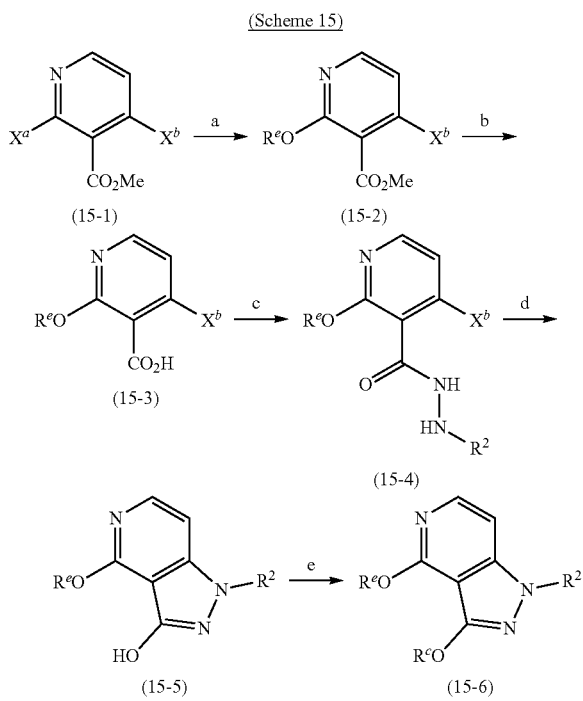

(Scheme 15)

wherein each symbol is as defined above.

Compound (15-1) and (15-2) may be a commercially available product, or can also be produced according to a method known per se or a method analogous thereto.

Compound (15-2) can be obtained by reacting compound (15-1) with a metal alkoxide corresponding to R$^e$.

This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, sulfoxides, aromatic organic bases, esters, ketones, mixed solvent thereof and the like.

Compound (15-3) can be obtained by subjecting compound (15-2) to an acid or alkali hydrolysis. The hydrolysis reaction can be carried out according to a method known per se, for example, the method described in "Protective Groups in Organic Synthesis, 4th Ed", Wiley-Interscience, Inc. (2006) (Theodora W. Greene, Peter G. M. Wuts) and the like.

Compound (15-4) can be obtained using compound (15-3) in the same manner as in Step b of Scheme 5.

Compound (15-5) can be obtained using compound (15-4) in the same manner as in Step c of Scheme 5.

Compound (15-6) can be obtained using compound (15-5) in the same manner as in Step d of Scheme 5.

The raw material compound and/or synthetic intermediate of compound (I) may be in the form of a salt. The salt is not particularly limited as long as the reaction is achieved, and examples thereof include those similar to the salts of compound (I) and the like.

The configurational isomer (E,Z form) of compound (I) can be isolated and purified by a conventional separation means such as extraction, recrystallization, distillation, chromatography and the like to give the pure compound, once the isomerization arises. In addition, the corresponding pure isomer can be obtained by promoting the isomerization of double bond by heating, an acid catalyst, a transition metal complex, a metal catalyst, a radical catalyst, light irradiation, a strong base catalyst and the like, according to the method described in Shin Jikken Kagaku Kouza, vol. 14, pages 251 to 253 (the Chemical Society of Japan ed.), Jikken Kagaku Kouza, 4th Edition, vol. 19, pages 273 to 274 (the Chemical Society of Japan ed.) or a method analogous thereto.

Compound (I) contains a stereoisomer depending on the kind of the substituent, and the single isomer and mixture thereof are also encompassed in the present invention.

In any case, compound (I) can be synthesized by deprotection reaction, acylation reaction, alkylation reaction, hydrogenation reaction, oxidation reaction, reduction reaction, reaction of carbon chain extension, substituent exchange reaction alone or two or more thereof in combination, if desired.

In the above-mentioned reaction, when the objective compound is obtained as a free form, it can be converted to a salt according to a method known per se. When the objective compound is obtained is a salt, it can be converted to the free form or the other salt according to a method known per se. The thus-obtained compound (I) can be isolated and purified from a reaction mixture according to a method known per se, for example, phase transfer, concentration, solvent extraction, fractional distillation, crystallization, recrystallization, column chromatography and the like.

In above-mentioned each reaction, when the compound has a functional group such as an amino group, a hydroxy group, a carboxy group and the like, the compound can be subjected to a reaction after introduction of a protecting group generally used in peptide chemistry and the like. By removing the protecting group as necessary after the reaction, the objective compound can be obtained.

Examples of the protecting group include a formyl group, and a C$_{1-6}$ alkyl-carbonyl group (e.g., acetyl, propionyl, etc.), a phenylcarbonyl group, a $C_{1-6}$ alkoxy-carbonyl group (e.g., methoxycarbonyl, ethoxycarbonyl, etc.), a phenyloxycarbonyl group, a $C_{7-10}$ aralkyloxy-carbonyl group (e.g., benzyloxycarbonyl, etc.), a trityl group and a phthaloyl group, each of which is optionally substituted, and the like. Examples of the substituent include a halogen atom (e.g., fluorine, chlorine, bromine, iodine, etc.), a $C_{1-6}$ alkyl-carbonyl group (e.g., acetyl, propionyl, valeryl, etc.), a nitro group and the like. The number of the substituent is, for example, 1 to 3.

The protecting groups can be removed according to a method known per se, for example, by employing a method treating acid, base, ultraviolet radiation, hydrazine, phenylhydrazine, sodium N-methyldithiocarbamate, tetrabutylammonium fluoride, palladium acetate and the like, a reduction method, and the like.

The thus-obtained compound (I), other reaction intermediate and a raw material compound thereof can be isolated and purified from a reaction mixture according to a method known per se, for example, means such as extraction, concentration, neutralization, filtration, distillation, recrystallization, column chromatography, thin layer chromatography, preparative high-performance liquid chromatography (preparative HPLC), medium-pressure preparative liquid chromatography (medium-pressure preparative LC) and the like.

The salt of compound (I) can be produced according to a method known per se, for example, by adding an inorganic acid or an organic acid in the case that compound (I) is a basic compound, or by adding an organic base or an inorganic base in the case that compound (I) is an acidic compound.

When compound (I) contains a configurational isomer, a diastereomer, a conformer and the like, each isomer can be isolated by the above-mentioned separation and purification means if desired. When compound (I) is racemic, it can be resolved into S-form and R-form by a conventional optical resolution.

Compound (I) may be used as a prodrug. The prodrug of compound (I) means a compound which is converted to compound (I) with a reaction due to an enzyme, gastric acid and the like under the physiological condition in the living body, that is, a compound which is converted to compound (I) by enzymatic oxidation, reduction, hydrolysis and the like; a compound which is converted to compound (I) by hydrolysis and the like due to gastric acid, and the like.

Examples of the prodrug for compound (I) include
(1) a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation, tert-butylation, ethoxycarbonylation, tert-butoxycarbonylation, acetylation or cyclopropylcarbonylation, and the like);
(2) a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation, and the like);
(3) a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, and the like)
and the like. These compounds can be produced from compound (I) according to a method known per se.

The prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, compound (I) and a prodrug thereof are sometimes collectively abbreviated as "the compound of the present invention".

When compound (I) contains an isomer such as an optical isomer, a stereoisomer, a regioisomer, a rotamer and the like, any isomer and a mixture thereof are also encompassed in compound (I). For example, when compound (I) contains an optical isomer, an optical isomer resolved from racemic compound is also encompassed in compound (I). These isomers can be obtained as a single product according to a synthetic method known per se, a separation means known per se (concentration, solvent extraction, column chromatography, recrystallization, etc.).

The compound (I) may be a crystal. Single crystal form and mixed crystal form are also encompassed in compound (I). The crystal can be produced by according to a crystallization method known per se.

Compound (I) may be a hydrate, a non-hydrate, a solvate or a non-solvate.

Compound (I) also encompasses a compound labeled with an isotope (e.g., $^3H$, $^{14}C$, $^{35}S$, $^{125}I$ etc.) and the like.

Compound (I) also encompasses a deuterium conversion form wherein $^1H$ is converted to $^2H(D)$.

Compound (I) also encompasses a tautomer thereof.

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity, solubility and stability etc.). The cocrystal or a salt thereof can be produced according to a cocrystallization a method known per se.

Compound (I) may also be used as a PET tracer.

Since the compound of the present invention has a superior JAK (JAK1, JAK2, JAK3, Tyk2) inhibitory action, it is also useful as safe medicaments based on such action.

Since the compound of the present invention also has an IFN-α inhibitory action, an IFN-β inhibitory action, an IFN-γ inhibitory action, an IL-2 inhibitory action, an IL-4 inhibitory action, an IL-7 inhibitory action, an IL-15 inhibitory action, an IL-21 inhibitory action, an IL-6 inhibitory action, an OSM inhibitory action, an IL-10 inhibitory action, an IL-19 inhibitory action, an IL-20 inhibitory action, an IL-22 inhibitory action, an IL-28 inhibitory action, an IL-29 inhibitory action, an IL-12 inhibitory action, and/or an IL-23 inhibitory action, it is also useful as safe medicaments based on such action.

For example, the medicament of the present invention containing the compound of the present invention can be used for a mammal (e.g., mouse, rat, hamster, rabbit, cat, dog, bovine, sheep, monkey, human etc.) as a prophylactic or therapeutic agent for JAK associated diseases, more specifically, the diseases described in (1)-(4) below.
(1) inflammatory diseases (e.g., acute pancreatitis, chronic pancreatitis, asthma, adult respiratory distress syndrome, chronic obstructive pulmonary disease (COPD), inflammatory bone disease, inflammatory pulmonary disease, inflammatory bowel disease, celiac disease, hepatitis, systemic inflammatory response syndrome (SIRS), postoperative or posttraumatic inflammation, pneumonia, nephritis, meningitis, cystitis, pharyngolaryngitis, gastric mucosal injury, meningitis, spondylitis, arthritis, dermatitis, chronic pneumonia, bronchitis, pulmonary infarction, silicosis, pulmonary sarcoidosis etc.), (2) autoimmune diseases (e.g., rheumatoid arthritis, psoriasis, inflammatory bowel disease (e.g., Crohn's disease, ulcerative colitis etc.), Sjogren's syndrome, Behcet's disease, multiple sclerosis, systemic lupus erythematosus, Castleman's disease, ankylopoietic spondylarthritis, polymyositis, dermatomyositis (DM), polyarteritis nodosa (PN), mixed connective tissue disease (MCTD), scleroderma, profundus lupus erythematosus, chronic thyroiditis, Graves' disease, autoimmune gastritis, type I and type II diabetes, autoimmune hemolytic anemia, autoimmune neutropenia, thrombocytopenia, atopic dermatitis, chronic active hepatitis, myasthenia gravis, graft versus host disease, Addison's disease, abnormal immunoresponse, arthritis, dermatitis, radiodermatitis etc.), (3) osteoarticular degenerative disease (e.g., rheumatoid arthritis, osteoporosis, osteoarthritis etc.), (4) neoplastic diseases [e.g., malignant tumor, angiogenesis glaucoma, infantile hemangioma, multiple myeloma, chronic sarcoma, multiple myeloma, metastasis melanoma, Kaposi's sacroma, vascular proliferation, cachexia, metastasis of the breast cancer, cancer (e.g., colorectal cancer (e.g., familial colorectal cancer, hereditary nonpolyposis colorectal cancer, gastrointestinal stromal tumor etc.), lung cancer (e.g., non-small cell lung cancer, small cell lung cancer, malignant mesothelioma etc.), mesothelioma, pancreatic cancer (e.g., pancreatic duct cancer etc.), gastric cancer (e.g., papillary adenocarcinoma, mucinous adenocarcinoma, adenosquamous carcinoma, etc.), breast cancer (e.g., invasive ductal carcinoma, ductal carcinoma in situ, inflammatory breast cancer etc.), ovarian cancer (e.g., ovarian epithelial carcinoma, extragonadal germ cell tumor, ovarian germ cell tumor, ovarian low malignant potential tumor etc.), prostate cancer (e.g., hormone-dependent prostate cancer, non-hormone dependent prostate cancer etc.), liver cancer (e.g., primary liver cancer, extrahepatic bile duct cancer etc.), thyroid cancer (e.g., medullary thyroid carcinoma etc.), kidney cancer (e.g., renal cell carcinoma, transitional cell carcinoma in kidney and urinary duct etc.), uterine cancer, brain tumor (e.g., pineal astrocytoma, pilocytic astrocytoma, diffuse astrocytoma, anaplastic astrocytoma etc.), melanoma, sarcoma, urinary bladder cancer, hematologic cancer and the like including multiple myeloma, hypophyseal adenoma, glioma, acoustic neurinoma, retinoblastoma, pharyngeal cancer, laryngeal cancer, cancer of the tongue, thymoma, esophagus cancer, duodenal cancer, colorectal cancer, rectal cancer, hepatoma, pancreatic endocrine tumor, bile duct cancer, gallbladder cancer, penile cancer, urinary duct cancer, testis tumor, vulvar cancer, cervix cancer, endometrial cancer, uterus sarcoma, cholionic disease, vaginal cancer, skin cancer, fungoid mycosis, basal cell tumor, soft tissue sarcoma, malignant lymphoma, Hodgkin's disease, myelodysplastic syndrome, adult T cell leukemia, chronic bone marrow proliferative disease, pancreatic endocrine tumor fibrous histiocytoma, leiomyosarcoma, rhabdomyosarcoma, cancer of unknown primary), leukemia (e.g., acute leukemia (e.g., acute lymphocytic leukemia, acute myelogenous leukemia etc.), chronic leukemia (e.g., chronic lymphocytic leukemia, chronic myelogenous leukemia etc.), myelodysplastic syndrome etc.), uterus sarcoma (e.g., mixed mesodermal tumor, uterine leiomyosarcoma, endometrial stromal tumor etc.), myelofibrosis and the like].

The medicament of the present invention can be preferably used as an agent for the prophylaxis or treatment of autoimmune disease, inflammatory disease, osteoarticular degenerative disease or neoplastic disease, particularly preferably rheumatoid arthritis, psoriasis, inflammatory bowel disease (preferably Crohn's disease or ulcerative colitis), Sjogren's syndrome, Behcet's disease, multiple sclerosis, systemic lupus erythematosus, Castleman's disease, leukemia, uterine leiomyosarcoma, prostate cancer, multiple myeloma, cachexia or myelofibrosi.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

The medicament of the present invention shows superior pharmacokinetics (e.g., a half-life of the drug in plasma), low toxicity (e.g., HERG inhibition, CYP inhibition, CYP induction), decreased side effect (e.g., adrenocortical hypofunction, gastrointestinal tract ulcer, induction/aggravation of diabetes, osteoporosis, cardiovascular/hematopoietic compromise), and decreased drug interaction. The compound of the present invention can be directly used as a medicament, or as the medicament of the present invention by producing a pharmaceutical composition by mixing with a pharmaceutically acceptable carrier by a means known per se and generally used in a production method of pharmaceutical preparations. The medicament of the present invention can be orally or parenterally administered safely to mammals (e.g., humans, monkeys, cows, horses, pigs, mice, rats, hamsters, rabbits, cats, dogs, sheep and goats).

A medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal etc.), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, cream, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor and direct administration to the lesion).

The content of the compound of the present invention in the medicament of the present invention is about 0.01 to 100% by weight of the entire medicament. The dose varies depending on administration subject, administration route, disease and the like. For example, for oral administration to patients (body weight about 60 kg) with rheumatoid arthritis, psoriasis, inflammatory bowel disease, Sjogren's syndrome, Behcet's disease, multiple sclerosis, systemic lupus erythematosus, Castleman's disease, leukemia, uterine leiomyosarcoma, prostate cancer, multiple myeloma, cachexia, myelofibrosis or the like, about 0.01 mg/kg body weight-about 500 mg/kg body weight, preferably about 0.1 mg/kg body weight-about 50 mg/kg body weight, more preferably about 1 mg/kg body weight-about 30 mg/kg body weight of an active ingredient (compound (I)) can be administered once to several portions per day.

The pharmaceutically acceptable carrier, which may be used for the production of the medicament of the present invention, may be exemplified by various organic or inorganic carrier materials that are conventionally used as preparation materials, for example, excipient, lubricant, bin ding agent and disintegrant for solid preparations; or solvent, solubilizing agent, suspending agent, isotonic agent, buffering agent, soothing agent and the like for liquid preparations. Furthermore, when necessary, ordinary additives such as preservative, antioxidant, colorant, sweetening agent, adsorbing agent, wetting agent and the like can be also used as appropriate in an appropriate amount.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidant include sulfites, ascorbic acid, α-tocopherol and the like.

For the prophylaxis or treatment of various diseases, the compound of the present invention can also be used together with other medicaments. In the following, a medicament to be used when the compound of the present invention is used together with other drug is referred to as "the combination agent of the present invention".

For example, the compound of the present invention is used as a JAK family inhibitor, an IFN-α inhibitor, an IFN-β inhibitor, an IFN-γ inhibitor, an IL-2 inhibitor, an IL-4 inhibitor, an IL-7 inhibitor, an IL-15 inhibitor, an IL-21 inhibitor, an IL-6 inhibitor, an OSM inhibitor, an IL-10 inhibitor, an IL-19 inhibitor, an IL-20 inhibitor, an IL-22 inhibitor, an IL-28 inhibitor, an IL-29 inhibitor, an IL-12 inhibitor, and/or an IL-23 inhibitor, it can be used in combination with the following drugs.

(1) non-steroidal anti-inflammatory drug (NSAIDs)
(i) Classical NSAIDs
  alcofenac, aceclofenac, sulindac, tolmetin, etodolac, fenoprofen, thiaprofenic acid, meclofenamic acid, meloxicam, tenoxicam, lornoxicam, nabumeton, acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesylate, camostat mesylate, ulinastatin, colchicine, probenecid, sulfinpyrazone, benzbromarone, allopurinol, sodium aurothiomalate, hyaluronate sodium, sodium salicylate, morphine hydrochloride, salicylic acid, atropine, scopolamine, morphine, pethidine, levorphanol, oxymorphone or a salt thereof and the like.
(ii) cyclooxygenase inhibitor (COX-1 selective inhibitor COX-2 selective inhibitor etc.)
  salicylic acid derivatives (e.g., celecoxib, aspirin), etoricoxib, valdecoxib, diclofenac, indomethacin, loxoprofen and the like.
(iii) nitric oxide-releasing NSAIDs.
(iv) JAK inhibitor
  tofacitinib, ruxolitinib and the like.
(2) disease-modifying anti-rheumatic drugs (DMARDs)
(i) Gold preparation
  auranofin and the like.
(ii) penicillamine
  D-penicillamine.
(iii) aminosalicylic acid preparation
  sulfasalazine, mesalamine, olsalazine, balsalazide.
(iv) antimalarial drug
  chloroquine and the like.
(v) pyrimidine synthesis inhibitor
  leflunomide and the like.
(vi) prograf
(3) anti-cytokine drug
(I) protein drug
(i) TNF inhibitor
  etanercept, infliximab, adalimumab, certolizumab pegol, golimumab, PASSTNF-α, soluble TNF-α receptor TNF-α binding protein, anti-TNF-α antibody and the like.
(ii) interleukin-1 inhibitor
  anakinra (interleukin-1 receptor antagonist), soluble interleukin-1 receptor and the like.
(iii) interleukin-6 inhibitor
  tocilizumab (anti-interleukin-6 receptor antibody), anti-interleukin-6 antibody and the like.
(iv) interleukin-10 drug
  interleukin-10 and the like.
(v) interleukin-12/23 inhibitor
  ustekinumab, briakinumab (anti-interleukin-12/23 antibody) and the like.
(II) non-protein drug
(i) MAPK inhibitor
  BMS-582949 and the like.
(ii) gene modulator inhibitor of molecule involved in signal transduction, such as NF-κ, NF-κB, IKK-1, IKK-2, AP-1 and the like, and the like.
(iii) cytokine production inhibitor
iguratimod, tetomilast and the like.
(iv) TNF-α converting enzyme inhibitor
(v) interleukin-1β converting enzyme inhibitor
VX-765 and the like.
(vi) interleukin-6 antagonist
HMPL-004 and the like.
(vii) interleukin-8 inhibitor
IL-8 antagonist, CXCR1 & CXCR2 antagonist, reparixin and the like.
(viii) chemokine antagonist
CCR9 antagonist (CCX-282, CCX-025), MCP-1 antagonist and the like.
(ix) interleukin-2 receptor antagonist
denileukin, diftitox and the like.
(x) therapeutic vaccines
TNF-α vaccine and the like.
(xi) gene therapy drug
gene therapy drugs aiming at promoting the expression of gene having an anti-inflammatory action such as interleukin-4, interleukin-10, soluble interleukin-1 receptor soluble TNF-α receptor and the like.
(xii) antisense compound
ISIS 104838 and the like.
(4) integrin inhibitor
natalizumab, vedolizumab, AJM300, TRK-170, E-6007 and the like.
(5) immunomodulator (immunosuppressant)
methotrexate, cyclophosphamide, MX-68, atiprimod dihydrochloride, BMS-188667, CKD-461, rimexolone, cyclosporine, tacrolimus, gusperimus, azathiopurine, anti-lymphocyte serum, freeze-dried sulfonated normal immunoglobulin, erythropoietin, colony stimulating factor interleukin, interferon and the like.
(6) steroid
dexamethasone, hexestrol, methimazole, betamethasone, triamcinolone, triamcinolone acetonide, fluocinonide, fluocinolone acetonide, predonisolone, methylpredonisolone, cortisone acetate, hydrocortisone, fluorometholone, beclomethasone dipropionate, estriol and the like.
(7) angiotensin converting enzyme inhibitor
enalapril, captopril, ramipril, lisinopril, cilazapril, perindopril and the like.
(8) angiotensin II receptor antagonist
candesartan, cilexetil (TCV-116), valsartan, irbesartan, olmesartan, eprosartan and the like.
(9) diuretic drug
hydrochlorothiazide, spironolactone, furosemide, indapamide, bendrofluazide, cyclopenthiazide and the like.
(10) cardiotonic drug
digoxin, dobutamine and the like.
(11) β receptor antagonist
carvedilol, metoprolol, atenolol and the like.
(12) Ca sensitizer
MCC-135 and the like.
(13) Ca channel antagonist
nifedipine, diltiazem, verapamil and the like.
(14) anti-platelet drug, anticoagulator
heparin, aspirin, warfarin and the like.
(15) HMG-CoA reductase inhibitor
atorvastatin, simvastatin and the like.
(16) contraceptive
(i) sex hormone or derivatives thereof
gestagen or a derivative thereof (progesterone, 17α-hydroxy progesterone, medroxyprogesterone, medroxyprogesterone acetate, norethisterone, norethisterone enanthate, norethindrone, norethindrone acetate, norethynodrel, levonorgestrel, norgestrel, ethynodiol diacetate, desogestrel, norgestimate, gestodene, progestin, etonogestrel, drospirenone, dienogest, trimegestone, nestorone, chlormadinone acetate, mifepristone, nomegestrol acetate, Org-30659, TX-525, EMM-310525) or a combination agent of a gestagen or a derivative thereof and an estrogen or a derivative thereof (estradiol, estradiol benzoate, estradiol cypionate, estradiol dipropionate, estradiol enanthate, estradiol hexahydrobenzoate, estradiol phenylpropionate, estradiol undecanoate, estradiol valerate, estrone, ethinylestradiol, mestranol) and the like.
(ii) antiestrogen
ormeloxifene, mifepristone, Org-33628 and the like.
(iii) spermatocide
ushercell and the like.
(17) others
(i) T cell inhibitors
(ii) inosine monophosphate dehydrogenase (IMPDH) inhibitor
mycophenolate mofetil and the like.
(iii) adhesion molecule inhibitor
ISIS-2302, selectin inhibitor ELAM-1, VCAM-1, ICAM-1 and the like.
(iv) thalidomide
(v) cathepsin inhibitor
(vi) matrix metalloprotease (MMPs) inhibitor
V-85546 and the like.
(vii) glucose-6-phosphate dehydrogenase inhibitor
(viii) Dihydroorotate dehydrogenase (DHODH) inhibitor
(ix) phosphodiesterase IV (PDE IV) inhibitor
roflumilast, CG-1088 and the like.
(x) phospholipase $A_2$ inhibitor
(xi) iNOS inhibitor
VAS-203 and the like.
(xii) microtubule stimulating drug
paclitaxel and the like.
(xiii) microtuble inhibitor
reumacon and the like.
(xiv) MHC class II antagonist
(xv) prostacyclin agonist
iloprost and the like.
(xvi) CD4 antagonist
zanolimumab and the like.
(xvii) CD23 antagonist
(xviii) LTB4 receptor antagonist
DW-1305 and the like.
(xix) 5-lipoxygenase inhibitor
zileuton and the like.
(xx) cholinesterase inhibitor
galanthamine and the like.
(xxi) tyrosine kinase inhibitor
Tyk2 inhibitor (WO2010142752) and the like.
(xxii) cathepsin B inhibitor
(xxvii) adenosine deaminase inhibitor
pentostatin and the like.
(xxiv) osteogenesis stimulator
(xxv) dipeptidylpeptidase inhibitor
(xxvi) collagen agonist
(xxvii) capsaicin cream
(xxviii) hyaluronic acid derivative
synvisc (hylan G-F 20), orthovisc and the like.
(xxii) glucosamine sulfate
(xxx) amiprilose (xxxi) CD-20 inhibitor
  rituximab, ibritumomab, tositumomab, ofatumumab and the like.
(xxxii) BAFF inhibitor
  belimumab, tabalumab, atacicept, A-623 and the like.
(xxxiii) CD52 inhibitor
  alemtuzumab and the like.
(xxxiv) IL-17 inhibitor
  secukinumab (AIN-457), LY-2439821, AMG827 and the like Other concomitant drugs besides the above-mentioned include for example, antibacterial agent, antifungal agent, antiprotozoal agent, antibiotic, antitussive and expectorant drug, sedative, anesthetic, antiulcer drug, antiarrhythmic agent, hypotensive diuretic drug, anticoagulant, tranquilizer, antipsychotic, antitumor drug, hypolipidemic drug, muscle relaxant, antiepileptic drug, antidepressant, antiallergic drug, cardiac stimulants, therapeutic drug for arrhythmia, vasodilator, vasoconstrictor, hypotensive diuretic, therapeutic drug for diabetes, antinarcotic, vitamin, vitamin derivative, antiasthmatic, therapeutic agent for pollakisuria/anischuria, antipruritic drug, therapeutic agent for atopic dermatitis, therapeutic agent for allergic rhinitis, hypertensor, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Specific examples thereof include the following.

(1) Antibacterial agent
(i) sulfa drug
  sulfamethizole, sulfisoxazole, sulfamonomethoxine, sulfamethizole, salazosulfapyridine, silver sulfadiazine and the like.
(ii) quinolone antibacterial agent
  nalidixic acid, pipemidic acid trihydrate, enoxacin, norfloxacin, ofloxacin, tosufloxacin tosylate, ciprofloxacin hydrochloride, lomefloxacin hydrochloride, sparfloxacin, fleroxacin and the like.
(iii) antiphthisic
  isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.
(iv) antiacidfast bacterium drug
  diaphenylsulfone, rifampicin and the like.
(v) antiviral drug
  idoxuridine, acyclovir, vidarabine, gancyclovir and the like.
(vi) anti-HIV agent
  zidovudine, didanosine, zalcitabine, indinavir sulfate ethanolate, ritonavir and the like.
(vii) antispirochetele
(viii) antibiotic
  tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cephalothin, cephapirin, cephaloridine, cefaclor, cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt a salt thereof, griseofulvin, lankacidin-group [Journal of Antibiotics (J. Antibiotics), 38, 877-885 (1985)], azole compound [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxyl)phenyl]-3(2H,4H)-1,2,4-triazolone, fluconazole, itraconazole and the like] and the like.

(2) antifungal agent
(i) polyethylene antibiotic (e.g., amphotericin B, nystatin, trichomycin)
(ii) griseofulvin, pyrrolnitrin and the like
(iii) cytosine metabolism antagonist (e.g., flucytosine)
(iv) imidazole derivative (e.g., econazole, clotrimazole, miconazole nitrate, bifonazole, croconazole)
(v) triazole derivative (e.g., fluconazole, itraconazole)
(vi) thiocarbamic acid derivative (e.g., trinaphthol) and the like.

(3) antiprotozoal agent
  metronidazole, tinidazole, diethylcarbamazine citrate, quinine hydrochloride, quinine sulfate and the like.

(4) antitussive and expectorant drug
  ephedrine hydrochloride, noscapine hydrochloride, codeine phosphate, dihydrocodeine phosphate, isoproterenol hydrochloride, ephedrine hydrochloride, methylephedrine hydrochloride, noscapine hydrochloride, alloclamide, chlophedianol, picoperidamine, cloperastine, protokylol, isoproterenol, salbutamol, terputaline, oxypetebanol, morphine hydrochloride, dextropethorfan hydrobromide, oxycodone hydrochloride, dimorphan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.

(5) sedative
  chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(6) anesthetic
(6-1) local anesthetic
  cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine and the like.
(6-2) general anesthetic
(i) inhalation anesthetic (e.g., ether, halothane, nitrous oxide, isoflurane, enflurane),
(ii) intravenous anesthetic (e.g., ketamine hydrochloride, droperidol, thiopental sodium, thiamylal sodium, pentobarbital) and the like.

(7) antiulcer drug
  histidine hydrochloride, lansoprazole, metoclopramide, pirenzepine, cimetidine, ranitidine, famotidine, urogastrine, oxethazaine, proglumide, omeprazole, sucralfate, sulpiride, cetraxate, gefarnate, aldioxa, teprenone, prostaglandin and the like.

(8) antiarrhythmic agent
(i) sodium channel blocker (e.g., quinidine, procainamide, disopyramide, ajmaline, lidocaine, mexiletine, phenytoin),
(ii) β-blocker (e.g., propranolol, alprenolol, bufetolol hydrochloride, oxprenolol, atenolol, acebutolol, metoprolol, bisoprolol, pindolol, carteolol, arotinolol hydrochloride),
(iii) potassium channel blocker (e.g., amiodarone),
(iv) calcium channel blocker (e.g., verapamil, diltiazem) and the like.

(9) hypotensive diuretic drug hexamethonium bromide, clonidine hydrochloride, hydrochlorothiazide, trichlormethiazide, furosemide, ethacrynic acid, bumetanide, mefruside, azosemide, spironolactone, potassium canrenoate, triamterene, amiloride, acetazolamide, D-mannitol, isosorbide, aminophylline and the like.

(10) anticoagulant heparin sodium, sodium citrate, activated protein C, tissue factor pathway inhibitor antithrombin III, dalteparin sodium, warfarin potassium, argatroban, gabexate, sodium citrate, ozagrel sodium, ethyl icosapentate, beraprost sodium, alprostadil, ticlopidine hydrochloride, pentoxifylline, dipyridamole, tisokinase, urokinase, streptokinase and the like.

(11) tranquilizer diazepam, lorazepam, oxazepam, chlordiazepoxide, medazepam, oxazolam, cloxazolam, clotiazepam, bromazepam, etizolam, fludiazepam, hydroxyzine and the like.

(12) antipsychotic chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine and the like.

(13) antitumor drug

6-O—(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, zusulfan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuprorelin acetate, buserelin acetate and the like.

(14) hypolipidemic drug clofibrate, ethyl 2-chloro-3-[4-(2-methyl-2-phenylpropoxy)phenyl]propionate [Chem. Pharm. Bull, 38, 2792-2796 (1990)], pravastatin, simvastatin, probucol, bezafibrate, clinofibrate, nicomol, cholestyramine, dextran sulfate sodium and the like.

(15) muscle relaxant pridinol, tubocurarine, pancuronium, tolperisone hydrochloride, chlorphenesin carbamate, baclofen, chlormezanone, mephenesin, chlorzoxazone, eperisone, tizanidine and the like.

(16) antiepileptic drug phenytoin, ethosuximide, acetazolamide, chlordiazepoxide, tripethadione, carbamazepine, phenobarbital, primidone, sulthiame, sodium valproate, clonazepam, diazepam, nitrazepam and the like.

(17) antidepressant imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride and the like.

(18) antiallergic drug diphenhydramine, chlorpheniramine, tripelennamine, metodilamine, clemizole, diphenylpyraline, methoxyphenamine, sodium cromoglicate, tranilast, repirinast, amlexanox, ibudilast, ketotifen, terfenadine, mequitazine, azelastine hydrochloride, epinastine, ozagrel hydrochloride, pranlukast hydrate, seratrodast and the like.

(19) cardiac stimulants trans-π-oxocamphor, terephyllol, aminophylline, etilefrine, dopamine, dobutamine, denopamine, aminophylline, vesinarine, amrinone, pimobendan, ubidecarenone, digitoxin, digoxin, methyldigoxin, lanatoside C, G-strophanthin and the like.

(20) vasodilator oxyfedrine, diltiazem, tolazoline, hexobendine, bamethan, clonidine, methyldopa, guanabenz and the like.

(21) vasoconstrictor dopamine, dobutamine denopamine and the like.

(22) hypotensive diuretic hexamethonium bromide, pentolinium, mecamylamine, ecarazine, clonidine, diltiazem, nifedipine and the like.

(23) therapeutic drug for diabetes tolbutamide, chlorpropamide, acetohexamide, glibenclamide, tolazamide, acarbose, epalrestat, troglitazone, glucagon, glymidine, glipuzide, phenformin, buformin, metformin and the like.

(24) antinarcotic levallorphan, nalorphine, naloxone or a salt thereof and the like.

(25) liposoluble vitamins (i) vitamin A: vitamin $A_1$, vitamin $A_2$ and retinol palmitate
(ii) vitamin D: vitamin $D_1$, $D_2$, $D_3$, $D_4$ and $D_5$
(iii) vitamin E: α-tocopherol, β-tocopherol, γ-tocopherol, δ-tocopherol, dl-α-tocopherol nicotinate
(iv) vitamin K: vitamin $K_1$, $K_2$, $K_3$ and $K_4$
(v) folic acid (vitamin M) and the like.

(26) vitamin derivative various derivatives of vitamins, for example, vitamin $D_3$ derivatives such as 5,6-trans-cholecalciferol, 2,5-hydroxycholecalciferol, 1-α-hydroxycholecalciferol and the like, vitamin $D_2$ derivatives such as 5,6-trans-ergocalciferol and the like, and the like.

(27) antiasthmatic isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranlkast hydrate, seratrodast, dexamethasone, prednisolone, hydrocortisone, hydrocortisone sodium succinate, beclometasone dipropionate and the like.

(28) therapeutic agent for pollakisuria/anischuria flavoxate hydrochloride and the like.

(29) therapeutic agent for atopic dermatitis sodium cromoglicate and the like.

(30) therapeutic agent for allergic rhinitis sodium cromoglicate, chlorpheniramine maleate, alimemazine tartrate, clemastine fumarate, homochlorcyclizine hydrochloride, fexofenadine, mequitazine and the like.

(31) hypertensor dopamine, dobutamine, denopamine, digitoxin, digoxin, methyldigoxin, lanatoside C, G-strophanthin and the like.

(32) others hydroxycam, diacerein, megestrol acetate, nicergoline, prostaglandins and the like.

For combined use, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:
(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 100% by weight, preferably about 0.1 to 50% by weight, further preferably about 0.5 to 20% by weight, of the entire preparation.

While the content of the additive such as a carrier and the like in the combination agent of the present invention varies depending on the form of a preparation, it is generally about 1 to 99.99% by weight, preferably about 10 to 90% by weight, based on the preparation.

When the compound of the present invention and the concomitant drug are separately prepared, the same content may be adopted.

The dose of the combination agent varies depending on the kind of the compound of the present invention, administration route, symptom, age of patients and the like. For example, for oral administration to patients (body weight about 60 kg) with rheumatoid arthritis, psoriasis, inflammatory bowel disease, Sjogren's syndrome, Behcet's disease, multiple sclerosis, systemic lupus erythematosus, leukemia, uterine leiomyosarcoma, prostate cancer, multiple myeloma, cachexia, myelofibrosis and the like, about 0.1 mg/kg body weight-about 50 mg/kg body weight, preferably about 1 mg/kg body weight-30 mg/kg body weight, of compound (I) can be administered once to several portions per day.

The dose of the pharmaceutical composition of the present invention as a sustained-release preparation varies depending on the kind and content of compound (I), dosage form, period of sustained drug release, subject animal of administration (e.g., mammals such as mouse, rat, hamster, guinea pig, rabbit, cat, dog, bovine, horse, swine, sheep, monkey, human etc.), and administration object. For example, for application by parenteral administration, about 0.1 to about 100 mg of compound (I) needs to be released from the administered preparation per 1 week.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times, divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example.

EXAMPLES

The present invention is explained in detail in the following by referring to Reference example, Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, "basic" means use of aminopropylsilane-bound silica gel. The ratios of elution solvents are volume mixing ratios, unless otherwise specified.

In Reference example and Examples, the following abbreviations are used.
DMF: N,N-dimethylformamide
DMA: N,N-dimethylacetamide
THF: tetrahydrofuran
EDCI: 1-ethyl-3-(3-dimethylaminopropyl)carbodiimide
DMSO: dimethyl sulfoxide
HOBt: 1-hydroxybenzotriazole
DIEA: N,N-diisopropylethylamine
DME: 1,2-dimethoxyethane
TMEDA: N,N,N',N'-tetramethylethylene diamine
NBS: N-bromosuccinimide
N: normal concentration
M: mol concentration
$^1$H NMR (protone nuclear magnetic resonance spectrum) was measured by Fourier-transform type NMR. For the analysis, ACD/SpecManager (trade name) and the like were used. Peaks with very mild protons such as a hydroxy group, an amino group and the like are not described.

In the measurement of $^1$H NMR, the following abbreviations are used.

s: singlet, d: doublet, dd: double doublet, dt: double triplet, t: triplet, q: quartet, m: multiplet, brs: broad singlet, quin: quintet, J: coupling constant, Hz: Hertz.

MS (mass spectrum) was measured by LC/MS (liquid chromatography mass spectrometer). As ionization method, ESI (Electro Spray Ionization) method or APCI (Atomospheric Pressure Chemical Ionization) method was used. The data indicates theoretical value and measured value (found).

Example 1

1-cyclopentyl-3-phenyl-1,5-dihydro-4H-pyrrolo[3,2-c]pyridin-4-one

A) 1-cyclopentyl-1H-pyrrole-2-carbaldehyde

To a solution of 1H-pyrrole-2-carbaldehyde (12.0 g) in DMSO (252 mL) was added sodium hydride (55% dispersion in mineral oil, 8.26 g) at 0° C., and the mixture was stirred for 30 min. To the reaction mixture was added bromocyclopentane (22.6 g) at 0° C., and the mixture was stirred overnight at room temperature. The reaction mixture was diluted with ethyl acetate (500 mL), and washed with water and saturated brine. The organic layer was dried over anhydrous magnesium sulfate, filtered, and concentrated under reduced pressure. The obtained residue was purified by silica gel column chromatography (hexane/ethyl acetate) to give the title compound (9.34 g).

$^1$H NMR (400 MHz, CDCl$_3$) δ 1.70-1.84 (6H, m), 2.15-2.34 (2H, m), 5.45-5.52 (1H, m), 6.23 (1H, dd, J=4.2, 2.6 Hz), 6.92 (1H, dd, J=4.2, 1.8 Hz), 7.12-7.13 (1H, m), 9.54 (1H, d, J=0.8 Hz).

B) (2E)-3-(1-cyclopentyl-1H-pyrrol-2-yl)acrylic acid

A solution of 1-cyclopentyl-1H-pyrrole-2-carbaldehyde (10.4 g), malonic acid (20.0 g) and piperidine (1.71 mL) in pyridine (64.0 mL) was refluxed overnight. The obtained reaction mixture was allowed to be cooled to room temperature, and then slowly poured into ice and 6N hydrochloric acid (300 mL). The mixture was extracted with dichloromethane, and the organic layer was dried over anhydrous magnesium sulfate, filtered, and concentrated under reduced pressure. The obtained residue was purified by silica gel column chromatography (hexane/ethyl acetate) to give the title compound (6.74 g).

$^1$H NMR (400 MHz, CDCl$_3$) δ 1.71-1.88 (6H, m), 2.14-2.20 (2H, m), 4.64-4.71 (1H, m), 6.17 (1H, d, J=15.6 Hz), 6.22 (1H, t, J=3.4 Hz), 6.73-6.75 (1H, m), 6.93-6.94 (1H, m), 7.78 (1H, d, J=15.2 Hz).

* CO$_2$H peak was not observed.

C) 1-cyclopentyl-1,5-dihydro-4H-pyrrolo[3,2-c]pyridin-4-one

To a solution of (2E)-3-(1-cyclopentyl-1H-pyrrol-2-yl)acrylic acid (6.74 g) and triethylamine (10.5 mL) in acetone (313 mL) was added dropwise a solution of ethyl chloroformate (8.63 mL) in acetone (193 mL) over 1 hr or more at 0° C. The mixture was stirred at 0° C. for 4 hr, and to the reaction mixture was added dropwise an aqueous solution (51.6 mL) of sodium azide (4.27 g) over 30 min or more. The reaction mixture was stirred at 0° C. for 2 hr, and poured into ice water (800 mL). The mixture was extracted with dichloromethane (400 mL, three times), and the organic layers were combined, and dried over anhydrous magnesium sulfate. The magnesium sulfate was filtered, and the filtrate was concentrated under reduced pressure to give an acyl azide compound.

To a solution of the acyl azide compound in dichloromethane (74.6 mL) was added dropwise a mixture of diphenyl ether (51.6 mL) and tributylamine (9.21 mL), and the reaction mixture was heated at 205° C. for 2 hr. The reaction mixture was allowed to be cooled to room temperature, and hexane was added thereto. The white precipitate was collected by filtration, and purified by silica gel column chromatography (hexane/ethyl acetate to ethyl acetate/methanol) to give the title compound (3.40 g).

$^1$H NMR (400 MHz, CDCl$_3$) δ 1.73-1.96 (6H, m), 2.18-2.25 (2H, m), 4.61-4.68 (1H, m), 6.47 (1H, d, J=7.2 Hz), 6.83 (1H, d, J=3.2 Hz), 7.00 (1H, d, J=3.2 Hz), 7.14-7.17 (1H, m), 11.75 (1H, brs).

D) 3-bromo-1-cyclopentyl-1,5-dihydro-4H-pyrrolo[3,2-c]pyridin-4-one

To a solution of 1-cyclopentyl-1,5-dihydro-4H-pyrrolo[3,2-c]pyridin-4-one (3.40 g) in DMF (42.0 mL) was added trimethylsilyl N-(trimethylsilyl)ethanimidate (7.52 g) at room temperature, and the mixture was stirred at 40° C. for 3 hr. The reaction mixture was allowed to be cooled to room temperature, and NBS (3.59 g) was added thereto at room temperature. The reaction mixture was stirred overnight at room temperature, water was added thereto, and the mixture was stirred at room temperature for 2 hr. The white precipitate was collected by filtration, and dried under reduced pressure to give the title compound (3.28 g).

$^1$H NMR (400 MHz, CDCl$_3$) δ 1.76-1.92 (6H, m), 2.16-2.21 (2H, m), 4.57-4.64 (1H, m), 6.40 (1H, d, J=7.6 Hz), 6.97 (1H, s), 7.12-7.15 (1H, m), 11.21 (1H, brs).

E) 1-cyclopentyl-3-phenyl-1,5-dihydro-4H-pyrrolo[3,2-c]pyridin-4-one

E-1) To a solution of 3-bromo-1-cyclopentyl-1,5-dihydro-4H-pyrrolo[3,2-c]pyridin-4-one (3.28 g) in DMF (233 mL) was added DIEA (2.65 mL) at room temperature, and (2-(chloromethoxy)ethyl) (trimethyl)silane (4.14 mL) was slowly added thereto. The reaction mixture was stirred overnight at room temperature, diluted with ethyl acetate, and washed with water and saturated brine. The organic layer was dried over anhydrous magnesium sulfate, filtered, and concentrated under reduced pressure. The obtained residue was purified by silica gel column chromatography (hexane/ethyl acetate) to give an oil (2.40 g).

$^1$H NMR (400 MHz, CDCl$_3$) δ −0.01 (9H, s), 0.91-0.95 (2H, m), 1.74-1.92 (6H, m), 2.15-2.22 (2H, m), 3.62-3.66 (2H, m), 4.55-4.61 (1H, m), 5.41 (2H, s), 6.37 (1H, d, J=7.6 Hz), 6.94 (1H, s), 7.16 (1H, d, J=7.2 Hz).

E-2) To a mixture of the obtained oil (474 mg) in DME (15.3 mL)/water (7.68 mL) were added 4,4,5,5-tetramethyl-2-phenyl-1,3,2-dioxaborolane (940 mg), tetrakis(triphenylphosphine)palladium(0) (133 mg) and potassium carbonate (637 mg). The reaction mixture was stirred under microwave irradiation at 100° C. for 10 min. The reaction mixture was diluted with water, and the mixture was extracted with ethyl acetate (10 mL, three times). The organic layers were combined, washed with saturated brine, dried over anhydrous magnesium sulfate, filtered, and concentrated under reduced pressure. The obtained residue was purified by silica gel column chromatography (hexane/ethyl acetate) to give a solid (384 mg).

$^1$H NMR (400 MHz, CDCl$_3$) δ −0.02 (9H, s), 0.91-0.95 (2H, m), 1.77-1.97 (6H, m), 2.17-2.27 (2H, m), 3.61-3.65 (2H, m), 4.62-4.69 (1H, m), 5.44 (2H, s), 6.44 (1H, d, J=7.2 Hz), 7.02 (1H, s), 7.21 (1H, d, J=7.6 Hz), 7.23-7.27 (1H, m), 7.36-7.40 (2H, m), 7.72-7.75 (2H, m).

E-3) To a solution of the obtained solid (384 mg) in trifluoroacetic acid (9.89 mL) was added triethylsilane (0.450 mL) at 0° C., and the mixture was stirred at room temperature for 1 hr. The reaction mixture was concentrated under reduced pressure, and the residue was dissolved in acetonitrile (7.00 mL). To the solution was added 28% aqueous ammonia solution (0.7 mL) at 0° C., and the mixture was stirred at room temperature for 2 hr. The white precipitate was collected by filtration, and dried under reduced pressure to give the title compound (135 mg).

$^1$H NMR (400 MHz, DMSO-d$_6$) δ 1.68-1.73 (2H, m), 1.83-1.92 (4H, m), 2.10-2.17 (2H, m), 4.75-4.82 (1H, m), 6.59 (1H, d, J=7.2 Hz), 7.05 (1H, t, J=6.4 Hz), 7.18 (1H, t, J=7.4 Hz), 7.31 (2H, t, J=7.6 Hz), 7.43 (1H, s), 7.84-7.86 (2H, m), 10.79 (1H, d, J=4.0 Hz).

Example 2

4-(1-cyclopentyl-4-oxo-4,5-dihydro-1H-pyrrolo[3,2-c]pyridin-3-yl)benzenesulfonamide To a mixture of the oil (500 mg) obtained in Step E-1 of Example 1 in DME (16.2 mL)/water (8.10 mL) were added 4-(4,4,5,5-tetramethyl-1,3,2-dioxaborolan-2-yl)benzenesulfonamide (1.37 g), tetrakis(triphenylphosphine)palladium(0) (140 mg) and potassium carbonate (672 mg). The reaction mixture was stirred under microwave irradiation at 100° C. for 10 min. The reaction mixture was diluted with water, and the mixture was extracted with ethyl acetate (10 mL, three times). The organic layers were combined, washed with saturated brine, dried over anhydrous magnesium sulfate, filtered, and concentrated under reduced pressure. The obtained residue was purified by silica gel column chromatography (hexane/ethyl acetate) to give a powder (387 mg).

$^1$H NMR (400 MHz, DMSO-d$_6$) δ −0.03 (9H, s), 0.84-0.91 (2H, m), 1.65-1.91 (6H, m), 2.12-2.18 (2H, m), 3.57 (2H, t, J=8.0 Hz), 4.79-4.86 (1H, H), 5.33 (2H, s), 6.74 (1H, d, J=7.6 Hz), 7.31 (2H, brs), 7.44 (1H, d, J=7.2 Hz), 7.62 (1H, s), 7.73-7.75 (2H, m), 7.98-8.00 (2H, m).

To a solution of the obtained powder (337 mg) in trifluoroacetic acid (7.27 mL) was added triethylsilane (0.331 mL) at 0° C., and the mixture was stirred at room temperature for 1 hr. The reaction mixture was concentrated under reduced pressure, and the residue was dissolved in acetonitrile (5.00 mL). 28% Aqueous ammonia solution (0.5 mL) was added thereto at 0° C., and the mixture was stirred at room temperature for 2 hr. The white precipitate was collected by filtration, and dried under reduced pressure to give the title compound (192 mg).

$^1$H NMR (400 MHz, DMSO-d$_6$) δ 1.69-1.72 (2H, m), 1.84-1.93 (4H, m), 2.11-2.18 (2H, m), 4.77-4.84 (1H, m), 6.63 (1H, d, J=6.8 Hz), 7.01 (1H, t, J=6.4 Hz), 7.30 (2H, brs), 7.62 (1H, s), 7.73-7.75 (2H, m), 8.06-8.09 (2H, m), 10.89 (1H, d, J=6.0 Hz).

Example 3 methyl 4-(1-cyclopentyl-4-oxo-4,5-dihydro-1H-pyrrolo[3,2-c]pyridin-3-yl)thiophene-2-carboxylate To a solution of the oil (100 mg) obtained in Step E-1 of Example 1 in DMF (2 mL)/water (0.30 mL) were added methyl 4-(4,4,5,5-tetramethyl-1,3,2-dioxaborolan-2-yl)thiophene-2-carboxylate (98.0 mg), tetrakis(triphenylphosphine)palladium(0) (28.0 mg) and potassium carbonate (34.0 mg). The reaction mixture was stirred under microwave irradiation at 130° C. for 1 hr. The reaction mixture was diluted with water, and the mixture was extracted with ethyl acetate. The organic layer was washed with saturated brine, dried over anhydrous magnesium sulfate, filtered, and concentrated under reduced pressure. The obtained residue was purified by silica gel column chromatography (hexane/ethyl acetate) to give a powder (88.5 mg).

MS (ESI+): [M+H]$^+$ 473.1.

MS (ESI+). found: 473.3.

The obtained powder (8.9 mg) and triethylsilane (0.00902 mL) were dissolved in trifluoroacetic acid (1 mL) at 0° C., and the solution was stirred at room temperature for 2 hr. The reaction mixture was concentrated under reduced pressure, and the residue was extracted with ethyl acetate and saturated aqueous sodium hydrogencarbonate solution. The organic layer was washed with saturated brine, dried over anhydrous magnesium sulfate, filtered, and concentrated under reduced pressure. The obtained residue was crystallized from ethyl acetate to give the title compound (5.5 mg).

$^1$H NMR (300 MHz, DMSO-d$_6$) δ 1.61-1.75 (2H, m), 1.79-1.94 (4H, m), 2.06-2.19 (2H, m), 3.84 (3H, s), 4.68-4.88 (1H, m), 6.59 (1H, d, J=7.2 Hz), 7.06 (1H, t, J=6.6 Hz), 7.82 (1H, s), 8.46 (1H, s), 8.87 (1H, s), 10.86 (1H, d, J=5.3 Hz).

MS (ESI+): [M+H]$^+$ 343.1.

MS (ESI+). found: 343.2.

Example 4

4-(1-cyclopentyl-4-oxo-4,5-dihydro-1H-pyrrolo[3,2-c]pyridin-3-yl)thiophene-2-carboxamide A) 4-(1-cyclopentyl-4-oxo-4,5-dihydro-1H-pyrrolo[3,2-c]pyridin-3-yl)thiophene-2-carboxylic acid To a solution of methyl 4-(1-cyclopentyl-4-oxo-4,5-dihydro-1H-pyrrolo[3,2-c]pyridin-3-yl)thiophene-2-carboxylate (27.0 mg) obtained in Example 3 in a mixed solvent of methanol (2 mL)/THF (2 mL)/water (2 mL) was added 8N aqueous sodium hydroxide solution (0.025 mL) at 0° C. The reaction mixture was stirred at 90° C. for 1 hr. The reaction mixture was diluted with water, and the mixture was extracted with ethyl acetate. The organic layer was washed with 0.1N hydrochloric acid, water and saturated brine, dried over anhydrous magnesium sulfate, filtered, and concentrated under reduced pressure to give the title compound (26.0 mg).

$^1$H NMR (300 MHz, DMSO-d$_6$) δ 1.60-1.76 (2H, m), 1.79-1.96 (4H, m), 2.04-2.21 (2H, m), 4.69-4.85 (1H, m), 6.59 (1H, d, J=6.8 Hz), 6.99-7.12 (1H, m), 7.77 (1H, s), 8.32 (1H, s), 8.77 (1H, d, J=1.1 Hz), 10.85 (1H, d, J=5.7 Hz), 12.98 (1H, brs).

B) 4-(1-cyclopentyl-4-oxo-4,5-dihydro-1H-pyrrolo[3,2-c]pyridin-3-yl)thiophene-2-carboxamide To a solution of 4-(1-cyclopentyl-4-oxo-4,5-dihydro-1H-pyrrolo[3,2-c]pyridin-3-yl)thiophene-2-carboxylic acid (62.5 mg) in DMA (2 mL) were added EDCI hydrochloride (43.8 mg) and HOBt ammonium salt (34.7 mg) at room temperature, and the mixture was stirred overnight at room temperature. The reaction mixture was diluted with water, the mixture was extracted with ethyl acetate, and the organic layer was washed with saturated brine, dried over anhydrous magnesium sulfate, filtered, and concentrated under reduced pressure. The obtained residue was purified by silica gel column chromatography (basic silica gel, ethyl acetate to ethyl acetate/methanol) to give the title compound (55.9 mg).

$^1$H NMR (300 MHz, DMSO-d$_6$) δ 1.66-1.92 (6H, m), 2.08-2.23 (2H, m), 4.80 (1H, quin, J=6.9 Hz), 6.59 (1H, d, J=6.8 Hz), 7.06 (1H, dd, J=7.0, 6.2 Hz), 7.34 (1H, brs), 7.48 (1H, s), 7.78 (1H, brs), 8.19 (1H, d, J=1.5 Hz), 8.66 (1H, d, J=1.5 Hz), 10.84 (1H, d, J=5.7 Hz).

MS (ESI+): [M+H]$^+$ 328.1.

MS (ESI+). found: 328.1.

Example 5

1-cyclopentyl-3-(3-thienyl)-1,5-dihydro-4H-pyrrolo [3,2-c]pyridin-4-one

To a solution of the oil (30.0 mg) obtained in Step E-1 of Example 1 in DMF (2 mL)/water (0.30 mL) were added 3-thienylboronic acid (98.0 mg), tetrakis(triphenylphosphine)palladium(0) (8.43 mg) and potassium carbonate (10.1 mg). The reaction mixture was stirred under microwave irradiation at 130° C. for 30 min. The reaction mixture was diluted with water, and the mixture was extracted with ethyl acetate. The organic layer was washed with saturated brine, dried over anhydrous magnesium sulfate, filtered, and concentrated under reduced pressure. The obtained residue was purified by silica gel column chromatography (hexane/ethyl acetate) to give a powder (23.4 mg).

$^1$H NMR (300 MHz, DMSO-d$_6$) δ −0.04 (9H, s), 0.81-0.92 (2H, m), 1.64-1.75 (2H, m), 1.80-1.93 (4H, m), 2.06-2.19 (2H, m), 3.53-3.62 (2H, m), 4.78 (1H, quin, J=7.3 Hz), 5.33 (2H, s), 6.68 (1H, d, J=7.6 Hz), 7.38 (1H, d, J=7.6 Hz), 7.45 (1H, dd, J=4.9, 3.0 Hz), 7.61 (1H, s), 7.63-7.69 (1H, m), 8.38 (1H, dd, J=3.0, 1.1 Hz).

The obtained powder (21.0 mg) and triethylsilane (0.024 mL) were dissolved in trifluoroacetic acid (2 mL) at 0° C., and the solution was stirred at room temperature for 2 hr. The reaction mixture was concentrated under reduced pressure, and the residue was extracted with ethyl acetate and saturated aqueous sodium hydrogencarbonate solution. The organic layer was washed with saturated brine, dried over anhydrous magnesium sulfate, filtered, and concentrated under reduced pressure. The obtained residue was purified by silica gel column chromatography (basic silica gel, ethyl acetate to ethyl acetate/methanol) to give the title compound (13.0 mg).

$^1$H NMR (300 MHz, DMSO-d$_6$) δ 1.61-1.76 (2H, m), 1.79-1.95 (4H, m), 2.05-2.20 (2H, m), 4.76 (1H, quin, J=7.3 Hz), 6.57 (1H, d, J=7.2 Hz), 7.00-7.09 (1H, m), 7.44 (1H, dd, J=4.9, 3.0 Hz), 7.60 (1H, s), 7.68 (1H, dd, J=5.3, 1.1 Hz), 8.50 (1H, dd, J=3.0, 1.1 Hz), 10.78 (1H, d, J=4.9 Hz).

Example 6

4-(1-cyclohexyl-4-oxo-4,5-dihydro-1H-pyrazolo[4,3-c]pyridin-3-yl)benzenesulfonamide A) 2-fluoro-3-iodopyridine To a solution of diisopropylamine (21.5 mL) in THF (300 mL) was added 1.6M n-butyllithium hexane solution (97 mL) under argon atmosphere at −20° C., and the mixture was stirred under argon atmosphere at 0° C. for 30 min. To the reaction mixture was added a solution of 2-fluoropyridine (15.0 g) in THF (20 mL) at −78° C., and the mixture was stirred under argon atmosphere at −78° C. for 3 hr. To the reaction mixture was added a solution of iodine (39.2 g) in THF (80 mL) at −78° C., and the mixture was stirred under argon atmosphere at −78° C. for 30 min. To the reaction mixture was added water, and then saturated aqueous sodium thiosulfate solution and saturated aqueous sodium hydrogencarbonate solution were added thereto, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (26.5 g).

$^1$H NMR (300 MHz, CDCl$_3$) δ 6.92-7.01 (1H, m), 8.11-8.23 (2H, m).

B) methyl 4-iodo-2-methoxynicotinate

To a solution of diisopropylamine (10.4 mL) in THF (150 mL) was added 1.6M n-butyllithium hexane solution (46 mL) under argon atmosphere at −10° C., and the mixture was stirred under argon atmosphere at −10° C. for 30 min. To the reaction mixture was slowly added a solution of 2-fluoro-3-iodopyridine (15 g) in THF (100 mL) at −78° C., and the mixture was stirred under argon atmosphere at −78° C. to −60° C. for 3 hr. To the reaction mixture was slowly added methyl chloroformate (7.21 g) at −78° C., and the mixture was stirred under argon atmosphere at −78° C. for 30 min. To the reaction mixture was slowly added a solution of sodium methoxide (3.90 g) in methanol (45 mL) at −78° C., and the mixture was allowed to be warmed to room temperature, and stirred at room temperature for 1 hr. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (10 g).

$^1$H NMR (300 MHz, DMSO-d$_6$) δ 3.86 (3H, s), 3.87 (3H, s), 7.53 (1H, d, J=5.3 Hz), 7.95 (1H, d, J=5.3 Hz).

C) 4-iodo-2-methoxynicotinic acid

To a solution of methyl 4-iodo-2-methoxynicotinate (10 g) in methanol (136 mL) was added 1N aqueous sodium hydroxide solution (136 mL) under ice-cooling, and the mixture was stirred overnight at room temperature. The reaction mixture was concentrated under reduced pressure to evaporate the methanol, and the remaining aqueous solution was washed twice with diethyl ether. The obtained aqueous layer was acidified with 1N hydrochloric acid (about 30 mL), and the mixture was extracted twice with ethyl acetate. The combined organic layers were washed with saturated brine, dried over anhydrous magnesium sulfate, and concentrated under reduced pressure to give the title compound (7.7 g).

$^1$H NMR (300 MHz, DMSO-d$_6$) δ 3.85 (3H, s), 7.49 (1H, d, J=5.3 Hz), 7.89 (1H, d, J=5.7 Hz), 13.59 (1H, brs).

D) N'-cyclohexyl-4-iodo-2-methoxynicotinohydrazide

A solution of 4-iodo-2-methoxynicotinic acid (558 mg), cyclohexyl hydrazine hydrochloride (362 mg), EDCI hydrochloride (575 mg), HOBt (405 mg) and triethylamine (304 mg) in DMF (10 mL) was stirred overnight at room temperature. To the reaction mixture was added water, and the mixture was extracted with ethyl acetate. The organic layer was dried over anhydrous sodium sulfate, and concentrated under reduced pressure. The residue was purified by silica gel column chromatography (ethyl acetate/hexane) to give the title compound (515 mg).

¹H NMR (300 MHz, CDCl₃) δ 1.10-1.40 (5H, m), 1.57-1.69 (1H, m), 1.72-1.85 (2H, m), 1.91-2.02 (2H, m), 2.96-3.09 (1H, m), 3.93 (3H, s), 4.89 (1H, brs), 7.23 (1H, brs), 7.36 (1H, d, J=5.7 Hz), 7.80 (1H, d, J=5.3 Hz).

E) 1-cyclohexyl-4-methoxy-1,2-dihydro-3H-pyrazolo[4,3-c]pyridin-3-one

A solution of N'-cyclohexyl-4-iodo-2-methoxynicotinohydrazide (220 mg), L-proline (13.5 mg), potassium carbonate (162 mg) and copper(I) iodide (11.2 mg) in DMSO (6 mL) was stirred overnight under nitrogen atmosphere at room temperature. To the reaction mixture was added water under ice-cooling, and the mixture was extracted with ethyl acetate. The organic layer was removed, to the obtained aqueous layer was added 1N hydrochloric acid (1.5 mL) under ice-cooling, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (100 mg).
¹H NMR (300 MHz, CDCl₃) δ 1.21-1.55 (3H, m), 1.76 (1H, d, J=11.3 Hz), 1.90-2.01 (6H, m), 4.02-4.19 (1H, m), 4.11 (3H, s), 6.79 (1H, d, J=6.4 Hz), 7.85 (1H, d, J=6.4 Hz), 10.06 (1H, brs).

F) 1-cyclohexyl-4-methoxy-1H-pyrazolo[4,3-c]pyridin-3-yl trifluoromethanesulfonate To a solution of 1-cyclohexyl-4-methoxy-1,2-dihydro-3H-pyrazolo[4,3-c]pyridin-3-one (78 mg) and pyridine (150 mg) in acetonitrile (10 mL) was added trifluoromethanesulfonic anhydride (356 mg), and the mixture was stirred at 0° C. for 30 min, and concentrated under reduced pressure. The residue was purified by silica gel column chromatography (ethyl acetate/hexane) to give the title compound (60 mg).
¹H NMR (300 MHz, CDCl₃) δ 1.18-1.55 (3H, m), 1.75 (1H, d, J=11.3 Hz), 1.82-2.07 (6H, m), 4.10 (3H, s), 4.18-4.31 (1H, m), 6.91 (1H, d, J=6.0 Hz), 7.93 (1H, d, J=6.4 Hz).

G) 4-(1-cyclohexyl-4-methoxy-1H-pyrazolo[4,3-c]pyridin-3-yl)benzenesulfonamide

A solution of 1-cyclohexyl-4-methoxy-1H-pyrazolo[4,3-c]pyridin-3-yl trifluoromethanesulfonate (60 mg), 4-(4,4,5,5-tetramethyl-1,3,2-dioxaborolan-2-yl)benzenesulfonamide (67 mg), tetrakis(triphenylphosphine)palladium(0) (18 mg) and 2M aqueous sodium carbonate solution (0.40 mL) in DME (10 mL) was stirred under nitrogen atmosphere at 100° C. for 3 hr. To the reaction mixture was added water, and the mixture was extracted with ethyl acetate. The organic layer was dried over anhydrous sodium sulfate, and concentrated under reduced pressure. The residue was purified by silica gel column chromatography (ethyl acetate/hexane) to give the title compound (60 mg).
¹H NMR (300 MHz, CDCl₃) δ 1.26-1.60 (3H, m), 1.69-1.85 (1H, m), 1.90-2.18 (6H, m), 4.06 (3H, s), 4.29-4.44 (1H, m), 5.08 (2H, brs), 7.00 (1H, d, J=6.0 Hz), 7.94 (1H, d, J=6.0 Hz), 7.97-8.03 (2H, m), 8.13-8.20 (2H, m).

H) 4-(1-cyclohexyl-4-oxo-4,5-dihydro-1H-pyrazolo[4,3-c]pyridin-3-yl)benzenesulfonamide To a solution of 4-(1-cyclohexyl-4-methoxy-1H-pyrazolo[4,3-c]pyridin-3-yl)benzenesulfonamide (53 mg) in acetonitrile (10 mL) were added sodium iodide (41 mg) and chloro(trimethyl)silane (119 mg), and the mixture was stirred at 60° C. for 20 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (methanol/ethyl acetate) to give the title compound (30 mg).
¹H NMR (300 MHz, DMSO-d₆) δ 1.19-1.36 (1H, m), 1.40-1.59 (2H, m), 1.65-1.77 (1H, m), 1.79-2.01 (6H, m), 4.45-4.58 (1H, m), 6.75 (1H, d, J=7.2 Hz), 7.22-7.29 (1H, m), 7.39 (2H, brs), 7.86 (2H, d, J=8.7 Hz), 8.49 (2H, d, J=8.3 Hz), 11.14 (1H, d, J=5.7 Hz).
MS (ESI+): [M+H]⁺ 373.1.
MS (ESI+). found: 373.3.

Example 7 methyl 4-(4-oxo-1-(pentan-3-yl)-4,5-dihydro-1H-pyrrolo[3,2-c]pyridin-3-yl)thiophene-2-carboxylate A) 1-((2-(trimethylsilyl)ethoxy)methyl)-1H-pyrrole-2-carbaldehyde To a solution of 1H-pyrrole-2-carbaldehyde (14.27 g) in DMF (143 mL) was added sodium hydride (60% dispersion in mineral oil, 6.6 g) at 0° C., and the mixture was stirred under argon atmosphere at 0° C. for 2 hr. To the reaction mixture was added a solution of (2-(chloromethoxy)ethyl)(trimethyl)silane (27.5 g) in DMF (20 mL), and the mixture was stirred at room temperature for 18 hr. The reaction mixture was added to water, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (30 g).
¹H NMR (300 MHz, CDCl₃) δ −0.03-0.02 (9H, m), 0.88-0.98 (2H, m), 3.52-3.62 (2H, m), 5.75 (2H, s), 6.34 (1H, dd, J=4.2, 2.6 Hz), 7.02 (1H, dd, J=4.0, 1.7 Hz), 7.18 (1H, dt, J=2.5, 1.4 Hz), 9.63 (1H, d, J=0.8 Hz).

B) 4-bromo-1-((2-(trimethylsilyl)ethoxy)methyl)-1H-pyrrole-2-carbaldehyde

To a solution of 1-((2-(trimethylsilyl)ethoxy)methyl)-1H-pyrrole-2-carbaldehyde (4.51 g) in THF (79 mL) was added NBS (4.27 g) at −20° C., and the mixture was stirred at 0° C. for 6 hr. To the reaction mixture was added hexane (240 mL), the precipitate was removed by filtration, and the filtrate was concentrated under reduced pressure. The residue was purified by silica gel column chromatography (ethyl acetate/hexane) to give the title compound (5.2 g).
¹H NMR (300 MHz, CDCl₃) δ 0.00 (9H, s), 0.89-0.96 (2H, m), 3.53-3.60 (2H, m), 5.69 (2H, s), 6.97 (1H, d, J=1.9 Hz), 7.15 (1H, s), 9.55 (1H, d, J=0.8 Hz).

C) ethyl (2E)-3-(4-bromo-1-((2-(trimethylsilyl)ethoxy)methyl)-1H-pyrrol-2-yl)acrylate To a solution of ethyl 3-(diethoxyphosphino)-3-oxopropanoate (3.7 g) in DMF (30 mL) was added sodium hydride (60% dispersion in mineral oil, 0.66 g) at 0° C., and the mixture was stirred under argon atmosphere at 0° C. for 1 hr. To the reaction mixture was added a solution of 4-bromo-1-((2-(trimethylsilyl)ethoxy)methyl)-1H-pyrrole-2-carbaldehyde (4.56 g) in DMF (7 mL) at 0° C., and the mixture was stirred at room temperature for 7 hr. The reaction mixture was added to water, and the mixture was extracted with ethyl acetate. The organic layer was washed with water and saturated brine, dried over anhydrous sodium sulfate, and concentrated under reduced pressure.

To a solution of the residue in THF (45 mL) were added 1N aqueous sodium hydroxide solution (45 mL) and methanol (70 mL) at room temperature, and the mixture was stirred at room temperature for 15 hr. The reaction mixture was concentrated under reduced pressure to evaporate the methanol and THF, and the remaining aqueous solution was washed with a mixed solvent of diethyl ether/hexane (1:1, 120 mL). The obtained aqueous layer was acidified with 1N hydrochloric acid (45 mL), and the mixture was extracted with ethyl acetate. The organic layer was washed with saturated brine, dried over anhydrous magnesium sulfate, and concentrated under reduced pressure to give the title compound (4.8 g).

$^1$H NMR (300 MHz, CDCl$_3$) δ 0.00 (9H, s), 0.88-0.97 (2H, m), 3.46-3.55 (2H, m), 5.28 (2H, s), 6.21 (1H, d, J=15.9 Hz), 6.74 (1H, d, J=1.5 Hz), 6.91 (1H, d, J=1.5 Hz), 7.70 (1H, d, J=15.9 Hz).

D) (2E)-3-(4-bromo-1-((2-(trimethylsilyl)ethoxy)methyl)-1H-pyrrol-2-yl)acryloyl azide To a solution of (2E)-3-(4-bromo-1-((2-(trimethylsilyl)ethoxy)methyl)-1H-pyrrol-2-yl)acrylic acid (4.5 g) in DMF (40 mL) was added a solution of triethylamine (2.0 mL) and diphenylphosphoryl azide (3.75 g) in DMF (5 mL) at 0° C., and the mixture was stirred at room temperature for 4 hr. The reaction mixture was added to water, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (4.56 g).

$^1$H NMR (300 MHz, CDCl$_3$) δ −0.03-0.01 (9H, m), 0.87-0.95 (2H, m), 3.45-3.54 (2H, m), 5.27 (2H, s), 6.18 (1H, d, J=15.5 Hz), 6.75 (1H, d, J=1.5 Hz), 6.92 (1H, d, J=1.5 Hz), 7.67 (1H, d, J=15.5 Hz).

E) 3-bromo-1-((2-(trimethylsilyl)ethoxy)methyl)-1,5-dihydro-4H-pyrrolo[3,2-c]pyridin-4-one A solution of (2E)-3-(4-bromo-1-((2-(trimethylsilyl)ethoxy)methyl)-1H-pyrrol-2-yl)acryloyl azide (3.39 g) and tributylamine (1.86 g) in diphenyl ether (33.9 mL) was stirred under nitrogen atmosphere at 90-105° C. for 15 min, and then at 155-160° C. for 2 hr. The reaction mixture was allowed to be cooled to room temperature, and the residue was purified by silica gel column chromatography (ethyl acetate/hexane) to give the title compound (2.01 g).

$^1$H NMR (300 MHz, DMSO-d$_6$) δ −0.07 (9H, s), 0.77-0.85 (2H, m), 3.41-3.49 (2H, m), 5.40 (2H, s), 6.56 (1H, d, J=7.2 Hz), 7.08 (1H, dd, J=7.0, 5.9 Hz), 7.39 (1H, s), 10.98 (1H, d, J=4.5 Hz).

F) 3-bromo-1,5-dihydro-4H-pyrrolo[3,2-c]pyridin-4-one

To a suspension of 3-bromo-1-((2-(trimethylsilyl)ethoxy)methyl)-1,5-dihydro-4H-pyrrolo[3,2-c]pyridin-4-one (2.0 g) and triethylsilane (1.27 g) was added trifluoroacetic acid (17.31 mL) at room temperature, and the mixture was stirred under nitrogen atmosphere at room temperature for 1 hr. The reaction mixture was concentrated under reduced pressure, to the residue were added acetonitrile (11 mL) and aqueous ammonia solution (25%, 11 mL), and the mixture was stirred at room temperature for 2 hr. The precipitate was collected by filtration, and washed with acetonitrile and ethyl acetate to give the title compound (1.06 g).

$^1$H NMR (300 MHz, DMSO-d$_6$) δ 6.34 (1H, d, J=7.2 Hz), 6.97 (1H, d, J=7.2 Hz), 7.19 (1H, s), 10.77 (1H, brs), 11.59 (1H, brs).

G) 3-bromo-1-(pentan-3-yl)-1,5-dihydro-4H-pyrrolo[3,2-c]pyridin-4-one

To a solution of 3-bromo-1,5-dihydro-4H-pyrrolo[3,2-c]pyridin-4-one (1.00 g) in DMF (30 mL) was added sodium hydride (60% dispersion in mineral oil, 0.207 g), and the mixture was stirred at room temperature for 1 hr. To the reaction mixture was added 3-bromopentane (0.851 g), and the mixture was stirred overnight at room temperature. The reaction mixture was extracted with water and ethyl acetate, and the organic layer was washed with saturated brine, dried over anhydrous magnesium sulfate, filtered, and concentrated under reduced pressure. The obtained residue was purified by silica gel column chromatography (hexane/ethyl acetate to ethyl acetate) to give the title compound (90.5 mg).

$^1$H NMR (300 MHz, DMSO-d$_6$) δ 0.65 (6H, t, J=7.4 Hz), 1.67-1.85 (4H, m), 4.03-4.20 (1H, m), 6.57 (1H, d, J=7.2 Hz), 7.00 (1H, dd, J=7.2, 5.7 Hz), 7.35 (1H, s), 10.83 (1H, d, J=4.5 Hz).

H) methyl 4-(4-oxo-1-(pentan-3-yl)-4,5-dihydro-1H-pyrrolo[3,2-c]pyridin-3-yl)thiophene-2-carboxylate H-1) To a solution of 3-bromo-1-(pentan-3-yl)-1,5-dihydro-4H-pyrrolo[3,2-c]pyridin-4-one (88.0 mg) in DMF (3 mL) was added sodium hydride (60% dispersion in mineral oil, 15.0 mg), and the mixture was stirred at room temperature for 2 hr. To the reaction mixture was added (2-(chloromethoxy)ethyl)(trimethyl)silane (0.066 mL), and the mixture was stirred overnight at room temperature. The reaction mixture was extracted with water and ethyl acetate, and the organic layer was washed with saturated brine, dried over anhydrous magnesium sulfate, filtered, and concentrated under reduced pressure. The obtained residue was purified by silica gel column chromatography (hexane/ethyl acetate) to give an oil (73.2 mg).

$^1$H NMR (300 MHz, DMSO-d$_6$) δ −0.05 (9H, s), 0.65 (6H, t, J=7.4 Hz), 0.81-0.88 (2H, m), 1.68-1.85 (4H, m), 3.52-3.61 (2H, m), 4.06-4.19 (1H, m), 5.26 (2H, s), 6.68 (1H, d, J=7.6 Hz), 7.34 (1H, d, J=7.6 Hz), 7.39 (1H, s).

MS (ESI+): [M+H]$^+$ 415.1.
MS (ESI+). found: 415.2.

H-2) To a solution of the obtained oil (70.0 mg) in DMF (2 mL)/water (0.20 mL) were added methyl 4-(4,4,5,5-tetramethyl-1,3,2-dioxaborolan-2-yl)thiophene-2-carboxylate (68.0 mg), tetrakis(triphenylphosphine)palladium(0) (20.1 mg) and potassium carbonate (23.3 mg). The reaction mixture was stirred under microwave irradiation at 130° C. for 1 hr. The reaction mixture was diluted with water, and the mixture was extracted with ethyl acetate. The organic layer was washed with saturated brine, dried over anhydrous magnesium sulfate, filtered, and concentrated under reduced pressure. The obtained residue was purified by silica gel column chromatography (hexane/ethyl acetate) to give a powder (47.1 mg).

$^1$H NMR (300 MHz, DMSO-d$_6$) δ −0.05 (9H, s), 0.68 (6H, t, J=7.4 Hz), 0.86 (2H, t, J=8.0 Hz), 1.84 (4H, quin, J=7.3 Hz), 3.59 (2H, t, J=7.8 Hz), 3.84 (3H, s), 4.17 (1H, quin, J=7.1 Hz), 5.34 (2H, s), 6.72 (1H, d, J=7.6 Hz), 7.38 (1H, d, J=7.2 Hz), 7.84 (1H, s), 8.42 (1H, d, J=1.5 Hz), 8.77 (1H, d, J=1.1 Hz).
MS (ESI+): [M+H]$^+$ 475.1.
MS (ESI+). found: 475.2.

H-3) The obtained powder (45.0 mg) and triethylsilane (0.045 mL) were dissolved in trifluoroacetic acid (2 mL) at 0° C., and the solution was stirred at room temperature for 1 hr. The reaction mixture was concentrated under reduced pressure, and the residue was extracted with ethyl acetate and saturated aqueous sodium hydrogencarbonate solution. The organic layer was washed with saturated brine, dried over anhydrous magnesium sulfate, filtered, and concentrated under reduced pressure. The obtained residue was purified by silica gel column chromatography (basic silica gel, ethyl acetate to ethyl acetate/methanol) to give the title compound (28.9 mg).

$^1$H NMR (300 MHz, DMSO-d$_6$) δ 0.68 (6H, t, J=7.4 Hz), 1.84 (4H, quin, J=7.3 Hz), 3.84 (3H, s), 4.15 (1H, quin, J=7.1 Hz), 6.60 (1H, d, J=7.2 Hz), 7.04 (1H, t, J=6.4 Hz), 7.84 (1H, s), 8.43 (1H, d, J=1.5 Hz), 8.93 (1H, d, J=1.5 Hz), 10.84 (1H, d, J=5.7 Hz).
MS (ESI+): [M+H]$^+$ 345.1.
MS (ESI+). found: 345.1.

Example 8

4-(4-oxo-1-(pentan-3-yl)-4,5-dihydro-1H-pyrrolo[3,2-c]pyridin-3-yl)thiophene-2-carboxamide A) 4-(4-oxo-1-(pentan-3-yl)-4,5-dihydro-1H-pyrrolo[3,2-c]pyridin-3-yl)thiophene-2-carboxylic acid To a solution of methyl 4-(4-oxo-1-(pentan-3-yl)-4,5-dihydro-1H-pyrrolo[3,2-c]pyridin-3-yl)thiophene-2-carboxylate (23.5 mg) obtained in Example 7 in a mixed solvent of methanol (1 mL)/THF (1 mL)/water (1 mL) was added 8N aqueous sodium hydroxide solution (0.021 mL) at 0° C. The reaction mixture was stirred at 90° C. for 1 hr. The reaction mixture was diluted with water, and the mixture was extracted with ethyl acetate. The organic layer was washed with 0.1N hydrochloric acid, water and saturated brine, dried over anhydrous magnesium sulfate, filtered, and concentrated under reduced pressure to give the title compound (23.0 mg).
MS (ESI+): [M+H]$^+$ 331.1.
MS (ESI+). found: 331.1.

B) 4-(4-oxo-1-(pentan-3-yl)-4,5-dihydro-1H-pyrrolo[3,2-c]pyridin-3-yl)thiophene-2-carboxamide To a solution of 4-(4-oxo-1-(pentan-3-yl)-4,5-dihydro-1H-pyrrolo[3,2-c]pyridin-3-yl)thiophene-2-carboxylic acid (23.0 mg) in DMA (2 mL) were added EDCI hydrochloride (16.0 mg) and HOBt ammonium salt (13.1 mg) at room temperature, and the mixture was stirred overnight at room temperature. The reaction mixture was diluted with water, the mixture was extracted with ethyl acetate, and the organic layer was washed with saturated brine, dried over anhydrous magnesium sulfate, filtered, and concentrated under reduced pressure. The obtained residue was purified by silica gel column chromatography (basic silica gel, ethyl acetate to ethyl acetate/methanol) to give the title compound (20.6 mg).

$^1$H NMR (300 MHz, DMSO-d$_6$) δ 0.70 (6H, t, J=7.2 Hz), 1.70-1.93 (4H, m), 4.09-4.24 (1H, m), 6.60 (1H, d, J=7.2 Hz), 6.99-7.09 (1H, m), 7.34 (1H, brs), 7.47 (1H, s), 7.79 (1H, brs), 8.17 (1H, d, J=1.1 Hz), 8.68 (1H, J=1.1 Hz), 10.83 (1H, d, J=5.7 Hz).
MS (ESI+): [M+H]$^+$ 330.1.
MS (ESI+). found: 330.2.

Example 9

4-(4-oxo-1-(pentan-3-yl)-4,5-dihydro-1H-pyrrolo[3,2-c]pyridin-3-yl)thiophene-2-carbonitrile To a solution of 4-(4-oxo-1-(pentan-3-yl)-4,5-dihydro-1H-pyrrolo[3,2-c]pyridin-3-yl)thiophene-2-carboxamide (13.0 mg) obtained in Example 8 in DMA (2 mL) was slowly added dropwise trifluoroacetic anhydride (8.36 μL) under nitrogen atmosphere at 0° C., and the mixture was allowed to be warmed to room temperature, and stirred overnight at room temperature. The reaction mixture was diluted with water, and the mixture was extracted three times with ethyl acetate. The combined organic layers were washed with saturated brine, dried over anhydrous magnesium sulfate, filtered, and concentrated under reduced pressure. The obtained residue was purified by silica gel column chromatography (basic silica gel, ethyl acetate) to give the title compound (9.2 mg).

$^1$H NMR (300 MHz, DMSO-d$_6$) δ 0.69 (6H, t, J=7.4 Hz), 1.71-1.93 (4H, m), 4.08-4.24 (1H, m), 6.62 (1H, d, J=6.8 Hz), 7.06 (1H, dd, J=7.2, 6.0 Hz), 7.80 (1H, s), 8.55 (1H, d, J=1.5 Hz), 8.98 (1H, d, J=1.5 Hz), 10.91 (1H, d, J=5.3 Hz).
MS (ESI+): [M+H]$^+$ 312.1.
MS (ESI+). found: 312.0.

Example 10

1,3-diphenyl-1,6-dihydro-7H-pyrazolo[3,4-c]pyridin-7-one

A) tert-butyl (4-benzyl-2-methoxypyridin-3-yl)carbamate

To a solution of tert-butyl (2-methoxypyridin-3-yl)carbamate (25.1 g) and N,N,N',N'-tetramethylethane-1,2-diamine (40.6 mL) in diethyl ether (374 mL) was added 1.6M n-butyllithium hexane solution (168 mL) at −78° C., and the mixture was stirred under argon atmosphere at 0° C. for 1 hr. To the reaction mixture was added benzyl bromide (24.9 g) at −78° C., and the mixture was stirred under argon atmosphere at room temperature for 4 hr. To the reaction mixture was added saturated aqueous sodium hydrogencarbonate solution at room temperature, and the mixture was extracted with ethyl acetate. The organic layer was washed with saturated brine, dried over anhydrous magnesium sulfate, and concentrated under reduced pressure. The residue was purified by silica gel column chromatography (basic silica gel, ethyl acetate/hexane), and crystallized from ethyl acetate and hexane to give the title compound (25.4 g).

$^1$H NMR (300 MHz, CDCl$_3$) δ 1.50 (9H, s), 3.96 (3H, s), 4.00 (2H, s), 5.99 (1H, brs), 6.60 (1H, d, J=5.3 Hz), 7.12-7.33 (5H, m), 7.88 (1H, d, J=5.3 Hz).

B) 4-benzyl-2-methoxypyridin-3-amine

To a solution of tert-butyl (4-benzyl-2-methoxypyridin-3-yl)carbamate (25.4 g) in ethyl acetate (202 mL) was added 4N hydrogen chloride/ethyl acetate solution (202 mL) at room temperature, and the mixture was stirred overnight at room temperature, and then at 50° C. for 1 hr. To the reaction mixture was added diisopropyl ether at room temperature, and the obtained precipitate was collected by filtration, and washed with diisopropyl ether. Saturated aqueous sodium hydrogencarbonate solution was added thereto, and the mixture was extracted with ethyl acetate. The organic layer was dried over anhydrous magnesium sulfate, and concentrated under reduced pressure. The residue was purified by silica gel column chromatography (basic silica gel, ethyl acetate/hexane) to give the title compound (8.8 g).
$^1$H NMR (300 MHz, CDCl$_3$) δ 3.66 (2H, brs), 3.88 (2H, s), 3.98 (3H, s), 6.62 (1H, d, J=5.3 Hz), 7.14-7.35 (5H, m), 7.56 (1H, d, J=5.3 Hz).

C) 7-methoxy-3-phenyl-1H-pyrazolo[3,4-c]pyridine

To a solution of 4-benzyl-2-methoxypyridin-3-amine (8.8 g) in acetic acid (310 mL) was added an aqueous solution prepared by dissolving sodium nitrite (2.83 g) in water (15.5 mL) at 0° C., and the mixture was stirred at 0° C. for 10 min, and then overnight at room temperature. The reaction mixture was concentrated under reduced pressure, to the residue was added saturated aqueous sodium hydrogencarbonate solution, and the mixture was extracted with ethyl acetate. The organic layer was washed with saturated brine, dried over anhydrous magnesium sulfate, and concentrated under reduced pressure. The residue was crystallized from ethanol and hexane to give the title compound (5.2 g).
$^1$H NMR (300 MHz, CDCl$_3$) δ 4.10 (3H, s), 7.38-7.46 (1H, m), 7.49-7.57 (2H, m), 7.62 (1H, d, J=6.1 Hz), 7.80 (1H, d, J=6.1 Hz), 8.00 (2H, d, J=7.2 Hz), 14.02 (1H, brs).

D) 4-benzyl-2-methoxypyridin-3-amine

A solution of 7-methoxy-3-phenyl-1H-pyrazolo[3,4-c]pyridine (113 mg), iodobenzene (1.02 g), L-proline (23.0 mg), potassium carbonate (346 mg) and copper(I) iodide (19.1 mg) in DMSO (10 mL) was stirred under nitrogen atmosphere at 180° C. for 1 hr. The reaction mixture was purified by silica gel column chromatography (ethyl acetate/hexane) to give the title compound (75 mg).
$^1$H NMR (300 MHz, CDCl$_3$) δ 4.01 (3H, s), 7.37-7.57 (7H, m), 7.63-7.68 (2H, m), 7.90 (1H, d, J=5.7 Hz), 7.96-8.02 (2H, m)

E) 1,3-diphenyl-1,6-dihydro-7H-pyrazolo[3,4-c]pyridin-7-one

To a solution of 7-methoxy-1,3-diphenyl-1H-pyrazolo[3,4-c]pyridine (75 mg) in acetonitrile (10 mL) were added sodium iodide (75 mg) and chloro(trimethyl)silane (216 mg), and the mixture was stirred at 60° C. for 1 hr. The reaction mixture was concentrated under reduced pressure, and the residue was purified by silica gel column chromatography (ethyl acetate/hexane), and crystallized from ethyl acetate and hexane to give the title compound (45 mg).
$^1$H NMR (300 MHz, DMSO-d$_6$) δ 6.88 (1H, d, J=7.2 Hz), 7.09-7.20 (1H, m), 7.38-7.61 (6H, m), 7.65-7.74 (2H, m), 7.87-7.95 (2H, m), 11.57 (1H, brs).

Example 11

3-phenyl-1-(3-thienyl)-1,6-dihydro-7H-pyrazolo[3,4-c]pyridin-7-one

A) 7-methoxy-3-phenyl-1-(3-thienyl)-1H-pyrazolo[3,4-c]pyridine

A solution of 7-methoxy-3-phenyl-1H-pyrazolo[3,4-c]pyridine (225 mg) obtained in Step C of Example 10, 3-iodothiophene (1.05 g), L-proline (46.1 mg), potassium carbonate (691 mg) and copper(I) iodide (38.1 mg) in DMSO (10 mL) was stirred under nitrogen atmosphere at 180° C. for 1 hr. The reaction mixture was purified by silica gel column chromatography (ethyl acetate/hexane) to give the title compound (28.5 mg).
$^1$H NMR (300 MHz, CDCl$_3$) δ 4.07 (3H, s), 7.34-7.58 (7H, m), 7.89 (1H, d, J=5.7 Hz), 7.95-8.00 (2H, m).

B) 3-phenyl-1-(3-thienyl)-1,6-dihydro-7H-pyrazolo[3,4-c]pyridin-7-one

To a solution of 7-methoxy-3-phenyl-1-(3-thienyl)-1H-pyrazolo[3,4-c]pyridine (28.5 mg) in acetonitrile (10 mL) were added sodium iodide (27.8 mg) and chloro(trimethyl)silane (81 mg), and the mixture was stirred at 60° C. for 1 hr. The reaction mixture was concentrated under reduced pressure, and the residue was purified by silica gel column chromatography (ethyl acetate/hexane), and crystallized from ethyl acetate and hexane to give the title compound (24.5 mg).
$^1$H NMR (300 MHz, DMSO-d$_6$) δ 6.86 (1H, d, J=6.8 Hz), 7.10-7.17 (1H, m), 7.43-7.50 (1H, m), 7.51-7.60 (3H, m), 7.61-7.66 (1H, m), 7.88-7.93 (2H, m), 7.97 (1H, dd, J=3.2, 1.3 Hz), 11.60 (1H, brs).

Example 12 methyl 4-(1-cyclopentyl-4-oxo-4,5-dihydro-1H-pyrazolo[4,3-c]pyridin-3-yl)thiophene-2-carboxylate A) N'-cyclopentyl-4-iodo-2-methoxynicotinohydrazide A solution of 4-iodo-2-methoxynicotinic acid (1.95 g) obtained in Step C of Example 6, cyclopentylhydrazine hydrochloride (1.05 g), EDCI hydrochloride (0.58 g), HOBt (2.01 g) and triethylamine (1.06 g) in DMF (30 mL) was stirred at room temperature for 3 days. To the reaction mixture was added water, and the mixture was extracted with ethyl acetate. The organic layer was dried over anhydrous sodium sulfate, and concentrated under reduced pressure. The residue was purified by silica gel column chromatography (ethyl acetate/hexane) to give the title compound (697 mg).
$^1$H NMR (300 MHz, CDCl$_3$) δ 1.49-1.65 (4H, m), 1.69-1.90 (4H, m), 3.66-3.76 (1H, m), 3.93 (3H, s), 4.85 (1H, brs), 7.36 (1H, d, J=5.7 Hz), 7.80 (1H, d, J=5.7 Hz).

B) 1-cyclopentyl-4-methoxy-1,2-dihydro-3H-pyrazolo[4,3-c]pyridin-3-one

A solution of N'-cyclopentyl-4-iodo-2-methoxynicotinohydrazide (695 mg), L-proline (44.3 mg), potassium carbonate (532 mg) and copper(I) iodide (36.6 mg) in DMSO (18 mL) was stirred under nitrogen atmosphere at room temperature for 5 hr. To the reaction mixture was added water under ice-cooling, and the mixture was extracted with ethyl acetate. The organic layer was removed, to the obtained aqueous layer was added 1N hydrochloric acid (7 mL) under ice-cooling, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (174 mg).
$^1$H NMR (300 MHz, CDCl$_3$) δ 1.62-1.82 (2H, m), 1.88-2.23 (6H, m), 4.11 (3H, s), 4.71 (1H, quin, J=7.7 Hz), 6.78 (1H, d, J=6.4 Hz), 7.86 (1H, d, J=6.4 Hz), 10.47 (1H, brs).

C) 1-cyclopentyl-4-methoxy-1H-pyrazolo[4,3-c]pyridin-3-yl trifluoromethanesulfonate To a solution of 1-cyclopentyl-4-methoxy-1,2-dihydro-3H-pyrazolo[4,3-c]pyridin-3-one (160 mg) and pyridine (326 mg) in acetonitrile (20 mL) was added trifluoromethanesulfonic anhydride (774 mg), the mixture was stirred at 0° C. for 2 hr, and the reaction mixture was concentrated under reduced pressure. The residue was purified by silica gel column chromatography (ethyl acetate/hexane) to give the title compound (140 mg).

$^1$H NMR (300 MHz, CDCl$_3$) δ 1.65-1.81 (2H, m), 1.86-2.02 (2H, m), 2.02-2.23 (4H, m), 4.11 (3H, s), 4.84 (1H, quin, J=6.9 Hz), 6.91 (1H, d, J 6.4 Hz), 7.94 (1H, d, J=6.4 Hz).

D) methyl 4-(1-cyclopentyl-4-methoxy-1H-pyrazolo [4,3-c]pyridin-3-yl)thiophene-2-carboxylate A solution of 1-cyclopentyl-4-methoxy-1H-pyrazolo[4,3-c]pyridin-3-yl trifluoromethanesulfonate (138 mg), methyl 4-(4,4,5,5-tetramethyl-1,3,2-dioxaborolan-2-yl)thiophene-2-carboxylate (152 mg), tetrakis(triphenylphosphine)palladium(0) (44 mg) and 2M aqueous sodium carbonate solution (0.94 mL) in DME (10 mL) was stirred under nitrogen atmosphere at 100° C. for 2 hr stirred. To the reaction mixture was added water, and the mixture was extracted with ethyl acetate. The organic layer was dried over anhydrous sodium sulfate, and concentrated under reduced pressure. The residue was purified by silica gel column chromatography (ethyl acetate/hexane) to give the title compound (132 mg).

$^1$H NMR (300 MHz, CDCl$_3$) δ 1.68-1.84 (2H, m), 1.92-2.30 (6H, m), 3.93 (3H, s), 4.14 (3H, s), 4.90 (1H, quin, J=7.2 Hz), 6.96 (1H, d, J=6.4 Hz), 7.91 (1H, d, J=6.0 Hz), 8.36 (1H, d, J=1.5 Hz), 8.49 (1H, d, J=1.5 Hz).

E) methyl 4-(1-cyclopentyl-4-oxo-4,5-dihydro-1H-pyrazolo[4,3-c]pyridin-3-yl)thiophene-2-carboxylate To a solution of methyl 4-(1-cyclopentyl-4-methoxy-1H-pyrazolo[4,3-c]pyridin-3-yl)thiophene-2-carboxylate (122 mg) in acetonitrile (20 mL) were added sodium iodide (102 mg) and chloro(trimethyl)silane (297 mg), and the mixture was stirred at 60° C. for 20 min. To the reaction mixture was added water, and the mixture was concentrated under reduced pressure to evaporate the acetonitrile. The precipitate in the remaining aqueous solution was collected by filtration to give the title compound (107 mg).

$^1$H NMR (300 MHz, DMSO-d$_6$) δ 1.63-1.77 (2H, m), 1.82-2.21 (6H, m), 3.86 (3H, s), 4.98-5.09 (1H, m), 6.68 (1H, d, J=6.4 Hz), 7.24 (1H, dd, J=7.2, 6.0 Hz), 8.49 (1H, d, J=1.5 Hz), 9.11 (1H, d, J=1.5 Hz), 11.15 (1H, d, J=5.7 Hz).
MS (ESI+): [M+H]$^+$ 344.1.
MS (ESI+). found: 344.0.

Example 13

4-(1-cyclopentyl-4-oxo-4,5-dihydro-1H-pyrazolo[4,3-c]pyridin-3-yl)thiophene-2-carboxamide A) 4-(1-cyclopentyl-4-oxo-4,5-dihydro-1H-pyrazolo [4,3-c]pyridin-3-yl)thiophene-2-carboxylic acid To a solution of methyl 4-(1-cyclopentyl-4-oxo-4,5-dihydro-1H-pyrazolo[4,3-c]pyridin-3-yl)thiophene-2-carboxylate (97 mg) obtained in Step E of Example 12 in a mixed solvent of THF (10 mL)/methanol (10 mL) was added 1N aqueous sodium hydroxide solution (2 mL) under ice-cooling, and the mixture was stirred at room temperature for 96 hr. To the reaction mixture was added 1N hydrochloric acid (2 mL) under ice-cooling, and the mixture was stirred, and extracted twice with ethyl acetate. The combined organic layers were washed with saturated brine, dried over anhydrous sodium sulfate, and concentrated under reduced pressure to give the title compound (83 mg).

$^1$H NMR (300 MHz, DMSO-d$_6$) δ 1.60-1.78 (2H, m), 1.82-2.21 (6H, m), 5.03 (1H, quin, J=7.1 Hz), 6.67 (1H, d, J=7.2 Hz), 7.24 (1H, dd, J=7.2, 6.0 Hz), 8.40 (1H, d, J=1.5 Hz), 9.05 (1H, d, J=1.5 Hz), 11.14 (1H, d, J=6.4 Hz), 13.19 (1H, brs).

B) 4-(1-cyclopentyl-4-oxo-4,5-dihydro-1H-pyrazolo [4,3-c]pyridin-3-yl)thiophene-2-carboxamide A solution of 4-(1-cyclopentyl-4-oxo-4,5-dihydro-1H-pyrazolo[4,3-c]pyridin-3-yl)thiophene-2-carboxylic acid (89 mg), HOBt ammonium salt (49 mg), EDCI hydrochloride (62 mg) and triethylamine (33 mg) in DMF (10 mL) was stirred at room temperature for 24 hr. To the reaction mixture was added water, and the mixture was extracted with ethyl acetate. The organic layer was washed with saturated brine, dried over anhydrous sodium sulfate, and concentrated under reduced pressure. The residue was crystallized from ethyl acetate to give the title compound (48 mg).

$^1$H NMR (300 MHz, DMSO-d$_6$) δ 1.64-1.75 (2H, m), 1.84-2.20 (6H, m), 5.03 (1H, quin, J=7.0 Hz), 6.67 (1H, d, J=7.6 Hz), 7.23 (1H, dd, J=6.8, 6.0 Hz), 7.41 (1H, brs), 8.16 (1H, brs), 8.33 (1H, d, J=1.1 Hz), 9.13 (1H, d, J=1.1 Hz), 11.12 (1H, d, J=5.7 Hz).
MS (ESI+): [M+H]$^+$ 329.1.
MS (ESI+). found: 328.9.

Example 14

4-(1-cyclopentyl-4-oxo-4,5-dihydro-1H-pyrazolo[4,3-c]pyridin-3-yl)thiophene-2-carbonitrile To a solution of 4-(1-cyclopentyl-4-oxo-4,5-dihydro-1H-pyrazolo[4,3-c]pyridin-3-yl)thiophene-2-carboxamide (25 mg) obtained in Example 13 in DMA (5 mL) was added trifluoroacetic anhydride (240 mg) under ice-cooling, and the mixture was stirred under nitrogen atmosphere at room temperature for 1 hr. To the reaction mixture was added water, the precipitate was collected by filtration, and the obtained solid was crystallized from ethyl acetate and hexane to give the title compound (16.7 mg).

$^1$H NMR (300 MHz, DMSO-d$_6$) δ 1.61-1.77 (2H, m), 1.82-2.21 (6H, m), 4.97-5.12 (1H, m), 6.70 (1H, d, J=7.2 Hz), 7.22-7.28 (1H, m), 8.62 (1H, d, J=1.1 Hz), 9.15 (1H, d, J=1.1 Hz), 11.20 (1H, d, J=5.7 Hz).
MS (ESI+): [M+H]$^+$ 311.1.
MS (ESI+). found: 310.9.

Example 15

4-(4-oxo-1-(tetrahydro-2H-pyran-4-yl)-4,5-dihydro-1H-pyrazolo[4,3-c]pyridin-3-yl)benzenesulfonamide A) tert-butyl 2-(tetrahydro-2H-pyran-4-yl)hydrazinecarboxylate A solution of tetrahydro-4H-pyran-4-one (2.50 g) and tert-butyl hydrazinecarboxylate (3.47 g) in methanol (10 mL) was stirred at room temperature for 1 hr, and concentrated under reduced pressure. The residue was dissolved in THF (25 mL), acetic acid (4.3 mL) and sodium borohydride (0.525 g) were added thereto, and the mixture was stirred at 0° C. for 1 hr. To the reaction mixture was added 8N aqueous sodium hydroxide solution, and the mixture was extracted with ethyl acetate. The organic layer was washed successively with saturated aqueous sodium hydrogencarbonate solution and saturated brine, dried over anhydrous sodium sulfate, and concentrated under reduced pressure. The residue was purified by silica gel column chromatography (ethyl acetate/hexane) to give the title compound (2.34 g).

$^1$H NMR (300 MHz, CDCl$_3$) δ 1.35-1.54 (11H, m), 1.77 (2H, dd, J=12.1 Hz, 2.3 Hz), 2.98-3.15 (1H, m), 3.40 (2H, td, J=11.3 Hz, 2.3 Hz), 3.96 (3H, dt, J=11.5 Hz, 3.7 Hz), 6.03 (1H, brs).

B) tetrahydro-2H-pyran-4-ylhydrazine dihydrochloride tert-Butyl 2-(tetrahydro-2H-pyran-4-yl)hydrazinecarboxylate (1.82 g) was dissolved in 4N hydrogen chloride-ethyl acetate solution (85 mL) under ice-cooling, and the solution was stirred overnight at room temperature. The reaction mixture was concentrated under reduced pressure to give the title compound (1.52 g).

$^1$H NMR (300 MHz, CDCl$_3$) δ 1.36-1.57 (2H, m), 1.89 (2H, dd, J=12.5 Hz, 2.3 Hz), 3.12 (1H, tt, J=11.0 Hz, 4.1 Hz), 3.28 (2H, td, J=11.6 Hz, 2.1 Hz), 3.89 (2H, dt, J=9.9 Hz, 2.0 Hz), 7.73 (3H, brs).

C) 4-iodo-2-methoxy-N'-(tetrahydro-2H-pyran-4-yl) nicotinohydrazide

A solution of 4-iodo-2-methoxynicotinic acid (1.75 g) obtained in Step C of Example 6, tetrahydro-2H-pyran-4-ylhydrazine dihydrochloride (0.957 g), DIEA (2.2 mL), EDCI hydrochloride (1.44 g) and HOBt (1.02 g) in DMF (100 mL) was stirred overnight at room temperature. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane/methanol), and the obtained solid was washed with ethyl acetate/diisopropyl ether to give the title compound (1.55 g).

$^1$H NMR (300 MHz, DMSO-d$_6$) δ 1.24-1.47 (2H, m), 1.82 (2H, dd, J=12.7 Hz, 2.8 Hz), 2.99-3.17 (1H, m), 3.23-3.39 (2H, m), 3.72-3.95 (5H, m), 5.09 (1H, dd, J=6.6 Hz, 4.0 Hz), 7.46 (1H, d, J=5.7 Hz), 7.85 (1H, d, J 5.7 Hz), 9.76 (1H, d, J=6.4 Hz).

MS (ESI+): [M+H]$^+$ 378.0.
MS (ESI+). found: 378.0.

D) 4-methoxy-1-(tetrahydro-2H-pyran-4-yl)-1,2-dihydro-3H-pyrazolo[4,3-c]pyridin-3-one A solution of 4-iodo-2-methoxy-N'-(tetrahydro-2H-pyran-4-yl)nicotinohydrazide (500 mg), L-proline (30.5 mg), potassium carbonate (366 mg) and copper(I) iodide (25.2 mg) in DMSO (25 mL) was stirred overnight at room temperature under nitrogen atmosphere. To the reaction mixture was added saturated aqueous ammonium chloride solution, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane) to give the title compound (223 mg).

$^1$H NMR (300 MHz, DMSO-d$_6$) δ 1.77 (2H, dd, J=12.3 Hz, 2.5 Hz), 1.91-2.11 (2H, m), 3.50 (2H, td, J=11.9 Hz, 1.9 Hz), 3.84-4.06 (5H, m), 4.52-4.70 (1H, m), 7.12 (1H, d, J=6.4 Hz), 7.77 (1H, d, J=6.0 Hz), 10.94 (1H, brs).

MS (ESI+): [M+H]$^+$ 250.1.
MS (ESI+). found: 250.0.

E) 4-methoxy-1-(tetrahydro-2H-pyran-4-yl)-1H-pyrazolo[4,3-c]pyridin-3-yl trifluoromethanesulfonate To a solution of 4-methoxy-1-(tetrahydro-2H-pyran-4-yl)-1,2-dihydro-3H-pyrazolo[4,3-c]pyridin-3-one (200 mg) and pyridine (0.260 mL) in acetonitrile (25 mL) was added trifluoromethanesulfonic anhydride (0.271 mL), and the mixture was stirred at 0° C. for 1 hr. To the reaction mixture was added saturated aqueous ammonium chloride solution, and the mixture was extracted with ethyl acetate. The organic layer was washed successively with 0.1N hydrochloric acid, water, saturated aqueous sodium hydrogencarbonate solution and saturated brine, dried over anhydrous sodium sulfate, and concentrated under reduced pressure. The residue was purified by silica gel column chromatography (ethyl acetate/hexane) to give the title compound (288 mg).

$^1$H NMR (300 MHz, DMSO-d$_6$) δ 1.85-2.08 (4H, m), 3.53 (2H, td, J=11.6 Hz, 2.8 Hz), 3.87-4.15 (5H, m), 4.85-5.04 (1H, m), 7.50 (1H, d, J=6.4 Hz), 8.04 (1H, d, J=6.4 Hz).

MS (ESI+): [M+H]$^+$ 382.1.
MS (ESI+). found: 382.1.

F) 4-(4-methoxy-1-(tetrahydro-2H-pyran-4-yl)-1H-pyrazolo[4,3-c]pyridin-3-yl)benzenesulfonamide A solution of 4-methoxy-1-(tetrahydro-2H-pyran-4-yl)-1H-pyrazolo[4,3-c]pyridin-3-yl trifluoromethanesulfonate (150 mg), 4-(4,4,5,5-tetramethyl-1,3,2-dioxaborolan-2-yl)benzenesulfonamide (167 mg), tetrakis(triphenylphosphine)palladium(0) (45.5 mg) and 2M aqueous sodium carbonate solution (1.0 mL) in DME (15 mL) was heated overnight with reflux under nitrogen atmosphere. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane), and the obtained solid was washed with ethyl acetate/diisopropyl ether to give the title compound (119 m).

$^1$H NMR (300 MHz, DMSO-d$_6$) δ 1.95 (2H, dd, J=12.3 Hz, 2.5 Hz), 2.19 (2H, qd, J=12.1 Hz, 4.5 Hz), 3.47-3.69 (2H, m), 3.90-4.15 (5H, m), 4.86-5.06 (1H, m), 7.42 (2H, s), 7.46 (1H, d, J=6.0 Hz), 7.88-7.96 (2H, m), 7.99 (1H, d, J=6.4 Hz), 8.07-8.17 (2H, m).

MS (ESI+): [M+H]$^+$ 389.1.
MS (ESI+). found: 389.1.

G) 4-(4-oxo-1-(tetrahydro-2H-pyran-4-yl)-4,5-dihydro-1H-pyrazolo[4,3-c]pyridin-3-yl)benzenesulfonamide To a solution of 4-(4-methoxy-1-(tetrahydro-2H-pyran-4-yl)-1H-pyrazolo[4,3-c]pyridin-3-yl)benzenesulfonamide (106 mg) in acetonitrile (10 mL) were added sodium iodide (82.0 mg) and chloro(trimethyl)silane (0.276 mL), and the mixture was stirred at 60° C. for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane), and the obtained solid was washed with ethyl acetate/diisopropyl ether to give the title compound (99.0 mg).

$^1$H NMR (300 MHz, DMSO-$d_6$) δ 1.81-1.97 (2H, m), 2.17 (2H, qd, J=12.0 Hz, 4.3 Hz), 3.56 (2H, t, J=11.1 Hz), 3.92-4.14 (2H, m), 4.73-4.92 (1H, m), 6.78 (1H, d, J=7.2 Hz), 7.19-7.51 (3H, m), 7.87 (2H, d, J=8.7 Hz), 8.50 (2H, d, J=8.3 Hz), 11.16 (1H, brs).

MS (ESI+): [M+H]$^+$ 375.1.
MS (ESI+). found: 375.1.

Example 16

4-(4-oxo-1-(tetrahydro-2H-pyran-4-yl)-4,5-dihydro-1H-pyrrolo[3,2-c]pyridin-3-yl)benzenesulfonamide

A) 3-iodo-4-methoxy-1-(tetrahydro-2H-pyran-4-yl)-1H-pyrrolo[3,2-c]pyridine

To a solution of 3-iodo-4-methoxy-1H-pyrrolo[3,2-c]pyridine (0.150 g) in DMF (10 mL) was added sodium hydride (60% dispersion in mineral oil, 55.0 mg), and the mixture was stirred at room temperature for 1 hr. Tetrahydro-2H-pyran-4-yl 4-methylbenzenesulfonate (0.351 g) was added thereto, and the mixture was stirred overnight at room temperature. The reaction mixture was extracted with water and ethyl acetate, and the organic layer was washed with saturated brine, dried over anhydrous magnesium sulfate, filtered, and concentrated under reduced pressure. The obtained residue was purified by silica gel column chromatography (hexane/ethyl acetate) to give the title compound (120 mg).

MS (ESI+): [M+H]$^+$ 359.0.
MS (ESI+). found: 359.0.

B) 4-(4-methoxy-1-(tetrahydro-2H-pyran-4-yl)-1H-pyrrolo[3,2-c]pyridin-3-yl)benzenesulfonamide To a solution of 3-iodo-4-methoxy-1-(tetrahydro-2H-pyran-4-yl)-1H-pyrrolo[3,2-c]pyridine (50.0 mg) in DMF (2 mL)/water (0.20 mL) were added 4-(4,4,5,5-tetramethyl-1,3,2-dioxaborolan-2-yl)benzenesulfonamide (59.0 mg), tetrakis(triphenylphosphine)palladium(0) (16.0 mg) and potassium carbonate (39.2 mg). The reaction mixture was stirred under microwave irradiation at 130° C. for 1 hr. The reaction mixture was diluted with water, and the mixture was extracted with ethyl acetate. The organic layer was washed with saturated brine, dried over anhydrous magnesium sulfate, filtered, and concentrated under reduced pressure. The obtained residue was purified by silica, gel column chromatography (hexane/ethyl acetate) to give the title compound (22.9 mg).

$^1$H NMR (300 MHz, DMSO-$d_6$) δ 1.87-1.98 (2H, m), 2.09 (2H, qd, J=12.1, 4.5 Hz), 3.58 (2H, t, J=11.0 Hz), 3.89-3.97 (3H, m), 3.98-4.05 (2H, m), 4.62-4.77 (1H, m), 7.32 (2H, s), 7.36 (1H, d, J=6.1 Hz), 7.79-7.86 (6H, m).

MS (ESI+): [M+H]$^+$ 388.1.
MS (ESI+). found: 388.1.

C) 4-(4-oxo-1-(tetrahydro-2H-pyran-4-yl)-4,5-dihydro-1H-pyrrolo[3,2-c]pyridin-3-yl)benzenesulfonamide To a solution of 4-(4-methoxy-1-(tetrahydro-2H-pyran-4-yl)-1H-pyrrolo[3,2-c]pyridin-3-yl)benzenesulfonamide (28.0 mg) in acetonitrile (3 mL) were added sodium iodide (28.2 mg) and chloro(trimethyl)silane (0.096 mL), and the mixture was stirred overnight at 50° C. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate to ethyl acetate/methanol), and the obtained solid was washed with ethyl acetate/diisopropyl ether to give the title compound (19.2 mg).

$^1$H NMR (300 MHz, DMSO-$d_6$) δ 1.83-1.94 (2H, m), 2.00-2.15 (2H, m), 3.55 (2H, t, J=11.0 Hz), 3.95-4.06 (2H, m), 4.57 (1H, tt, J=11.5, 4.4 Hz), 6.70 (1H, d, J 7.2 Hz), 7.07-7.17 (1H, m), 7.27 (2H, s), 7.68-7.79 (3H, m), 8.08 (2H, d, J=8.3 Hz), 10.89 (1H, d, J=5.7 Hz).

MS (ESI+): [M+H]$^+$ 374.1.
MS (ESI+). found: 374.1.

Example 17

4-(1-(1-methoxybutan-2-yl)-4-oxo-4,5-dihydro-1H-pyrrolo[3,2-c]pyridin-3-yl)benzenesulfonamide

A-1) To a solution of 1-methoxybutan-2-yl 4-methylbenzenesulfonate

To a solution of 1-methoxybutan-2-ol (1.10 mL) in pyridine (5 mL) was added dropwise a solution of 4-methylbenzenesulfonyl chloride (2.75 g) in pyridine (15 mL) over 30 min or more at 0° C. The reaction mixture was stirred overnight at room temperature, and poured into ice-water. The reaction mixture was stirred at 0° C. for 1 hr, and the precipitate was collected by filtration, and washed with cold water. The obtained solid was purified by silica gel column chromatography (hexane/ethyl acetate) to give the title compound (2.23 g).

$^1$H NMR (300 MHz, DMSO-$d_6$) δ 0.74 (3H, t, J=7.4 Hz), 1.45-1.66 (2H, m), 2.42 (3H, s), 3.12 (3H, s), 3.33-3.40 (2H, m), 4.46-4.60 (1H, m), 7.46 (2H, d, J=7.9 Hz), 7.74-7.84 (2H, m).

A-2) 3-iodo-4-methoxy-1-(1-methoxybutan-2-yl)-1H-pyrrolo[3,2-c]pyridine

To a solution of 3-iodo-4-methoxy-1H-pyrrolo[3,2-c]pyridine (0.500 g) in DMF (15 mL) was added sodium hydride (60% dispersion in mineral oil, 18.3 mg), and the mixture was stirred at room temperature for 1 hr, 1-methoxybutan-2-yl 4-methylbenzenesulfonate (1.18 g) was added thereto, and the mixture was stirred overnight at room temperature. The reaction mixture was extracted with water and ethyl acetate, and the organic layer was washed with saturated brine, dried over anhydrous magnesium sulfate, filtered, and concentrated under reduced pressure. The obtained residue was purified by silica gel column chromatography (hexane/ethyl acetate) to give the title compound (589 mg).

MS (ESI+): [M+H]$^+$ 361.0.
MS (ESI+). found: 361.0.

B) 4-(4-methoxy-1-(1-methoxybutan-2-yl)-1H-pyrrolo[3,2-c]pyridin-3-yl)benzenesulfonamide To a solution of 3-iodo-4-methoxy-1-(1-methoxybutan-2-yl)-1H-pyrrolo[3,2-c]pyridine (70.8 mg) in DMF (2 mL)/water (0.20 mL) were added 4-(4,4,5,5-tetramethyl-1,3,2-dioxaborolan-2-yl)benzenesulfonamide (60.0 mg), tetrakis(triphenylphosphine)palladium(0) (19.2 mg) and potassium carbonate (46.0 mg). The reaction mixture was stirred under microwave irradiation at 130° C. for 1 hr. The reaction mixture was diluted with water, and the mixture was extracted with ethyl acetate. The organic layer was washed with saturated brine, dried over anhydrous magnesium sulfate, filtered, and concentrated under reduced pressure. The obtained residue was purified by silica gel column chromatography (hexane/ethyl acetate) to give the title compound (24.2 mg).
MS (ESI+): [M+H]+ 390.1.
MS (ESI+). found: 390.1.

C) 4-(1-(1-methoxybutan-2-yl)-4-oxo-4,5-dihydro-1H-pyrrolo[3,2-c]pyridin-3-yl)benzenesulfonamide To a solution of 4-(4-methoxy-1-(1-methoxybutan-2-yl)-1H-pyrrolo[3,2-c]pyridin-3-yl)benzenesulfonamide (21.0 mg) in acetonitrile (2 mL) were added sodium iodide (20.2 mg) and chloro(trimethyl)silane (0.068 mL), and the mixture was stirred overnight at 50° C. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate to ethyl acetate/methanol) to give the title compound (10.9 mg).
$^1$H NMR (300 MHz, DMSO-$d_6$) δ 0.73 (3H, t, J=7.2 Hz), 1.74-1.91 (2H, m), 3.21 (3H, s), 3.57-3.69 (1H, m), 3.70-3.82 (1H, m), 4.50 (1H, brs), 6.64 (1H, d, J=6.8 Hz), 7.02-7.12 (1H, m), 7.28 (2H, s), 7.65 (1H, s), 7.75 (2H, d, J=8.3 Hz), 8.07 (2H, d, J=8.7 Hz), 10.85 (1H, d, J=5.7 Hz).
MS (ESI+): [M+H]+ 376.1.
MS (ESI+). found: 376.1.

Example 18

4-(4-oxo-1-(tetrahydrofuran-3-yl)-4,5-dihydro-1H-pyrrolo[3,2-c]pyridin-3-yl)benzenesulfonamide A) 3-iodo-4-methoxy-1-(tetrahydrofuran-3-yl)-1H-pyrrolo[3,2-c]pyridine To a solution of 3-iodo-4-methoxy-1H-pyrrolo[3,2-c]pyridine (0.100 g) in DMF (5 mL) was added sodium hydride (60% dispersion in mineral oil, 36.1 mg), and the mixture was stirred at room temperature for 1 hr. Tetrahydrofuran-3-yl 4-methylbenzenesulfonate (221 mg) was added thereto, and the mixture was stirred overnight at room temperature. The reaction mixture was extracted with water and ethyl acetate, and the organic layer was washed with saturated brine, dried over anhydrous magnesium sulfate, filtered, and concentrated under reduced pressure. The obtained residue was purified by silica gel column chromatography (hexane/ethyl acetate) to give the title compound (115 mg).
MS (ESI+): [M+H]+ 345.0.
MS (ESI+). found: 344.9.

B) 4-(4-methoxy-1-(tetrahydrofuran-3-yl)-1H-pyrrolo[3,2-c]pyridin-3-yl)benzenesulfonamide To a solution of 3-iodo-4-methoxy-1-(tetrahydrofuran-3-yl)-1H-pyrrolo[3,2-c]pyridine (60.0 mg) in DMF (2 mL)/water (0.20 mL) were added 4-(4,4,5,5-tetramethyl-1,3,2-dioxaborolan-2-yl)benzenesulfonamide (74.0 mg), tetrakis(triphenylphosphine)palladium(0) (20.1 mg) and potassium carbonate (48.2 mg). The reaction mixture was stirred under microwave irradiation at 130° C. for 1 hr. The reaction mixture was diluted with water, and the mixture was extracted with ethyl acetate. The organic layer was washed with saturated brine, dried over anhydrous magnesium sulfate, filtered, and concentrated under reduced pressure. The obtained residue was purified by silica gel column chromatography (hexane/ethyl acetate) to give the title compound (19.6 mg).
$^1$H NMR (300 MHz, DMSO-$d_6$) δ 2.19 (1H, dd, J=9.8, 5.3 Hz), 2.55 (1H, d, J=6.1 Hz), 3.84 (1H, td, J=8.5, 6.4 Hz), 3.92 (3H, s), 3.96-4.01 (2H, m), 4.07-4.18 (1H, m), 5.29 (1H, dd, J=8.3, 4.5 Hz), 7.29-7.36 (3H, m), 7.64 (1H, s), 7.76-7.83 (4H, m), 7.86 (1H, d, J=5.7 Hz).

C) 4-(4-oxo-1-(tetrahydrofuran-3-yl)-4,5-dihydro-1H-pyrrolo[3,2-c]pyridin-3-yl)benzenesulfonamide To a solution of 4-(4-methoxy-1-(tetrahydrofuran-3-yl)-1H-pyrrolo[3,2-c]pyridin-3-yl)benzenesulfonamide (17.1 mg) in acetonitrile (2 mL) were added sodium iodide (17.1 mg) and chloro(trimethyl)silane (0.058 mL), and the mixture was stirred overnight at 50° C. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate to ethyl acetate/methanol) to give the title compound (11.1 mg).
$^1$H NMR (300 MHz, DMSO-$d_6$) δ 1.11-1.27 (1H, m), 2.08-2.25 (1H, m), 3.76-3.87 (1H, m), 3.96 (2H, d, J=5.3 Hz), 4.05-4.17 (1H, m), 5.18 (1H, dq, J=8.3, 4.4 Hz), 6.66 (1H, d, J=7.2 Hz), 7.08-7.18 (1H, m), 7.28 (2H, s), 7.52 (1H, s), 7.74 (2H, d, J=8.3 Hz), 8.05 (2H, d, J=8.7 Hz), 10.93 (1H, d, J=5.3 Hz).
MS (ESI+): [M+H]+ 360.1.
MS (ESI+). found: 360.1.

Example 19

4-((7-oxo-3-phenyl-6,7-dihydro-1H-pyrazolo[3,4-c]pyridin-1-yl)methyl)benzenesulfonamide A) 4-((7-methoxy-3-phenyl-1H-pyrazolo[3,4-c]pyridin-1-yl)methyl)benzenesulfonamide To a solution of 7-methoxy-3-phenyl-1H-pyrazolo[3,4-c]pyridine (193 mg) obtained in Step C of Example 10 in THF (30 mL) was added sodium hydride (60% dispersion in mineral oil, 70 mg) at room temperature, and the mixture was stirred at room temperature for 10 min. 4-(Bromomethyl)benzenesulfonamide (220 mg) was added thereto at room temperature, and the mixture was stirred at room temperature for 3 days, and then overnight at 60° C. Sodium hydride (60% dispersion in mineral oil, 70 mg) and 4-(bromomethyl)benzenesulfonamide (220 mg) were added thereto, and the mixture was stirred at 60° C. for 10 hr. To the reaction mixture was added water, and the mixture was extracted with ethyl acetate. The organic layer was dried over anhydrous sodium sulfate, and concentrated under reduced pressure. The residue was purified by silica gel column chromatography (ethyl acetate/hexane) to give the title compound (173 mg).
$^1$H NMR (300 MHz, DMSO-$d_6$) δ 4.07 (3H, s), 5.94 (2H, s), 7.31 (2H, brs), 7.39-7.48 (3H, m), 7.50-7.58 (2H, m), 7.65 (1H, d, J=5.7 Hz), 7.74-7.80 (2H, m), 7.84 (1H, s), 7.97 (2H, dd, J=8.5, 1.3 Hz).

B) 4-((7-oxo-3-phenyl-6,7-dihydro-1H-pyrazolo[3,4-c]pyridin-1-yl)methyl)benzenesulfonamide To a solution of 4-((7-methoxy-3-phenyl-1H-pyrazolo[3,4-c]pyridin-1-yl)methyl)benzenesulfonamide (155 mg) in acetonitrile (30 mL) were added sodium iodide (118 mg) and chloro(trimethyl)silane (342 mg), and the mixture was stirred at 60° C. for 1 hr. The reaction mixture was concentrated under reduced pressure, and the residue was purified by silica gel column chromatography (methanol/ethyl acetate). To the obtained residue was added water, and the mixture was extracted with ethyl acetate. The organic layer was washed with water and saturated brine, dried over anhydrous sodium sulfate, and concentrated under reduced pressure. The residue was crystallized from ethyl acetate and hexane to give the title compound (147 mg).

$^1$H NMR (300 MHz, DMSO-d$_6$) δ 6.02 (2H, s), 6.83 (1H, d, J=7.2 Hz), 7.05 (1H, d, J=7.2 Hz), 7.31 (2H, brs), 7.35-7.55 (5H, m), 7.78 (2H, d, J=8.3 Hz), 7.80-7.88 (2H, m), 11.55 (1H, brs).

Example 20

(4-(1-(1-methoxybutan-2-yl)-4-oxo-4,5-dihydro-1H-pyrrolo[3,2-c]pyridin-3-yl)phenyl)acetonitrile A) (4-(1-(1-methoxybutan-2-yl)-4-oxo-4,5-dihydro-1H-pyrrolo[3,2-c]pyridin-3-yl)phenyl)acetonitrile To a solution of 3-iodo-4-methoxy-1-(1-methoxybutan-2-yl)-1H-pyrrolo[3,2-c]pyridine (50.0 mg) obtained in Step A-2 of Example 17 in DMF (2 mL)/water (0.20 mL) were added (4-(cyanomethyl)phenyl)boronic acid (33.8 mg), tetrakis(triphenylphosphine)palladium(0) (15.9 mg) and potassium carbonate (38.3 mg). The reaction mixture was stirred under microwave irradiation at 130° C. for 30 min. The reaction mixture was diluted with water, and the mixture was extracted with ethyl acetate. The organic layer was washed with saturated brine, dried over anhydrous magnesium sulfate, filtered, and concentrated under reduced pressure. The obtained residue was purified by silica gel column chromatography (hexane/ethyl acetate) to give the title compound (20.2 mg).

$^1$H NMR (300 MHz, DMSO-d$_6$) δ 0.67-0.77 (3H, m), 1.87 (2H, quin, J=7.2 Hz), 3.20 (3H, s), 3.61-3.71 (1H, m), 3.72-3.83 (1H, m), 3.90 (3H, s), 4.06 (2H, s), 4.52-4.69 (1H, m), 7.26 (1H, d, J=6.1 Hz), 7.35 (2H, d, J=8.0 Hz), 7.58-7.68 (3H, m), 7.78 (1H, d, J=6.1 Hz).

MS (ESI+): [M+H]$^+$ 350.2.
MS (ESI+). found: 350.1.

B) (4-(1-(1-methoxybutan-2-yl)-4-oxo-4,5-dihydro-1H-pyrrolo[3,2-c]pyridin-3-yl)phenyl)acetonitrile To a solution of (4-(4-methoxy-1-(1-methoxybutan-2-yl)-1H-pyrrolo[3,2-c]pyridin-3-yl)phenyl)acetonitrile (18.0 mg) in acetonitrile (2 mL) were added sodium iodide (19.3 mg) and chloro(trimethyl)silane (0.065 mL), and the mixture was stirred overnight at 50° C. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate to ethyl acetate/methanol) to give the title compound (11.6 mg).

$^1$H NMR (300 MHz, DMSO-d$_6$) δ 0.73 (3H, t, J=7.4 Hz), 1.73-1.91 (2H, m), 3.21 (3H, s), 3.56-3.67 (1H, m), 3.67-3.80 (1H, m), 4.02 (2H, s), 4.40-4.55 (1H, m), 6.60 (1H, d, J=7.2 Hz), 6.98-7.09 (1H, m), 7.29 (2H, d, J=8.3 Hz), 7.49 (1H, s), 7.89 (1H, d, J=8.3 Hz), 10.77 (1H, d, J=5.7 Hz).

MS (ESI+): [M+H]$^+$ 336.2.
MS (ESI+). found: 336.1.

Example 21 methyl 4-(4-oxo-1-(tetrahydro-2H-pyran-4-yl)-4,5-dihydro-1H-pyrazolo[4,3-c]pyridin-3-yl)thiophene-2-carboxylate A) methyl 4-(4-methoxy-1-(tetrahydro-2H-pyran-4-yl)-1H-pyrazolo[4,3-c]pyridin-3-yl)thiophene-2-carboxylate A solution of 4-methoxy-1-(tetrahydro-2H-pyran-4-yl)-1H-pyrazolo[4,3-c]pyridin-3-yl trifluoromethanesulfonate (250 mg) obtained in Step A of Example 15, methyl 4-(4,4,5,5-tetramethyl-1,3,2-dioxaborolan-2-yl)thiophene-2-carboxylate (264 mg), tetrakis(triphenylphosphine)palladium (0) (76.0 mg) and 2M aqueous sodium carbonate solution (1.60 mL) in DME (15 mL) was heated overnight with reflux under nitrogen atmosphere. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane) to give the title compound (167 mg).

$^1$H NMR (300 MHz, DMSO-d$_6$) δ 1.92 (2H, dd, J=12.7 Hz, 2.5 Hz), 2.18 (2H, qd, J=12.1 Hz, 4.5 Hz), 3.50-3.66 (2H, m), 3.88 (3H, s), 3.96-4.15 (5H, m), 4.82-5.01 (1H, m), 7.43 (1H, d, J=6.4 Hz), 7.96 (1H, d, J, =6.4 Hz), 8.35 (1H, d, J=1.5 Hz), 8.57 (1H, d, J=1.5 Hz).

MS (ESI+): [M+H]$^+$ 374.1.
MS (ESI+). found: 374.1.

B) methyl 4-(4-oxo-1-(tetrahydro-2H-pyran-4-yl)-4,5-dihydro-1H-pyrazolo[4,3-c]pyridin-3-yl)thiophene-2-carboxylate To a solution of methyl 4-(4-methoxy-1-(tetrahydro-2H-pyran-4-yl)-1H-pyrazolo[4,3-c]pyridin-3-yl)thiophene-2-carboxylate (146 mg) in acetonitrile (10 mL) were added sodium iodide (117 mg) and chloro(trimethyl)silane (0.396 mL)(and the mixture was stirred at 60° C. for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane), and the obtained solid was washed with ethyl acetate/diisopropyl ether to give the title compound (131 mg).

$^1$H NMR (300 MHz, DMSO-d$_6$) δ 1.88 (2H, dd, J=12.5 Hz, 2.3 Hz), 2.15 (2H, qd, J=12.1 Hz, 4.5 Hz), 3.44-3.64 (2H, m), 3.86 (3H, s), 4.01 (2H, dd, J=11.0 Hz, 3.8 Hz), 4.79 (1H, tt, J=11.3 Hz, 4.2 Hz), 6.75 (1H, d, J=6.8 Hz), 7.27 (1H, dd, J=7.4 Hz, 5.9 Hz), 8.53 (1H, d, J=1.1 Hz), 9.11 (1H, d, J=1.5 Hz), 11.16 (1H, d, J=5.7 Hz).

MS (ESI+): [M+H]$^+$ 360.1.
MS (ESI+). found: 360.1.

Example 22

(4-(4-oxo-1-(tetrahydrofuran-3-yl)-4,5-dihydro-1H-pyrrolo[3,2-c]pyridin-3-yl)phenyl)acetonitrile A) (4-(4-methoxy-1-(tetrahydrofuran-3-yl)-1H-pyrrolo[3,2-c]pyridin-3-yl)phenyl)acetonitrile To a solution of 3-iodo-4-methoxy-1-(tetrahydrofuran-3-yl)-1H-pyrrolo[3,2-c]pyridine (50.0 mg) obtained in Step A of Example 19 in DMF (2 mL)/water (0.20 mL) were added (4-(cyanomethyl)phenyl)boronic acid (35.1 mg), tetrakis(triphenylphosphine)palladium(0) (16.8 mg) and potassium carbonate (40.2 mg). The reaction mixture was stirred under microwave irradiation at 130° C. for 30 min. The reaction mixture was diluted with water, and the mixture was extracted with ethyl acetate. The organic layer was washed with saturated brine, dried over anhydrous magnesium sulfate, filtered, and concentrated under reduced pressure. The obtained residue was purified by silica gel column chromatography (hexane/ethyl acetate) to give the title compound (16.8 mg).

MS (ESI+): [M+H]$^+$ 334.2.
MS (ESI+). found: 334.1.

B) (4-(4-oxo-1-(tetrahydrofuran-3-yl)-4,5-dihydro-1H-pyrrolo[3,2-c]pyridin-3-yl)phenyl)acetonitrile To a solution of (4-(4-methoxy-1-(tetrahydrofuran-3-yl)-1H-pyrrolo[3,2-c]pyridin-3-yl)phenyl)acetonitrile (14.0 mg) in acetonitrile (2 mL) were added sodium iodide (15.7 mg) and chloro(trimethyl)silane (0.053 mL), and the mixture was stirred overnight at 50° C. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate to ethyl acetate/methanol) to give the title compound (7.2 mg).

$^1$H NMR (300 MHz, DMSO-d$_6$) δ 2.07-2.22 (1H, m), 2.41-2.47 (1H, m), 3.81 (1H, td, J=8.5, 6.4 Hz), 3.92-3.97 (2H, m), 4.02 (2H, s), 4.05-4.15 (1H, m), 5.08-5.23 (1H, m), 6.64 (1H, d, J=6.8 Hz), 7.04-7.14 (1H, m), 7.29 (2H, d, J=8.3 Hz), 7.38 (1H, s), 7.86 (2H, d, J=8.3 Hz), 10.85 (1H, d, J=5.7 Hz).

MS (ESI+): [M+H]$^+$ 320.1.
MS (ESI+). found: 320.1.

Example 23

4-(4-oxo-1-(tetrahydro-2H-pyran-4-yl)-4,5-dihydro-1H-pyrazolo[4,3-c]pyridin-3-yl)thiophene-2-carboxylic acid To a solution of methyl 4-(4-oxo-1-(tetrahydro-2H-pyran-4-yl)-4,5-dihydro-1H-pyrazolo[4,3-c]pyridin-3-yl)thiophene-2-carboxylate (125 mg) obtained in Example 21 in methanol (20 mL) was added 1N aqueous sodium hydroxide solution (5 mL) under ice-cooling, and the mixture was stirred at 50° C. for 6 hr. The reaction mixture was concentrated under reduced pressure to evaporate the methanol, and the residue was partitioned between ethyl acetate and 1N hydrochloric acid (6 mL). The organic layer was washed with saturated brine, dried over anhydrous sodium sulfate, and concentrated under reduced pressure to give the title compound (119 mg).

$^1$H NMR (300 MHz, DMSO-d$_6$) δ 1.77-1.97 (2H, m), 2.15 (2H, dd, J=11.9 Hz, 4.0 Hz), 3.55 (2H, t, J=11.0 Hz), 4.01 (2H, dd, J=10.8 Hz, 3.6 Hz), 4.67-4.90 (1H, m), 6.75 (1H, d, J=6.8 Hz), 7.26 (1H, dd, J=7.2 Hz, 6.0 Hz), 8.44 (1H, d, J=1.5 Hz), 9.06 (1H, d, J=1.5 Hz), 11.17 (1H, d, J=5.7 Hz), 13.09 (1H, brs).

MS (ESI+): [M+H]$^+$ 346.1.
MS (ESI+). found: 346.0.

Example 24

4-(1-(1-methoxybutan-2-yl)-4-oxo-4,5-dihydro-1H-pyrrolo[3,2-c]pyridin-3-yl)benzonitrile A) 4-(4-methoxy-1-(1-methoxybutan-2-yl)-1H-pyrrolo[3,2-c]pyridin-3-yl)benzonitrile To a solution of 3-iodo-4-methoxy-1-(1-methoxybutan-2-yl)-1H-pyrrolo[3,2-c]pyridine (200 mg) obtained in Step A-2 of Example 17 in DMF (4 mL)/water (0.40 mL) were added 4-(4,4,5,5-tetramethyl-1,3,2-dioxaborolan-2-yl)benzonitrile (191 mg), tetrakis(triphenylphosphine)palladium(0) (64.2 mg) and potassium carbonate (154 mg). The reaction mixture was stirred under microwave irradiation at 130° C. for 30 min. The reaction mixture was diluted with water, and the mixture was extracted with ethyl acetate. The organic layer was washed with saturated brine, dried over anhydrous magnesium sulfate, filtered, and concentrated under reduced pressure. The obtained residue was purified by silica gel column chromatography (hexane/ethyl acetate) to give the title compound (40.0 mg).

$^1$H NMR (300 MHz, DMSO-d$_6$) δ 0.72 (3H, t, J=7.4 Hz), 1.88 (2H, quin, J=7.3 Hz), 3.20 (3H, s), 3.61-3.70 (1H, m), 3.74-3.84 (1H, m), 3.93 (3H, s), 4.58-4.70 (1H, m), 7.30 (1H, d, J=6.1 Hz), 7.79-7.87 (6H, m).

MS (ESI+): [M+H]$^+$ 336.2.
MS (ESI+). found: 336.1.

B) 4-(1-(1-methoxybutan-2-yl)-4-oxo-4,5-dihydro-1H-pyrrolo[3,2-c]pyridin-3-yl)benzonitrile To a solution of 4-(4-methoxy-1-(1-methoxybutan-2-yl)-1H-pyrrolo[3,2-c]pyridin-3-yl)benzonitrile (38.0 mg) in acetonitrile (3 mL) were added sodium iodide (42.5 mg) and chloro(trimethyl)silane (0.144 mL), and the mixture was stirred overnight at 50° C. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate to ethyl acetate/methanol) to give the title compound (26.2 mg).

$^1$H NMR (300 MHz, DMSO-d$_6$) δ 0.73 (3H, t, J=7.2 Hz), 1.76-1.90 (2H, m), 3.21 (3H, s), 3.58-3.67 (1H, m), 3.69-3.80 (1H, m), 4.44-4.58 (1H, m), 6.64 (1H, d, J=7.2 Hz), 7.04-7.13 (1H, m), 7.71-7.80 (3H, m), 8.15-8.23 (2H, m), 10.92 (1H, d, J=5.3 Hz).

MS (ESI+): [M+H]$^+$ 322.2.
MS (ESI+). found: 322.1.

Example 25

(4-(4-oxo-1-(tetrahydro-2H-pyran-4-yl)-4,5-dihydro-1H-pyrrolo[3,2-c]pyridin-3-yl)phenyl)acetonitrile A) (4-(4-methoxy-1-(tetrahydro-2H-pyran-4-yl)-1H-pyrrolo[3,2-c]pyridin-3-yl)phenyl)acetonitrile To a solution of 3-iodo-4-methoxy-1-(tetrahydro-2H-pyran-4-yl)-1H-pyrrolo[3,2-c]pyridine (20.0 mg) obtained in Step A of Example 16 in DMF (2 mL)/water (0.20 mL) were added (4-(cyanomethyl)phenyl)boronic acid (13.5 mg), tetrakis(triphenylphosphine)palladium(0) (6.45 mg) and potassium carbonate (15.4 mg). The reaction mixture was stirred under microwave irradiation at 130° C. for 1 hr. The reaction mixture was diluted with water, and the mixture was extracted with ethyl acetate. The organic layer was washed with saturated brine, dried over anhydrous magnesium sulfate, filtered, and concentrated under reduced pressure. The obtained residue was purified by silica gel column chromatography (hexane/ethyl acetate=4/1 to 2/1) to give the title compound (12.0 mg) as a white solid.

$^1$H NMR (300 MHz, DMSO-$d_6$) δ 1.89-1.94 (2H, m), 2.01-2.15 (2H, m), 3.54-3.61 (2H, m), 3.90 (3H, s), 3.99-4.03 (2H, m), 4.05 (2H, s), 4.60-4.75 (1H, m), 7.30-7.37 (2H, m), 7.61-7.68 (4H, m), 7.81 (1H, d, J=6.1 Hz).

B) (4-(4-oxo-1-(tetrahydro-2H-pyran-4-yl)-4,5-dihydro-1H-pyrrolo[3,2-c]pyridin-3-yl)phenyl)acetonitrile To a solution of (4-(4-methoxy-1-(tetrahydro-2H-pyran-4-yl)-1H-pyrrolo[3,2-c]pyridin-3-yl)phenyl)acetonitrile (10.2 mg) in acetonitrile (1 mL) were added sodium iodide (10.8 mg) and chloro(trimethyl)silane (0.037 mL), and the mixture was stirred overnight at 50° C. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate to ethyl acetate/methanol) to give the title compound (5.7 mg).

$^1$H NMR (300 MHz, DMSO-$d_6$) δ 1.82-1.93 (2H, m), 1.96-2.14 (2H, m), 3.55 (2H, t, J=11.0 Hz), 3.93-4.07 (4H, m), 4.47-4.62 (1H, m), 6.67 (1H, d, J=7.2 Hz), 7.03-7.13 (1H, m), 7.28 (2H, d, J=8.3 Hz), 7.55 (1H, s), 7.89 (2H, d, J=8.3 Hz), 10.81 (1H, d, J=5.7 Hz).

MS (ESI+): [M+H]$^+$ 334.2.
MS (ESI+). found: 334.1.

Example 26

4-(1-(1-methoxybutan-2-yl)-4-oxo-4,5-dihydro-1H-pyrrolo[3,2-c]pyridin-3-yl)benzamide To a solution of 4-(1-(1-methoxybutan-2-yl)-4-oxo-4,5-dihydro-1H-pyrrolo[3,2-c]pyridin-3-yl)benzonitrile (20.0 mg) obtained in Example 24 in DMSO (0.5 mL) was added potassium carbonate (10.3 mg) at 0° C., 30% aqueous hydrogen peroxide (0.019 mL) was added thereto, and the mixture was stirred overnight at room temperature. The reaction mixture was diluted with water, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate to ethyl acetate/methanol) to give the title compound (18.1 mg).

$^1$H NMR (300 MHz, DMSO-$d_6$) δ 0.73 (3H, t, J=7.2 Hz), 1.76-1.93 (2H, m), 3.21 (3H, s), 3.59-3.68 (1H, m), 3.70-3.80 (1H, m), 4.43-4.57 (1H, m), 6.62 (1H, d, J=7.2 Hz), 7.01-7.10 (1H, m), 7.26 (1H, brs), 7.61 (1H, s), 7.83 (2H, d, J=8.7 Hz), 7.92 (1H, brs), 7.99 (2H, d, J=8.3 Hz), 10.82 (1H, d, J=5.7 Hz).

MS (ESI+): [M+H]$^+$ 340.2.
MS (ESI+). found: 340.1.

Example 27

4-(4-oxo-1-(tetrahydro-2H-pyran-4-yl)-4,5-dihydro-1H-pyrazolo[4,3-c]pyridin-3-yl)thiophene-2-carboxamide A solution of 4-(4-oxo-1-(tetrahydro-2H-pyran-4-yl)-4,5-dihydro-1H-pyrazolo[4,3-c]pyridin-3-yl)thiophene-2-carboxylic acid (105 mg) obtained in Example 23, HOBt ammonium salt (139 mg) and EDCI hydrochloride (175 mg) in DMF (15 mL) was stirred overnight at room temperature. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane/methanol) to give the title compound (91 mg).

$^1$H NMR (300 MHz, DMSO-$d_6$) δ 1.88 (2H, dd, J=12.5 Hz, 2.6 Hz), 2.18 (2H, qd, J=12.1 Hz, 4.5 Hz), 3.55 (2H, t, J=11.0 Hz), 3.93-4.11 (2H, m), 4.78 (1H, tt, J=11.2 Hz, 4.2 Hz), 6.73 (1H, d, J=6.4 Hz), 7.26 (1H, dd, J=7.2 Hz, 6.0 Hz), 7.39 (1H, brs), 8.14 (1H, brs), 8.37 (1H, d, J=1.1 Hz), 9.15 (1H, d, J=1.1 Hz), 11.13 (1H, d, J=5.7 Hz).

MS (ESI+): [M-NH$_2$]$^+$ 328.1.
MS (ESI+). found: 328.0.

Example 28

4-(4-oxo-1-(tetrahydro-2H-pyran-3-yl)-4,5-dihydro-1H-pyrazolo[4,3-c]pyridin-3-yl)benzenesulfonamide A) tert-butyl 2-(tetrahydro-2H-pyran-3-yl)hydrazinecarboxylate A solution of tert-butyl dihydro-2H-pyran-3(4H)-one (4.00 g) and hydrazinecarboxylate (5.54 g) in methanol (20 mL) was stirred at room temperature for 1 hr, and the mixture was concentrated under reduced pressure. The residue was dissolved in THF (50 mL), acetic acid (6.86 mL) and sodium borohydride (0.840 g) were added thereto, and the mixture was stirred at 0° C. for 1 hr. To the reaction mixture was added 8N aqueous sodium hydroxide solution, and the mixture was extracted with ethyl acetate. The organic layer was washed successively with saturated aqueous sodium hydrogencarbonate solution and saturated brine, dried over anhydrous sodium sulfate, and concentrated under reduced pressure. The residue was purified by silica gel column chromatography (ethyl acetate/hexane) to give the title compound (4.18 g).

$^1$H NMR (300 MHz, DMSO-$d_6$) δ 1.13-1.31 (1H, m), 1.32-1.51 (10H, m), 1.55-1.69 (1H, m), 1.70-1.84 (1H, m), 2.66-2.81 (1H, m), 3.01 (1H, dd, J=11.0 Hz, 8.7 Hz), 3.24 (1H, td, J=10.7 Hz, 2.8 Hz), 3.59-3.78 (2H, m), 4.28 (1H, dd, J=4.3 Hz, 3.6 Hz), 8.18 (1H, brs).

B) tetrahydro-2H-pyran-3-ylhydrazine dihydrochloride tert-Butyl 2-(tetrahydro-2H-pyran-3-yl)hydrazinecarboxylate (3.65 g) was dissolved in 4N hydrogen chloride-ethyl acetate solution (85 mL) under ice-cooling, and the solution was stirred overnight, at room temperature. The reaction mixture was concentrated under reduced pressure to give the title compound (2.40 g).

¹H NMR (300 MHz, DMSO-d₆) δ 1.32-1.63 (2H, m), 1.63-1.80 (1H, m), 1.85-2.04 (1H, m), 2.98 (1H, tt, J=7.9 Hz, 3.8 Hz), 3.25-3.48 (2H, m), 3.64 (1H, dt, J=11.1 Hz, 4.4 Hz), 3.78-3.97 (1H, m), 7.20 (3H, brs).

C) 4-iodo-2-methoxy-N'-(tetrahydro-2H-pyran-3-yl) nicotinohydrazide

A solution of 4-iodo-2-methoxynicotinic acid (3.0 g) obtained in Step C of Example 6, tetrahydro-2H-pyran-3-ylhydrazine dihydrochloride (2.44 g), DIEA (5.63 mL), EDCI hydrochloride (2.47 g) and HOBt (1.74 g) in DMF (50 mL) was stirred overnight at room temperature. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane) to give the title compound (2.36 g).

¹H NMR (300 MHz, DMSO-d₆) δ 1.37-1.58 (2H, m), 1.61-1.78 (1H, m), 1.84-2.03 (1H, m), 2.94-3.08 (1H, m), 3.18-3.41 (2H, m), 3.61-3.72 (1H, m), 3.83 (3H, s), 3.86-3.96 (1H, m), 7.48 (1H, d, J=5.3 Hz), 7.87 (1H, d, J=5.7 Hz), 10.08 (1H, brs).

MS (ESI+): [M+H]⁺ 377.9.
MS (ESI+). found: 378.0.

D) 4-methoxy-1-(tetrahydro-2H-pyran-3-yl)-1,2-dihydro-3H-pyrazolo[4,3-c]pyridin-3-one A solution of 4-iodo-2-methoxy-N'-(tetrahydro-2H-pyran-3-yl)nicotinohydrazide (484 mg), L-proline (29.5 mg), potassium carbonate (355 mg) and copper(I) iodide (24.4 mg) in DMSO (25 mL) was stirred under nitrogen atmosphere at room temperature for 3 hr. The reaction mixture was purified by silica gel column chromatography (ethyl acetate/hexane) to give the title compound (100 mg).

¹H NMR (300 MHz, DMSO-d₆) δ 1.76 (2H, d, J=3.4 Hz), 1.94-2.15 (2H, m), 3.23-3.42 (1H, m), 3.50-3.64 (1H, m), 3.79-4.00 (5H, m), 4.36-4.57 (1H, m), 7.15 (1H, d, J=6.4 Hz), 7.77 (1H, d, J=6.0 Hz), 10.95 (1H, brs).

MS (ESI+): [M+H]⁺ 250.1.
MS (ESI+). found: 250.1.

E) 4-methoxy-1-(tetrahydro-2H-pyran-3-yl)-1H-pyrazolo[4,3-c]pyridin-3-yl trifluoromethanesulfonate To a solution of 4-methoxy-1-(tetrahydro-2H-pyran-3-yl)-1,2-dihydro-3H-pyrazolo[4,3-c]pyridin-3-one (187 mg) and pyridine (0.243 mL) in acetonitrile (25 mL) was added trifluoromethanesulfonic anhydride (0.203 mL), and the mixture was stirred at 0° C. for 1 hr. To the reaction mixture was added saturated aqueous ammonium chloride solution, and the mixture was extracted with ethyl acetate. The organic layer was washed successively with 0.1N hydrochloric acid, water, saturated aqueous sodium hydrogencarbonate solution and saturated brine, dried over anhydrous sodium sulfate, and concentrated under reduced pressure. The residue was purified by silica gel column chromatography (ethyl acetate/hexane) to give the title compound (268 mg).

¹H NMR (300 MHz, DMSO-d₆) δ 1.66-1.88 (2H, m), 1.96-2.22 (2H, m), 3.42 (1H, td, J=10.8 Hz, 3.8 Hz), 3.57 (1H, t, J=10.4 Hz), 3.82-3.92 (1H, m), 3.93-4.02 (1H, m), 4.03 (3H, s), 4.80 (1H, tt, J=10.0 Hz, 4.7 Hz), 7.53 (1H, d, J=6.4 Hz), 8.04 (1H, d, J=6.0 Hz).

MS (ESI+): [M+H]⁺ 382.1.
MS (ESI+). found: 382.1.

F) 4-(4-methoxy-1-(tetrahydro-2H-pyran-3-yl)-1H-pyrazolo[4,3-c]pyridin-3-yl)benzenesulfonamide A solution of 4-methoxy-1-(tetrahydro-2H-pyran-3-yl)-1H-pyrazolo[4,3-c]pyridin-3-yl trifluoromethanesulfonate (254 mg), 4-(4,4,5,5-tetramethyl-1,3,2-dioxaborolan-2-yl)benzenesulfonamide (207 mg), tetrakis(triphenylphosphine)palladium(0) (77.0 mg) and 2M aqueous sodium carbonate solution (1.0 mL) in DME (15 mL) was heated overnight with reflux under nitrogen atmosphere. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane), and the obtained solid was washed with ethyl acetate/diisopropyl ether to give the title compound (181 mg).

¹H NMR (300 MHz, DMSO-d₆) δ 1.68-1.94 (2H, m), 2.07-2.37 (2H, m), 3.38-3.55 (1H, m), 3.65-3.81 (1H, m), 3.85-4.11 (5H, m), 4.73-4.89 (1H, m), 7.42 (2H, s), 7.49 (1H, d, J=6.4 Hz), 7.88-7.96 (2H, m), 7.98 (1H, d, J=6.0 Hz), 8.04-8.15 (2H, m).

MS (ESI+): [M+H]⁺ 389.1.
MS (ESI+). found: 389.2.

G) 4-(4-oxo-1-(tetrahydro-2H-pyran-3-yl)-4,5-dihydro-1H-pyrazolo[4,3-c]pyridin-3-yl)benzenesulfonamide To a solution of 4-(4-methoxy-1-(tetrahydro-2H-pyran-3-yl)-1H-pyrazolo[4,3-c]pyridin-3-yl)benzenesulfonamide (160 mg) in acetonitrile (15 mL) were added sodium iodide (124 mg) and chloro(trimethyl)silane (0.418 mL), and the mixture was stirred at 60° C. for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane), and the obtained solid was washed with ethyl acetate/diisopropyl ether to give the title compound (153 mg).

¹H NMR (300 MHz, DMSO-d₆) δ 1.72-1.91 (2H, m), 2.05-2.31 (2H, m), 3.36-3.52 (1H, m), 3.65-3.79 (1H, m), 3.91 (1H, d, J=11.3 Hz), 3.95-4.06 (1H, m), 4.59-4.77 (1H, m), 6.79 (1H, d, J=7.6 Hz), 7.28 (1H, dd, J=7.0 Hz, 5.9 Hz), 7.39 (2H, s), 7.78-7.93 (2H, m), 8.37-8.59 (2H, m), 11.17 (1H, d, J=5.3 Hz).

MS (ESI+): [M+H]⁺ 375.1.
MS (ESI+). found: 375.1.

Example 29 methyl 3-(4-carbamoyl phenyl)-1-cyclopentyl-4-oxo-4,5-dihydro-1H-pyrrolo[3,2-c]pyridine-7-carboxylate A) 2-(carboxymethyl)-1-cyclopentyl-1H-pyrrole-3-carboxylic acid To a solution of cyclopentanamine (175 g) in water (150 mL) was added 3-oxopentanedioic acid (30 g) at 20° C. or lower, 2-chloroacetaldehyde (40% aqueous solution, 43 mL) was added dropwise thereto at 10° C. or lower, and the mixture was stirred at room temperature for 14 hr. 6N Hydrochloric acid (150 mL) was added thereto at 0° C., and the black precipitate was removed by filtration. To the filtrate was added 6N hydrochloric acid (50 mL) at 0° C., and the precipitate was collected by filtration to give the title compound (40 g).

$^1$H NMR (300 MHz, DMSO-d$_6$) δ 1.62-1.83 (6H, m), 2.04 (2H, dd, J=7.7, 4.3 Hz), 4.09 (2H, s), 4.36-4.51 (1H, m), 6.39 (1H, d, J=3.4 Hz), 6.77-6.86 (1H, m), 11.22-12.53 (2H, m).

MS (ESI+): [M+H]$^+$ 238.2.
MS (ESI+). found: 238.1.

B) methyl 1-cyclopentyl-2-(2-methoxy-2-oxoethyl)-1H-pyrrole-3-carboxylate

To a solution of 2-(carboxymethyl)-1-cyclopentyl-1H-pyrrole-3-carboxylic acid (20 g) in methanol (400 mL) was added conc. sulfuric acid (8.99 mL), and the mixture was stirred at 70° C. for 24 hr. To the reaction mixture was added saturated aqueous sodium bicarbonate solution, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (10.7 g).

$^1$H NMR (300 MHz, CDCl$_3$) δ 1.64-1.90 (6H, m), 2.06-2.20 (2H, m), 3.65-3.83 (6H, m), 4.19 (2H, s), 4.41 (1H, t, J=7.2 Hz), 6.58 (1H, d, J=3.0 Hz), 6.67 (1H, d, J=3.0 Hz).

MS (ESI+): [M+H]$^+$ 265.3.
MS (ESI+). found: 266.2.

C) methyl 2-(1-amino-3-methoxy-3-oxoprop-1-en-2-yl)-1-cyclopentyl-1H-pyrrole-3-carboxylate To a solution of methyl 1-cyclopentyl-2-(2-methoxy-2-oxoethyl)-1H-pyrrole-3-carboxylate (20 g) in THF (300 mL) was added sodium hydride (60% dispersion in mineral oil, 12.06 g) at 0° C., and methyl formate was added dropwise thereto at 0° C. The reaction mixture was stirred at room temperature for 5 hr. To the reaction mixture was added methanol at 10° C., and 6N hydrochloric acid was added thereto at 0° C. To the reaction mixture was added water, and the mixture was extracted with ethyl acetate. The organic layer was washed with saturated brine, dried over anhydrous sodium sulfate, and concentrated under reduced pressure. To a solution (240 mL) of the residue (22.15 g) in methanol was added ammonium acetate (27.7 g) at room temperature, and the mixture was stirred at 0° C. for 2 hr, and then at room temperature for 14 hr. The precipitate was collected by filtration to give the title compound (18.26 g).

$^1$H NMR (300 MHz, CDCl$_3$) δ 1.67-1.84 (6H, m), 1.97-2.09 (2H, m), 3.65 (3H, s), 3.73 (3H, s), 4.31 (1H, t, J=7.6 Hz), 4.49 (2H, d, J=10.6 Hz), 6.69 (1H, d, J=3.0 Hz), 6.78 (1H, d, J=3.0 Hz), 7.82 (1H, t, J=11.1 Hz).

MS (ESI+): [M+H]$^+$ 293.3.
MS (ESI+). found: 293.2.

D) methyl 1-cyclopentyl-4-oxo-4,5-dihydro-1H-pyrrolo[3,2-c]pyridine-7-carboxylate To a solution of methyl 2-(1-amino-3-methoxy-3-oxoprop-1-en-2-yl)-1-cyclopentyl-1H-pyrrole-3-carboxylate (20.45 g) in DMF (205 mL) was added sodium tert-butoxide (6.72 g), and the mixture was stirred at 160° C. for 1 hr. The reaction mixture was allowed to be cooled to room temperature, water was added thereto, and the mixture was extracted with ethyl acetate. The organic layer was washed with saturated brine, dried over anhydrous sodium sulfate, and concentrated under reduced pressure. The residue was washed with ethyl acetate and hexane to give the title compound (7.83 g).

$^1$H NMR (300 MHz, CDCl$_3$) δ 1.72-1.89 (6H, m), 2.14-2.28 (2H, m), 3.89 (3H, s), 5.33-5.47 (1H, m), 6.90 (1H, d, J=3.4 Hz), 7.10 (1H, d, J=3.4 Hz), 7.92 (1H, s), 11.68 (1H, brs).

MS (ESI+): [M+H]$^+$ 261.2.
MS (ESI+). found: 261.2.

E) methyl 3-(4-carbamoyl phenyl)-1-cyclopentyl-4-oxo-4,5-dihydro-1H-pyrrolo[3,2-c]pyridine-7-carboxylate E-1) To a solution of methyl 1-cyclopentyl-4-oxo-4,5-dihydro-1H-pyrrolo[3,2-c]pyridine-7-carboxylate (1.3 g) in DMF (15 mL) was added sodium hydride (60% dispersion in mineral oil, 0.28 g) at 0° C., and the mixture was stirred for 20 min. To the reaction mixture was added (2-(chloromethoxy)ethyl)(trimethyl)silane (1.32 mL) at 0° C., and the mixture was stirred at room temperature for 14 hr. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give an oil (0.95 g).

$^1$H NMR (300 MHz, CDCl$_3$) δ −0.02-0.03 (9H, m), 0.91-0.99 (2H, m), 1.70-1.89 (6H, m), 2.14-2.25 (2H, m), 3.56-3.72 (2H, m), 3.91 (3H, s), 5.32-5.37 (1H, m), 5.46 (2H, s), 6.89 (1H, d, J=3.4 Hz), 7.06 (1H, d, J=3.4 Hz), 7.95 (1H, s).

MS (ESI+): [M+H]$^+$ 391.5.
MS (ESI+). found: 391.1.

E-2) To a solution of the obtained, oil (0.95 g) in DMF (10 mL) was added dropwise a solution of NBS (0.45 g) in DMF (5 mL) at 0° C., and the mixture was stirred for 2 hr. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give a powder (0.99 g).

$^1$H NMR (300 MHz, CDCl$_3$) δ −0.04-0.03 (9H, m), 0.85-1.00 (2H, m), 1.62-1.91 (5H, m), 1.97-2.36 (3H, m), 3.58-3.73 (2H, m), 3.84-3.94 (3H, m), 5.14-5.32 (1H, m), 5.35-5.47 (2H, m), 6.90-7.09 (1H, m), 7.85-8.10 (1H, m).

MS (ESI+): [M]$^+$ 469.4.
MS (ESI+). found: 469.1.

E-3) A mixture of the obtained powder (60 mg), (4-carbamoyl phenyl)boronic acid (63 mg), (1,1'-bis(diphenylphosphino)ferrocene)dichloropalladium(II) (10 mg), 2M aqueous sodium carbonate solution (0.128 mL) and DME (1 mL) was stirred under microwave irradiation at 120° C. 15 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give a powder (40 mg).

$^1$H NMR (300 MHz, CDCl$_3$) δ −0.01-0.02 (9H, m), 0.91-1.00 (2H, m), 1.73-1.93 (6H, m), 2.19-2.33 (2H, m), 3.60-3.70 (2H, m), 3.93 (3H, s), 5.29-5.31 (1H, m), 5.42-5.48 (2H, m), 7.15 (1H, s), 7.71-7.76 (2H, m), 7.80-7.86 (2H, m), 8.00 (1H, s).

MS (ESI+): [M+H]$^+$ 510.6.
MS (ESI+). found: 510.2.

E-4) To the obtained powder (40 mg) in THF (0.3 mL) was added 1M tetra-n-butylammonium fluoride THF solution (0.314 mL), and the mixture was stirred at 70° C. for 14 hr. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane). To a solution of the obtained residue in methanol (1 mL) was added ethylene diamine (0.026 mL), and the mixture was stirred at 50° C. for 5 hr. To the reaction mixture was added water, and the mixture was extracted with ethyl acetate. The organic layer was washed with saturated brine, dried over anhydrous sodium sulfate, and concentrated under reduced pressure to give the title compound (1 mg).

$^1$H NMR (300 MHz, CDCl$_3$) δ 1.84-1.92 (6H, m), 2.24 (2H, brs), 3.90 (3H, s), 5.28 (1H, brs), 5.76 (2H, brs), 7.17 (1H, s), 7.80 (5H, d, J=7.9 Hz), 10.41 (1H, brs).

MS (ESI+): [M+H]$^+$ 380.4.

MS (ESI+). found: 380.2.

Example 30

4-(4-oxo-1-phenyl-4,5-dihydro-1H-pyrazolo[4,3-c]pyridin-3-yl)benzenesulfonamide

A) 4-iodo-2-methoxy-N'-phenylnicotinohydrazide

A solution of 4-iodo-2-methoxynicotinic acid (1.5 g) obtained in Step C of Example 6, phenylhydrazine hydrochloride (0.933 g), DIEA (3.0 mL), EDCI hydrochloride (1.24 g) and HOBt (0.872 g) in DMF (100 mL) was stirred overnight at room temperature. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane) to give the title compound (1.06 g).

$^1$H NMR (300 MHz, DMSO-d$_6$) δ 3.91 (3H, s), 6.72 (1H, s), 6.89-7.03 (2H, m), 7.07-7.25 (2H, m), 7.52 (1H, d, J=5.3 Hz), 7.90 (1H, d, J=5.7 Hz), 8.00 (1H, d, J=1.5 Hz), 10.12 (1H, d, J=1.9 Hz).

MS (ESI+): [M+H]$^+$ 370.0.

MS (ESI+). found: 370.0.

B) 4-methoxy-1-phenyl-1,2-dihydro-3H-pyrazolo[4,3-c]pyridin-3-one

A solution of 4-iodo-2-methoxy-N'-phenylnicotinohydrazide (640 mg), L-proline (39.9 mg), potassium carbonate (479 mg) and copper(I) iodide (33.0 mg) in DMSO (25 mL) was stirred overnight at 60° C. under nitrogen atmosphere. The reaction mixture was purified by silica gel column chromatography (ethyl acetate/hexane) to give the title compound (266 mg).

$^1$H NMR (300 MHz, DMSO-d$_6$) δ 3.99 (3H, s), 7.28 (1H, d, J=6.4 Hz), 7.30-7.39 (1H, m), 7.48-7.60 (2H, m), 7.62-7.73 (2H, m), 7.93 (1H, d, J=6.4 Hz), 11.48 (1H, brs).

MS (ESI+): [M+H]$^+$ 242.1.

MS (ESI+). found: 242.1.

C) 4-methoxy-1-phenyl-1H-pyrazolo[4,3-c]pyridin-3-yl trifluoromethanesulfonate

To a solution of 4-methoxy-1-phenyl-1,2-dihydro-3H-pyrazolo[4,3-c]pyridin-3-one (405 mg) and pyridine (0.544 mL) in acetonitrile (50 mL) was added trifluoromethanesulfonic anhydride (0.568 mL), and the mixture was stirred at 0° C. for 1 hr. To the reaction mixture was added saturated aqueous ammonium chloride solution, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (406 mg).

$^1$H NMR (300 MHz, DMSO-d$_6$) δ 4.10 (3H, s), 7.46 (1H, d, J=6.4 Hz), 7.49-7.58 (1H, m), 7.59-7.69 (2H, m), 7.70-7.79 (2H, m), 8.14 (1H, d, J=6.0 Hz).

MS (ESI+): [M+H]$^+$ 374.0.

MS (ESI+). found: 374.0.

D) 4-(4-methoxy-1-phenyl-1H-pyrazolo[4,3-c]pyridin-3-yl)benzenesulfonamide

A solution of 4-methoxy-1-phenyl-1H-pyrazolo[4,3-c]pyridin-3-yl trifluoromethanesulfonate (100 mg), 4-(4,4,5,5-tetramethyl-1,3,2-dioxaborolan-2-yl)benzenesulfonamide (83 mg), tetrakis(triphenylphosphine)palladium(0) (31.0 mg) and 2M aqueous sodium carbonate solution (1.0 mL) in DME (10 mL) was heated overnight with reflux under nitrogen atmosphere. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane) to give the title compound (101 mg).

$^1$H NMR (300 MHz, DMSO-d$_6$) δ 4.05 (3H, s), 7.37-7.57 (4H, m), 7.59-7.72 (2H, m), 7.77-7.88 (2H, m), 7.91-8.02 (2H, m), 8.09 (1H, d, J=6.4 Hz), 8.14-8.26 (2H, m).

MS (ESI+): [M+H]$^+$ 381.1.

MS (ESI+). found: 381.1.

E) 4-(4-oxo-1-phenyl-4,5-dihydro-1H-pyrazolo[4,3-c]pyridin-3-yl)benzenesulfonamide To a solution of 4-(4-methoxy-1-phenyl-1H-pyrazolo[4,3-c]pyridin-3-yl)benzenesulfonamide (82.0 mg) in acetonitrile (10 mL) were added sodium iodide (64.6 mg) and chloro(trimethyl)silane (0.218 mL), and the mixture was stirred at 60° C. for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane/methanol), and the obtained solid was washed with ethyl acetate to give the title compound (79.0 mg).

$^1$H NMR (300 MHz, DMSO-d$_6$) δ 6.63 (1H, d, J=7.2 Hz), 7.28-7.47 (3H, m), 7.48-7.57 (1H, m), 7.58-7.70 (2H, m), 7.71-7.82 (2H, m), 7.85-8.00 (2H, m), 8.43-8.61 (2H, m), 11.39 (1H, brs).

MS (ESI+): [M+H]$^+$ 367.1.

MS (ESI+). found: 367.1.

Example 31

4-(1-(trans-4-hydroxycyclohexyl)-4-oxo-4,5-dihydro-1H-pyrrolo[3,2-c]pyridin-3-yl)benzenesulfonamide A) 1-(trans-4-((tert-butyl(dimethyl)silyl)oxy)cyclohexyl)-3-iodo-4-methoxy-1H-pyrrolo[3,2-c]pyridine A-1) cis-4-((tert-butyl(dimethyl)silyl)oxy)cyclohexanol and trans-4-((tert-butyl(dimethyl)silyl)oxy)cyclohexanol To a solution of cyclohexane-1,4-diol (cis/trans mixture, 5.00 g) in DMF (40 mL) were added triethylamine (6.60 mL) and tert-butyl(chloro)dimethylsilane (7.79 g) at 0° C., and the mixture was stirred at room temperature for 1 hr. The reaction mixture was extracted with ethyl acetate and water, and the obtained organic layer was washed with water and saturated brine, dried over anhydrous magnesium sulfate, filtered, and concentrated under reduced pressure. The obtained residue was purified by silica gel column chromatography (hexane/ethyl acetate) to give the title cis form (2.55 g) and trans form 1.53 g).

cis-4-((tert-butyl(dimethyl)silyl)oxy)cyclohexanol $^1$H NMR (300 MHz, DMSO-$d_6$) δ 0.03 (6H, d, J=6.0 Hz), 0.83-0.90 (9H, m), 1.35-1.63 (8H, m), 3.47 (1H, tq, J=7.4, 3.4 Hz), 3.75 (1H, tt, J=5.8, 2.9 Hz), 4.37 (1H, d, J=3.8 Hz).

trans-4-((tert-butyl(dimethyl)silyl)oxy)cyclohexanol $^1$H NMR (300 MHz, DMSO-$d_6$) δ 0.00-0.04 (6H, m), 0.80-0.89 (9H, m), 1.09-1.32 (4H, m), 1.74 (4H, d, J=8.7 Hz), 3.35-3.49 (1H, m), 3.53-3.66 (1H, m), 4.45 (1H, d, J=4.2 Hz).

A-2) cis-4-((tert-butyl(dimethyl)silyl)oxy)cyclohexyl 4-methylbenzenesulfonate

The title compound (736 mg) was obtained using cis-4-((tert-butyl(dimethyl)silyl)oxy)cyclohexanol (527 mg) obtained in Step A-1 of Example 31 in the same manner as in Step A-1 of Example 17.

$^1$H NMR (300 MHz, DMSO-$d_6$) δ 0.01 (6H, s), 0.79-0.89 (9H, m), 1.40-1.59 (6H, m), 1.61-1.78 (2H, m), 2.42 (3H, s), 3.67-3.79 (1H, m), 4.45-4.57 (1H, m), 7.47 (2H, d, J=7.9 Hz), 7.75-7.84 (2H, m).

A-3) 1-(trans-4-((tert-butyl(dimethyl)silyl)oxy)cyclohexyl)-3-iodo-4-methoxy-1H-pyrrolo[3,2-c]pyridine To a solution of 3-iodo-4-methoxy-1H-pyrrolo[3,2-c]pyridine (0.100 g) in DMF (5 mL) was added sodium hydride (60% dispersion in mineral oil, 36.5 mg), and the mixture was stirred at room temperature for 1 hr. cis-4-((tert-Butyl(dimethyl)silyl)oxy)cyclohexyl 4-methylbenzenesulfonate (351 mg) was added thereto, and the mixture was stirred overnight at room temperature. The reaction mixture was extracted with water and ethyl acetate, and the organic layer was washed with saturated brine, dried over anhydrous magnesium sulfate, filtered, and concentrated under reduced pressure. The obtained residue was purified by silica gel column chromatography (hexane/ethyl acetate) to give the title compound (31.1 mg).

$^1$H NMR (300 MHz, DMSO-$d_6$) δ 0.07 (6H, s), 0.88 (9H, s), 1.53-1.57 (2H, m), 1.84-1.92 (6H, m), 3.71-3.76 (1H, m), 3.94 (3H, s), 4.33-4.42 (1H, m), 7.27 (1H, d, J=6.1 Hz), 7.58 (1H, s), 7.75 (1H, d, J=6.1 Hz).

B) 4-(1-(trans-4-((tert-butyl(dimethyl)silyl)oxy)cyclohexyl)-4-methoxy-1H-pyrrolo[3,2-c]pyridin-3-yl)benzenesulfonamide To a solution of 1-(trans-4-((tert-butyl(dimethyl)silyl)oxy)cyclohexyl)-3-iodo-4-methoxy-1H-pyrrolo[3,2-c]pyridine (30.0 mg) in DMF (2 mL)/water (0.20 mL) were added 4-(4,4,5,5-tetramethyl-1,3,2-dioxaborolan-2-yl)benzenesulfonamide (25.8 mg), tetrakis(triphenylphosphine)palladium(0) (7.13 mg) and potassium carbonate (17.2 mg). The reaction mixture was stirred under microwave irradiation at 130° C. for 1 hr. The reaction mixture was diluted with water, and the mixture was extracted with ethyl acetate. The organic layer was washed with saturated brine, dried over anhydrous magnesium sulfate, filtered, and concentrated under reduced pressure. The obtained residue was purified by silica gel column chromatography (hexane/ethyl acetate) to give the title compound (13.1 mg).

$^1$H NMR (300 MHz, DMSO-$d_6$) δ 0.09 (6H, s), 0.92 (9H, s), 1.72-1.84 (6H, m), 2.08-2.27 (2H, m), 3.92 (3H, s), 4.09-4.13 (1H, m), 4.43 (1H, t, J=11.5 Hz), 7.29 (1H, d, J=6.1 Hz), 7.32 (2H, s), 7.59 (1H, s), 7.78-7.82 (5H, m).

C) 4-(1-(trans-4-hydroxycyclohexyl)-4-oxo-4,5-dihydro-1H-pyrrolo[3,2-c]pyridin-3-yl)benzenesulfonamide To a solution of 4-(1-(trans-4-((tert-butyl(dimethyl)silyl)oxy)cyclohexyl)-4-methoxy-1H-pyrrolo[3,2-c]pyridin-3-yl)benzenesulfonamide (10.0 mg) in acetonitrile (1 mL) were added sodium iodide (7.3 mg) and chloro(trimethyl)silane (0.025 mL), and the mixture was stirred overnight at 50° C. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate to ethyl acetate/methanol) to give the title compound (5.8 mg).

$^1$H NMR (300 MHz, DMSO-$d_6$) δ 1.36-1.56 (2H, m), 1.81-2.01 (6H, m), 3.46-3.65 (1H, m), 4.19-4.35 (1H, m), 4.70 (1H, d, J=4.5 Hz), 6.66 (1H, d, J=7.2 Hz), 7.02-7.13 (1H, m), 7.27 (2H, s), 7.65 (1H, s), 7.73 (2H, d, J=8.3 Hz), 8.07 (2H, d, J=8.7 Hz), 10.86 (1H, d, J=6.1 Hz).

MS (ESI+): [M+H]$^+$ 388.1.
MS (ESI+). found: 388.2.

Example 32

4-(1-(cis-4-hydroxycyclohexyl)-4-oxo-4,5-dihydro-1H-pyrrolo[3,2-c]pyridin-3-yl)benzenesulfonamide A) 1-(cis-4-((tert-butyl(dimethyl)silyl)oxy)cyclohexyl)-3-iodo-4-methoxy-1H-pyrrolo[3,2-c]pyridine A-1) trans-4-((tert-butyl(dimethyl)silyl)oxy)cyclohexyl 4-methylbenzenesulfonate The title compound (408 mg) was obtained using trans-4-((tert-butyl(dimethyl)silyl)oxy)cyclohexanol (325 mg) obtained in Step A-1 of Example 31 in the same manner as in Step A-1 of Example 17.

$^1$H NMR (300 MHz, DMSO-d$_6$) δ 0.01 (6H, brs), 0.78-0.86 (9H, m), 1.22-1.37 (2H, m), 1.40-1.55 (2H, m), 1.62-1.83 (4H, m), 2.42 (3H, s), 3.67-3.80 (1H, m), 4.47-4.61 (1H, m), 7.46 (2H, d, J=7.9 Hz), 7.74-7.83 (2H, m).

A-2) 1-(cis-4-((tert-butyl(dimethyl)silyl)oxy)cyclohexyl)-3-iodo-4-methoxy-1H-pyrrolo[3,2-c]pyridine To a solution of 3-iodo-4-methoxy-1H-pyrrolo[3,2-c]pyridine (0.100 g) in DMF (5 mL) was added sodium hydride (60% dispersion in mineral oil, 36.5 mg), and the mixture was stirred at room temperature for 1 hr. trans-4-((tert-Butyl(dimethyl)silyl)oxy)cyclohexyl 4-methylbenzenesulfonate (351 mg) was added thereto, and the mixture was stirred overnight at room temperature. The reaction mixture was extracted with water and ethyl acetate, and the organic layer was washed with saturated brine, dried over anhydrous magnesium sulfate, filtered, and concentrated under reduced pressure. The obtained residue was purified by silica gel column chromatography (hexane/ethyl acetate) to give the title compound (100 mg).
$^1$H NMR (300 MHz, DMSO-d$_6$) δ 0.08 (6H, s), 0.93 (9H, s), 1.67-1.73 (6H, m), 2.00-2.18 (2H, m), 3.94 (3H, s), 4.05-4.09 (1H, m), 4.33-4.42 (1H, m), 7.25 (1H, d, =6.1 Hz), 7.45 (1H, s), 7.74 (1H, d, J=6.1 Hz).

B) 4-(1-(cis-4-((tert-butyl(dimethyl)silyl)oxy)cyclohexyl)-4-methoxy-1H-pyrrolo[3,2-c]pyridin-3-yl)benzenesulfonamide To a solution of 1-(cis-4-((tert-butyl(dimethyl)silyl)oxy)cyclohexyl)-3-iodo-4-methoxy-1H-pyrrolo[3,2-c]pyridine (100 mg) in DMF (2 mL)/water (0.20 mL) were added 4-(4,4,5,5-tetramethyl-1,3,2-dioxaborolan-2-yl)benzenesulfonamide (70.6 mg), tetrakis(triphenylphosphine)palladium(0) (23.8 mg) and potassium carbonate (56.8 mg). The reaction mixture was stirred under microwave irradiation at 130° C. for 1 hr. The reaction mixture was diluted with water, and the mixture was extracted with ethyl acetate. The organic layer was washed with saturated brine, dried over anhydrous magnesium sulfate, filtered, and concentrated under reduced pressure. The obtained residue was purified by silica gel column chromatography (hexane/ethyl acetate) to give the title compound (22.7 mg).
$^1$H NMR (300 MHz, DMSO-d$_6$) δ 0.09 (6H, s), 0.92 (9H, s), 1.76-1.82 (6H, m), 2.08-2.27 (2H, m), 3.92 (3H, s), 4.09-4.12 (1H, m), 4.39-4.47 (1H, m), 7.29 (1H, d, J=6.1 Hz), 7.32 (2H, s), 7.59 (1H, s), 7.79-7.83 (5H, m).

C) 4-(1-(cis-4-hydroxycyclohexyl)-4-oxo-4,5-dihydro-1H-pyrrolo[3,2-c]pyridin-3-yl)benzenesulfonamide To a solution of 4-(1-(cis-4-((tert-butyl(dimethyl)silyl)oxy)cyclohexyl)-4-methoxy-1H-pyrrolo[3,2-c]pyridin-3-yl)benzenesulfonamide (20.0 mg) in acetonitrile (2 mL) were added sodium iodide (14.5 mg) and chloro(trimethyl)silane (0.049 mL), and the mixture was stirred overnight at 50° C. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate to ethyl acetate/methanol) to give the title compound (12.3 mg).

$^1$H NMR (300 MHz, DMSO-d$_6$) δ 1.60-1.89 (6H, m), 2.07-2.28 (2H, m), 3.90-3.93 (1H, m), 4.21-4.37 (1H, m), 4.53 (1H, d, J=3.4 Hz), 6.64 (1H, d, J=7.2 Hz), 7.04-7.15 (1H, m), 7.27 (2H, s), 7.61 (1H, s), 7.73 (2H, d, J=8.7 Hz), 8.10 (2H, d, J=8.3 Hz), 10.86 (1H, d, J=5.7 Hz).

Example 33

4-(7-cyano-1-cyclopentyl-4-oxo-4,5-dihydro-1H-pyrrolo[3,2-c]pyridin-3-yl)thiophene-2-carboxamide A) 4-bromothiophene-2-carboxamide To a solution of 4-bromothiophene-2-carboxylic acid (15 g), HOBt ammonium salt (16.5 g) and triethylamine (20.08 mL) in acetonitrile (250 mL) was added EDCI hydrochloride (16.87 g), and the mixture was stirred overnight. The reaction mixture was washed with saturated aqueous sodium bicarbonate solution and saturated brine, dried over anhydrous sodium sulfate, and concentrated under reduced pressure. The residue was purified by silica gel column chromatography (ethyl acetate/hexane) to give the title compound (8.0 g).
$^1$H NMR (300 MHz, CDCl$_3$) δ 5.87 (2H, brs), 7.43 (2H, q, J=1.4 Hz).

B) 4-(4,4,5,5-tetramethyl-1,3,2-dioxaborolan-2-yl)thiophene-2-carboxamide

To a solution of 4-bromothiophene-2-carboxamide (2 g) in DME (20 mL) were added (1,1'-bis(diphenylphosphino)ferrocene)dichloropalladium(II) (0.793 g), potassium acetate (2.86 g) and 4,4,4',4',5,5,5',5'-octamethyl-2,2-bi-1,3,2-dioxaborolane (4.93 g), and the mixture was stirred overnight at 90° C. under argon atmosphere. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (1.2 g).
$^1$H NMR (300 MHz, CDCl$_3$) δ 1.23-1.41 (12H, m), 5.82 (2H, brs), 7.75 (1H, d, J=0.8 Hz), 8.04 (1H, s).

C) methyl 4-chloro-1-cyclopentyl-4,5-dihydro-1H-pyrrolo[3,2-c]pyridine-7-carboxylate To a solution of methyl 1-cyclopentyl-4-oxo-4,5-dihydro-1H-pyrrolo[3,2-c]pyridine-7-carboxylate (1.83 g) obtained in Step D of Example 29 in acetonitrile (20 mL) was added phosphoryl chloride (4 mL), and the mixture was stirred at 80° C. for 4 hr. To the reaction mixture was added 8N aqueous sodium hydroxide solution at 0° C., and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (1.37 g).
$^1$H NMR (300 MHz, CDCl$_3$) δ 1.72-1.89 (6H, m), 2.14-2.27 (2H, m), 3.99 (3H, s), 5.20-5.37 (1H, m), 6.76 (1H, d, J=3.4 Hz), 7.34 (1H, d, J=3.4 Hz), 8.47 (1H, s).
MS (ESI+): [M+H]$^+$ 279.7.
MS (ESI+). found: 279.1.

D) methyl 1-cyclopentyl-4-methoxy-4,5-dihydro-1H-pyrrolo[3,2-c]pyridine-7-carboxylate To a solution of methyl 4-chloro-1-cyclopentyl-4,5-dihydro-1H-pyrrolo[3,2-c]pyridine-7-carboxylate (1.37 g) in methanol (5 mL) was added sodium methoxide (28% methanol solution, 5 mL), and the mixture was stirred at 70° C. for 3 hr. The reaction mixture was concentrated under reduced pressure, to the residue was added water, and the mixture was extracted with ethyl acetate. The organic layer was washed with saturated brine, dried over anhydrous sodium sulfate, and concentrated under reduced pressure to give the title compound (879 mg).
$^1$H NMR (300 MHz, CDCl$_3$) δ 1.71-1.88 (6H, m), 2.11-2.25 (2H, m), 3.94 (3H, s), 4.06-4.15 (3H, m), 5.29-5.47 (1H, m), 6.68 (1H, d, J=3.4 Hz), 7.18 (1H, d, J=3.4 Hz), 8.29-8.46 (1H, m).
MS (ESI+): [M+H]$^+$ 275.3.
MS (ESI+). found: 275.2.

E) methyl 3-bromo-1-cyclopentyl-4-methoxy-4,5-dihydro-1H-pyrrolo[3,2-c]pyridine-7-carboxylate The title compound (878 mg) was obtained using methyl 1-cyclopentyl-4-methoxy-4,5-dihydro-1H-pyrrolo[3,2-c]pyridine-7-carboxylate (879 mg) in the same manner as in Step E-2 of Example 29.
$^1$H NMR (300 MHz, CDCl$_3$) δ 1.71-1.86 (6H, m), 2.13-2.25 (2H, m), 3.94 (3H, s), 4.12 (3H, s), 5.20-5.41 (1H, m), 7.17 (1H, s), 8.28-8.39 (1H, m).
MS (ESI+): [M]$^+$ 353.2.
MS (ESI+). found: 353.0.

F) 3-bromo-1-cyclopentyl-4-methoxy-4,5-dihydro-1H-pyrrolo[3,2-c]pyridine-7-carboxylic acid To a solution of methyl 3-bromo-1-cyclopentyl-4-methoxy-4,5-dihydro-1H-pyrrolo[3,2-c]pyridine-7-carboxylate (874 mg) in methanol (8 mL) was added 1N aqueous sodium hydroxide solution (8 mL), and the mixture was stirred at room temperature for 3 hr. To the reaction mixture was added 1N hydrochloric acid at 0° C., and the precipitate was collected by filtration, and dried to give the title compound (894 mg).
$^1$H NMR (300 MHz, CDCl$_3$) δ 1.68-1.86 (6H, m), 2.18-2.24 (2H, m), 4.11-4.20 (3H, m), 5.45 (1H, t, J 6.2 Hz), 7.19 (1H, s), 8.56 (1H, s).
MS (ESI+): [M]$^+$ 339.1.
MS (ESI+). found: 339.1.

G) 3-bromo-1-cyclopentyl-4-methoxy-4,5-dihydro-1H-pyrrolo[3,2-c]pyridine-7-carboxamide To a solution of 3-bromo-1-cyclopentyl-4-methoxy-4,5-dihydro-1H-pyrrolo[3,2-c]pyridine-7-carboxylic acid (894 mg), HOBt ammonium salt (1155 mg) and triethylamine (1.41 mL) in acetonitrile (8 mL) was added EDCI hydrochloride (1179 mg), and the mixture was stirred overnight. The reaction mixture was washed with saturated aqueous sodium bicarbonate solution and saturated brine, dried over anhydrous sodium sulfate, and concentrated under reduced pressure to give the title compound (654 mg).
$^1$H NMR (300 MHz, CDCl$_3$) δ 1.71-1.91 (6H, m), 2.10-2.26 (2H, m), 4.10 (3H, s), 5.13-5.30 (1H, m), 5.75 (1H, brs), 6.01 (1H, brs), 7.17 (1H, s), 8.03 (1H, s).
MS (ESI+): [M]$^+$ 338.2.
MS (ESI+). found: 338.0.

H) 3-bromo-1-cyclopentyl-4-methoxy-4,5-dihydro-1H-pyrrolo[3,2-c]pyridine-7-carbonitrile To a solution of 3-bromo-1-cyclopentyl-4-methoxy-4,5-dihydro-1H-pyrrolo[3,2-c]pyridine-7-carboxamide (654 mg) in THF (8 mL) was added Burgess reagent (1152 mg at 0° C.), and the mixture was stirred at 0° C. for 2 hr. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (522 mg).
$^1$H NMR (300 MHz, CDCl$_3$) δ 1.81-1.93 (6H, m), 2.25-2.37 (2H, m), 4.13 (3H, s), 5.40 (1H, dd, J=8.3, 4.5 Hz), 7.17 (1H, s), 8.22 (1H, s).
MS (ESI+): [M]$^+$ 320.1.
MS (ESI+). found: 320.0.

I) 4-(7-cyano-1-cyclopentyl-4-methoxy-1H-pyrrolo[3,2-c]pyridin-3-yl)thiophene-2-carboxamide A mixture of 3-bromo-1-cyclopentyl-4-methoxy-4,5-dihydro-1H-pyrrolo[3,2-c]pyridine-7-carbonitrile (400 mg), 4-(4,4,5,5-tetramethyl-1,3,2-dioxaborolan-2-yl)thiophene-2-carboxamide (553 mg) obtained in Step B of Example 33, (1,1'-bis(diphenylphosphino)ferrocene)dichloropalladium (II) (102 mg), 2M aqueous sodium carbonate solution (1.24 mL) and DME (3.5 mL) was stirred under microwave irradiation at 120° C. for 1 hr 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (310 mg).
$^1$H NMR (300 MHz, DMSO-d$_6$) δ 1.69-1.80 (2H, m), 1.83-2.04 (4H, m), 2.24 (2H, dd, J=13.0, 5.5 Hz), 4.04 (3H, s), 5.34 (1H, quin, J=6.7 Hz), 7.41 (1H, brs), 7.79 (1H, s), 7.85-7.93 (2H, m), 8.02-8.09 (1H, m), 8.39 (1H, s).
MS (ESI+): [M+H]$^+$ 367.4.
MS (ESI+). found: 367.0.

J) 4-(7-cyano-1-cyclopentyl-4-oxo-4,5-dihydro-1H-pyrrolo[3,2-c]pyridin-3-yl)thiophene-2-carboxamide To a solution of 4-(7-cyano-1-cyclopentyl-4-methoxy-1H-pyrrolo[3,2-c]pyridin-3-yl)thiophene-2-carboxamide (310 mg) in acetonitrile (40 mL) were added sodium iodide (254 mg) and chloro(trimethyl)silane (536 mL), and the mixture was stirred at 80° C. for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (methanol/ethyl acetate) to give the title compound (143 mg).
$^1$H NMR (300 MHz, DMSO-d$_6$) δ 1.66-1.80 (2H, m), 1.82-2.05 (4H, m), 2.15-2.31 (2H, m), 5.19-5.33 (1H, m), 7.37 (1H, brs), 7.59 (1H, s), 7.81 (1H, brs), 8.01 (1H, s), 8.16 (1H, d, J=1.5 Hz), 8.42 (1H, d, J=1.5 Hz), 11.89 (1H, brs).
MS (ESI+): [M+H]$^+$ 353.4.
MS (ESI+). found: 353.2.

Example 34 methyl 3-(5-carbamoyl-3-thienyl)-1-cyclopentyl-4-oxo-4,5-dihydro-1H-pyrrolo[3,2-c]pyridine-7-carboxylate The title compound was obtained using the powder obtained in Step E-2 of Example 29 and 4-(4,4,5,5-tetramethyl-1,3,2-dioxaborolan-2-yl)thiophene-2-carboxamide obtained in Step B of Example 33, in the same manner as in Step E-3 of Example 29 and Step H-3 of Example V.

MS (ESI+): [M+H]+ 386.4.
MS (ESI+). found: 386.0.

Example 35

4-(1-(2,6-difluorophenyl)-4-oxo-4,5-dihydro-1H-pyrazolo[4,3-c]pyridin-3-yl)benzenesulfonamide A) N'-(2,6-difluorophenyl)-4-iodo-2-methoxynicotinohydrazide To a solution of 4-iodo-2-methoxynicotinic acid (1.00 g) obtained in Step C of Example 6 in DMA (10 mL) were added (2,6-difluorophenyl)hydrazine hydrochloride (647 mg), EDCI hydrochloride (824 mg) and HOBt (581 mg) at 0° C., and the mixture was stirred overnight at room temperature. To the reaction mixture was added water, and the mixture was extracted with ethyl acetate. The organic layer was dried over anhydrous sodium sulfate, filtered, and concentrated under reduced pressure. The residue was purified by silica gel column chromatography (basic silica gel, hexane/ethyl acetate) to give the title compound (1.32 g).

$^1$H NMR (300 MHz, DMSO-$d_6$) δ 3.82 (3H, s), 6.88-7.06 (3H, m), 7.41-7.49 (2H, m), 7.86 (1H, d, J=5.3 Hz), 10.42 (1H, d, J=2.3 Hz).

B) 1-(2,6-difluorophenyl)-4-methoxy-1,2-dihydro-3H-pyrazolo[4,3-c]pyridin-3-one

To a solution of N'-(2,6-difluorophenyl)-4-iodo-2-methoxynicotinohydrazide (1.32 g) in DMSO (20 mL) were added L-proline (75.0 mg) and potassium carbonate (901 mg) at room temperature. Copper(I) iodide (62.1 mg) was added thereto under nitrogen atmosphere at 60° C., and the mixture was stirred overnight at 60° C. The reaction mixture was purified by silica gel column chromatography (hexane/ethyl acetate) to give the title compound (278 mg).

$^1$H NMR (300 MHz, DMSO-$d_6$) δ 4.00 (3H, s), 6.76 (1H, d, J=6.1 Hz), 7.35-7.48 (2H, m), 7.58-7.73 (1H, m), 7.91 (1H, d, J=6.1 Hz), 11.55 (1H, brs).

C) 1-(2,6-difluorophenyl)-4-methoxy-1H-pyrazolo[4,3-c]pyridin-3-yl trifluoromethanesulfonate To a solution of 1-(2,6-difluorophenyl)-4-methoxy-1,2-dihydro-3H-pyrazolo[4,3-c]pyridin-3-one (276 mg) and pyridine (0.321 mL) in acetonitrile (25 mL) was added trifluoromethanesulfonic anhydride (0.336 mL), and the mixture was stirred at 0° C. for 1 hr. To the reaction mixture was added saturated aqueous ammonium chloride solution, and the mixture was extracted with ethyl acetate. The organic layer was washed with saturated brine, dried over anhydrous sodium sulfate, filtered, and concentrated under reduced pressure. The residue was purified by silica gel column chromatography (hexane/ethyl acetate) to give the title compound (408 mg).

MS (ESI+): [M+H]+ 410.0.
MS (ESI+). found: 409.9.

D) 4-(1-(2,6-difluorophenyl)-4-methoxy-1H-pyrazolo[4,3-c]pyridin-3-yl)benzenesulfonamide To a solution of 1-(2,6-difluorophenyl)-4-methoxy-1H-pyrazolo[4,3-c]pyridin-3-yl trifluoromethanesulfonate (80 mg) in DMF (2 mL)/water (0.20 mL) were added 4-(4,4,5,5-tetramethyl-1,3,2-dioxaborolan-2-yl)benzenesulfonamide (83.0 mg), tetrakis(triphenylphosphine)palladium(0) (22.6 mg) and potassium carbonate (54.0 mg). The reaction mixture was stirred under microwave irradiation at 130° C. for 30 min. The reaction mixture was diluted with water, and the mixture was extracted with ethyl acetate. The organic layer was washed with saturated brine, dried over anhydrous magnesium sulfate, filtered, and concentrated under reduced pressure. The obtained residue was purified by silica gel column chromatography (hexane/ethyl acetate) to give the title compound (46.2 mg).

$^1$H NMR (300 MHz, DMSO-$d_6$) δ 4.06 (3H, s), 6.85-6.90 (1H, m), 7.09 (1H, s), 7.48 (2H, d, J=3.8 Hz), 7.51-7.55 (1H, m), 7.61-7.66 (1H, m), 7.94-8.00 (2H, m), 8.10 (1H, d, J=6.1 Hz), 8.14-8.19 (2H, m).

E) 4-(1-(2,6-difluorophenyl)-4-oxo-4,5-dihydro-1H-pyrazolo[4,3-c]pyridin-3-yl)benzenesulfonamide To a solution of 4-(1-(2,6-difluorophenyl)-4-methoxy-1H-pyrazolo[4,3-c]pyridin-3-yl)benzenesulfonamide (46.0 mg) in acetonitrile (4 mL) were added sodium iodide (41.4 mg) and chloro(trimethyl)silane (0.140 mL), and the mixture was stirred at 50° C. for 30 min. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate to ethyl acetate/methanol) to give the title compound (28.5 mg).

$^1$H NMR (300 MHz, DMSO-$d_6$) δ 6.31 (1H, d, J=7.2 Hz), 7.38 (2H, d, J=7.2 Hz), 7.50 (3H, t, J=8.3 Hz), 7.78 (1H, tt, J=8.7, 6.4 Hz), 7.87-7.96 (2H, m), 8.44-8.55 (2H, m), 11.45 (1H, brs).

MS (ESI+): [M+H]+ 403.1.
MS (ESI+). found: 403.1.

Example 36 methyl 4-(1-(2,6-difluorophenyl)-4-oxo-4,5-dihydro-1H-pyrazolo[4,3-c]pyridin-3-yl)thiophene-2-carboxylate A) methyl 4-(1-(2,6-difluorophenyl)-4-methoxy-1H-pyrazolo[4,3-c]pyridin-3-yl)thiophene-2-carboxylate To a solution of 1-(2,6-difluorophenyl)-4-methoxy-1H-pyrazolo[4,3-c]pyridin-3-yl trifluoromethanesulfonate (100 mg) obtained in Step C of Example 35 in DMF (4 mL)/water (0.40 mL) were added methyl 4-(4,4,5,5-tetramethyl-1,3,2-dioxaborolan-2-yl)thiophene-2-carboxylate (98.3 mg), tetrakis(triphenylphosphine)palladium(0) (28.2 mg) and potassium carbonate (67.5 mg). The reaction mixture was stirred under microwave irradiation at 130° C. for 30 min. The reaction mixture was diluted with water, and the mixture was extracted with ethyl acetate. The organic layer was washed with saturated brine, dried over anhydrous magnesium sulfate, filtered, and concentrated under reduced pressure. The obtained residue was purified by silica gel column chromatography (hexane/ethyl acetate) to give the title compound (44.9 mg).

$^1$H NMR (300 MHz, DMSO-$d_6$) δ 3.87 (3H, s), 4.13 (3H, s), 7.04 (1H, d, J=6.1 Hz), 7.46-7.55 (2H, m), 7.77 (1H, tt, J=8.7, 6.4 Hz), 8.07 (1H, d, J=6.1 Hz), 8.35 (1H, d, J=1.5 Hz), 8.70 (1H, d, J=1.5 Hz).

MS (ESI+): [M+H]⁺ 402.1.
MS (ESI+). found: 402.1.

B) methyl 4-(1-(2,6-difluorophenyl)-4-oxo-4,5-dihydro-1H-pyrazolo[4,3-c]pyridin-3-yl)thiophene-2-carboxylate To a solution of methyl 4-(1-(2,6-difluorophenyl)-4-methoxy-1H-pyrazolo[4,3-c]pyridin-3-yl)thiophene-2-carboxylate (42.5 mg) in acetonitrile (4 mL) were added sodium iodide (39.7 mg) and chloro(trimethyl)silane (0.134 mL), and the mixture was stirred at 50° C. for 30 min. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, hexane/ethyl acetate to ethyl acetate) to give the title compound (37.2 mg).
$^1$H NMR (300 MHz, DMSO-$d_6$) δ 3.86 (3H, s), 6.29 (1H, d, J=7.2 Hz), 7.37 (1H, d, J=7.2 Hz), 7.43-7.55 (2H, m), 7.77 (1H, tt, J=8.6, 6.3 Hz), 8.54 (1H, d, J=1.5 Hz), 9.18 (1H, d, J=1.1 Hz), 11.52 (1H, brs).
MS (ESI+): [M+H]⁺ 388.1.
MS (ESI+). found: 388.1.

Example 37

4-(1-(2,6-difluorophenyl)-4-oxo-4,5-dihydro-1H-pyrazolo[4,3-c]pyridin-3-yl)thiophene-2-carboxylic acid To a mixture of methyl 4-(1-(2,6-difluorophenyl)-4-oxo-4,5-dihydro-1H-pyrazolo[4,3-c]pyridin-3-yl)thiophene-2-carboxylate (32.0 mg) obtained in Example 36 in methanol (2 mL)/THF (2 mL)/water (2 mL) was added 8 M aqueous sodium hydroxide solution (0.026 mL) at 0° C. The reaction mixture was stirred at 90° C. for 2 hr. The reaction mixture was diluted with water, and the mixture was extracted with ethyl acetate. The organic layer was washed with 0.1 N hydrochloric acid, water and saturated brine, dried over anhydrous magnesium sulfate, filtered, and concentrated under reduced pressure to give the title compound (31.1 mg).
MS (ESI+): [M+H]⁺ 374.0.
MS (ESI+). found: 374.1.

Example 38

4-(1-(2,6-difluorophenyl)-4-oxo-4,5-dihydro-1H-pyrazolo[4,3-c]pyridin-3-yl)thiophene-2-carboxamide To a solution of 4-(1-(2,6-difluorophenyl)-4-oxo-4,5-dihydro-1H-pyrazolo[4,3-c]pyridin-3-yl)thiophene-2-carboxylic acid (30.0 mg) obtained in Example 37 in DMA (2 mL) were added EDCI hydrochloride (18.5 mg) and HOBt ammonium salt (14.7 mg) at room temperature, and the mixture was stirred overnight at room temperature. The reaction mixture was diluted with water, the mixture was extracted with ethyl acetate, and the organic layer was washed with saturated brine, dried over magnesium sulfate, filtered, and concentrated under reduced pressure. The obtained residue was purified by silica gel column chromatography (basic silica gel, hexane/ethyl acetate to ethyl acetate) to give the title compound (21.2 mg).
$^1$H NMR (300 MHz, DMSO-$d_6$) δ 6.28 (1H, d, J=7.2 Hz), 7.36 (1H, d, J=7.2 Hz), 7.42 (1H, brs), 7.49 (2H, t, J=8.5 Hz), 7.77 (1H, tt, J=8.5, 6.4 Hz), 8.11 (1H, brs), 8.39 (1H, d, J=1.1 Hz), 9.30 (1H, d, J=1.1 Hz), 11.51 (1H, brs).
MS (ESI+): [M+H]⁺ 373.1.
MS (ESI+). found: 373.1.

Example 39

(4-(1-(2,6-difluorophenyl)-4-oxo-4,5-dihydro-1H-pyrazolo[4,3-c]pyridin-3-yl)phenyl)acetonitrile A) (4-(1-(2,6-difluorophenyl)-4-methoxy-1H-pyrazolo[4,3-c]pyridin-3-yl)phenyl)acetonitrile To a solution of 1-(2,6-difluorophenyl)-4-methoxy-1H-pyrazolo[4,3-c]pyridin-3-yl trifluoromethanesulfonate (150 mg) obtained in Step C of Example 35 in DMF (4 mL)/water (0.40 mL) were added (4-(cyanomethyl)phenyl)boronic acid (156 mg), tetrakis(triphenylphosphine)palladium(0) (42.4 mg) and potassium carbonate (101 mg). The reaction mixture was stirred under microwave irradiation at 130° C. for 1 hr. The reaction mixture was diluted with water, and the mixture was extracted with ethyl acetate. The organic layer was washed with saturated brine, dried over anhydrous magnesium sulfate, filtered, and concentrated under reduced pressure. The obtained residue was purified by silica gel column chromatography (hexane/ethyl acetate) to give the title compound (107 mg).
$^1$H NMR (300 MHz, DMSO-$d_6$) δ 4.04 (3H, s), 4.15 (2H, s), 7.04 (1H, d, J=5.7 Hz), 7.49-7.54 (3H, m), 7.69-7.83 (2H, m), 8.00 (2H, d, J=8.0 Hz), 8.07 (1H, d, J=6.1 Hz).
MS (ESI+): [M+H]⁺ 377.1.
MS (ESI+). found: 377.1.

B) (4-(1-(2,6-difluorophenyl)-4-oxo-4,5-dihydro-1H-pyrazolo[4,3-c]pyridin-3-yl)phenyl)acetonitrile To a solution of (4-(1-(2,6-difluorophenyl)-4-methoxy-1H-pyrazolo[4,3-c]pyridin-3-yl)phenyl)acetonitrile (140 mg) in acetonitrile (6 mL) were added sodium iodide (139 mg) and chloro(trimethyl)silane (0.475 mL), and the mixture was stirred at 50° C. for 1 hr. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, hexane/ethyl acetate to ethyl acetate) to give the title compound (80.2 mg).
$^1$H NMR (300 MHz, DMSO-$d_6$) δ 4.12 (2H, s), 6.27 (1H, d, J=6.8 Hz), 7.30-7.38 (1H, m), 7.41-7.56 (4H, m), 7.69-7.85 (1H, m), 8.33 (2H, d, J=8.3 Hz), 11.43 (1H, d, J=5.3 Hz).
MS (ESI+): [M+H]⁺ 363.1.
MS (ESI+). found: 363.1.

Example 40

4-(1-cyclopentyl-7-(hydroxymethyl)-4-oxo-4,5-dihydro-1H-pyrrolo[3,2-c]pyridin-3-yl)thiophene-2-carboxamide To a solution of methyl 3-(5-carbamoyl-3-thienyl)-1-cyclopentyl-4-oxo-4,5-dihydro-1H-pyrrolo[3,2-c]pyridine-7-carboxylate (30 mg) obtained in Example 34 in a mixed solvent of THF (0.5 mL) and methanol (0.5 mL) was added lithium borohydride (4.4 mg), and the mixture was stirred overnight at room temperature. To the reaction mixture was added water, and the mixture was extracted with ethyl acetate.

The organic layer was washed with saturated brine, dried over anhydrous sodium sulfate, and concentrated under reduced pressure. The residue was purified by silica gel column chromatography (ethyl acetate/hexane) to give the title compound (8 mg).

MS (ESI+): [M+H]$^+$ 358.4.
MS (ESI+). found: 358.1.

Example 41

3-(cyclohex-1-en-1-yl)-1-cyclopentyl-1,5-dihydro-4H-pyrazolo[4,3-c]pyridin-4-one To a solution (1.0 mL) of 1-cyclopentyl-4-methoxy-1H-pyrazolo[4,3-c]pyridin-3-yl trifluoromethanesulfonate (29.2 mg) obtained in Step C of Example 12, 2-(cyclohex-1-en-1-yl)-4,4,5,5-tetramethyl-1,3,2-dioxaborolane (16.7 mg) and tetrakistriphenylphosphine palladium (18.5 mg) in DME was added 2N sodium carbonate (120 μl), and the mixture was reacted at 100° C. for 6 hr. To the reaction mixture were added ethyl acetate (4 mL), THF (1 mL) and water (1 mL), the mixture was stirred for 5 min, and the organic layer was separated, and concentrated by air-blowing. The residue was purified by preparative high-performance liquid chromatography (C18, mobile phase: acetonitrile/10 mM aqueous ammonium bicarbonate solution) to give 3-(cyclohex-1-en-1-yl)-1-cyclopentyl-4-methoxy-1H-pyrazolo[4,3-c]pyridine. A solution (1.0 mL) of chloro(trimethyl)silane (10.2 μl) and sodium iodide (12.0 mg) in acetonitrile was added to 3-(cyclohex-1-en-1-yl)-1-cyclopentyl-4-methoxy-1H-pyrazolo[4,3-c]pyridine, and the mixture was reacted at 60° C. for 1 hr. To the reaction mixture were added ethyl acetate (4 mL), THF (1 mL) and water (1 mL), the mixture was stirred for 5 min, and the organic layer was separated, and concentrated by air-blowing. The residue was purified by preparative high-performance liquid chromatography (C18, mobile phase: acetonitrile/10 mM aqueous ammonium bicarbonate solution) to give the title compound (13.0 mg).

MS (ESI/APCI+): [M+H]$^+$ 284.2.
MS (ESI/APCI+). found: 284.3.

Example 42-59

The following compounds 42-59 were synthesized using the corresponding boronic acid or boronate ester, in the same manner as in Example 41. The compounds are shown in Table 1.

TABLE 1

| Ex. | Structure | Compound Name | MS: M+ | MS (ESI+), found: M + H |
|---|---|---|---|---|
| 42 | 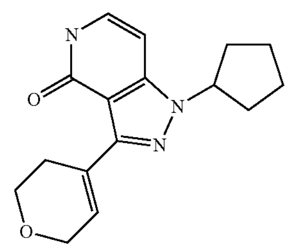 [SMILES: O=c1[nH]ccc2c1c(C1=CCOCC1)nn2C1CCCC1] | 1-cyclopentyl-3-(3,6-dihydro-2H-pyran-4-yl)-1,5-dihydro-4H-pyrazolo[4,3-c]pyridin-4-one | 285.3 | 286.3 |
| 43 | 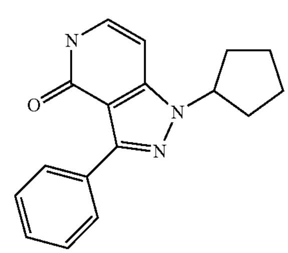 | 1-cyclopentyl-3-phenyl-1,5-dihydro-4H-pyrazolo[4,3-c]pyridin-4-one | 279.3 | 280.3 |
| 44 | 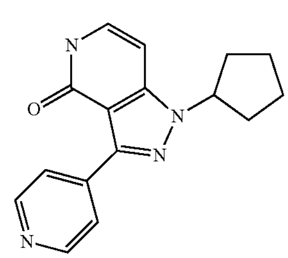 [SMILES: O=c1[nH]ccc2c1c(-c1ccncc1)nn2C1CCCC1] | 1-cyclopentyl-3-(pyridin-4-yl)-1,5-dihydro-4H-pyrazolo[4,3-c]pyridin-4-one | 280.3 | 281.2 |

TABLE 1-continued

| Ex. | Structure | Compound Name | MS: M+ | MS (ESI+), found: M + H |
|---|---|---|---|---|
| 45 | 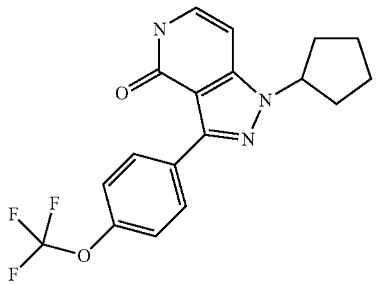 [SMILES: O=c1[nH]ccc2c1c(-c1ccc(OC(F)(F)F)cc1)nn2C1CCCC1] | 1-cyclopentyl-3-(4-(trifluoromethoxy)phenyl)-1,5-dihydro-4H-pyrazolo[4,3-c]pyridin-4-one | 363.3 | 364.3 |
| 46 | 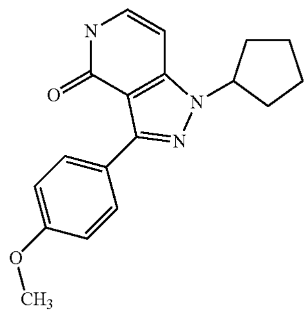 [SMILES: COc1ccc(-c2nn(C3CCCC3)c3cc[nH]c(=O)c23)cc1] | 1-cyclopentyl-3-(4-methoxyphenyl)-1,5-dihydro-4H-pyrazolo[4,3-c]pyridin-4-one | 309.4 | 310.2 |
| 47 | 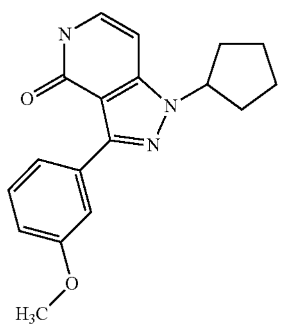 [SMILES: COc1cccc(-c2nn(C3CCCC3)c3cc[nH]c(=O)c23)c1] | 1-cyclopentyl-3-(3-methoxyphenyl)-1,5-dihydro-4H-pyrazolo[4,3-c]pyridin-4-one | 309.4 | 310.3 |
| 48 | 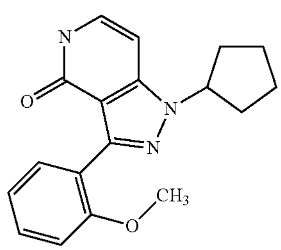 [SMILES: COc1ccccc1-c1nn(C2CCCC2)c2cc[nH]c(=O)c12] | 1-cyclopentyl-3-(2-methoxyphenyl)-1,5-dihydro-4H-pyrazolo[4,3-c]pyridin-4-one | 309.4 | 310.3 |
| 49 | 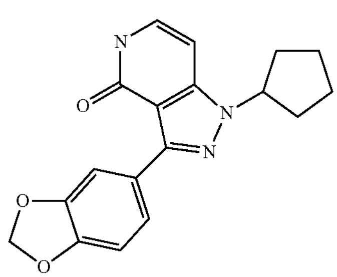 [SMILES: O=c1[nH]ccc2c1c(-c1ccc3c(c1)OCO3)nn2C1CCCC1] | 3-(1,3-benzodioxol-5-yl)-1-cyclopentyl-1,5-dihydro-4H-pyrazolo[4,3-c]pyridin-4-one | 323.3 | 324.3 |

TABLE 1-continued

| Ex. | Structure | Compound Name | MS: M+ | MS (ESI+), found: M + H |
|---|---|---|---|---|
| 50 | 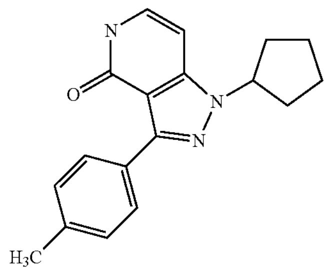 [SMILES: Cc1ccc(-c2nn(C3CCCC3)c3cc[nH]c(=O)c23)cc1] | 1-cyclopentyl-3-(4-methylphenyl)-1,5-dihydro-4H-pyrazolo[4,3-c]pyridin-4-one | 293.4 | 294.3 |
| 51 | 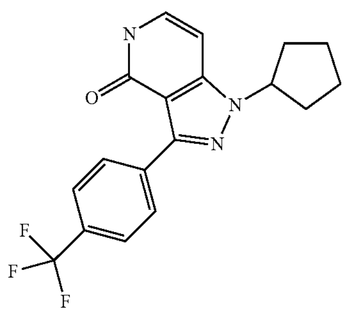 [SMILES: O=c1[nH]ccc2c1c(-c1ccc(C(F)(F)F)cc1)nn2C1CCCC1] | 1-cyclopentyl-3-(4-(trifluoromethyl)phenyl)-1,5-dihydro-4H-pyrazolo[4,3-c]pyridin-4-one | 347.3 | 348.2 |
| 52 | 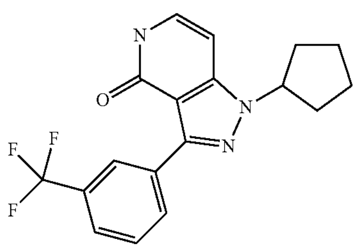 [SMILES: O=c1[nH]ccc2c1c(-c1cccc(C(F)(F)F)c1)nn2C1CCCC1] | 1-cyclopentyl-3-(3-(trifluoromethyl)phenyl)-1,5-dihydro-4H-pyrazolo[4,3-c]pyridin-4-one | 347.3 | 348.3 |
| 53 | 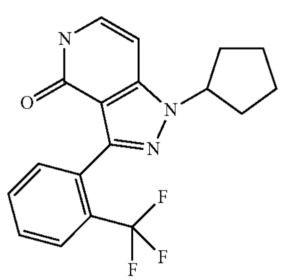 [SMILES: O=c1[nH]ccc2c1c(-c1ccccc1C(F)(F)F)nn2C1CCCC1] | 1-cyclopentyl-3-(2-(trifluoromethyl)phenyl)-1,5-dihydro-4H-pyrazolo[4,3-c]pyridin-4-one | 347.3 | 348.2 |
| 54 | 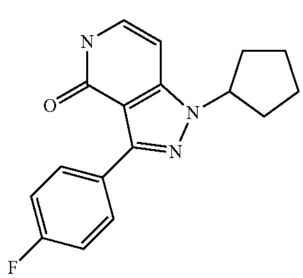 [SMILES: O=c1[nH]ccc2c1c(-c1ccc(F)cc1)nn2C1CCCC1] | 1-cyclopentyl-3-(4-fluorophenyl)-1,5-dihydro-4H-pyrazolo[4,3-c]pyridin-4-one | 297.3 | 298.2 |

TABLE 1-continued

| Ex. | Structure | Compound Name | MS: M+ | MS (ESI+), found: M + H |
|---|---|---|---|---|
| 55 | 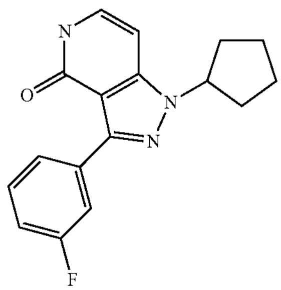 [SMILES: O=c1[nH]ccc2c1c(-c1cccc(F)c1)nn2C1CCCC1] | 1-cyclopentyl-3-(3-fluorophenyl)-1,5-dihydro-4H-pyrazolo[4,3-c]pyridin-4-one | 297.3 | 298.3 |
| 56 | 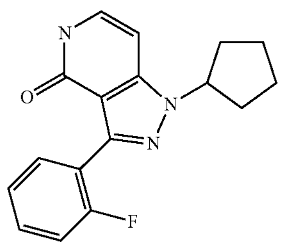 [SMILES: O=c1[nH]ccc2c1c(-c1ccccc1F)nn2C1CCCC1] | 1-cyclopentyl-3-(2-fluorophenyl)-1,5-dihydro-4H-pyrazolo[4,3-c]pyridin-4-one | 297.3 | 298.2 |
| 57 | 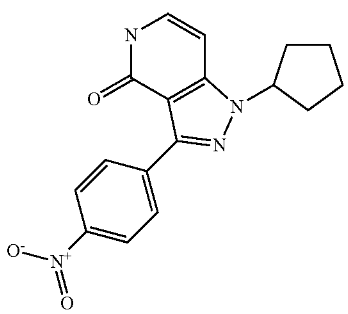 [SMILES: O=c1[nH]ccc2c1c(-c1ccc([N+](=O)[O-])cc1)nn2C1CCCC1] | 1-cyclopentyl-3-(4-nitrophenyl)-1,5-dihydro-4H-pyrazolo[4,3-c]pyridin-4-one | 324.3 | 325.3 |
| 58 | 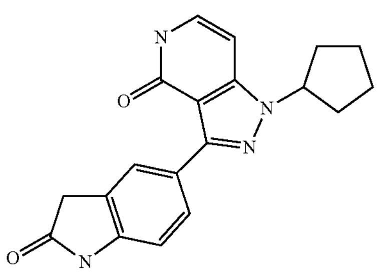 [SMILES: O=C1Cc2cc(-c3nn(C4CCCC4)c4cc[nH]c(=O)c34)ccc2N1] | 1-cyclopentyl-3-(2-oxo-2,3-dihydro-1H-indol-5-yl)-1,5-dihydro-4H-pyrazolo[4,3-c]pyridin-4-one | 334.4 | 335.3 |
| 59 | 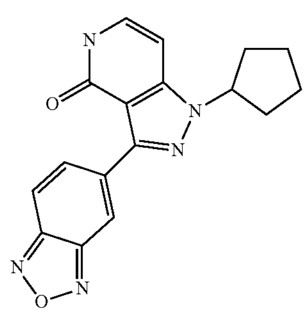 [SMILES: O=c1[nH]ccc2c1c(-c1ccc3nonc3c1)nn2C1CCCC1] | 3-(2,1,3-benzoxadiazol-5-yl)-1-cyclopentyl-1,5-dihydro-4H-pyrazolo[4,3-c]pyridin-4-one | 321.3 | 322.2 |

Example 60

4-(7-acetyl-1-cyclopentyl-4-oxo-4,5-dihydro-1H-pyrrolo[3,2-c]pyridin-3-yl)thiophene-2-carboxamide To a solution of the powder obtained in Step E-2 of Example 29 (100 mg) in THF (1 mL) was added methylmagnesium bromide (0.176 mL, 3M THF solution) at room temperature, and the mixture was stirred at 60° C. for 2 hr. To the reaction mixture was added saturated aqueous ammonium chloride solution, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give a powder (40 mg).

$^1$H NMR (300 MHz, CDCl$_3$) δ −0.01-0.00 (9H, m), 0.91-1.01 (2H, m), 1.65-1.84 (6H, m), 2.04-2.19 (2H, m), 2.56 (3H, s), 3.62-3.70 (2H, m), 5.03 (1H, t, J=7.0 Hz), 5.44 (2H, s), 7.05 (1H, s), 7.81 (1H, s).

The title compound was obtained using the obtained powder and 4-(4,4,5,5-tetramethyl-1,3,2-dioxaborolan-2-yl)thiophene-2-carboxamide obtained in Step B of Example 33, in the same manner as in Step E-3 and Step E-4 of Example 29.

MS (ESI+): [M+H]$^+$ 370.4.
MS (ESI+). found: 370.1.

Example 61

3-(5-carbamoyl-3-thienyl)-1-cyclopentyl-4-oxo-4,5-dihydro-1H-pyrrolo[3,2-c]pyridine-7-carboxylic acid The title compound was obtained using methyl 3-(5-carbamoyl-3-thienyl)-1-cyclopentyl-4-oxo-4,5-dihydro-1H-pyrrolo[3,2-c]pyridine-7-carboxylate obtained in Example 34, in the same manner as in Step F of Example 33.

MS (ESI+): [M+H]$^+$ 372.4.
MS (ESI+). found: 372.1.

Example 62

3-(5-carbamoyl-3-thienyl)-1-cyclopentyl-4-oxo-4,5-dihydro-1H-pyrrolo[3,2-c]pyridine-7-carboxamide The title compound was obtained using 3-(5-carbamoyl-3-thienyl)-1-cyclopentyl-4-oxo-4,5-dihydro-1H-pyrrolo[3,2-c]pyridine-7-carboxylic acid obtained in Example 61, in the same manner as in Step G of Example 33.

MS (ESI+): [M+H]$^+$ 371.4.
MS (ESI+). found: 371.2.

Example 63

1-cyclopentyl-N-methyl-3-(5-(methylcarbamoyl)-3-thienyl)-4-oxo-4,5-dihydro-1H-pyrrolo[3,2-c]pyridine-7-carboxamide The title compound was obtained using 3-(5-carbamoyl-3-thienyl)-1-cyclopentyl-4-oxo-4,5-dihydro-1H-pyrrolo[3,2-c]pyridine-7-carboxylic acid obtained in Example 61 and methylamine hydrochloride, in the same manner as in Step G of Example 33.

MS (ESI+): [M+H]$^+$ 399.4.
MS (ESI+). found: 399.1.

Example 64

1-cyclopentyl-3-(5-(dimethylcarbamoyl)-3-thienyl)-N,N-dimethyl-4-oxo-4,5-dihydro-1H-pyrrolo[3,2-c]pyridine-7-carboxamide The title compound was obtained using 3-(5-carbamoyl-3-thienyl)-1-cyclopentyl-4-oxo-4,5-dihydro-1H-pyrrolo[3,2-c]pyridine-7-carboxylic acid obtained in Example 61 and dimethylamine hydrochloride, in the same manner as in Step G of Example 33.

MS (ESI+): [M+H]$^+$ 427.5.
MS (ESI+). found: 427.1.

Example 65

4-(4-cyano-3-cyclopentyl-7-oxo-6,7-dihydro-1H-pyrazolo[3,4-c]pyridin-1-yl)thiophene-2-carboxylic acid

A) (5-bromo-3-fluoro-2-methoxypyridin-4-yl)(cyclopentyl)methanol

To a solution of DIEA (0.827 mL) in THF (90 mL) was added 1.6 M n-butyllithium hexane solution (3.64 mL) at −78° C., and the mixture was stirred under argon atmosphere at −78° C. for 30 min. To the reaction mixture was added a solution of 5-bromo-3-fluoro-2-methoxypyridine (1.00 g) in THF (30 mL) at −78° C., and the mixture was stirred under argon atmosphere at −78° C. for 1 hr. To the reaction mixture was added cyclopentanecarbaldehyde (0.572 g) at −78° C., and the mixture was stirred under argon atmosphere at −78° C. for 1 hr. To the reaction mixture was added saturated aqueous ammonium chloride solution at −78° C., and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (430 mg).

MS (ESI+): [M+H]$^+$ 304.0.
MS (ESI+). found: 304.0.

B) (5-bromo-3-fluoro-2-methoxypyridin-4-yl)(cyclopentyl)methanone

To a solution of (5-bromo-3-fluoro-2-methoxypyridin-4-yl)(cyclopentyl)methanol (430 mg) in acetonitrile (10 mL) was added Dess-Martin reagent (720 mg) at room temperature, and the mixture was stirred for 3 hr, and the reaction mixture was concentrated under reduced pressure. The residue was purified by silica gel column chromatography (basic silica gel, ethyl acetate/hexane) to give the title compound (440 mg).

MS (ESI+): [M+H]$^+$ 301.0.
MS (ESI+). found: 304.0.

C) 4-bromo-3-cyclopentyl-7-methoxy-1H-pyrazolo[3,4-c]pyridine

To a solution of (5-bromo-3-fluoro-2-methoxypyridin-4-yl)(cyclopentyl)methanone (440 mg) in methanol (10 mL) was added hydrazine monohydrate (2.06 mL) at room temperature, the mixture was stirred for 3 hr, and the reaction mixture was concentrated under reduced pressure. The residue was purified by silica gel column chromatography (basic silica gel, ethyl acetate/hexane) to give the title compound (100 mg).

¹H NMR (300 MHz, DMSO-d₆) δ 1.59-1.96 (6H, m), 1.97-2.18 (2H, m), 3.82 (1H, quin, J=7.8 Hz), 4.03 (3H, s), 7.76 (1H, s), 13.77 (1H, brs).

D) methyl 4-(4-bromo-3-cyclopentyl-7-methoxy-1H-pyrazolo[3,4-c]pyridin-1-yl)thiophene-2-carboxylate A suspension of 4-bromo-3-cyclopentyl-7-methoxy-1H-pyrazolo[3,4-c]pyridine (100 mg), methyl 4-(4,4,5,5-tetramethyl-1,3,2-dioxaborolan-2-yl)thiophene-2-carboxylate (181 mg), copper(II) acetate (73.6 mg) and pyridine (37.4 mg) in DMF (10 mL) was stirred at room temperature for 4 days. To the reaction mixture was added water, and the mixture was extracted with ethyl acetate. The organic layer was washed with water, dried over anhydrous sodium sulfate, and concentrated under reduced pressure. The residue was purified by silica gel column chromatography (ethyl acetate/hexane) to give the title compound (65 mg).
MS (ESI+): [M+H]⁺ 436.0.
MS (ESI+). found: 438.0.

E) methyl 4-(4-cyano-3-cyclopentyl-7-methoxy-1H-pyrazolo[3,4-c]pyridin-1-yl)thiophene-2-carboxylate A suspension of methyl 4-(4-bromo-3-cyclopentyl-7-methoxy-1H-pyrazolo[3,4-c]pyridin-1-yl)thiophene-2-carboxylate (65 mg), tetrakis(triphenylphosphine)palladium(0) (34.4 mg) and zinc cyanide (26.2 mg) in DMA (3 mL) was stirred under microwave irradiation at 120° C. for 30 min. To the reaction mixture were added ethyl acetate and water, and the mixture was filtered through Celite. The filtrate was purified by silica gel column chromatography (ethyl acetate/hexane) to give the title compound (40 mg).
¹H NMR (300 MHz, DMSO-d₆) δ 1.60-1.87 (4H, m), 1.87-2.05 (2H, m), 2.05-2.24 (2H, m), 3.71 (1H, quin, J=7.8 Hz), 3.88 (3H, s), 4.03 (3H, s), 8.05 (1H, d, J=1.5 Hz), 8.18 (1H, d, J=1.5 Hz), 8.46 (1H, s).

F) methyl 4-(4-cyano-3-cyclopentyl-7-oxo-6,7-dihydro-1H-pyrazolo[3,4-c]pyridin-1-yl)thiophene-2-carboxylate To a solution of methyl 4-(4-cyano-3-cyclopentyl-7-methoxy-1H-pyrazolo[3,4-c]pyridin-1-yl)thiophene-2-carboxylate (40 mg) in acetonitrile (5 mL) were added sodium iodide (31.4 mg) and chloro(trimethyl)silane (0.066 mL), and the mixture was stirred at 60° C. for 30 min. To the reaction mixture was added water, and the mixture was extracted with ethyl acetate. The organic layer was washed with saturated aqueous sodium hydrogencarbonate solution and saturated brine, dried over anhydrous sodium sulfate, and concentrated under reduced pressure to give the title compound (20 mg).
¹H NMR (300 MHz, DMSO-d₆) δ 1.57-1.98 (6H, m), 2.04-2.18 (2H, m), 3.61 (1H, quin, J=7.8 Hz), 3.86 (3H, s), 8.03 (1H, s), 8.10 (1H, d, J=1.9 Hz), 8.21 (1H, d, J=1.9 Hz), 12.39 (1H, brs).

G) 4-(4-cyano-3-cyclopentyl-7-oxo-6,7-dihydro-1H-pyrazolo[3,4-c]pyridin-1-yl)thiophene-2-carboxylic acid To a solution of methyl 4-(4-cyano-3-cyclopentyl-7-oxo-6,7-dihydro-1H-pyrazolo[3,4-c]pyridin-1-yl)thiophene-2-carboxylate (18 mg) in a mixed solvent of THF (1 mL), methanol (1 mL) and water (1 mL) was added 1N aqueous sodium hydroxide solution (0.195 mL), and the mixture was stirred at room temperature for 15 hr. To the reaction mixture was added 1N hydrochloric acid (0.195 mL), and the reaction mixture was concentrated under reduced pressure. To the residue was added water, and the resulting solid was washed with water and hexane to give the title compound (17 mg).
¹H NMR (300 MHz, DMSO-d₆) δ 1.60-2.01 (6H, m), 2.02-2.19 (2H, m), 3.61 (1H, quin, J=7.8 Hz), 7.96 (1H, s), 8.03 (1H, brs), 8.10 (1H, d, J=1.1 Hz), 12.38 (1H, brs), 13.43 (1H, brs).
MS (ESI+): [M+H]⁺ 355.1.
MS (ESI+). found: 355.1.

Example 66

4-(4-cyano-3-cyclopentyl-7-oxo-6,7-dihydro-1H-pyrazolo[3,4-c]pyridin-1-yl)thiophene-2-carboxamide A solution of 4-(4-cyano-3-cyclopentyl-7-oxo-6,7-dihydro-1H-pyrazolo[3,4-c]pyridin-1-yl)thiophene-2-carboxylic acid (14 mg) obtained in Example 65, EDCI (7.36 mg) and HOBt ammonium salt (18 mg) in DMA (3 mL) was stirred at room temperature for 60 hr. To the reaction mixture was added water, and the mixture was extracted with ethyl acetate. The organic layer was washed with saturated aqueous sodium hydrogencarbonate solution and saturated brine, dried over anhydrous sodium sulfate, and concentrated under reduced pressure. The residue was purified by silica gel column chromatography (ethyl acetate/hexane), and crystallized from ethyl acetate/hexane to give the title compound (6.4 mg).
¹H NMR (300 MHz, DMSO-d₆) δ 1.62-2.01 (6H, m), 2.04-2.19 (2H, m), 3.61 (1H, quin, J=7.9 Hz), 7.52 (1H, brs), 8.00-8.03 (2H, m), 8.06 (1H, s), 8.12 (1H, brs), 12.34 (1H, brs).
MS (ESI+): [M+H]⁺ 354.1.
MS (ESI+). found: 354.1.

Example 67

4-(4-bromo-3-cyclopentyl-7-oxo-6,7-dihydro-1H-pyrazolo[3,4-c]pyridin-1-yl)thiophene-2-carboxamide A) 4-(4-bromo-3-cyclopentyl-7-methoxy-1H-pyrazolo[3,4-c]pyridin-1-yl)thiophene-2-carboxamide The title compound was obtained using 4-bromo-3-cyclopentyl-7-methoxy-1H-pyrazolo[3,4-c]pyridine obtained in Step C of Example 65 and 4-(4,4,5,5-tetramethyl-1,3,2-dioxaborolan-2-yl)thiophene-2-carboxamide obtained in Step B of Example 33, in the same manner as in Step D of Example 65.
¹H NMR (300 MHz, DMSO-d₆) δ, 1.60-1.85 (4H, m), 1.85-1.98 (2H, m), 2.05-2.23 (2H, m), 3.93 (3H, s), 7.54 (1H, brs), 7.93 (1H, d, J=1.1 Hz), 7.95 (1H, s), 8.03 (1H, d, J=1.5 Hz), 8.10 (1H, brs).

B) 4-(4-bromo-3-cyclopentyl-7-oxo-6,7-dihydro-1H-pyrazolo[3,4-c]pyridin-1-yl)thiophene-2-carboxamide The title compound was obtained using 4-(4-bromo-3-cyclopentyl-7-methoxy-1H-pyrazolo[3,4-c]pyridin-1-yl)thiophene-2-carboxamide, in the same manner as in Step F of Example 65.
¹H NMR (300 MHz, DMSO-d₆) δ 1.58-1.98 (6H, m), 2.01-2.20 (2H, m), 3.84 (1H, quin, J=7.9 Hz), 7.27 (1H, s), 7.50 (1H, brs), 8.00 (1H, d, J=1.5 Hz), 8.04 (1H, d, J=1.5 Hz), 8.10 (1H, brs), 11.74 (1H, brs).
MS (ESI+): [M+H]⁺ 407.0.
MS (ESI+). found: 408.7.

Example 68 methyl 4-(4-cyano-3-(2-methylphenyl)-7-oxo-6,7-dihydro-1H-pyrazolo[3,4-c]pyridin-1-yl)thiophene-2-carboxylate The title compound was obtained using 5-bromo-3-fluoro-2-methoxypyridine and 2-methylbenzaldehyde, in the same manner as in Step A to Step F of Example 65.
¹H NMR (300 MHz, DMSO-d₆) δ 2.23 (3H, s), 3.87 (3H, s), 7.25-7.47 (4H, m), 8.05 (1H, s), 8.19 (1H, d, J=1.5 Hz), 8.31 (1H, d, J=1.5 Hz), 12.48 (1H, brs).
MS (ESI+): [M+H]⁺ 391.1.
MS (ESI+). found: 391.1.

Example 69

4-(4-cyano-3-(2-methylphenyl)-7-oxo-6,7-dihydro-1H-pyrazolo[3,4-c]pyridin-1-yl)thiophene-2-carboxylic acid The title, compound was obtained using methyl 4-(4-cyano-3-(2-methylphenyl)-7-oxo-6,7-dihydro-1H-pyrazolo[3,4-c]pyridin-1-yl)thiophene-2-carboxylate obtained in Example 68, in the same manner as in Step G of Example 65.
¹H NMR (300 MHz, DMSO-d₆) δ 2.23 (3H, s), 7.24-7.51 (4H, m), 8.06 (2H, d, J=15.5 Hz), 8.24 (1H, s), 12.47 (1H, brs), 13.41 (1H, brs).
MS (ESI+): [M+H]⁺ 377.1.
MS (ESI+). found: 377.1.

Example 70

4-(4-cyano-3-(2-methylphenyl)-7-oxo-6,7-dihydro-1H-pyrazolo[3,4-c]pyridin-1-yl)thiophene-2-carboxamide The title compound was obtained using 4-(4-cyano-3-(2-methylphenyl)-7-oxo-6,7-dihydro-1H-pyrazolo[3,4-c]pyridin-1-yl)thiophene-2-carboxylic acid obtained in Example 69, in the same manner as in Example 66.
¹H NMR (300 MHz, DMSO-d₆) δ 2.23 (3H, s), 7.25-7.47 (4H, m), 7.54 (1H, brs), 8.04 (1H, s), 8.12 (1H, brs), 8.18 (2H, d, J=4.5 Hz), 12.48 (1H, brs).
MS (ESI+): [M+H]⁺ 376.1.
MS (ESI+). found: 376.1.

Example 71

4-(1-((cis-2-methylcyclopentyl)-4-oxo-4,5-dihydro-1H-pyrrolo[3,2-c]pyridin-3-yl)benzenesulfonamide A) ethyl (2E)-3-(4-bromo-1H-pyrrol-2-yl)acrylate A mixture of ethyl (2E)-3-(4-bromo-1-((2-(trimethylsilyl)ethoxy)methyl)-1H-pyrrol-2-yl)acrylate (200 mg) obtained in Step C of Example 7 and tetra-n-butylammonium fluoride (698 mg) in DME (2 mL) was stirred at 85° C. for 2.5 hr. The reaction mixture was diluted with ethyl acetate, and the mixture was washed with water and saturated brine, dried over anhydrous sodium sulfate, and concentrated under reduced pressure. The residue was purified by silica gel column chromatography (ethyl acetate/hexane) to give the title compound (102 mg).
¹H NMR (300 MHz, CDCl₃) δ 1.32 (3H, t, J=7.2 Hz), 4.24 (2H, q, J=7.2 Hz), 6.02 (1H, d, J=15.9 Hz), 6.54 (1H, dd, J=2.8, 1.7 Hz), 6.89 (1H, dd, J=2.8, 1.7 Hz), 7.44 (1H, d, J=15.9 Hz), 8.63 (1H, brs).

B) ethyl (2E)-3-(4-bromo-1-(cis-2-methylcyclopentyl)-1H-pyrrol-2-yl)acrylate

A solution of ethyl (2E)-3-(4-bromo-1H-pyrrol-2-yl)acrylate (1.3 g), trans-2-methylcyclopentanol (0.64 g) and 2-(tributylphosphoranylidene)acetonitrile (1.928 g) in toluene (12.6 mL) was stirred with heating under reflux for 22 hr under argon atmosphere. The reaction mixture was purified by silica gel column chromatography (ethyl acetate/hexane) to give the title compound (608 mg).
¹H NMR (300 MHz, CDCl₃) δ 0.56 (3H, d, J=6.8 Hz), 1.32 (3H, t, J=7.2 Hz), 1.36-1.50 (1H, m), 1.61-1.78 (1H, m), 1.85-2.11 (3H, m), 2.15-2.34 (2H, m), 4.24 (2H, q, J=7.2 Hz), 4.63 (1H, q, J=7.2 Hz), 6.15 (1H, d, J=15.5 Hz), 6.64 (1H, d, J=1.5 Hz), 6.78 (1H, d, J=1.5 Hz), 7.57 (1H, d, J=15.5 Hz).

C) (2E)-3-(4-bromo-1-(cis-2-methylcyclopentyl)-1H-pyrrol-2-yl)acrylic acid

To a solution of ethyl (2E)-3-(4-bromo-1-(cis-2-methylcyclopentyl)-1H-pyrrol-2-yl)acrylate (800 mg) in THF (7.36 mL) were added 1N aqueous sodium hydroxide solution (7.36 mL) and methanol (10 mL) at room temperature, and the mixture was stirred at room temperature for 18 hr. The reaction mixture was concentrated under reduced pressure to evaporate the methanol and THF, and the remaining aqueous solution was washed with diethyl ether (100 mL). The obtained aqueous layer was acidified with 1N hydrochloric acid (7.36 mL), and the mixture was extracted with ethyl acetate. The organic layer was washed with saturated brine, dried over anhydrous magnesium sulfate, and concentrated under reduced pressure to give the title compound (711 mg).
¹H NMR (300 MHz, CDCl₃) δ 0.56 (3H, d, J=7.2 Hz), 1.36-1.50 (1H, m), 1.62-1.78 (1H, m), 1.85-2.12 (3H, m), 2.16-2.36 (2H, m), 4.63 (1H, q, J=7.2 Hz), 6.15 (1H, d, J=15.5 Hz), 6.70 (1H, d, J=1.5 Hz), 6.81 (1H, d, J=1.9 Hz), 7.65 (1H, d, J=15.5 Hz).

D) (2E)-3-(4-bromo-1-(cis-2-methylcyclopentyl)-1H-pyrrol-2-yl)acryloyl azide

To a solution of (2E)-3-(4-bromo-1-(cis-2-methylcyclopentyl)-1H-pyrrol-2-yl)acrylic acid (700 mg) in DMF (7 mL) was added a solution of triethylamine (0.36 mL) and diphenylphosphoryl azide (0.678 g) in DMF (1 mL) at room temperature, and the mixture was stirred at room temperature for 4 hr. The reaction mixture was added to water, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (685 mg).
¹H NMR (300 MHz, CDCl₃) δ 0.56 (3H, d, J=6.8 Hz), 1.35-1.50 (1H, m), 1.65-1.79 (1H, m), 1.87-2.12 (3H, m), 2.17-2.34 (2H, m), 4.63 (1H, q, J=7.2 Hz), 6.11 (1H, d, J=15.5 Hz), 6.72 (1H, d, J=1.5 Hz), 6.84 (1H, d, J=1.5 Hz), 7.64 (1H, d, J=15.5 Hz).

E) 3-bromo-1-((cis-2-methylcyclopentyl)-1,5-dihydro-4H-pyrrolo[3,2-c]pyridin-4-one A solution of (2E)-3-(4-bromo-1-(cis-2-methylcyclopentyl)-1H-pyrrol-2-yl)acryloyl azide (221 mg) and tributylamine (139 mg) in diphenyl ether (2.2 mL) was stirred under nitrogen atmosphere at 90-105° C. for 15 min, and then at 155-160° C. for 2 hr. The reaction mixture was allowed to be cooled to room temperature, and the residue was purified by silica gel column chromatography (ethyl acetate/hexane) to give the title compound (93 mg).

$^1$H NMR (300 MHz, CDCl$_3$) δ 0.59 (3H, d, J=6.8 Hz), 1.48 (1H, dq, J=13.1, 9.0 Hz), 1.68-1.84 (1H, m), 1.90-2.03 (2H, m), 2.05-2.17 (1H, m), 2.23-2.39 (2H, m), 4.55-4.64 (1H, m), 6.38 (1H, d, J=7.2 Hz), 6.90 (1H, s), 7.11 (1H, d, J=7.2 Hz), 10.90 (1H, brs).

F) 4-(1-(cis-2-methylcyclopentyl)-4-oxo-4,5-dihydro-1H-pyrrolo[3,2-c]pyridin-3-yl)benzenesulfonamide F-1) To a solution of 3-bromo-1-(cis-2-methylcyclopentyl)-1,5-dihydro-4H-pyrrolo[3,2-c]pyridin-4-one (120 mg) in THF (2.4 mL) was added sodium hydride (60% dispersion in mineral oil, 17.9 mg), and the mixture was stirred under argon atmosphere at 0° C. for 1 hr. To the reaction mixture was added a solution of (2-(chloromethoxy)ethyl)(trimethyl)silane (74.6 mg) in THF (0.5 mL) at 0° C., and the mixture was stirred at room temperature for 18 hr. The reaction mixture was added to water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give an oil (124 mg).

$^1$H NMR (300 MHz, CDCl$_3$) δ −0.05-0.01 (9H, m), 0.59 (3H, d, J=6.8 Hz), 0.89-0.97 (2H, m), 1.40-1.55 (1H, m), 1.68-1.84 (1H, m), 1.88-2.02 (2H, m), 2.04-2.16 (1H, m), 2.23-2.38 (2H, m), 3.61-3.70 (2H, m), 4.52-4.62 (1H, m), 5.40 (2H, q, J=10.1 Hz), 6.35 (1H, d, J=7.6 Hz), 6.87 (1H, s), 7.15 (1H, d, J=7.6 Hz).

F-2) A mixture of the obtained oil (53 mg), 4-(4,4,5,5-tetramethyl-1,3,2-dioxaborolan-2-yl)benzenesulfonamide (52.9 mg), tetrakis(triphenylphosphine)palladium(0) (21.6 mg) and potassium carbonate (17.3 mg) in DMF (2 mL)/water (0.2 mL) was stirred under microwave irradiation at 130° C. for 1 hr. The reaction mixture was diluted with ethyl acetate, and the mixture was washed with water and saturated brine, dried over anhydrous sodium sulfate, and concentrated under reduced pressure. The residue was purified by silica gel column chromatography (ethyl acetate/hexane) to give an oil (45 mg).

$^1$H NMR (300 MHz, CDCl$_3$) δ −0.05-0.01 (9H, m), 0.64 (3H, d, J=7.2 Hz), 0.89-0.98 (2H, m), 1.46-1.57 (1H, m), 1.79 (1H, dt, J=13.2, 8.7 Hz), 1.93-2.09 (2H, m), 2.12-2.27 (1H, m), 2.27-2.46 (2H, m), 3.60-3.70 (2H, m), 4.66 (1H, q, J=7.1 Hz), 4.86 (2H, s), 5.37-5.50 (2H, m), 6.46 (1H, d, J=7.6 Hz), 7.03 (1H, s), 7.24 (1H, d, J=7.6 Hz), 7.90 (4H, s).

F-3) To a suspension of the obtained oil (45 mg) and triethylsilane (20 mg) was added trifluoroacetic acid (0.27 mL) at room temperature, and the mixture was stirred at room temperature for 1 hr under nitrogen atmosphere. The reaction mixture was concentrated under reduced pressure, to the residue were added acetonitrile (0.5 mL) and aqueous ammonia solution (25%, 0.5 mL), and the mixture was stirred at room temperature for 2 hr. The precipitate was collected by filtration, and washed with acetonitrile and ethyl acetate to give the title compound (24 mg).

$^1$H NMR (300 MHz, DMSO-d$_6$) δ 0.50 (3H, d, J=6.8 Hz), 1.38-1.53 (1H, m), 1.66 (1H, dt, J=12.7, 8.5 Hz), 1.83-2.04 (2H, m), 2.18-2.28 (2H, m), 2.34 (1H, dt, J=14.7, 7.4 Hz), 4.83 (1H, q, J=7.4 Hz), 6.63 (1H, d, J=7.2 Hz), 7.05-7.12 (1H, m), 7.26 (2H, brs), 7.50 (1H, s), 7.70-7.77 (2H, m), 8.06-8.13 (2H, m), 10.86 (1H, d, J=5.3 Hz).

MS (ESI+): [M+H]$^+$ 372.1.
MS (ESI+). found: 372.1.

Example 72

2-(4-(1-(2,6-difluorophenyl)-4-oxo-4,5-dihydro-1H-pyrazolo[4,3-c]pyridin-3-yl)phenyl)acetamide To a solution of (4-(1-(2,6-difluorophenyl)-4-oxo-4,5-dihydro-1H-pyrazolo[4,3-c]pyridin-3-yl)phenyl)acetonitrile (80.0 mg) obtained in Example 39 in DMSO (0.8 mL) was added potassium carbonate (36.6 mg), and then 30% aqueous hydrogen peroxide (0.068 mL) was added thereto. The reaction mixture was stirred overnight at room temperature. To the reaction mixture was added water, and the white precipitate was collected by filtration, washed with water, and dried in vacuum to give the title compound (7.5 mg).

$^1$H NMR (300 MHz, DMSO-d$_6$) δ 3.44 (2H, s), 6.25 (1H, d, J=7.2 Hz), 6.91 (1H, brs), 7.35 (3H, d, =8.3 Hz), 7.43-7.59 (3H, m), 7.67-7.86 (1H, m), 8.22 (2H, d, J=7.9 Hz), 11.40 (1H, brs).

MS (ESI+): [M+H]$^+$ 381.1.
MS (ESI+). found: 381.1.

Example 73 methyl 3-(5-cyano-3-thienyl)-1-cyclopentyl-4-oxo-4,5-dihydro-1H-pyrrolo[3,2-c]pyridine-7-carboxylate A-1) A powder was obtained using the powder obtained in Step E-2 of Example 29 and 4-(4,4,5,5-tetramethyl-1,3,2-dioxaborolan-2-yl)thiophene-2-carboxamide obtained in Step B of Example 33, in the same manner as in Step E-3 of Example 29.

MS (ESI+): [M+H]$^+$ 516.7.
MS (ESI+). found: 516.1.

A-2) The title compound was obtained using the obtained powder, in the same manner as in Step H of Example 33 and Step H-3 of Example 7.

MS (ESI+): [M+H]$^+$ 368.4.
MS (ESI+). found: 368.2.

Example 74 methyl 1-cyclopentyl-4-oxo-3-(5-(5-oxo-4,5-dihydro-1,2,4-oxadiazol-3-yl)-3-thienyl)-4,5-dihydro-1H-pyrrolo[3,2-c]pyridine-7-carboxylate To a solution of methyl 3-(5-cyano-3-thienyl)-1-cyclopentyl-4-oxo-4,5-dihydro-1H-pyrrolo[3,2-c]pyridine-7-carboxylate (111 mg) obtained in Example 73 in DMSO (2 mL) were added sodium hydrogencarbonate (127 mg) and hydroxylamine hydrochloride (84 mg) at room temperature, and the mixture was stirred at 90° C. for 30 min. To the reaction mixture was added water, and the mixture was extracted with ethyl acetate. The organic layer was washed with saturated brine, dried over anhydrous sodium sulfate, and concentrated under reduced pressure. To a solution of the residue in THF (2 mL) were added 1,1'-carbonyldiimidazole (73.5 mg) and 1,8-diazabicyclo[5.4.0]undec-7-ene (0.068 mL) at room temperature, and the mixture was stirred overnight. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (90 mg).
MS (ESI+): [M+H]+ 427.4.
MS (ESI+). found: 427.1.

Example 75

4-(3-cyclopentyl-7-oxo-6,7-dihydro-1H-pyrazolo[3,4-c]pyridin-1-yl)benzenesulfonamide A) 3-iodo-2-methoxyisonicotinic acid To a 28% methanol solution (5 g) of sodium methoxide was added 2-bromo-3-iodoisonicotinic acid (880 mg), and the mixture was stirred at 80° C. for 2 hr. To the reaction mixture was added 1N hydrochloric acid under ice-cooling, and the mixture was extracted with ethyl acetate. The organic layer was washed with saturated brine, dried over anhydrous sodium sulfate, and concentrated under reduced pressure to give the title compound (780 mg).
MS (ESI+): [M+H]+ 279.9.
MS (ESI+). found: 279.7.

B) 3-iodo-2-methoxy-N-(4-sulfamoylphenyl)pyridine-4-carbohydrazone acid

A solution of 3-iodo-2-methoxyisonicotinic acid (748 mg), 4-hydrazinobenzenesulfonamide hydrochloride (1.20 g), EDCI hydrochloride (2.57 g), HOBt (1.23 g) and triethylamine (1.36 g) in DMF (30 mL) was stirred overnight at room temperature. To the reaction mixture was added water, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (600 mg).
MS (ESI+): [M+H]+ 449.0.
MS (ESI+). found: 448.9.

C) 4-(3-hydroxy-7-methoxy-1H-pyrazolo[3,4-c]pyridin-1-yl)benzenesulfonamide

A solution of 3-iodo-2-methoxy-N-(4-sulfamoylphenyl)pyridine-4-carbohydrazone acid (100 mg), L-proline (5.1 mg), potassium carbonate (92 mg) and copper(I) iodide (4.3 mg) in DMSO (5 mL) was stirred at 100° C. for 2 hr. To the reaction mixture was added 1N hydrochloric acid under ice-cooling, and the mixture was extracted with ethyl acetate. The organic layer was washed with saturated aqueous sodium thiosulfate solution and saturated brine, dried over anhydrous magnesium sulfate, and concentrated under reduced pressure to give the title compound (80 mg).
$^1$H NMR (300 MHz, DMSO-$d_6$) δ 3.96 (3H, s), 7.34 (1H, d, J=5.7 Hz), 7.42 (2H, s), 7.73 (2H, d, J=9.1 Hz), 7.83 (1H, d, J=5.7 Hz), 7.90 (2H, d, J=8.7 Hz), 11.60 (1H, s).

D) 7-methoxy-1-(4-sulfamoylphenyl)-1H-pyrazolo[3,4-c]pyridin-3-yl trifluoromethanesulfonate To a solution of 4-(3-hydroxy-7-methoxy-1H-pyrazolo[3,4-c]pyridin-1-yl)benzenesulfonamide (70.5 mg) in pyridine (5 mL) was added trifluoromethanesulfonic anhydride (186 mg) under ice-cooling, and the mixture was stirred under nitrogen atmosphere at room temperature for 3 hr. To the reaction mixture was added saturated aqueous sodium hydrogencarbonate solution under ice-cooling, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate) to give the title compound (59 mg).
$^1$H NMR (300 MHz, DMSO-$d_6$) δ 3.97 (3H, s), 7.47 (1H, d, J=5.7 Hz), 7.54 (2H, s), 7.86-8.03 (4H, m), 8.05 (1H, d, J=5.7 Hz).

E) 4-(3-(cyclopent-1-en-1-yl)-7-methoxy-1H-pyrazolo[3,4-c]pyridin-1-yl)benzenesulfonamide A solution of 7-methoxy-1-(4-sulfamoylphenyl)-1H-pyrazolo[3,4-c]pyridin-3-yl trifluoromethanesulfonate (59 mg), 2-(cyclopent-1-en-1-yl)-4,4,5,5-tetramethyl-1,3,2-dioxaborolane (25.3 mg), tetrakis(triphenylphosphine)palladium (0) (7.5 mg) and 2M aqueous sodium carbonate solution (0.33 mL) in DME (5 mL) was stirred under argon atmosphere at 100° C. for 3 hr. To the reaction mixture was added water, and the mixture was extracted with ethyl acetate. The organic layer was washed with water and saturated brine, dried over anhydrous sodium sulfate, and concentrated under reduced pressure. The residue was purified by silica gel column chromatography (ethyl acetate/hexane) to give the title compound (22 mg).
MS (ESI+): [M+H]+ 371.1.
MS (ESI+). found: 371.0.

F) 4-(3-cyclopentyl-7-methoxy-1H-pyrazolo[3,4-c]pyridin-1-yl)benzenesulfonamide

To a solution of 4-(3-(cyclopent-1-en-1-yl)-7-methoxy-1H-pyrazolo[3,4-c]pyridin-1-yl)benzenesulfonamide (22 mg) in methanol (10 mL) was added 10% palladium/carbon (6.32 mg) containing water, and the mixture was stirred overnight under hydrogen atmosphere at room temperature. The reaction mixture was filtered, and the filtrate was concentrated under reduced pressure to give the title compound (30 mg).
MS (ESI+): [M+H]+ 373.1.
MS (ESI+). found: 373.0.

G) 4-(3-cyclopentyl-7-oxo-6,7-dihydro-1H-pyrazolo[3,4-c]pyridin-1-yl)benzenesulfonamide To a solution of 4-(3-cyclopentyl-7-methoxy-1H-pyrazolo[3,4-c]pyridin-1-yl)benzenesulfonamide (22.4 mg) in acetonitrile (10 mL) were added sodium iodide (18.0 mg) and chloro(trimethyl)silane (52.1 mg), and the mixture was stirred at 80° C. for 5 hr. To the reaction mixture was added water at room temperature, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (20 mg).
$^1$H NMR (300 MHz, DMSO-$d_6$) δ 1.64-1.92 (6H, m), 2.00-2.24 (2H, m), 3.36-3.45 (1H, m), 6.65 (1H, d, J=6.8 Hz), 7.08 (1H, d, J=6.8 Hz), 7.44 (2H, brs), 7.78-7.93 (4H, m), 11.52 (1H, brs).
MS (ESI+): [M+H]+ 359.1.
MS (ESI+). found: 358.9.

Example 76 methyl 4-(7-cyano-1-cyclopentyl-4-oxo-4,5-dihydro-1H-pyrrolo[3,2-c]pyridin-3-yl)thiophene-2-carboxylate A) methyl 4-(7-cyano-1-cyclopentyl-4-methoxy-1H-pyrrolo[3,2-c]pyridin-3-yl)thiophene-2-carboxylate The title compound was obtained using 3-bromo-1-cyclopentyl-4-methoxy-4,5-dihydro-1H-pyrrolo[3,2-c]pyridine-7-carbonitrile obtained in Step H of Example 33 and methyl 4-(4,4,5,5-tetramethyl-1,3,2-dioxaborolan-2-yl)thiophene-2-carboxylate, in the same manner as in Step I of Example 33.
MS (ESI+): [M+H]$^+$ 382.4.
MS (ESI+). found: 382.1.

B) methyl 4-(7-cyano-1-cyclopentyl-4-oxo-4,5-dihydro-1H-pyrrolo[3,2-c]pyridin-3-yl)thiophene-2-carboxylate The title compound was obtained using methyl 4-(7-cyano-1-cyclopentyl-4-methoxy-1H-pyrrolo[3,2-c]pyridin-3-yl)thiophene-2-carboxylate, in the same manner as in Step J of Example 33.
MS (ESI+): [M+H]$^+$ 368.4.
MS (ESI+). found: 368.2.

Example 77

4-(7-cyano-1-cyclopentyl-4-oxo-4,5-dihydro-1H-pyrrolo[3,2-c]pyridin-3-yl)thiophene-2-carboxylic acid The title compound was obtained using methyl 4-(7-cyano-1-cyclopentyl-4-oxo-4,5-dihydro-1H-pyrrolo[3,2-c]pyridin-3-yl)thiophene-2-carboxylate obtained in Example 76, in the same manner as in Step F of Example 33.
MS (ESI+): [M+H]$^+$ 354.4.
MS (ESI+). found: 354.1.

Example 78 methyl 4-(4-bromo-3-(2-methylphenyl)-7-oxo-6,7-dihydro-1H-pyrazolo[3,4-c]pyridin-1-yl)thiophene-2-carboxylate The title compound was obtained using methyl 4-(4-bromo-7-methoxy-3-(2-methylphenyl)-1H-pyrazolo[3,4-c]pyridin-1-yl)thiophene-2-carboxylate obtained in Step D of Example 68, in the same manner as in Step F of Example 65.
$^1$H NMR (300 MHz, DMSO-d$_6$) δ 2.14 (3H, s), 3.86 (3H, s), 7.23-7.45 (5H, m), 8.19 (1H, d, J=1.9 Hz), 8.31 (1H, d, J=1.9 Hz), 11.88 (1H, brs).
MS (ESI+): [M+H]$^+$ 444.0.
MS (ESI+). found: 446.1.

Example 79

4-(4-bromo-3-(2-methylphenyl)-7-oxo-6,7-dihydro-1H-pyrazolo[3,4-c]pyridin-1-yl)thiophene-2-carboxylic acid The title compound was obtained using methyl 4-(4-bromo-3-(2-methylphenyl)-7-oxo-6,7-dihydro-1H-pyrazolo[3,4-c]pyridin-1-yl)thiophene-2-carboxylate obtained in Example 78, in the same manner as in Step G of Example 65.
$^1$H NMR (300 MHz, DMSO-d$_6$) δ 2.14 (3H, s), 7.15-7.51 (5H, m), 8.05 (1H, d, J=0.8 Hz), 8.20 (1H, d, J=1.1 Hz), 11.86 (1H, d, J=5.7 Hz), 13.41 (1H, brs).
MS (ESI+): [M+H]$^+$ 430.0.
MS (ESI+). found: 432.2.

Example 80

4-(4-bromo-3-(2-methylphenyl)-7-oxo-6,7-dihydro-1H-pyrazolo[3,4-c]pyridin-1-yl)thiophene-2-carboxamide The title compound was obtained using 4-(4-bromo-3-(2-methylphenyl)-7-oxo-6,7-dihydro-1H-pyrazolo[3,4-c]pyridin-1-yl)thiophene-2-carboxylic acid obtained in Example 79, in the same manner as in Example 66.
$^1$H NMR (300 MHz, DMSO-d$_6$) δ 2.14 (3H, s), 7.23-7.45 (5H, m), 7.51 (1H, brs), 8.05-8.17 (2H, m), 8.18 (1H, s), 11.88 (1H, brs).
MS (ESI+): [M+H]$^+$ 429.0.
MS (ESI+). found: 428.9.

Example 81

4-(7-cyano-1-cyclopentyl-4-oxo-4,5-dihydro-1H-pyrrolo[3,2-c]pyridin-3-yl)benzamide The title compound was obtained using 3-bromo-1-cyclopentyl-4-methoxy-4,5-dihydro-1H-pyrrolo[3,2-c]pyridine-7-carbonitrile obtained in Step H of Example 33 and (4-(ethoxycarbonyl)phenyl)boronic acid, in the same manner as in Step E-3 of Example 29, Step F of Example 33, Step G of Example 33 and Step J of Example 33.
MS (ESI+): [M+H]$^+$ 347.3.
MS (ESI+). found: 347.2.

Example 82

4-(4-oxo-1-(tetrahydrofuran-3-yl)-4,5-dihydro-1H-pyrazolo[4,3-c]pyridin-3-yl)benzenesulfonamide A) 4-iodo-2-methoxy-N'-(tetrahydrofuran-3-yl)nicotinohydrazide A solution of 4-iodo-2-methoxynicotinic acid (1.6 g 1.5 g) obtained in Step C of Example 6, tetrahydrofuran-3-ylhydrazine dihydrochloride (1.00 g), DIEA (3.0 mL), EDCI hydrochloride (1.32 g) and HOBt (0.930 g) in DMF (75 mL) was stirred overnight at room temperature. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane) to give the title compound (1.06 g).
$^1$H NMR (300 MHz, DMSO-d$_6$) δ 1.79-1.98 (2H, m), 3.56-3.92 (8H, m), 5.22 (1H, dd, J=6.4 Hz, 3.8 Hz), 7.46 (1H, d, J=5.7 Hz), 7.86 (1H, d, J=5.7 Hz), 9.83 (1H, d, J=6.0 Hz).
MS (ESI+): [M+H]$^+$ 364.0.
MS (ESI+). found: 364.0.

B) 4-methoxy-1-(tetrahydrofuran-3-yl)-1,2-dihydro-3H-pyrazolo[4,3-c]pyridin-3-one A solution of 4-iodo-2-methoxy-N'-(tetrahydrofuran-3-yl)nicotinohydrazide (1.26 g), L-proline (0.080 g), potassium carbonate (0.957 g) and copper(I) iodide (0.066 g) in DMSO (25 mL) was stirred under nitrogen atmosphere at room temperature for 3 hr. The reaction mixture was purified by silica gel column chromatography (ethyl acetate/hexane) to give the title compound (0.263 g).

$^1$H NMR (300 MHz, DMSO-$d_6$) δ 2.07-2.23 (1H, m), 2.33 (1H, dq, J=12.7 Hz, 7.6 Hz), 3.75-3.88 (2H, m), 3.93 (3H, s), 3.96-4.07 (2H, m), 5.17-5.30 (1H, m), 7.11 (1H, d, J=6.4 Hz), 7.79 (1H, d, J=6.0 Hz), 11.04 (1H, brs).

MS (ESI+): [M+H]$^+$ 236.1.
MS (ESI+). found: 236.1.

C) 4-methoxy-1-(tetrahydrofuran-3-yl)-1H-pyrazolo[4,3-c]pyridin-3-yl trifluoromethanesulfonate To a solution of 4-methoxy-1-(tetrahydrofuran-3-yl)-1,2-dihydro-3H-pyrazolo[4,3-c]pyridin-3-one (250 mg) and pyridine (0.344 mL) in acetonitrile (25 mL) was added trifluoromethanesulfonic anhydride (0.360 mL), and the mixture was stirred at 0° C. for 1 hr. To the reaction mixture was added saturated aqueous ammonium chloride solution, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (259 mg).

$^1$H NMR (300 MHz, DMSO-$d_6$) δ 2.15-2.30 (1H, m), 2.37-2.48 (1H, m), 3.81-3.92 (2H, m), 3.96-4.13 (5H, m), 5.42-5.58 (1H, m), 7.45 (1H, d, J=6.0 Hz), 8.05 (1H, d, J=6.4 Hz).

MS (ESI+): [M+H]$^+$ 368.1.
MS (ESI+). found: 367.9.

D) 4-(4-methoxy-1-(tetrahydrofuran-3-yl)-1H-pyrazolo[4,3-c]pyridin-3-yl)benzenesulfonamide A solution of 4-methoxy-1-(tetrahydrofuran-3-yl)-1H-pyrazolo[4,3-c]pyridin-3-yl trifluoromethanesulfonate (225 mg), 4-(4,4,5,5-tetramethyl-1,3,2-dioxaborolan-2-yl)benzenesulfonamide (260 mg), tetrakis(triphenylphosphine)palladium(0) (70.8 mg) and 2M aqueous sodium carbonate solution (1.53 mL) in DME (15 mL) was heated overnight with reflux under nitrogen atmosphere. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane), and the obtained solid was washed with ethyl acetate/diisopropyl ether to give the title compound (176 mg).

$^1$H NMR (300 MHz, DMSO-$d_6$) δ 2.31-2.57 (2H, m), 3.90 (1H, td, J=8.0 Hz, 5.9 Hz), 3.95-4.06 (4H, m), 4.07-4.19 (2H, m), 5.48-5.60 (1H, m), 7.32-7.49 (3H, m), 7.88-7.97 (2H, m), 8.00 (1H, d, J=6.0 Hz), 8.07-8.17 (2H, m).

MS (ESI+): [M+H]$^+$ 375.1.
MS (ESI+). found: 375.2.

E) 4-(4-oxo-1-(tetrahydrofuran-3-yl)-4,5-dihydro-1H-pyrazolo[4,3-c]pyridin-3-yl)benzenesulfonamide To a solution of 4-(4-methoxy-1-(tetrahydrofuran-3-yl)-1H-pyrazolo[4,3-c]pyridin-3-yl)benzenesulfonamide (167 mg) in acetonitrile (15 mL) were added sodium iodide (134 mg) and chloro(trimethyl)silane (0.452 mL), and the mixture was stirred at 60° C. for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane/methanol), and the obtained solid was washed with ethyl acetate to give the title compound (142 mg).

$^1$H NMR (300 MHz, DMSO-$d_6$) δ 2.29-2.49 (2H, m), 3.83-4.00 (2H, m), 4.01-4.18 (2H, m), 5.34-5.50 (1H, m), 6.74 (1H, d, J=6.4 Hz), 7.30 (1H, dd, J=7.2 Hz, 6.0 Hz), 7.40 (2H, s), 7.80-7.96 (2H, m), 8.38-8.60 (2H, m), 11.20 (1H, d, J=6.0 Hz).

MS (ESI+): [M+H]$^+$ 361.1.
MS (ESI+). found: 361.1.

Example 83

4-(4-oxo-1-(tetrahydrofuran-3-yl)-4,5-dihydro-1H-pyrazolo[4,3-c]pyridin-3-yl)benzenesulfonamide Racemic 4-(4-oxo-1-(tetrahydrofuran-3-yl)-4,5-dihydro-1H-pyrazolo[4,3-c]pyridin-3-yl)benzenesulfonamide (135 mg) obtained in Example 82 was resolved by HPLC (column: CHIRALCEL OD (trade name), 50 mmID×500 mmL, manufactured by Daicel Chemical Industries, mobile phase: methanol 100%) to give the title compound (54.3 mg) having a shorter retention time.

MS (ESI+): [M+H]$^+$ 361.1.
MS (ESI+). found: 360.9.

Example 84

4-(4-oxo-1-(tetrahydrofuran-3-yl)-4,5-dihydro-1H-pyrazolo[4,3-c]pyridin-3-yl)benzenesulfonamide Racemic 4-(4-oxo-1-(tetrahydrofuran-3-yl)-4,5-dihydro-1H-pyrazolo[4,3-c]pyridin-3-yl)benzenesulfonamide (135 mg) obtained in Example 82 was resolved by HPLC (column: CHIRALCEL OD (trade name), 50 mmID×500 mmL, manufactured by Daicel Chemical Industries, mobile phase: methanol 100%) to give the title compound (45.7 mg) having a longer retention time.

MS (ESI+): [M+H]$^+$ 361.1.
MS (ESI+). found: 360.9.

Example 85

4-(1-(cis-2-methylcyclopentyl)-4-oxo-4,5-dihydro-1H-pyrrolo[3,2-c]pyridin-3-yl)thiophene-2-carboxamide A mixture of the oil (122 mg) obtained in Step F-1 of Example 71, 4-(4,4,5,5-tetramethyl-1,3,2-dioxaborolan-2-yl)thiophene-2-carboxamide obtained in Step B of Example 33 (109 mg), (1,1'-bis(diphenylphosphino)ferrocene)dichloropalladium(II) (21 mg) and 2 M aqueous sodium carbonate solution (0.287 mL) in DME (2 mL) was stirred under microwave irradiation at 120° C. for 1 hr. The reaction mixture was added to water, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give a powder (85 mg).

$^1$H NMR (300 MHz, CDCl$_3$) δ −0.02 (9H, s), 0.61 (3H, d, J=6.8 Hz), 0.91-0.98 (2H, m), 1.44-1.55 (1H, m), 1.70-1.87 (1H, m), 1.93-2.10 (2H, m), 2.18 (1H, dt, J=14.4, 7.7 Hz), 2.27-2.42 (2H, m), 3.62-3.69 (2H, m), 4.63 (1H, q, J=6.9 Hz), 5.37-5.48 (2H, m), 5.76 (2H, brs), 6.42 (1H, d, J=7.6 Hz), 7.10 (1H, s), 7.20 (1H, d, J=7.6 Hz), 8.06 (1H, d, J=1.5 Hz), 8.28 (1H, d, J=1.5 Hz).

To a suspension of the obtained powder (84 mg) and triethylsilane (38.8 mg) was added trifluoroacetic acid (0.53 mL) at room temperature, and the mixture was stirred under nitrogen atmosphere at room temperature for 1 hr. The reaction mixture was concentrated under reduced pressure, to the residue were added acetonitrile (1.3 mL) and 25% aqueous ammonia solution (1.3 mL), and the mixture was stirred at room temperature for 2 hr. The reaction mixture was added to water, and the mixture was extracted with ethyl acetate. The organic layer was washed with saturated brine, dried over anhydrous sodium sulfate, and concentrated under reduced pressure. The residue was purified by silica gel column chromatography (methanol/ethyl acetate) to give the title compound (48 mg).

$^1$H NMR (300 MHz, DMSO-$d_6$) δ 0.50 (3H, d, J=6.8 Hz), 1.45 (1H, dq, J=12.4, 8.6 Hz), 1.62-1.79 (1H, m), 1.86-2.07 (2H, m), 2.08-2.40 (3H, m), 4.81 (1H, q, J=7.2 Hz), 6.60 (1H, d, J=6.8 Hz), 7.05 (1H, dd, J=7.2, 6.0 Hz), 7.36 (1H, brs), 7.37 (1H, s), 7.79 (1H, brs), 8.19 (1H, d, J=1.5 Hz), 8.71 (1H, d, J=1.5 Hz), 10.85 (1H, d, J=6.0 Hz).

MS (ESI+): [M+H]$^+$ 342.1.
MS (ESI+). found: 341.9.

Example 86

4-(1-tert-butyl-4-oxo-4,5-dihydro-1H-pyrazolo[4,3-c]pyridin-3-yl)benzenesulfonamide A) N'-tert-butyl-4-iodo-2-methoxynicotinohydrazide A solution of 4-iodo-2-methoxynicotinic acid (3.00 g) obtained in Step C of Example 6, tert-butylhydrazine hydrochloride (1.61 g), DIEA (5.63 mL), EDCI hydrochloride (2.47 g) and HOBt (1.74 g) in DMF (100 mL) was stirred overnight at room temperature. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (3.23 g).

$^1$H NMR (300 MHz, DMSO-$d_6$) δ 1.10 (9H, s), 3.83 (3H, s), 4.78 (1H, d, J=7.9 Hz), 7.47 (1H, d, J=5.7 Hz), 7.85 (1H, d, J=5.3 Hz), 9.65 (1H, d, J=7.9 Hz).

MS (ESI+): [M+H]$^+$ 350.0.
MS (ESI+). found: 350.0.

B) 1-tert-butyl-4-methoxy-1,2-dihydro-3H-pyrazolo[4,3-c]pyridin-3-one

A solution of N'-tert-butyl-4-iodo-2-methoxynicotinohydrazide (1.00 g), L-proline (0.066 g), potassium carbonate (0.792 g) and copper(I) iodide (0.055 g) in DMSO (30 mL) was stirred under nitrogen atmosphere at room temperature for 6 hr. The reaction mixture was purified by silica gel column chromatography (ethyl acetate/hexane) to give the title compound (341 mg).

$^1$H NMR (300 MHz, DMSO-$d_6$) δ 1.60 (9H, s), 3.92 (3H, s), 7.17 (1H, d, J=6.4 Hz), 7.71 (1H, d, J=6.4 Hz), 10.73 (1H, brs).

MS (ESI+): [M+H]$^+$ 222.1.
MS (ESI+). found: 222.1.

C) 1-tert-butyl-4-methoxy-1H-pyrazolo[4,3-c]pyridin-3-yl trifluoromethanesulfonate To a solution of 1-tert-butyl-4-methoxy-1,2-dihydro-3H-pyrazolo[4,3-c]pyridin-3-one (337 mg) and pyridine (0.493 mL) in acetonitrile (30 mL) was added trifluoromethanesulfonic anhydride (0.203 mL), and the mixture was stirred at 0° C. for 1 hr. To the reaction mixture was added saturated aqueous ammonium chloride solution, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (525 mg).

$^1$H NMR (300 MHz, DMSO-$d_6$) δ 1.68 (9H, s), 4.03 (3H, s), 7.54 (1H, d, J=6.4 Hz), 7.98 (1H, d, J=6.4 Hz).

MS (ESI+): [M+H]$^+$ 354.1.
MS (ESI+). found: 354.0.

D) 4-(1-tert-butyl-4-methoxy-1H-pyrazolo[4,3-c]pyridin-3-yl)benzenesulfonamide

A solution of 1-tert-butyl-4-methoxy-1H-pyrazolo[4,3-c]pyridin-3-yl trifluoromethanesulfonate (521 mg), 4-(4,4,5,5-tetramethyl-1,3,2-dioxaborolan-2-yl)benzenesulfonamide (501 mg), tetrakis(triphenylphosphine)palladium(0) (170 mg) and 2M aqueous sodium carbonate solution (3.69 mL) in DME (40 mL) was heated overnight with reflux under nitrogen atmosphere. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane), and the obtained solid was washed with ethyl acetate/diisopropyl ether to give the title compound (433 mg).

$^1$H NMR (300 MHz, DMSO-$d_6$) δ 1.75 (9H, s), 3.99 (3H, s), 7.42 (2H, s), 7.53 (1H, d, J=6.1 Hz), 7.86-8.00 (3H, m), 8.06 (2H, d, J=8.7 Hz).

MS (ESI+): [M+H]$^+$ 361.1.
MS (ESI+). found: 361.1.

E) 4-(1-tert-butyl-4-oxo-4,5-dihydro-1H-pyrazolo[4,3-c]pyridin-3-yl)benzenesulfonamide To a solution of 4-(1-tort-butyl-4-methoxy-1H-pyrazolo[4,3-c]pyridin-3-yl)benzenesulfonamide (80.0 mg) in acetonitrile (10 mL) were added sodium iodide (66.5 mg) and chloro(trimethyl)silane (0.225 mL), and the mixture was stirred at 60° C. for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane/methanol) to give the title compound (73.7 mg).

$^1$H NMR (300 MHz, DMSO-$d_6$) δ 1.71 (9H, s), 6.84 (1H, d, J=7.6 Hz), 7.20 (1H, d, J=7.6 Hz), 7.86 (2H, d, J=8.3 Hz), 8.42 (2H, d, J=8.3 Hz).

MS (ESI+): [M+H]$^+$ 367.1.
MS (ESI+). found: 346.9.

Example 87

4-(4-oxo-1-(tetrahydro-2H-pyran-3-yl)-4,5-dihydro-1H-pyrazolo[4,3-c]pyridin-3-yl)benzenesulfonamide Racemic 4-(4-oxo-1-(tetrahydro-2H-pyran-3-yl)-4,5-dihydro-1H-pyrazolo[4,3-c]pyridin-3-yl)benzenesulfonamide (125 mg) obtained in Example 28 was resolved by HPLC (column: CHIRALCEL OD (trade name), 50 mmID×500 mmL, manufactured by Daicel Chemical Industries, mobile phase: hexane/ethanol=500/500) to give, the title compound (58.9 mg) having a shorter retention time.

MS (ESI+): [M+H]$^+$ 375.1.

MS (ESI+). found: 374.9.

Example 88

4-(4-oxo-1-(tetrahydro-2H-pyran-3-yl)-4,5-dihydro-1H-pyrazolo[4,3-c]pyridin-3-yl)benzenesulfonamide Racemic 4-(4-oxo-1-(tetrahydro-2H-pyran-3-yl)-4,5-dihydro-1H-pyrazolo[4,3-c]pyridin-3-yl)benzenesulfonamide (125 mg) obtained in Example 28 was resolved by HPLC (column: CHIRALCEL OD (trade name), 50 mmID×500 mmL, was resolved by Daicel Chemical Industries, mobile phase: hexane/ethanol=500/500) to give the title compound (54.0 mg) having a longer retention time.

MS (ESI+): [M+H]$^+$ 375.1.

MS (ESI+). found: 375.0.

Example 89

3-(7-cyano-1-cyclopentyl-4-oxo-4,5-dihydro-1H-pyrrolo[3,2-c]pyridin-3-yl)benzamide The title compound was obtained using 3-bromo-1-cyclopentyl-4-methoxy-4,5-dihydro-1H-pyrrolo[3,2-c]pyridine-7-carbonitrile obtained in Step H of Example 33 and (3-carbamoyl phenyl)boronic acid, in the same manner as in Step I of Example 33 and Step J of Example 33.

MS (ESI+): [M+H]$^+$ 347.4.

MS (ESI+). found: 347.3.

Example 90

4-(1-((2,2-dimethyl-1,3-dioxolan-4-yl)methyl)-4-oxo-4,5-dihydro-1H-pyrrolo[3,2-c]pyridin-3-yl)benzenesulfonamide Example 91

4-(1-(2,3-dihydroxypropyl)-4-oxo-4,5-dihydro-1H-pyrrolo[3,2-c]pyridin-3-yl)benzenesulfonamide A) 1-((2,2-dimethyl-1,3-dioxolan-4-yl)methyl)-3-iodo-4-methoxy-1H-pyrrolo[3,2-c]pyridine To a solution of 3-iodo-4-methoxy-1H-pyrrolo[3,2-c]pyridine in DMF (5 mL) was added sodium hydride (60% dispersion in mineral oil, 73.0 mg), and the mixture was stirred at room temperature for 1 hr, (2,2-Dimethyl-1,3-dioxolan-4-yl) methyl 4-methylbenzenesulfonate (523 mg) was added thereto, and the mixture was stirred overnight at room temperature. The reaction mixture was extracted with water and ethyl acetate, and the organic layer was washed with saturated brine, dried over anhydrous magnesium sulfate, filtered, and concentrated under reduced pressure. The obtained residue was purified by silica gel column chromatography (hexane/ethyl acetate) to give the title compound (122 mg).

$^1$H NMR (300 MHz, DMSO-d$_6$) δ 1.24 (6H, d, J=11.7 Hz), 3.62 (1H, dd, J=8.7, 5.7 Hz), 3.95 (3H, s), 3.99-4.07 (1H, m), 4.16-4.27 (1H, m), 4.30-4.42 (2H, m), 7.24 (1H, d, J=6.0 Hz), 7.47 (1H, s), 7.76 (1H, d, J=6.0 Hz).

MS (ESI+): [M+H]$^+$ 389.0

MS (ESI+). found: 389.1.

B) 4-(1-((2,2-dimethyl-1,3-dioxolan-4-yl)methyl)-4-methoxy-1H-pyrrolo[3,2-c]pyridin-3-yl)benzenesulfonamide To a solution of 1-((2,2-dimethyl-1,3-dioxolan-4-yl)methyl)-3-iodo-4-methoxy-1H-pyrrolo[3,2-c]pyridine (120 mg) in DMF (3 mL)/water (0.30 mL) were added 4-(4,4,5,5-tetramethyl-1,3,2-dioxaborolan-2-yl)benzenesulfonamide (131 mg), tetrakis(triphenylphosphine)palladium(0) (35.7 mg) and potassium carbonate (85.4 mg). The reaction mixture was stirred under microwave irradiation at 130° C. for 1 hr. The reaction mixture was diluted with water, and the mixture was extracted with ethyl acetate. The organic layer was washed with saturated brine, dried over anhydrous magnesium sulfate, filtered, and concentrated under reduced pressure. The obtained residue was purified by silica gel column chromatography (hexane/ethyl acetate) to give the title compound (32.0 mg).

MS (ESI+): [M+H]$^+$ 418.1.

MS (ESI+). found: 418.2.

C) 4-(1-((2,2-dimethyl-1,3-dioxolan-4-yl)methyl)-4-oxo-4,5-dihydro-1H-pyrrolo[3,2-c]pyridin-3-yl)benzenesulfonamide (Example 90)

4-(1-(2,3-dihydroxypropyl)-4-oxo-4,5-dihydro-1H-pyrrolo[3,2-c]pyridin-3-yl)benzenesulfonamide (Example 91)

To a solution of 4-(1-((2,2-dimethyl-1,3-dioxolan-4-yl) methyl)-4-methoxy-1H-pyrrolo[3,2-c]pyridin-3-yl)benzenesulfonamide (32.0 mg) in acetonitrile (3 mL) were added sodium iodide (28.7 mg) and chloro(trimethyl)silane (0.097 mL), and the mixture was stirred overnight at 50° C. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate to ethyl acetate/methanol) to give the title compound (Example 90)(4.5 mg) and the title compound (Example 91) (5.7 mg).

Example 90

$^1$H NMR (300 MHz, DMSO-d$_6$) δ 1.15 (3H, s), 1.46 (3H, s), 3.17 (1H, d, J=4.5 Hz), 3.59 (2H, dd, J=9.1, 4.2 Hz), 4.12-4.26 (2H, m), 4.95 (1H, brs), 6.47 (1H, d, J=7.2 Hz), 7.01 (1H, t, J=6.4 Hz), 7.35-7.46 (4H, m), 7.78 (2H, d, J=7.9 Hz), 10.71 (1H, d, J=5.3 Hz).

MS (ESI+): [M+H]$^+$ 404.1.

MS (ESI+). found: 403.8.

Example 91

$^1$H NMR (300 MHz, DMSO-d$_6$) δ 3.37-3.47 (2H, m), 3.77 (1H, brs), 3.90-4.06 (1H, m), 4.23 (1H, dd, J=14.2, 3.6 Hz), 4.84 (1H, brs), 5.07 (1H, d, J=4.9 Hz), 6.54 (1H, d, J=7.2 Hz), 7.02-7.16 (1H, m), 7.27 (2H, s), 7.47 (1H, s), 7.75 (2H, d, J=8.7 Hz), 8.04 (2H, d, J=8.7 Hz), 10.85 (1H, d, J=5.7 Hz).

MS (ESI+): [M+H]$^+$ 364.1.

MS (ESI+). found: 363.8.

Example 92

4-(1-cyclopentyl-4-oxo-4,5-dihydro-1H-pyrazolo[4,3-c]pyridin-3-yl)benzenesulfonamide

A) 4-(1-cyclopentyl-4-methoxy-1H-pyrazolo[4,3-c]pyridin-3-yl)benzenesulfonamide A solution of 1-cyclopentyl-4-methoxy-1H-pyrazolo[4,3-c]pyridin-3-yl trifluoromethanesulfonate (150 mg) obtained in Step C of Example 12, 4-(4,4,5,5-tetramethyl-1,3,2-dioxaborolan-2-yl)benzenesulfonamide (145 mg), tetrakis(triphenylphosphine)palladium(0) (47.4 mg) and 2M aqueous sodium carbonate solution (1.03 mL) in DME (10 mL) was heated overnight with reflux under nitrogen atmosphere. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane) to give the title compound (147 mg).

$^1$H NMR (300 MHz, DMSO-$d_6$) δ 1.62-1.80 (2H, m), 1.82-2.25 (6H, m), 4.00 (3H, s), 5.20 (1H, quin, J=7.1 Hz), 7.35-7.46 (3H, m), 7.88-7.95 (2H, m), 7.97 (1H, d, J=6.0 Hz), 8.06-8.14 (2H, m).

MS (ESI+): [M+H]$^+$ 373.1.
MS (ESI+). found: 372.9.

B) 4-(1-cyclopentyl-4-oxo-4,5-dihydro-1H-pyrazolo[4,3-c]pyridin-3-yl)benzenesulfonamide To a solution of 4-(1-cyclopentyl-4-methoxy-1H-pyrazolo[4,3-c]pyridin-3-yl)benzenesulfonamide (61.2 mg) in acetonitrile (10 mL) were added sodium iodide (49.3 mg) and chloro(trimethyl)silane (0.166 mL), and the mixture was stirred at 60° C. for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane), and the obtained solid was washed with ethyl acetate to give the title compound (53.4 mg).

$^1$H NMR (300 MHz, DMSO-$d_6$) δ 1.60-1.79 (2H, m), 1.81-2.23 (6H, m), 5.07 (1H, quin, J=7.1 Hz), 6.71 (1H, d, J=7.2 Hz), 7.31 (3H, m), 7.86 (2H, d, J=8.7 Hz), 8.49 (2H, d, J=8.3 Hz), 11.16 (1H, brs).

MS (ESI+): [M+H]$^+$ 359.1.
MS (ESI+). found: 359.0.

Example 93

3-(5-(cyanomethyl)-3-thienyl)-1-cyclopentyl-4-oxo-4,5-dihydro-1H-pyrrolo[3,2-c]pyridine-7-carbonitrile

A) (4-(4,4,5,5-tetramethyl-1,3,2-dioxaborolan-2-yl)-2-thienyl)acetonitrile

A mixture of (4-bromo-2-thienyl)acetonitrile (1.70 g) synthesized according to the method described in WO 2006/138264, 4,4,4',4',5,5,5',5'-octamethyl-2,2'-bi-1,3,2-dioxaborolane (2.56 g), (1,1'-bis(diphenylphosphino)ferrocene)dichloropalladium(II) (308 mg), potassium acetate (1.65 g) and DMF (10 mL) was stirred at 80° C. for 3 hr. To the reaction mixture was added water, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (2.01 g).

$^1$H NMR (300 MHz, CDCl$_3$) δ 1.33 (12H, s), 3.91 (2H, d, J=1.1 Hz), 7.32-7.34 (1H, m), 7.77-7.87 (1H, m).

B) 3-(5-(cyanomethyl)-3-thienyl)-1-cyclopentyl-4-methoxy-1H-pyrrolo[3,2-c]pyridine-7-carbonitrile A mixture of 3-bromo-1-cyclopentyl-4-methoxy-4,5-dihydro-1H-pyrrolo[3,2-c]pyridine-7-carbonitrile (250 mg) obtained in Step H of Example 33, (4-(4,4,5,5-tetramethyl-1,3,2-dioxaborolan-2-yl)-2-thienyl)acetonitrile (292 mg), tetrakis(triphenylphosphine)palladium(0) (90 mg), 2M aqueous sodium carbonate solution (0.781 mL) and DME (3.0 mL) was stirred overnight at 80° C. To the reaction mixture was added water, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (220 mg).

MS (ESI+): [M+H]$^+$ 363.1.
MS (ESI+). found: 363.2.

C) 3-(5-(cyanomethyl)-3-thienyl)-1-cyclopentyl-4-oxo-4,5-dihydro-1H-pyrrolo[3,2-c]pyridine-7-carbonitrile To a solution of 3-(5-(cyanomethyl)-3-thienyl)-1-cyclopentyl-4-methoxy-1H-pyrrolo[3,2-c]pyridine-7-carbonitrile (220 mg) in acetonitrile (5 mL) were added sodium iodide (182 mg) and chloro(trimethyl)silane (0.388 mL), and the mixture was stirred at 50° C. for 3 hr. The reaction mixture was allowed to be cooled to room temperature, and filtered, and the obtained solid was washed with acetonitrile and water, and dried under reduced pressure to give the title compound (146 mg).

$^1$H NMR (300 MHz, DMSO-$d_6$) δ 1.58-2.04 (6H, m), 2.17 (2H, d, J=6.0 Hz), 4.27 (2H, s), 5.24 (1H, s), 7.49-7.77 (2H, m), 8.00 (1H, s), 8.24 (1H, d, J=1.5 Hz), 11.74-11.98 (1H, m).

MS (ESI+): [M+H]$^+$ 349.1.
MS (ESI+). found: 349.2.

Example 94

4-(1-(4-methoxybenzyl)-4-oxo-4,5-dihydro-1H-pyrazolo[4,3-c]pyridin-3-yl)benzenesulfonamide

A) 4-iodo-2-methoxy-N'-(4-methoxybenzyl)nicotinohydrazide

To a solution of 4-iodo-2-methoxynicotinic acid (3.00 g) obtained in Step C of Example 6 in DMF (100 mL) were added DIEA (1.88 mL), (4-methoxybenzyl)hydrazine hydrochloride (2.06 g), EDCI hydrochloride (2.03 g) and HOBt (1.45 g) at 0° C., and the mixture was stirred overnight at room temperature. To the reaction mixture was added water, and the mixture was extracted with ethyl acetate. The organic layer was dried over anhydrous sodium sulfate, filtered, and concentrated under reduced pressure. The residue was washed with ethyl acetate/diisopropyl ether to give the title compound (1.52 g).

¹H NMR (300 MHz, DMSO-d₆) δ 3.74 (3H, s), 3.81 (3H, s), 3.92 (2H, d, J=4.9 Hz), 5.35 (1H, d, J=6.0 Hz), 6.89 (2H, d, J=8.7 Hz), 7.31 (2H, d, J 8.7 Hz), 7.44 (1H, d, J=5.3 Hz), 7.84 (1H, d, J 5.3 Hz), 9.78 (1H, d, J=6.4 Hz).
MS (ESI+): [M+H]⁺ 413.0.
MS (ESI+). found: 413.7.

B) 4-methoxy-1-(4-methoxybenzyl)-1,2-dihydro-3H-pyrazolo[4,3-c]pyridin-3-one

To a solution of 4-iodo-2-methoxy-NT-(4-methoxybenzyl) nicotinohydrazide (1.50 g) in DMSO (15 mL) were added L-proline (84.0 mg) and potassium carbonate (1.00 g) at room temperature. Then copper(I) iodide (69.0 mg) was added thereto under nitrogen atmosphere at 60° C., and the mixture was stirred overnight at 60° C. The reaction mixture was purified by silica gel column chromatography (hexane/ethyl acetate) to give the title compound (393 mg).
¹H NMR (300 MHz, DMSO-d₆) δ 3.70 (3H, s), 3.92 (3H, s), 5.24 (2H, s), 6.82-6.90 (2H, m), 7.11-7.19 (3H, m), 7.78 (1H, d, J=6.4 Hz), 10.73-11.22 (1H, m).
MS (ESI+): [M+H]⁺ 286.1.
MS (ESI+). found: 286.2.

C) 4-methoxy-1-(4-methoxybenzyl)-1H-pyrazolo[4,3-c]pyridin-3-yl trifluoromethanesulfonate To a solution of 4-methoxy-1-(4-methoxybenzyl)-1,2-dihydro-3H-pyrazolo[4,3-c]pyridin-3-one (393 mg) and pyridine (0.444 mL) in acetonitrile (25 mL) was added trifluoromethanesulfonic anhydride (0.465 mL), and the mixture was stirred at 0° C. for 1 hr. To the reaction mixture was added saturated aqueous ammonium chloride solution, and the mixture was extracted with ethyl acetate. The organic layer was washed with saturated brine, dried over anhydrous sodium sulfate, filtered, and concentrated under reduced pressure. The residue was purified by silica gel column chromatography (hexane/ethyl acetate) to give the title compound (472 mg).
¹H NMR (300 MHz, DMSO-d₆) δ 3.71 (3H, s), 4.03 (3H, s), 5.55 (2H, s), 6.89 (2H, d, J=8.7 Hz), 7.23 (2H, d, J=9.1 Hz), 7.48 (1H, d, J=6.0 Hz), 8.03 (1H, d, J=6.0 Hz).
MS (ESI+): [M+H]⁺ 417.1.
MS (ESI+). found: 417.7.

D) 4-(4-methoxy-1-(4-methoxybenzyl)-1H-pyrazolo[4,3-c]pyridin-3-yl)benzenesulfonamide To a solution of 4-methoxy-1-(4-methoxybenzyl)-1H-pyrazolo[4,3-c]pyridin-3-yl trifluoromethanesulfonate (100 mg) in DMF (4 mL)/water (0.30 mL) were added 4-(4,4,5,5-tetramethyl-1,3,2-dioxaborolan-2-yl)benzenesulfonamide (102 mg), tetrakis(triphenylphosphine)palladium(0) (27.7 mg) and potassium carbonate (66.2 mg). The reaction mixture was stirred under microwave irradiation at 130° C. for 30 min. The reaction mixture was diluted with water, and the mixture was extracted with ethyl acetate. The organic layer was washed with saturated brine, dried over anhydrous magnesium sulfate, filtered and concentrated under reduced pressure. The obtained residue was purified by silica gel column chromatography (hexane/ethyl acetate) to give the title compound (45.0 mg).
¹H NMR (300 MHz, DMSO-d₆) δ 3.70 (3H, s), 4.00 (3H, s), 5.63 (2H, s), 6.89 (2H, d, J=8.7 Hz), 7.28 (2H, d, J=8.7 Hz), 7.43 (2H, s), 7.45 (1H, s), 7.94 (2H, s), 7.98 (1H, d, J=6.0 Hz), 8.11 (2H, d, J=8.3 Hz).
MS (ESI+): [M+H]⁺ 425.1.
MS (ESI+). found: 425.3.

E) 4-(1-(4-methoxybenzyl)-4-oxo-4,5-dihydro-1H-pyrazolo[4,3-c]pyridin-3-yl)benzenesulfonamide To a solution of 4-(4-methoxy-1-(4-methoxybenzyl)-1H-pyrazolo[4,3-c]pyridin-3-yl)benzenesulfonamide (42.0 mg) in acetonitrile (3 mL) were added sodium iodide (37.1 mg) and chloro(trimethyl)silane (0.126 mL), and the mixture was stirred at 50° C. for 1 hr. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate to ethyl acetate/methanol) to give the title compound (33.1 mg).
¹H NMR (300 MHz, DMSO-d₆) δ 3.71 (3H, s), 5.53 (2H, s), 6.75 (1H, d, J=7.2 Hz), 6.83-6.95 (2H, m), 7.21-7.32 (3H, m), 7.39 (2H, brs), 7.81-7.95 (2H, m), 8.43-8.55 (2H, m), 11.18 (1H, brs).
MS (ESI+): [M+H]⁺ 411.1.
MS (ESI+). found: 411.3.

Example 95

2-(4-(7-cyano-1-cyclopentyl-4-oxo-4,5-dihydro-1H-pyrrolo[3,2-c]pyridin-3-yl)phenyl)acetamide A) 2-(4-(4,4,5,5-tetramethyl-1,3,2-dioxaborolan-2-yl)phenyl)acetamide To a solution of (4-(4,4,5,5-tetramethyl-1,3,2-dioxaborolan-2-yl)phenyl)acetic acid (500 mg) and HOBt ammonium salt (435 mg) in DMF (5 mL) was added EDCI hydrochloride (539 mg), and the mixture was stirred at room temperature for 3 hr. To the reaction mixture was added water, and the mixture was extracted with ethyl acetate. The organic layer was washed with saturated aqueous sodium hydrogencarbonate solution and saturated brine, dried over anhydrous magnesium sulfate, and concentrated under reduced pressure to give the title compound (420 mg).
MS (ESI+): [M+H]⁺ 262.1.
MS (ESI+). found: 262.3.

B) 2-(4-(7-cyano-1-cyclopentyl-4-methoxy-1H-pyrrolo[3,2-c]pyridin-3-yl)phenyl)acetamide The title compound (130 mg) was obtained using 2-(4-(4,4,5,5-tetramethyl-1,3,2-dioxaborolan-2-yl)phenyl)acetamide (428 mg) and 3-bromo-1-cyclopentyl-4-methoxy-4,5-dihydro-1H-pyrrolo[3,2-c]pyridine-7-carbonitrile (350 mg) obtained in Step H of Example 33, in the same manner as in Step I of Example 33.
MS (ESI+): [M+H]⁺ 375.2.
MS (ESI+). found: 375.3.

C) 2-(4-(7-cyano-1-cyclopentyl-4-oxo-4,5-dihydro-1H-pyrrolo[3,2-c]pyridin-3-yl)phenyl)acetamide The title compound (104 mg) was obtained using 2-(4-(7-cyano-1-cyclopentyl-4-methoxy-1H-pyrrolo[3,2-c]pyridin-3-yl)phenyl)acetamide (126 mg), in the same manner as in Step J of Example 33.
MS (ESI+): [M+H]⁺ 361.2.
MS (ESI+). found: 361.2.

Example 96

3-(4-(cyanomethyl)phenyl)-1-cyclopentyl-4-oxo-4,5-dihydro-1H-pyrrolo[3,2-c]pyridine-7-carbonitrile To a solution of 2-(4-(7-cyano-1-cyclopentyl-4-oxo-4,5-dihydro-1H-pyrrolo[3,2-c]pyridin-3-yl)phenyl)acetamide (50 mg) to obtained in Example 95 and pyridine (34 μL) in THF (3 mL) was added trifluoroacetic anhydride (59 μL), and the mixture was stirred overnight at 60° C. To the reaction mixture was added water. The mixture was filtered, and the obtained solid was washed with water, and dried under reduced pressure to give the title compound (44 mg).
MS (ESI+): [M+H]$^+$ 343.2.
MS (ESI+). found: 343.2.

Example 97

2-(4-(7-cyano-1-cyclopentyl-4-oxo-4,5-dihydro-1H-pyrrolo[3,2-c]pyridin-3-yl)-2-thienyl)acetamide To a solution of 3-(5-(cyanomethyl)-3-thienyl)-1-cyclopentyl-4-oxo-4,5-dihydro-1H-pyrrolo[3,2-c]pyridine-7-carbonitrile (80 mg) obtained in Example 93 and 2M aqueous potassium carbonate solution (0.574 mL) in DMSO (3 mL) was added 30% hydrogen peroxide aqueous solution (0.235 mL) at 0° C., and the mixture was stirred at room temperature for 5 hr. To the reaction mixture was added water, and the mixture was extracted with ethyl acetate. The organic layer was washed with water and saturated brine, dried over anhydrous magnesium sulfate, and concentrated under reduced pressure to give the title compound (13 mg).
$^1$H NMR (300 MHz, DMSO-d$_6$) δ 1.56-1.77 (2H, m), 1.79-2.05 (4H, m), 2.09-2.26 (2H, m), 3.53-3.62 (2H, m), 5.14-5.33 (1H, m), 6.91-7.04 (1H, m), 7.32-7.44 (1H, m), 7.44-7.56 (1H, m), 7.60-7.70 (1H, m), 7.92-8.04 (1H, m), 8.11-8.20 (1H, m), 11.70-11.93 (1H, m).
MS (ESI+): [M+H]$^+$ 367.1.
MS (ESI+). found: 367.2.

Example 98

2-(4-(7-cyano-1-cyclopentyl-4-oxo-4,5-dihydro-1H-pyrrolo[3,2-c]pyridin-3-yl)-1H-pyrazol-1-yl)acetamide A) 1-cyclopentyl-4-methoxy-3-(1H-pyrazol-4-yl)-1H-pyrrolo[3,2-c]pyridine-7-carbonitrile The title compound was obtained using 3-bromo-1-cyclopentyl-4-methoxy-4,5-dihydro-1H-pyrrolo[3,2-c]pyridine-7-carbonitrile obtained in Step H of Example 33 and tert-butyl 4-(4,4,5,5-tetramethyl-1,3,2-dioxaborolan-2-yl)-1H-pyrazole-1-carboxylate, in the same manner as in Step I of Example 33.
MS (ESI+): [M+H]$^+$ 308.4.
MS (ESI+). found: 308.2.

B) 2-(4-(7-cyano-1-cyclopentyl-4-methoxy-1H-pyrrolo[3,2-c]pyridin-3-yl)-1H-pyrazol-1-yl)acetamide To a solution of 1-cyclopentyl-4-methoxy-3-(1H-pyrazol-4-yl)-1H-pyrrolo[3,2-c]pyridine-7-carbonitrile (55.3 mg) in THF (2 mL) was added sodium hydride (dispersion in mineral oil, 14.4 mg) at 0° C., and the mixture was stirred for 1 hr. To the reaction mixture was added 2-bromoacetamide (29.8 mg) at 0° C., and the reaction mixture was stirred overnight. The reaction mixture was poured into water, and the mixture was extracted twice with ethyl acetate and THF. The combined organic layers was washed with saturated brine, and dried over anhydrous magnesium sulfate, and the solvent was evaporated under reduced pressure. The residue was purified by silica gel column chromatography (ethyl acetate/hexane/methanol) to give the title compound (27.5 mg).
MS (ESI+): [M+H]$^+$ 365.4.
MS (ESI+). found: 365.3.

C) 2-(4-(7-cyano-1-cyclopentyl-4-oxo-4,5-dihydro-1H-pyrrolo[3,2-c]pyridin-3-yl)-1H-pyrazol-1-yl)acetamide The title compound was obtained using 2-(4-(7-cyano-1-cyclopentyl-4-methoxy-1H-pyrrolo[3,2-c]pyridin-3-yl)-1H-pyrazol-1-yl)acetamide, in the same manner as in Step J of Example 33.
MS (ESI+): [M+H]$^+$ 351.4.
MS (ESI+). found: 351.2.

Example 99

3-(1-(cyanomethyl)-1H-pyrazol-4-yl)-1-cyclopentyl-4-oxo-4,5-dihydro-1H-pyrrolo[3,2-c]pyridine-7-carbonitrile A) 3-(1-(cyanomethyl)-1H-pyrazol-4-yl)-1-cyclopentyl-4-methoxy-1H-pyrrolo[3,2-c]pyridine-7-carbonitrile To a solution of 1-cyclopentyl-4-methoxy-3-(1H-pyrazol-4-yl)-1H-pyrrolo[3,2-c]pyridine-7-carbonitrile (152.2 mg) obtained in Step A of Example 98 in THF (2 mL) was added sodium hydride (dispersion in mineral oil, 39.6 mg) at 0° C., and the mixture was stirred for 1 hr. To the reaction mixture was added 2-bromoacetonitrile (38 μL) at 0° C., and the mixture was allowed to be warmed to room temperature, and stirred overnight. The reaction mixture was added to water, and the mixture was extracted twice with ethyl acetate. The organic layers were combined, washed with saturated brine, and dried over magnesium sulfate, and the solvent was evaporated under reduced pressure. The residue was purified by silica gel column chromatography (ethyl acetate/hexane) to give the title compound (13.7 mg).
$^1$H NMR (300 MHz, DMSO-d$_6$) δ 1.65-2.06 (6H, m), 2.14-2.30 (2H, m), 4.08 (3H, s), 5.24-5.39 (1H, m), 5.54 (2H, s), 7.86 (1H, s), 7.98 (1H, d, J=0.8 Hz), 8.17 (1H, s), 8.36 (1H, s).
MS (ESI+): [M+H]$^+$ 347.4.
MS (ESI+). found: 347.2.

B) 3-(1-(cyanomethyl)-1H-pyrazol-4-yl)-1-cyclopentyl-4-oxo-4,5-dihydro-1H-pyrrolo[3,2-c]pyridine-7-carbonitrile 3-(1-(Cyanomethyl)-1H-pyrazol-4-yl)-1-cyclopentyl-4-methoxy-1H-pyrrolo[3,2-c]pyridine-7-carbonitrile (13.7 mg), sodium iodide (11.9 mg) and chloro(trimethyl)silane (25 μL) were stirred at 50° C. for 1 hr. The precipitated crystals were collected by filtration, and washed with ethyl acetate to give the title compound (3.3 mg).
$^1$H NMR (300 MHz, DMSO-d$_6$) δ 1.61-2.04 (6H, m), 2.10-2.29 (2H, m), 5.13-5.30 (1H, m), 5.52 (2H, s), 7.69 (1H, s), 7.96 (1H, s), 8.11 (1H, s), 8.54 (1H, s), 11.75-11.89 (1H, m).

MS (ESI+): [M+H]⁺ 333.4.
MS (ESI+). found: 333.2.

Example 100

4-(1-((3-methyloxetan-3-yl)methyl)-4-oxo-4,5-dihydro-1H-pyrazolo[4,3-c]pyridin-3-yl)benzenesulfonamide A) 4-(4-methoxy-1H-pyrazolo[4,3-c]pyridin-3-yl)benzenesulfonamide 4-(1-tert-Butyl-4-methoxy-1H-pyrazolo[4,3-c]pyridin-3-yl)benzenesulfonamide (878 mg) obtained in Step D of Example 86 was dissolved in a mixed solvent of trifluoroacetic acid (50 mL)/water (5 mL), and the solution was heated with reflux for 24 hr. The reaction mixture was allowed to be cooled to room temperature, and concentrated under reduced pressure. The residue was extracted with ethyl acetate and saturated aqueous sodium hydrogencarbonate solution, and the organic layer was washed with saturated brine, dried over anhydrous magnesium sulfate, filtered, and concentrated under reduced pressure. The obtained residue was purified by silica gel column chromatography (hexane/ethyl acetate) to give the title compound (561 mg).
¹H NMR (300 MHz, DMSO-$d_6$) δ 4.01 (3H, s), 7.20 (1H, d, J=6.0 Hz), 7.42 (2H, s), 7.87-8.02 (3H, m), 8.05-8.20 (2H, m), 13.75 (1H, s).
MS (ESI+): [M+H]⁺ 305.1.
MS (ESI+). found: 305.2.

B) 4-(4-oxo-4,5-dihydro-1H-pyrazolo[4,3-c]pyridin-3-yl)benzenesulfonamide

To a solution of 4-(4-methoxy-1H-pyrazolo[4,3-c]pyridin-3-yl)benzenesulfonamide (60.0 mg) in acetonitrile (3 mL) were added sodium iodide (73.8 mg) and chloro(trimethyl)silane (0.250 mL), and the mixture was stirred at 50° C. for 1 hr. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate to ethyl acetate/methanol) to give the title compound (46.7 mg).
¹H NMR (300 MHz, DMSO-$d_6$) δ 6.48 (1H, d, J=7.2 Hz), 7.21 (1H, d, J=3.8 Hz), 7.38 (2H, brs), 7.87 (2H, d, J=8.3 Hz), 8.55 (2H, s), 11.05 (1H, brs), 12.88-14.31 (1H, m).
MS (ESI+): [M+H]⁺ 291.1.
MS (ESI+). found: 291.2.

C) 4-(1-((3-methyloxetan-3-yl)methyl)-4-oxo-4,5-dihydro-1H-pyrazolo[4,3-c]pyridin-3-yl)benzenesulfonamide To a solution of 4-(4-oxo-4,5-dihydro-1H-pyrazolo[4,3-c]pyridin-3-yl)benzenesulfonamide (34.5 mg) in DMF (2 mL) was added sodium hydride (60% dispersion in mineral oil, 7.13 mg), and the mixture was stirred at room temperature for 1 hr. To the reaction mixture was added (3-methyloxetan-3-yl)methyl 4-methylbenzenesulfonate (45.7 mg), and the mixture was stirred overnight at room temperature. The reaction mixture was extracted with water and ethyl acetate, and the organic layer was washed with saturated brine, dried over anhydrous magnesium sulfate, filtered, and concentrated under reduced pressure. The obtained residue was purified by silica gel column chromatography (basic silica gel, ethyl acetate/methanol) to give the title compound (14.2 mg).
¹H NMR (300 MHz, DMSO-$d_6$) δ 1.18 (3H, s), 4.28 (2H, d, J=5.7 Hz), 4.57 (2H, s), 4.70 (2H, d, J=6.0 Hz), 6.73 (1H, d, J=7.2 Hz), 7.30 (1H, d, J=7.2 Hz), 7.34-7.64 (2H, m), 7.83-7.92 (2H, m), 8.43-8.53 (2H, m), 10.80-11.63 (1H, br.s).
MS (ESI+): [M+H]⁺ 375.1.
MS (ESI+). found: 374.9.

Example 101

4-(7-bromo-1-cyclopentyl-4-oxo-4,5-dihydro-1H-pyrazolo[4,3-c]pyridin-3-yl)benzenesulfonamide A) 4-(7-bromo-1-cyclopentyl-4-methoxy-1H-pyrazolo[4,3-c]pyridin-3-yl)benzenesulfonamide To a solution of 4-(1-cyclopentyl-4-methoxy-1H-pyrazolo[4,3-c]pyridin-3-yl)benzenesulfonamide (72.4 mg) obtained in Step A of Example 92 in DMF (5 mL) was added NBS (38.1 mg) at 0° C., and the mixture was stirred overnight at room temperature. To the reaction mixture was added saturated aqueous sodium thiosulfate solution, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane) to give the title compound (67.8 mg).
¹H NMR (300 MHz, DMSO-$d_6$) δ 1.72 (2H, dd, J=7.0 Hz, 4.7 Hz), 1.81-1.97 (2H, m), 2.07-2.28 (4H, m), 3.97 (3H, s), 5.91 (1H, quin, J=6.8 Hz), 7.43 (2H, s), 7.89-7.96 (2H, m), 7.97-8.05 (2H, m), 8.13 (1H, s).
MS (ESI+): [M+H]⁺ 451.0.
MS (ESI+). found: 452.5.

B) 4-(7-bromo-1-cyclopentyl-4-oxo-4,5-dihydro-1H-pyrazolo[4,3-c]pyridin-3-yl)benzenesulfonamide To a solution of 4-(7-bromo-1-cyclopentyl-4-methoxy-1H-pyrazolo[4,3-c]pyridin-3-yl)benzenesulfonamide (60.0 mg) in acetonitrile (10 mL) were added sodium iodide (40.0 mg) and chloro(trimethyl)silane (0.135 mL), and the mixture was stirred at 60° C. for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (35.2 mg).
¹H NMR (300 MHz, DMSO-$d_6$) δ 1.60-1.81 (2H, m), 1.82-2.01 (2H, m), 2.15 (4H, q, J=5.9 Hz), 5.82 (1H, quin, J=6.9 Hz), 7.43 (2H, brs), 7.54 (1H, s), 7.87 (2H, d, J=8.7 Hz), 8.31 (2H, d, J=8.3 Hz).
MS (ESI+): [M+H]⁺ 437.0.
MS (ESI+). found: 436.7.

Example 102

3-bromo-7-methoxy-1-((2-(trimethylsilyl)ethoxy)methyl)-1H-pyrrolo[2,3-c]pyridine-4-carbonitrile A) 4-bromo-7-methoxy-1-((2-(trimethylsilyl)ethoxy)methyl)-1H-pyrrolo[2,3-c]pyridine To a solution of 4-bromo-7-methoxy-1H-pyrrolo[2,3-c]pyridine (2.27 g) obtained according to the method described in Journal of Organic Chemistry, 2002, vol. 67, #7, p. 2345-2347 or Journal of Medicinal Chemistry, 2009, vol. 52, #23, p. 7778-7787 in THF (50 mL) was added sodium hydride (dispersion in mineral oil, 0.48 g) at 0° C., and the mixture was stirred at 0° C. for 30 min. (2-(Chloromethoxy)ethyl)(trimethyl)silane (2.12 mL) was added thereto, and the mixture was stirred at 0° C. for 2 hr. To the reaction mixture was added saturated aqueous ammonium chloride solution at 0° C., and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (3.27 g).

MS (ESI+): [M+H]$^+$ 357.1.
MS (ESI+). found: 357.0, 358.9.

B) 7-methoxy-1-((2-(trimethylsilyl)ethoxy)methyl)-1H-pyrrolo[2,3-c]pyridine-4-carbonitrile To a solution of 4-bromo-7-methoxy-1-((2-(trimethylsilyl)ethoxy)methyl)-1H-pyrrolo[2,3-c]pyridine (1.80 g) in DMA (20.15 mL) were added tetrakis(triphenylphosphine)palladium(0) (0.58 g) and zinc cyanide (0.88 g) at room temperature, and the mixture was stirred at 100° C. for 1 hr. The reaction mixture was concentrated under reduced pressure, and the obtained residue was purified by silica gel column chromatography (ethyl acetate/hexane) to give the title compound (1.51 g).

MS (ESI+): [M+H]$^+$ 304.1.
MS (ESI+). found: 304.0.

C) 3-bromo-7-methoxy-1-((2-(trimethylsilyl)ethoxy)methyl)-1H-pyrrolo[2,3-c]pyridine-4-carbonitrile To a solution of 7-methoxy-1-((2-(trimethylsilyl)ethoxy)methyl)-1H-pyrrolo[2,3-c]pyridine-4-carbonitrile (1.34 g) in ethyl acetate (20.15 mL) was added NBS (1.97 g) at room temperature, and the mixture was stirred at 60° C. for 2 hr. The reaction mixture was concentrated under reduced pressure, and the obtained residue was purified by silica gel column chromatography (ethyl acetate/hexane) to give the title compound (1.30 g).

$^1$H NMR (400 MHz, CDCl$_3$) δ −0.05 (9H, s), 0.84-0.94 (2H, m), 3.47-3.56 (2H, m), 4.16 (3H, s), 5.71 (2H, s), 7.41 (1H, s), 8.21 (1H, s).

D) 7-methoxy-3-(2-methylphenyl)-1-((2-(trimethylsilyl)ethoxy)methyl)-1H-pyrrolo[2,3-c]pyridine-4-carbonitrile To a solution of 3-bromo-7-methoxy-1-((2-(trimethylsilyl)ethoxy)methyl)-1H-pyrrolo[2,3-c]pyridine-4-carbonitrile (1.30 g) in toluene (17 mL) were added 2-dicyclohexyl phosphino-2',4',6'-triisopropylbiphenyl (0.486 g), tris(dibenzylideneacetone)dipalladium(0) (0.311 g), (2-methylphenyl)boronic acid (0.693 g) and 2M aqueous sodium carbonate solution (5.10 mL) at room temperature, and the mixture was stirred at 90° C. for 3 hr. The reaction mixture was concentrated under reduced pressure, and the obtained residue was purified by silica gel column chromatography (ethyl acetate/hexane). The obtained fraction was treated with activated carbon, and concentrated under reduced pressure to give the title compound (1.20 g).

MS (ESI+): [M+H]$^+$ 394.2.
MS (ESI+). found: 394.1.

E) 7-methoxy-3-(2-methylphenyl)-1H-pyrrolo[2,3-c]pyridine-4-carbonitrile

To a solution of 7-methoxy-3-(2-methylphenyl)-1-((2-(trimethylsilyl)ethoxy)methyl)-1H-pyrrolo[2,3-c]pyridine-4-carbonitrile (1.20 g) in trifluoroacetic acid (15.25 mL) was added triethylsilane (1.46 mL) at room temperature, and the mixture was stirred at room temperature for 3 hr. The reaction mixture was concentrated under reduced pressure, and the obtained residue was purified by silica gel column chromatography (basic silica gel, ethyl acetate/hexane), and crystallized from ethyl acetate and hexane to give the title compound (1.20 g).

MS (ESI+): [M+H]$^+$ 264.1.
MS (ESI+). found: 264.0.

F) 4-(4-cyano-3-(2-methylphenyl)-7-oxo-6,7-dihydro-1H-pyrrolo[2,3-c]pyridin-1-yl)thiophene-2-carboxamide A mixture of 7-methoxy-3-(2-methylphenyl)-1H-pyrrolo[2,3-c]pyridine-4-carbonitrile (50 mg), 4-bromothiophene-2-carboxamide (47 mg), copper(I) iodide (3.6 mg), potassium carbonate (31.5 mg) and N-methylpyrrolidone (2 mL) was stirred under microwave irradiation at 200° C. for 1 hr. To the reaction mixture was added water, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane, methanol/ethyl acetate). The obtained fraction was purified by HPLC (C18, mobile phase: water/acetonitrile (containing 5 mM ammonium carbonate)), to the obtained fraction was added saturated aqueous sodium hydrogencarbonate solution, and the mixture was extracted with ethyl acetate. The organic layer was dried over anhydrous magnesium sulfate, and concentrated under reduced pressure to give the title compound (2.5 mg).

MS (ESI+): [M+H]$^+$ 375.1.
MS (ESI+). found: 375.2.

Example 103

1-cyclopentyl-4-oxo-3-phenyl-4,5-dihydro-1H-pyrrolo[3,2-c]pyridine-7-carbonitrile

A) 1-cyclopentyl-4-methoxy-3-phenyl-1H-pyrrolo[3,2-c]pyridine-7-carbonitrile The title compound (67 mg) was obtained using 3-bromo-1-cyclopentyl-4-methoxy-4,5-dihydro-1H-pyrrolo[3,2-c]pyridine-7-carbonitrile (80 mg) obtained in Step H of Example 33 and phenylboronic acid (45.7 mg), in the same manner as in Step I of Example 33.

MS (ESI+): [M+H]$^+$ 318.2.
MS (ESI+). found: 318.2.

B) 1-cyclopentyl-4-oxo-3-phenyl-4,5-dihydro-1H-pyrrolo[3,2-c]pyridine-7-carbonitrile The title compound (39 mg) was obtained using 1-cyclopentyl-4-methoxy-3-phenyl-1H-pyrrolo[3,2-c]pyridine-7-carbonitrile (65 mg), in the same manner as in Step J of Example 33.

MS (ESI+): [M+H]$^+$ 304.1.
MS (ESI+). found: 304.2.

Example 104

(4-(7-bromo-1-(2,6-difluorophenyl)-4-oxo-4,5-dihydro-1H-pyrazolo[4,3-c]pyridin-3-yl)phenyl)acetonitrile A) (4-(7-bromo-1-(2,6-difluorophenyl)-4-methoxy-1H-pyrazolo[4,3-c]pyridin-3-yl)phenyl)acetonitrile To a solution of (4-(1-(2,6-difluorophenyl)-4-methoxy-1H-pyrazolo[4,3-c]pyridin-3-yl)phenyl)acetonitrile (148.1 mg) obtained in Step A of Example 39 in DMF (5 mL) was added NBS (77 mg) at 0° C., and the mixture was allowed to be warmed to room temperature, and stirred overnight. The reaction mixture was poured into water, and the mixture was extracted twice with ethyl acetate. The organic layers were combined, washed with saturated brine, and dried over sodium sulfate, and the solvent was evaporated under reduced pressure. The residue was purified by silica gel column chromatography (ethyl acetate/hexane) to give the title compound (161 mg).
MS (ESI+): [M+H]$^+$ 456.3.
MS (ESI+). found: 456.2.

B) (4-(7-bromo-1-(2,6-difluorophenyl)-4-oxo-4,5-dihydro-1H-pyrazolo[4,3-c]pyridin-3-yl)phenyl)acetonitrile The title compound was obtained using (4-(7-bromo-1-(2,6-difluorophenyl)-4-methoxy-1H-pyrazolo[4,3-c]pyridin-3-yl)phenyl)acetonitrile, in the same manner as in Step J of Example 33.
MS (ESI+): [M+H]$^+$ 442.2.
MS (ESI+). found: 442.2.

Example 105

4-(1-(oxetan-3-ylmethyl)-4-oxo-4,5-dihydro-1H-pyrazolo[4,3-c]pyridin-3-yl)benzenesulfonamide A) oxetan-3-ylmethyl 4-methylbenzenesulfonate The title compound (287 mg) was obtained using oxetan-3-ylmethanol (500 mg), in the same manner as in Step A-1 of Example 17.
$^1$H NMR (300 MHz, DMSO-d$_6$) δ 2.43 (3H, s), 3.18-3.28 (1H, m), 4.16-4.26 (4H, m), 4.56 (2H, dd, J=7.9, 6.4 Hz), 7.50 (2H, d, J=7.9 Hz), 7.78-7.84 (2H, m).

B) 4-(1-(oxetan-3-ylmethyl)-4-oxo-4,5-dihydro-1H-pyrazolo[4,3-c]pyridin-3-yl)benzenesulfonamide To a solution of 4-(4-oxo-4,5-dihydro-1H-pyrazolo[4,3-c]pyridin-3-yl)benzenesulfonamide (52.0 mg) obtained in Step B of Example 100 in DMF (3 mL) was added sodium hydride (60% dispersion in mineral oil, 8.60 mg), and the mixture was stirred at room temperature for 1 hr. To the reaction mixture was added oxetan-3-ylmethyl 4-methylbenzenesulfonate (52.1 mg), and the mixture was stirred overnight at room temperature. The reaction mixture was extracted with water and ethyl acetate, and the organic layer was washed with saturated brine, dried over anhydrous magnesium sulfate, filtered, and concentrated under reduced pressure. The obtained residue was purified by silica gel column chromatography (basic silica gel, ethyl acetate/methanol) to give the title compound (10.0 mg).
$^1$H NMR (300 MHz, DMSO-d$_6$) δ 3.44-3.59 (1H, m), 4.49 (2H, t, J=6.2 Hz), 4.61-4.72 (4H, m), 6.75 (1H, d, J=7.2 Hz), 7.30 (1H, d, J=7.2 Hz), 7.39 (2H, brs), 7.87 (2H, d, J=8.7 Hz), 8.48 (2H, d, J=8.7 Hz), 11.19 (1H, brs).
MS (ESI+): [M+H]$^+$ 361.1.
MS (ESI+). found: 360.9.

Example 106

1-cyclopentyl-4-oxo-3-(3-thienyl)-4,5-dihydro-1H-pyrrolo[3,2-c]pyridine-7-carbonitrile The title compound was obtained using 3-bromo-1-cyclopentyl-4-methoxy-4,5-dihydro-1H-pyrrolo[3,2-c]pyridine-7-carbonitrile obtained in Step H of Example 33 and 3-thienylboronic acid, in the same manner as in Step I of Example 33 and Step J of Example 33.
MS (ESI+): [M+H]$^+$ 310.4.
MS (ESI+). found: 310.2.

Example 107

4-(7-cyano-1-cyclopentyl-4-oxo-4,5-dihydro-1H-pyrrolo[3,2-c]pyridin-3-yl)-N,N-dimethylthiophene-2-carboxamide A) N,N-dimethyl-4-(4,4,5,5-tetramethyl-1,3,2-dioxaborolan-2-yl)thiophene-2-carboxamide The title compound was obtained using 4-bromothiophene-2-carboxylic acid and dimethylamine hydrochloride, in the same manner as in Step A of Example 33 and Step B of Example 33.
MS (ESI+): [M]$^+$ 281.1.
MS (ESI+). found: 281.8.

B) 4-(7-cyano-1-cyclopentyl-4-oxo-4,5-dihydro-1H-pyrrolo[3,2-c]pyridin-3-yl)-N,N-dimethylthiophene-2-carboxamide The title compound was obtained using N,N-dimethyl-4-(4,4,5,5-tetramethyl-1,3,2-dioxaborolan-2-yl)thiophene-2-carboxamide and 3-bromo-1-cyclopentyl-4-methoxy-4,5-dihydro-1H-pyrrolo[3,2-c]pyridine-7-carbonitrile obtained in Step H of Example 33, in the same manner as in Step I of Example 33 and Step J of Example 33.
MS (ESI+): [M]$^+$ 380.4.
MS (ESI+). found: 380.8.

Example 108

4-(7-cyano-1-cyclopentyl-4-oxo-4,5-dihydro-1H-pyrrolo[3,2-c]pyridin-3-yl)-N-methylthiophene-2-carboxamide A) N-methyl-4-(4,4,5,5-tetramethyl-1,3,2-dioxaborolan-2-yl)thiophene-2-carboxamide The title compound was obtained using 4-bromothiophene-2-carboxylic acid and methylamine hydrochloride, in the same manner as in Step A of Example 33 and Step B of Example 33.
MS (ESI+): [M]$^+$ 267.1.
MS (ESI+). found: 267.8.

B) 4-(7-cyano-1-cyclopentyl-4-oxo-4,5-dihydro-1H-pyrrolo[3,2-c]pyridin-3-yl)-N-methylthiophene-2-carboxamide The title compound was obtained using N-methyl-4-(4,4,5,5-tetramethyl-1,3,2-dioxaborolan-2-yl)thiophene-2-carboxamide and 3-bromo-1-cyclopentyl-4-methoxy-4,5-dihydro-1H-pyrrolo[3,2-c]pyridine-7-carbonitrile obtained in Step H of Example 33, in the same manner as in Step I of Example 33 and Step J of Example 33.
MS (ESI+): [M]$^+$ 366.7.
MS (ESI+). found: 366.4.

Example 109

3-(3-(cyanomethyl)phenyl)-1-cyclopentyl-4-oxo-4,5-dihydro-1H-pyrrolo[3,2-c]pyridine-7-carbonitrile A) 3-(3-(cyanomethyl)phenyl)-1-cyclopentyl-4-methoxy-1H-pyrrolo[3,2-c]pyridine-7-carbonitrile The title compound (320 mg) was obtained using 3-bromo-1-cyclopentyl-4-methoxy-4,5-dihydro-1H-pyrrolo[3,2-c]pyridine-7-carbonitrile (300 mg) obtained in Step H of Example 33 and (3-(4,4,5,5-tetramethyl-1,3,2-dioxaborolan-2-yl)phenyl)acetonitrile, in the same manner as in Step I of Example 33.
MS (ESI+): [M+H]$^+$ 357.2.
MS (ESI+). found: 357.2.

B) 3-(3-(cyanomethyl)phenyl)-1-cyclopentyl-4-oxo-4,5-dihydro-1H-pyrrolo[3,2-c]pyridine-7-carbonitrile The title compound (180 mg) was obtained using 3-(3-(cyanomethyl)phenyl)-1-cyclopentyl-4-methoxy-1H-pyrrolo[3,2-c]pyridine-7-carbonitrile (320 mg), in the same manner as in Step J of Example 33.
MS (ESI+): [M+H]$^+$ 343.2.
MS (ESI+). found: 343.2.

Example 110

2-(3-(7-cyano-1-cyclopentyl-4-oxo-4,5-dihydro-1H-pyrrolo[3,2-c]pyridin-3-yl)phenyl)acetamide The title compound (4.0 mg) was obtained using 3-(3-(cyanomethyl)phenyl)-1-cyclopentyl-4-oxo-4,5-dihydro-1H-pyrrolo[3,2-c]pyridine-7-carbonitrile (80 mg) obtained in Example 109, in the same manner as in Example 97.
MS (ESI+): [M+H]$^+$ 361.2.
MS (ESI+). found: 361.3.

Example 111

1-cyclopentyl-4-oxo-3-(1H-pyrazol-4-yl)-4,5-dihydro-1H-pyrrolo[3,2-c]pyridine-7-carbonitrile The title compound was obtained using 1-cyclopentyl-4-methoxy-3-(1H-pyrazol-4-yl)-1H-pyrrolo[3,2-c]pyridine-7-carbonitrile obtained in Step A of Example 98, in the same manner as in Step J of Example 33.
MS (ESI+): [M+H]$^+$ 294.3.
MS (ESI+). found: 294.2.

Example 112

2-(4-(7-bromo-1-(2,6-difluorophenyl)-4-oxo-4,5-dihydro-1H-pyrazolo[4,3-c]pyridin-3-yl)phenyl)acetamide To a solution of (4-(7-bromo-1-(2,6-difluorophenyl)-4-oxo-4,5-dihydro-1H-pyrazolo[4,3-c]pyridin-3-yl)phenyl)acetonitrile (126.2 mg) obtained in Example 104 and potassium carbonate (47.4 mg) in DMSO (2 mL) was added 30% aqueous hydrogen peroxide (131 µL) at room temperature, and the mixture was stirred overnight. The reaction mixture was poured into water, and the precipitated crystals were collected by filtration, and washed with water. The obtained crystals were purified by HPLC (C18, mobile phase: water/acetonitrile (containing 0.1% TFA)) to give the title compound (92 mg).
$^1$H NMR (300 MHz, DMSO-d$_6$) δ 3.43 (2H, s), 6.91 (1H, brs), 7.34 (2H, d, J=7.9 Hz), 7.40-7.55 (3H, m), 7.65 (1H, s), 7.72-7.87 (1H, m), 8.09 (2H, d, J=8.3 Hz), 11.79 (1H, brs)
MS (ESI+): [M+H]$^+$ 460.2.
MS (ESI+). found: 460.2.

Example 113 methyl 4-(1-(4-methoxybenzyl)-4-oxo-4,5-dihydro-1H-pyrazolo[4,3-c]pyridin-3-yl)thiophene-2-carboxylate A) methyl 4-(4-methoxy-1-(4-methoxybenzyl)-1H-pyrazolo[4,3-c]pyridin-3-yl)thiophene-2-carboxylate To a solution of 4-methoxy-1-(4-methoxybenzyl)-1H-pyrazolo[4,3-c]pyridin-3-yl trifluoromethanesulfonate (157 mg) obtained in Step C of Example 94 in DME (4 mL) were added methyl 4-(4,4,5,5-tetramethyl-1,3,2-dioxaborolan-2-yl)thiophene-2-carboxylate (121 mg) and 2M aqueous sodium carbonate solution (0.940 mL), and then tetrakis(triphenylphosphine)palladium(0) (42.8 mg) was added thereto under nitrogen atmosphere. The reaction mixture was stirred overnight under nitrogen atmosphere at 100° C. To the reaction mixture was added water, and the mixture was extracted with ethyl acetate. The organic layer was washed with saturated brine, dried over anhydrous magnesium sulfate, filtered, and concentrated under reduced pressure. The obtained residue was purified by silica gel column chromatography (hexane/ethyl acetate) to give the title compound (77.9 mg).
$^1$H NMR (300 MHz, DMSO-d$_6$) δ 3.70 (3H, s), 3.87 (3H, s), 4.06 (3H, s), 5.59 (2H, s), 6.88 (2H, d, J=8.7 Hz), 7.26 (2H, d, J=8.7 Hz), 7.41 (1H, d, J=6.4 Hz), 7.95 (1H, d, J=6.0 Hz), 8.33 (1H, d, J=1.5 Hz), 8.58 (1H, d, J=1.5 Hz).
MS (ESI+): [M+H]$^+$ 410.1.
MS (ESI+). found: 409.8.

B) methyl 4-(1-(4-methoxybenzyl)-4-oxo-4,5-dihydro-1H-pyrazolo[4,3-c]pyridin-3-yl)thiophene-2-carboxylate To a solution of methyl 4-(4-methoxy-1-(4-methoxybenzyl)-1H-pyrazolo[4,3-c]pyridin-3-yl)thiophene-2-carboxylate (75.0 mg) in acetonitrile (5 mL) were added sodium iodide (68.6 mg) and chloro(trimethyl)silane (0.232 mL), and the mixture was stirred at 50° C. for 1 hr. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate to ethyl acetate/methanol) to give the title compound (49.7 mg).

$^1$H NMR (300 MHz, DMSO-$d_6$) δ 3.71 (3H, s), 3.86 (3H, s), 5.49 (2H, s), 6.73 (1H, d, J=6.8 Hz), 6.85-6.95 (2H, m), 7.19-7.32 (3H, m), 8.51 (1H, d, J=1.1 Hz), 9.10 (1H, d, J=1.5 Hz), 11.20 (1H, d, J=5.7 Hz).

MS (ESI+): [M+H]$^+$ 396.1.
MS (ESI+). found: 396.2.

Example 114 methyl 4-(1-(4-methoxybenzyl)-4-oxo-4,5-dihydro-1H-pyrazolo[4,3-c]pyridin-3-yl)thiophene-2-carboxylate

A) 4-(1-(4-methoxybenzyl)-4-oxo-4,5-dihydro-1H-pyrazolo[4,3-c]pyridin-3-yl)thiophene-2-carboxylic acid A mixture of methyl 4-(1-(4-methoxybenzyl)-4-oxo-4,5-dihydro-1H-pyrazolo[4,3-c]pyridin-3-yl)thiophene-2-carboxylate (46.5 mg) obtained in Example 113 in a mixed solvent of methanol (2 mL)/THF (2 mL)/water (2 mL) was added 8 M aqueous sodium hydroxide solution (0.037 mL) at 0° C. The reaction mixture was stirred at 90° C. for 2 hr. The reaction mixture was diluted with water, and the mixture was extracted with ethyl acetate. The organic layer was washed with 0.1 N hydrochloric acid, water and saturated brine, dried over anhydrous magnesium sulfate, filtered, and concentrated under reduced pressure to give the title compound (40.8 mg).

MS (ESI+): [M+H]$^+$ 382.1.
MS (ESI+). found: 382.2.

B) methyl 4-(1-(4-methoxybenzyl)-4-oxo-4,5-dihydro-1H-pyrazolo[4,3-c]pyridin-3-yl)thiophene-2-carboxylate To a solution of 4-(1-(4-methoxybenzyl)-4-oxo-4,5-dihydro-1H-pyrazolo[4,3-c]pyridin-3-yl)thiophene-2-carboxylic acid (38.8 mg) in DMA (3 mL) were added EDCI hydrochloride (23.4 mg) and HOBt ammonium salt (18.6 mg) at room temperature, and the mixture was stirred overnight at room temperature. The reaction mixture was diluted with water, and the mixture was extracted with ethyl acetate. The organic layer was washed with saturated brine, dried over anhydrous magnesium sulfate, filtered, and concentrated under reduced pressure. The obtained residue was purified by silica gel column chromatography (basic silica gel, ethyl acetate/methanol) to give the title compound (31.4 mg).

$^1$H NMR (300 MHz, DMSO-$d_6$) δ 3.71 (3H, s), 5.49 (2H, s), 6.70 (1H, d, J=7.2 Hz), 6.83-6.95 (2H, m), 7.16-7.30 (3H, m), 7.40 (1H, brs), 8.14 (1H, brs), 8.34 (1H, d, J=1.1 Hz), 9.18 (1H, d, J=1.1 Hz), 11.18 (1H, brs).

MS (ESI+): [M+H]$^+$ 381.1.
MS (ESI+). found: 381.2.

Example 115

4-(4-oxo-1-(tetrahydrofuran-3-ylmethyl)-4,5-dihydro-1H-pyrazolo[4,3-c]pyridin-3-yl)benzenesulfonamide To a solution of 4-(4-oxo-4,5-dihydro-1H-pyrazolo[4,3-c]pyridin-3-yl)benzenesulfonamide (28.7 mg) obtained in Step B of Example 100 in DMF (2 mL) was added sodium hydride (60% dispersion in mineral oil, 4.35 mg), and the mixture was stirred at room temperature for 1 hr. To the reaction mixture was added tetrahydrofuran-3-ylmethyl 4-methylbenzenesulfonate (27.8 mg), and the mixture was stirred overnight at room temperature. The reaction mixture was extracted with water and ethyl acetate, and the organic layer was washed with saturated brine, dried over anhydrous magnesium sulfate, filtered, and concentrated under reduced pressure. The obtained residue was purified by silica gel column chromatography (basic silica gel, ethyl acetate/methanol) to give the title compound (11.8 mg).

$^1$H NMR (300 MHz, DMSO-$d_6$) δ 1.60-1.75 (1H, m), 1.86-2.03 (1H, m), 2.74-2.86 (1H, m), 3.52 (1H, dd, J=8.7, 5.7 Hz), 3.59-3.74 (2H, m), 3.81 (1H, td, J=8.1, 5.7 Hz), 4.28-4.42 (2H, m), 6.73 (1H, d, J=7.6 Hz), 7.29 (1H, d, J=7.2 Hz), 7.40 (2H, brs), 7.81-7.91 (2H, m), 8.43-8.56 (2H, m), 11.18 (1H, brs).

MS (ESI+): [M+H]$^+$ 375.1.
MS (ESI+). found: 375.2.

Example 116

(4-(7-chloro-1-(2,6-difluorophenyl)-4-oxo-4,5-dihydro-1H-pyrazolo[4,3-c]pyridin-3-yl)phenyl)acetonitrile To a solution of (4-(1-(2,6-difluorophenyl)-4-methoxy-1H-pyrazolo[4,3-c]pyridin-3-yl)phenyl)acetonitrile (322.3 mg) obtained in Step A of Example 39 in DMF (10 mL) was added N-chlorosuccinimide (252 mg) at 0° C., and the mixture was allowed to be warmed to room temperature, and stirred for 1 day, and then at 100° C. for 1 day, and cooled to room temperature. The reaction mixture was added to water, and the mixture was extracted twice with ethyl acetate. The organic layers were combined, washed with saturated brine, and dried over sodium sulfate, and the solvent was evaporated under reduced pressure. The residue was purified by silica gel column chromatography (basic silica gel, ethyl acetate/hexane/methanol) to give the title compound (156 mg).

MS (ESI+): [M+H]$^+$ 397.8.
MS (ESI+). found: 397.1.

Example 117

4-(3-cyclopentyl-7-oxo-6,7-dihydro-1H-pyrazolo[3,4-c]pyridin-1-yl)thiophene-2-carboxamide

A) 4-(3-cyclopentyl-7-methoxy-1H-pyrazolo[3,4-c]pyridin-1-yl)thiophene-2-carboxamide A mixture of 4-(4-bromo-3-cyclopentyl-7-methoxy-1H-pyrazolo[3,4-c]pyridin-1-yl)thiophene-2-carboxamide (60 mg) obtained in Step A of Example 67 and 10% palladium/carbon (50% wet, 15 mg) in a mixed solvent of ethanol (10 mL) and DMF (3 mL) was stirred under hydrogen atmosphere at room temperature for 15 hr. The reaction mixture was filtered, and the filtrate was concentrated under reduced pressure to give the title compound (60 mg).

MS (ESI+): [M+H]$^+$ 343.1.
MS (ESI+). found: 342.9.

B) 4-(3-cyclopentyl-7-oxo-6,7-dihydro-1H-pyrazolo[3,4-c]pyridin-1-yl)thiophene-2-carboxamide To a solution of 4-(3-cyclopentyl-7-methoxy-1H-pyrazolo[3,4-c]pyridin-1-yl)thiophene-2-carboxamide (60 mg) in acetonitrile (5 mL) were added sodium iodide (52.5 mg) and chloro(trimethyl)silane (0.111 mL), and the mixture was stirred at room temperature for 30 min. To the reaction mixture was added water, and the mixture was extracted with ethyl acetate. The organic layer was washed with saturated aqueous sodium hydrogencarbonate solution and saturated brine, dried over anhydrous sodium sulfate, and concentrated under reduced pressure. The residue was purified by HPLC (L-Column 2 ODS, mobile phase: water/acetonitrile (containing 0.1% trifluoroacetic acid)), to the obtained fraction was added saturated aqueous sodium hydrogencarbonate solution, and the mixture was extracted with ethyl acetate and THF. The organic layer was dried over anhydrous sodium sulfate, and concentrated under reduced pressure. The suspension of the residue in ethanol was stirred at 100° C. for 2 hr, allowed to be cooled to room temperature, and the solid was washed with ethanol to give the title compound (35 mg).
$^1$H NMR (300 MHz, DMSO-$d_6$) δ 1.58-1.95 (6H, m), 1.98-2.21 (2H, m), 3.34-3.49 (1H, m), 6.62 (1H, d, J=6.8 Hz), 7.04 (1H, d, J=6.8 Hz), 7.50 (1H, brs), 7.85-8.36 (3H, m), 11.49 (1H, brs).
MS (ESI+): [M+H]$^+$ 329.1.
MS (ESI+). found: 328.9.

Example 118

4-(4-cyano-3-cyclopentyl-7-oxo-6,7-dihydro-1H-pyrrolo[2,3-c]pyridin-1-yl)thiophene-2-carboxamide A) 3-(cyclopent-1-en-1-yl)-7-methoxy-1-((2-(trimethylsilyl)ethoxy)methyl)-1H-pyrrolo[2,3-c]pyridine-4-carbonitrile The title compound (368 mg) was obtained using 3-bromo-7-methoxy-1-((2-(trimethylsilyl)ethoxy)methyl)-1H-pyrrolo[2,3-c]pyridine-4-carbonitrile (600 mg) obtained in Step C of Example 102 and 2-(cyclopent-1-en-1-yl)-4,4,5,5-tetramethyl-1,3,2-dioxaborolane, in the same manner as in Step D of Example 102.
MS (ESI+): [M+H]$^+$ 370.2.
MS (ESI+). found: 370.2.

B) 3-cyclopentyl-7-methoxy-1-((2-(trimethylsilyl)ethoxy)methyl)-1H-pyrrolo[2,3-c]pyridine-4-carbonitrile To a solution of 3-(cyclopent-1-en-1-yl)-7-methoxy-1-((2-(trimethylsilyl)ethoxy)methyl)-1H-pyrrolo[2,3-c]pyridine-4-carbonitrile (690 mg) in methanol (5 mL) was added 10% palladium/carbon (100 mg). The reaction mixture was stirred overnight under hydrogen atmosphere (1 atm) at 50° C., and the insoluble substance was removed by filtration through Celite. The filtrate was concentrated under reduced pressure, and the obtained residue was purified by silica gel column chromatography (ethyl acetate/hexane) to give the title compound (519 mg).
MS (ESI+): [M+H]$^+$ 372.2.
MS (ESI+). found: 372.0.

C) 3-cyclopentyl-7-methoxy-1H-pyrrolo[2,3-c]pyridine-4-carbonitrile

The title compound (320 mg) was obtained using 3-cyclopentyl-7-methoxy-1-((2-(trimethylsilyl)ethoxy)methyl)-1H-pyrrolo[2,3-c]pyridine-4-carbonitrile (515 mg), in the same manner as in Step E of Example 102.
MS (ESI+): [M+H]$^+$ 242.1.
MS (ESI+). found: 242.2.

D) 4-(4-cyano-3-cyclopentyl-7-oxo-6,7-dihydro-1H-pyrrolo[2,3-c]pyridin-1-yl)thiophene-2-carboxamide The title compound (8.0 mg) was obtained using 3-cyclopentyl-7-methoxy-1H-pyrrolo[2,3-c]pyridine-4-carbonitrile (100 mg), in the same manner as in Step F of Example 102.
$^1$H NMR (300 MHz, DMSO-$d_6$) δ 1.50-1.83 (6H, m), 2.00-2.18 (2H, m), 3.36-3.50 (1H, m), 7.53 (2H, s), 7.82 (1H, d, J=1.5 Hz), 7.86 (1H, d, J=1.5 Hz), 7.90 (1H, s), 7.94-8.02 (1H, m), 11.85-12.02 (1H, m).

Example 119

4-(1-(4-hydroxycyclohexyl)-4-oxo-4,5-dihydro-1H-pyrazolo[4,3-c]pyridin-3-yl)benzenesulfonamide A) 4-(1-(4-((tert-butyl(dimethyl)silyl)oxy)cyclohexyl)-4-methoxy-1H-pyrazolo[4,3-c]pyridin-3-yl)benzenesulfonamide To a solution of 4-(4-methoxy-1H-pyrazolo[4,3-c]pyridin-3-yl)benzenesulfonamide (50.0 mg) obtained in Step A of Example 100 in DMF (2 mL) was added sodium hydride (60% dispersion in mineral oil, 7.89 mg), and the mixture was stirred at room temperature for 1 hr. To the reaction mixture was added 4-((tert-butyl(dimethyl)silyl)oxy)cyclohexyl 4-methylbenzenesulfonate (76.0 mg), and the mixture was stirred overnight at room temperature. The reaction mixture was extracted with water and ethyl acetate, and the organic layer was washed with saturated brine, dried over anhydrous magnesium sulfate, filtered, and concentrated under reduced pressure. The obtained residue was purified by silica gel column chromatography (hexane/ethyl acetate) to give the title compound (52.8 mg).
$^1$H NMR (300 MHz, DMSO-$d_6$) δ 0.03-0.12 (6H, m), 0.77-0.88 (1H, m), 0.89-0.98 (9H, m), 1.66-1.83 (6H, m), 2.25-2.45 (2H, m), 4.00 (3H, s), 4.65-4.73 (1H, m), 7.39 (1H, d, J=6.0 Hz), 7.43 (2H, brs), 7.88-8.00 (3H, m), 8.09 (2H, d, J=8.3 Hz).
MS (ESI+): [M+H]$^+$ 517.1.
MS (ESI+). found: 517.4.

B) 4-(1-(4-hydroxycyclohexyl)-4-oxo-4,5-dihydro-1H-pyrazolo[4,3-c]pyridin-3-yl)benzenesulfonamide To a solution of 4-(1-(4-((tert-butyl(dimethyl)silyl)oxy)cyclohexyl)-4-methoxy-1H-pyrazolo[4,3-c]pyridin-3-yl)benzenesulfonamide (50.0 mg) in 0.5 acetonitrile (3 mL) were added sodium iodide (36.0 mg) and chloro(trimethyl)silane (0.123 mL), and the mixture was stirred at 50° C. for 1 hr. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate to ethyl acetate/methanol) to give the title compound (28.1 mg).
$^1$H NMR (300 MHz, DMSO-$d_6$) δ 1.68 (4H, d, J=12.1 Hz), 1.75-1.90 (2H, m), 2.26-2.41 (2H, m), 3.91 (1H, brs), 4.45-4.59 (2H, m), 6.72 (1H, d, J=7.2 Hz), 7.26 (1H, d, J=7.2 Hz), 7.40 (2H, brs), 7.83-7.91 (2H, m), 8.46-8.54 (2H, m), 11.13 (1H, brs).
MS (ESI+): [M+H]$^+$ 389.1.
MS (ESI+). found: 389.3.

Example 120

2-(4-(7-cyano-1-cyclopentyl-4-oxo-4,5-dihydro-1H-pyrrolo[3,2-c]pyridin-3-yl)phenoxy)acetamide A) 1-cyclopentyl-3-(4-hydroxyphenyl)-4-methoxy-1H-pyrrolo[3,2-c]pyridine-7-carbonitrile The title compound (270 mg) was obtained using 3-bromo-1-cyclopentyl-4-methoxy-4,5-dihydro-1H-pyrrolo[3,2-c]pyridine-7-carbonitrile (800 mg) obtained in Step H of Example 33 and 4-(4,4,5,5-tetramethyl-1,3,2-dioxaborolan-2-yl)phenol, in the same manner as in Step I of Example 33.
MS (ESI+): [M+H]$^+$ 334.2.
MS (ESI+). found: 334.2.

B) 2-(4-(7-cyano-1-cyclopentyl-4-methoxy-1H-pyrrolo[3,2-c]pyridin-3-yl)phenoxy)acetamide To a solution of 1-cyclopentyl-3-(4-hydroxyphenyl)-4-methoxy-1H-pyrrolo[3,2-c]pyridine-7-carbonitrile (120 mg) and sodium hydride (dispersion in mineral oil, 22 mg) in DMF (3.0 mL) was added 2-bromoacetamide (120 mg) at 0° C., and the mixture was stirred at room temperature for 1 hr. To the reaction mixture was added water, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (37 mg).
MS (ESI+): [M+H]$^+$ 391.2.
MS (ESI+). found: 391.3.

C) 2-(4-(7-cyano-1-cyclopentyl-4-oxo-4,5-dihydro-1H-pyrrolo[3,2-c]pyridin-3-yl)phenoxy)acetamide The title compound (12 mg) was obtained using 2-(4-(7-cyano-1-cyclopentyl-4-methoxy-1H-pyrrolo[3,2-c]pyridin-3-yl)phenoxy)acetamide (32 mg), in the same manner as in Step J of Example 33.
MS (ESI+): [M+H]$^+$ 377.2.
MS (ESI+). found: 377.3.

Example 121

3-(4-(cyanomethoxy)phenyl)-1-cyclopentyl-4-oxo-4,5-dihydro-1H-pyrrolo[3,2-c]pyridine-7-carbonitrile A) 3-(4-(cyanomethoxy)phenyl)-1-cyclopentyl-4-methoxy-1H-pyrrolo[3,2-c]pyridine-7-carbonitrile The title compound (135 mg) was obtained using 1-cyclopentyl-3-(4-hydroxyphenyl)-4-methoxy-1H-pyrrolo[3,2-c]pyridine-7-carbonitrile (150 mg) obtained in Step A of Example 120 and 2-bromoacetonitrile, in the same manner as in Step B of Example 120.
MS (ESI+): [M+H]$^+$ 373.2.
MS (ESI+). found: 373.3.

B) 3-(4-(cyanomethoxy)phenyl)-1-cyclopentyl-4-oxo-4,5-dihydro-1H-pyrrolo[3,2-c]pyridine-7-carbonitrile The title compound (34 mg) was obtained using 3-(4-(cyanomethoxy)phenyl)-1-cyclopentyl-4-methoxy-1H-pyrrolo[3,2-c]pyridine-7-carbonitrile (130 mg), in the same manner as in Step J of Example 33.
MS (ESI+): [M+H]$^+$ 359.1.
MS (ESI+). found: 359.2.

Example 122

4-(7-cyano-1-cyclopentyl-4-oxo-4,5-dihydro-1H-pyrrolo[3,2-c]pyridin-3-yl)-N-ethylthiophene-2-carboxamide The title compound was obtained using methyl 4-(7-cyano-1-cyclopentyl-4-methoxy-1H-pyrrolo[3,2-c]pyridin-3-yl)thiophene-2-carboxylate obtained in Step A of Example 76 and ethylamine, in the same manner as in Step F of Example 33, Step G of Example 33 and Step J of Example 33.
MS (ESI+): [M]$^+$ 380.4.
MS (ESI+). found: 380.8.

Example 123

N-tert-butyl-4-(7-cyano-1-cyclopentyl-4-oxo-4,5-dihydro-1H-pyrrolo[3,2-c]pyridin-3-yl)thiophene-2-carboxamide The title compound was obtained using methyl 4-(7-cyano-1-cyclopentyl-4-methoxy-1H-pyrrolo[3,2-c]pyridin-3-yl)thiophene-2-carboxylate obtained in Step A of Example 76 and tert-butylamine, in the same manner as in Step F of Example 33, Step G of Example 33 and Step J of Example 33.
MS (ESI+): [M]$^+$ 408.5.
MS (ESI+). found: 408.7.

Example 124

2-(4-(7-chloro-1-(2,6-difluorophenyl)-4-oxo-4,5-dihydro-1H-pyrazolo[4,3-c]pyridin-3-yl)phenyl)acetamide To a solution of (4-(7-chloro-1-(2,6-difluorophenyl)-4-oxo-4,5-dihydro-1H-pyrazolo[4,3-c]pyridin-3-yl)phenyl)acetonitrile (134.5 mg) obtained in Example 116 and potassium carbonate (94 mg) in DMSO (2 mL) was added 30% aqueous hydrogen peroxide (139 µL) at room temperature. The reaction mixture was stirred overnight, and poured into water. The precipitated crystals were collected by filtration, and purified by HPLC (C18, mobile phase: water/acetonitrile (containing 0.1% TFA)), to the obtained fraction was added saturated aqueous sodium hydrogencarbonate solution, and the mixture was extracted with ethyl acetate, dried over anhydrous magnesium sulfate, concentrated under reduced pressure, and purified to give the title compound (105 mg).
$^1$H NMR (300 MHz, DMSO-d$_6$) δ 3.44 (2H, s), 6.91 (1H, brs), 7.35 (2H, d, J=8.3 Hz), 7.40-7.55 (3H, m), 7.62 (1H, s), 7.71-7.85 (1H, m), 8.10 (2H, d, J=8.3 Hz), 11.79 (1H, brs).
MS (ESI+): [M+H]$^+$ 415.8.
MS (ESI+). found: 415.2.

Example 125

1-cyclopentyl-4-oxo-3-(1H-pyrazol-5-yl)-4,5-dihydro-1H-pyrrolo[3,2-c]pyridine-7-carbonitrile hydrochloride A) 1-cyclopentyl-4-oxo-3-(1-(tetrahydro-2H-pyran-2-yl)-1H-pyrazol-5-yl)-4,5-dihydro-1H-pyrrolo[3,2-c]pyridine-7-carbonitrile The title compound was obtained using 3-bromo-1-cyclopentyl-4-methoxy-4,5-dihydro-1H-pyrrolo[3,2-c]pyridine- 7-carbonitrile obtained in Step H of Example 33 and 1-(tetrahydro-2H-pyran-2-yl)-5-(4,4,5,5-tetramethyl-1,3,2-dioxaborolan-2-yl)-1H-pyrazole, in the same manner as in Step I of Example 33.
MS (ESI+): [M+H]$^+$ 392.5.
MS (ESI+). found: 392.3.

B) 1-cyclopentyl-4-oxo-3-(1H-pyrazol-5-yl)-4,5-dihydro-1H-pyrrolo[3,2-c]pyridine-7-carbonitrile hydrochloride A solution of 1-cyclopentyl-4-oxo-3-(1-(tetrahydro-2H-pyran-2-yl)-1H-pyrazol-5-yl)-4,5-dihydro-1H-pyrrolo[3,2-c]pyridine-7-carbonitrile and 4N hydrogen chloride/ethyl acetate solution (1.31 mL) in ethanol (2 mL) was stirred overnight at 50° C., and the solvent was evaporated under reduced pressure. The residue was crystallized from ethanol and diisopropyl ether to give the title compound (136 mg).
MS (ESI+): [M+H—HCl]$^+$ 294.3.
MS (ESI+). found: 294.2.

Example 126

4-(1-(4-hydroxycyclohexyl)-4-oxo-4,5-dihydro-1H-pyrazolo[4,3-c]pyridin-3-yl)benzenesulfonamide To a solution of 4-(1-(4-((tert-butyl(dimethyl)silyl)oxy)cyclohexyl)-4-methoxy-1H-pyrazolo[4,3-c]pyridin-3-yl)benzenesulfonamide (42.8 mg) obtained in Step A of Example 119 in acetonitrile (3 mL) were added sodium iodide (31.0 mg) and chloro(trimethyl)silane (0.105 mL), and the mixture was stirred at 50° C. for 1 hr. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate to ethyl acetate/methanol) to give the title compound (24.6 mg).
$^1$H NMR (300 MHz, DMSO-d$_6$) δ 1.68 (4H, d, J=11.3 Hz), 1.77-1.91 (2H, m), 2.25-2.44 (2H, m), 3.91 (1H, brs), 4.46-4.61 (2H, m), 6.72 (1H, d, J=7.2 Hz), 7.26 (1H, d, J=5.7 Hz), 7.39 (2H, s), 7.87 (2H, d, J=8.3 Hz), 8.45-8.56 (2H, m), 11.14 (1H, brs).
MS (ESI+): [M]$^+$ 389.1.
MS (ESI+). found: 389.2.

Example 127

(4-(1-cyclopentyl-4-oxo-4,5-dihydro-1H-pyrazolo[4,3-c]pyridin-3-yl)phenyl)acetonitrile

A) (4-(1-cyclopentyl-4-methoxy-1H-pyrazolo[4,3-c]pyridin-3-yl)phenyl)acetonitrile A solution of 1-cyclopentyl-4-methoxy-1H-pyrazolo[4,3-c]pyridin-3-yl trifluoromethanesulfonate (160 mg) obtained in Step C of Example 12, (4-(4,4,5,5-tetramethyl-1,3,2-dioxaborolan-2-yl)phenyl)acetonitrile (160 mg), tetrakis(triphenylphosphine)palladium(0) (50.6 mg) and 2M aqueous sodium carbonate solution (1.10 mL) in DME (10 mL) was heated overnight with reflux under nitrogen atmosphere. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane) to give the title compound (91.0 mg).
$^1$H NMR (300 MHz, DMSO-d$_6$) δ 1.62-1.80 (2H, m), 1.82-2.23 (6H, m), 3.98 (3H, s), 4.12 (2H, s), 5.18 (1H, quin, J=7.1 Hz), 7.37 (1H, d, J=6.0 Hz), 7.45 (2H, d, J=8.7 Hz), 7.88-8.00 (3H, m).
MS (ESI+): [M+H]$^+$ 333.2.
MS (ESI+). found: 332.9.

B) (4-(1-cyclopentyl-4-oxo-4,5-dihydro-1H-pyrazolo[4,3-c]pyridin-3-yl)phenyl)acetonitrile To a solution of (4-(1-cyclopentyl-4-methoxy-1H-pyrazolo[4,3-c]pyridin-3-yl)phenyl)acetonitrile (81.6 mg) in acetonitrile (10 mL) were added sodium iodide (73.6 mg) and chloro(trimethyl)silane (0.249 mL), and the mixture was stirred at 60° C. for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane), and the obtained solid was washed with ethyl acetate/diisopropyl ether to give the title compound (73.4 mg).
$^1$H NMR (300 MHz, DMSO-d$_6$) δ 1.58-1.80 (2H, m), 1.81-2.22 (6H, m), 4.08 (2H, s), 5.04 (1H, quin, J=7.1 Hz), 6.67 (1H, d, J=7.2 Hz), 7.16-7.30 (1H, m), 7.40 (2H, d, J=7.9 Hz), 8.32 (2H, d, J=8.3 Hz), 11.07 (1H, brs).
MS (ESI+): [M+H]$^+$ 319.2.
MS (ESI+). found: 318.9.

Example 128

(3-(1-cyclopentyl-4-oxo-4,5-dihydro-1H-pyrazolo[4,3-c]pyridin-3-yl)phenyl)acetonitrile

A) (3-(1-cyclopentyl-4-methoxy-1H-pyrazolo[4,3-c]pyridin-3-yl)phenyl)acetonitrile A solution of 1-cyclopentyl-4-methoxy-1H-pyrazolo[4,3-c]pyridin-3-yl trifluoromethanesulfonate (160 mg) obtained in Step C of Example 12, (3-(4,4,5,5-tetramethyl-1,3,2-dioxaborolan-2-yl)phenyl)acetonitrile (160 mg), tetrakis(triphenylphosphine)palladium(0) (50.6 mg) and 2M aqueous sodium carbonate solution (1.10 mL) in DME (10 mL) was heated overnight with reflux under nitrogen atmosphere. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane) to give the title compound (127 mg).
$^1$H NMR (300 MHz, DMSO-d$_6$) δ 1.62-1.80 (2H, m), 1.83-2.25 (6H, m), 4.00 (3H, s), 4.15 (2H, s), 5.18 (1H, quin, J=7.2 Hz), 7.31-7.43 (2H, m), 7.45-7.54 (1H, m), 7.88 (1H, d, J=7.9 Hz), 7.92-8.00 (2H, m).
MS (ESI+): [M+H]$^+$ 333.2.
MS (ESI+). found: 332.9.

B) (3-(1-cyclopentyl-4-oxo-4,5-dihydro-1H-pyrazolo[4,3-c]pyridin-3-yl)phenyl)acetonitrile To a solution of (3-(1-cyclopentyl-4-methoxy-1H-pyrazolo[4,3-c]pyridin-3-yl)phenyl)acetonitrile (120 mg) in acetonitrile (10 mL) were added sodium iodide (108 mg) and chloro(trimethyl)silane (0.366 mL), and the mixture was stirred at 60° C. for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane), and the obtained solid was washed with ethyl acetate to give the title compound (105 mg).

$^1$H NMR (300 MHz, DMSO-$d_6$) δ 1.61-1.79 (2H, m), 1.82-2.22 (6H, m), 4.11 (2H, s), 5.05 (1H, quin, J=7.1 Hz), 6.68 (1H, d, J=7.2 Hz), 7.24 (1H, d, J=7.2 Hz), 7.30-7.39 (1H, m), 7.40-7.52 (1H, m), 8.22 (1H, s), 8.35 (1H, d, J=7.9 Hz), 11.07 (1H, brs).

MS (ESI+): [M+H]$^+$ 319.2.
MS (ESI+). found: 318.9.

Example 129

4-(1-tert-butyl-4-oxo-4,5-dihydro-1H-pyrazolo[4,3-c]pyridin-3-yl)thiophene-2-carboxamide A) methyl 4-(1-tert-butyl-4-methoxy-1H-pyrazolo[4,3-c]pyridin-3-yl)thiophene-2-carboxylate To a solution of 1-tert-butyl-4-methoxy-1H-pyrazolo[4,3-c]pyridin-3-yl trifluoromethanesulfonate (1.60 g) obtained in Step C of Example 86 in DME (100 mL) were added methyl 4-(4,4,5,5-tetramethyl-1,3,2-dioxaborolan-2-yl)thiophene-2-carboxylate (1.46 g) and 2M aqueous sodium carbonate solution (11.3 mL), and then tetrakis(triphenylphosphine)palladium(0) (523 mg) was added thereto under nitrogen atmosphere. The reaction mixture was stirred overnight under nitrogen atmosphere at 100° C. To the reaction mixture was added water, and the mixture was extracted with ethyl acetate. The organic layer was washed with saturated brine, dried over anhydrous magnesium sulfate, filtered, and concentrated under reduced pressure. The obtained residue was purified by silica gel column chromatography (hexane/ethyl acetate) to give the title compound (1.88 g).

$^1$H NMR (300 MHz, DMSO-$d_6$) δ 1.74 (9H, s), 3.87 (3H, s), 4.06 (3H, s), 7.50 (1H, d, J=6.4 Hz), 7.90 (1H, d, J=6.0 Hz), 8.31 (1H, d, J=1.5 Hz), 8.52 (1H, d, J=1.5 Hz).

B) 4-(1-tert-butyl-4-methoxy-1H-pyrazolo[4,3-c]pyridin-3-yl)thiophene-2-carboxylic acid To a mixture of methyl 4-(1-tert-butyl-4-methoxy-1H-pyrazolo[4,3-c]pyridin-3-yl)thiophene-2-carboxylate (1.88 g) in a mixed solvent of methanol (30 mL)/THF (30 mL)/water (25 mL) was added 1N aqueous sodium hydroxide solution (5.44 mL) at room temperature, and the mixture was stirred overnight at room temperature. To the reaction mixture was added 1N hydrochloric acid, and the mixture was concentrated under reduced pressure. The residue was washed with water, and dried in vacuum to give the title compound (1.50 g).

$^1$H NMR (300 MHz, DMSO-$d_6$) δ 1.73 (9H, s), 4.05 (3H, s), 7.49 (1H, d, J=6.4 Hz), 7.90 (1H, d, J=6.4 Hz), 8.24 (1H, d, J=1.1 Hz), 8.45 (1H, d, J=1.1 Hz), 13.23 (1H, brs).

C) 4-(1-tert-butyl-4-methoxy-1H-pyrazolo[4,3-c]pyridin-3-yl)thiophene-2-carboxamide To a solution of 4-(1-tert-butyl-4-methoxy-1H-pyrazolo[4,3-c]pyridin-3-yl)thiophene-2-carboxylic acid (1.50 g) in DMF (200 mL) were added EDCI hydrochloride (4.34 mg) and HOBt ammonium salt (3.44 g) at room temperature, and the mixture was stirred at room temperature for 5 hr. To the reaction mixture was added water at 0° C., and the white precipitate was collected by filtration. The obtained white solid was washed with water and saturated aqueous sodium hydrogencarbonate solution, and dried in vacuum to give the title compound (1.46 g).

$^1$H NMR (300 MHz, DMSO-$d_6$) δ 1.74 (9H, s), 4.05 (3H, s), 7.44 (1H, brs), 7.48 (1H, d, J=6.4 Hz), 7.89 (1H, d, J=6.4 Hz), 8.15 (1H, brs), 8.31 (2H, dd, J=8.3, 1.5 Hz).

D) 4-(1-tert-butyl-4-oxo-4,5-dihydro-1H-pyrazolo[4,3-c]pyridin-3-yl)thiophene-2-carboxamide To a solution of 4-(1-tert-butyl-4-methoxy-1H-pyrazolo[4,3-c]pyridin-3-yl)thiophene-2-carboxamide (500 mg) in acetonitrile (30 mL) were added sodium iodide (567 mg) and chloro(trimethyl)silane (1.92 mL), and the mixture was stirred at 50° C. for 1 hr. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate/methanol) to give the title compound (475 mg).

$^1$H NMR (300 MHz, DMSO-$d_6$) δ 1.70 (9H, s), 6.80 (1H, d, J=7.6 Hz), 7.17 (1H, dd, J=7.4, 5.9 Hz), 7.40 (1H, brs), 8.13 (1H, brs), 8.34 (1H, d, J=1.1 Hz), 9.06 (1H, d, J=1.1 Hz), 11.16 (1H, d, J=5.3 Hz).

MS (ESI+): [M]$^+$ 317.1.
MS (ESI+). found: 317.2.

Example 130

N-(3-(7-cyano-1-cyclopentyl-4-oxo-4,5-dihydro-1H-pyrrolo[3,2-c]pyridin-3-yl)phenyl)acetamide A) N-(3-(7-cyano-1-cyclopentyl-4-methoxy-1H-pyrrolo[3,2-c]pyridin-3-yl)phenyl)acetamide The title compound was obtained using 3-bromo-1-cyclopentyl-4-methoxy-4,5-dihydro-1H-pyrrolo[3,2-c]pyridine-7-carbonitrile (32 mg) obtained in Step H of Example 33 and (3-acetamidophenyl)boronic acid, in the same manner as in Step I of Example 33.

B) N-(3-(7-cyano-1-cyclopentyl-4-oxo-4,5-dihydro-1H-pyrrolo[3,2-c]pyridin-3-yl)phenyl)acetamide The title compound (40.2 mg) was obtained using N-(3-(7-cyano-1-cyclopentyl-4-methoxy-1H-pyrrolo[3,2-c]pyridin-3-yl)phenyl)acetamide, in the same manner as in Step J of Example 33.

MS (ESI+): [M+H]$^+$ 361.2.
MS (ESI+). found: 362.0.

Example 131

1-cyclopentyl-3-(1-methyl-1H-pyrazol-4-yl)-4-oxo-4,5-dihydro-1H-pyrrolo[3,2-c]pyridine-7-carbonitrile A) 1-cyclopentyl-4-methoxy-3-(1-methyl-1H-pyrazol-4-yl)-1H-pyrrolo[3,2-c]pyridine-7-carbonitrile The title compound was obtained using 3-bromo-1-cyclopentyl-4-methoxy-4,5-dihydro-1H-pyrrolo[3,2-c]pyridine- 7-carbonitrile (32 mg) obtained in Step H of Example 33 and 1-methyl-4-(4,4,5,5-tetramethyl-1,3,2-dioxaborolan-2-yl)-1H-pyrazole, in the same manner as in Step I of Example 33.

B) 1-cyclopentyl-3-(1-methyl-1H-pyrazol-4-yl)-4-oxo-4,5-dihydro-1H-pyrrolo[3,2-c]pyridine-7-carbonitrile The title compound (6.5 mg) was obtained using 1-cyclopentyl-4-methoxy-3-(1-methyl-1H-pyrazol-4-yl)-1H-pyrrolo[3,2-c]pyridine-7-carbonitrile, in the same manner as in Step J of Example 33.
MS (ESI+): [M+H]$^+$ 308.1.
MS (ESI+). found: 307.9.

Example 132

1-cyclopentyl-4-oxo-3-(pyridin-2-yl)-4,5-dihydro-1H-pyrrolo[3,2-c]pyridine-7-carbonitrile A) 1-cyclopentyl-4-methoxy-3-(pyridin-2-yl)-1H-pyrrolo[3,2-c]pyridine-7-carbonitrile The title compound was obtained using 3-bromo-1-cyclopentyl-4-methoxy-4,5-dihydro-1H-pyrrolo[3,2-c]pyridine-7-carbonitrile (32 mg) obtained in Step H of Example 33 and (2-pyridine)cyclic triolborate lithium salt, in the same manner as in Step I of Example 33.

B) 1-cyclopentyl-4-oxo-3-(pyridin-2-yl)-4,5-dihydro-1H-pyrrolo[3,2-c]pyridine-7-carbonitrile The title compound (9.2 mg) was obtained using 1-cyclopentyl-4-methoxy-3-(pyridin-2-yl)-1H-pyrrolo[3,2-c]pyridine-7-carbonitrile, in the same manner as in Step J of Example 33.
MS (ESI+): [M+H]$^+$ 305.1.
MS (ESI+). found: 304.9.

Example 133

1-cyclopentyl-4-oxo-3-(pyridin-3-yl)-4,5-dihydro-1H-pyrrolo[3,2-c]pyridine-7-carbonitrile A) 1-cyclopentyl-4-methoxy-3-(pyridin-3-yl)-1H-pyrrolo[3,2-c]pyridine-7-carbonitrile The title compound was obtained using 3-bromo-1-cyclopentyl-4-methoxy-4,5-dihydro-1H-pyrrolo[3,2-c]pyridine-7-carbonitrile (32 mg) obtained in Step H of Example 33 and pyridin-3-ylboronic acid, in the same manner as in Step I of Example 33.

B) 1-cyclopentyl-4-oxo-3-(pyridin-3-yl)-4,5-dihydro-1H-pyrrolo[3,2-c]pyridine-7-carbonitrile The title compound (28.9 mg) was obtained using 1-cyclopentyl-4-methoxy-3-(pyridin-3-yl)-1H-pyrrolo[3,2-c]pyridine-7-carbonitrile, in the same manner as in Step J of Example 33.
MS (ESI+): [M+H]$^+$ 305.1.
MS (ESI+). found: 304.9.

Example 134

1-cyclopentyl-4-oxo-3-(2-thienyl)-4,5-dihydro-1H-pyrrolo[3,2-c]pyridine-7-carbonitrile A) 1-cyclopentyl-4-methoxy-3-(2-thienyl)-1H-pyrrolo[3,2-c]pyridine-7-carbonitrile The title compound was obtained using 3-bromo-1-cyclopentyl-4-methoxy-4,5-dihydro-1H-pyrrolo[3,2-c]pyridine-7-carbonitrile (32 mg) obtained in Step H of Example 33 and 6-methyl-2-(2-thienyl)-1,3,6,2-dioxazaborocine-4,8-dione, in the same manner as in Step I of Example 33.

B) 1-cyclopentyl-4-oxo-3-(2-thienyl)-4,5-dihydro-1H-pyrrolo[3,2-c]pyridine-7-carbonitrile The title compound (40.1 mg) was obtained using 1-cyclopentyl-4-methoxy-3-(2-thienyl)-1H-pyrrolo[3,2-c]pyridine-7-carbonitrile, in the same manner as in Step J of Example 33.
MS (ESI+): [M+H]$^+$ 310.1.
MS (ESI+). found: 310.9.

Example 135

1-cyclopentyl-3-(1-isobutyl-1H-pyrazol-4-yl)-4-oxo-4,5-dihydro-1H-pyrrolo[3,2-c]pyridine-7-carbonitrile A) 1-cyclopentyl-3-(1-isobutyl-1H-pyrazol-4-yl)-4-methoxy-1H-pyrrolo[3,2-c]pyridine-7-carbonitrile The title compound was obtained using 3-bromo-1-cyclopentyl-4-methoxy-4,5-dihydro-1H-pyrrolo[3,2-c]pyridine-7-carbonitrile (32 mg) obtained in Step H of Example 33 and 1-isobutyl-4-(4,4,5,5-tetramethyl-1,3,2-dioxaborolan-2-yl)-1H-pyrazole, in the same manner as in Step I of Example 33.

B) 1-cyclopentyl-3-(1-isobutyl-1H-pyrazol-4-yl)-4-oxo-4,5-dihydro-1H-pyrrolo[3,2-c]pyridine-7-carbonitrile The title compound (38.1 mg) was obtained using 1-cyclopentyl-3-(1-isobutyl-1H-pyrazol-4-yl)-4-methoxy-1H-pyrrolo[3,2-c]pyridine-7-carbonitrile, in the same manner as in Step J of Example 33.
MS (ESI+): [M+H]$^+$ 350.2.
MS (ESI+). found: 350.0.

Example 136

1-cyclopentyl-3-(1-methyl-1H-pyrazol-3-yl)-4-oxo-4,5-dihydro-1H-pyrrolo[3,2-c]pyridine-7-carbonitrile A) 1-cyclopentyl-4-methoxy-3-(1-methyl-1H-pyrazol-3-yl)-1H-pyrrolo[3,2-c]pyridine-7-carbonitrile The title compound was obtained using 3-bromo-1-cyclopentyl-4-methoxy-4,5-dihydro-1H-pyrrolo[3,2-c]pyridine-7-carbonitrile (32 mg) obtained in Step H of Example 33 and 1-methyl-3-(4,4,5,5-tetramethyl-1,3,2-dioxaborolan-2-yl)-1H-pyrazole, in the same manner as in Step I of Example 33.

B) 1-cyclopentyl-3-(1-methyl-1H-pyrazol-3-yl)-4-oxo-4,5-dihydro-1H-pyrrolo[3,2-c]pyridine-7-carbonitrile The title compound (2.3 mg) was obtained using 1-cyclopentyl-4-methoxy-3-(1-methyl-1H-pyrazol-3-yl)-1H-pyrrolo[3,2-c]pyridine-7-carbonitrile, in the same manner as in Step J of Example 33.
MS (ESI+): [M+H]$^+$ 308.1.
MS (ESI+). found: 307.9.

Example 137

1-cyclopentyl-3-(1-cyclopentyl-1H-pyrazol-4-yl)-4-oxo-4,5-dihydro-1H-pyrrolo[3,2-c]pyridine-7-carbonitrile A) 1-cyclopentyl-3-(1-cyclopentyl-1H-pyrazol-4-yl)-4-methoxy-1H-pyrrolo[3,2-c]pyridine-7-carbonitrile The title compound was obtained using 3-bromo-1-cyclopentyl-4-methoxy-4,5-dihydro-1H-pyrrolo[3,2-c]pyridine-7-carbonitrile (32 mg) obtained in Step H of Example 33 and 1-cyclopentyl-4-(4,4,5,5-tetramethyl-1,3,2-dioxaborolan-2-yl)-1H-pyrazole, in the same manner as in Step I of Example 33.

B) 1-cyclopentyl-3-(1-cyclopentyl-1H-pyrazol-4-yl)-4-oxo-4,5-dihydro-1H-pyrrolo[3,2-c]pyridine-7-carbonitrile The title compound (20.8 mg) was obtained using 1-cyclopentyl-3-(1-cyclopentyl-1H-pyrazol-4-yl)-4-methoxy-1H-pyrrolo[3,2-c]pyridine-7-carbonitrile, in the same manner as in Step J of Example 33.
MS (ESI+): [M+H]$^+$ 362.2.
MS (ESI+). found: 362.0.

Example 138

1-cyclopentyl-3-(1-cyclopropyl-1H-pyrazol-4-yl)-4-oxo-4,5-dihydro-1H-pyrrolo[3,2-c]pyridine-7-carbonitrile A) 1-cyclopentyl-3-(1-cyclopropyl-1H-pyrazol-4-yl)-4-methoxy-1H-pyrrolo[3,2-c]pyridine-7-carbonitrile The title compound was obtained using 3-bromo-1-cyclopentyl-4-methoxy-4,5-dihydro-1H-pyrrolo[3,2-c]pyridine-7-carbonitrile (32 mg) obtained in Step H of Example 33 and 1-cyclopropyl-4-(4,4,5,5-tetramethyl-1,3,2-dioxaborolan-2-yl)-1H-pyrazole, in the same manner as in Step I of Example 33.

B) 1-cyclopentyl-3-(1-cyclopropyl-1H-pyrazol-4-yl)-4-oxo-4,5-dihydro-1H-pyrrolo[3,2-c]pyridine-7-carbonitrile The title compound (20.4 mg) was obtained using 1-cyclopentyl-3-(1-cyclopropyl-1H-pyrazol-4-yl)-4-methoxy-1H-pyrrolo[3,2-c]pyridine-7-carbonitrile, in the same manner as in Step J of Example 33.
MS (ESI+): [M+H]$^+$ 334.2.
MS (ESI+). found: 333.9.

Example 139

3-(4-(2-cyanopropan-2-yl)phenyl)-1-cyclopentyl-4-oxo-4,5-dihydro-1H-pyrrolo[3,2-c]pyridine-7-carbonitrile A) 3-(4-(2-cyanopropan-2-yl)phenyl)-1-cyclopentyl-4-methoxy-1H-pyrrolo[3,2-c]pyridine-7-carbonitrile The title compound was obtained using 3-bromo-1-cyclopentyl-4-methoxy-4,5-dihydro-1H-pyrrolo[3,2-c]pyridine-7-carbonitrile (32 mg) obtained in Step H of Example 33 and (4-(2-cyanopropan-2-yl)phenyl)boronic acid, in the same manner as in Step I of Example 33.

B) 3-(4-(2-cyanopropan-2-yl)phenyl)-1-cyclopentyl-4-oxo-4,5-dihydro-1H-pyrrolo[3,2-c]pyridine-7-carbonitrile The title compound (42.4 mg) was obtained using 3-(4-(2-cyanopropan-2-yl)phenyl)-1-cyclopentyl-4-methoxy-1H-pyrrolo[3,2-c]pyridine-7-carbonitrile, in the same manner as in Step J of Example 33.
MS (ESI+): [M+H]$^+$ 371.2.
MS (ESI+). found: 371.0.

Example 140

1-cyclopentyl-3-(3-(morpholin-4-yl)phenyl)-4-oxo-4,5-dihydro-1H-pyrrolo[3,2-c]pyridine-7-carbonitrile A) 1-cyclopentyl-4-methoxy-3-(3-(morpholin-4-yl)phenyl)-1H-pyrrolo[3,2-c]pyridine-7-carbonitrile The title compound was obtained using 3-bromo-1-cyclopentyl-4-methoxy-4,5-dihydro-1H-pyrrolo[3,2-c]pyridine-7-carbonitrile (32 mg) obtained in Step H of Example 33 and 4-(3-(4,4,5,5-tetramethyl-1,3,2-dioxaborolan-2-yl)phenyl)morpholine, in the same manner as in Step I of Example 33.

B) 1-cyclopentyl-3-(3-(morpholin-4-yl)phenyl)-4-oxo-4,5-dihydro-1H-pyrrolo[3,2-c]pyridine-7-carbonitrile The title compound (26.5 mg) was obtained using 1-cyclopentyl-4-methoxy-3-(3-(morpholin-4-yl)phenyl)-1H-pyrrolo[3,2-c]pyridine-7-carbonitrile, in the same manner as in Step J of Example 33.
MS (ESI+): [M+H]$^+$ 389.2.
MS (ESI+). found: 390.1.

Example 141

4-(1-((3-methyloxetan-3-yl)methyl)-4-oxo-4,5-dihydro-1H-pyrazolo[4,3-c]pyridin-3-yl)thiophene-2-carboxamide A) 4-(4-oxo-4,5-dihydro-1H-pyrazolo[4,3-c]pyridin-3-yl)thiophene-2-carboxamide 4-(1-tert-Butyl-4-oxo-4,5-dihydro-1H-pyrazolo[4,3-c]pyridin-3-yl)thiophene-2-carboxamide (475 mg) obtained in Example 129 was dissolved in a mixed solvent of trifluoroacetic acid (60 mL)/water (6 mL), and the mixture was heated with reflux at 24 hr. The reaction mixture was allowed to be cooled to room temperature, and concentrated under reduced pressure. The residue was extracted with ethyl acetate and saturated aqueous sodium hydrogencarbonate solution, and the organic layer was washed with saturated brine, dried over anhydrous magnesium sulfate, filtered, and concentrated under reduced pressure. The obtained residue was crystallized from DMF-ethyl acetate, and dried in vacuum to give the title compound (240 mg).

$^1$H NMR (300 MHz, DMSO-$d_6$) δ 6.45 (1H, d, J=6.4 Hz), 7.13-7.27 (1H, m), 7.41 (1H, brs), 8.11 (1H, brs), 8.40 (1H, d, J=1.1 Hz), 9.16 (1H, d, J=0.8 Hz), 11.07 (1H, d, J=5.7 Hz), 13.36 (1H, s).

MS (ESI+): [M]$^+$ 261.1.
MS (ESI+). found: 261.2.

B) 4-(1-((3-methyloxetan-3-yl)methyl)-4-oxo-4,5-dihydro-1H-pyrazolo[4,3-c]pyridin-3-yl)thiophene-2-carboxamide To a solution of 4-(4-oxo-4,5-dihydro-1H-pyrazolo[4,3-c]pyridin-3-yl)thiophene-2-carboxamide (60.0 mg) in DMF (3 mL) was added sodium hydride (60% dispersion in mineral oil, 23.0 mg), and the mixture was stirred at room temperature for 1 hr. To the reaction mixture was added (3-methyloxetan-3-yl)methyl 4-methylbenzenesulfonate (148 mg), and the mixture was stirred overnight at room temperature. The reaction mixture was extracted with water and ethyl acetate, and the organic layer was washed with saturated brine, dried over anhydrous magnesium sulfate, filtered, and concentrated under reduced pressure. The obtained residue was purified by silica gel column chromatography (basic silica gel, ethyl acetate/methanol) to give the title compound (2.3 mg).

MS (ESI+): [M]$^+$ 345.1.
MS (ESI+). found: 345.2.

Example 142

4-(1-cyclopentyl-4-oxo-4,5-dihydro-1H-pyrazolo[4,3-c]pyridin-3-yl)benzamide

A) 4-(1-cyclopentyl-4-methoxy-1H-pyrazolo[4,3-c]pyridin-3-yl)benzamide

A solution of 1-cyclopentyl-4-methoxy-1H-pyrazolo[4,3-c]pyridin-3-yl trifluoromethanesulfonate (120 mg) obtained in Step C of Example 12, 4-(4,4,5,5-tetramethyl-1,3,2-dioxaborolan-2-yl)benzamide (122 mg), tetrakis(triphenylphosphine)palladium(0) (38.0 mg) and 2M aqueous sodium carbonate solution (0.821 mL) in DME (10 mL) was heated overnight with reflux under nitrogen atmosphere. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane) to give the title compound (100 mg).

$^1$H NMR (300 MHz, DMSO-$d_6$) δ 1.60-1.81 (2H, m), 1.83-2.26 (6H, m), 4.00 (3H, s), 5.19 (1H, quin, J=7.1 Hz), 7.31-7.48 (2H, m), 7.84-8.15 (6H, m).

MS (ESI+): [M+H]$^+$ 337.2.
MS (ESI+). found: 336.9.

B) 4-(1-cyclopentyl-4-oxo-4,5-dihydro-1H-pyrazolo[4,3-c]pyridin-3-yl)benzamide

To a solution of 4-(1-cyclopentyl-4-methoxy-1H-pyrazolo[4,3-c]pyridin-3-yl)benzamide (83.4 mg) in acetonitrile (10 mL) were added sodium iodide (74.3 mg) and chloro(trimethyl)silane (0.251 mL), and the mixture was stirred at 60° C. for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/methanol), and the obtained solid was washed with ethyl acetate to give the title compound (75.0 mg).

$^1$H NMR (300 MHz, DMSO-$d_6$) δ 1.57-1.80 (2H, m), 1.83-2.23 (6H, m), 5.06 (1H, quin, J=7.1 Hz), 6.69 (1H, d, J=7.2 Hz), 7.25 (1H, d, J=5.7 Hz), 7.38 (1H, brs), 7.92 (2H, d, J=8.7 Hz), 8.01 (1H, br s), 8.40 (2H, d, J=8.7 Hz), 11.11 (1H, brs).

MS (ESI+): [M]$^+$ 323.2.
MS (ESI+). found: 322.9.

Example 143

3-(1-cyclopentyl-4-oxo-4,5-dihydro-1H-pyrazolo[4,3-c]pyridin-3-yl)benzamide

A) 3-(1-cyclopentyl-4-methoxy-1H-pyrazolo[4,3-c]pyridin-3-yl)benzamide

A solution of 1-cyclopentyl-4-methoxy-1H-pyrazolo[4,3-c]pyridin-3-yl trifluoromethanesulfonate (120 mg) obtained in Step C of Example 12, (3-carbamoyl phenyl)boronic acid (81.0 mg), tetrakis(triphenylphosphine)palladium(0) (38.0 mg) and 2M aqueous sodium carbonate solution (0.821 mL) in DME (10 mL) was heated overnight with reflux under nitrogen atmosphere. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane) to give the title compound (103 mg).

$^1$H NMR (300 MHz, DMSO-$d_6$) δ 1.60-1.80 (2H, m), 1.81-2.25 (6H, m), 3.97 (3H, s), 5.19 (1H, quin, J=7.3 Hz), 7.27-7.47 (2H, m), 7.55 (1H, t, J=7.9 Hz), 7.82-7.99 (2H, m), 8.00-8.12 (2H, m), 8.43 (1H, t, J=1.7 Hz).

MS (ESI+): [M+H]$^+$ 337.2.
MS (ESI+). found: 336.9.

B) 3-(1-cyclopentyl-4-oxo-4,5-dihydro-1H-pyrazolo[4,3-c]pyridin-3-yl)benzamide

To a solution of 3-(1-cyclopentyl-4-methoxy-1H-pyrazolo[4,3-c]pyridin-3-yl)benzamide (61.2 mg) in acetonitrile (10 mL) were added sodium iodide (54.5 mg) and chloro(trimethyl)silane (0.184 mL), and the mixture was stirred at 60° C. for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (methanol/ethyl acetate), and the obtained solid was washed with ethyl acetate to give the title compound (50.6 mg).

$^1$H NMR (300 MHz, DMSO-$d_6$) δ 1.56-1.80 (2H, m), 1.82-2.24 (6H, m), 5.06 (1H, quin, J=7.2 Hz), 6.69 (1H, d, J=7.2 Hz), 7.12-7.30 (1H, m), 7.39 (1H, brs), 7.50 (1H, t, J=7.7 Hz), 7.84 (1H, d, J=7.9 Hz), 7.97 (1H, brs), 8.50 (1H, d, J=7.9 Hz), 8.54-8.69 (1H, m), 11.07 (1H, d, J=4.5 Hz).

MS (ESI+): [M+H]$^+$ 323.2.
MS (ESI+). found: 323.7.

Example 144

4-(7-bromo-1-(2,6-difluorophenyl)-4-oxo-4,5-dihydro-1H-pyrazolo[4,3-c]pyridin-3-yl)thiophene-2-carboxamide The title compound was obtained using methyl 4-(1-(2,6-difluorophenyl)-4-methoxy-1H-pyrazolo[4,3-c]pyridin-3-yl)thiophene-2-carboxylate obtained in Step A of Example 36, in the same manner as in Step E of Example 33, Step F of Example 33, Step G of Example 33 and Step J of Example 33.

$^1$H NMR (300 MHz, DMSO-$d_6$) δ 7.46 (3H, t, J=8.3 Hz), 7.64-7.87 (2H, m), 8.10 (1H, brs), 8.37 (1H, d, J=1.1 Hz), 9.28 (1H, d, J=0.8 Hz), 11.90 (1H, brs).

Example 145

4-(7-bromo-1-(2,6-difluorophenyl)-4-oxo-4,5-dihydro-1H-pyrazolo[4,3-c]pyridin-3-yl)-N-methylthiophene-2-carboxamide The title compound was obtained using methyl 4-(1-(2,6-difluorophenyl)-4-methoxy-1H-pyrazolo[4,3-c]pyridin-3-yl)thiophene-2-carboxylate obtained in Step A of Example 36 and methylamine hydrochloride, in the same manner as in Step E of Example 33, Step F of Example 33 and Step G of Example 33, Step J of Example 33.

MS (ESI+): [M+H]$^+$ 466.2.
MS (ESI+). found: 466.6.

Example 146

(3-(7-bromo-1-(2,6-difluorophenyl)-4-oxo-4,5-dihydro-1H-pyrazolo[4,3-c]pyridin-3-yl)phenyl)acetonitrile A) (3-(1-(2,6-difluorophenyl)-4-methoxy-1H-pyrazolo[4,3-c]pyridin-3-yl)phenyl)acetonitrile The title compound (180 mg) was obtained using 1-(2,6-difluorophenyl)-4-methoxy-1H-pyrazolo[4,3-c]pyridin-3-yl trifluoromethanesulfonate (200 mg) obtained in Step C of Example 35 and (3-(4,4,5,5-tetramethyl-1,3,2-dioxaborolan-2-yl)phenyl)acetonitrile, in the same manner as in Step A of Example 39.

MS (ESI+): [M+H]$^+$ 377.1.
MS (ESI+). found: 377.2.

B) (3-(7-bromo-1-(2,6-difluorophenyl)-4-methoxy-1H-pyrazolo[4,3-c]pyridin-3-yl)phenyl)acetonitrile The title compound (160 mg) was obtained using (3-(1-(2,6-difluorophenyl)-4-methoxy-1H-pyrazolo[4,3-c]pyridin-3-yl)phenyl)acetonitrile (175 mg), in the same manner as in Step A of Example 104.

MS (ESI+): [M+H]$^+$ 455.2.
MS (ESI+). found: 455.2

C) (3-(7-bromo-1-(2,6-difluorophenyl)-4-oxo-4,5-dihydro-1H-pyrazolo[4,3-c]pyridin-3-yl)phenyl)acetonitrile The title compound (134 mg) was obtained using (3-(7-bromo-1-(2,6-difluorophenyl)-4-methoxy-1H-pyrazolo[4,3-c]pyridin-3-yl)phenyl)acetonitrile (160 mg), in the same manner as in Step J of Example 33.

MS (ESI+): [M+H]$^+$ 441.1.
MS (ESI+). found: 441.2.

Example 147

2-(3-(7-bromo-1-(2,6-difluorophenyl)-4-oxo-4,5-dihydro-1H-pyrazolo[4,3-c]pyridin-3-yl)phenyl)acetamide The title compound (9.0 mg) was obtained using (3-(7-bromo-1-(2,6-difluorophenyl)-4-oxo-4,5-dihydro-1H-pyrazolo[4,3-c]pyridin-3-yl)phenyl)acetonitrile (47 mg) obtained in Example 146, in the same manner as in Example 97.

MS (ESI+): [M+H]$^+$ 459.0.
MS (ESI+). found: 459.2.

Example 148

4-(1-(1,4-dioxaspiro[4.5]dec-8-yl)-4-oxo-4,5-dihydro-1H-pyrazolo[4,3-c]pyridin-3-yl)thiophene-2-carboxamide A) 4-(4-methoxy-1H-pyrazolo[4,3-c]pyridin-3-yl)thiophene-2-carboxamide 4-(1-tert-Butyl-4-methoxy-1H-pyrazolo[4,3-c]pyridin-3-yl)thiophene-2-carboxamide (150 mg) obtained in Step C of Example 129 was dissolved in a mixed solvent of trifluoroacetic acid (20 mL)/water (2 mL), and the mixture was heated with reflux for 24 hr. The reaction mixture was allowed to be cooled to room temperature, and concentrated under reduced pressure. The residue was extracted with ethyl acetate and saturated aqueous sodium hydrogencarbonate solution, and the organic layer was washed with saturated brine, dried over anhydrous magnesium sulfate, filtered, and concentrated under reduced pressure. The residue was purified by silica gel column chromatography (hexane/ethyl acetate to ethyl acetate) to give the title compound (68.1 mg).

$^1$H NMR (300 MHz, DMSO-$d_6$) δ 4.07 (3H, s), 7.15 (1H, d, J=6.0 Hz), 7.45 (1H, brs), 7.91 (1H, d, J=6.0 Hz), 8.13 (1H, brs), 8.40 (2H, dd, J=17.2, 1.3 Hz), 13.56 (1H, brs).

MS (ESI+): [M]$^+$ 275.1.
MS (ESI+). found: 275.2.

B) 4-(1-(1,4-dioxaspiro[4.5]dec-8-yl)-4-methoxy-1H-pyrazolo[4,3-c]pyridin-3-yl)thiophene-2-carboxamide To a solution of 4-(4-methoxy-1H-pyrazolo[4,3-c]pyridin-3-yl)thiophene-2-carboxamide (65.0 mg) in DMF (3 mL) was added sodium hydride (60% dispersion in mineral oil, 19.0 mg), and the mixture was stirred at room temperature for 1 hr. To the reaction mixture was added 1,4-dioxaspiro[4.5]dec-8-yl 4-methylbenzenesulfonate (148 mg), and the mixture was stirred overnight at room temperature. The reaction mixture was extracted with water and ethyl acetate, and the organic layer was washed with saturated brine, dried over anhydrous magnesium sulfate, filtered, and concentrated under reduced pressure. The obtained residue was purified by silica gel column chromatography (hexane/ethyl acetate) to give the title compound (53.9 mg).

$^1$H NMR (300 MHz, DMSO-$d_6$) δ 1.72-1.98 (6H, m), 2.24 (2H, qd, J=12.1, 5.3 Hz), 3.83-4.00 (4H, m), 4.02-4.09 (3H, m), 4.76 (1H, tt, J=11.5, 3.8 Hz), 7.37 (1H, d, J=6.0 Hz), 7.44

(1H, brs), 7.94 (1H, d, J=6.0 Hz), 8.22 (1H, brs), 8.30 (1H, d, J=1.5 Hz), 8.40 (1H, d, J=1.5 Hz).
MS (ESI+): [M]$^+$ 415.1.
MS (ESI+). found: 415.3.

C) 4-(1-(1,4-dioxaspiro[4.5]dec-8-yl)-4-oxo-4,5-dihydro-1H-pyrazolo[4,3-c]pyridin-3-yl)thiophene-2-carboxamide To a solution of 4-(1-(1,4-dioxaspiro[4.5]dec-8-yl)-4-methoxy-1H-pyrazolo[4,3-c]pyridin-3-yl)thiophene-2-carboxamide (20.0 mg) in acetonitrile (5 mL) were added sodium iodide (18.1 mg) and chloro(trimethyl)silane (0.027 mL), and the mixture was stirred at 50° C. for 1 hr. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, ethyl acetate/methanol) to give the title compound (3.4 mg).
MS (ESI+): [M]$^+$ 401.1.
MS (ESI+). found: 400.8.

Example 149

4-(4-oxo-1-(pentan-3-yl)-4,5-dihydro-1H-pyrazolo[4,3-c]pyridin-3-yl)thiophene-2-carboxamide To a solution of 4-(4-oxo-4,5-dihydro-1H-pyrazolo[4,3-c]pyridin-3-yl)thiophene-2-carboxamide (80.0 mg) obtained in Step A of Example 141 in DMF (3 mL) was added sodium hydride (60% dispersion in mineral oil, 24.6 mg), and the mixture was stirred at room temperature for 1 hr. To the reaction mixture was added 3-bromopentane (93.0 mg), and the mixture was stirred overnight at room temperature. The reaction mixture was extracted with water and ethyl acetate, and the organic layer was washed with saturated brine, dried over anhydrous magnesium sulfate, filtered, and concentrated under reduced pressure. The obtained residue was purified by silica gel column chromatography (basic silica gel, ethyl acetate/methanol) to give the title compound (51.8 mg).
$^1$H NMR (300 MHz, DMSO-d$_6$) δ 0.68 (6H, t, J=7.4 Hz), 1.76-2.06 (4H, m), 4.35 (1H, tt, J=9.3, 4.3 Hz), 6.69 (1H, d, J=7.6 Hz), 7.22 (1H, t, J=6.6 Hz), 7.40 (1H, brs), 8.15 (1H, brs), 8.33 (1H, d, J=1.1 Hz), 9.16 (1H, s), 11.11 (1H, d, J=5.3 Hz).
MS (ESI+): [M]$^+$ 331.1.
MS (ESI+). found: 331.2.

Example 150

4-(1-(1-methoxybutan-2-yl)-4-oxo-4,5-dihydro-1H-pyrazolo[4,3-c]pyridin-3-yl)thiophene-2-carboxamide To a solution of 4-(4-oxo-4,5-dihydro-1H-pyrazolo[4,3-c]pyridin-3-yl)thiophene-2-carboxamide (50.0 mg) obtained in Step A of Example 141 in DMF (2 mL) was added sodium hydride (60% dispersion in mineral oil, 15.4 mg), and the mixture was stirred at room temperature for 1 hr. To the reaction mixture was added 1-methoxybutan-2-yl 4-methylbenzenesulfonate (99.0 mg) obtained in Step A-1 of Example 17, and the mixture was stirred overnight at room temperature. The reaction mixture was extracted with water and ethyl acetate, and the organic layer was washed with saturated brine, dried over anhydrous magnesium sulfate, filtered, and concentrated under reduced pressure. The obtained residue was purified by silica gel column chromatography (basic silica gel, ethyl acetate/methanol) to give the title compound (21.8 mg).
$^1$H NMR (300 MHz, DMSO-d$_6$) δ 0.70 (3H, t, J=7.4 Hz), 1.76-1.97 (2H, m), 3.18 (3H, s), 3.62-3.73 (1H, m), 3.75-3.88 (1H, m), 4.67 (1H, tt, J=9.3, 4.7 Hz), 6.69 (1H, d, J=7.2 Hz), 7.22 (1H, dd, J=7.0, 5.9 Hz), 7.40 (1H, brs), 8.15 (1H, brs), 8.31-8.36 (1H, m), 9.15 (1H, d, J=1.1 Hz), 11.12 (1H, d, J=5.7 Hz).
MS (ESI+): [M]$^+$ 347.1.
MS (ESI+). found: 347.2.

Example 151

1-(2,6-difluorophenyl)-3-(1H-pyrazol-4-yl)-1,5-dihydro-4H-pyrazolo[4,3-c]pyridin-4-one The title compound was obtained using 1-(2,6-difluorophenyl)-4-methoxy-1H-pyrazolo[4,3-c]pyridin-3-yl trifluoromethanesulfonate obtained in Step C of Example 35, in the same manner as in Step I of Example 33 and Step J of Example 33.
MS (ESI+): [M+H]$^+$ 314.3.
MS (ESI+). found: 314.1.

Example 152

(4-(7-chloro-1-(2,6-difluorophenyl)-4-oxo-4,5-dihydro-1H-pyrazolo[4,3-c]pyridin-3-yl)-2-thienyl)acetonitrile A) 7-chloro-1-(2,6-difluorophenyl)-4-methoxy-1H-pyrazolo[4,3-c]pyridin-3-yl trifluoromethanesulfonate To a solution (10 mL) of 1-(2,6-difluorophenyl)-4-methoxy-1H-pyrazolo[4,3-c]pyridin-3-yl trifluoromethanesulfonate (500 mg) obtained in Step C of Example 35 in DMF was added N-chlorosuccinimide (215 mg) at room temperature. The reaction mixture was heated at 50° C. for 21 hr, and the mixture was allowed to be cooled to room temperature. To the reaction mixture was added water under ice-cooling, and the mixture was extracted with ethyl acetate. The organic layer was washed with saturated brine, dried over anhydrous magnesium sulfate, and concentrated under reduced pressure. The residue was purified by silica gel column chromatography (ethyl acetate/methanol) to give the title compound (259 mg).
MS (ESI+): [M+H]$^+$ 444.0.
MS (ESI+). found: 444.1.

B) (4-(7-chloro-1-(2,6-difluorophenyl)-4-methoxy-1H-pyrazolo[4,3-c]pyridin-3-yl)-2-thienyl)acetonitrile A mixture of 7-chloro-1-(2,6-difluorophenyl)-4-methoxy-1H-pyrazolo[4,3-c]pyridin-3-yl trifluoromethanesulfonate (100 mg), (4-(4,4,5,5-tetramethyl-1,3,2-dioxaborolan-2-yl)-2-thienyl)acetonitrile (84.0 mg) obtained in Step A of Example 93, tetrakis(triphenylphosphine)palladium(0) (13.0 mg) and 2M aqueous sodium carbonate solution (0.200 mL) in DMF (2 mL) was stirred under microwave irradiation at 130° C. for 1.5 hr. The reaction mixture was added to water, and the mixture was extracted with ethyl acetate. The organic layer was washed with saturated brine, dried over anhydrous magnesium sulfate, and concentrated under reduced pressure.

The residue was purified by silica gel column chromatography (ethyl acetate/hexane) to give the title compound (70.2 mg).
MS (ESI+): [M+H]+ 417.0.
MS (ESI+). found: 417.2.

C) (4-(7-chloro-1-(2,6-difluorophenyl)-4-oxo-4,5-dihydro-1H-pyrazolo[4,3-c]pyridin-3-yl)-2-thienyl)acetonitrile To a mixture of (4-(7-chloro-1-(2,6-difluorophenyl)-4-methoxy-1H-pyrazolo[4,3-c]pyridin-3-yl)-2-thienyl)acetonitrile (70.2 mg) and sodium iodide (50.5 mg) in acetonitrile (3 mL) was added chloro(trimethyl)silane (0.108 mL) at room temperature, and the mixture was stirred at 50° C. for 1 hr. To the reaction mixture was added saturated aqueous sodium hydrogencarbonate solution, and the mixture was extracted with ethyl acetate. The organic layer was washed with saturated brine, dried over anhydrous magnesium sulfate, and concentrated under reduced pressure. The residue was purified by silica gel column chromatography (basic silica gel, methanol/ethyl acetate) to give the title compound (38.1 mg).
MS (ESI+): [M+H]+ 403.0.
MS (ESI+). found: 403.1.

Example 153

2-(4-(7-bromo-1-(2,6-difluorophenyl)-4-methoxy-1H-pyrazolo[4,3-c]pyridin-3-yl)phenyl)-N-methylacetamide A) methyl (4-(1-(2,6-difluorophenyl)-4-methoxy-1H-pyrazolo[4,3-c]pyridin-3-yl)phenyl)acetate The title compound (243 mg) was obtained using 1-(2,6-difluorophenyl)-4-methoxy-1H-pyrazolo[4,3-c]pyridin-3-yl trifluoromethanesulfonate (700 mg) obtained in Step C of Example 35 and methyl (4-(4,4,5,5-tetramethyl-1,3,2-dioxaborolan-2-yl)phenyl)acetate, in the same manner as in Step A of Example 39.
MS (ESI+): [M+H]+ 411.1.
MS (ESI+). found: 410.2.

B) methyl (4-(7-bromo-1-(2,6-difluorophenyl)-4-methoxy-1H-pyrazolo[4,3-c]pyridin-3-yl)phenyl)acetate The title compound (272 mg) was obtained using methyl (4-(1-(2,6-difluorophenyl)-4-methoxy-1H-pyrazolo[4,3-c]pyridin-3-yl)phenyl)acetate (240 mg), in the same manner as in Step A of Example 104.
MS (ESI+): [M+H]+ 488.0.
MS (ESI+). found: 488.2.

C) (4-(7-bromo-1-(2,6-difluorophenyl)-4-methoxy-1H-pyrazolo[4,3-c]pyridin-3-yl)phenyl)acetic acid To a mixture to methyl (4-(7-bromo-1-(2,6-difluorophenyl)-4-methoxy-1H-pyrazolo[4,3-c]pyridin-3-yl)phenyl)acetate (270 mg) in a mixed solvent of DME (1.0 mL), THF (1.0 mL) and water (0.5 mL) was added 8N aqueous sodium hydroxide solution (0.346 mL), and the mixture was stirred at 60° C. for 4 hr. To the reaction mixture was added water, and the mixture was extracted with ethyl acetate. The aqueous layer was neutralized with 1N hydrochloric acid at 0° C., and the mixture was extracted with ethyl acetate. The organic layer was washed with water and saturated brine, dried over anhydrous magnesium sulfate, and concentrated under reduced pressure to give the title compound (235 mg).
MS (ESI+): [M+H]+ 474.0.
MS (ESI+). found: 474.2.

D) 2-(4-(7-bromo-1-(2,6-difluorophenyl)-4-methoxy-1H-pyrazolo[4,3-c]pyridin-3-yl)phenyl)-N-methylacetamide To a solution of (4-(7-bromo-1-(2,6-difluorophenyl)-4-methoxy-1H-pyrazolo[4,3-c]pyridin-3-yl)phenyl)acetic acid (60 mg), methylamine hydrochloride (12.8 mg), HOBt (25 mg) and triethylamine (26 μL) in DMF (3 mL) was added EDCI hydrochloride (36 mg), and the mixture was stirred overnight at room temperature. To the reaction mixture was added water, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (57 mg).
MS (ESI+): [M+H]+ 487.1.
MS (ESI+). found: 487.3.

E) 2-(4-(7-bromo-1-(2,6-difluorophenyl)-4-methoxy-1H-pyrazolo[4,3-c]pyridin-3-yl)phenyl)-N-methylacetamide The title compound (24 mg) was obtained using 2-(4-(7-bromo-1-(2,6-difluorophenyl)-4-methoxy-1H-pyrazolo[4,3-c]pyridin-3-yl)phenyl)-N-methylacetamide (55 mg), in the same manner as in Step J of Example 33.
MS (ESI+): [M+H]+ 473.0.
MS (ESI+). found: 473.1.

Example 154

2-(4-(7-bromo-1-(2,6-difluorophenyl)-4-methoxy-1H-pyrazolo[4,3-c]pyridin-3-yl)phenyl)-N-cyclopropylacetamide A) 2-(4-(7-bromo-1-(2,6-difluorophenyl)-4-methoxy-1H-pyrazolo[4,3-c]pyridin-3-yl)phenyl)-N-cyclopropylacetamide The title compound (62 mg) was obtained using Step C of Example 153 obtained in (4-(7-bromo-1-(2,6-difluorophenyl)-4-methoxy-1H-pyrazolo[4,3-c]pyridin-3-yl)phenyl)acetic acid (60 mg) and cyclopropylamine, in the same manner as in Step D of Example 153.
MS (ESI+): [M+H]+ 513.1.
MS (ESI+). found: 513.3.

B) 2-(4-(7-bromo-1-(2,6-difluorophenyl)-4-methoxy-1H-pyrazolo[4,3-c]pyridin-3-yl)phenyl)-N-cyclopropylacetamide The title compound (40 mg) was obtained using 2-(4-(7-bromo-1-(2,6-difluorophenyl)-4-methoxy-1H-pyrazolo[4,3-c]pyridin-3-yl)phenyl)-N-cyclopropylacetamide (60 mg), in the same manner as in Step J of Example 33.
MS (ESI+): [M+H]+ 499.1.
MS (ESI+). found: 499.3.

Example 155

4-(1-cyclopentyl-4-oxo-4,5-dihydro-1H-pyrazolo[4,3-c]pyridin-3-yl)-N-methylthiophene-2-carboxamide

A) 4-(1-cyclopentyl-4-methoxy-1H-pyrazolo[4,3-c]pyridin-3-yl)thiophene-2-carboxylic acid To a solution of methyl 4-(1-cyclopentyl-4-methoxy-1H-pyrazolo[4,3-c]pyridin-3-yl)thiophene-2-carboxylate (250 mg) obtained in Step D of Example 12 in methanol (20 mL) was added 1N aqueous sodium hydroxide solution (4 mL) under ice-cooling, and the mixture was stirred at 50° C. for 4 hr. The reaction mixture was concentrated under reduced pressure to evaporate the methanol, and the mixture was partitioned between ethyl acetate and 1N hydrochloric acid (8 mL). The organic layer was washed with saturated brine, dried over anhydrous sodium sulfate, and concentrated under reduced pressure to give the title compound (238 mg).

$^1$H NMR (300 MHz, DMSO-$d_6$) δ 1.60-1.80 (2H, m), 1.82-2.25 (6H, m), 4.06 (3H, s), 5.16 (1H, quin, J=7.0 Hz), 7.36 (1H, d, J=6.0 Hz), 7.94 (1H, d, J=6.0 Hz), 8.26 (1H, d, J=1.5 Hz), 8.49 (1H, d, J=1.5 Hz), 13.23 (1H, brs).

MS (ESI+): [M+H]$^+$ 344.1.

MS (ESI+). found: 343.9.

B) 4-(1-cyclopentyl-4-methoxy-1H-pyrazolo[4,3-c]pyridin-3-yl)-N-methylthiophene-2-carboxamide A solution of 4-(1-cyclopentyl-4-methoxy-1H-pyrazolo[4,3-c]pyridin-3-yl)thiophene-2-carboxylic acid (75.0 mg), methylamine hydrochloride (22.1 mg), DIEA (0.153 mL), EDCI hydrochloride (62.8 mg) and HOBt (44.3 mg) in DMF (10 mL) was stirred overnight at room temperature. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane) to give the title compound (76.0 mg).

$^1$H NMR (300 MHz, DMSO-$d_6$) δ 1.60-1.82 (2H, m), 1.83-2.24 (6H, m), 2.79 (3H, d, J=4.5 Hz), 4.06 (3H, s), 5.16 (1H, quin, J=7.1 Hz), 7.35 (1H, d, J=6.4 Hz), 7.93 (1H, d, J=6.0 Hz), 8.27 (1H, d, J=1.1 Hz), 8.40 (1H, d, J=1.1 Hz), 8.64 (1H, d, J=4.5 Hz).

MS (ESI+): [M+H]$^+$ 357.1.

MS (ESI+). found: 356.8.

C) 4-(1-cyclopentyl-4-oxo-4,5-dihydro-1H-pyrazolo[4,3-c]pyridin-3-yl)-N-methylthiophene-2-carboxamide To a solution of 4-(1-cyclopentyl-4-methoxy-1H-pyrazolo[4,3-c]pyridin-3-yl)-N-methylthiophene-2-carboxamide (67.4 mg) in acetonitrile (10 mL) were added sodium iodide (56.7 mg) and chloro(trimethyl)silane (0.192 mL), and the mixture was stirred at 60° C. for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane), and the obtained solid was washed with ethyl acetate/diisopropyl ether to give the title compound (57.4 mg).

$^1$H NMR (300 MHz, DMSO-$d_6$) δ 1.58-1.80 (2H, m), 1.83-2.24 (6H, m), 2.78 (3H, d, J=4.2 Hz), 5.03 (1H, quin, J=7.1 Hz), 6.67 (1H, d, J=7.2 Hz), 7.12-7.35 (1H, m), 8.29 (1H, s), 8.62 (1H, d, J=4.5 Hz), 9.13 (1H, s), 11.12 (1H, brs).

MS (ESI+): [M+H]$^+$ 343.1.

MS (ESI+). found: 342.9.

Example 156

4-(1-cyclopentyl-4-oxo-4,5-dihydro-1H-pyrazolo[4,3-c]pyridin-3-yl)-N-cyclopropylthiophene-2-carboxamide

A) 4-(1-cyclopentyl-4-methoxy-1H-pyrazolo[4,3-c]pyridin-3-yl)-N-cyclopropylthiophene-2-carboxamide A solution of 4-(1-cyclopentyl-4-methoxy-1H-pyrazolo[4,3-c]pyridin-3-yl)thiophene-2-carboxylic acid (75.0 mg) obtained in Step A of Example 155, cyclopropylamine (0.023 mL), EDCI hydrochloride (62.8 mg) and HOBt (44.3 mg) in DMF (10 mL) was stirred overnight at room temperature. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane) to give the title compound (78.0 mg).

$^1$H NMR (300 MHz, DMSO-$d_6$) δ 0.54-0.65 (2H, m), 0.65-0.77 (2H, m), 1.61-1.81 (2H, m), 1.83-2.25 (6H, m), 2.83 (1H, tq, J=7.3 Hz, 3.8 Hz), 4.06 (3H, s), 5.15 (1H, quin, J=7.3 Hz), 7.35 (1H, d, J=6.0 Hz), 7.93 (1H, d, J=6.0 Hz), 8.26 (1H, d, J=1.1 Hz), 8.41 (1H, d, J=1.5 Hz), 8.69 (1H, d, J=3.8 Hz).

MS (ESI+): [M+H]$^+$ 383.2.

MS (ESI+). found: 382.9.

B) 4-(1-cyclopentyl-4-oxo-4,5-dihydro-1H-pyrazolo[4,3-c]pyridin-3-yl)-N-cyclopropylthiophene-2-carboxamide To a solution of 4-(1-cyclopentyl-4-methoxy-1H-pyrazolo[4,3-c]pyridin-3-yl)-N-cyclopropylthiophene-2-carboxamide (68.4 mg) in acetonitrile (10 mL) were added sodium iodide (53.6 mg) and chloro(trimethyl)silane (0.181 mL), and the mixture was stirred at 60° C. for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane), and the obtained solid was washed with ethyl acetate/diisopropyl ether to give the title compound (56.8 mg).

$^1$H NMR (300 MHz, DMSO-$d_6$) δ 0.53-0.79 (4H, m), 1.56-1.80 (2H, m), 1.82-2.23 (6H, m), 2.82 (1H, tq, J=7.3 Hz, 3.9 Hz), 5.02 (1H, quin, J=7.4 Hz), 6.67 (1H, d, J=7.2 Hz), 7.08-7.35 (1H, m), 8.28 (1H, s), 8.68 (1H, d, J=3.8 Hz), 9.16 (1H, s), 11.12 (1H, d, J=5.7 Hz).

MS (ESI+): [M+H]$^+$ 369.1.

MS (ESI+). found: 368.9.

Example 157

4-(1-cyclopentyl-4-oxo-4,5-dihydro-1H-pyrazolo[4,3-c]pyridin-3-yl)-N-(2-hydroxyethyl)thiophene-2-carboxamide

A) 4-(1-cyclopentyl-4-methoxy-1H-pyrazolo[4,3-c]pyridin-3-yl)-N-(2-hydroxyethyl)thiophene-2-carboxamide A solution of 4-(1-cyclopentyl-4-methoxy-1H-pyrazolo[4,3-c]pyridin-3-yl)thiophene-2-carboxylic acid (90.0 mg) obtained in Step A of Example 155, 2-aminoethanol (0.024 mL), EDCI hydrochloride (75.0 mg) and HOBt (53.1 mg) in DMF (10 mL) was stirred overnight at room temperature. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane) to give the title compound (67.3 mg).

$^1$H NMR (300 MHz, DMSO-$d_6$) δ 1.60-1.82 (2H, m), 1.85-2.26 (6H, m), 3.32 (2H, brs), 3.53 (2H, brs), 4.06 (3H, s), 4.77 (1H, brs), 5.16 (1H, quin, J=7.4 Hz), 7.35 (1H, d, J=6.4 Hz), 7.93 (1H, d, J=6.0 Hz), 8.32 (1H, s), 8.41 (1H, s), 8.70 (1H, t, J=4.9 Hz).

MS (ESI+): [M+H]$^+$ 387.1.
MS (ESI+). found: 386.9.

B) 4-(1-cyclopentyl-4-oxo-4,5-dihydro-1H-pyrazolo[4,3-c]pyridin-3-yl)-N-(2-hydroxyethyl)thiophene-2-carboxamide To a solution of 4-(1-cyclopentyl-4-methoxy-1H-pyrazolo[4,3-c]pyridin-3-yl)-N-(2-hydroxyethyl)thiophene-2-carboxamide (62.6 mg) in acetonitrile (10 mL) were added sodium iodide (48.6 mg) and chloro(trimethyl)silane (0.164 mL), and the mixture was stirred at 60° C. for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane/methanol), and the obtained solid was washed with ethyl acetate/diisopropyl ether to give the title compound (49.0 mg).

$^1$H NMR (300 MHz, DMSO-$d_6$) δ 1.60-1.80 (2H, m), 1.82-2.23 (6H, m), 3.23-3.39 (2H, m), 3.52 (2H, q, J=5.8 Hz), 4.76 (1H, t, J=5.5 Hz), 5.03 (1H, quin, J=7.2 Hz), 6.67 (1H, d, J=7.2 Hz), 7.16-7.31 (1H, m), 8.34 (1H, d, J=1.5 Hz), 8.68 (1H, t, J=5.7 Hz), 9.16 (1H, d, J=1.1 Hz), 11.12 (1H, d, J=4.2 Hz).

MS (ESI+): [M+H]$^+$ 373.1.
MS (ESI+). found: 372.8.

Example 158

2-(3-(1-cyclopentyl-4-oxo-4,5-dihydro-1H-pyrazolo[4,3-c]pyridin-3-yl)phenyl)acetamide To a solution of (3-(1-cyclopentyl-4-oxo-4,5-dihydro-1H-pyrazolo[4,3-c]pyridin-3-yl)phenyl)acetonitrile (58.3 mg) obtained in Example 128 in DMSO (5 mL) were added potassium carbonate (30.4 mg) and 30% aqueous hydrogen peroxide (0.056 mL), and the mixture was stirred for 3 days. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (methanol/ethyl acetate), and the obtained solid was washed with ethyl acetate/diisopropyl ether to give the title compound (43.2 mg).

$^1$H NMR (300 MHz, DMSO-$d_6$) δ 1.56-1.79 (2H, m), 1.81-2.23 (6H, m), 3.43 (2H, s), 5.04 (1H, quin, J=7.2 Hz), 6.67 (1H, d, J=7.2 Hz), 6.90 (1H, brs), 7.16-7.30 (2H, m), 7.30-7.40 (1H, m), 7.48 (1H, brs), 8.03 (1H, s), 8.21 (1H, d, J=7.6 Hz), 11.01 (1H, d, J=5.7 Hz).

MS (ESI+): [M+H]$^+$ 337.2.
MS (ESI+). found: 336.9.

Example 159

3-(1-cyclopentyl-4-oxo-4,5-dihydro-1H-pyrazolo[4,3-c]pyridin-3-yl)benzenesulfonamide

A) 3-(1-cyclopentyl-4-methoxy-1H-pyrazolo[4,3-c]pyridin-3-yl)benzenesulfonamide A solution of 1-cyclopentyl-4-methoxy-1H-pyrazolo[4,3-c]pyridin-3-yl trifluoromethanesulfonate (80.0 mg) obtained in Step C of Example 12, 3-(4,4,5,5-tetramethyl-1,3,2-dioxaborolan-2-yl)benzenesulfonamide (93.0 mg), tetrakis(triphenylphosphine)palladium(0) (25.3 mg) and 2M aqueous sodium carbonate solution (0.550 mL) in DME (10 mL) was heated overnight with reflux under nitrogen atmosphere. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane) to give the title compound (35.7 mg).

$^1$H NMR (300 MHz, DMSO-$d_6$) δ 1.60-1.82 (2H, m), 1.83-2.30 (6H, m), 4.00 (3H, s), 5.21 (1H, quin, J=7.1 Hz), 7.31-7.53 (3H, m), 7.62-7.75 (1H, m), 7.86 (1H, d, J=7.6 Hz), 7.97 (1H, d, J=6.0 Hz), 8.15 (1H, d, J=7.6 Hz), 8.46 (1H, s).

MS (ESI+): [M+H]$^+$ 373.1.
MS (ESI+). found: 372.8.

B) 3-(1-cyclopentyl-4-oxo-4,5-dihydro-1H-pyrazolo[4,3-c]pyridin-3-yl)benzenesulfonamide To a solution of 3-(1-cyclopentyl-4-methoxy-1H-pyrazolo[4,3-c]pyridin-3-yl)benzenesulfonamide (28.5 mg) in acetonitrile (5 mL) were added sodium iodide (22.9 mg) and chloro(trimethyl)silane (0.078 mL), and the mixture was stirred at 60° C. for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane), and the obtained solid was washed with ethyl acetate/diisopropyl ether to give the title compound (21.2 mg).

$^1$H NMR (300 MHz, DMSO-$d_6$) δ 1.57-1.80 (2H, m), 1.81-2.24 (6H, m), 5.07 (1H, quin, J=7.2 Hz), 6.71 (1H, d, J=7.2 Hz), 7.18-7.31 (1H, m), 7.41 (2H, s), 7.56-7.70 (1H, m), 7.81 (1H, d, J=7.6 Hz), 8.62 (1H, s), 8.71 (1H, d, J=7.9 Hz), 11.13 (1H, brs).

MS (ESI+): [M+H]$^+$ 359.1.
MS (ESI+). found: 358.8.

Example 160

2-(4-(7-chloro-1-(2,6-difluorophenyl)-4-oxo-4,5-dihydro-1H-pyrazolo[4,3-c]pyridin-3-yl)-2-thienyl)acetamide To a mixture of (4-(7-chloro-1-(2,6-difluorophenyl)-4-oxo-4,5-dihydro-1H-pyrazolo[4,3-c]pyridin-3-yl)-2-thienyl)acetonitrile (69.4 mg) obtained in Example 152 and 2M aqueous potassium carbonate solution (0.431 mL) in DMSO (3 mL) was added 30% aqueous hydrogen peroxide (0.176 mL) under ice-cooling, and the reaction mixture was stirred at room temperature for 5 hr. The reaction mixture was allowed to be cooled to room temperature, water was added thereto under ice-cooling, and the mixture was extracted with ethyl acetate. The organic layer was washed with saturated brine, dried over anhydrous magnesium sulfate, and concentrated under reduced pressure. The obtained solid was washed with ethyl acetate and diisopropyl ether to give the title compound (55.8 mg).
MS (ESI+): [M+H]$^+$ 421.0.
MS (ESI+). found: 421.2.

Example 161

7-chloro-1-(2,6-difluorophenyl)-3-(4-(morpholin-4-yl)phenyl)-1,5-dihydro-4H-pyrazolo[4,3-c]pyridin-4-one The title compound (26.4 mg) was obtained using 7-chloro-1-(2,6-difluorophenyl)-4-methoxy-1H-pyrazolo[4,3-c]pyridin-3-yl trifluoromethanesulfonate obtained in Step A of Example 152 and 4-(4-(4,4,5,5-tetramethyl-1,3,2-dioxaborolan-2-yl)phenyl)morpholine, in the same manner as in Step B of Example 152 and Step C of Example 152.
MS (ESI+): [M+H]$^+$ 443.1.
MS (ESI+). found: 443.2.

Example 162

4-(7-chloro-1-(2,6-difluorophenyl)-4-oxo-4,5-dihydro-1H-pyrazolo[4,3-c]pyridin-3-yl)-N-methylthiophene-2-carboxamide The title compound was obtained using 7-chloro-1-(2,6-difluorophenyl)-4-methoxy-1H-pyrazolo[4,3-c]pyridin-3-yl trifluoromethanesulfonate obtained in Step A of Example 152, methyl 4-(4,4,5,5-tetramethyl-1,3,2-dioxaborolan-2-yl)thiophene-2-carboxylate and methylamine hydrochloride, in the same manner as in Step I of Example 33, Step F of Example 33, Step J of Example 33 and Step G of Example 33.
MS (ESI+): [M]$^+$ 420.8.
MS (ESI+). found: 420.6.

Example 163

4-(7-chloro-1-(2,6-difluorophenyl)-4-oxo-4,5-dihydro-1H-pyrazolo[4,3-c]pyridin-3-yl)-N-(1-cyanocyclopropyl)thiophene-2-carboxamide The title compound was obtained using 7-chloro-1-(2,6-difluorophenyl)-4-methoxy-1H-pyrazolo[4,3-c]pyridin-3-yl trifluoromethanesulfonate obtained in Step A of Example 152, methyl 4-(4,4,5,5-tetramethyl-1,3,2-dioxaborolan-2-yl)thiophene-2-carboxylate and 1-aminocyclopropanecarbonitrile hydrochloride, in the same manner as in Step I of Example 33, Step F of Example 33, Step J of Example 33 and Step G of Example 33.
MS (ESI+): [M]$^+$ 471.8.
MS (ESI+). found: 471.7.

Example 164

7-chloro-1-(2,6-difluorophenyl)-3-(6-(morpholin-4-yl)pyridin-3-yl)-1,5-dihydro-4H-pyrazolo[4,3-c]pyridin-4-one The title compound (116 mg) was obtained using 7-chloro-1-(2,6-difluorophenyl)-4-methoxy-1H-pyrazolo[4,3-c]pyridin-3-yl trifluoromethanesulfonate obtained in Step A of Example 152 and 4-(5-(4,4,5,5-tetramethyl-1,3,2-dioxaborolan-2-yl)pyridin-2-yl)morpholine, in the same manner as in Step B of Example 152 and Step C of Example 152.
MS (ESI+): [M+H]$^+$ 444.1.
MS (ESI+). found: 444.2.

Example 165

4-(7-cyano-1-cyclopentyl-4-oxo-4,5-dihydro-1H-pyrazolo[4,3-c]pyridin-3-yl)thiophene-2-carboxamide A) methyl 4-(7-bromo-1-cyclopentyl-4-methoxy-1H-pyrazolo[4,3-c]pyridin-3-yl)thiophene-2-carboxylate To a solution of methyl 4-(1-cyclopentyl-4-methoxy-1H-pyrazolo[4,3-c]pyridin-3-yl)thiophene-2-carboxylate (103 mg) obtained in Step D of Example 12 in DMF (5 mL) was added NBS (56.4 mg) at 0° C., and the mixture was stirred overnight at room temperature. To the reaction mixture was added saturated aqueous sodium thiosulfate solution, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane) to give the title compound (117 mg).
$^1$H NMR (300 MHz, DMSO-d$_6$) δ 1.61-1.80 (2H, m), 1.81-2.01 (2H, m), 2.14 (4H, d, J=3.8 Hz), 3.79-3.93 (3H, m), 3.98-4.10 (3H, m), 5.87 (1H, quin, J=6.8 Hz), 8.06-8.13 (1H, m), 8.22-8.30 (1H, m), 8.47-8.55 (1H, m).
MS (ESI+): [M+H]$^+$ 436.0.
MS (ESI+). found: 436.3.

B) 4-(7-bromo-1-cyclopentyl-4-methoxy-1H-pyrazolo[4,3-c]pyridin-3-yl)thiophene-2-carboxylic acid To a solution of methyl 4-(7-bromo-1-cyclopentyl-4-methoxy-1H-pyrazolo[4,3-c]pyridin-3-yl)thiophene-2-carboxylate (111 mg) in methanol (10 mL) was added 1N aqueous sodium hydroxide solution (2 mL) under ice-cooling, and the mixture was stirred at 50° C. for 4 hr. The reaction mixture was concentrated under reduced pressure to evaporate the methanol, and the mixture was partitioned between ethyl acetate and 1N hydrochloric acid (5 mL). The organic layer was washed with saturated brine, dried over anhydrous sodium sulfate, and concentrated under reduced pressure to give the title compound (107 mg).
$^1$H NMR (300 MHz, DMSO-d$_6$) δ 1.63-1.79 (2H, m), 1.81-2.00 (1H, m), 2.02-2.29 (5H, m), 4.04 (3H, s), 5.87 (1H, quin, J=6.8 Hz), 8.09 (1H, s), 8.19 (1H, d, J=1.5 Hz), 8.44 (1H, d, J=1.5 Hz), 13.29 (1H, brs).

MS (ESI+): [M+H]+ 422.0.
MS (ESI+). found: 423.6.

C) 4-(7-bromo-1-cyclopentyl-4-methoxy-1H-pyrazolo[4,3-c]pyridin-3-yl)thiophene-2-carboxamide A solution of 4-(7-bromo-1-cyclopentyl-4-methoxy-1H-pyrazolo[4,3-c]pyridin-3-yl)thiophene-2-carboxylic acid (100 mg), HOBt ammonium salt (227 mg) and EDCI hydrochloride (180 mg) in DMF (15 mL) was stirred overnight at room temperature. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane/methanol) to give the title compound (88 mg).
$^1$H NMR (300 MHz, DMSO-$d_6$) δ 1.64-1.80 (2H, m), 1.83-2.01 (2H, m), 2.06-2.24 (4H, m), 4.04 (3H, s), 5.87 (1H, quin, J=7.0 Hz), 7.46 (1H, brs), 8.09 (1H, s), 8.18 (1H, brs), 8.27 (1H, d, J=1.1 Hz), 8.34 (1H, d, J=1.5 Hz).
MS (ESI+): [M-NH$_2$]+ 321.0.
MS (ESI+). found: 422.6.

D) 4-(7-cyano-1-cyclopentyl-4-methoxy-1H-pyrazolo[4,3-c]pyridin-3-yl)thiophene-2-carboxamide A suspension of 4-(7-bromo-1-cyclopentyl-4-methoxy-1H-pyrazolo[4,3-c]pyridin-3-yl)thiophene-2-carboxamide (100 mg), zinc cyanide (41.8 mg) and tetrakis(triphenylphosphine)palladium(0) (54.9 mg) in DMA was stirred under microwave irradiation at 120° C. for 30 min. The reaction mixture was purified by silica gel column chromatography (ethyl acetate/hexane) to give the title compound (61.7 mg).
$^1$H NMR (300 MHz, DMSO-$d_6$) δ 1.60-1.83 (2H, m), 1.85-2.05 (2H, m), 2.08-2.31 (4H, m), 4.15 (3H, s), 5.45 (1H, quin, J=6.7 Hz), 7.36-7.71 (1H, m), 8.20 (1H, brs), 8.29 (1H, d, J=1.1 Hz), 8.38 (1H, d, J=1.5 Hz), 8.59 (1H, s).
MS (ESI+): [M+H]+ 368.1.
MS (ESI+). found: 367.8.

E) 4-(7-cyano-1-cyclopentyl-4-oxo-4,5-dihydro-1H-pyrazolo[4,3-c]pyridin-3-yl)thiophene-2-carboxamide To a solution of 4-(7-cyano-1-cyclopentyl-4-methoxy-1H-pyrazolo[4,3-c]pyridin-3-yl)thiophene-2-carboxamide (53.3 mg) in acetonitrile (10 mL) were added sodium iodide (43.5 mg) and chloro(trimethyl)silane (0.147 mL), and the mixture was stirred at 60° C. for 30 min. The reaction mixture was concentrated under reduced pressure, and the residue was washed successively with water and ethyl acetate to give the title compound (50.3 mg).
$^1$H NMR (300 MHz, DMSO-$d_6$) δ 1.59-1.81 (2H, m), 1.84-2.04 (2H, m), 2.05-2.32 (4H, m), 5.36 (1H, quin, J=6.7 Hz), 7.44 (1H, brs), 8.19 (1H, brs), 8.25 (1H, d, J=6.4 Hz), 8.32 (1H, d, J=1.5 Hz), 8.96 (1H, d, J=1.1 Hz), 12.19 (1H, d, J=6.8 Hz).

Example 166

4-(7-chloro-1-(2,6-difluorophenyl)-4-oxo-4,5-dihydro-1H-pyrazolo[4,3-c]pyridin-3-yl)-N-(1-methyl-1H-pyrazol-4-yl)thiophene-2-carboxamide The title compound was obtained using 7-chloro-1-(2,6-difluorophenyl)-4-methoxy-1H-pyrazolo[4,3-c]pyridin-3-yl trifluoromethanesulfonate obtained in Step A of Example 152, methyl 4-(4,4,5,5-tetramethyl-1,3,2-dioxaborolan-2-yl)thiophene-2-carboxylate and 1-methyl-1H-pyrazol-4-amine, in the same manner as in Step I of Example 33, Step F of Example 33, Step J of Example 33 and Step G of Example 33.
MS (ESI+): [M]+ 486.8.
MS (ESI+). found: 486.7.

Example 167

(4-(7-chloro-1-(2,6-difluorophenyl)-4-oxo-4,5-dihydro-1H-pyrazolo[4,3-c]pyridin-3-yl)phenoxy)acetonitrile

A) (4-(7-chloro-1-(2,6-difluorophenyl)-4-methoxy-1H-pyrazolo[4,3-c]pyridin-3-yl)phenoxy)acetonitrile The title compound (96 mg) was obtained using 7-chloro-1-(2,6-difluorophenyl)-4-methoxy-1H-pyrazolo[4,3-c]pyridin-3-yl trifluoromethanesulfonate obtained in Step A of Example 152 and (4-(4,4,5,5-tetramethyl-1,3,2-dioxaborolan-2-yl)phenoxy)acetonitrile, in the same manner as in Step B of Example 152.
MS (ESI+): [M+H]+ 427.1.
MS (ESI+). found: 427.2.

B) (4-(7-chloro-1-(2,6-difluorophenyl)-4-oxo-4,5-dihydro-1H-pyrazolo[4,3-c]pyridin-3-yl)phenoxy)acetonitrile The title compound (32 mg) was obtained using (4-(7-chloro-1-(2,6-difluorophenyl)-4-methoxy-1H-pyrazolo[4,3-c]pyridin-3-yl)phenoxy)acetonitrile (96 mg), in the same manner as in Step C of Example 152.
MS (ESI+): [M+H]+ 413.1.
MS (ESI+). found: 413.2.

Example 168

7-chloro-1-(2,6-difluorophenyl)-3-(3-(2-hydroxyethoxyl)phenyl)-1,5-dihydro-4H-pyrazolo[4,3-c]pyridin-4-one

A) 3-(4,4,5,5-tetramethyl-1,3,2-dioxaborolan-2-yl)phenyl benzoate

To a solution of 3-(4,4,5,5-tetramethyl-1,3,2-dioxaborolan-2-yl)phenol (2.0 g), triethylamine (1.90 mL) and N,N-dimethylaminopyridine (56 mg) in THF (10 mL) was added benzoyl chloride (1.16 mL) at 0° C., and the mixture was stirred at room temperature for 2 hr. To the reaction mixture was added water, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (2.74 g).
$^1$H NMR (300 MHz, CDCl$_3$) δ 1.34 (12H, s), 7.28-7.35 (1H, m), 7.40-7.47 (1H, m), 7.51 (2H, s), 7.59-7.67 (2H, m), 7.68-7.76 (1H, m), 8.21 (2H, s).

B) 3-(7-chloro-1-(2,6-difluorophenyl)-4-methoxy-1H-pyrazolo[4,3-c]pyridin-3-yl)phenol The title compound (222 mg) was obtained using 7-chloro-1-(2,6-difluorophenyl)-4-methoxy-1H-pyrazolo[4,3-c]pyridin-3-yl trifluoromethanesulfonate obtained in Step A of Example 152 (450 mg) and 3-(4,4,5,5-tetramethyl-1,3,2-dioxaborolan-2-yl)phenyl benzoate, in the same manner as in Step B of Example 152.

MS (ESI+): [M+H]$^+$ 388.1.
MS (ESI+). found: 388.2.

C) 2-(3-(7-chloro-1-(2,6-difluorophenyl)-4-methoxy-1H-pyrazolo[4,3-c]pyridin-3-yl)phenoxy)ethanol A solution of 3-(7-chloro-1-(2,6-difluorophenyl)-4-methoxy-1H-pyrazolo[4,3-c]pyridin-3-yl)phenol (30 mg), potassium carbonate (7 mg) and 2-bromoethanol (21 μL) in DMF (3 mL) was stirred at 70° C. for 5 hr. The mixture was allowed to be cooled to room temperature, potassium carbonate (107 mg) and 2-bromoethanol (55 μL) were added thereto, and the mixture was stirred overnight at 7° C. To the reaction mixture was added water, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (15 mg).

MS (ESI+): [M+H]$^+$ 432.1.
MS (ESI+). found: 432.2.

D) 7-chloro-1-(2,6-difluorophenyl)-3-(3-(2-hydroxyethoxy)phenyl)-1,5-dihydro-4H-pyrazolo[4,3-c]pyridin-4-one The title compound (6 mg) was obtained using (3-(7-chloro-1-(2,6-difluorophenyl)-4-methoxy-1H-pyrazolo[4,3-c]pyridin-3-yl)phenoxy)ethanol (15 mg), in the same manner as in Step C of Example 152.

MS (ESI+): [M+H]$^+$ 418.1.
MS (ESI+). found: 418.2.

Example 169

2-(4-(7-chloro-1-(2,6-difluorophenyl)-4-oxo-4,5-dihydro-1H-pyrazolo[4,3-c]pyridin-3-yl)phenoxy)acetamide The title compound (13 mg) was obtained using (4-(7-chloro-1-(2,6-difluorophenyl)-4-oxo-4,5-dihydro-1H-pyrazolo[4,3-c]pyridin-3-yl)phenoxy)acetonitrile (28 mg) obtained in Example 167, in the same manner as in Example 97.

MS (ESI+): [M+H]$^+$ 431.1.
MS (ESI+). found: 431.2.

Example 170

4-(4-oxo-1-(4-oxocyclohexyl)-4,5-dihydro-1H-pyrazolo[4,3-c]pyridin-3-yl)thiophene-2-carboxamide To a solution of 4-(1-(1,4-dioxaspiro[4.5]dec-8-yl)-4-methoxy-1H-pyrazolo[4,3-c]pyridin-3-yl)thiophene-2-carboxamide (20.0 mg) obtained in Step B of Example 148 in a mixed solvent of THF (5 mL) and water (0.50 mL) was added 6N hydrochloric acid (0.032 mL), and the mixture was stirred at 60° C. overnight. The reaction mixture was extracted with ethyl acetate, and the organic layer was washed with saturated aqueous sodium hydrogencarbonate solution and saturated brine, dried over anhydrous magnesium sulfate, filtered, and concentrated under reduced pressure. The obtained residue was purified by silica gel column chromatography (ethyl acetate/methanol) to give the title compound (16.1 mg).

$^1$H NMR (300 MHz, DMSO-d$_6$) δ 2.15-2.48 (6H, m), 2.61-2.76 (2H, m), 5.02-5.16 (1H, m), 6.77 (1H, d, J=6.8 Hz), 7.29 (1H, dd, J=7.2, 6.0 Hz), 7.41 (1H, brs), 8.12 (1H, brs), 8.34 (1H, d, J=1.5 Hz), 9.15 (1H, d, J=1.1 Hz), 11.18 (1H, d, J=6.0 Hz).

MS (ESI+): [M]$^+$ 357.1.
MS (ESI+). found: 357.1.

Example 171

4-(1-(4-hydroxycyclohexyl)-4-oxo-4,5-dihydro-1H-pyrazolo[4,3-c]pyridin-3-yl)thiophene-2-carboxamide To a solution of 4-(4-oxo-1-(4-oxocyclohexyl)-4,5-dihydro-1H-pyrazolo[4,3-c]pyridin-3-yl)thiophene-2-carboxamide (40.0 mg) obtained in Example 170 in methanol (5 mL) was added sodium borohydride (8.49 mg) at 0° C., and the mixture was stirred overnight under nitrogen atmosphere at room temperature. To the reaction mixture was added saturated aqueous ammonium chloride, and the mixture was extracted with ethyl acetate. The organic layer was washed with saturated brine, dried over anhydrous magnesium sulfate, filtered, and concentrated under reduced pressure. The obtained residue was purified by silica gel column chromatography (basic silica gel, ethyl acetate/methanol) to give the title compound (cis/trans mixture, 30.9 mg).

$^1$H NMR (300 MHz, DMSO-d$_6$) δ 1.77-2.11 (8H, m), 2.24-2.41 (1H, m), 3.47-3.61 (1H, m), 4.71 (1H, d, J=4.5 Hz), 6.72 (1H, d, J=7.6 Hz), 7.23 (1H, d, J=5.3 Hz), 7.40 (1H, brs), 8.14 (1H, brs), 8.30-8.35 (1H, m), 9.12 (1H, d, J=1.1 Hz), 11.12 (1H, brs).

MS (ESI+): [M]$^+$ 359.1.
MS (ESI+). found: 359.1.

Example 172

4-(1-(4-hydroxy-4-phenylcyclohexyl)-4-oxo-4,5-dihydro-1H-pyrazolo[4,3-c]pyridin-3-yl)thiophene-2-carboxamide To a solution of 4-(4-oxo-1-(4-oxocyclohexyl)-4,5-dihydro-1H-pyrazolo[4,3-c]pyridin-3-yl)thiophene-2-carboxamide (30.0 mg) obtained in Example 170 in THF (10 mL) was added dropwise 1.6 M phenyllithium butyl ether solution (0.210 mL) at −78° C., and the mixture was stirred overnight at room temperature. To the reaction mixture was added dropwise 1N hydrochloric acid at 0° C., and the mixture was extracted with ethyl acetate. The organic layer was washed with saturated aqueous sodium hydrogencarbonate solution and saturated brine, dried over anhydrous magnesium sulfate, filtered, and concentrated under reduced pressure. The obtained residue was purified by silica gel column chromatography (ethyl acetate/methanol) to give the title compound (cis/trans mixture, 11.2 mg).

$^1$H NMR (300 MHz, DMSO-d$_6$) δ 1.72-1.86 (5H, m), 2.00-2.16 (2H, m), 4.66 (1H, tt, J=11.8, 3.3 Hz), 5.00 (1H, s), 6.72 (1H, d, J=7.6 Hz), 7.18-7.45 (6H, m), 7.53-7.59 (2H, m), 8.24 (1H, br. s.), 8.35 (1H, d, J=1.5 Hz), 9.17 (1H, d, J=1.1 Hz), 11.14 (1H, d, J=4.9 Hz).

MS (ESI+): [M]$^+$ 435.5.
MS (ESI+). found: 435.3.

Example 173

4-(4-oxo-1-(4-oxocyclohexyl)-4,5-dihydro-1H-pyrazolo[4,3-c]pyridin-3-yl)benzenesulfonamide A) 4-(1-(1,4-dioxaspiro[4.5]dec-8-yl)-4-methoxy-1H-pyrazolo[4,3-c]pyridin-3-yl)benzenesulfonamide To a solution of 4-(4-methoxy-1H-pyrazolo[4,3-c]pyridin-3-yl)benzenesulfonamide (500 mg) obtained in Step A of Example 100 in DMF (8 mL) was added sodium hydride (60% dispersion in mineral oil, 131 mg), and the mixture was stirred at room temperature for 1 hr. To the reaction mixture was added 1,4-dioxaspiro[4.5]dec-8-yl 4-methylbenzenesulfonate (1.03 g), and the mixture was stirred overnight at 60° C. The reaction mixture was extracted with ethyl acetate and water. The organic layer was washed with saturated brine, dried over anhydrous magnesium sulfate, filtered, and concentrated under reduced pressure. The obtained residue was purified by silica gel column chromatography (ethyl acetate/methanol) to give the title compound (283 mg).

$^1$H NMR (300 MHz, DMSO-$d_6$) δ 1.69-1.96 (6H, m), 2.12-2.36 (2H, m), 3.89-3.96 (4H, m), 3.97-4.04 (3H, m), 4.75-4.91 (1H, m), 7.42 (3H, d, J=6.4 Hz), 7.89-8.02 (3H, m), 8.11 (2H, d, J=8.3 Hz).

MS (ESI+): [M]$^+$ 445.2.

MS (ESI+). found: 445.1.

B) 4-(4-oxo-1-(4-oxocyclohexyl)-4,5-dihydro-1H-pyrazolo[4,3-c]pyridin-3-yl)benzenesulfonamide To a solution of 4-(1-(1,4-dioxaspiro[4.5]dec-8-yl)-4-methoxy-1H-pyrazolo[4,3-c]pyridin-3-yl)benzenesulfonamide (280 mg) in a mixed solvent of THF (15 mL) and water (1.5 mL) was added 1N hydrochloric acid (0.420 mL) at 0° C., and the mixture was stirred overnight at room temperature. To the reaction mixture was added 1N aqueous sodium hydroxide solution at 0° C., and the mixture was extracted with ethyl acetate. The organic layer was washed with saturated aqueous sodium hydrogencarbonate solution and saturated brine, dried over anhydrous magnesium sulfate, filtered, and concentrated under reduced pressure. The obtained residue was purified by silica gel column chromatography (hexane/ethyl acetate) to give the title compound (219 mg).

$^1$H NMR (300 MHz, DMSO-$d_6$) δ 2.23-2.47 (6H, m), 2.60-2.72 (2H, m), 5.05-5.22 (1H, m), 6.81 (1H, d, J=7.6 Hz), 7.33 (1H, d, J=7.6 Hz), 7.41 (2H, brs), 7.86 (2H, d, J=8.7 Hz), 8.49 (2H, d, J=8.7 Hz), 11.18 (1H, brs).

MS (ESI+): [M]$^+$ 387.1.

MS (ESI+). found: 387.2.

Example 174

4-(1-(4-hydroxy-4-phenylcyclohexyl)-4-oxo-4,5-dihydro-1H-pyrazolo[4,3-c]pyridin-3-yl)benzenesulfonamide To a solution of 4-(4-oxo-1-(4-oxocyclohexyl)-4,5-dihydro-1H-pyrazolo[4,3-c]pyridin-3-yl)benzenesulfonamide (30.0 mg) obtained in Example 173 in THF was added 1.6M phenyllithium butyl ether solution (0.194 mL) at −78° C., and the mixture was stirred overnight at room temperature under nitrogen atmosphere. To the reaction mixture was added 1N hydrochloric acid at 0° C., and the mixture was extracted with ethyl acetate. The organic layer was washed with saturated aqueous sodium hydrogencarbonate solution and saturated brine, dried over anhydrous magnesium sulfate, filtered, and concentrated under reduced pressure. The obtained residue was purified by silica gel column chromatography (ethyl acetate/methanol) to give the title compound (15.1 mg).

$^1$H NMR (300 MHz, DMSO-$d_6$) δ 1.81 (4H, d, J=11.3 Hz), 2.08 (2H, t, J=11.7 Hz), 4.65-4.82 (1H, m), 5.03 (1H, s), 6.76 (1H, d, J=7.2 Hz), 7.15-7.44 (8H, m), 7.56 (2H, d, J=7.2 Hz), 7.88 (2H, d, J=8.7 Hz), 8.46-8.57 (2H, m), 11.17 (1H, brs).

MS (ESI+): [M]$^+$ 465.2.

MS (ESI+). found: 465.3.

Example 175

2-(4-(7-bromo-1-(2,6-difluorophenyl)-4-oxo-4,5-dihydro-1H-pyrazolo[4,3-c]pyridin-3-yl)-1H-pyrazol-1-yl)acetamide The title compound was obtained using 1-(2,6-difluorophenyl)-4-methoxy-1H-pyrazolo[4,3-c]pyridin-3-yl trifluoromethanesulfonate obtained in Step C of Example 35, in the same manner as in Step I of Example 33, Step B of Example 98, Step A of Example 104 and Step J of Example 33.

MS (ESI+): [M+H]$^+$ 450.2.

MS (ESI+). found: 450.1.

Example 176

7-bromo-1-(2,6-difluorophenyl)-3-(1H-pyrazol-4-yl)-1,5-dihydro-4H-pyrazolo[4,3-c]pyridin-4-one The title compound was obtained using 1-(2,6-difluorophenyl)-4-methoxy-1H-pyrazolo[4,3-c]pyridin-3-yl trifluoromethanesulfonate obtained in Step C of Example 35, in the same manner as in Step I of Example 33, Step A of Example 104 and Step J of Example 33.

MS (ESI+): [M+H]$^+$ 393.2.

MS (ESI+). found: 393.0.

Example 177

7-chloro-1-(2,6-difluorophenyl)-3-(1H-pyrazol-4-yl)-1,5-dihydro-4H-pyrazolo[4,3-c]pyridin-4-one A) 7-chloro-1-(2,6-difluorophenyl)-4-methoxy-3-(1H-pyrazol-4-yl)-1H-pyrazolo[4,3-c]pyridine The title compound was obtained using 7-chloro-1-(2,6-difluorophenyl)-4-methoxy-1H-pyrazolo[4,3-c]pyridin-3-yl trifluoromethanesulfonate obtained in Step A of Example 152, in the same manner as in Step I of Example 33.

$^1$H NMR (300 MHz, DMSO-$d_6$) δ 4.13 (3H, s), 7.34-7.53 (2H, m), 7.78 (1H, tt, J=8.6, 6.5 Hz), 7.97-8.22 (2H, m), 8.25-8.53 (1H, m), 13.21 (1H, brs).

B) 7-chloro-1-(2,6-difluorophenyl)-3-(1H-pyrazol-4-yl)-1,5-dihydro-4H-pyrazolo[4,3-c]pyridin-4-one The title compound was obtained using 7-chloro-1-(2,6-difluorophenyl)-4-methoxy-3-(1H-pyrazol-4-yl)-1H-pyrazolo[4,3-c]pyridine, in the same manner as in Step J of Example 33.

MS (ESI+): [M+H]$^+$ 348.7.

MS (ESI+). found: 348.1.

Example 178

3-((7-cyano-1-cyclopentyl-4-oxo-4,5-dihydro-1H-pyrrolo[3,2-c]pyridin-3-yl)amino)benzamide A) methyl 3-((7-cyano-1-cyclopentyl-4-methoxy-1H-pyrrolo[3,2-c]pyridin-3-yl)amino)benzoate To a solution of 3-bromo-1-cyclopentyl-4-methoxy-4,5-dihydro-1H-pyrrolo[3,2-c]pyridine-7-carbonitrile (1.5 g) obtained in Step H of Example 33, methyl 3-aminobenzoate (0.85 g), 4,5'-bis(diphenylphosphino)-9,9'-dimethylxanthene (0.54 g) and tris(dibenzylideneacetone)dipalladium(0) (0.43 g) in toluene (10 mL) was added sodium tert-butoxide (0.90 g), and the mixture was stirred at 110° C. for 4 hr. To the reaction mixture was added water, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (190 mg).
MS (ESI+): [M+H]$^+$ 391.4.
MS (ESI+). found: 391.3.

B) 3-((7-cyano-1-cyclopentyl-4-methoxy-1H-pyrrolo[3,2-c]pyridin-3-yl)amino)benzoic acid To a mixture of methyl 3-((7-cyano-1-cyclopentyl-4-methoxy-1H-pyrrolo[3,2-c]pyridin-3-yl)amino)benzoate (90 mg) in a mixed solvent of methanol (1 mL) and THF (1 mL) was added 8N aqueous sodium hydroxide solution (0.288 mL), and the mixture was stirred at 80° C. for 4 hr. To the reaction mixture was added water, and the mixture was extracted with ethyl acetate. The aqueous layer was neutralized with 1N hydrochloric acid at 0° C., and the mixture was extracted with ethyl acetate. The organic layer was washed with water and saturated brine, dried over anhydrous magnesium sulfate, and concentrated under reduced pressure to give the title compound (80 mg).
MS (ESI+): [M+H]$^+$ 377.4.
MS (ESI+). found: 377.2.

C) 3-((7-cyano-1-cyclopentyl-4-methoxy-1H-pyrrolo[3,2-c]pyridin-3-yl)amino)benzamide To a solution of 3-((7-cyano-1-cyclopentyl-4-methoxy-1H-pyrrolo[3,2-c]pyridin-3-yl)amino)benzoic acid (80 mg) and HOBt ammonium salt (52 mg) in DMF (2 mL) was added EDCI hydrochloride (65 mg), and the mixture was stirred overnight at room temperature. To the reaction mixture was added water, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (65 mg).
MS (ESI+): [M+H]$^+$ 376.4.
MS (ESI+). found: 376.3.

D) 3-((7-cyano-1-cyclopentyl-4-oxo-4,5-dihydro-1H-pyrrolo[3,2-c]pyridin-3-yl)amino)benzamide The title compound (5 mg) was obtained using 3-((7-cyano-1-cyclopentyl-4-methoxy-1H-pyrrolo[3,2-c]pyridin-3-yl)amino)benzamide (34 mg), in the same manner as in Step J of Example 33.
MS (ESI+): [M+H]$^+$ 362.4.
MS (ESI+). found: 362.3.

Example 179

1-(2,6-difluorophenyl)-3-(4-(morpholin-4-yl)phenyl)-1,5-dihydro-4H-pyrazolo[4,3-c]pyridin-4-one A) 1-(2,6-difluorophenyl)-4-methoxy-3-(4-(morpholin-4-yl)phenyl)-1H-pyrazolo[4,3-c]pyridine A mixture of 1-(2,6-difluorophenyl)-4-methoxy-1H-pyrazolo[4,3-c]pyridin-3-yl trifluoromethanesulfonate (250 mg) obtained in Step C of Example 35, 4-(4-(4,4,5,5-tetramethyl-1,3,2-dioxaborolan-2-yl)phenyl)morpholine (265 mg), tetrakis(triphenylphosphine)palladium(0) (35.3 mg) and 2M aqueous potassium carbonate solution (169 mg) in DMF (2 mL) was stirred under microwave irradiation at 130° C. for 1.5 hr. The reaction mixture was added to water, and the filtrate was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (240 mg).
$^1$H NMR (300 MHz, CDCl$_3$) δ 3.23-3.30 (4H, m), 3.84-3.93 (4H, m), 4.11 (3H, s), 6.75 (1H, dt, J=6.0, 1.3 Hz), 7.01 (2H, d, J=8.7 Hz), 7.09-7.18 (2H, m), 7.48 (1H, tt, J=8.5, 6.0 Hz), 7.94-8.03 (3H, m).
MS (ESI+): [M+H]$^+$ 423.2.
MS (ESI+). found: 423.3

B) 1-(2,6-difluorophenyl)-3-(4-(morpholin-4-yl)phenyl)-1,5-dihydro-4H-pyrazolo[4,3-c]pyridin-4-one To a mixture of 1-(2,6-difluorophenyl)-4-methoxy-3-(4-(morpholin-4-yl)phenyl)-1H-pyrazolo[4,3-c]pyridine (50.0 mg) and sodium iodide (35.5 mg) in acetonitrile (3 mL) was added chloro(trimethyl)silane (0.0760 mL) at room temperature, and the mixture was stirred at 50° C. for 16 hr. To the reaction mixture was added saturated aqueous sodium hydrogencarbonate solution, and the mixture was extracted with ethyl acetate. The organic layer was washed with saturated brine, dried over anhydrous magnesium sulfate, and concentrated under reduced pressure. The residue was purified by silica gel column chromatography (basic silica gel, methanol/ethyl acetate) to give the title compound (36.5 mg).
$^1$H NMR (300 MHz, DMSO-d$_6$) δ 3.14-3.24 (4H, m), 3.70-3.82 (4H, m), 6.21 (1H, d, J=7.2 Hz), 7.01 (2H, d, J=9.1 Hz), 7.25-7.35 (1H, m), 7.42-7.54 (2H, m), 7.74 (1H, tt, J=8.6, 6.3 Hz), 8.24 (2H, d, J=9.1 Hz), 11.34 (1H, d, J=3.4 Hz).
MS (ESI+): [M+H]$^+$ 409.1.
MS (ESI+). found: 409.3

Example 180

4-(1-(2,6-difluorophenyl)-4-oxo-4,5-dihydro-1H-pyrazolo[4,3-c]pyridin-3-yl)-N-methylbenzamide A) methyl 4-(1-(2,6-difluorophenyl)-4-methoxy-1H-pyrazolo[4,3-c]pyridin-3-yl)benzoate To a solution of 1-(2,6-difluorophenyl)-4-methoxy-1H-pyrazolo[4,3-c]pyridin-3-yl trifluoromethanesulfonate (3.20 g) obtained in Step C of Example 35 in DMF (20 mL)/water (2.0 mL) were added methyl 4-(4,4,5,5-tetramethyl-1,3,2- dioxaborolan-2-yl)benzoate (2.87 g), (1,1'-bis(diphenylphosphino)ferrocene)dichloropalladium(II) (319 mg) and potassium carbonate (2.16 g). The reaction mixture was stirred overnight at 90° C. The reaction mixture was diluted with water, and the mixture was extracted with ethyl acetate. The organic layer was washed with saturated brine, dried over anhydrous magnesium sulfate, filtered, and concentrated under reduced pressure. The obtained residue was purified by silica gel column chromatography (hexane/ethyl acetate) to give the title compound (2.75 g).

$^1$H NMR (300 MHz, CDCl$_3$) δ 3.96 (3H, s), 4.11 (3H, s), 6.72-6.84 (1H, m), 7.11-7.22 (2H, m), 7.51 (1H, s), 8.04 (1H, d, J=6.0 Hz), 8.15 (4H, s).

MS (ESI+): [M+H]$^+$ 396.1.

MS (ESI+). found: 396.2.

B) 4-(1-(2,6-difluorophenyl)-4-methoxy-1H-pyrazolo[4,3-c]pyridin-3-yl)benzoic acid To a solution of methyl 4-(1-(2,6-difluorophenyl)-4-methoxy-1H-pyrazolo[4,3-c]pyridin-3-yl)benzoate (2.70 g) in a mixed solvent of methanol (20 mL) THF (20 mL) and water (10 mL) was added 8N aqueous sodium hydroxide solution (4.27 mL), and the mixture was stirred at 50° C. for 4 hr. To the reaction mixture was added water, and the mixture was extracted with ethyl acetate. The aqueous layer was neutralized with 1N hydrochloric acid at 0° C., and the mixture was extracted with ethyl acetate. The organic layer was washed with water and saturated brine, dried over anhydrous magnesium sulfate, and concentrated under reduced pressure to give the title compound (2.59 g).

$^1$H NMR (300 MHz, CDCl$_3$) δ 4.13 (3H, s), 6.80 (1H, d, J=6.0 Hz), 7.07-7.23 (2H, m), 7.42-7.62 (1H, m), 8.06 (1H, d, J=6.0 Hz), 8.14-8.30 (4H, m).

MS (ESI+): [M+H]$^+$ 382.1.

MS (ESI+). found: 382.2.

C) 4-(1-(2,6-difluorophenyl)-4-methoxy-1H-pyrazolo[4,3-c]pyridin-3-yl)-N-methylbenzamide To a solution of 4-(1-(2,6-difluorophenyl)-4-methoxy-1H-pyrazolo[4,3-c]pyridin-3-yl)benzoic acid (2.59 g), methylamine hydrochloride (688 mg), HOBt monohydrate (1.56 g) and triethylamine (1.89 mL) in DMF (20 mL) was added EDCI hydrochloride (1.95 g) at 0° C., and the mixture was stirred overnight at room temperature. To the reaction mixture was added water, and the white precipitate was filtered, washed with water and hexane, and dried in vacuum to give the title compound (2.68 g).

$^1$H NMR (300 MHz, CDCl$_3$) δ 3.06 (3H, d, J=4.9 Hz), 4.11 (3H, s), 6.15-6.28 (1H, m), 6.7.4-6.83 (1H, m), 7.11-7.22 (2H, m), 7.51 (1H, s), 7.84-7.90 (2H, m), 8.03 (1H, d, J=6.0 Hz), 8.09-8.17 (1H, m).

MS (ESI+): [M+H]$^+$ 395.1.

MS (ESI+). found: 395.3.

D) 4-(1-(2,6-difluorophenyl)-4-oxo-4,5-dihydro-1H-pyrazolo[4,3-c]pyridin-3-yl)-N-methylbenzamide To a solution of 4-(1-(2,6-difluorophenyl)-4-methoxy-1H-pyrazolo[4,3-c]pyridin-3-yl)-N-methylbenzamide (2.68 g) in acetonitrile (50 mL) were added sodium iodide (2.04 g) and chloro(trimethyl)silane (4.34 mL) was added, and the mixture was stirred at 60° C. for 3 hr. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (basic silica gel, hexane/ethyl acetate to ethyl acetate/methanol). 1.60 g of the obtained title compound (2.15 g) was dissolved in 2-propanol (240 mL) at 80° C. To the solution was added heptane (160 mL) over 15 min, the mixture was stirred for 15 min, and allowed overnight to be cooled. The white precipitate was collected by filtration, washed with a mixed solvent of 2-propanol-heptane (3:4), and dried in vacuum to give the title compound (1.49 g).

$^1$H NMR (300 MHz, DMSO-d$_6$) δ 2.82 (3H, d, J=4.5 Hz), 6.29 (1H, d, J=7.2 Hz), 7.37 (1H, d, J=7.2 Hz), 7.50 (2H, t, J=8.3 Hz), 7.68-7.84 (1H, m), 7.92 (2H, d, J=8.7 Hz), 8.41 (2H, d, J=8.7 Hz), 8.48-8.58 (1H, m), 11.48 (1H, s).

MS (ESI+): [M+H]$^+$ 381.1.

MS (ESI+). found: 381.3.

The structure formulas and compound names of the compounds obtained in Examples 1 to 180 are shown in Table 2.

TABLE 2

| Ex. | Structural Formula | Compound Name |
| --- | --- | --- |
| 1 |  | 1-cyclopentyl-3-phenyl-1,5-dihydro-4H-pyrrolo[3,2-c]pyridin-4-one |

TABLE 2-continued

| Ex. | Structural Formula | Compound Name |
|---|---|---|
| 2 | | 4-(1-cyclopentyl-4-oxo-4,5-dihydro-1H-pyrrolo[3,2-c]pyridin-3-yl)benzenesulfonamide |
| 3 | | methyl 4-(1-cyclopentyl-4-oxo-4,5-dihydro-1H-pyrrolo[3,2-c]pyridin-3-yl)thiophene-2-carboxylate |
| 4 | | 4-(1-cyclopentyl-4-oxo-4,5-dihydro-1H-pyrrolo[3,2-c]pyridin-3-yl)thiophene-2-carboxamide |
| 5 | | 1-cyclopentyl-3-(3-thienyl)-1,5-dihydro-4H-pyrrolo[3,2-c]pyridin-4-one |
| 6 | | 4-(1-cyclohexyl-4-oxo-4,5-dihydro-1H-pyrazolo[4,3-c]pyridin-3-yl)benzenesulfonamide |

TABLE 2-continued

| Ex. | Structural Formula | Compound Name |
|---|---|---|
| 7 | 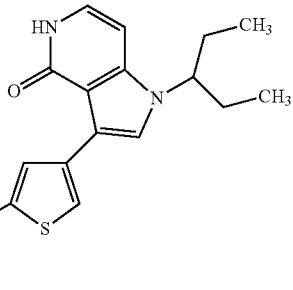 | methyl 4-(4-oxo-1-(pentan-3-yl)-4,5-dihydro-1H-pyrrolo[3,2-c]pyridin-3-yl)thiophene-2-carboxylate |
| 8 | 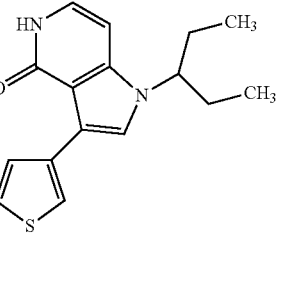 | 4-(4-oxo-1-(pentan-3-yl)-4,5-dihydro-1H-pyrrolo[3,2-c]pyridin-3-yl)thiophene-2-carboxamide |
| 9 | 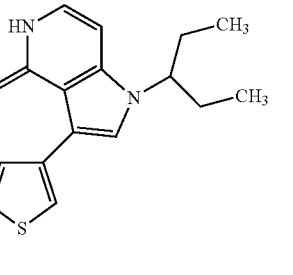 | 4-(4-oxo-1-(pentan-3-yl)-4,5-dihydro-1H-pyrrolo[3,2-c]pyridin-3-yl)thiophene-2-carbonitrile |
| 10 | 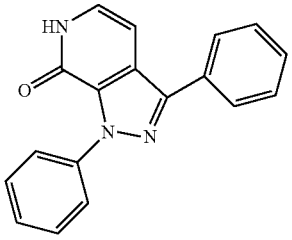 [SMILES: O=c1[nH]ccc2c(-c3ccccc3)nn(-c3ccccc3)c12] | 1,3-diphenyl-1,6-dihydro-7H-pyrazolo[3,4-c]pyridin-7-one |
| 11 | 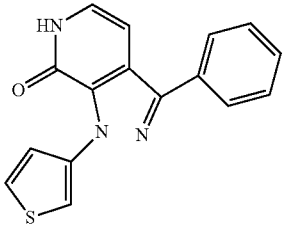 [SMILES: N=C(c1ccccc1)c1cc[nH]c(=O)c1Nc1ccsc1] | 3-phenyl-1-(3-thienyl)-1,6-dihydro-7H-pyrazolo[3,4-c]pyridin-7-one |
| 12 | 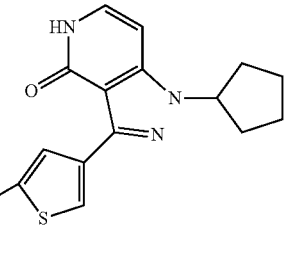 | methyl 4-(1-cyclopentyl-4-oxo-4,5-dihydro-1H-pyrazolo[4,3-c]pyridin-3-yl)thiophene-2-carboxylate |

TABLE 2-continued

| Ex. | Structural Formula | Compound Name |
| --- | --- | --- |
| 13 | | 4-(1-cyclopentyl-4-oxo-4,5-dihydro-1H-pyrazolo[4,3-c]pyridin-3-yl)thiophene-2-carboxamide |
| 14 | | 4-(1-cyclopentyl-4-oxo-4,5-dihydro-1H-pyrazolo[4,3-c]pyridin-3-yl)thiophene-2-carbonitrile |
| 15 | | 4-(4-oxo-1-(tetrahydro-2H-pyran-4-yl)-4,5-dihydro-1H-pyrazolo[4,3-c]pyridin-3-yl)benzenesulfonamide |
| 16 | | 4-(4-oxo-1-(tetrahydro-2H-pyran-4-yl)-4,5-dihydro-1H-pyrrolo[3,2-c]pyridin-3-yl)benzenesulfonamide |
| 17 | | 4-(1-(1-methoxybutan-2-yl)-4-oxo-4,5-dihydro-1H-pyrrolo[3,2-c]pyridin-3-yl)benzenesulfonamide |

TABLE 2-continued

| Ex. | Structural Formula | Compound Name |
|---|---|---|
| 18 | | 4-(4-oxo-1-(tetrahydrofuran-3-yl)-4,5-dihydro-1H-pyrrolo[3,2-c]pyridin-3-yl)benzenesulfonamide |
| 19 | | 4-((7-oxo-3-phenyl-6,7-dihydro-1H-pyrazolo[3,4-c]pyridin-1-yl)methyl)benzenesulfonamide |
| 20 | | (4-(1-(1-methoxybutan-2-yl)-4-oxo-4,5-dihydro-1H-pyrrolo[3,2-c]pyridin-3-yl)phenyl)acetonitrile |
| 21 | | methyl 4-(4-oxo-1-(tetrahydro-2H-pyran-4-yl)-4,5-dihydro-1H-pyrazolo[4,3-c]pyridin-3-yl)thiophene-2-carboxylate |
| 22 | | (4-(4-oxo-1-(tetrahydrofuran-3-yl)-4,5-dihydro-1H-pyrrolo[3,2-c]pyridin-3-yl)phenyl)acetonitrile |

TABLE 2-continued

| Ex. | Structural Formula | Compound Name |
|---|---|---|
| 23 | | 4-(4-oxo-1-(tetrahydro-2H-pyran-4-yl)-4,5-dihydro-1H-pyrazolo[4,3-c]pyridin-3-yl)thiophene-2-carboxylic acid |
| 24 | | 4-(1-(1-methoxybutan-2-yl)-4-oxo-4,5-dihydro-1H-pyrrolo[3,2-c]pyridin-3-yl)benzonitrile |
| 25 | | (4-(4-oxo-1-(tetrahydro-2H-pyran-4-yl)-4,5-dihydro-1H-pyrrolo[3,2-c]pyridin-3-yl)phenyl)acetonitrile |
| 26 | | 4-(1-(1-methoxybutan-2-yl)-4-oxo-4,5-dihydro-1H-pyrrolo[3,2-c]pyridin-3-yl)benzamide |
| 27 | | 4-(4-oxo-1-(tetrahydro-2H-pyran-4-yl)-4,5-dihydro-1H-pyrazolo[4,3-c]pyridin-3-yl)thiophene-2-carboxamide |

TABLE 2-continued

| Ex. | Structural Formula | Compound Name |
|---|---|---|
| 28 | 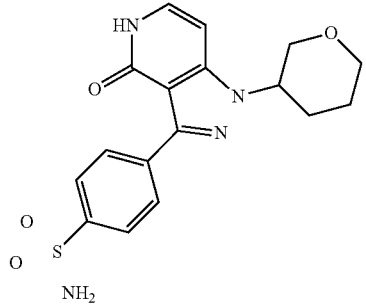 | 4-(4-oxo-1-(tetrahydro-2H-pyran-3-yl)-4,5-dihydro-1H-pyrazolo[4,3-c]pyridin-3-yl)benzenesulfonamide |
| 29 | 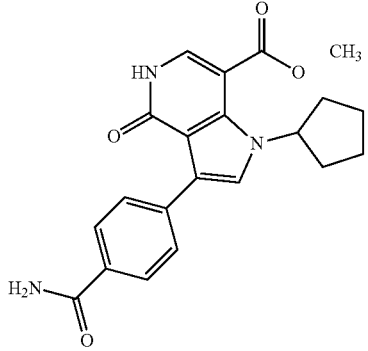 | methyl 3-(4-carbamoylphenyl)-1-cyclopentyl-4-oxo-4,5-dihydro-1H-pyrrolo[3,2-c]pyridine-7-carboxylate |
| 30 | 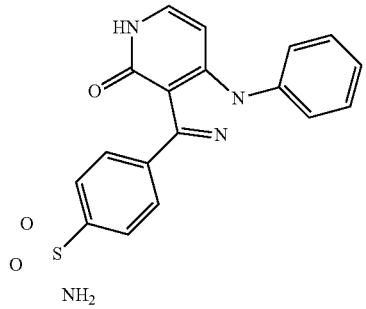 | 4-(4-oxo-1-phenyl-4,5-dihydro-1H-pyrazolo[4,3-c]pyridin-3-yl)benzenesulfonamide |
| 31 | 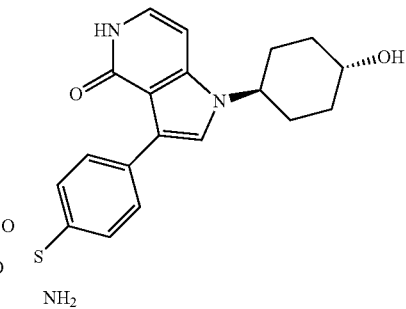 | 4-(1-(trans-4-hydroxycyclohexyl)-4-oxo-4,5-dihydro-1H-pyrrolo[3,2-c]pyridin-3-yl)benzenesulfonamide |

TABLE 2-continued

| Ex. | Structural Formula | Compound Name |
|---|---|---|
| 32 | | 4-(1-(cis-4-hydroxycyclohexyl)-4-oxo-4,5-dihydro-1H-pyrrolo[3,2-c]pyridin-3-yl)benzenesulfonamide |
| 33 | | 4-(7-cyano-1-cyclopentyl-4-oxo-4,5-dihydro-1H-pyrrolo[3,2-c]pyridin-3-yl)thiophene-2-carboxamide |
| 34 | | methyl 3-(5-carbamoyl-3-thienyl)-1-cyclopentyl-4-oxo-4,5-dihydro-1H-pyrrolo[3,2-c]pyridine-7-carboxylate |
| 35 | | 4-(1-(2,6-difluorophenyl)-4-oxo-4,5-dihydro-1H-pyrazolo[4,3-c]pyridin-3-yl)benzenesulfonamide |
| 36 | | methyl 4-(1-(2,6-difluorophenyl)-4-oxo-4,5-dihydro-1H-pyrazolo[4,3-c]pyridin-3-yl)thiophene-2-carboxylate |

TABLE 2-continued

| Ex. | Structural Formula | Compound Name |
|---|---|---|
| 37 | | 4-(1-(2,6-difluorophenyl)-4-oxo-4,5-dihydro-1H-pyrazolo[4,3-c]pyridin-3-yl)thiophene-2-carboxylic acid |
| 38 | | 4-(1-(2,6-difluorophenyl)-4-oxo-4,5-dihydro-1H-pyrazolo[4,3-c]pyridin-3-yl)thiophene-2-carboxamide |
| 39 | | (4-(1-(2,6-difluorophenyl)-4-oxo-4,5-dihydro-1H-pyrazolo[4,3-c]pyridin-3-yl)phenyl)acetonitrile |
| 40 | | 4-(1-cyclopentyl-7-(hydroxymethyl)-4-oxo-4,5-dihydro-1H-pyrrolo[3,2-c]pyridin-3-yl)thiophene-2-carboxamide |
| 41 | | 3-(cyclohex-1-en-1-yl)-1-cyclopentyl-1,5-dihydro-4H-pyrazolo[4,3-c]pyridin-4-one |
| 42 | | 1-cyclopentyl-3-(3,6-dihydro-2H-pyran-4-yl)-1,5-dihydro-4H-pyrazolo[4,3-c]pyridin-4-one |

TABLE 2-continued

| Ex. | Structural Formula | Compound Name |
|---|---|---|
| 43 | | 1-cyclopentyl-3-phenyl-1,5-dihydro-4H-pyrazolo[4,3-c]pyridin-4-one |
| 44 | | 1-cyclopentyl-3-(pyridin-4-yl)-1,5-dihydro-4H-pyrazolo[4,3-c]pyridin-4-one |
| 45 | | 1-cyclopentyl-3-(4-(trifluoromethoxy)phenyl)-1,5-dihydro-4H-pyrazolo[4,3-c]pyridin-4-one |
| 46 | | 1-cyclopentyl-3-(4-methoxyphenyl)-1,5-dihydro-4H-pyrazolo[4,3-c]pyridin-4-one |
| 47 | | 1-cyclopentyl-3-(3-methoxyphenyl)-1,5-dihydro-4H-pyrazolo[4,3-c]pyridin-4-one |

TABLE 2-continued

| Ex. | Structural Formula | Compound Name |
|---|---|---|
| 48 | | 1-cyclopentyl-3-(2-methoxyphenyl)-1,5-dihydro-4H-pyrazolo[4,3-c]pyridin-4-one |
| 49 | | 3-(1,3-benzodioxol-5-yl)-1-cyclopentyl-1,5-dihydro-4H-pyrazolo[4,3-c]pyridin-4-one |
| 50 | | 1-cyclopentyl-3-(4-methylphenyl)-1,5-dihydro-4H-pyrazolo[4,3-c]pyridin-4-one |
| 51 | | 1-cyclopentyl-3-(4-(trifluoromethyl)phenyl)-1,5-dihydro-4H-pyrazolo[4,3-c]pyridin-4-one |
| 52 | | 1-cyclopentyl-3-(3-(trifluoromethyl)phenyl)-1,5-dihydro-4H-pyrazolo[4,3-c]pyridin-4-one |

TABLE 2-continued

| Ex. | Structural Formula | Compound Name |
|---|---|---|
| 53 | | 1-cyclopentyl-3-(2-(trifluoromethyl)phenyl)-1,5-dihydro-4H-pyrazolo[4,3-c]pyridin-4-one |
| 54 | | 1-cyclopentyl-3-(4-fluorophenyl)-1,5-dihydro-4H-pyrazolo[4,3-c]pyridin-4-one |
| 55 | | 1-cyclopentyl-3-(3-fluorophenyl)-1,5-dihydro-4H-pyrazolo[4,3-c]pyridin-4-one |
| 56 | | 1-cyclopentyl-3-(2-fluorophenyl)-1,5-dihydro-4H-pyrazolo[4,3-c]pyridin-4-one |
| 57 | | 1-cyclopentyl-3-(4-nitrophenyl)-1,5-dihydro-4H-pyrazolo[4,3-c]pyridin-4-one |

TABLE 2-continued

| Ex. | Structural Formula | Compound Name |
|---|---|---|
| 58 | | 1-cyclopentyl-3-(2-oxo-2,3-dihydro-1H-indol-5-yl)-1,5-dihydro-4H-pyrazolo[4,3-c]pyridin-4-one |
| 59 | | 3-(2,1,3-benzoxadiazol-5-yl)-1-cyclopentyl-1,5-dihydro-4H-pyrazolo[4,3-c]pyridin-4-one |
| 60 | | 4-(7-acetyl-1-cyclopentyl-4-oxo-4,5-dihydro-1H-pyrrolo[3,2-c]pyridin-3-yl)thiophene-2-carboxamide |
| 61 | | 3-(5-carbamoyl-3-thienyl)-1-cyclopentyl-4-oxo-4,5-dihydro-1H-pyrrolo[3,2-c]pyridine-7-carboxylic acid |
| 62 | | 3-(5-carbamoyl-3-thienyl)-1-cyclopentyl-4-oxo-4,5-dihydro-1H-pyrrolo[3,2-c]pyridine-7-carboxamide |

TABLE 2-continued

| Ex. | Structural Formula | Compound Name |
|---|---|---|
| 63 | 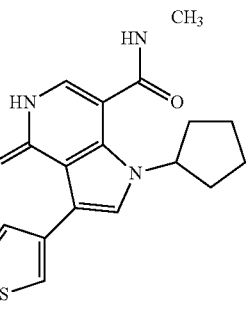 | 1-cyclopentyl-N-methyl-3-(5-(methylcarbamoyl)-3-thienyl)-4-oxo-4,5-dihydro-1H-pyrrolo[3,2-c]pyridine-7-carboxamide |
| 64 | 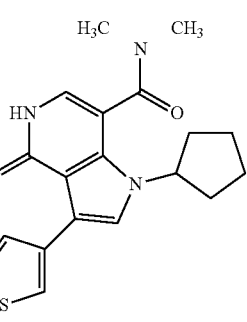 | 1-cyclopentyl-3-(5-(dimethylcarbamoyl)-3-thienyl)-N,N-dimethyl-4-oxo-4,5-dihydro-1H-pyrrolo[3,2-c]pyridine-7-carboxamide |
| 65 | 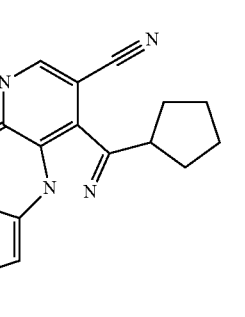 | 4-(4-cyano-3-cyclopentyl-7-oxo-6,7-dihydro-1H-pyrazolo[3,4-c]pyridin-1-yl)thiophene-2-carboxylic acid |
| 66 | 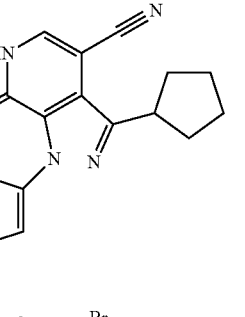 | 4-(4-cyano-3-cyclopentyl-7-oxo-6,7-dihydro-1H-pyrazolo[3,4-c]pyridin-1-yl)thiophene-2-carboxamide |
| 67 | 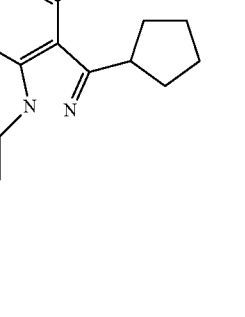 | 4-(4-bromo-3-cyclopentyl-7-oxo-6,7-dihydro-1H-pyrazolo[3,4-c]pyridin-1-yl)thiophene-2-carboxamide |

TABLE 2-continued

| Ex. | Structural Formula | Compound Name |
|---|---|---|
| 68 | | methyl 4-(4-cyano-3-(2-methylphenyl)-7-oxo-6,7-dihydro-1H-pyrazolo[3,4-c]pyridin-1-yl)thiophene-2-carboxylate |
| 69 | | 4-(4-cyano-3-(2-methylphenyl)-7-oxo-6,7-dihydro-1H-pyrazolo[3,4-c]pyridin-1-yl)thiophene-2-carboxylic acid |
| 70 | | 4-(4-cyano-3-(2-methylphenyl)-7-oxo-6,7-dihydro-1H-pyrazolo[3,4-c]pyridin-1-yl)thiophene-2-carboxamide |
| 71 | | 4-(1-(cis-2-methylcyclopentyl)-4-oxo-4,5-dihydro-1H-pyrrolo[3,2-c]pyridin-3-yl)benzenesulfonamide |
| 72 | | 2-(4-(1-(2,6-difluorophenyl)-4-oxo-4,5-dihydro-1H-pyrazolo[4,3-c]pyridin-3-yl)phenyl)acetamide |

TABLE 2-continued

| Ex. | Structural Formula | Compound Name |
| --- | --- | --- |
| 73 | | methyl 3-(5-cyano-3-thienyl)-1-cyclopentyl-4-oxo-4,5-dihydro-1H-pyrrolo[3,2-c]pyridine-7-carboxylate |
| 74 | | methyl 1-cyclopentyl-4-oxo-3-(5-(5-oxo-4,5-dihydro-1,2,4-oxadiazol-3-yl)-3-thienyl)-4,5-dihydro-1H-pyrrolo[3,2-c]pyridine-7-carboxylate |
| 75 | | 4-(3-cyclopentyl-7-oxo-6,7-dihydro-1H-pyrazolo[3,4-c]pyridin-1-yl)benzenesulfonamide |
| 76 | | methyl 4-(7-cyano-1-cyclopentyl-4-oxo-4,5-dihydro-1H-pyrrolo[3,2-c]pyridin-3-yl)thiophene-2-carboxylate |
| 77 | | 4-(7-cyano-1-cyclopentyl-4-oxo-4,5-dihydro-1H-pyrrolo[3,2-c]pyridin-3-yl)thiophene-2-carboxylic acid |

TABLE 2-continued

| Ex. | Structural Formula | Compound Name |
|---|---|---|
| 78 | | methyl 4-(4-bromo-3-(2-methylphenyl)-7-oxo-6,7-dihydro-1H-pyrazolo[3,4-c]pyridin-1-yl)thiophene-2-carboxylate |
| 79 | | 4-(4-bromo-3-(2-methylphenyl)-7-oxo-6,7-dihydro-1H-pyrazolo[3,4-c]pyridin-1-yl)thiophene-2-carboxylic acid |
| 80 | | 4-(4-bromo-3-(2-methylphenyl)-7-oxo-6,7-dihydro-1H-pyrazolo[3,4-c]pyridin-1-yl)thiophene-2-carboxamide |
| 81 | | 4-(7-cyano-1-cyclopentyl-4-oxo-4,5-dihydro-1H-pyrrolo[3,2-c]pyridin-3-yl)benzamide |
| 82 | | 4-(4-oxo-1-(tetrahydrofuran-3-yl)-4,5-dihydro-1H-pyrazolo[4,3-c]pyridin-3-yl)benzenesulfonamide |

TABLE 2-continued
| Ex. | Structural Formula | Compound Name |
|---|---|---|
| 83 | 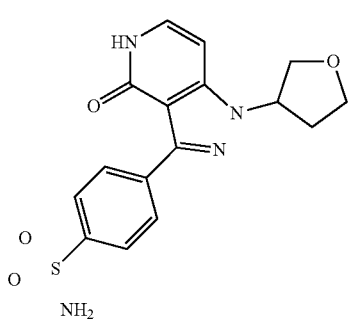 | 4-(4-oxo-1-(tetrahydrofuran-3-yl)-4,5-dihydro-1H-pyrazolo[4,3-c]pyridin-3-yl)benzenesulfonamide |
| 84 | 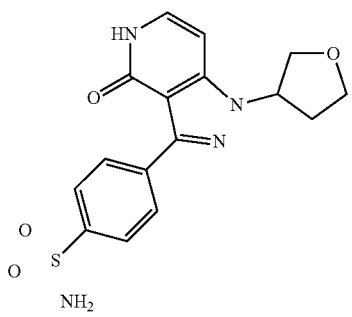 | 4-(4-oxo-1-(tetrahydrofuran-3-yl)-4,5-dihydro-1H-pyrazolo[4,3-c]pyridin-3-yl)benzenesulfonamide |
| 85 | 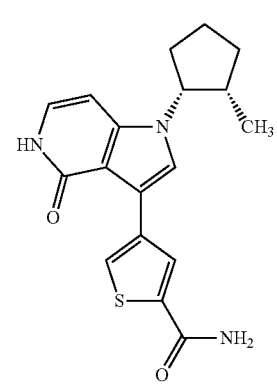 [SMILES: C[C@H]1CCC[C@H]1n1cc(-c2csc(C(N)=O)c2)c2c(=O)[nH]ccc21] | 4-(1-(cis-2-methylcyclopentyl)-4-oxo-4,5-dihydro-1H-pyrrolo[3,2-c]pyridin-3-yl)thiophene-2-carboxamide |
| 86 | 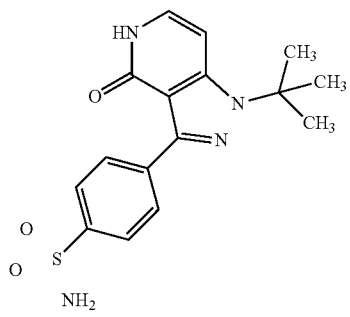 | 4-(1-tert-butyl-4-oxo-4,5-dihydro-1H-pyrazolo[4,3-c]pyridin-3-yl)benzenesulfonamide |

TABLE 2-continued

| Ex. | Structural Formula | Compound Name |
|---|---|---|
| 87 | | 4-(4-oxo-1-(tetrahydro-2H-pyran-3-yl)-4,5-dihydro-1H-pyrazolo[4,3-c]pyridin-3-yl)benzenesulfonamide |
| 88 | | 4-(4-oxo-1-(tetrahydro-2H-pyran-3-yl)-4,5-dihydro-1H-pyrazolo[4,3-c]pyridin-3-yl)benzenesulfonamide |
| 89 | | 3-(7-cyano-1-cyclopentyl-4-oxo-4,5-dihydro-1H-pyrrolo[3,2-c]pyridin-3-yl)benzamide |
| 90 | | 4-(1-((2,2-dimethyl-1,3-dioxolan-4-yl)methyl)-4-oxo-4,5-dihydro-1H-pyrrolo[3,2-c]pyridin-3-yl)benzenesulfonamide |
| 91 | | 4-(1-(2,3-dihydroxypropyl)-4-oxo-4,5-dihydro-1H-pyrrolo[3,2-c]pyridin-3-yl)benzenesulfonamide |

TABLE 2-continued
| Ex. | Structural Formula | Compound Name |
|---|---|---|
| 92 | 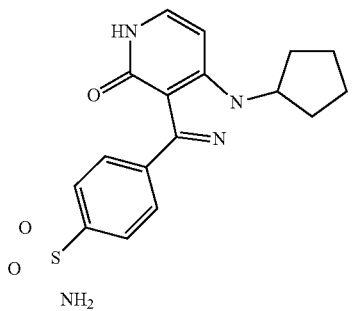 | 4-(1-cyclopentyl-4-oxo-4,5-dihydro-1H-pyrazolo[4,3-c]pyridin-3-yl)benzenesulfonamide |
| 93 | 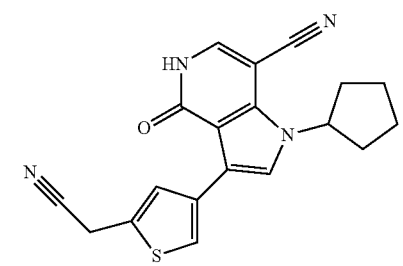 [SMILES: N#CCc1cc(-c2cn(C3CCCC3)c3c(C#N)c[nH]c(=O)c23)cs1] | 3-(5-(cyanomethyl)-3-thienyl)-1-cyclopentyl-4-oxo-4,5-dihydro-1H-pyrrolo[3,2-c]pyridine-7-carbonitrile |
| 94 | 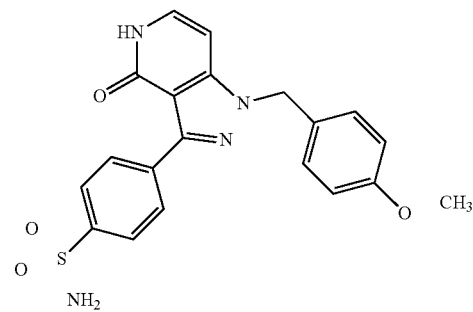 | 4-(1-(4-methoxybenzyl)-4-oxo-4,5-dihydro-1H-pyrazolo[4,3-c]pyridin-3-yl)benzenesulfonamide |
| 95 | 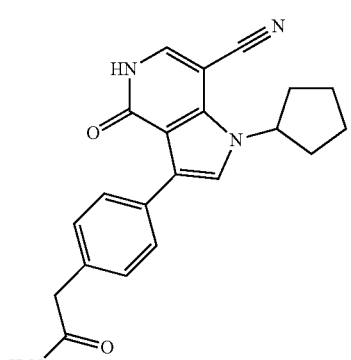 | 2-(4-(7-cyano-1-cyclopentyl-4-oxo-4,5-dihydro-1H-pyrrolo[3,2-c]pyridin-3-yl)phenyl)acetamide |

TABLE 2-continued

| Ex. | Structural Formula | Compound Name |
|---|---|---|
| 96 | | 3-(4-(cyanomethyl)phenyl)-1-cyclopentyl-4-oxo-4,5-dihydro-1H-pyrrolo[3,2-c]pyridine-7-carbonitrile |
| 97 | | 2-(4-(7-cyano-1-cyclopentyl-4-oxo-4,5-dihydro-1H-pyrrolo[3,2-c]pyridin-3-yl)-2-thienyl)acetamide |
| 98 | | 2-(4-(7-cyano-1-cyclopentyl-4-oxo-4,5-dihydro-1H-pyrrolo[3,2-c]pyridin-3-yl)-1H-pyrazol-1-yl)acetamide |
| 99 | | 3-(1-(cyanomethyl)-1H-pyrazol-4-yl)-1-cyclopentyl-4-oxo-4,5-dihydro-1H-pyrrolo[3,2-c]pyridine-7-carbonitrile |
| 100 | | 4-(1-((3-methyloxetan-3-yl)methyl)-4-oxo-4,5-dihydro-1H-pyrazolo[4,3-c]pyridin-3-yl)benzenesulfonamide |

TABLE 2-continued

| Ex. | Structural Formula | Compound Name |
|---|---|---|
| 101 | | 4-(7-bromo-1-cyclopentyl-4-oxo-4,5-dihydro-1H-pyrazolo[4,3-c]pyridin-3-yl)benzenesulfonamide |
| 102 | | 4-(4-cyano-3-(2-methylphenyl)-7-oxo-6,7-dihydro-1H-pyrrolo[2,3-c]pyridin-1-yl)thiophene-2-carboxamide |
| 103 | | 1-cyclopentyl-4-oxo-3-phenyl-4,5-dihydro-1H-pyrrolo[3,2-c]pyridine-7-carbonitrile |
| 104 | | (4-(7-bromo-1-(2,6-difluorophenyl)-4-oxo-4,5-dihydro-1H-pyrazolo[4,3-c]pyridin-3-yl)phenyl)acetonitrile |
| 105 | | 4-(1-(oxetan-3-ylmethyl)-4-oxo-4,5-dihydro-1H-pyrazolo[4,3-c]pyridin-3-yl)benzenesulfonamide |

TABLE 2-continued

| Ex. | Structural Formula | Compound Name |
| --- | --- | --- |
| 106 | | 1-cyclopentyl-4-oxo-3-(3-thienyl)-4,5-dihydro-1H-pyrrolo[3,2-c]pyridine-7-carbonltrile |
| 107 | | 4-(7-cyano-1-cyclopentyl-4-oxo-4,5-dihydro-1H-pyrrolo[3,2-c]pyridin-3-yl)-N,N-dimethylthiophene-2-carboxamide |
| 108 | | 4-(7-cyano-1-cyclopentyl-4-oxo-4,5-dihydro-1H-pyrrolo[3,2-c]pyridin-3-yl)-N-methylthiophene-2-carboxamide |
| 109 | | 3-(3-(cyanomethyl)phenyl)-1-cyclopentyl-4-oxo-4,5-dihydro-1H-pyrrolo[3,2-c]pyridine-7-carbonitrile |
| 110 | | 2-(3-(7-cyano-1-cyclopentyl-4-oxo-4,5-dihydro-1H-pyrrolo[3,2-c]pyridin-3-yl)phenyl)acetamide |

TABLE 2-continued

| Ex. | Structural Formula | Compound Name |
|---|---|---|
| 111 | | 1-cyclopentyl-4-oxo-3-(1H-pyrazol-4-yl)-4,5-dihydro-1H-pyrrolo[3,2-c]pyridine-7-carbonitrile |
| 112 | | 2-(4-(7-bromo-1-(2,6-difluorophenyl)-4-oxo-4,5-dihydro-1H-pyrazolo[4,3-c]pyridin-3-yl)phenyl)acetamide |
| 113 | | methyl 4-(1-(4-methoxybenzyl)-4-oxo-4,5-dihydro-1H-pyrazolo[4,3-c]pyridin-3-yl)thiophene-2-carboxylate |
| 114 | | 4-(1-(4-methoxybenzyl)-4-oxo-4,5-dihydro-1H-pyrazolo[4,3-c]pyridin-3-yl)thiophene-2-carboxamide |
| 115 | | 4-(4-oxo-1-(tetrahydrofuran-3-ylmethyl)-4,5-dihydro-1H-pyrazolo[4,3-c]pyridin-3-yl)benzenesulfonamide |

TABLE 2-continued

| Ex. | Structural Formula | Compound Name |
|---|---|---|
| 116 | | (4-(7-chloro-1-(2,6-difluorophenyl)-4-oxo-4,5-dihydro-1H-pyrazolo[4,3-c]pyridin-3-yl)phenyl)acetonitrile |
| 117 | | 4-(3-cyclopentyl-7-oxo-6,7-dihydro-1H-pyrazolo[3,4-c]pyridin-1-yl)thiophene-2-carboxamide |
| 118 | | 4-(4-cyano-3-cyclopentyl-7-oxo-6,7-dihydro-1H-pyrrolo[2,3-c]pyridin-1-yl)thiophene-2-carboxamide |
| 119 | | 4-(1-(4-hydroxycyclohexyl)-4-oxo-4,5-dihydro-1H-pyrazolo[4,3-c]pyridin-3-yl)benzenesulfonamide |

TABLE 2-continued

| Ex. | Structural Formula | Compound Name |
|---|---|---|
| 120 | 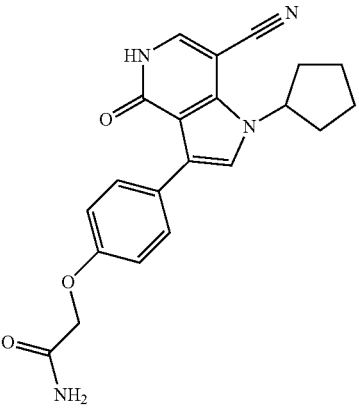 [SMILES: N#Cc1c[nH]c(=O)c2c(-c3ccc(OCC(N)=O)cc3)cn(C3CCCC3)c12] | 2-(4-(7-cyano-1-cyclopentyl-4-oxo-4,5-dihydro-1H-pyrrolo[3,2-c]pyridin-3-yl)phenoxy)acetamide |
| 121 | 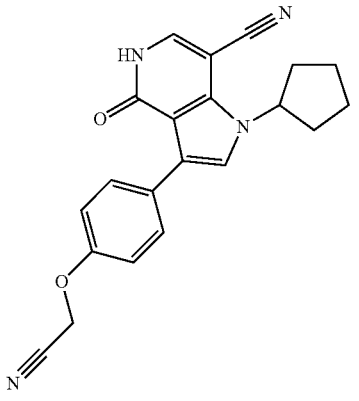 [SMILES: N#CCOc1ccc(-c2cn(C3CCCC3)c3c(C#N)c[nH]c(=O)c23)cc1] | 3-(4-(cyanomethoxy)phenyl)-1-cyclopentyl-4-oxo-4,5-dihydro-1H-pyrrolo[3,2-c]pyridine-7-carbonitrile |
| 122 | 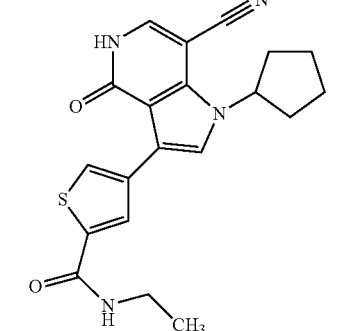 | 4-(7-cyano-1-cyclopentyl-4-oxo-4,5-dihydro-1H-pyrrolo[3,2-c]pyridin-3-yl)-N-ethylthiophene-2-carboxamide |
| 123 | 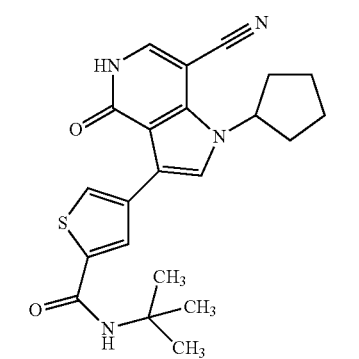 [SMILES: CC(C)(C)NC(=O)c1cc(-c2cn(C3CCCC3)c3c(C#N)c[nH]c(=O)c23)cs1] | N-tert-butyl-4-(7-cyano-1-cyclopentyl-4-oxo-4,5-dihydro-1H-pyrrolo[3,2-c]pyridin-3-yl)thiophene-2-carboxamide |

TABLE 2-continued

| Ex. | Structural Formula | Compound Name |
|---|---|---|
| 124 | 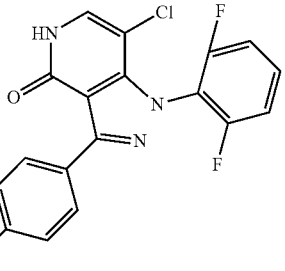 | 2-(4-(7-chloro-1-(2,6-difluorophenyl)-4-oxo-4,5-dihydro-1H-pyrazolo[4,3-c]pyridin-3-yl)phenyl)acetamide |
| 125 | 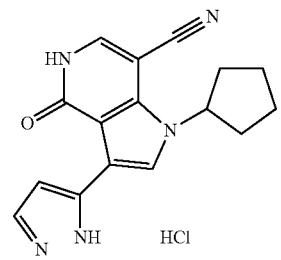 [SMILES: N#Cc1c[nH]c(=O)c2c(/C(N)=C/C=N)cn(C3CCCC3)c12 ; Cl] | 1-cyclopentyl-4-oxo-3-(1H-pyrazol-5-yl)-4,5-dihydro-1H-pyrrolo[3,2-c]pyridine-7-carbonitrile hydrochloride |
| 126 | 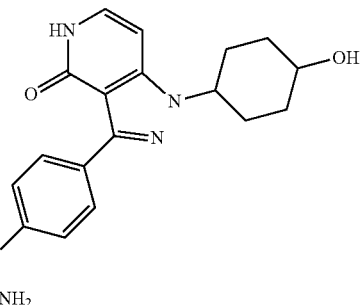 | 4-(1-(4-hydroxycyclohexyl)-4-oxo-4,5-dihydro-1H-pyrazolo[4,3-c]pyridin-3-yl)benzenesulfonamide |
| 127 | 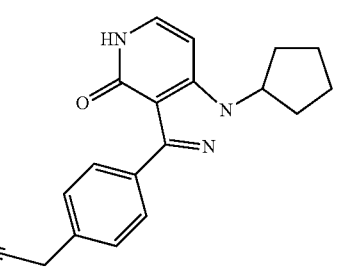 | (4-(1-cyclopentyl-4-oxo-4,5-dihydro-1H-pyrazolo[4,3-c]pyridin-3-yl)phenyl)acetonitrile |
| 128 | 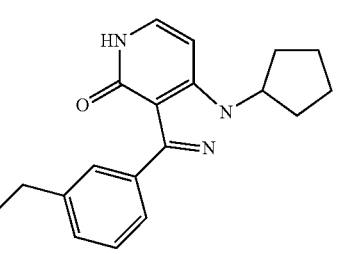 | (3-(1-cyclopentyl-4-oxo-4,5-dihydro-1H-pyrazolo[4,3-c]pyridin-3-yl)phenyl)acetonitrile |

TABLE 2-continued

| Ex. | Structural Formula | Compound Name |
|---|---|---|
| 129 | | 4-(1-tert-butyl-4-oxo-4,5-dihydro-1H-pyrazolo[4,3-c]pyridin-3-yl)thiophene-2-carboxamide |
| 130 | | N-(3-(7-cyano-1-cyclopentyl-4-oxo-4,5-dihydro-1H-pyrrolo[3,2-c]pyridin-3-yl)phenyl)acetamide |
| 131 | | 1-cyclopentyl-3-(1-methyl-1H-pyrazol-4-yl)-4-oxo-4,5-dihydro-1H-pyrrolo[3,2-c]pyridine-7-carbonitrile |
| 132 | | 1-cyclopentyl-4-oxo-3-(pyridin-2-yl)-4,5-dihydro-1H-pyrrolo[3,2-c]pyridine-7-carbonitrile |
| 133 | | 1-cyclopentyl-4-oxo-3-(pyridin-3-yl)-4,5-dihydro-1H-pyrrolo[3,2-c]pyridine-7-carbonitrile |

TABLE 2-continued

| Ex. | Structural Formula | Compound Name |
|---|---|---|
| 134 | | 1-cyclopentyl-4-oxo-3-(2-thienyl)-4,5-dihydro-1H-pyrrolo[3,2-c]pyridine-7-carbonitrile |
| 135 | | 1-cyclopentyl-3-(1-isobutyl-1H-pyrazol-4-yl)-4-oxo-4,5-dihydro-1H-pyrrolo[3,2-c]pyridine-7-carbonitrile |
| 136 | | 1-cyclopentyl-3-(1-methyl-1H-pyrazol-3-yl)-4-oxo-4,5-dihydro-1H-pyrrolo[3,2-c]pyridine-7-carbonitrile |
| 137 | | 1-cyclopentyl-3-(1-cyclopentyl-1H-pyrazol-4-yl)-4-oxo-4,5-dihydro-1H-pyrrolo[3,2-c]pyridine-7-carbonitrile |
| 138 | | 1-cyclopentyl-3-(1-cyclopropyl-1H-pyrazol-4-yl)-4-oxo-4,5-dihydro-1H-pyrrolo[3,2-c]pyridine-7-carbonitrile |

TABLE 2-continued

| Ex. | Structural Formula | Compound Name |
|---|---|---|
| 139 | | 3-(4-(2-cyanopropan-2-yl)phenyl)-1-cyclopentyl-4-oxo-4,5-dihydro-1H-pyrrolo[3,2-c]pyridine-7-carbonitrile |
| 140 | | 1-cyclopentyl-3-(3-(morpholin-4-yl)phenyl)-4-oxo-4,5-dihydro-1H-pyrrolo[3,2-c]pyridine-7-carbonitrile |
| 141 | | 4-(1-((3-methyloxetan-3-yl)methyl)-4-oxo-4,5-dihydro-1H-pyrazolo[4,3-c]pyridin-3-yl)thiophene-2-carboxamide |
| 142 | | 4-(1-cyclopentyl-4-oxo-4,5-dihydro-1H-pyrazolo[4,3-c]pyridin-3-yl)benzamide |
| 143 | | 3-(1-cyclopentyl-4-oxo-4,5-dihydro-1H-pyrazolo[4,3-c]pyridin-3-yl)benzamide |

TABLE 2-continued

| Ex. | Structural Formula | Compound Name |
|---|---|---|
| 144 | | 4-(7-bromo-1-(2,6-difluorophenyl)-4-oxo-4,5-dihydro-1H-pyrazolo[4,3-c]pyridin-3-yl)thiophene-2-carboxamide |
| 145 | | 4-(7-bromo-1-(2,6-difluorophenyl)-4-oxo-4,5-dihydro-1H-pyrazolo[4,3-c]pyridin-3-yl)-N-methylthiophene-2-carboxamide |
| 146 | | (3-(7-bromo-1-(2,6-difluorophenyl)-4-oxo-4,5-dihydro-1H-pyrazolo[4,3-c]pyridin-3-yl)phenyl)acetonitrile |
| 147 | | 2-(3-(7-bromo-1-(2,6-difluorophenyl)-4-oxo-4,5-dihydro-1H-pyrazolo[4,3-c]pyridin-3-yl)phenyl)acetamide |
| 148 | | 4-(1-(1,4-dioxaspiro[4.5]dec-8-yl)-4-oxo-4,5-dihydro-1H-pyrazolo[4,3-c]pyridin-3-yl)thiophene-2-carboxamide |

TABLE 2-continued

| Ex. | Structural Formula | Compound Name |
|---|---|---|
| 149 | | 4-(4-oxo-1-(pentan-3-yl)-4,5-dihydro-1H-pyrazolo[4,3-c]pyridin-3-yl)thiophene-2-carboxamide |
| 150 | | 4-(1-(1-methoxybutan-2-yl)-4-oxo-4,5-dihydro-1H-pyrazolo[4,3-c]pyridin-3-yl)thiophene-2-carboxamide |
| 151 | | 1-(2,6-difluorophenyl)-3-(1H-pyrazol-4-yl)-1,5-dihydro-4H-pyrazolo[4,3-c]pyridin-4-one |
| 152 | | (4-(7-chloro-1-(2,6-difluorophenyl)-4-oxo-4,5-dihydro-1H-pyrazolo[4,3-c]pyridin-3-yl)-2-thienyl)acetonitrile |
| 153 | | 2-(4-(7-bromo-1-(2,6-difluorophenyl)-4-oxo-4,5-dihydro-1H-pyrazolo[4,3-c]pyridin-3-yl)phenyl)-N-methylacetamide |

TABLE 2-continued

| Ex. | Structural Formula | Compound Name |
|---|---|---|
| 154 | 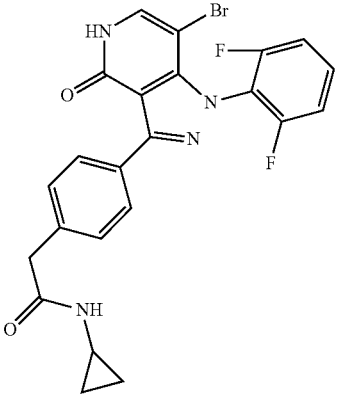 [SMILES: N=C(c1ccc(CC(=O)NC2CC2)cc1)c1c(Nc2c(F)cccc2F)c(Br)c[nH]c1=O] | 2-(4-(7-bromo-1-(2,6-difluorophenyl)-4-oxo-4,5-dihydro-1H-pyrazolo[4,3-c]pyridin-3-yl)phenyl)-N-cyclopropylacetamide |
| 155 | 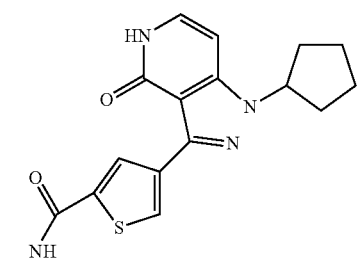 | 4-(1-cyclopentyl-4-oxo-4,5-dihydro-1H-pyrazolo[4,3-c]pyridin-3-yl)-N-methylthiophene-2-carboxamide |
| 156 | 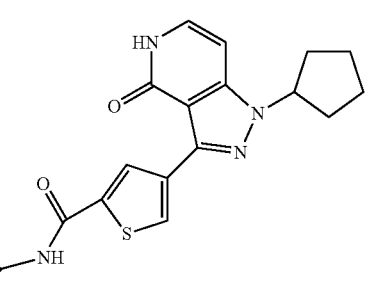 | 4-(1-cyclopentyl-4-oxo-4,5-dihydro-1H-pyrazolo[4,3-c]pyridin-3-yl)-N-cyclopropylthiophene-2-carboxamide |
| 157 | 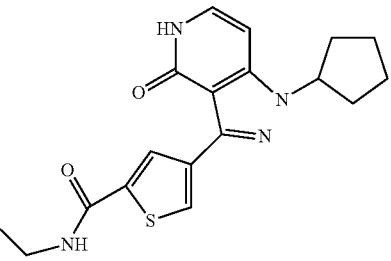 | 4-(1-cyclopentyl-4-oxo-4,5-dihydro-1H-pyrazolo[4,3-c]pyridin-3-yl)-N-(2-hydroxyethyl)thiophene-2-carboxamide |
| 158 | 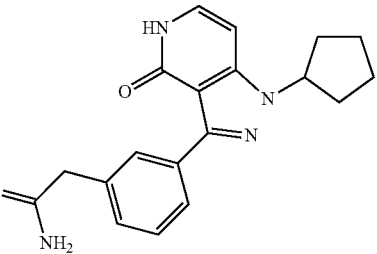 | 2-(3-(1-cyclopentyl-4-oxo-4,5-dihydro-1H-pyrazolo[4,3-c]pyridin-3-yl)phenyl)acetamide |

TABLE 2-continued

| Ex. | Structural Formula | Compound Name |
|---|---|---|
| 159 | | 3-(1-cyclopentyl-4-oxo-4,5-dihydro-1H-pyrazolo[4,3-c]pyridin-3-yl)benzenesulfonamide |
| 160 | | 2-(4-(7-chloro-1-(2,6-difluorophenyl)-4-oxo-4,5-dihydro-1H-pyrazolo[4,3-c]pyridin-3-yl)-2-thienyl)acetamide |
| 161 | | 7-chloro-1-(2,6-difluorophenyl)-3-(4-(morpholin-4-yl)phenyl)-1,5-dihydro-4H-pyrazolo[4,3-c]pyridin-4-one |
| 162 | | 4-(7-chloro-1-(2,6-difluorophenyl)-4-oxo-4,5-dihydro-1H-pyrazolo[4,3-c]pyridin-3-yl)-N-methylthiophene-2-carboxamide |

TABLE 2-continued

| Ex. | Structural Formula | Compound Name |
|---|---|---|
| 163 | | 4-(7-chloro-1-(2,6-difluorophenyl)-4-oxo-4,5-dihydro-1H-pyrazolo[4,3-c]pyridin-3-yl)-N-(1-cyanocyclopropyl)thiophene-2-carboxamide |
| 164 | | 7-chloro-1-(2,6-difluorophenyl)-3-(6-(morpholin-4-yl)pyridin-3-yl)-1,5-dihydro-4H-pyrazolo[4,3-c]pyridin-4-one |
| 165 | | 4-(7-cyano-1-cyclopentyl-4-oxo-4,5-dihydro-1H-pyrazolo[4,3-c]pyridin-3-yl)thiophene-2-carboxamide |
| 166 | | 4-(7-chloro-1-(2,6-difluorophenyl)-4-oxo-4,5-dihydro-1H-pyrazolo[4,3-c]pyridin-3-yl)-N-(1-methyl-1H-pyrazol-4-yl)thiophene-2-carboxamide |

TABLE 2-continued

| Ex. | Structural Formula | Compound Name |
|---|---|---|
| 167 | | (4-(7-chloro-1-(2,6-difluorophenyl)-4-oxo-4,5-dihydro-1H-pyrazolo[4,3-c]pyridin-3-yl)phenoxy)acetonitrile |
| 168 | | 7-chloro-1-(2,6-difluorophenyl)-3-(3-(2-hydroxyethoxy)phenyl)-1,5-dihydro-4H-pyrazolo[4,3-c]pyridin-4-one |
| 169 | | 2-(4-(7-chloro-1-(2,6-difluorophenyl)-4-oxo-4,5-dihydro-1H-pyrazolo[4,3-c]pyridin-3-yl)phenoxy)acetamide |
| 170 | | 4-(4-oxo-1-(4-oxocyclohexyl)-4,5-dihydro-1H-pyrazolo[4,3-c]pyridin-3-yl)thiophene-2-carboxamide |
| 171 | | 4-(1-(4-hydroxycyclohexyl)-4-oxo-4,5-dihydro-1H-pyrazolo[4,3-c]pyridin-3-yl)thiophene-2-carboxamide |

TABLE 2-continued

| Ex. | Structural Formula | Compound Name |
| --- | --- | --- |
| 172 | | 4-(1-(4-hydroxy-4-phenylcyclohexyl)-4-oxo-4,5-dihydro-1H-pyrazolo[4,3-c]pyridin-3-yl)thiophene-2-carboxamide |
| 173 | | 4-(4-oxo-1-(4-oxocyclohexyl)-4,5-dihydro-1H-pyrazolo[4,3-c]pyridin-3-yl)benzenesulfonamide |
| 174 | | 4-(1-(4-hydroxy-4-phenylcyclohexyl)-4-oxo-4,5-dihydro-1H-pyrazolo[4,3-c]pyridin-3-yl)benzenesulfonamide |
| 175 | | 2-(4-(7-bromo-1-(2,6-difluorophenyl)-4-oxo-4,5-dihydro-1H-pyrazolo[4,3-c]pyridin-3-yl)-1H-pyrazol-1-yl)acetamide |
| 176 | | 7-bromo-1-(2,6-difluorophenyl)-3-(1H-pyrazol-4-yl)-1,5-dihydro-4H-pyrazolo[4,3-c]pyridin-4-one |

TABLE 2-continued

| Ex. | Structural Formula | Compound Name |
|---|---|---|
| 177 | | 7-chloro-1-(2,6-difluorophenyl)-3-(1H-pyrazol-4-yl)-1,5-dihydro-4H-pyrazolo[4,3-c]pyridin-4-one |
| 178 | | 3-((7-cyano-1-cyclopentyl-4-oxo-4,5-dihydro-1H-pyrrolo[3,2-c]pyridin-3-yl)amino)benzamide |
| 179 | | 1-(2,6-difluorophenyl)-3-(4-(morpholin-4-yl)phenyl)-1,5-dihydro-4H-pyrazolo[4,3-c]pyridin-4-one |
| 180 | | 4-(1-(2,6-difluorophenyl)-4-oxo-4,5-dihydro-1H-pyrazolo[4,3-c]pyridin-3-yl)-N-methylbenzamide |

Example 181

1-(2,6-difluorophenyl)-3-(4-(morpholin-4-yl)phenyl)-1,5-dihydro-4H-pyrazolo[4,3-c]pyridin-4-one hydrochloride To a solution of 1-(2,6-difluorophenyl)-3-(4-(morpholin-4-yl)phenyl)-1,5-dihydro-4H-pyrazolo[4,3-c]pyridin-4-one (500 mg) obtained in Example 179 in ethanol (4 mL) was added 4M hydrogen chloride ethyl acetate (0.612 mL), and the mixture was stirred at room temperature for 30 min. The reaction mixture was concentrated, and the residue was crystallized from DMSO and ethyl acetate to give the title compound (433 mg).

MS (ESI+): [M+H]$^+$ 409.4.

MS (ESI+). found: 409.3.

Example 182

2-(4-(1-cyclopentyl-4-oxo-4,5-dihydro-1H-pyrazolo[4,3-c]pyridin-3-yl)phenyl)acetamide The title compound was obtained using (4-(1-cyclopentyl-4-oxo-4,5-dihydro-1H-pyrazolo[4,3-c]pyridin-3-yl)phenyl)acetonitrile obtained in Example 127, in the same manner as in Example 158.
MS (ESI+): [M+H]$^+$ 337.2.
MS (ESI+). found: 336.9.

Example 183

4-(1-(trans-4-hydroxycyclohexyl)-4-oxo-4,5-dihydro-1H-pyrazolo[4,3-c]pyridin-3-yl)thiophene-2-carboxamide To a solution of 4-(4-oxo-1-(4-oxocyclohexyl)-4,5-dihydro-1H-pyrazolo[4,3-c]pyridin-3-yl)thiophene-2-carboxamide (40.0 mg) obtained in Example 170 in THF was added sodium borohydride (8.49 mg) at 0° C., and the mixture was stirred overnight at room temperature under nitrogen atmosphere. To the reaction solution was added 1N hydrochloric acid at 0° C., and the mixture was extracted with ethyl acetate. The organic layer was washed with saturated aqueous sodium hydrogencarbonate solution and saturated brine, dried over anhydrous magnesium sulfate, filtered, and concentrated under reduced pressure. The obtained residue was purified by silica gel column chromatography (ethyl acetate/methanol) to give a cis/trans mixture (30.9 mg) of the title compound. The obtained cis/trans mixture was purified by HPLC (column: L-column2 ODS (trade name) 20 mmID×150 mmL, 5 μm, manufactured by Daicel Chemical Industries, mobile phase: water/acetonitrile (containing 10 mM ammonium carbonate)) to give the title compound having a shorter retention time.
MS (ESI+): [M+H]$^+$ 359.1.
MS (ESI+). found: 359.3.

Example 184

4-(1-(cis-4-hydroxycyclohexyl)-4-oxo-4,5-dihydro-1H-pyrazolo[4,3-c]pyridin-3-yl)thiophene-2-carboxamide The cis/trans mixture (30.9 mg) obtained in Example 183 was purified by HPLC (column: L-column2 ODS (trade name) 20 mmID×150 mmL, 5 μm, manufactured by Daicel Chemical Industries, mobile phase: water/acetonitrile (containing 10 mM ammonium carbonate)) to give the title compound having a longer retention time.
MS (ESI+): [M+H]$^+$ 359.1.
MS (ESI+). found: 359.3.

Example 185

7-chloro-1-(2,6-difluorophenyl)-3-(4-(morpholin-4-ylmethyl)phenyl)-1,5-dihydro-4H-pyrazolo[4,3-c]pyridin-4-one A) (4-(morpholino methyl)phenyl)boronic acid To a mixture of (4-(bromomethyl)phenyl)boronic acid (500 mg) and potassium carbonate (643 mg) in acetonitrile (10 mL) was added morpholine (0.304 mL), and the mixture was stirred at room temperature for 60 hr. To the reaction mixture was added water, and the mixture was extracted with ethyl acetate. The organic layer was washed with saturated brine, dried over anhydrous magnesium sulfate, and concentrated under reduced pressure. The obtained solid was washed with diisopropyl ether and ethyl acetate to give the title compound (449 mg).
MS(ESI+): [M+H]$^+$ 222.1.
MS(ESI+). found: 222.2.

B) 7-chloro-1-(2,6-difluorophenyl)-3-(4-(morpholin-4-ylmethyl)phenyl)-1,5-dihydro-4H-pyrazolo[4,3-c]pyridin-4-one The title compound (64.0 mg) was obtained using 7-chloro-1-(2,6-difluorophenyl)-4-methoxy-1H-pyrazolo[4,3-c]pyridin-3-yl trifluoromethanesulfonate obtained in Step A of Example 152 (200 mg) and (4-(morpholino methyl)phenyl)boronic acid (149 mg), in the same manner as in Step B of Example 152 and Step C of Example 152.
MS(ESI+): [M+H]$^+$ 457.1.
MS(ESI+). found: 457.3.

Example 186

7-chloro-1-(2,6-difluorophenyl)-3-(4-((2-oxo-1,3-oxazolidin-3-yl)methyl)phenyl)-1,5-dihydro-4H-pyrazolo[4,3-c]pyridin-4-one A) (4-((2-oxo-1,3-oxazolidin-3-yl)methyl)phenyl)boronic acid To a solution of oxazolidin-2-one (243 mg) in anhydrous DMF (10 mL) was added sodium hydride (60% dispersion in mineral oil, 140 mg) in small portions under ice-cooling. The reaction mixture was stirred at room temperature for 2 hr, to the reaction mixture was added (4-(bromomethyl)phenyl)boronic acid (500 mg), and the mixture was stirred for 60 hr. To the reaction mixture was added ice water, and the aqueous layer was neutralized with 1N hydrochloric acid under ice-cooling, and the mixture was extracted with ethyl acetate. The organic layer was washed with saturated brine, dried over anhydrous magnesium sulfate, and concentrated under reduced pressure. The residue was washed with diisopropyl ether and ethyl acetate to give the title compound (273 mg).
MS(ESI+): [M+H]$^+$ 222.1.
MS(ESI+). found: 222.1.

B) 7-chloro-1-(2,6-difluorophenyl)-3-(4-((2-oxo-1,3-oxazolidin-3-yl)methyl)phenyl)-1,5-dihydro-4H-pyrazolo[4,3-c]pyridin-4-one The title compound (151 mg) was obtained using 7-chloro-1-(2,6-difluorophenyl)-4-methoxy-1H-pyrazolo[4,3-c]pyridin-3-yl trifluoromethanesulfonate obtained in Step A of Example 152 (200 mg) and (4-((2-oxo-1,3-oxazolidin-3-yl)methyl)phenyl)boronic acid (149 mg), in the same manner as in Step B of Example 152 and Step C of Example 152.
MS(ESI+): [M+H]$^+$ 457.1.
MS(ESI+). found: 457.2.

Example 187

2-(4-(7-chloro-1-(2,6-difluorophenyl)-4-oxo-4,5-dihydro-1H-pyrazolo[4,3-c]pyridin-3-yl)phenyl)-2-methylpropanenitrile The title compound was obtained using 7-chloro-1-(2,6-difluorophenyl)-4-methoxy-1H-pyrazolo[4,3-c]pyridin-3-yl trifluoromethanesulfonate obtained in Step A of Example 152 and (4-(2-cyanopropan-2-yl)phenyl)boronic acid, in the same manner as in Step D of Example 35 and Step C of Example 93.

MS (ESI+): [M+H]+ 425.1.
MS (ESI+). found: 425.3.

Example 188

2-(4-(7-chloro-1-(2,6-difluorophenyl)-4-oxo-4,5-dihydro-1H-pyrazolo[4,3-c]pyridin-3-yl)phenyl)-2-methylpropanamide The title compound was obtained using 2-(4-(7-chloro-1-(2,6-difluorophenyl)-4-oxo-4,5-dihydro-1H-pyrazolo[4,3-c]pyridin-3-yl)phenyl)-2-methylpropanenitrile obtained in Example 187, in the same manner as in Example 72.

MS (ESI+): [M+H]+ 443.1.
MS (ESI+). found: 443.1.

Example 189

7-chloro-1-(2,6-difluorophenyl)-3-(1-methyl-1H-pyrazol-4-yl)-1,5-dihydro-4H-pyrazolo[4,3-c]pyridin-4-one The title compound was obtained using 7-chloro-1-(2,6-difluorophenyl)-4-methoxy-1H-pyrazolo[4,3-c]pyridin-3-yl trifluoromethanesulfonate obtained in Step A of Example 152, in the same manner as in Step A of Example 131 and Step J of Example 33.

MS (ESI+): [M+H]+ 361.7.
MS (ESI+). found: 361.1.

Example 190

2-(4-(7-chloro-1-(2,6-difluorophenyl)-4-oxo-4,5-dihydro-1H-pyrazolo[4,3-c]pyridin-3-yl)-1H-pyrazol-1-yl)acetamide The title compound was obtained using 7-chloro-1-(2,6-difluorophenyl)-4-methoxy-1H-pyrazolo[4,3-c]pyridin-3-yl trifluoromethanesulfonate obtained in Step A of Example 152, in the same manner as in Step A to Step C of Example 98.

MS (ESI+): [M+H]+ 405.8.
MS (ESI+). found: 405.2.

Example 191

4-(7-chloro-1-(2,6-difluorophenyl)-4-oxo-4,5-dihydro-1H-pyrazolo[4,3-c]pyridin-3-yl)-N-(cyanomethyl)thiophene-2-carboxamide The title compound was obtained using 7-chloro-1-(2,6-difluorophenyl)-4-methoxy-1H-pyrazolo[4,3-c]pyridin-3-yl trifluoromethanesulfonate obtained in Step A of Example 152, methyl 4-(4,4,5,5-tetramethyl-1,3,2-dioxaborolan-2-yl)thiophene-2-carboxylate and aminoacetonitrile, in the same manner as in Step I of Example 33, Step F of Example 33, Step J of Example 33 and Step G of Example 33.

MS (ESI+): [M+H]+ 445.8.
MS (ESI+). found: 445.7.

Example 192

7-chloro-1-(2,6-difluorophenyl)-3-(5-(morpholin-4-ylcarbonyl)-3-thienyl)-1,5-dihydro-4H-pyrazolo[4,3-c]pyridin-4-one The title compound was obtained using 7-chloro-1-(2,6-difluorophenyl)-4-methoxy-1H-pyrazolo[4,3-c]pyridin-3-yl trifluoromethanesulfonate obtained in Step A of Example 152, methyl 4-(4,4,5,5-tetramethyl-1,3,2-dioxaborolan-2-yl)thiophene-2-carboxylate and morpholine, in the same manner as in Step I of Example 33, Step F of Example 33, Step J of Example 33 and Step G of Example 33.

MS (ESI+): [M+H]+ 476.8.
MS (ESI+). found: 476.7.

Example 193

4-(7-chloro-1-(2,6-difluorophenyl)-4-oxo-4,5-dihydro-1H-pyrazolo[4,3-c]pyridin-3-yl)-N-(morpholin-4-yl)thiophene-2-carboxamide The title compound was obtained using 7-chloro-1-(2,6-difluorophenyl)-4-methoxy-1H-pyrazolo[4,3-c]pyridin-3-yl trifluoromethanesulfonate obtained in Step A of Example 152, methyl 4-(4,4,5,5-tetramethyl-1,3,2-dioxaborolan-2-yl)thiophene-2-carboxylate and morpholin-4-amine, in the same manner as in Step I of Example 33, Step F of Example 33, Step J of Example 33 and Step G of Example 33.

MS (ESI+): [M+H]+ 492.9.
MS (ESI+). found: 493.1.

Example 194

4-(7-chloro-1-(2,6-difluorophenyl)-4-oxo-4,5-dihydro-1H-pyrazolo[4,3-c]pyridin-3-yl)-N-methylbenzamide A) methyl 4-(7-chloro-1-(2,6-difluorophenyl)-4-methoxy-1H-pyrazolo[4.3-c]pyridin-3-yl)benzoate The title compound (118 mg) was obtained using 7-chloro-1-(2,6-difluorophenyl)-4-methoxy-1H-pyrazolo[4,3-c]pyridin-3-yl trifluoromethanesulfonate obtained in Step A of Example 152 (200 mg) and (4-(methoxycarbonyl)phenyl)boronic acid (122 mg), in the same manner as in Step B of Example 152.

MS(ESI+): [M+H]+ 430.1.
MS(ESI+). found: 430.2.

B) 4-(7-chloro-1-(2,6-difluorophenyl)-4-methoxy-1H-pyrazolo[4,3-c]pyridin-3-yl)benzoic acid To a mixture of methyl 4-(7-chloro-1-(2,6-difluorophenyl)-4-methoxy-1H-pyrazolo[4.3-c]pyridin-3-yl)benzoate (118 mg) in a mixed solvent of methanol (2 mL) and THF (1 mL) was added 1N aqueous sodium hydroxide solution (1 mL) at room temperature, and the mixture was stirred at room temperature for 4 hr. The reaction mixture was neutralized with 1N hydrochloric acid under ice-cooling, and the mixture was concentrated under reduced pressure. The obtained solid was washed with water to give the title compound (78.0 mg).

MS(ESI+): [M+H]+ 416.1.
MS(ESI+). found: 416.2.

C) 4-(7-chloro-1-(2,6-difluorophenyl)-4-methoxy-1H-pyrazolo[4,3-c]pyridin-3-yl)-N-methylbenzamide To a solution of 4-(7-chloro-1-(2,6-difluorophenyl)-4-methoxy-1H-pyrazolo[4,3-c]pyridin-3-yl)benzoic acid (78.3 mg) in anhydrous DMF (3 mL) were added methylammonium chloride (25.4 mg), EDCI hydrochloride (72.2 mg), HOBt (57.7 mg) and triethylamine (0.052 mL) at room temperature, and the mixture was stirred at room temperature for 96 hr. The reaction mixture was diluted with water, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (72.0 mg).
MS(ESI+): [M+H]$^+$ 429.1.
MS(ESI+). found: 429.2.

D) 4-(7-chloro-1-(2,6-difluorophenyl)-4-oxo-4,5-dihydro-1H-pyrazolo[4,3-c]pyridin-3-yl)-N-methylbenzamide The title compound (47 mg) was obtained using 4-(7-chloro-1-(2,6-difluorophenyl)-4-methoxy-1H-pyrazolo[4,3-c]pyridin-3-yl)-N-methylbenzamide (72 mg), in the same manner as in Step C of Example 152.
MS(ESI+): [M+H]$^+$ 415.1.
MS(ESI+). found: 415.2.

Example 195

7-chloro-1-(2,6-difluorophenyl)-3-(4-(2-oxopyrrolidin-1-yl)phenyl)-1,5-dihydro-4H-pyrazolo[4,3-c]pyridin-4-one The title compound was obtained using 7-chloro-1-(2,6-difluorophenyl)-4-methoxy-1H-pyrazolo[4,3-c]pyridin-3-yl trifluoromethanesulfonate obtained in Step A of Example 152 and 1-(4-(4,4,5,5-tetramethyl-1,3,2-dioxaborolan-2-yl)phenyl)pyrrolidin-2-one, in the same manner as in Step A of Example 39 and Step B.
MS (ESI+): [M+H]$^+$ 441.8.
MS (ESI+). found: 441.3.

Example 196

(cis) or (trans)-4-(1-(4-hydroxy-4-methylcyclohexyl)-4-oxo-4,5-dihydro-1H-pyrazolo[4,3-c]pyridin-3-yl)benzenesulfonamide To a solution of 4-(4-oxo-1-(4-oxocyclohexyl)-4,5-dihydro-1H-pyrazolo[4,3-c]pyridin-3-yl)benzenesulfonamide (50.0 mg) obtained in Example 173 in THF (15 ml) was added 1.0M methyllithium-ethyl ether solution (0.518 mL) at 0° C., and the mixture was stirred overnight at room temperature under nitrogen atmosphere. To the reaction solution was added 1N hydrochloric acid at 0° C., and the mixture was extracted with ethyl acetate. The organic layer was washed with saturated aqueous sodium hydrogencarbonate solution and saturated brine, dried over anhydrous magnesium sulfate, filtered, and concentrated under reduced pressure. The obtained residue was purified by silica gel column chromatography (ethyl acetate/methanol) to give the racemic form of the title compound. The obtained racemic form was resolved by HPLC (column: L-column2 ODS (trade name) 20 mmID× 150 mmL, 5 μm, manufactured by Daicel Chemical Industries, mobile phase: water/acetonitrile (containing 10 mM ammonium carbonate)) to give the title compound (6.30 mg) having a shorter retention time.
MS (ESI+): [M+H]$^+$ 403.1.
MS (ESI+). found: 403.3.

Example 197

(cis) or (trans)-4-(1-(4-hydroxy-4-methylcyclohexyl)-4-oxo-4,5-dihydro-1H-pyrazolo[4,3-c]pyridin-3-yl)benzenesulfonamide The racemic form obtained in Example 196 was resolved by HPLC (column: L-column2 ODS (trade name) 20 mmID× 150 mmL, 5 μm, manufactured by Daicel Chemical Industries, mobile phase: water/acetonitrile (containing 10 mM ammonium carbonate)) to give the title compound (10.0 mg) having a longer retention time.
MS (ESI+): [M+H]$^+$ 403.1.
MS (ESI+). found: 403.3.

Example 198

(cis) or (trans)-4-(1-(4-hydroxy-4-methylcyclohexyl)-4-oxo-4,5-dihydro-1H-pyrazolo[4,3-c]pyridin-3-yl)thiophene-2-carboxamide The racemic form of the title compound was obtained using 4-(4-oxo-1-(4-oxocyclohexyl)-4,5-dihydro-1H-pyrazolo[4,3-c]pyridin-3-yl)thiophene-2-carboxamide obtained in Example 170, in the same manner as in Example 196. The obtained racemic form was resolved by HPLC (column: L-column2 ODS (trade name) 20 mmID×150 mmL, 5 μm, manufactured by Daicel Chemical Industries, mobile phase: water/acetonitrile (containing 10 mM ammonium carbonate)) to give the title compound having a shorter retention time.
MS (ESI+): [M+H]$^+$ 373.1.
MS (ESI+). found: 373.3.

Example 199

(cis) or (trans)-4-(1-(4-hydroxy-4-methylcyclohexyl)-4-oxo-4,5-dihydro-1H-pyrazolo[4,3-c]pyridin-3-yl)thiophene-2-carboxamide The racemic form of the title compound obtained in Example 198 was resolved by HPLC (column: L-column2 ODS (trade name) 20 mmID×150 mmL, 5 μm, manufactured by Daicel Chemical Industries, mobile phase: water/acetonitrile (containing 10 mM ammonium carbonate)) to give the title compound having a longer retention time.
MS (ESI+): [M+H]$^+$ 373.1.
MS (ESI+). found: 373.3.

Example 200

5-(7-chloro-1-(2,6-difluorophenyl)-4-oxo-4,5-dihydro-1H-pyrazolo[4,3-c]pyridin-3-yl)-2-(morpholin-4-yl)benzonitrile The title compound was obtained using 7-chloro-1-(2,6-difluorophenyl)-4-methoxy-1H-pyrazolo[4,3-c]pyridin-3-yl trifluoromethanesulfonate obtained in Step A of Example 152 and 2-(morpholin-4-yl)-5-(4,4,5,5-tetramethyl-1,3,2-dioxaborolan-2-yl)benzonitrile, in the same manner as in Step I of Example 33 and Step J of Example 33.
MS (ESI+): [M+H]⁺ 468.8.
MS (ESI+). found: 468.3.

Example 201

4-(1-cyclopentyl-4-oxo-4,5-dihydro-1H-pyrazolo[4,3-c]pyridin-3-yl)benzonitrile

To a solution of 4-(1-cyclopentyl-4-oxo-4,5-dihydro-1H-pyrazolo[4,3-c]pyridin-3-yl)benzamide (32.0 mg) obtained in Example 142 in THF (10 ml) were added pyridine (0.032 mL) and trifluoroacetic anhydride (0.028 mL) at 0° C., and the mixture was stirred overnight at room temperature. Pyridine (0.032 mL) and trifluoroacetic anhydride (0.028 mL) were added thereto, and the mixture was stirred at room temperature for 2 hr. To the reaction mixture was added saturated aqueous ammonium chloride solution, and the mixture was extracted with ethyl acetate. The organic layer was washed with saturated brine, dried over anhydrous sodium sulfate, and concentrated under reduced pressure. The residue was purified by silica gel column chromatography (methanol/ethyl acetate) to give a mixture containing the title compound and the raw material (4-(1-cyclopentyl-4-oxo-4,5-dihydro-1H-pyrazolo[4,3-c]pyridin-3-yl)benzamide. To a solution of the obtained 4-(1-cyclopentyl-4-oxo-4,5-dihydro-1H-pyrazolo[4,3-c]pyridin-3-yl)benzamide in THF were added triethylamine (0.055 mL) and trifluoroacetic anhydride (0.028 mL) at 0° C., and the mixture was stirred overnight at room temperature. To the reaction mixture was added saturated aqueous ammonium chloride solution, and the mixture was extracted with ethyl acetate. The organic layer was washed with saturated brine, dried over anhydrous sodium sulfate, and concentrated under reduced pressure. The obtained residue was combined with the mixture containing the title compound, and purified by silica gel column chromatography (ethyl acetate/hexane) to give the title compound (6.10 mg).
MS (ESI+): [M+H]⁺ 305.1.
MS (ESI+). found: 304.9.

Example 202

3-(1-cyclopentyl-4-oxo-4,5-dihydro-1H-pyrazolo[4,3-c]pyridin-3-yl)benzonitrile

The title compound (3.0 mg) was obtained using 3-(1-cyclopentyl-4-oxo-4,5-dihydro-1H-pyrazolo[4,3-c]pyridin-3-yl)benzamide obtained in Example 143, in the same manner as in Example 201.
MS (ESI+): [M+H]⁺ 305.1.
MS (ESI+). found: 304.9.

Example 203

7-chloro-1-(2,6-difluorophenyl)-3-(5-(morpholin-4-ylmethyl)-3-thienyl)-1,5-dihydro-4H-pyrazolo[4,3-c]pyridin-4-one The title compound was obtained using 7-chloro-1-(2,6-difluorophenyl)-4-methoxy-1H-pyrazolo[4,3-c]pyridin-3-yl trifluoromethanesulfonate obtained in Step A of Example 152 and 4-((4-(4,4,5,5-tetramethyl-1,3,2-dioxaborolan-2-yl)-2-thienyl)methyl)morpholine, in the same manner as in Step I of Example 33 and Step J of Example 33.
MS (ESI+): [M+H]⁺ 463.9.
MS (ESI+). found: 463.2.

Example 204

1-cyclopentyl-3-(1H-pyrazol-4-yl)-1,5-dihydro-4H-pyrazolo[4,3-c]pyridin-4-one

The title compound was obtained using 1-cyclopentyl-4-methoxy-1H-pyrazolo[4,3-c]pyridin-3-yl trifluoromethanesulfonate obtained in Step C of Example 12 and tert-butyl 4-(4,4,5,5-tetramethyl-1,3,2-dioxaborolan-2-yl)-1H-pyrazole-1-carboxylate, in the same manner as in Step D of Example 12 and Step E of Example 12.
MS (ESI+): [M+H]⁺ 270.1.
MS (ESI+). found: 270.2.

Example 205

7-chloro-1-(2,6-difluorophenyl)-3-(1-(tetrahydro-2H-pyran-4-yl)-1H-pyrazol-4-yl)-1,5-dihydro-4H-pyrazolo[4,3-c]pyridin-4-one A) 7-chloro-1-(2,6-difluorophenyl)-4-methoxy-3-(1H-pyrazol-4-yl)-1H-pyrazolo[4,3-c]pyridine The title compound was obtained using 7-chloro-1-(2,6-difluorophenyl)-4-methoxy-1H-pyrazolo[4,3-c]pyridin-3-yl trifluoromethanesulfonate, in the same manner as in Step A of Example 98.
MS (ESI+): [M+H]⁺ 362.7.
MS (ESI+). found: 362.2.

B) 7-chloro-1-(2,6-difluorophenyl)-4-methoxy-3-(1-(tetrahydro-2H-pyran-4-yl)-1H-pyrazol-4-yl)-1H-pyrazolo[4,3-c]pyridine To a solution of 7-chloro-1-(2,6-difluorophenyl)-4-methoxy-3-(1H-pyrazol-4-yl)-1H-pyrazolo[4,3-c]pyridine in tetrahydrofuran (3 mL) were added tetrahydro-2H-pyran-4-ol (0.160 ml), triphenylphosphine (527 mg) and di-tert-butyl (E)-diazene-1,2-dicarboxylate (2.505 ml) at room temperature, and the mixture was stirred overnight at room temperature. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (140 mg).
MS (ESI+): [M+H]⁺ 446.8.
MS (ESI+). found: 446.3.

C) 7-chloro-1-(2,6-difluorophenyl)-3-(1-(tetrahydro-2H-pyran-4-yl)-1H-pyrazol-4-yl)-1,5-dihydro-4H-pyrazolo[4,3-c]pyridin-4-one The title compound was obtained using 7-chloro-1-(2,6-difluorophenyl)-4-methoxy-3-(1-(tetrahydro-2H-pyran-4-yl)-1H-pyrazol-4-yl)-1H-pyrazolo[4,3-c]pyridine, in the same manner as in Step J of Example 33.
MS (ESI+): [M+H]⁺ 432.8.
MS (ESI+). found: 432.2.

Example 206

7-chloro-1-(2,6-difluorophenyl)-3-(3-fluoro-4-(morpholin-4-yl)phenyl)-1,5-dihydro-4H-pyrazolo[4,3-c]pyridin-4-one The title compound was obtained using 7-chloro-1-(2,6-difluorophenyl)-4-methoxy-1H-pyrazolo[4,3-c]pyridin-3-yl trifluoromethanesulfonate obtained in Step A of Example 152 and 4-(2-fluoro-4-(4,4,5,5-tetramethyl-1,3,2-dioxaborolan-2-yl)phenyl)morpholine, in the same manner as in Step I of Example 33 and Step J of Example 33.

MS (ESI+): [M+H]$^+$ 461.8.
MS (ESI+). found: 461.3.

Example 207

7-chloro-1-(2,6-difluorophenyl)-3-(4-(1,4-oxazepan-4-yl)phenyl)-1,5-dihydro-4H-pyrazolo[4,3-c]pyridin-4-one The title compound was obtained using 7-chloro-1-(2,6-difluorophenyl)-4-methoxy-1H-pyrazolo[4,3-c]pyridin-3-yl trifluoromethanesulfonate obtained in Step A of Example 152 and 4-(4-(4,4,5,5-tetramethyl-1,3,2-dioxaborolan-2-yl)phenyl)-1,4-oxazepane, in the same manner as in Step I of Example 33 and Step J of Example 33.

MS (ESI+): [M+H]$^+$ 457.8.
MS (ESI+). found: 457.3.

Example 208

7-chloro-3-cyclopropyl-1-(2,6-difluorophenyl)-1,5-dihydro-4H-pyrazolo[4,3-c]pyridin-4-one The title compound was obtained using 7-chloro-1-(2,6-difluorophenyl)-4-methoxy-1H-pyrazolo[4,3-c]pyridin-3-yl trifluoromethanesulfonate obtained in Step A of Example 152 and 2-cyclopropyl-4,4,5,5-tetramethyl-1,3,2-dioxaborolane, in the same manner as in Step D of Example 35 and Step J of Example 33.

MS (ESI+): [M+H]$^+$ 322.1.
MS (ESI+). found: 322.1.

Example 209

(cis) or (trans)-4-(1-(4-ethyl-4-hydroxycyclohexyl)-4-oxo-4,5-dihydro-1H-pyrazolo[4,3-c]pyridin-3-yl)benzenesulfonamide To a solution of 4-(4-oxo-1-(4-oxocyclohexyl)-4,5-dihydro-1H-pyrazolo[4,3-c]pyridin-3-yl)benzenesulfonamide (50.0 mg) obtained in Example 173 in THF (20 ml) was added 1.0M bromo(ethyl)magnesium-THF solution (0.518 mL) at 0° C., and the mixture was stirred overnight at room temperature under nitrogen atmosphere. To the reaction solution was added 1N hydrochloric acid at 0° C., and the mixture was extracted with ethyl acetate. The organic layer was washed with saturated aqueous sodium hydrogencarbonate solution and saturated brine, dried over anhydrous magnesium sulfate, filtered, and concentrated under reduced pressure. The obtained residue was purified by silica gel column chromatography (ethyl acetate/methanol) to give the racemic form of the title compound. The obtained racemic form was resolved by HPLC (column: L-column2 ODS (trade name) 20 mmID×150 mmL, 5 μm, manufactured by Daicel Chemical Industries, mobile phase: water/acetonitrile (containing 10 mM ammonium carbonate)) to give the title compound (5.3 mg) having a shorter retention time.

MS (ESI+): [M+H]$^+$ 417.2.
MS (ESI+). found: 417.4.

Example 210

(cis) or (trans)-4-(1-(4-ethyl-4-hydroxycyclohexyl)-4-oxo-4,5-dihydro-1H-pyrazolo[4,3-c]pyridin-3-yl)benzenesulfonamide The racemic form of the title compound obtained in Example 209 was resolved by HPLC (column: L-column2 ODS (trade name) 20 mmID×150 mmL, 5 μm, manufactured by Daicel Chemical Industries, mobile phase: water/acetonitrile (containing 10 mM ammonium carbonate)) to give the title compound (5.1 mg) having a longer retention time.

MS (ESI+): [M+H]$^+$ 417.2.
MS (ESI+). found: 417.4.

Example 211

4-(1-(2-methylphenyl)-4-oxo-4,5-dihydro-1H-pyrazolo[4,3-c]pyridin-3-yl)benzenesulfonamide The title compound was obtained using 4-iodo-2-methoxynicotinic acid and (2-methylphenyl)hydrazine hydrochloride obtained in Step C of Example 6, in the same manner as in Step A to Step E of Example 30.

MS (ESI+): [M+H]$^+$ 381.1.
MS (ESI+). found: 381.2.

Example 212

4-(4-oxo-1-(2-(trifluoromethyl)phenyl)-4,5-dihydro-1H-pyrazolo[4,3-c]pyridin-3-yl)benzenesulfonamide The title compound was obtained using 4-iodo-2-methoxynicotinic acid obtained in Step C of Example 6 and ((2-(trifluoromethyl)phenyl)hydrazine hydrochloride, in the same manner as in Step A to Step E of Example 30.

MS (ESI+): [M+H]$^+$ 435.1.
MS (ESI+). found: 435.2.

Example 213

4-(1-(2-fluorophenyl)-4-oxo-4,5-dihydro-1H-pyrazolo[4,3-c]pyridin-3-yl)benzenesulfonamide The title compound was obtained using 4-iodo-2-methoxynicotinic acid obtained in Step C of Example 6 and (2-fluorophenyl)hydrazine hydrochloride, in the same manner as in Step A to Step E of Example 30.

MS (ESI+): [M+H]$^+$ 385.1.
MS (ESI+). found: 385.2.

Example 214

4-(1-(2-chlorophenyl)-4-oxo-4,5-dihydro-1H-pyrazolo[4,3-c]pyridin-3-yl)benzenesulfonamide The title compound was obtained using 4-iodo-2-methoxynicotinic acid obtained in Step C of Example 6 and (2-chlorophenyl)hydrazine, in the same manner as in Step A to Step E of Example 30.

MS (ESI+): [M]$^+$ 401.0.
MS (ESI+). found: 401.2.

Example 215

4-(7-chloro-1-(2,6-difluorophenyl)-4-oxo-4,5-dihydro-1H-pyrazolo[4,3-c]pyridin-3-yl)-2-fluorobenzamide

A) ethyl 4-bromo-2-fluorobenzoate

To a solution of 4-bromo-2-fluorobenzoic acid (3.0 g) in ethanol (20 mL) was added thionyl chloride (2.0 mL) at 0° C., and the mixture was stirred overnight at 70° C. To the reaction mixture was added saturated aqueous sodium hydrogencarbonate solution, the mixture was concentrated under reduced pressure, and the residue was extracted with ethyl acetate. The organic layer was washed successively with water and saturated brine, dried over anhydrous magnesium sulfate, and concentrated under reduced pressure to give the title compound (3.30 g).

$^1$H NMR (300 MHz, CDCl$_3$) δ 1.39 (3H, t, J=7.2 Hz), 4.39 (2H, q, J=7.2 Hz), 7.30-7.40 (2H, m), 7.82 (1H, dd, J=8.7, 7.9 Hz).

B) ethyl 2-fluoro-4-(4,4,5,5-tetramethyl-1,3,2-dioxaborolan-2-yl)benzoate

To a solution of ethyl 4-bromo-2-fluorobenzoate (2.0 g), 4,4,4',4',5,5,5',5'-octamethyl-2,2-bi-1,3,2-dioxaborolane (2.47 g) and potassium acetate (1.59 g) in DMF (10 mL) was added 1,1'-bis(diphenylphosphino)ferrocene)dichloropalladium(II) (296 mg), and the mixture was stirred overnight at 80° C. The reaction mixture was filtered to remove the insoluble substance. To the filtrate was added water, and the mixture was extracted with ethyl acetate. The organic layer was washed successively with saturated aqueous sodium hydrogencarbonate solution and saturated brine, dried over anhydrous magnesium sulfate, and concentrated under reduced pressure. The residue was purified by silica gel column chromatography (ethyl acetate/hexane) to give the title compound (2.1 g).

$^1$H NMR (300 MHz, CDCl$_3$) δ 1.35 (12H, s), 1.40 (3H, t, J=7.0 Hz), 4.40 (2H, d, J=7.2 Hz), 7.51-7.62 (2H, m), 7.83-7.99 (1H, m).

C) 4-(7-chloro-1-(2,6-difluorophenyl)-4-methoxy-1H-pyrazolo[4,3-c]pyridin-3-yl)-2-fluorobenzoic acid The title compound was obtained using 7-chloro-1-(2,6-difluorophenyl)-4-methoxy-1H-pyrazolo[4,3-c]pyridin-3-yl trifluoromethanesulfonate obtained in Step A of Example 152 and ethyl 2-fluoro-4-(4,4,5,5-tetramethyl-1,3,2-dioxaborolan-2-yl)benzoate, in the same manner as in Step A of Example 180 and Step B of Example 180.

MS (ESI+): [M+H]$^+$ 434.0.
MS (ESI+). found: 434.2.

D) 4-(7-chloro-1-(2,6-difluorophenyl)-4-oxo-4,5-dihydro-1H-pyrazolo[4,3-c]pyridin-3-yl)-2-fluorobenzamide The title compound was obtained using 4-(7-chloro-1-(2,6-difluorophenyl)-4-methoxy-1H-pyrazolo[4,3-c]pyridin-3-yl)-2-fluorobenzoic acid, in the same manner as in Step C of Example 129 and Step C of Example 93.

MS (ESI+): [M+H]$^+$ 419.0.
MS (ESI+). found: 419.2.

Example 216

4-(7-chloro-1-(2,6-difluorophenyl)-4-oxo-4,5-dihydro-1H-pyrazolo[4,3-c]pyridin-3-yl)-2-fluoro-N-methylbenzamide The title compound was obtained using 4-(7-chloro-1-(2,6-difluorophenyl)-4-methoxy-1H-pyrazolo[4,3-c]pyridin-3-yl)-2-fluorobenzoic acid obtained in Step 0.0 of Example 215 and methylamine hydrochloride, in the same manner as in Step C of Example 180 and Step C of Example 93.

MS (ESI+): [M+H]$^+$ 433.1.
MS (ESI+). found: 433.2.

Example 217

2-(4-(7-chloro-1-(2,6-difluorophenyl)-4-oxo-4,5-dihydro-1H-pyrazolo[4,3-c]pyridin-3-yl)phenoxy)-N-(2-methoxyethyl)acetamide

A) ethyl (4-(4,4,5,5-tetramethyl-1,3,2-dioxaborolan-2-yl)phenoxy)acetate

To a solution of 4-(4,4,5,5-tetramethyl-1,3,2-dioxaborolan-2-yl)phenol (1.5 g) and ethyl bromoacetate (0.91 mL) in DMF (10 mL) was added potassium carbonate (1.41 g), and the mixture was stirred at 80° C. for 5 hr. The reaction mixture was added water, and the mixture was extracted with ethyl acetate. The organic layer was washed successively with saturated aqueous sodium hydrogencarbonate solution and saturated brine, dried over anhydrous magnesium sulfate, and concentrated under reduced pressure. The residue was purified by silica gel column chromatography (ethyl acetate/hexane) to give the title compound (1.77 g).

$^1$H NMR (300 MHz, CDCl$_3$) δ 1.29 (3H, t, J=7.2 Hz), 1.33 (12H, s), 4.26 (2H, d, J=7.2 Hz), 4.64 (2H, s), 6.90 (2H, d, J=8.7 Hz), 7.75 (2H, d, J=8.7 Hz).

B) (4-(7-chloro-1-(2,6-difluorophenyl)-4-methoxy-1H-pyrazolo[4,3-c]pyridin-3-yl)phenoxy)acetic acid To a solution of 7-chloro-1-(2,6-difluorophenyl)-4-methoxy-1H-pyrazolo[4,3-c]pyridin-3-yl trifluoromethanesulfonate obtained in Step A of Example 152 (250 mg) in DMF (3 mL)/water (0.3 mL) were added ethyl (4-(4,4,5,5-tetramethyl-1,3,2-dioxaborolan-2-yl)phenoxy)acetate (241 mg), (1,1'-bis(diphenylphosphino)ferrocene)dichloropalladium(II) (23 mg) and cesium carbonate (367 mg). The reaction mixture was stirred overnight at 90° C. The reaction mixture was diluted with water, and the aqueous layer was washed with ethyl acetate, and neutralized 1M hydrochloric acid at 0° C., and the mixture was extracted with ethyl acetate. The organic layer was washed with saturated brine, dried over anhydrous magnesium sulfate, filtered, and concentrated under reduced pressure. The obtained residue was purified by silica gel column chromatography (ethyl acetate/hexane) to give the title compound (166 mg).

MS (ESI+): [M+H]$^+$ 446.1.
MS (ESI+). found: 446.2.

C) 2-(4-(7-chloro-1-(2,6-difluorophenyl)-4-oxo-4,5-dihydro-1H-pyrazolo[4,3-c]pyridin-3-yl)phenoxy)-N-(2-methoxyethyl)acetamide The title compound was obtained using (4-(7-chloro-1-(2,6-difluorophenyl)-4-methoxy-1H-pyrazolo[4,3-c]pyridin-3- yl)phenoxy)acetic acid and 2-methoxyethanamine, in the same manner as in Step C of Example 180 and Step J of Example 33.
MS (ESI+): [M+H]$^+$ 489.1.
MS (ESI+). found: 489.3.

Example 218

7-bromo-1-(2,6-difluorophenyl)-3-(4-(morpholin-4-yl)phenyl)-1,5-dihydro-4H-pyrazolo[4,3-c]pyridin-4-one A) 4-(4-(1-(2,6-difluorophenyl)-4-methoxy-1H-pyrazolo[4,3-c]pyridin-3-yl)phenyl)morpholine The title compound (240 mg) was obtained using 1-(2,6-difluorophenyl)-4-methoxy-1H-pyrazolo[4,3-c]pyridin-3-yl trifluoromethanesulfonate (250 mg) obtained in Step C of Example 35 and 4-(4-(4,4,5,5-tetramethyl-1,3,2-dioxaborolan-2-yl)phenyl)morpholine (265 mg), in the same manner as in Step B of Example 152.
MS(ESI+): [M+H]$^+$ 423.2.
MS(ESI+). found: 423.3.

B) 4-(4-(7-bromo-1-(2,6-difluorophenyl)-4-methoxy-1H-pyrazolo[4,3-c]pyridin-3-yl)phenyl)morpholine The title compound (143 mg) was obtained using 4-(4-(1-(2,6-difluorophenyl)-4-methoxy-1H-pyrazolo[4,3-c]pyridin-3-yl)phenyl)morpholine (190 mg), in the same manner as in Step A of Example 104.
MS(ESI+): [M+H]$^+$ 501.1.
MS(ESI+). found: 501.3.

C) 7-bromo-1-(2,6-difluorophenyl)-3-(4-(morpholin-4-yl)phenyl)-1,5-dihydro-4H-pyrazolo[4,3-c]pyridin-4-one The title compound (38 mg) was obtained using 4-(4-(7-bromo-1-(2,6-difluorophenyl)-4-methoxy-1H-pyrazolo[4,3-c]pyridin-3-yl)phenyl)morpholine (50 mg), in the same manner as in Step C of Example 152.
MS(ESI+): [M+H]$^+$ 487.1.
MS(ESI+). found: 487.3.

Example 219

1-(4-(7-chloro-1-(2,6-difluorophenyl)-4-oxo-4,5-dihydro-1H-pyrazolo[4,3-c]pyridin-3-yl)benzyl)pyrrolidine-2,5-dione A) (4-((2,5-dioxopyrrolidin-1-yl)methyl)phenyl)boronic acid To a solution (10 mL) of pyrrolidine-2,5-dione (500 mg) in DMF was added sodium hydride (60% dispersion in mineral oil, 252 mg) at 0° C., and the mixture was stirred for 1 hr. (4-(Bromomethyl)phenyl)boronic acid (903 mg) was added thereto, and the mixture was stirred overnight at room temperature. The reaction mixture was extracted with water and ethyl acetate, and the organic layer was washed with saturated brine, dried over anhydrous magnesium sulfate, and crystallized from ethyl acetate and diisopropyl ether to give the title compound (520 mg).

B) 1-(4-(7-chloro-1-(2,6-difluorophenyl)-4-oxo-4,5-dihydro-1H-pyrazolo[4,3-c]pyridin-3-yl)benzyl)pyrrolidine-2,5-dione The title compound was obtained using 7-chloro-1-(2,6-difluorophenyl)-4-methoxy-1H-pyrazolo[4,3-c]pyridin-3-yl trifluoromethanesulfonate obtained in Step A of Example 152 and (4-((2,5-dioxopyrrolidin-1-yl)methyl)phenyl)boronic acid obtained in Step A of Example 219, in the same manner as in Step A of Example 39 and Step B of Example 39.
MS (ESI+): [M+H]$^+$ 469.8.
MS (ESI+). found: 469.3.

Example 220

7-chloro-1-(2,6-difluorophenyl)-3-(5-((2-oxopyrrolidin-1-yl)methyl)-3-thienyl)-1,5-dihydro-4H-pyrazolo[4,3-c]pyridin-4-one A) 1-((4-(4,4,5,5-tetramethyl-1,3,2-dioxaboran-2-yl)thiophen-2-yl)methyl)pyrrolidin-2-one The title compound was obtained using 1-((4-bromothiophen-2-yl)methyl)pyrrolidin-2-one, in the same manner as in Step B of Example 33.
MS (ESI+): [M+H]$^+$ 308.2.
MS (ESI+). found: 308.2.

B) 7-chloro-1-(2,6-difluorophenyl)-3-(5-((2-oxopyrrolidin-1-yl)methyl)-3-thienyl)-1,5-dihydro-4H-pyrazolo[4,3-c]pyridin-4-one The title compound was obtained using 7-chloro-1-(2,6-difluorophenyl)-4-methoxy-1H-pyrazolo[4,3-c]pyridin-3-yl trifluoromethanesulfonate obtained in Step A of Example 152 and 1-((4-(4,4,5,5-tetramethyl-1,3,2-dioxaboran-2-yl)thiophen-2-yl)methyl)pyrrolidin-2-one, in the same manner as in Step E-3 of Example 29 and Step J of Example 33.
MS (ESI+): [M+H]$^+$ 461.9.
MS (ESI+). found: 461.2.

Example 221

2-(4-(7-chloro-1-(2,6-difluorophenyl)-4-oxo-4,5-dihydro-1H-pyrazolo[4,3-c]pyridin-3-yl)phenoxy)-N-methylacetamide The title compound was obtained using (4-(7-chloro-1-(2,6-difluorophenyl)-4-methoxy-1H-pyrazolo[4,3-c]pyridin-3-yl)phenoxy)acetic acid obtained in Step B of Example 217, in the same manner as in Step C of Example 180 and Step C of Example 93.
MS (ESI+): [M+H]$^+$ 445.1.
MS (ESI+). found: 445.3.

Example 222

4-(7-chloro-1-(2,6-difluorophenyl)-4-oxo-4,5-dihydro-1H-pyrazolo[4,3-c]pyridin-3-yl)-N-ethyl-1H-pyrazole-1-carboxamide A) 4-(7-chloro-1-(2,6-difluorophenyl)-4-methoxy-1H-pyrazolo[4,3-c]pyridin-3-yl)-N-ethyl-1H-pyrazole-1-carboxamide To a solution of 7-chloro-1-(2,6-difluorophenyl)-4-methoxy-3-(1H-pyrazol-4-yl)-1H-pyrazolo[4,3-c]pyridine (40 mg) obtained in Step A of Example 177 in THF (3 mL) was added isocyanatoethane (0.018 mL), and the mixture was stirred overnight at room temperature. To the reaction mixture was added water, and the mixture was extracted with ethyl acetate. The organic layer was washed successively with water and saturated brine, dried over anhydrous magnesium sulfate, and concentrated under reduced pressure to give the title compound (45 mg).
MS (ESI+): [M+H]$^+$ 433.1.
MS (ESI+). found: 433.3.

B) 4-(7-chloro-1-(2,6-difluorophenyl)-4-oxo-4,5-dihydro-1H-pyrazolo[4,3-c]pyridin-3-yl)-N-ethyl-1H-pyrazole-1-carboxamide The title compound was obtained using 4-(7-chloro-1-(2,6-difluorophenyl)-4-methoxy-1H-pyrazolo[4,3-c]pyridin-3-yl)-N-ethyl-1H-pyrazole-1-carboxamide, in the same manner as in Step C of Example 93.
MS (ESI+): [M+H]$^+$ 419.1.
MS (ESI+). found: 419.3.

Example 223

4-(1-cyclopentyl-4-oxo-4,5-dihydro-1H-pyrazolo[4,3-c]pyridin-3-yl)-N-methylbenzenesulfonamide A) 4-(1-cyclopentyl-4-methoxy-1H-pyrazolo[4,3-c]pyridin-3-yl)-N-methylbenzenesulfonamide To a solution of 4-(1-cyclopentyl-4-methoxy-1H-pyrazolo[4,3-c]pyridin-3-yl)benzenesulfonamide (50.0 mg) obtained in Step A of Example 92 in DMF (3 ml) was added sodium hydride (60% dispersion in mineral oil, 5.91 mg), and the mixture was stirred at room temperature for 1 hr. To the reaction mixture was added iodomethane (0.0126 ml), and the mixture was stirred overnight at room temperature. The reaction mixture was extracted with water and ethyl acetate, and the organic layer was washed with saturated brine, dried over anhydrous magnesium sulfate, filtered, and concentrated under reduced pressure. The obtained residue was purified by silica gel column chromatography (ethyl acetate/hexane) to give the title compound (10.9 mg).
MS (ESI+): [M+H]$^+$ 387.2.
MS (ESI+). found: 387.3.

B) 4-(1-cyclopentyl-4-oxo-4,5-dihydro-1H-pyrazolo[4,3-c]pyridin-3-yl)-N-methylbenzenesulfonamide The title compound was obtained using 4-(1-cyclopentyl-4-methoxy-1H-pyrazolo[4,3-c]pyridin-3-yl)-N-methylbenzenesulfonamide, in the same manner as in Step B of Example 92.
MS (ESI+): [M+H]$^+$ 373.1.
MS (ESI+). found: 373.3.

Example 224

7-chloro-1-(2,6-difluorophenyl)-3-(4-((2-oxopyrrolidin-1-yl)methyl)phenyl)-1,5-dihydro-4H-pyrazolo[4,3-c]pyridin-4-one The title compound was obtained using 1-(4-bromobenzyl)pyrrolidin-2-one, in the same manner as in Step A of Example 220 and Step B of Example 220.
MS (ESI+): [M+H]$^+$ 455.9.
MS (ESI+). found: 455.3.

Example 225

7-chloro-1-(2,6-difluorophenyl)-3-(4-(2-oxoimidazolidin-1-yl)phenyl)-1,5-dihydro-4H-pyrazolo[4,3-c]pyridin-4-one A) tert-butyl 2-oxo-3-(4-(4,4,5,5-tetramethyl-1,3,2-dioxaborolan-2-yl)phenyl)imidazolidine-1-carboxylate A-1) 1-(4-(4,4,5,5-tetramethyl-1,3,2-dioxaborolan-2-yl)phenyl)imidazolidin-2-one To a solution of 4-(4,4,5,5-tetramethyl-1,3,2-dioxaborolan-2-yl)aniline (1.05 g) and triethylamine (1.34 mL) in THF (20 mL) was added 1-chloro-2-isocyanatoethane (0.409 mL) at 0° C., and the mixture was stirred overnight at room temperature. To the reaction mixture was added water, and the mixture was extracted with ethyl acetate. The organic layer was washed with saturated brine, dried over anhydrous magnesium sulfate, and concentrated under reduced pressure to give a powder. A mixture of the obtained powder and potassium tert-butoxide (1.08 g) in THF (20 mL) was stirred overnight at room temperature. To the reaction mixture was added water, and the mixture was extracted with ethyl acetate. The organic layer was washed with saturated brine, dried over anhydrous magnesium sulfate, and concentrated under reduced pressure. The obtained residue was crystallized from ethyl acetate and diisopropyl ether to give the title compound (0.98 g).
MS (ESI+): [M+H]$^+$ 289.2.
MS (ESI+). found: 289.2.

A-2) tert-butyl 2-oxo-3-(4-(4,4,5,5-tetramethyl-1,3,2-dioxaborolan-2-yl)phenyl)imidazolidine-1-carboxylate To a solution of 1-(4-(4,4,5,5-tetramethyl-1,3,2-dioxaborolan-2-yl)phenyl)imidazolidin-2-one (0.98 g) and dimethylaminopyridine (0.062 g) in acetonitrile (15 mL) was added di-tert-butyl dicarbonate (0.854 g) at 0° C., and the mixture was stirred overnight at room temperature. The reaction mixture was extracted with water and ethyl acetate, and the organic layer was washed with saturated brine, and dried over anhydrous magnesium sulfate, and the solvent was evaporated under reduced pressure. The residue was purified by silica gel column chromatography (ethyl acetate/hexane) to give the title compound (0.95 g).
$^1$H NMR (300 MHz, DMSO-d$_6$) δ 1.29 (12H, s), 1.47 (9H, s), 3.77-3.85 (4H, m), 7.56-7.71 (4H, m).
MS (ESI+): [M+H]$^+$ 389.3
MS (ESI+). found: not observed.

B) 7-chloro-1-(2,6-difluorophenyl)-3-(4-(2-oxoimidazolidin-1-yl)phenyl)-1,5-dihydro-4H-pyrazolo[4,3-c]pyridin-4-one The title compound was obtained using tert-butyl 2-oxo-3-(4-(4,4,5,5-tetramethyl-1,3,2-dioxaborolan-2-yl)phenyl)imidazolidine-1-carboxylate, in the same manner as in Step B of Example 220.
MS (ESI+): [M+H]$^+$ 442.8.
MS (ESI+). found: 442.3.

Example 226

7-chloro-1-(2,6-difluorophenyl)-3-(1-methyl-1H-benzimidazol-5-yl)-1,5-dihydro-4H-pyrazolo[4,3-c]pyridin-4-one The title compound was obtained using 7-chloro-1-(2,6-difluorophenyl)-4-methoxy-1H-pyrazolo[4,3-c]pyridin-3-yl trifluoromethanesulfonate obtained in Step A of Example 152 and (1-methyl-1H-benzimidazol-5-yl)boronic acid, in the same manner as in Step I of Example 33, Step J of Example 33.

MS (ESI+): [M+H]$^+$ 412.7.
MS (ESI+). found: 412.2.

Example 227

7-chloro-1-(2,6-difluorophenyl)-3-(2-oxo-2,3-dihydro-1H-indol-6-yl)-1,5-dihydro-4H-pyrazolo[4,3-c]pyridin-4-one The title compound was obtained using 7-chloro-1-(2,6-difluorophenyl)-4-methoxy-1H-pyrazolo[4,3-c]pyridin-3-yl trifluoromethanesulfonate obtained in Step A of Example 152 and (2-oxo-2,3-dihydro-1H-indol-6-yl)boronic acid, in the same manner as in Step I of Example 33 and Step J of Example 33.

MS (ESI+): [M+H]$^+$ 413.7.
MS (ESI+). found: 413.2.

Example 228

1-(2,6-difluorophenyl)-4-oxo-3-(1H-pyrazol-4-yl)-4,5-dihydro-1H-pyrazolo[4,3-c]pyridine-7-carbonitrile

A) 7-bromo-1-(2,6-difluorophenyl)-4-methoxy-3-(1H-pyrazol-4-yl)-1H-pyrazolo[4,3-c]pyridine The title compound was obtained using 1-(2,6-difluorophenyl)-4-methoxy-1H-pyrazolo[4,3-c]pyridin-3-yl trifluoromethanesulfonate obtained in Step C of Example 35 and tert-butyl 4-(4,4,5,5-tetramethyl-1,3,2-dioxaborolan-2-yl)-1H-pyrazole-1-carboxylate, in the same manner as in Step I of Example 33 and Step A of Example 104.

MS (ESI+): [M+H]$^+$ 407.1.
MS (ESI+). found: 407.1.

B) 7-bromo-1-(2,6-difluorophenyl)-4-methoxy-3-(1-((2-(trimethylsilyl)ethoxy)methyl)-1H-pyrazol-4-yl)-1H-pyrazolo[4,3-c]pyridine The title compound was obtained using 7-bromo-1-(2,6-difluorophenyl)-4-methoxy-3-(1H-pyrazol-4-yl)-1H-pyrazolo[4,3-c]pyridine, in the same manner as in Step E-1 of Example 29.

MS (ESI+): [M+H]$^+$ 537.4.
MS (ESI+). found: 537.3.

C) 1-(2,6-difluorophenyl)-4-methoxy-3-(1-((2-(trimethylsilyl)ethoxy)methyl)-1H-pyrazol-4-yl)-1H-pyrazolo[4,3-c]pyridine-7-carbonitrile The title compound was obtained using 7-bromo-1-(2,6-difluorophenyl)-4-methoxy-3-(1-((2-(trimethylsilyl)ethoxy)methyl)-1H-pyrazol-4-yl)-1H-pyrazolo[4,3-c]pyridine, in the same manner as in Step E of Example 65.

MS (ESI+): [M+H]$^+$ 483.2.
MS (ESI+). found: 483.4.

D) 1-(2,6-difluorophenyl)-4-oxo-3-(1H-pyrazol-4-yl)-4,5-dihydro-1H-pyrazolo[4,3-c]pyridine-7-carbonitrile The title compound was obtained using 1-(2,6-difluorophenyl)-4-methoxy-3-(1-((2-(trimethylsilyl)ethoxy)methyl)-1H-pyrazol-4-yl)-1H-pyrazolo[4,3-c]pyridine-7-carbonitrile, in the same manner as in Step E-4 of Example 29 and Step J of Example 33.

MS (ESI+): [M+H]$^+$ 339.2.
MS (ESI+). found: 339.2.

Example 229

1-(2,6-difluorophenyl)-3-(4-(morpholin-4-yl)phenyl)-4-oxo-4,5-dihydro-1H-pyrazolo[4,3-c]pyridine-7-carbonitrile

A) 1-(2,6-difluorophenyl)-4-methoxy-3-(4-(morpholin-4-yl)phenyl)-1H-pyrazolo[4,3-c]pyridine-7-carbonitrile To a solution of 4-(4-(7-bromo-1-(2,6-difluorophenyl)-4-methoxy-1H-pyrazolo[4,3-c]pyridin-3-yl)phenyl)morpholine (93 mg) obtained in Step B of Example 218 in DMA (3 mL) were added tetrakis(triphenylphosphine)palladium(0) (43 mg) and zinc cyanide (33 mg) at room temperature, and the mixture was stirred under microwave irradiation at 120° C. for 30 min. The reaction mixture was purified by silica gel column chromatography (ethyl acetate/hexane) to give the title compound (77 mg).

MS(ESI+): [M+H]$^+$ 448.2.
MS(ESI+). found: 448.3.

B) 1-(2,6-difluorophenyl)-3-(4-(morpholin-4-yl)phenyl)-4-oxo-4,5-dihydro-1H-pyrazolo[4,3-c]pyridine-7-carbonitrile The title compound (43 mg) was obtained using 1-(2,6-difluorophenyl)-4-methoxy-3-(4-(morpholin-4-yl)phenyl)-1H-pyrazolo[4,3-c]pyridine-7-carbonitrile (77 mg), in the same manner as in Step C of Example 152.

MS(ESI+): [M+H]$^+$ 434.1.
MS(ESI+). found: 434.3.

Example 230

4-(1-(2,6-difluorophenyl)-4-oxo-4,5-dihydro-1H-pyrazolo[4,3-c]pyridin-3-yl)benzamide The title compound was obtained using 4-(1-(2,6-difluorophenyl)-4-methoxy-1H-pyrazolo[4,3-c]pyridin-3-yl)benzoic acid obtained in Step B of Example 180, in the same manner as in Step 0.0 of Example 129 and Step J of Example 33.

MS (ESI+): [M+H]$^+$ 367.1.
MS (ESI+). found: 367.2.

Example 231

4-(7-chloro-1-(2,6-difluorophenyl)-4-oxo-4,5-dihydro-1H-pyrazolo[4,3-c]pyridin-3-yl)-N-(2-methoxyethyl)benzamide A) 4-(7-chloro-1-(2,6-difluorophenyl)-4-methoxy-1H-pyrazolo[4,3-c]pyridin-3-yl)benzoic acid The title compound was obtained using 7-chloro-1-(2,6-difluorophenyl)-4-methoxy-1H-pyrazolo[4,3-c]pyridin-3-yl trifluoromethanesulfonate obtained in Step A of Example 152 and methyl 4-(4,4,5,5-tetramethyl-1,3,2-dioxaborolan-2-yl)benzoate, in the same manner as in Step A of Example 180 and Step B of Example 180.
MS (ESI+): [M+H]$^+$ 416.1.
MS (ESI+). found: 416.2.

B) 4-(7-chloro-1-(2,6-difluorophenyl)-4-oxo-4,5-dihydro-1H-pyrazolo[4,3-c]pyridin-3-yl)-N-(2-methoxyethyl)benzamide The title compound was obtained using 4-(7-chloro-1-(2,6-difluorophenyl)-4-methoxy-1H-pyrazolo[4,3-c]pyridin-3-yl)benzoic acid and 2-methoxyethanamine, in the same manner as in Step C of Example 180 and Step J of Example 33.
MS (ESI+): [M+H]$^+$ 459.1.
MS (ESI+). found: 459.3.

Example 232

4-(7-chloro-1-(2,6-difluorophenyl)-4-oxo-4,5-dihydro-1H-pyrazolo[4,3-c]pyridin-3-yl)-N-(2-hydroxyethyl)benzamide A) 4-(7-chloro-1-(2,6-difluorophenyl)-4-methoxy-1H-pyrazolo[4,3-c]pyridin-3-yl)-N-(2-hydroxyethyl)benzamide To a solution of 4-(7-chloro-1-(2,6-difluorophenyl)-4-methoxy-1H-pyrazolo[4,3-c]pyridin-3-yl)benzoic acid (100 mg) obtained in Step A of Example 231, 2-aminoethanol (0.022 mL) and triethylamine (0.050 mL) in DMF (3 mL) was added 2-(7-azabenzotriazol-1-yl)-1,1,3,3-hexafluorophosphate (137 mg), and the mixture was stirred overnight at room temperature. To the reaction mixture was added water, and the mixture was extracted with ethyl acetate. The organic layer was washed successively with water and saturated brine, dried over anhydrous magnesium sulfate, and concentrated under reduced pressure to give the title compound (105 mg).
MS (ESI+): [M+H]$^+$ 459.1.
MS (ESI+). found: 459.3.

B) 4-(7-chloro-1-(2,6-difluorophenyl)-4-oxo-4,5-dihydro-1H-pyrazolo[4,3-c]pyridin-3-yl)-N-(2-hydroxyethyl)benzamide The title compound was obtained using 4-(7-chloro-1-(2,6-difluorophenyl)-4-methoxy-1H-pyrazolo[4,3-c]pyridin-3-yl)-N-(2-hydroxyethyl)benzamide, in the same manner as in Step J of Example 33.
MS (ESI+): [M+H]$^+$ 445.1.
MS (ESI+). found: 445.3.

Example 233

7-chloro-1-(2,6-difluorophenyl)-3-(4-(morpholin-4-yl)phenyl)-1,5-dihydro-4H-pyrazolo[4,3-c]pyridin-4-one hydrochloride To a solution of 7-chloro-1-(2,6-difluorophenyl)-3-(4-(morpholin-4-yl)phenyl)-1,5-dihydro-4H-pyrazolo[4,3-c]pyridin-4-one (100 mg) obtained in Example 161 in ethanol (10 mL) was added 6M hydrochloric acid (0.102 mL) at room temperature, and the reaction mixture was concentrated. The residue was crystallized from ethanol to give the title compound (82 mg).
MS (ESI+): [M+H]$^+$ 443.8.
MS (ESI+). found: 443.3.

Example 234

1-(2,6-difluorophenyl)-3-(5-(morpholin-4-yl)-3-thienyl)-1,5-dihydro-4H-pyrazolo[4,3-c]pyridin-4-one The title compound was obtained using 1-(2,6-difluorophenyl)-4-methoxy-1H-pyrazolo[4,3-c]pyridin-3-yl trifluoromethanesulfonate obtained in Step C of Example 35 and 4-(4-(4,4,5,5-tetramethyl-1,3,2-dioxaborolan-2-yl)-2-thienyl)morpholine, in the same manner as in Step I of Example 33 and Step J of Example 33.
MS (ESI+): [M+H]$^+$ 415.4.
MS (ESI+). found: 415.3.

Example 235

1-(2,6-difluorophenyl)-7-methyl-3-(4-(morpholin-4-yl)phenyl)-1,5-dihydro-4H-pyrazolo[4,3-c]pyridin-4-one A) 7-bromo-1-(2,6-difluorophenyl)-4-methoxy-3-(4-(morpholin-4-yl)phenyl)-1H-pyrazolo[4,3-c]pyridine The title compound was obtained using 1-(2,6-difluorophenyl)-4-methoxy-1H-pyrazolo[4,3-c]pyridin-3-yl trifluoromethanesulfonate obtained in Step C of Example 35 and 4-(4-(4,4,5,5-tetramethyl-1,3,2-dioxaborolan-2-yl)phenyl)morpholine, in the same manner as in Step I of Example 33 and Step A of Example 104.
MS (ESI+): [M+H]$^+$ 502.3.
MS (ESI+). found: 502.3.

B) 1-(2,6-difluorophenyl)-7-methyl-3-(4-(morpholin-4-yl)phenyl)-1,5-dihydro-4H-pyrazolo[4,3-c]pyridin-4-one The title compound was obtained using 7-bromo-1-(2,6-difluorophenyl)-4-methoxy-3-(4-(morpholin-4-yl)phenyl)-1H-pyrazolo[4,3-c]pyridine and methylboronic acid, in the same manner as in Step I of Example 33 and Step J of Example 33.
MS (ESI+): [M+H]$^+$ 423.4.
MS (ESI+). found: 423.3.

Example 236

7-chloro-1-(2,6-difluorophenyl)-3-(4-(thiomorpholin-4-yl)phenyl)-1,5-dihydro-4H-pyrazolo[4,3-c]pyridin-4-one A) 4-(4-bromophenyl)thiomorpholine A mixture of 1,4-dibromobenzene (1.0 g), thiomorpholine (0.44 g), tris(dibenzylideneacetone)dipalladium(0) (0.097 g), 2,2'-bis(diphenylphosphino)-1,1'-binaphthyl (0.20 g) and sodium tert-butoxide (0.49 g) in toluene (10 mL) was stirred at 80° C. for 16 hr. To the reaction mixture was added water, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (0.82 g).
MS(ESI+): [M+H]$^+$ 258.0.
MS(ESI+). found: 258.1.

B) 4-(4-(4,4,5,5-tetramethyl-1,3,2-dioxaborolan-2-yl)phenyl)thiomorpholine

To a mixture of 4-(4-bromophenyl)thiomorpholine (0.40 g), 4,4,5,5-tetramethyl-1,3,2-dioxaborolane (0.40 g) and triethylamine (0.65 mL) in 1,4-dioxane (15 mL) was added dichlorobis(triphenylphosphine)palladium(II) (0.054 g) under argon atmosphere. The reaction mixture was stirred at 100° C. for 16 hr. To the reaction mixture was added water, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (0.40 g).
MS(ESI+): [M+H]$^+$ 306.2.
MS(ESI+). found: 306.3.

C) 7-chloro-1-(2,6-difluorophenyl)-3-(4-(thiomorpholin-4-yl)phenyl)-1,5-dihydro-4H-pyrazolo[4,3-c]pyridin-4-one The title compound (53 mg) was obtained using 7-chloro-1-(2,6-difluorophenyl)-4-methoxy-1H-pyrazolo[4,3-c]pyridin-3-yl trifluoromethanesulfonate obtained in Step A of Example 152 (250 mg) and 4-(4-(4,4,5,5-tetramethyl-1,3,2-dioxaborolan-2-yl)phenyl)thiomorpholine (258 mg), in the same manner as in Step B of Example 152 and Step C of Example 152.
MS(ESI+): [M+H]$^+$ 459.1.
MS(ESI+). found: 459.3.

Example 237

4-(1-(2,6-difluorophenyl)-4-oxo-4,5-dihydro-1H-pyrazolo[4,3-c]pyridin-3-yl)-N-(2-hydroxyethyl)benzamide The title compound was obtained using 4-(1-(2,6-difluorophenyl)-4-methoxy-1H-pyrazolo[4,3-c]pyridin-3-yl)benzoic acid obtained in Step B of Example 180, in the same manner as in Step A of Example 232 and Step J of Example 33.
MS (ESI+): [M+H]$^+$ 411.1.
MS (ESI+). found: 411.3.

Example 238

1-(2,6-difluorophenyl)-3-(1-methyl-6-oxo-1,6-dihydropyridin-3-yl)-1,5-dihydro-4H-pyrazolo[4,3-c]pyridin-4-one The title compound was obtained using 1-(2,6-difluorophenyl)-4-methoxy-1H-pyrazolo[4,3-c]pyridin-3-yl trifluoromethanesulfonate obtained in Step C of Example 35 and (1-methyl-6-oxo-1,6-dihydropyridin-3-yl)boronic acid, in the same manner as in Step A of Example 180 and Step J of Example 33.
MS (ESI+): [M+H]$^+$ 355.1.
MS (ESI+). found: 355.2.

Example 239

7-chloro-1-(2,6-difluorophenyl)-3-(4-(3-methyl-2-oxoimidazolidin-1-yl)phenyl)-1,5-dihydro-4H-pyrazolo[4,3-c]pyridin-4-one A) 1-methyl-3-(4-(4,4,5,5-tetramethyl-1,3,2-dioxaborolan-2-yl)phenyl)imidazolidin-2-one The title compound was obtained using 1-(4-(4,4,5,5-tetramethyl-1,3,2-dioxaborolan-2-yl)phenyl)imidazolidin-2-one obtained in Step A-1 of Example 225 and methyl iodide, in the same manner as in Step B of Example 98.
MS (ESI+): [M+H]$^+$ 303.2.
MS (ESI+). found: 303.2.

B) 7-chloro-1-(2,6-difluorophenyl)-3-(4-(3-methyl-2-oxoimidazolidin-1-yl)phenyl)-1,5-dihydro-4H-pyrazolo[4,3-c]pyridin-4-one The title compound was obtained using 1-methyl-3-(4-(4,4,5,5-tetramethyl-1,3,2-dioxaborolan-2-yl)phenyl)imidazolidin-2-one obtained in Step A of Example 239, in the same manner as in Step B of Example 220.
MS (ESI+): [M+H]$^+$ 456.8.
MS (ESI+). found: 456.3.

Example 240

1-(2,6-difluorophenyl)-3-(4-(3-methyl-2-oxoimidazolidin-1-yl)phenyl)-1,5-dihydro-4H-pyrazolo[4,3-c]pyridin-4-one The title compound was obtained using 1-(2,6-difluorophenyl)-4-methoxy-1H-pyrazolo[4,3-c]pyridin-3-yl trifluoromethanesulfonate obtained in Step C of Example 35 and 1-methyl-3-(4-(4,4,5,5-tetramethyl-1,3,2-dioxaborolan-2-yl)phenyl)imidazolidin-2-one obtained in Step A of Example 239, in the same manner as in Step B of Example 220.
MS (ESI+): [M+H]$^+$ 422.4.
MS (ESI+). found: 422.4.

Example 241

7-chloro-1-(2,6-difluorophenyl)-3-(4-((2-methoxyethyl)(methyl)amino)phenyl)-1,5-dihydro-4H-pyrazolo[4,3-c]pyridin-4-one The title compound (118 mg) was obtained using 7-chloro-1-(2,6-difluorophenyl)-4-methoxy-1H-pyrazolo[4,3-c]pyridin-3-yl trifluoromethanesulfonate obtained in Step A of Example 152 (427 mg) and 2-methoxy-N-methylethanamine (0.455 mL), in the same manner as in Step A of Example 236, Step B of Example 236, Step B of Example 152 and Step C of Example 152.
MS(ESI+): [M+H]$^+$ 445.1.
MS(ESI+). found: 445.3.

Example 242

7-chloro-1-(2,6-difluorophenyl)-3-(4-(1,1-dioxidothiomorpholin-4-yl)phenyl)-1,5-dihydro-4H-pyrazolo[4,3-c]pyridin-4-one To a mixture of 7-chloro-1-(2,6-difluorophenyl)-3-(4-(thiomorpholin-4-yl)phenyl)-1,5-dihydro-4H-pyrazolo[4,3-c]pyridin-4-one (30 mg) obtained in Example 236 in a mixed solvent of methanol (3 mL) and water (0.15 mL) was added Oxone (registered trademark) (80 mg) at room temperature. The reaction mixture was stirred at 80° C. for 16 hr. To the reaction mixture was added water, and the mixture was extracted with THF. The organic layer was washed with saturated brine, dried over anhydrous magnesium sulfate, and concentrated under reduced pressure. The residue was purified by silica gel column chromatography (NH, ethyl acetate/hexane) to give the title compound (5.7 mg).
MS(ESI+): [M+H]$^+$ 491.1.
MS(ESI+). found: 491.3.

Example 243

1-tert-butyl-3-(4-(morpholin-4-yl)phenyl)-1,5-dihydro-4H-pyrazolo[4,3-c]pyridin-4-one The title compound was obtained using 4-iodo-2-methoxynicotinic acid and tert-butylhydrazine hydrochloride obtained in Step C of Example 6 and 4-(4-(4,4,5,5-tetramethyl-1,3,2-dioxaborolan-2-yl)phenyl)morpholine, in the same manner as in Step A to Step C of Example 35, Step I of Example 33 and Step J of Example 33.
MS (ESI+): [M+H]$^+$ 353.4.
MS (ESI+). found: 353.3.

Example 244

3,5-difluoro-4-(3-(4-(morpholin-4-yl)phenyl)-4-oxo-4,5-dihydro-1H-pyrazolo[4,3-c]pyridin-1-yl)benzonitrile A) 1-tert-butyl-4-methoxy-3-(4-(morpholin-4-yl)phenyl)-1H-pyrazolo[4,3-c]pyridine The title compound was obtained using 4-iodo-2-methoxynicotinic acid obtained in Step C of Example 6, tert-butylhydrazine hydrochloride and 4-(4-(4,4,5,5-tetramethyl-1,3,2-dioxaborolan-2-yl)phenyl)morpholine, in the same manner as in Step A to Step C of Example 35 and Step I of Example 33.
MS (ESI+): [M+H]$^+$ 367.4.
MS (ESI+). found: 367.3.

B) 4-methoxy-3-(4-(morpholin-4-yl)phenyl)-1H-pyrazolo[4,3-c]pyridine

To a solution of 1-tert-butyl-4-methoxy-3-(4-(morpholin-4-yl)phenyl)-1H-pyrazolo[4,3-c]pyridine (2.2 g) in trifluoroacetic acid (50 mL) was added water (5 mL), and the mixture was stirred overnight at 130° C. The reaction mixture was concentrated under reduced pressure. To the obtained residue was added saturated aqueous sodium bicarbonate solution, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (0.332 g).
MS (ESI+): [M+H]$^+$ 311.3.
MS (ESI+). found: 311.2.

C) 3,5-difluoro-4-(4-methoxy-3-(4-(morpholin-4-yl)phenyl)-1H-pyrazolo[4,3-c]pyridin-1-yl)benzonitrile To a solution of 4-methoxy-3-(4-(morpholin-4-yl)phenyl)-1H-pyrazolo[4,3-c]pyridine (250 mg), 1,4,7,10,13-pentaoxacyclopentadecane (266 mg) and 3,4,5-trifluorobenzonitrile (152 mg) in DMF (5 ml) was added sodium hydride (60%, 48.03 mg) at 0° C., and the mixture was stirred at 0° C. for 1 hr. To the reaction mixture was added saturated aqueous sodium bicarbonate solution, and the mixture was extracted with ethyl acetate. The organic layer was washed with, saturated brine, dried over anhydrous magnesium sulfate, and concentrated under reduced pressure. The residue was purified by silica gel column chromatography (ethyl acetate/hexane) to give the title compound (250 mg).
MS (ESI+): [M+H]$^+$ 448.4.
MS (ESI+). found: 448.4.

D) 3,5-difluoro-4-(3-(4-(morpholin-4-yl)phenyl)-4-oxo-4,5-dihydro-1H-pyrazolo[4,3-c]pyridin-1-yl)benzonitrile The title compound was obtained using 3,5-difluoro-4-(4-methoxy-3-(4-(morpholin-4-yl)phenyl)-1H-pyrazolo[4,3-c]pyridin-1-yl)benzonitrile, in the same manner as in Step J of Example 33.
MS (ESI+): [M+H]$^+$ 434.4.
MS (ESI+). found: 434.3.

Example 245

1-(2,6-difluorophenyl)-3-(4-((3S)-3-methylmorpholin-4-yl)phenyl)-1,5-dihydro-4H-pyrazolo[4,3-c]pyridin-4-one A) (3S)-4-(4-bromophenyl)-3-methylmorpholine A solution of 1,4-dibromobenzene (1.0 g), (3S)-3-methylmorpholine p-toluenesulfate (1.16 g), tris(dibenzylideneacetone)dipalladium(0) (97 mg), 2,2'-bis(diphenylphosphino)-1,1'-binaphthyl (198 mg) and sodium tert-butoxide (1.0 g) in toluene (20 mL) was stirred at 80° C. for 16 hr. To the reaction mixture was added water, and the insoluble substance was removed by filtration through Celite. The filtrate was extracted with ethyl acetate. The organic layer was washed successively with water and saturated brine, dried over anhydrous magnesium sulfate, and concentrated under reduced pressure. The residue was purified by silica gel column chromatography (ethyl acetate/hexane) to give the title compound (635 mg).
MS (ESI+): [M+H]$^+$ 256.0, 258.0.
MS (ESI+). found: 256.1, 258.1.

B) (3S)-3-methyl-4-(4-(4,4,5,5-tetramethyl-1,3,2-dioxaborolan-2-yl)phenyl)morpholine To a solution of (3S)-4-(4-bromophenyl)-3-methylmorpholine (630 mg), 4,4,5,5-tetramethyl-1,3,2-dioxaborolane (630 mg) and triethylamine (1.03 mL) in 1,4-dioxane (10 mL) was added dichlorobis(triphenylphosphine)palladium(II) (86 mg), and the mixture was stirred overnight at 100° C. To the reaction mixture was added water, and the mixture was extracted with ethyl acetate. The organic layer was washed successively with water and saturated brine, dried over anhydrous magnesium sulfate, and concentrated under reduced pressure. The residue was purified by silica gel column chromatography (ethyl acetate/hexane) to give the title compound (470 mg).

MS (ESI+): [M+H]$^+$ 304.2.
MS (ESI+). found: 304.3.

C) 1-(2,6-difluorophenyl)-3-(4-((3S)-3-methylmorpholin-4-yl)phenyl)-1,5-dihydro-4H-pyrazolo[4,3-c]pyridin-4-one The title compound was obtained using 1-(2,6-difluorophenyl)-4-methoxy-1H-pyrazolo[4,3-c]pyridin-3-yl trifluoromethanesulfonate obtained in Step C of Example 35 and (3S)-3-methyl-4-(4-(4,4,5,5-tetramethyl-1,3,2-dioxaborolan-2-yl)phenyl)morpholine, in the same manner as in Step I of Example 33 and Step J of Example 33.

$^1$H NMR (300 MHz, DMSO-d$_6$) δ 1.05 (3H, d, J=6.4 Hz), 2.95-3.12 (1H, m), 3.27-3.32 (1H, m), 3.49-3.64 (1H, m), 3.72 (2H, d, J=2.3 Hz), 3.88-4.07 (2H, m), 6.22 (1H, s), 6.95 (2H, d, J=9.1 Hz), 7.21-7.35 (1H, m), 7.40-7.56 (2H, m), 7.67-7.88 (1H, m), 8.24 (2H, d, J=9.1 Hz), 11.23-11.42 (1H, m).

Example 246

1-(2,6-difluorophenyl)-3-(4-((3R)-3-methylmorpholin-4-yl)phenyl)-1,5-dihydro-4H-pyrazolo[4,3-c]pyridin-4-one The title compound was obtained using (3R)-3-methylmorpholine p-toluenesulfate, in the same manner as in Step A to Step C of Example 245.

MS (ESI+): [M+H]$^+$ 423.2.
MS (ESI+). found: 423.3.

Example 247

4-(4-oxo-1-(pyridin-2-yl)-4,5-dihydro-1H-pyrazolo[4,3-c]pyridin-3-yl)thiophene-2-carboxamide The title compound was obtained using 4-(4-methoxy-1H-pyrazolo[4,3-c]pyridin-3-yl)thiophene-2-carboxamide obtained in Step A of Example 148 and 2-iodopyridine, in the same manner as in Step B of Example 148 and Step C of Example 148.

MS (ESI+): [M+H]$^+$ 338.1.
MS (ESI+). found: 338.2.

Example 248

3-((l-tert-butyl-4-oxo-4,5-dihydro-1H-pyrazolo[4,3-c]pyridin-3-yl)amino)benzenesulfonamide A) 3-((l-tert-butyl-4-methoxy-1H-pyrazolo[4,3-c]pyridin-3-yl)amino)benzenesulfonamide To a solution of 1-tert-butyl-4-methoxy-1H-pyrazolo[4,3-c]pyridin-3-yl trifluoromethanesulfonate (200 mg) obtained in Step C of Example 86 in toluene (20 ml) were added 3-aminobenzenesulfonamide (146 mg), tris(dibenzylideneacetone)dipalladium (51.8 mg), (9,9-dimethyl-9H-xanthene-4,5-diyl)bis(diphenylphosphine)(92.6 mg) and cesium carbonate (369 mg), and the mixture was heated overnight with reflux under nitrogen atmosphere. The reaction mixture was extracted with water and ethyl acetate, and the organic layer was washed with saturated brine, dried over anhydrous sodium sulfate, filtered, and concentrated under reduced pressure. The obtained residue was purified by silica gel column chromatography (ethyl acetate/hexane) to give the title compound (29.6 mg).

MS (ESI+): [M+H]$^+$ 376.1.
MS (ESI+). found: 376.2.

B) 3-((1-tert-butyl-4-oxo-4,5-dihydro-1H-pyrazolo[4,3-c]pyridin-3-yl)amino)benzenesulfonamide The title compound was obtained using 3-((1-tert-butyl-4-methoxy-1H-pyrazolo[4,3-c]pyridin-3-yl)amino)benzenesulfonamide, in the same manner as in Step E of Example 86.

MS (ESI+): [M+H]$^+$ 362.1.
MS (ESI+). found: 362.3.

Example 249

1-tert-butyl-3-((4-methoxybenzyl)amino)-1,5-dihydro-4H-pyrazolo[4,3-c]pyridin-4-one The title compound was obtained using 1-tert-butyl-4-methoxy-1H-pyrazolo[4,3-c]pyridin-3-yl trifluoromethanesulfonate obtained in Step C of Example 86, in the same manner as in Step A of Example 248 and Step E of Example 86.

MS (ESI+): [M+H]$^+$ 327.2.
MS (ESI+). found: 327.3.

Example 250

3-anilino-1-tert-butyl-1,5-dihydro-4H-pyrazolo[4,3-c]pyridin-4-one

The title compound was obtained using 1-tert-butyl-4-methoxy-1H-pyrazolo[4,3-c]pyridin-3-yl trifluoromethanesulfonate obtained in Step C of Example 86, in the same manner as in Step A of Example 248 and Step E of Example 86.

MS (ESI+): [M+H]$^+$ 283.2.
MS (ESI+). found: 283.2.

Example 251

3,5-difluoro-4-(3-(4-(morpholin-4-yl)phenyl)-4-oxo-4,5-dihydro-1H-pyrazolo[4,3-c]pyridin-1-yl)benzamide To a solution of 3,5-difluoro-4-(3-(4-(morpholin-4-yl)phenyl)-4-oxo-4,5-dihydro-1H-pyrazolo[4,3-c]pyridin-1-yl)benzonitrile (120 mg) obtained in Step D of Example 244 in a mixed solvent of DMSO (3 mL) and water (0.25 mL) were added potassium carbonate (45.9 mg) and aqueous hydrogen peroxide (concentration 30 w/v %, 0.085 mL), and the mixture was stirred overnight at room temperature. The precipitate was collected by filtration, and washed with DMSO and water to give the title compound (64 mg).

MS (ESI+): [M+H]$^+$ 452.4.
MS (ESI+). found: 452.4.

Example 252

2-(3-(1-(2,6-difluorophenyl)-4-oxo-4,5-dihydro-1H-pyrazolo[4,3-c]pyridin-3-yl)phenyl)acetamide A) methyl (3-(4,4,5,5-tetramethyl-1,3,2-dioxaborolan-2-yl)phenyl)acetate The title compound was obtained using methyl (3-bromophenyl)acetate, in the same manner as in Step B of Example 215.
MS (ESI+): [M+H]$^+$ 277.1.
MS (ESI+). found: 277.3.

B) (3-(1-(2,6-difluorophenyl)-4-methoxy-1H-pyrazolo[4,3-c]pyridin-3-yl)phenyl)acetic acid To a solution of 1-(2,6-difluorophenyl)-4-methoxy-1H-pyrazolo[4,3-c]pyridin-3-yl trifluoromethanesulfonate (600 mg) obtained in Step C of Example 35 in a mixed solvent of DMF (5 mL)/water (0.5 mL) were added methyl (3-(4,4,5,5-tetramethyl-1,3,2-dioxaborolan-2-yl)phenyl)acetate (567 mg), (1,1'-bis(diphenylphosphino)ferrocene)dichloropalladium(II) (60 mg) and potassium carbonate (405 mg). The reaction mixture was stirred overnight at 90° C. The reaction mixture was diluted with water, and the aqueous layer was washed with ethyl acetate. The aqueous layer was neutralized with 1M hydrochloric acid at 0° C., and the mixture was extracted with ethyl acetate. The organic layer was washed with saturated brine, dried over anhydrous magnesium sulfate, filtered, and concentrated under reduced pressure. The obtained residue was purified by silica gel column chromatography (ethyl acetate/hexane) to give the title compound (205 mg).
MS (ESI+): [M+H]$^+$ 397.1.
MS (ESI+). found: 397.2.

C) 2-(3-(1-(2,6-difluorophenyl)-4-oxo-4,5-dihydro-1H-pyrazolo[4,3-c]pyridin-3-yl)phenyl)acetamide The title compound was obtained using (3-(1-(2,6-difluorophenyl)-4-methoxy-1H-pyrazolo[4,3-c]pyridin-3-yl)phenyl)acetic acid, in the same manner as in Step C of Example 129 and Step C of Example 93.
MS (ESI+): [M+H]$^+$ 381.1.
MS (ESI+). found: 381.3.

Example 253

2-(3-(1-(2,6-difluorophenyl)-4-oxo-4,5-dihydro-1H-pyrazolo[4,3-c]pyridin-3-yl)phenyl)-N-methylacetamide The title compound was obtained using (3-(1-(2,6-difluorophenyl)-4-methoxy-1H-pyrazolo[4,3-c]pyridin-3-yl)phenyl)acetic acid obtained in Step B of Example 252, in the same manner as in Step C of Example 180 and Step J of Example 33.
MS (ESI+): [M+H]$^+$ 396.1.
MS (ESI+). found: 396.3.

Example 254

3-(7-chloro-1-(2,6-difluorophenyl)-4-oxo-4,5-dihydro-1H-pyrazolo[4,3-c]pyridin-3-yl)benzamide The title compound was obtained using 7-chloro-1-(2,6-difluorophenyl)-4-methoxy-1H-pyrazolo[4,3-c]pyridin-3-yl trifluoromethanesulfonate obtained in Step A of Example 152 and (3-carbamoyl phenyl)boronic acid, in the same manner as in Step B of Example 220.
MS (ESI+): [M+H]$^+$ 401.8.
MS (ESI+). found: 401.2.

Example 255

3-(1-(2,6-difluorophenyl)-4-oxo-4,5-dihydro-1H-pyrazolo[4,3-c]pyridin-3-yl)benzamide The title compound was obtained using 1-(2,6-difluorophenyl)-4-methoxy-1H-pyrazolo[4,3-c]pyridin-3-yl trifluoromethanesulfonate obtained in Step C of Example 35 and (3-carbamoyl phenyl)boronic acid, in the same manner as in Step B of Example 220.
MS (ESI+): [M+H]$^+$ 367.3.
MS (ESI+). found: 367.2.

Example 256

1-(2,6-difluorophenyl)-3-(4-(3,6-dihydro-2H-pyran-4-yl)phenyl)-1,5-dihydro-4H-pyrazolo[4,3-c]pyridin-4-one The title compound was obtained using 1-(2,6-difluorophenyl)-4-methoxy-1H-pyrazolo[4,3-c]pyridin-3-yl trifluoromethanesulfonate obtained in Step C of Example 35 and 4-(4-(4,4,5,5-tetramethyl-1,3,2-dioxaborolan-2-yl)phenyl)-3,6-dihydro-2H-pyran, in the same manner as in Step I of Example 33 and Step J of Example 33.
MS (ESI+): [M+H]$^+$ 406.4.
MS (ESI+). found: 406.3.

Example 257

1-(2,6-difluorophenyl)-3-(4-(tetrahydro-2H-pyran-4-yl)phenyl)-1,5-dihydro-4H-pyrazolo[4,3-c]pyridin-4-one The title compound was obtained using 1-(2,6-difluorophenyl)-4-methoxy-1H-pyrazolo[4,3-c]pyridin-3-yl trifluoromethanesulfonate obtained in Step C of Example 35 and 4-(4-(4,4,5,5-tetramethyl-1,3,2-dioxaborolan-2-yl)phenyl)tetrahydro-2H-pyran, in the same manner as in Step I of Example 33 and Step J of Example 33.
MS (ESI+): [M+H]$^+$ 408.4.
MS (ESI+). found: 408.3.

Example 258

1-(2,6-difluorophenyl)-3-(3-((dimethylamino)methyl)phenyl)-1,5-dihydro-4H-pyrazolo[4,3-c]pyridin-4-one A) (3-(1-(2,6-difluorophenyl)-4-methoxy-1H-pyrazolo[4,3-c]pyridin-3-yl)phenyl)methanol The title compound was obtained using 1-(2,6-difluorophenyl)-4-methoxy-1H-pyrazolo[4,3-c]pyridin-3-yl trifluoromethanesulfonate obtained in Step C of Example 35 and (3-(4,4,5,5-tetramethyl-1,3,2-dioxaborolan-2-yl)phenyl)methanol, in the same manner as in Step A of Example 180.
MS (ESI+): [M+H]$^+$ 368.1.
MS (ESI+). found: 368.2.

B) 3-(1-(2,6-difluorophenyl)-4-methoxy-1H-pyrazolo[4,3-c]pyridin-3-yl)benzyl methanesulfonate, and 3-(3-(chloromethyl)phenyl)-1-(2,6-difluorophenyl)-4-methoxy-1H-pyrazolo[4,3-c]pyridine To a solution of (3-(1-(2,6-difluorophenyl)-1H-pyrazolo[4,3-c]pyridin-3-yl)phenyl)methanol (400 mg) and triethylamine (0.228 mL) in THF (3 mL) was added methanesulfonyl chloride (0.126 mL) at 0° C., and the mixture was stirred overnight at room temperature. To the reaction mixture was added saturated aqueous sodium hydrogencarbonate solution, and the mixture was extracted with ethyl acetate. The organic layer was washed successively with water and saturated brine, dried over anhydrous magnesium sulfate, and concentrated under reduced pressure. The residue was purified by silica gel column chromatography (ethyl acetate/hexane) to give 3-(1-(2,6-difluorophenyl)-4-methoxy-1H-pyrazolo[4,3-c]pyridin-3-yl)benzyl methanesulfonate (386 mg) and 3-(3-(chloromethyl)phenyl)-1-(2,6-difluorophenyl)-4-methoxy-1H-pyrazolo[4,3-c]pyridine (48 mg).

3-(1-(2,6-difluorophenyl)-4-methoxy-1H-pyrazolo[4,3-c]pyridin-3-yl)benzyl methanesulfonate MS (ESI+): [M+H]$^+$ 446.1.
MS (ESI+). found: 446.3.

3-(3-(chloromethyl)phenyl)-1-(2,6-difluorophenyl)-4-methoxy-1H-pyrazolo[4,3-c]pyridine MS (ESI+): [M+H]$^+$ 386.1.
MS (ESI+). found: 386.2.

C) 1-(3-(1-(2,6-difluorophenyl)-4-methoxy-1H-pyrazolo[4,3-c]pyridin-3-yl)phenyl)-N,N-dimethylmethanamine To a solution of 3-(1-(2,6-difluorophenyl)-4-methoxy-1H-pyrazolo[4,3-c]pyridin-3-yl)benzyl methanesulfonate (75 mg), dimethylamine hydrochloride (79 mg) and sodium iodide (29 mg) in DMF (1 mL) was added triethylamine (0.135 mL), and the mixture was stirred at 90° C. for 2 hr. To the reaction mixture was added saturated aqueous sodium hydrogencarbonate solution, and the mixture was extracted with ethyl acetate. The organic layer was washed successively with water and saturated brine, dried over anhydrous magnesium sulfate, and concentrated under reduced pressure. The residue was purified by silica gel column chromatography (basic silica gel, ethyl acetate/hexane) to give the title compound (62 mg).

MS (ESI+): [M+H]$^+$ 395.2.
MS (ESI+). found: 395.3.

D) 1-(2,6-difluorophenyl)-3-(3-((dimethylamino)methyl)phenyl)-1,5-dihydro-4H-pyrazolo[4,3-c]pyridin-4-one The title compound was obtained using 1-(3-(1-(2,6-difluorophenyl)-4-methoxy-1H-pyrazolo[4,3-c]pyridin-3-yl)phenyl)-N,N-dimethylmethanamine, in the same manner as in Step J of Example 33.

MS (ESI+): [M+H]$^+$ 381.1.
MS (ESI+). found: 381.3.

Example 259 ethyl 5-(1-(2,6-difluorophenyl)-4-oxo-4,5-dihydro-1H-pyrazolo[4,3-c]pyridin-3-yl)pyridine-2-carboxylate A) ethyl 5-(4,4,5,5-tetramethyl-1,3,2-dioxaborolan-2-yl)pyridine-2-carboxylate The title compound was obtained using ethyl 5-bromopyridine-2-carboxylate, in the same manner as in Step B of Example 215.

MS (ESI+): [M+H]$^+$ 278.2.
MS (ESI+). found: 278.2.

B) ethyl 5-(1-(2,6-difluorophenyl)-4-oxo-4,5-dihydro-1H-pyrazolo[4,3-c]pyridin-3-yl)pyridine-2-carboxylate The title compound was obtained using 1-(2,6-difluorophenyl)-4-methoxy-1H-pyrazolo[4,3-c]pyridin-3-yl trifluoromethanesulfonate obtained in Step C of Example 35 and ethyl 5-(4,4,5,5-tetramethyl-1,3,2-dioxaborolan-2-yl)pyridine-2-carboxylate, in the same manner as in Step A of Example 180 and Step J of Example 33.

MS (ESI+): [M+H]$^+$ 397.1.
MS (ESI+). found: 397.2.

Example 260 methyl 4-(1-(2,6-difluorophenyl)-4-oxo-4,5-dihydro-1H-pyrazolo[4,3-c]pyridin-3-yl)benzoate The title compound was obtained using methyl 4-(1-(2,6-difluorophenyl)-4-methoxy-1H-pyrazolo[4,3-c]pyridin-3-yl)benzoate obtained in Step A of Example 180, in the same manner as in Step J of Example 33.

MS (ESI+): [M+H]$^+$ 382.1.
MS (ESI+). found: 382.2.

Example 261

1-(2,6-difluorophenyl)-3-(3-((3,3-difluoropyrrolidin-1-yl)methyl)phenyl)-1,5-dihydro-4H-pyrazolo[4,3-c]pyridin-4-one The title compound was obtained using 3-(3-(chloromethyl)phenyl)-1-(2,6-difluorophenyl)-4-methoxy-1H-pyrazolo[4,3-c]pyridine obtained in Step B of Example 258 and 3,3-difluoropyrrolidine hydrochloride, in the same manner as in Step C of Example 258 and Step J of Example 33.

MS (ESI+): [M+H]$^+$ 443.1.
MS (ESI+). found: 443.3.

Example 262

4-(1-((2S)-1-methoxybutan-2-yl)-4-oxo-4,5-dihydro-1H-pyrazolo[4,3-c]pyridin-3-yl)thiophene-2-carboxamide The racemic form of the title compound was obtained using 4-(4-methoxy-1H-pyrazolo[4,3-c]pyridin-3-yl)thiophene-2-carboxamide obtained in Step A of Example 148 and 1-methoxybutan-2-yl 4-methylbenzenesulfonate, in the same manner as in Step B of Example 148 and Step C of Example 148.

The obtained racemic form was resolved by HPLC (column: L-column2 ODS (trade name) 20 mmID×150 mmL, 5 μm, manufactured by Daicel Chemical Industries, mobile phase: water/acetonitrile (containing 10 mM ammonium carbonate)) to give the title compound having a shorter retention time.

MS (ESI+): [M+H]$^+$ 347.1.
MS (ESI+). found: 347.2.

Example 263

4-(1-((2R)-1-methoxybutan-2-yl)-4-oxo-4,5-dihydro-1H-pyrazolo[4,3-c]pyridin-3-yl)thiophene-2-carboxamide The racemic form obtained in Example 262 was resolved by HPLC (column: L-column2 ODS (trade name) 20 mmID× 150 mmL, 5 μm, manufactured by Daicel Chemical Industries, mobile phase: water/acetonitrile (containing 10 mM ammonium carbonate)) to give the title compound having a longer retention time.

MS (ESI+): [M+H]$^+$ 347.1.
MS (ESI+). found: 347.2.

Example 264

3-amino-1-tert-butyl-1,5-dihydro-4H-pyrazolo[4,3-c]pyridin-4-one

To a solution of 1-tert-butyl-3-((4-methoxybenzyl)amino)-1,5-dihydro-4H-pyrazolo[4,3-c]pyridin-4-one (250 mg) obtained in Example 249 in TFA (5 ml) was added triethylsilane (0.306 ml), and the mixture was stirred overnight at room temperature. The reaction mixture was concentrated under reduced pressure, and the obtained residue was purified by silica gel column chromatography (ethyl acetate/methanol) to give the title compound (155 mg).

MS (ESI+): [M+H]$^+$ 207.1.
MS (ESI+). found: 207.2.

Example 265

N-(1-tert-butyl-4-oxo-4,5-dihydro-1H-pyrazolo[4,3-c]pyridin-3-yl)benzamide

To a solution of 3-amino-1-tert-butyl-1,5-dihydro-4H-pyrazolo[4,3-c]pyridin-4-one (20.0 mg) obtained in Example 264 and pyridine (0.016 ml) in THF (3 ml) was added benzoyl chloride (0.023 ml), and the mixture was stirred overnight at room temperature. The reaction mixture was extracted with water and ethyl acetate, and the organic layer was washed with saturated brine, dried over anhydrous sodium sulfate, filtered, and concentrated under reduced pressure. The obtained residue was purified by silica gel column chromatography (ethyl acetate/methanol) to give the title compound (28.8 mg).

MS (ESI+): [M+H]$^+$ 311.2.
MS (ESI+). found: 311.2.

Example 266

1-(4,4-difluorocyclohexyl)-3-(4-(morpholin-4-yl)phenyl)-1,5-dihydro-4H-pyrazolo[4,3-c]pyridin-4-one The title compound was obtained using 4-methoxy-3-(4-(morpholin-4-yl)phenyl)-1H-pyrazolo[4,3-c]pyridine obtained in Step B of Example 244 and 4,4-difluorocyclohexyl 4-methylbenzenesulfonate, in the same manner as in Step C of Example 244 and Step J of Example 33.

MS (ESI+): [M+H]$^+$ 414.4.
MS (ESI+). found: 415.4.

Example 267

3-(1-(2,6-difluorophenyl)-4-oxo-4,5-dihydro-1H-pyrazolo[4,3-c]pyridin-3-yl)-4-fluorobenzamide The title compound was obtained using methyl 3-bromo-4-fluorobenzoate, in the same manner as in Step A of Example 220, Step D of Example 35 and Steps F, G and J of Example 33.

MS (ESI+): [M+H]$^+$ 385.3.
MS (ESI+). found: 385.2.

Example 268

3-(1-(2,6-difluorophenyl)-4-oxo-4,5-dihydro-1H-pyrazolo[4,3-c]pyridin-3-yl)-5-fluorobenzamide The title compound was obtained using methyl 3-bromo-5-fluorobenzoate, in the same manner as in Step A of Example 220, Step D of Example 35, Step F of Example 33, Step G of Example 33 and Step J of Example 33.

MS (ESI+): [M+H]$^+$ 385.3.
MS (ESI+). found: 385.2.

Example 269

3-(7-chloro-1-(2,6-difluorophenyl)-4-oxo-4,5-dihydro-1H-pyrazolo[4,3-c]pyridin-3-yl)-4-fluorobenzamide The title compound was obtained using methyl 3-bromo-4-fluorobenzoate, in the same manner as in Step A of Example 220, Step E-3 of Example 29, Step F of Example 33, Step G of Example 33 and Step J of Example 33.

MS (ESI+): [M+H]$^+$ 419.8.
MS (ESI+). found: 419.2.

Example 270

3-(7-chloro-1-(2,6-difluorophenyl)-4-oxo-4,5-dihydro-1H-pyrazolo[4,3-c]pyridin-3-yl)-5-fluorobenzamide The title compound was obtained using methyl 3-bromo-5-fluorobenzoate, in the same manner as in Step A of Example 220, Step E-3 of Example 29, Step F of Example 33, Step G of Example 33 and Step J of Example 33.

MS (ESI+): [M+H]$^+$ 419.8.
MS (ESI+). found: 419.2.

Example 271

3-(7-chloro-1-(2,6-difluorophenyl)-4-oxo-4,5-dihydro-1H-pyrazolo[4,3-c]pyridin-3-yl)-4-fluoro-N-methylbenzamide The title compound was obtained using methyl 3-bromo-4-fluorobenzoate and methylamine hydrochloride, in the same manner as in Step A of Example 220, Step E-3 of Example 29, Step F of Example 33, Step G of Example 33 and Step J of Example 33.

MS (ESI+): [M+H]⁺ 433.8.
MS (ESI+). found: 433.2.

Example 272

3-(1-(2,6-difluorophenyl)-4-oxo-4,5-dihydro-1H-pyrazolo[4,3-c]pyridin-3-yl)-4-fluoro-N-methylbenzamide The title compound was obtained using methyl 3-bromo-4-fluorobenzoate and methylamine hydrochloride, in the same manner as in Step A of Example 220, Step D of Example 35, Step F of Example 33, Step G of Example 33 and Step J of Example 33.
MS (ESI+): [M+H]⁺ 399.3.
MS (ESI+). found: 399.2.

Example 273

3-(7-chloro-1-(2,6-difluorophenyl)-4-oxo-4,5-dihydro-1H-pyrazolo[4,3-c]pyridin-3-yl)-5-fluoro-N-methylbenzamide The title compound was obtained using methyl 3-bromo-5-fluorobenzoate and methylamine hydrochloride, in the same manner as in Step A of Example 220, Step E-3 of Example 29, Step F of Example 33, Step G of Example 33 and Step J of Example 33.
MS (ESI+): [M+H]⁺ 433.8.
MS (ESI+). found: 433.2.

Example 274

3-(1-(2,6-difluorophenyl)-4-oxo-4,5-dihydro-1H-pyrazolo[4,3-c]pyridin-3-yl)-5-fluoro-N-methylbenzamide The title compound was obtained using methyl 3-bromo-5-fluorobenzoate and methylamine hydrochloride, in the same manner as in Step A of Example 220, Step D of Example 35, Step F of Example 33, Step G of Example 33 and Step J of Example 33.
MS (ESI+): [M+H]⁺ 399.3.
MS (ESI+). found: 399.2.

Example 275

1-(2,6-difluorophenyl)-3-(4-((2-oxopyrrolidin-1-yl)methyl)phenyl)-1,5-dihydro-4H-pyrazolo[4,3-c]pyridin-4-one The title compound was obtained using 1-(4-bromobenzyl)pyrrolidin-2-one, in the same manner as in Step A of Example 220, Step D of Example 35 and Step J of Example 33.
MS (ESI+): [M+H]⁺ 421.4.
MS (ESI+). found: 421.3.

Example 276

1-(2,6-difluorophenyl)-3-(4-(2-oxoimidazolidin-1-yl)phenyl)-1,5-dihydro-4H-pyrazolo[4,3-c]pyridin-4-one The title compound was obtained using tert-butyl 2-oxo-3-(4-(4,4,5,5-tetramethyl-1,3,2-dioxaborolan-2-yl)phenyl)imidazolidine-1-carboxylate obtained in Step A of Example 225, in the same manner as in Step D of Example 35 and Step J of Example 33.
MS (ESI+): [M+H]⁺ 408.4.
MS (ESI+). found: 408.3.

Example 277

N-(4-(1-(2,6-difluorophenyl)-4-oxo-4,5-dihydro-1H-pyrazolo[4,3-c]pyridin-3-yl)phenyl)acetamide The title compound was obtained using N-(4-(4,4,5,5-tetramethyl-1,3,2-dioxaborolan-2-yl)phenyl)acetamide, in the same manner as in Step D of Example 35 and Step J of Example 33.
MS (ESI+): [M+H]⁺ 381.3.
MS (ESI+). found: 381.2.

Example 278

1-(2,6-difluorophenyl)-3-(3-(hydroxymethyl)phenyl)-1,5-dihydro-4H-pyrazolo[4,3-c]pyridin-4-one The title compound was obtained using (3-(1-(2,6-difluorophenyl)-4-methoxy-1H-pyrazolo[4,3-c]pyridin-3-yl)phenyl)methanol obtained in Step A of Example 258, in the same manner as in Step J of Example 33.
MS (ESI+): [M+H]⁺ 354.1.
MS (ESI+). found: 354.2.

Example 279

3-(4-(4-acetylpiperazin-1-yl)phenyl)-1-(2,6-difluorophenyl)-1,5-dihydro-4H-pyrazolo[4,3-c]pyridin-4-one The title compound was obtained using 1-(2,6-difluorophenyl)-4-methoxy-1H-pyrazolo[4,3-c]pyridin-3-yl trifluoromethanesulfonate obtained in Step C of Example 35 and 1-(4-(4-(4,4,5,5-tetramethyl-1,3,2-dioxaborolan-2-yl)phenyl)piperazin-1-yl)ethanone, in the same manner as in Step A of Example 180 and Step J of Example 33.
MS (ESI+): [M+H]⁺ 450.2.
MS (ESI+). found: 450.4.

Example 280

4-(7-bromo-1-cyclopentyl-4-oxo-4,5-dihydro-1H-pyrazolo[4,3-c]pyridin-3-yl)thiophene-2-carboxamide The title compound was obtained using 4-(7-bromo-1-cyclopentyl-4-methoxy-1H-pyrazolo[4,3-c]pyridin-3-yl)thiophene-2-carboxamide obtained in Step C of Example 165, in the same manner as in Step E of Example 165 (3.0 mg).
¹H NMR (300 MHz, DMSO-d₆) δ 1.66 (2H, d, J=15.5 Hz), 1.84-2.03 (2H, m), 2.06-2.24 (4H, m), 5.78 (1H, quin, J=7.0 Hz), 7.42 (1H, brs), 7.52 (1H, s), 8.17 (1H, brs), 8.32 (1H, d, J=1.1 Hz), 9.06 (1H, d, J=1.1 Hz).

Example 281

4-(1-cyclopentyl-7-methyl-4-oxo-4,5-dihydro-1H-pyrazolo[4,3-c]pyridin-3-yl)thiophene-2-carboxamide A suspension of 4-(7-bromo-1-cyclopentyl-4-methoxy-1H-pyrazolo[4,3-c]pyridin-3-yl)thiophene-2-carboxamide (52.8 mg) obtained in Step C of Example 165, methylboronic acid (22.5 mg), 2M aqueous sodium carbonate solution (0.313 mL) and tetrakis(triphenylphosphine)palladium(0) (29.0 mg) in DMA was stirred under microwave irradiation at 130° C. for 1 hr. The reaction mixture was purified by silica gel column chromatography (ethyl acetate/hexane) to give a residue (34.0 mg) containing 4-(1-cyclopentyl-4-methoxy-7-methyl-1H-pyrazolo[4,3-c]pyridin-3-yl)thiophene-2-carboxamide.

To a solution of the obtained residue (31.2 mg) in acetonitrile (10 mL) were added sodium iodide (26.2 mg) and chloro(trimethyl)silane (0.089 mL), and the mixture was stirred at 60° C. for 30 min. The reaction mixture was concentrated under reduced pressure, and the residue was washed successively with water and ethyl acetate, dried over anhydrous sodium sulfate, and concentrated under reduced pressure. The residue was purified by silica gel column chromatography (ethyl acetate/hexane), and the residue was purified by HPLC (column: L-column2 ODS (trade name) 20 mmID× 150 mmL, 5 μm, manufactured by Daicel Chemical Industries, mobile phase: water/acetonitrile (containing 10 mM ammonium carbonate)) to give the title compound (3.5 mg).

MS (ESI+): [M+H]$^+$ 343.1.
MS (ESI+). found: 343.2.

Example 282

4-(1-cyclopentyl-7-cyclopropyl-4-oxo-4,5-dihydro-1H-pyrazolo[4,3-c]pyridin-3-yl)thiophene-2-carboxamide The title compound (11.0 mg) was obtained using 4-(7-bromo-1-cyclopentyl-4-methoxy-1H-pyrazolo[4,3-c]pyridin-3-yl)thiophene-2-carboxamide (46.5 mg) obtained in Step C of Example 165 and cyclopropylboronic acid (28.4 mg), in the same manner as in Example 281.

MS (ESI+): [M+H]$^+$ 369.1.
MS (ESI+). found: 369.2.

Example 283

3-anilino-1-cyclopentyl-1,5-dihydro-4H-pyrazolo[4,3-c]pyridin-4-one

A) 1-cyclopentyl-4-methoxy-N-phenyl-1H-pyrazolo[4,3-c]pyridin-3-amine

To a solution of 1-cyclopentyl-4-methoxy-1H-pyrazolo[4,3-c]pyridin-3-yl trifluoromethanesulfonate (100 mg) obtained in Step C of Example 12 in toluene (3 ml) were added aniline (0.075 mL), tris(dibenzylideneacetone)dipalladium (25.1 mg), 2-dicyclohexyl phosphino-2',4',6'-triisopropylbiphenyl (26.1 mg) and sodium tert-butoxide (132 mg), and the mixture was stirred under microwave irradiation at 100° C. for 1 hr. The reaction mixture was partitioned between water and ethyl acetate, and the organic layer was washed successively with water and saturated brine, dried over anhydrous sodium sulfate, and concentrated under reduced pressure. The obtained residue was purified by silica gel column chromatography (ethyl acetate/hexane), and then HPLC (column: L-column2 ODS (trade name) 20 mmID× 150 mmL, 5 μm, manufactured by Daicel Chemical Industries, mobile phase: water/acetonitrile (containing 10 mM ammonium carbonate)) to give the title compound (9.6 mg).

MS (ESI+): [M+H]$^+$ 309.2.
MS (ESI+). found: 309.2.

B) 3-anilino-1-cyclopentyl-1,5-dihydro-4H-pyrazolo[4,3-c]pyridin-4-one

The title compound (6.5 mg) was obtained using 1-cyclopentyl-4-methoxy-N-phenyl-1H-pyrazolo[4,3-c]pyridin-3-amine (7.1 mg), in the same manner as in Step B of Example 92.

MS (ESI+): [M+H]$^+$ 295.2.
MS (ESI+). found: 295.2.

Example 284

3-((1-cyclopentyl-4-oxo-4,5-dihydro-1H-pyrazolo[4,3-c]pyridin-3-yl)amino)benzenesulfonamide A) 3-((1-cyclopentyl-4-methoxy-1H-pyrazolo[4,3-c]pyridin-3-yl)amino)benzenesulfonamide To a solution of 1-cyclopentyl-4-methoxy-1H-pyrazolo[4,3-c]pyridin-3-yl trifluoromethanesulfonate (150 mg) obtained in Step C of Example 12 in toluene were added 3-aminobenzenesulfonamide (106 mg), tris(dibenzylideneacetone)dipalladium (37.6 mg), (9,9-dimethyl-9H-xanthene-4,5-diyl)bis(diphenylphosphine) (47.5 mg) and cesium carbonate (401 mg), and the mixture was heated overnight with reflux under nitrogen atmosphere. The reaction mixture was extracted with water and ethyl acetate, and the organic layer was washed with saturated brine, dried over anhydrous sodium sulfate, filtered, and concentrated under reduced pressure. The obtained residue was purified by silica gel column chromatography (ethyl acetate/hexane) to give the title compound (52.6 mg).

$^1$H NMR (300 MHz, DMSO-d$_6$) 51.54-1.80 (2H, m), 1.83-2.20 (6H, m), 4.03 (3H, s), 4.93-5.11 (1H, m), 7.17 (1H, d, J=6.0 Hz), 7.25 (2H, s), 7.31 (1H, d, J=8.3 Hz), 7.45 (1H, t, J=7.9 Hz), 7.75-7.93 (2H, m), 8.20-8.38 (2H, m).

MS (ESI+): [M+H]$^+$ 388.1.
MS (ESI+). found: 388.3.

B) 3-((1-cyclopentyl-4-oxo-4,5-dihydro-1H-pyrazolo[4,3-c]pyridin-3-yl)amino)benzenesulfonamide To a solution of 3-((1-cyclopentyl-4-methoxy-1H-pyrazolo[4,3-c]pyridin-3-yl)amino)benzenesulfonamide (14.4 mg) in acetonitrile (5 mL) were added sodium iodide (11.1 mg) and chloro(trimethyl)silane (0.038 mL), and the mixture was stirred at 60° C. for 1 hr. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane), and the obtained solid was washed with ethyl acetate/diisopropyl ether to give the title compound (10.4 mg).

$^1$H NMR (300 MHz, DMSO-d$_6$) δ 1.53-1.81 (2H, m), 1.83-2.16 (6H, m), 4.82-5.00 (1H, m), 6.55 (1H, d, J=7.2 Hz), 7.17 (1H, dd, J=7.2, 6.0 Hz), 7.25 (2H, s), 7.31 (1H, d, J=8.3 Hz), 7.44 (1H, t, J=7.9 Hz), 7.77 (1H, dd, J=7.9, 1.5 Hz), 8.22-8.40 (2H, m), 11.02 (1H, d, J=5.7 Hz).

MS (ESI+): [M+H]$^+$ 374.1.
MS (ESI+). found: 374.2.

Example 285

3-((7-bromo-1-cyclopentyl-4-oxo-4,5-dihydro-1H-pyrazolo[4,3-c]pyridin-3-yl)amino)benzenesulfonamide A) 3-((7-bromo-1-cyclopentyl-4-methoxy-1H-pyrazolo[4,3-c]pyridin-3-yl)amino)benzenesulfonamide The title compound (14.6 mg) was obtained using 3-((1-cyclopentyl-4-methoxy-1H-pyrazolo[4,3-c]pyridin-3-yl)amino)benzenesulfonamide (28.3 mg) obtained in Step A of Example 284, in the same manner as in Step A of Example 165.

MS (ESI+): [M+H]$^+$ 466.1.
MS (ESI+). found: 466.2.

B) 3-((7-bromo-1-cyclopentyl-4-oxo-4,5-dihydro-1H-pyrazolo[4,3-c]pyridin-3-yl)amino)benzenesulfonamide The title compound (7.3 mg) was obtained using 3-((7-bromo-1-cyclopentyl-4-methoxy-1H-pyrazolo[4,3-c]pyridin-3-yl)amino)benzenesulfonamide (12.0 mg), in the same manner as in Step B of Example 92.

MS (ESI+): [M+H]$^+$ 452.0.
MS (ESI+). found: 452.2.

Example 286

4-(1-cyclopentyl-4-oxo-4,5-dihydro-1H-pyrazolo[4,3-c]pyridin-3-yl)-N,N-dimethylthiophene-2-carboxamide A) 4-(1-cyclopentyl-4-methoxy-1H-pyrazolo[4,3-c]pyridin-3-yl)thiophene-2-carboxamide The title compound (282 mg) was obtained using 4-(1-cyclopentyl-4-methoxy-1H-pyrazolo[4,3-c]pyridin-3-yl)thiophene-2-carboxylic acid (328 mg) obtained in Step A of Example 155, in the same manner as in Example 27.

MS (ESI+): [M+H]$^+$ 343.1.
MS (ESI+). found: 343.2.

B) 4-(1-cyclopentyl-4-methoxy-1H-pyrazolo[4,3-c]pyridin-3-yl)-N,N-dimethylthiophene-2-carboxamide 4-(1-Cyclopentyl-4-methoxy-1H-pyrazolo[4,3-c]pyridin-3-yl)thiophene-2-carboxamide (51.0 mg) was added to a solution of sodium hydride (60% dispersion in mineral oil, 30.0 mg) in DMF (10 ml), and the mixture was stirred at room temperature for 30 min. To the reaction mixture was added iodomethane (0.023 mL), and the mixture was stirred overnight at room temperature. To the reaction mixture was added saturated aqueous ammonium chloride solution, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane) to give the title compound (55.0 mg).

MS (ESI+): [M+H]$^+$ 371.2,
MS (ESI+). found: 371.2.

C) 4-(1-cyclopentyl-4-methoxy-1H-pyrazolo[4,3-c]pyridin-3-yl)thiophene-2-carboxamide The title compound (36.0 mg) was obtained using 4-(1-cyclopentyl-4-methoxy-1H-pyrazolo[4,3-c]pyridin-3-yl)-N,N-dimethylthiophene-2-carboxamide (49.1 mg), in the same manner as in Step B of Example 92.

MS (ESI+): [M+H]$^+$ 357.1.
MS (ESI+). found: 357.2.

Example 287

1-(2,6-difluorophenyl)-3-(3-((3,3-difluoropyrrolidin-1-yl)methyl)phenyl)-1,5-dihydro-4H-pyrazolo[4,3-c]pyridin-4-one hydrochloride To a solution of 1-(2,6-difluorophenyl)-3-(3-((3,3-difluoropyrrolidin-1-yl)methyl)phenyl)-1,5-dihydro-4H-pyrazolo[4,3-c]pyridin-4-one (41 mg) obtained in Example 261 in ethyl acetate (2 mL) was added 4M hydrogen chloride ethyl acetate (0.024 mL), and the mixture was stirred at room temperature for 5 min. The precipitate was collected by filtration, and washed with ethyl acetate and hexane to give the title compound (34 mg).

MS (ESI+): [M+H]$^+$ 443.1.
MS (ESI+). found: 443.3.

Example 288

1-(2,6-difluorophenyl)-3-(3-(pyrrolidin-1-ylmethyl)phenyl)-1,5-dihydro-4H-pyrazolo[4,3-c]pyridin-4-one A) 1-(2,6-difluorophenyl)-4-methoxy-3-(3-(pyrrolidin-1-ylmethyl)phenyl)-1H-pyrazolo[4,3-c]pyridine To a solution of 3-(1-(2,6-difluorophenyl)-4-methoxy-1H-pyrazolo[4,3-c]pyridin-3-yl)benzyl methanesulfonate (100 mg) obtained in Step B of Example 258 and pyrrolidine (0.028 mL) in DMF (3 mL) was added triethylamine (0.047 mL) at room temperature, and the mixture was stirred at 60° C. for 4 hr. To the reaction mixture was added saturated aqueous sodium hydrogencarbonate solution, and the mixture was extracted with ethyl acetate. The organic layer was washed successively with water and saturated brine, dried over anhydrous magnesium sulfate, and concentrated under reduced pressure. The residue was purified by silica gel column chromatography (basic silica gel, ethyl acetate/hexane) to give the title compound (70 mg).

MS (ESI+): [M+H]$^+$ 420.3.
MS (ESI+). found: 421.4.

B) 1-(2,6-difluorophenyl)-3-(3-(pyrrolidin-1-ylmethyl)phenyl)-1,5-dihydro-4H-pyrazolo[4,3-c]pyridin-4-one The title compound was obtained using 1-(2,6-difluorophenyl)-4-methoxy-3-(3-(pyrrolidin-1-ylmethyl)phenyl)-1H-pyrazolo[4,3-c]pyridine, in the same manner as in Step J of Example 33.

MS (ESI+): [M+H]$^+$ 407.2.
MS (ESI+). found: 407.3.

Example 289

4-(1-(2,6-difluorophenyl)-4-oxo-4,5-dihydro-1H-pyrazolo[4,3-c]pyridin-3-yl)-N',N'-dimethylbenzhydrazide The title compound was obtained using 4-(1-(2,6-difluorophenyl)-4-methoxy-1H-pyrazolo[4,3-c]pyridin-3-yl)benzoic acid obtained in Step B of Example 180 and 1,1-dimethylhydrazine, in the same manner as in Step C of Example 180 and Step J of Example 33.
MS (ESI+): [M+H]$^+$ 410.1.
MS (ESI+). found: 410.2.

Example 290

4-(1-(4,4-difluorocyclohexyl)-4-oxo-4,5-dihydro-1H-pyrazolo[4,3-c]pyridin-3-yl)benzenesulfonamide The title compound was obtained using 4-(4-methoxy-1H-pyrazolo[4,3-c]pyridin-3-yl)benzenesulfonamide obtained in Step A of Example 100, in the same manner as in Step A of Example 119 and Step B of Example 119.
MS (ESI+): [M+H]$^+$ 409.1.
MS (ESI+). found: 409.3.

Example 291

2-(3-(1-(2,6-difluorophenyl)-4-oxo-4,5-dihydro-1H-pyrazolo[4,3-c]pyridin-3-yl)-4-fluorophenyl)acetamide The title compound was obtained using methyl 2-(4-fluoro-3-(4,4,5,5-tetramethyl-1,3,2-dioxaborolan-2-yl)phenyl)acetate, in the same manner as in Step D of Example 35, Step F of Example 33, Step G of Example 33 and Step J of Example 33.
MS (ESI+): [M+H]$^+$ 399.3.
MS (ESI+). found: 399.2.

Example 292

1-(2,6-difluorophenyl)-3-(4-(2-oxopyrrolidin-1-yl)phenyl)-1,5-dihydro-4H-pyrazolo[4,3-c]pyridin-4-one The title compound was obtained using 1-(4-(4,4,5,5-tetramethyl-1,3,2-dioxaborolan-2-yl)phenyl)pyrrolidin-2-one, in the same manner as in Step D of Example 35 and Step J of Example 33.
MS (ESI+): [M+H]$^+$ 407.4.
MS (ESI+). found: 407.3.

Example 293

2-(3-(1-(2,6-difluorophenyl)-4-oxo-4,5-dihydro-1H-pyrazolo[4,3-c]pyridin-3-yl)-4-fluorophenyl)-N-methylacetamide The title compound was obtained using methyl 2-(4-fluoro-3-(4,4,5,5-tetramethyl-1,3,2-dioxaborolan-2-yl)phenyl)acetate and methylamine hydrochloride, in the same manner as in Step D of Example 35, Step F of Example 33, Step G of Example 33 and Step J of Example 33.
MS (ESI+): [M+H]$^+$ 413.4.
MS (ESI+). found: 413.3.

Example 294

4-(1-(2,6-difluorophenyl)-4-oxo-4,5-dihydro-1H-pyrazolo[4,3-c]pyridin-3-yl)-3-fluoro-N-methylbenzamide The title compound was obtained using methyl 3-fluoro-4-(4,4,5,5-tetramethyl-1,3,2-dioxaborolan-2-yl)benzoate and methylamine hydrochloride, in the same manner as in Step D of Example 35, Step F of Example 33, Step G of Example 33 and Step J of Example 33.
MS (ESI+): [M+H]$^+$ 399.3.
MS (ESI+). found: 399.2.

Example 295

3-chloro-4-(1-(2,6-difluorophenyl)-4-oxo-4,5-dihydro-1H-pyrazolo[4,3-c]pyridin-3-yl)-N-methylbenzamide The title compound was obtained using methyl 3-chloro-4-(4,4,5,5-tetramethyl-1,3,2-dioxaborolan-2-yl)benzoate and methylamine hydrochloride, in the same manner as in Step D of Example 35, Step F of Example 33, Step G of Example 33 and Step J of Example 33.
MS (ESI+): [M+H]$^+$ 415.8.
MS (ESI+). found: 415.2.

Example 296

4-(7-chloro-1-cyclopentyl-4-oxo-4,5-dihydro-1H-pyrazolo[4,3-c]pyridin-3-yl)thiophene-2-carboxamide A) 4-(7-chloro-1-cyclopentyl-4-methoxy-1H-pyrazolo[4,3-c]pyridin-3-yl)thiophene-2-carboxamide To a solution of 4-(1-cyclopentyl-4-methoxy-1H-pyrazolo[4,3-c]pyridin-3-yl)thiophene-2-carboxamide (30.3 mg) obtained in Step A of Example 286 in DMF (2 mL) was added N-chlorosuccinimide (13.0 mg) at 0° C., and the mixture was stirred overnight at 80° C. To the reaction mixture was added N-chlorosuccinimide (6.0 mg), and the mixture was stirred at 80° C. for 3 hr. To the reaction mixture was added N-chlorosuccinimide (6.0 mg), and the mixture was stirred at 80° C. for 3 hr. To the reaction mixture was added water, and the mixture was extracted with ethyl acetate. The organic layer was washed successively with water and saturated brine, dried over anhydrous sodium sulfate, and concentrated under reduced pressure. The residue was purified by silica gel column chromatography (ethyl acetate/hexane), and then HPLC (column: L-column2 ODS (trade name) 20 mmID×150 mmL, 5 μm, manufactured by Daicel Chemical Industries, mobile phase: water/acetonitrile (containing 10 mM ammonium carbonate)) to give the title compound (19.5 mg).
MS (ESI+): [M+H]$^+$ 377.1.
MS (ESI+). found: 377.2.

B) 4-(7-chloro-1-cyclopentyl-4-oxo-4,5-dihydro-1H-pyrazolo[4,3-c]pyridin-3-yl)thiophene-2-carboxamide The title compound (5.0 mg) was obtained using 4-(7-chloro-1-cyclopentyl-4-methoxy-1H-pyrazolo[4,3-c]pyridin-3-yl)thiophene-2-carboxamide (29.5 mg), in the same manner as in Step B of Example 92.
MS (ESI+): [M+H]+ 363.1.
MS (ESI+). found: 363.2.

Example 297

4-((1-cyclopentyl-4-oxo-4,5-dihydro-1H-pyrazolo[4,3-c]pyridin-3-yl)amino)benzenesulfonamide To a solution of 1-cyclopentyl-4-methoxy-1H-pyrazolo[4,3-c]pyridin-3-yl trifluoromethanesulfonate (150 mg) obtained in Step C of Example 12 in toluene (20 ml) were added 4-aminobenzenesulfonamide (212 mg), tris(dibenzylideneacetone)dipalladium (37.6 mg), (9,9-dimethyl-9H-xanthene-4,5-diyl)bis(diphenylphosphine)(47.5 mg) and cesium carbonate (669 mg), and the mixture was heated overnight with reflux under nitrogen atmosphere. The reaction mixture was partitioned between water and ethyl acetate, and the organic layer was washed successively with hydrochloric acid, water, saturated aqueous sodium hydrogencarbonate solution and saturated brine, dried over anhydrous sodium sulfate, and concentrated under reduced pressure. The obtained residue was purified by silica gel column chromatography (ethyl acetate/hexane) to give a residue (105 mg) containing 4-((1-cyclopentyl-4-methoxy-1H-pyrazolo[4,3-c]pyridin-3-yl)amino)benzenesulfonamide. To a solution of the obtained residue (102 mg) in acetonitrile (10 mL) were added sodium iodide (64.8 mg) and chloro(trimethyl)silane (0.219 mL), and the mixture was stirred at 60° C. for 30 min. The reaction mixture was concentrated under reduced pressure, and the residue was washed successively with water and ethyl acetate, dried over anhydrous sodium sulfate, and concentrated under reduced pressure. The residue was purified by silica gel column chromatography (ethyl acetate/hexane), and the obtained solid was washed with ethyl acetate/diisopropyl ether to give the title compound (68.1 mg).
1H NMR (300 MHz, DMSO-d6) δ 1.56-1.79 (2H, m), 1.82-2.17 (6H, m), 4.82-5.02 (1H, m), 6.56 (1H, d, J=7.2 Hz), 7.12 (2H, s), 7.18 (1H, dd, J=7.2, 6.0 Hz), 7.62-7.74 (2H, m), 7.74-7.84 (2H, m), 8.44 (1H, s), 11.04 (1H, d, J=5.7 Hz).
MS (ESI+): [M+H]+ 374.1.
MS (ESI+). found: 374.2.

Example 298

4-(1-(cis-4-aminocyclohexyl)-4-oxo-4,5-dihydro-1H-pyrazolo[4,3-c]pyridin-3-yl)thiophene-2-carboxamide A) tert-butyl (cis-4-(3-(5-carbamoyl-3-thienyl)-4-methoxy-1H-pyrazolo[4,3-c]pyridin-1-yl)cyclohexyl)carbamate and tert-butyl (trans-4-(3-(5-carbamoyl-3-thienyl)-4-methoxy-1H-pyrazolo[4,3-c]pyridin-1-yl)cyclohexyl)carbamate The two kinds of the title compounds were each obtained using 4-(4-oxo-4,5-dihydro-1H-pyrazolo[4,3-c]pyridin-3-yl)thiophene-2-carboxamide obtained in Step A of Example 148 and 4-(tert-butoxycarbonylamino)cyclohexyl trans-4-methylbenzenesulfonate, in the same manner as in Step B of Example 148.
cis
MS (ESI+): [M+H]+ 472.2.
MS (ESI+). found: 472.5.
trans
MS (ESI+): [M+H]+ 472.2.
MS (ESI+). found: 472.5.

B) 4-(1-(cis-4-aminocyclohexyl)-4-oxo-4,5-dihydro-1H-pyrazolo[4,3-c]pyridin-3-yl)thiophene-2-carboxamide To a solution of tert-butyl (cis-4-(3-(5-carbamoyl-3-thienyl)-4-methoxy-1H-pyrazolo[4,3-c]pyridin-1-yl)cyclohexyl)carbamate (33.0 mg) in a mixed solvent of acetonitrile (2 ml) and THF (1 ml) were added sodium iodide (26.2 mg) and chloro(trimethyl)silane (0.089 ml), and the mixture was stirred at 50° C. for 1 hr. Trifluoroacetic acid (2 mL) was added thereto, and the mixture was stirred at 50° C. for additional 2 hr. The reaction mixture was concentrated under reduced pressure, and the obtained residue was purified by silica gel column chromatography (basic silica gel, ethyl acetate/methanol) to give the title compound (155 mg).
MS (ESI+): [M+H]+ 358.1.
MS (ESI+). found: 358.3.

Example 299

4-(1-(trans-4-aminocyclohexyl)-4-oxo-4,5-dihydro-1H-pyrazolo[4,3-c]pyridin-3-yl)thiophene-2-carboxamide The title compound was obtained using tert-butyl (trans-4-(3-(5-carbamoyl-3-thienyl)-4-methoxy-1H-pyrazolo[4,3-c]pyridin-1-yl)cyclohexyl)carbamate obtained in Step A of Example 298, in the same manner as in Step B of Example 298.
MS (ESI+): [M+H]+ 358.1.
MS (ESI+). found: 358.3.

Example 300

3-(2-aminopyrimidin-5-yl)-1-(2,6-difluorophenyl)-1,5-dihydro-4H-pyrazolo[4,3-c]pyridin-4-one The title compound was obtained using 1-(2,6-difluorophenyl)-4-methoxy-1H-pyrazolo[4,3-c]pyridin-3-yl trifluoromethanesulfonate obtained in Step C of Example 35 and 5-(4,4,5,5-tetramethyl-1,3,2-dioxaborolan-2-yl)pyrimidin-2-amine, in the same manner as in Step A of Example 180 and Step J of Example 33.
MS (ESI+): [M+H]+ 341.1.
MS (ESI+). found: 341.2.

Example 301

3-(4-(1-acetylpiperidin-4-yl)phenyl)-1-(2,6-difluorophenyl)-1,5-dihydro-4H-pyrazolo[4,3-c]pyridin-4-one A) 1-benzyl-4-(4-bromophenyl)piperidin-4-ol To a solution of magnesium (1.77 g) and iodine (0.81 g) in THF (60 mL) was added a solution of 1,4-dibromobenzene (8.94 mL) in THF (5 mL), and the mixture was stirred at room temperature for 30 min. The reaction mixture was cooled to 0° C., a solution of 1-benzylpiperidin-4-one (13.2 mL) in THF (5 mL) was slowly added dropwise thereto, and the reaction mixture was stirred at room temperature for 2 hr. To the reaction mixture was added water, and the mixture was extracted with ethyl acetate. The organic layer was washed successively with water and saturated brine, dried over anhydrous magnesium sulfate, and concentrated under reduced pressure. The residue was purified by silica gel column chromatography (ethyl acetate/hexane) to give the title compound (9.19 g).
MS (ESI+): [M+H]⁺ 346.1, 348.1.
MS (ESI+). found: 346.2, 348.2.

B) 1-benzyl-4-(4-bromophenyl)-1,2,3,6-tetrahydropyridine

To a solution of 1-benzyl-4-(4-bromophenyl)piperidin-4-ol (3.0 g) in toluene (20 mL) was added p-toluenesulfonic acid monohydrate (1.98 g) at room temperature. The reaction mixture was stirred at 130° C. for 2 hr. To the reaction mixture was added saturated aqueous sodium hydrogencarbonate solution at 0° C., and the mixture was extracted with ethyl acetate-THF. The organic layer was washed successively with water and saturated brine, dried over anhydrous magnesium sulfate, and concentrated under reduced pressure to give the title compound (2.80 g).
¹H NMR (300 MHz, CDCl₃) δ 2.45-2.57 (2H, m), 2.66-2.75 (2H, m), 3.15 (2H, q, J=2.8 Hz), 3.63 (2H, s), 6.06 (1H, tt, J=3.5, 1.6 Hz), 7.10-7.24 (2H, m), 7.25-7.48 (7H, m).

C) 1-benzyl-4-(4-(4,4,5,5-tetramethyl-1,3,2-dioxaborolan-2-yl)phenyl)-1,2,3,6-tetrahydropyridine The title compound was obtained using 1-benzyl-4-(4-bromophenyl)-1,2,3,6-tetrahydropyridine, in the same manner as in Step B of Example 215.
MS (ESI+): [M+H]⁺ 376.2.
MS (ESI+). found: 375.3.

D) 3-(4-(1-benzyl-1,2,3,6-tetrahydropyridin-4-yl)phenyl)-1-(2,6-difluorophenyl)-4-methoxy-1H-pyrazolo[4,3-c]pyridine The title compound was obtained using 1-(2,6-difluorophenyl)-4-methoxy-1H-pyrazolo[4,3-c]pyridin-3-yl trifluoromethanesulfonate obtained in Step C of Example 35 and 1-benzyl-4-(4-(4,4,5,5-tetramethyl-1,3,2-dioxaborolan-2-yl)phenyl)-1,2,3,6-tetrahydropyridine, in the same manner as in Step A of Example 180.
MS (ESI+): [M+H]⁺ 509.2.
MS (ESI+). found: 509.4.

E) 1-(2,6-difluorophenyl)-4-methoxy-3-(4-(piperidin-4-yl)phenyl)-1H-pyrazolo[4,3-c]pyridine To a solution of 3-(4-(1-benzyl-1,2,3,6-tetrahydropyridin-4-yl)phenyl)-1-(2,6-difluorophenyl)-4-methoxy-1H-pyrazolo[4,3-c]pyridine (670 mg) in methanol (10 mL) was added 10% palladium carbon (80 mg), and the mixture was stirred overnight at 50° C. under hydrogen atmosphere. The reaction mixture was filtered, and the filtrate was concentrated to give the title compound (540 mg).
MS (ESI+): [M+H]⁺ 421.2.
MS (ESI+). found: 421.3.

F) 1-(4-(4-(1-(2,6-difluorophenyl)-4-methoxy-1H-pyrazolo[4,3-c]pyridin-3-yl)phenyl)piperidin-1-yl)ethanone To a solution of 1-(2,6-difluorophenyl)-4-methoxy-3-(4-(piperidin-4-yl)phenyl)-1H-pyrazolo[4,3-c]pyridine (120 mg), triethylamine (0.080 mL) and N,N-dimethylaminopyridine (1.7 mg) in THF (4 mL) was added acetyl chloride (0.080 mL). The reaction mixture was stirred at room temperature for 1 hr. To the reaction mixture was added saturated aqueous sodium hydrogencarbonate solution at 0° C., and the mixture was extracted with ethyl acetate. The organic layer was washed successively with water and saturated brine, dried over anhydrous magnesium sulfate, and concentrated under reduced pressure. The residue was purified by silica gel column chromatography (ethyl acetate/hexane) to give the title compound (117 mg).
MS (ESI+): [M+H]⁺ 463.2.
MS (ESI+). found: 463.4.

G) 3-(4-(1-acetylpiperidin-4-yl)phenyl)-1-(2,6-difluorophenyl)-1,5-dihydro-4H-pyrazolo[4,3-c]pyridin-4-one To a solution of 1-(4-(4-(1-(2,6-difluorophenyl)-4-methoxy-1H-pyrazolo[4,3-c]pyridin-3-yl)phenyl)piperidin-1-yl)ethanone (112 mg) in acetonitrile (3 mL) were added sodium iodide (73 mg) and chloro(trimethyl)silane (0.155 mL), and the mixture was stirred at 60° C. for 3 hr. To the reaction mixture was added saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (silica gel, hexane/ethyl acetate to ethyl acetate/methanol). The obtained fraction was purified by HPLC (L-Column 2 ODS, mobile phase: water/acetonitrile (containing 10 mM ammonium carbonate)) to give the title compound (51 mg).
MS (ESI+): [M+H]⁺ 449.2.
MS (ESI+). found: 449.4.

Example 302

4-(1-(4-amino-2-fluoro-6-methoxyphenyl)-4-oxo-4,5-dihydro-1H-pyrrolo[3,2-c]pyridin-3-yl)thiophene-2-carboxamide

A) 1-(2,6-difluoro-4-nitrophenyl)-3-iodo-4-methoxy-1H-pyrrolo[3,2-c]pyridine To a solution of 3-iodo-4-methoxy-1H-pyrrolo[3,2-c]pyridine (200 mg) in DMF (6 ml) were added 15-crown-5 (0.159 ml) and sodium hydride (60% dispersion in mineral oil, 32.1 mg), and the mixture was stirred at room temperature for 1 hr. To the reaction mixture was added 1,2,3-trifluoro-5-nitrobenzene (0.101 ml), and the mixture was stirred overnight at room temperature under nitrogen atmosphere. The reaction mixture was extracted with water and ethyl acetate, and the organic layer was washed with saturated brine, dried over anhydrous sodium sulfate, filtered, and concentrated under reduced pressure. The obtained residue was purified by silica gel column chromatography (ethyl acetate/hexane) to give the title compound (258 mg).
MS (ESI+): [M+H]⁺ 432.0.
MS (ESI+). found: 432.1.

B) methyl 4-(1-(2,6-difluoro-4-nitrophenyl)-4-methoxy-1H-pyrrolo[3,2-c]pyridin-3-yl)thiophene-2-carboxylate The title compound was obtained using 1-(2,6-difluoro-4-nitrophenyl)-3-iodo-4-methoxy-1H-pyrrolo[3,2-c]pyridine, in the same manner as in Step A of Example 113.
MS (ESI+): [M+H]⁺ 446.1.
MS (ESI+). found: 446.3.

C) methyl 4-(1-(2,6-difluoro-4-nitrophenyl)-4-oxo-4, 5-dihydro-1H-pyrrolo[3,2-c]pyridin-3-yl)thiophene-2-carboxylate The title compound was obtained using methyl 4-(1-(2,6-difluoro-4-nitrophenyl)-4-methoxy-1H-pyrrolo[3,2-c]pyridin-3-yl)thiophene-2-carboxylate, in the same manner as in Step B of Example 113.
MS (ESI+): [M+H]$^+$ 432.1.
MS (ESI+). found: 432.2.

D) 4-(1-(2-fluoro-6-methoxy-4-nitrophenyl)-4-oxo-4,5-dihydro-1H-pyrrolo[3,2-c]pyridin-3-yl)thiophene-2-carboxylic acid The title compound was obtained using methyl 4-(1-(2,6-difluoro-4-nitrophenyl)-4-oxo-4,5-dihydro-1H-pyrrolo[3,2-c]pyridin-3-yl)thiophene-2-carboxylate, in the same manner as in Step A of Example 114.
MS (ESI+): [M+H]$^+$ 430.1.
MS (ESI+). found: 430.2.

E) 4-(1-(2-fluoro-6-methoxy-4-nitrophenyl)-4-oxo-4, 5-dihydro-1H-pyrrolo[3,2-c]pyridin-3-yl)thiophene-2-carboxamide The title compound was obtained using 4-(1-(2-fluoro-6-methoxy-4-nitrophenyl)-4-oxo-4,5-dihydro-1H-pyrrolo[3, 2-c]pyridin-3-yl)thiophene-2-carboxylic acid, in the same manner as in Step B of Example 114.
MS (ESI+): [M+H]$^+$ 429.1.
MS (ESI+). found: 429.2.

F) 4-(1-(4-amino-2-fluoro-6-methoxyphenyl)-4-oxo-4,5-dihydro-1H-pyrrolo[3,2-c]pyridin-3-yl)thiophene-2-carboxamide To a solution of 4-(1-(2-fluoro-6-methoxy-4-nitrophenyl)-4-oxo-4,5-dihydro-1H-pyrrolo[3,2-c]pyridin-3-yl)thiophene-2-carboxamide (45.0 mg) and calcium chloride (11.7 mg) in a mixed solvent of ethanol (5 ml) and water (1 ml) was added reduced iron (29.3 mg), and the mixture was stirred at 100° C. for 2 hr. The insoluble substance was removed by the filtration, and washed with water and ethyl acetate. The filtrate was extracted with ethyl acetate, and the organic layer was washed with saturated brine, dried over anhydrous sodium sulfate, filtered, and concentrated under reduced pressure. The obtained residue was purified by silica gel column chromatography (ethyl acetate/hexane) to give the title compound (30.0 mg).
MS (ESI+): [M+H]$^+$ 399.1.
MS (ESI+). found: 399.2.

Example 303

4-(1-(4-amino-2,6-difluorophenyl)-4-oxo-4,5-dihydro-1H-pyrazolo[4,3-c]pyridin-3-yl)benzenesulfonamide A) 4-(1-(2,6-difluoro-4-nitrophenyl)-4-methoxy-1H-pyrazolo[4,3-c]pyridin-3-yl)benzenesulfonamide The title compound was obtained using 4-(4-methoxy-1H-pyrazolo[4,3-c]pyridin-3-yl)benzenesulfonamide obtained in Step A of Example 100 and 3,4,5-trifluoronitrobenzene, in the same manner as in Step A of Example 119.
MS (ESI+): [M+H]$^+$ 462.1.
MS (ESI+). found: 462.3.

B) 4-(1-(4-amino-2,6-difluorophenyl)-4-methoxy-1H-pyrazolo[4,3-c]pyridin-3-yl)benzenesulfonamide The title compound was obtained using 4-(1-(2,6-difluoro-4-nitrophenyl)-4-methoxy-1H-pyrazolo[4,3-c]pyridin-3-yl) benzenesulfonamide, in the same manner as in Step F of Example 302.
MS (ESI+): [M+H]$^+$ 432.1.
MS (ESI+). found: 432.3.

C) 4-(1-(4-amino-2,6-difluorophenyl)-4-oxo-4,5-dihydro-1H-pyrazolo[4,3-c]pyridin-3-yl)benzenesulfonamide The title compound was obtained using 4-(1-(4-amino-2, 6-difluorophenyl)-4-methoxy-1H-pyrazolo[4,3-c]pyridin-3-yl)benzenesulfonamide, in the same manner as in Step B of Example 119.
MS (ESI+): [M+H]$^+$ 418.1.
MS (ESI+). found: 418.2.

Example 304

1-(2,6-difluorophenyl)-3-(4-(3-oxomorpholin-4-yl) phenyl)-1,5-dihydro-4H-pyrazolo[4,3-c]pyridin-4-one A) 4-(4-bromophenyl)morpholin-3-one To a mixture of morpholin-3-one (100 mg), 1-bromo-4-iodobenzene (282 mg), cesium carbonate (326 mg) and N1,N2-dimethylethane-1,2-diamine (9 mg) in DMF (2 mL) was added copper(I) iodide (10 mg) at room temperature under nitrogen atmosphere. The reaction mixture was stirred under microwave irradiation at 100° C. for 30 min. The reaction mixture was added to water, and the mixture was extracted with ethyl acetate. The organic layer was washed with saturated brine, dried over anhydrous sodium sulfate, and concentrated under reduced pressure. The residue was purified by silica gel column chromatography (ethyl acetate/ petroleum ether) to give the title compound (210 mg).
MS(ESI+): [M+H]$^+$ 256.0.
MS(ESI+). found: 256.0.

B) 4-(4-(4,4,5,5-tetramethyl-1,3,2-dioxaborolan-2-yl)phenyl)morpholin-3-one

To a mixture of 4-(4-bromophenyl)morpholin-3-one, bis (pinacolato)diboron (120 mg) and potassium acetate (120 mg) in DMSO (1 mL) was added dichlorobis(triphenylphosphine)palladium(II) (14 mg) under nitrogen atmosphere. The reaction mixture was stirred under microwave irradiation at 105° C. for 30 min. The insoluble substance was removed by the filtration, and the filtrate was added to water, and the mixture was extracted with ethyl acetate. The organic layer was washed with saturated brine, dried over anhydrous sodium sulfate, and concentrated under reduced pressure. The residue was purified by silica gel column chromatography (ethyl acetate/petroleum ether) to give the title compound (145 mg).
MS(ESI+): [M+H]$^+$ 304.2.
MS(ESI+). found: 304.2.

C) 4-(4-(1-(2,6-difluorophenyl)-4-methoxy-1H-pyrazolo[4,3-c]pyridin-3-yl)phenyl)morpholin-3-one To a mixture of 1-(2,6-difluorophenyl)-4-methoxy-1H-pyrazolo[4,3-c]pyridin-3-yl trifluoromethanesulfonate (150 mg) obtained in Step C of Example 35, 4-(4-(4,4,5,5-tetramethyl-1,3,2-dioxaborolan-2-yl)phenyl)morpholin-3-one (145 mg) and sodium carbonate (78 mg) in DME/water (1.5 mL/0.070 mL) was added dichloro(1,1'-bis(diphenylphosphino)ferrocene)palladium(II) (21 mg) under nitrogen atmosphere. The reaction mixture was stirred under microwave irradiation at 120° C. for 1 hr. The insoluble substance was removed by the filtration, the filtrate was added to water, and the mixture was extracted with ethyl acetate. The organic layer was washed with saturated brine, dried over anhydrous sodium sulfate, and concentrated under reduced pressure. The residue was purified by thin layer silica gel chromatography (ethyl acetate/petroleum ether) to give the title compound (143 mg).
MS(ESI+): [M+H]$^+$ 437.1.
MS(ESI+). found: 437.1.

D) 1-(2,6-difluorophenyl)-3-(4-(3-oxomorpholin-4-yl)phenyl)-1,5-dihydro-4H-pyrazolo[4,3-c]pyridin-4-one The title compound (105 mg) was obtained using 4-(4-(1-(2,6-difluorophenyl)-4-methoxy-1H-pyrazolo[4,3-c]pyridin-3-yl)phenyl)morpholin-3-one (228 mg) and 2-methoxy-N-methylethanamine (0.455 mL), in the same manner as in Step C of Example 152.
MS(ESI+): [M+H]$^+$ 423.1.
MS(ESI+). found: 423.1.

Example 305

3-fluoro-2-(3-(4-(morpholin-4-yl)phenyl)-4-oxo-4,5-dihydro-1H-pyrazolo[4,3-c]pyridin-1-yl)benzonitrile

A) 2,4-dichloropyridine-3-carbaldehyde

To a solution of 2,4-dichloropyridine (10 g) in THF (100 mL) was added dropwise lithium diisopropylamide solution (2M, 37 mL) at −78° C. The reaction mixture was stirred at −78° C. for 1 hr. To the reaction mixture was added dropwise 1-formylpiperidine (7.7 g) at −78° C. The reaction mixture was stirred at −78° C. for 2 hr. The reaction mixture was added to 10% aqueous acetic acid solution, and the mixture was extracted with ethyl acetate. The organic layer was washed with saturated aqueous sodium hydrogencarbonate solution and saturated brine, dried over anhydrous sodium sulfate, and concentrated under reduced pressure. The residue was purified by silica gel column chromatography (ethyl acetate/petroleum ether) to give the title compound (7.0 g).
$^1$H NMR (400 MHz, DMSO-d$_6$) δ 7.78 (1H, d, J=5.6 Hz), 8.56 (1H, d, J=5.6 Hz), 10.32 (1H, s).

B) 4-chloro-1H-pyrazolo[4,3-c]pyridine

To a solution of 2,4-dichloropyridine-3-carbaldehyde (7.0 g) in DME (70 mL) was added hydrazine monohydrate (8.0 g) at room temperature. The reaction mixture was stirred overnight at 75° C., and concentrated under reduced pressure. The residue was purified by silica gel column chromatography (ethyl acetate/petroleum ether) to give the title compound (4.0 g).
$^1$H NMR (400 MHz, DMSO-d$_6$) δ 7.60 (1H, d, J=6.0 Hz), 8.14 (1H, d, J=6.0 Hz), 8.33 (1H, s), 13.89 (1H, brs).

C) 4-chloro-3-iodo-1H-pyrazolo[4,3-c]pyridine

To a mixture of 4-chloro-1H-pyrazolo[4,3-c]pyridine (4.0 g) and potassium hydroxide (4.4 g) in DME (50 mL) was added iodine (13.3 g) at room temperature. The reaction mixture was stirred at 75° C. for 4 hr. The reaction mixture was added to aqueous sodium thiosulfate solution, and the mixture was left stand overnight, and the resulting solid was collected by filtration to give the title compound (6.3 g).
MS(ESI+): [M+H]$^+$ 279.9.
MS(ESI+). found: 280.1.

D) 1-benzyl-4-chloro-3-iodo-1H-pyrazolo[4,3-c]pyridine

To a mixture of 4-chloro-3-iodo-1H-pyrazolo[4,3-c]pyridine (6.3 g) and potassium hydroxide (2.5 g) in DMF (60 mL) was added benzyl bromide (4.6 g) at room temperature. The reaction mixture was stirred at room temperature for 4 hr. The reaction mixture was neutralized with saturated aqueous sodium hydrogencarbonate solution under ice-cooling, and the mixture was extracted with ethyl acetate. The organic layer was washed with water and saturated brine, dried over anhydrous sodium sulfate, and concentrated under reduced pressure. The residue was purified by silica gel column chromatography (ethyl acetate/petroleum ether) to give the title compound (5.0 g).
$^1$H NMR (400 MHz, DMSO-d$_6$) δ 5.72 (2H, s), 7.25-7.27 (2H, m), 7.30-7.37 (3H, m), 7.96 (1H, d, J=6.0 Hz), 8.21 (1H, d, J=6.0 Hz).

E) 1-benzyl-3-iodo-4-methoxy-1H-pyrazolo[4,3-c]pyridine

To a mixture of 1-benzyl-4-chloro-3-iodo-1H-pyrazolo[4,3-c]pyridine (3.7 g) in methanol (40 mL) was added sodium methoxide methanol solution (1.5 M, 27 mL) at room temperature, and the reaction mixture was refluxed overnight. The reaction mixture was added to water at room temperature, and the mixture was extracted with ethyl acetate. The organic layer was washed with water and saturated brine, dried over anhydrous sodium sulfate, and concentrated under reduced pressure. The obtained residue was washed with petroleum ether to give the title compound (3.6 g).
MS(ESI+): [M+H]$^+$ 366.0.
MS(ESI+). found: 366.0.

F) 1-benzyl-4-methoxy-3-(4-(morpholin-4-yl)phenyl)-1H-pyrazolo[4,3-c]pyridine To a mixture of 1-benzyl-3-iodo-4-methoxy-1H-pyrazolo[4,3-c]pyridine (0.75 g), 4-(4-(4,4,5,5-tetramethyl-1,3,2-dioxaborolan-2-yl)phenyl)morpholine (0.60 g) and sodium carbonate (0.44 g) in DME/water (6 mL/3 mL) was added dichloro(1,1'-bis(diphenylphosphino)ferrocene)palladium(II) (73 mg) under nitrogen atmosphere. The reaction mixture was stirred overnight at 85° C. To the reaction mixture was added water, and the mixture was extracted with ethyl acetate. The organic layer was washed with water and saturated brine, dried over anhydrous sodium sulfate, and concentrated under reduced pressure. The residue was purified by silica gel chromatography (ethyl acetate/petroleum ether) to give the title compound (0.72 g).
MS(ESI+): [M+H]$^+$ 401.2.
MS(ESI+). found: 401.2.

G) 4-methoxy-3-(4-(morpholin-4-yl)phenyl)-1H-pyrazolo[4,3-c]pyridine

To a solution of 1-benzyl-4-methoxy-3-(4-(morpholin-4-yl)phenyl)-1H-pyrazolo[4,3-c]pyridine (0.68 g) in DMSO/THF (10 mL/2.5 mL) was added potassium tert-butoxide (1.90 g) under ice-cooling. The reaction mixture was stirred at room temperature for 5 hr. The reaction mixture was added to saturated aqueous ammonium chloride solution, and the mixture was extracted with ethyl acetate. The organic layer was washed with saturated brine, dried over anhydrous sodium sulfate, and concentrated under reduced pressure. The residue was purified by silica gel chromatography (ethyl acetate/petroleum ether) to give the title compound (0.37 g).
MS(ESI+): [M+H]$^+$ 311.1.
MS(ESI+). found: 311.2.

H) 3-fluoro-2-(4-methoxy-3-(4-(morpholin-4-yl)phenyl)-1H-pyrazolo[4,3-c]pyridin-1-yl)benzonitrile A solution of 4-methoxy-3-(4-(morpholin-4-yl)phenyl)-1H-pyrazolo[4,3-c]pyridine (355 mg), 2,3-difluorobenzonitrile (180 mg) and potassium carbonate in DMF (5 mL) was stirred at 100° C. for 2.5 hr. The reaction mixture was added to water, and the mixture was extracted with ethyl acetate. The organic layer was washed with saturated brine, dried over anhydrous sodium sulfate, and concentrated under reduced pressure. The resulting solid was washed with petroleum ether to give the title compound (380 mg).
MS(ESI+): [M+H]$^+$ 430.2.
MS(ESI+). found: 430.2.

I) 3-fluoro-2-(3-(4-(morpholin-4-yl)phenyl)-4-oxo-4,5-dihydro-1H-pyrazolo[4,3-c]pyridin-1-yl)benzonitrile The title compound (120 mg) was obtained using 3-fluoro-2-(4-methoxy-3-(4-(morpholin-4-yl)phenyl)-1H-pyrazolo[4,3-c]pyridin-1-yl)benzonitrile (360 mg), in the same manner as in Step C of Example 152.
MS(ESI+): [M+H]$^+$ 416.1.
MS(ESI+). found: 416.2.

Example 306

3-fluoro-2-(3-(6-(morpholin-4-yl)pyridin-3-yl)-4-oxo-4,5-dihydro-1H-pyrazolo[4,3-c]pyridin-1-yl)benzonitrile The title compound (55 mg) was obtained using 1-benzyl-3-iodo-4-methoxy-1H-pyrazolo[4,3-c]pyridine (0.75 g) obtained in Step E of Example 305 and 4-(5-(4,4,5,5-tetramethyl-1,3,2-dioxaborolan-2-yl)pyridin-2-yl)morpholine (0.60 g), in the same manner as in Step F of Example 305, Step G of Example 305, Step H of Example 305 and Step C of Example 152.
MS(ESI+): [M+H]$^+$ 417.1.
MS(ESI+). found: 417.2.

Example 307

4-(1-(2-cyano-6-fluorophenyl)-4-oxo-4,5-dihydro-1H-pyrazolo[4,3-c]pyridin-3-yl)-N-methylbenzamide The title compound (0.20 g) was obtained using 1-benzyl-3-iodo-4-methoxy-1H-pyrazolo[4,3-c]pyridine (0.91 g) obtained in Step E of Example 305 and N-methyl-4-(4,4,5,5-tetramethyl-1,3,2-dioxaborolan-2-yl)benzamide (0.65 g), in the same manner as in Step F of Example 305, Step G of Example 305, Step H of Example 305 and Step C of Example 152.
MS(ESI+): [M+H]$^+$ 388.1.
MS(ESI+). found: 388.2.

Example 308

3-(4-(morpholin-4-yl)phenyl)-1-(2,4,6-trifluorophenyl)-1,5-dihydro-4H-pyrazolo[4,3-c]pyridin-4-one The title compound (102 mg) was obtained using 4-iodo-2-methoxynicotinic acid (860 mg), (2,4,6-trifluorophenyl)hydrazine (500 mg) and 4-(4-(4,4,5,5-tetramethyl-1,3,2-dioxaborolan-2-yl)phenyl)morpholine (265 mg), in the same manner as in Example 35.
MS(ESI+): [M+H]$^+$ 427.1.
MS(ESI+). found: 427.2.

Example 309

1-(2,6-difluorophenyl)-3-(6-(morpholin-4-yl)pyridin-3-yl)-1,5-dihydro-4H-pyrazolo[4,3-c]pyridin-4-one The title compound (240 mg) was obtained using 1-(2,6-difluorophenyl)-4-methoxy-1H-pyrazolo[4,3-c]pyridin-3-yl trifluoromethanesulfonate (250 mg) obtained in Step C of Example 35 and 4-(5-(4,4,5,5-tetramethyl-1,3,2-dioxaborolan-2-yl)pyridin-2-yl)morpholine (213 mg), in the same manner as in Example 179.
MS(ESI+): [M+H]$^+$ 410.1.
MS(ESI+). found: 410.2.

Example 310

1-(4-(1-(2,6-difluorophenyl)-4-oxo-4,5-dihydro-1H-pyrazolo[4,3-c]pyridin-3-yl)phenyl)-N-methylpiperidine-4-carboxamide

A) methyl 1-(4-nitrophenyl)piperidine-4-carboxylate

A mixture of methyl piperidine-4-carboxylate (2.70 g), 1-fluoro-4-nitrobenzene (6.00 g) and triethylamine (6.80 g) in acetonitrile (60 mL) was refluxed overnight, and concentrated under reduced pressure. To the residue was added ethyl acetate, and the mixture was washed with water, dried over anhydrous sodium sulfate, and concentrated under reduced pressure. The residue was purified by silica gel chromatography (ethyl acetate/petroleum ether) to give the title compound (3.80 g).
MS(ESI+): [M+H]$^+$ 265.1.
MS(ESI+). found: 265.2.

B) methyl 1-(4-aminophenyl)piperidine-4-carboxylate

To a mixture of methyl 1-(4-nitrophenyl)piperidine-4-carboxylate (3.80 g) and iron powder (3.20 g) in methanol/water (40 mL/10 mL) was added conc. hydrochloric acid (2 mL) at room temperature. The reaction mixture was stirred at 65° C. for 3 hr. The reaction mixture was adjusted to pH=9 with saturated sodium carbonate, and the insoluble substance was removed by the filtration. The filtrate was concentrated under reduced pressure, and the residue was extracted with ethyl acetate. The organic layer was washed with saturated brine, dried over anhydrous sodium sulfate, and concentrated under reduced pressure to give the title compound (3.20 g).
MS(ESI+): [M+H]$^+$ 235.1.
MS(ESI+). found: 235.3.

C) methyl 1-(4-bromophenyl)piperidine-4-carboxylate

To a solution of methyl 1-(4-aminophenyl)piperidine-4-carboxylate (1.50 g) in acetonitrile (15 mL) were successively added tetraethylammonium bromide (1.05 g), isoamyl nitrite (1.05 g) and copper(I) bromide (0.09 g) at room temperature. The reaction mixture was stirred at room temperature for 40 min, and then at 60° C. for 2 hr. The reaction mixture was added to water, and the mixture was extracted with diethyl ether. The organic layer was dried over anhydrous sodium sulfate, and concentrated under reduced pressure. The residue was purified by silica gel chromatography (ethyl acetate/petroleum ether) to give the title compound (0.95 g).
MS(ESI+): [M+H]$^+$ 298.0.
MS(ESI+). found: 298.1.

D) N-methyl-1-(4-bromophenyl)piperidine-4-carboxamide

To methyl 1-(4-bromophenyl)piperidine-4-carboxylate (950 mg) was added methylamine methanol solution (25%, 20 mL) at room temperature. The reaction mixture was stirred overnight at room temperature, and concentrated under reduced pressure. To a solution of the residue in acetonitrile (15 mL) were successively added tetraethylammonium bromide (1.05 g), isoamyl nitrite (1.05 g) and copper(I) bromide (0.09 g) at room temperature. The reaction mixture was stirred at room temperature for 40 min, and then at 60° C. for 2 hr. The reaction mixture was added to water, and the mixture was extracted with diethyl ether. The organic layer was dried over anhydrous sodium sulfate, and concentrated under reduced pressure. The residue was purified by silica gel chromatography (ethyl acetate/petroleum ether) to give the title compound (800 mg).
MS(ESI+): [M+H]$^+$ 297.1.
MS(ESI+). found: 297.1.

E) N-methyl-1-(4-(4,4,5,5-tetramethyl-1,3,2-dioxaborolan-2-yl)phenyl)piperidine-4-carboxamide To a mixture of N-methyl-1-(4-bromophenyl)piperidine-4-carboxamide (680 mg), bis(pinacolato)diboron (700 mg) and potassium acetate (676 mg) in 1,4-dioxane (15 mL) was added dichlorobis(triphenylphosphine)palladium(II) (68 mg) under nitrogen atmosphere. The reaction mixture was stirred at 90° C. overnight. The insoluble substance was removed by the filtration, and the filtrate was concentrated under reduced pressure. The residue was purified by silica gel column chromatography (ethyl acetate/petroleum ether) to give the title compound (400 mg).
MS(ESI+): [M+H]$^+$ 345.2.
MS(ESI+). found: 345.3.

F) 1-(4-(1-(2,6-difluorophenyl)-4-oxo-4,5-dihydro-1H-pyrazolo[4,3-c]pyridin-3-yl)phenyl)-N-methylpiperidine-4-carboxamide The title compound (104 mg) was obtained using N-methyl-1-(4-(4,4,5,5-tetramethyl-1,3,2-dioxaborolan-2-yl)phenyl)piperidine-4-carboxamide (222 mg) and 1-(2,6-difluorophenyl)-4-methoxy-1H-pyrazolo[4,3-c]pyridin-3-yl trifluoromethanesulfonate (220 mg) obtained in Step C of Example 35, in the same manner as in Example 179.
MS(ESI+): [M+H]$^+$ 464.2.
MS(ESI+). found: 464.3.

Example 311

1-(2,6-difluorophenyl)-3-(4-(4-(methylsulfonyl)piperazin-1-yl)phenyl)-1,5-dihydro-4H-pyrazolo[4,3-c]pyridin-4-one A) tert-butyl 4-(4-bromophenyl)piperazine-1-carboxylate A mixture of 4-bromoaniline (10.9 g) and bis(2-chloroethyl)amine hydrochloride (11.3 g) in ethane-1,2-diol (80 mL) was stirred overnight at 150° C. To the reaction mixture were added triethylamine (25.7 g) and di-tert-butyl dicarbonate (19.3 g) under ice-cooling, and the mixture was stirred at room temperature for 2 hr. The reaction mixture was added to water, and the mixture was extracted with ethyl acetate. The organic layer was washed with saturated brine, dried over anhydrous sodium sulfate, and concentrated under reduced pressure. The residue was purified by silica gel chromatography (ethyl acetate/petroleum ether) to give the title compound (7.10 g).
MS(ESI+): [M+H]$^+$ 341.1.
MS(ESI+). found: 341.0.

B) tert-butyl 4-(4-(4,4,5,5-tetramethyl-1,3,2-dioxaborolan-2-yl)phenyl)piperazine-1-carboxylate The title compound (2.24 g) was obtained using tert-butyl 4-(4-bromophenyl)piperazine-1-carboxylate (2.00 g), in the same manner as in Step E of Example 310.
MS(ESI+): [M+H]+389.3.
MS(ESI+). found: 389.3.

C) tert-butyl 4-(4-(1-(2,6-difluorophenyl)-4-methoxy-1H-pyrazolo[4,3-c]pyridin-3-yl)phenyl)piperazine-1-carboxylate The title compound (240 mg) was obtained using tert-butyl 4-(4-(4,4,5,5-tetramethyl-1,3,2-dioxaborolan-2-yl)phenyl) piperazine-1-carboxylate (213 mg) and 1-(2,6-difluorophenyl)-4-methoxy-1H-pyrazolo[4,3-c]pyridin-3-yl trifluoromethanesulfonate (205 mg) obtained in Step C of Example 35, in the same manner as in Step A of Example 179.
MS(ESI+): [M+H]$^+$ 522.2.
MS(ESI+). found: 522.3.

D) 1-(2,6-difluorophenyl)-4-methoxy-3-(4-(piperazin-1-yl)phenyl)-1H-pyrazolo[4,3-c]pyridine To a solution of tert-butyl 4-(4-(1-(2,6-difluorophenyl)-4-methoxy-1H-pyrazolo[4,3-c]pyridin-3-yl)phenyl)piperazine-1-carboxylate (920 mg) in dichloromethane (10 mL)

was added trifluoroacetic acid (4 mL) under ice-cooling, and the mixture was stirred at room temperature for 5 hr, and concentrated under reduced pressure. The residue was diluted with dichloromethane, and the mixture was adjusted to pH=9 with saturated aqueous sodium carbonate solution, and extracted with dichloromethane. The organic layer was dried over anhydrous sodium sulfate, and concentrated under reduced pressure to give the title compound (744 mg).
MS(ESI+): [M+H]$^+$ 422.2.
MS(ESI+). found: 422.2.

E) 1-(2,6-difluorophenyl)-4-methoxy-3-(4-(4-(methylsulfonyl)piperazin-1-yl)phenyl)-1H-pyrazolo[4,3-c]pyridine To a solution of 1-(2,6-difluorophenyl)-4-methoxy-3-(4-(piperazin-1-yl)phenyl)-1H-pyrazolo[4,3-c]pyridine (260 mg) and triethylamine (112 mg) in dichloromethane (5 mL) was added methanesulfonyl chloride (99.0 mg) under ice-cooling. The reaction mixture was stirred at room temperature for 2 hr, and diluted with dichloromethane. The organic layer was washed with water, dried over anhydrous sodium sulfate, and concentrated under reduced pressure to give the title compound (240 mg).
MS(ESI+): [M+H]$^+$ 500.2.
MS(ESI+). found: 500.1.

F) 1-(2,6-difluorophenyl)-3-(4-(4-(methylsulfonyl)piperazin-1-yl)phenyl)-1,5-dihydro-4H-pyrazolo[4,3-c]pyridin-4-one The title compound (155 mg) was obtained using 1-(2,6-difluorophenyl)-4-methoxy-3-(4-(4-(methylsulfonyl)piperazin-1-yl)phenyl)-1H-pyrazolo[4,3-c]pyridine (230 mg), in the same manner as in Step C of Example 152.
MS(ESI+): [M+H]+486.1.
MS(ESI+). found: 486.3.

Example 312

1-(2,6-difluorophenyl)-3-(4-(4-glycoloylpiperazin-1-yl)phenyl)-1,5-dihydro-4H-pyrazolo[4,3-c]pyridin-4-one A) 1-(4-(4-(1-(2,6-difluorophenyl)-4-methoxy-1H-pyrazolo[4,3-c]pyridin-3-yl)phenyl)piperazin-1-yl)-2-hydroxyethanone To a solution of 1-(2,6-difluorophenyl)-4-methoxy-3-(4-(piperazin-1-yl)phenyl)-1H-pyrazolo[4,3-c]pyridine (220 mg) obtained in Step D of Example 311, 2-hydroxyacetic acid (42 mg) and triethylamine (158 mg) in anhydrous THF (5 mL) was added O-(7-azabenzotriazol-1-yl)-N,N,N',N'-tetramethyluronium hexafluorophosphate (297 mg) under ice-cooling, and the mixture was stirred at room temperature for 2 hr. The reaction mixture was added to water, and the mixture was extracted with ethyl acetate. The organic layer was dried over anhydrous sodium sulfate, and the residue was purified by thin layer silica gel chromatography (ethyl acetate) to give the title compound (220 mg).
MS(ESI+): [M+H]$^+$ 480.2.
MS(ESI+). found: 480.0.

B) 1-(2,6-difluorophenyl)-3-(4-(4-glycoloylpiperazin-1-yl)phenyl)-1,5-dihydro-4H-pyrazolo[4,3-c]pyridin-4-one The title compound (72 mg) was obtained using 1-(4-(4-(1-(2,6-difluorophenyl)-4-methoxy-1H-pyrazolo[4,3-c]pyridin-3-yl)phenyl)piperazin-1-yl)-2-hydroxethanone (220 mg), in the same manner as in Step C of Example 152.
MS(ESI+): [M+H]$^+$ 466.2.
MS(ESI+). found: 466.2.

Example 313

1-(2,6-difluorophenyl)-3-(4-(4-(methoxyacetyl)piperazin-1-yl)phenyl)-1,5-dihydro-4H-pyrazolo[4,3-c]pyridin-4-one The title compound (155 mg) was obtained using 1-(2,6-difluorophenyl)-4-methoxy-3-(4-(piperazin-1-yl)phenyl)-1H-pyrazolo[4,3-c]pyridine (260 mg) obtained in Step D of Example 311 and 2-methoxyacetic acid (67.0 mg), in the same manner as in Step A of Example 312 and Step C of Example 152.
MS(ESI+): [M+H]$^+$ 480.2.
MS(ESI+). found: 480.3.

Example 314

1-(2,2-dimethylcyclopentyl)-3-(4-(morpholin-4-yl)phenyl)-1,5-dihydro-4H-pyrazolo[4,3-c]pyridin-4-one A) tert-butyl 2-(2,2-dimethylcyclopentylidene)hydrazinecarboxylate A solution of tert-butyl hydrazinecarboxylate (4.1 g) and 2,2-dimethylcyclopentanone (3.5 g) in methanol (50 mL) was stirred at 70° C. for 4 hr. The reaction mixture was concentrated under reduced pressure, and the residue was washed with diethyl ether to give the title compound (5.4 g). 1H NMR (400 MHz, CDCl$_3$) δ 1.17 (6H, s), 1.50 (9H, s), 1.61-1.64 (2H, t, J=6.8 Hz), 1.80-1.87 (2H, m), 2.24-2.27 (2H, t, J=7.2 Hz), 7.12 (1H, brs).

B) tert-butyl 2-(2,2-dimethylcyclopentyl)hydrazinecarboxylate

To a solution of tert-butyl 2-(2,2-dimethylcyclopentylidene)hydrazinecarboxylate (4.6 g) and acetic acid (9.4 g) in THF (80 mL) was added sodium cyanoborohydride (5.1 g) at room temperature. The reaction mixture was stirred at 85° C. for 10 hr, aqueous sodium hypochlorite solution was added thereto, and the mixture was extracted with ethyl acetate. The organic layer was washed with saturated brine, dried over anhydrous sodium sulfate, and concentrated under reduced pressure. The residue was purified by silica gel chromatography (ethyl acetate/petroleum ether) to give the title compound (2.4 g).
$^1$H NMR (400 MHz, CDCl$_3$) δ 0.94 (3H, s), 1.01 (3H, s), 1.36-1.56 (13H, m), 1.58-1.66 (1H, m), 1.87-1.92 (1H, m), 2.94-3.02 (1H, m), 3.96 (1H, brs), 6.16 (1H, brs).

C) (2,2-dimethylcyclopentyl)hydrazine trihydrochloride

A mixture of tert-butyl 2-(2,2-dimethylcyclopentyl)hydrazinecarboxylate (2.4 g) and hydrogen chloride in saturated methanol solution (30 mL) was stirred overnight at room temperature. The reaction mixture was concentrated under reduced pressure, and the obtained solid was washed with diethyl ether to give the title compound (2.0 g).

$^1$H NMR (400 MHz, DMSO-d$_6$) δ 0.94 (3H, s), 1.06 (3H, s), 1.41-1.54 (3H, m), 1.62-1.72 (2H, m), 2.01-2.04 (1H, m), 2.96-3.00 (1H, m), 7.31 (6H, brs).

D) N'-(2,2-dimethylcyclopentyl)-4-iodo-2-methoxynicotinohydrazide

To a mixture of 4-iodo-2-methoxy-3-pyridinecarboxylic acid (2.8 g) and triethylamine (4.5 g) in DMA (40 mL) was added O-(7-azabenzotriazol-1-yl)-N,N,N',N'-tetramethyluronium hexafluorophosphate (5.7 g) under ice-cooling. The reaction mixture was stirred at room temperature for 30 min, and (2,2-dimethylcyclopentyl)hydrazine trihydrochloride (2.8 g) was added thereto under ice-cooling. The reaction mixture was stirred at room temperature for 1 hr, and added to water, and the mixture was extracted with ethyl acetate. The organic layer was dried over anhydrous sodium sulfate, and concentrated under reduced pressure. The residue was purified by silica gel chromatography (ethyl acetate/petroleum ether) to give the title compound (3.0 g).
MS(ESI+): [M+H]$^+$ 390.1.
MS(ESI+). found: 390.0.

E) 1-(2,2-dimethylcyclopentyl)-3-(4-(morpholin-4-yl)phenyl)-1,5-dihydro-4H-pyrazolo[4,3-c]pyridin-4-one The title compound (290 mg) was obtained using N'-(2,2-dimethylcyclopentyl)-4-iodo-2-methoxynicotinohydrazide (3.00 g), in the same manner as in Step B of Example 35, Step C of Example 35, Step A of Example 179 and Step B of Example 179.
MS(ESI+): [M+H]$^+$ 392.2.
MS(ESI+). found: 393.3.

Example 315

3-fluoro-2-(4-oxo-3-(1H-pyrazol-4-yl)-4,5-dihydro-1H-pyrazolo[4,3-c]pyridin-1-yl)benzonitrile A) 4-(4,4,5,5-tetramethyl-1,3,2-dioxaborolan-2-yl)-1-((2-(trimethylsilyl)ethoxy)methyl)-1H-pyrazole To a solution of 4-(4,4,5,5-tetramethyl-1,3,2-dioxaborolan-2-yl)-1H-pyrazole (770 mg) in DMF (10 mL) was added sodium hydride (60%, 114 mg) under ice-cooling. The reaction mixture was stirred at room temperature for 1 hr. To the reaction mixture was added dropwise (2-(chloromethoxy)ethyl)(trimethyl)silane (990 mg) at room temperature, and the mixture was stirred for 15 hr. The reaction mixture was diluted with ethyl acetate, and the mixture was washed with 5% aqueous lithium chloride solution, dried over anhydrous sodium sulfate, and concentrated under reduced pressure to give the title compound (0.90 g).
MS(ESI+): [M+H]$^+$ 325.2.
MS(ESI+). found: 325.2.

B) 4-chloro-3-iodo-1-trityl-1H-pyrazolo[4,3-c]pyridine

To a solution of 4-chloro-3-iodo-1H-pyrazolo[4,3-c]pyridine (1.0 g) obtained in Step C of Example 305 in DMF (10 mL) was added sodium hydride (60%, 130 mg) under ice-cooling, and the mixture was stirred at room temperature for 1 hr. To the reaction mixture was added trityl chloride (1.1 g) at room temperature, and the mixture was stirred for 15 hr. To the reaction mixture was added water, and the resulting solid was collected by filtration, and dried to give the title compound (1.7 g).
MS(ESI+): [M+H]$^+$ 522.0.
MS(ESI+). found: 522.0.

C) 3-iodo-4-methoxy-1-trityl-1H-pyrazolo[4,3-c]pyridine

To a solution of 4-chloro-3-iodo-1-trityl-1H-pyrazolo[4,3-c]pyridine (1.7 g) in THF (20 mL) was added sodium methoxide methanol solution (1.5 M, 2.7 mL) at room temperature, and the mixture was stirred at 50° C. for 2 hr. To the reaction mixture was added water, and the mixture was extracted with ethyl acetate. The organic layer was washed with saturated brine, dried over anhydrous sodium sulfate, and concentrated under reduced pressure to give the title compound (1.6 g).
MS(ESI+): [M+H]$^+$ 518.1.
MS(ESI+). found: 518.0.

D) 3-fluoro-2-(3-iodo-4-methoxy-1H-pyrazolo[4,3-c]pyridin-1-yl)benzonitrile

To a solution of 3-iodo-4-methoxy-1-trityl-1H-pyrazolo[4,3-c]pyridine (1.6 g) in dichloromethane (15 mL) was added trifluoroacetic acid (5 mL) at room temperature, and the mixture was stirred for 5 hr. To the reaction mixture was added aqueous sodium carbonate solution. The organic layer was separated, and concentrated under reduced pressure. A mixture of the obtained residue (0.80 g), 2,3-difluorobenzonitrile (0.50 g) and potassium carbonate (0.60 g) in DMF (3 mL) was stirred at 100° C. for 5 hr. To the reaction mixture was added water, and the mixture was extracted with ethyl acetate. The organic layer was washed with saturated brine, dried over anhydrous sodium sulfate, and concentrated under reduced pressure. The residue was purified by silica gel chromatography (ethyl acetate/petroleum ether) to give the title compound (0.80 g).
MS(ESI+): [M+H]$^+$ 395.0.
MS(ESI+). found: 395.0.

E) 3-fluoro-2-(4-methoxy-3-(1-((2-(trimethylsilyl)ethoxy)methyl)-1H-pyrazol-4-yl)-1H-pyrazolo[4,3-c]pyridin-1-yl)benzonitrile The title compound (0.40 g) was obtained using 3-fluoro-2-(3-iodo-4-methoxy-1H-pyrazolo[4,3-c]pyridin-1-yl)benzonitrile (0.63 g) and 4-(4,4,5,5-tetramethyl-1,3,2-dioxaborolan-2-yl)-1-((2-(trimethylsilyl)ethoxy)methyl)-1H-pyrazole (0.62 g), in the same manner as in Step B of Example 152.
MS(ESI+): [M+H]$^+$ 465.2.
MS(ESI+). found: 465.2.

F) 3-fluoro-2-(4-methoxy-3-(1H-pyrazol-4-yl)-1H-pyrazolo[4,3-c]pyridin-1-yl)benzonitrile To a solution of 3-fluoro-2-(4-methoxy-3-(1-((2-(trimethylsilyl)ethoxy)methyl)-1H-pyrazol-4-yl)-1H-pyrazolo[4,3-c]pyridin-1-yl)benzonitrile (400 mg) in dichloromethane (4 mL) was added trifluoroacetic acid (1 mL), and the mixture was stirred at room temperature for 5 hr. To the reaction mixture was added aqueous sodium carbonate solution. The organic layer was separated, and concentrated under reduced pressure. The residue was purified by silica gel chromatography (ethyl acetate/petroleum ether) to give the title compound (115 mg).
MS(ESI+): [M+H]$^+$ 335.1.
MS(ESI+). found: 335.1.

G) 3-fluoro-2-(4-oxo-3-(1H-pyrazol-4-yl)-4,5-dihydro-1H-pyrazolo[4,3-c]pyridin-1-yl)benzonitrile The title compound (59.0 mg) was obtained using 3-fluoro-2-(4-methoxy-3-(1H-pyrazol-4-yl)-1H-pyrazolo[4,3-c]pyridin-1-yl)benzonitrile (110 mg), in the same manner as in Step C of Example 152.
MS(ESI+): [M+H]$^+$ 321.1.
MS(ESI+). found: 321.1.

Example 316

3-(4-(1-acetyl-3,3-difluoropiperidin-4-yl)phenyl)-1-(2,6-difluorophenyl)-1,5-dihydro-4H-pyrazolo[4,3-c]pyridin-4-one A) ethyl N-benzyl-N-(3-ethoxy-2,2-difluoro-3-oxopropyl)-β-alaninate To a solution of 1H-benzotriazole (2.38 g) in methanol (20 mL) were added ethyl N-benzyl-β-alaninate (4.14 g) and aqueous formaldehyde solution (37%, 2 mL) at room temperature. The reaction mixture was stirred overnight at room temperature, and concentrated under reduced pressure. The residue was purified by silica gel chromatography (ethyl acetate/petroleum ether) to give ethyl N-(1H-benzotriazol-1-ylmethyl)-N-benzyl-β-alaninate (5.60 g). To a mixture of zinc powder (1.74 g) in anhydrous THF (16 mL) was added chlorotrimethylsilane (1.58 g) under nitrogen atmosphere, and the mixture was stirred at room temperature for 10 min. To the reaction mixture was added ethyl bromodifluoroacetate (2.97 g) at room temperature, and then a solution of ethyl N-(1H-benzotriazol-1-ylmethyl)-N-benzyl-β-alaninate (4.50 g) in THF (8 mL) was added thereto at room temperature. The reaction mixture was stirred at room temperature for 18 hr, and added to water. The insoluble substance was removed by the filtration, and the filtrate was extracted with ethyl acetate. The organic layer was dried over anhydrous sodium sulfate, and concentrated under reduced pressure. The residue was purified by silica gel chromatography (ethyl acetate/petroleum ether) to give the title compound (3.23 g).
MS(ESI+): [M+H]$^+$ 344.2.
MS(ESI+). found: 344.2.

B) ethyl 1-benzyl-5,5-difluoro-4-hydroxy-1,2,5,6-tetrahydropyridine-3-carboxylate To a solution of ethyl N-benzyl-N-(3-ethoxy-2,2-difluoro-3-oxopropyl)-β-alaninate (25.0 g) in anhydrous THF (200 mL) was added dropwise lithium diisopropylamide (2M, 72.8 mL) at −78° C. The reaction mixture was stirred at room temperature for 2 hr, and added to saturated aqueous ammonium chloride solution, and the mixture was extracted with ethyl acetate. The organic layer was dried over anhydrous sodium sulfate, and concentrated under reduced pressure to give the title compound (27.4 g).
MS(ESI+): [M+H]$^+$ 298.1.
MS(ESI+). found: 298.1.

C) 1-benzyl-3,3-difluoropiperidine-4,4-diol

A mixture of ethyl 1-benzyl-5,5-difluoro-4-hydroxy-1,2,5,6-tetrahydropyridine-3-carboxylate (5.0 g) and conc. hydrochloric acid (40 mL) in 1,4-dioxane (15 mL) was stirred at 80° C. for 3 hr. The reaction mixture was concentrated under reduced pressure, and diluted with ethyl acetate, and the mixture was adjusted to pH-9 with saturated aqueous sodium carbonate solution. The aqueous layer was extracted with ethyl acetate, and the organic layer was dried over anhydrous sodium sulfate, and concentrated under reduced pressure. The residue was washed with dichloromethane to give the title compound (1.40 g).
MS(ESI+): [M+H]$^+$ 244.1.
MS(ESI+). found: 244.1.

D) 1-benzyl-3,3-difluoro-1,2,3,6-tetrahydropyridin-4-yl trifluoromethanesulfonate To a mixture of ethyl 1-benzyl-5,5-difluoro-4-hydroxy-1,2,5,6-tetrahydropyridine-3-carboxylate (2.43 g) and 1,8-diazabicyclo[5.4.0]undec-7-ene (7.61 g) in anhydrous 1,4-dioxane (30 mL) was added 1,1,1-trifluoro-N-phenyl-N-((trifluoromethyl)sulfonyl)methanesulfonamide (10.7 g) at room temperature. The reaction mixture was stirred at 80° C. overnight, and added to water, and the mixture was extracted with ethyl acetate. The organic layer was dried over anhydrous sodium sulfate, and concentrated under reduced pressure. The residue was purified by silica gel chromatography (ethyl acetate/petroleum ether) to give the title compound (1.86 g).
MS(ESI+): [M+H]$^+$ 358.1.
MS(ESI+). found: 358.1.

E) 4-(1-benzyl-3,3-difluoro-1,2,3,6-tetrahydropyridin-4-yl)phenol

To a mixture of 1-benzyl-3,3-difluoro-1,2,3,6-tetrahydropyridin-4-yl trifluoromethanesulfonate (1.13 g), 4-hydroxyphenylboronic acid (0.43 g) and sodium carbonate (1.01 g) in DMF (10 mL) was added dichloro(1,1'-bis(diphenylphosphino)ferrocene)palladium(II) (73 mg) under nitrogen atmosphere. The reaction mixture was stirred at 90° C. for 3 hr. The reaction mixture was added to water, and the mixture was adjusted to pH=5 with acetic acid, and extracted with ethyl acetate. The organic layer was washed with saturated aqueous sodium hydrogencarbonate solution, dried over anhydrous sodium sulfate, and concentrated under reduced pressure. The residue was purified by silica gel chromatography (ethyl acetate/petroleum ether) to give the title compound (725 mg).
MS(ESI+): [M+H]$^+$ 302.1.
MS(ESI+). found: 302.2.

F) tert-butyl 3,3-difluoro-4-(4-hydroxyphenyl)piperidine-1-carboxylate

A mixture of 4-(1-benzyl-3,3-difluoro-1,2,3,6-tetrahydropyridin-4-yl)phenol (740 mg), di-tert-butyl dicarbonate (985 mg) and 10% palladium on carbon (360 mg) in methanol (15 mL) was stirred under hydrogen atmosphere at room temperature for 3 hr. The insoluble substance was removed by the filtration, and the filtrate was concentrated under reduced pressure. The resulting solid was washed with hexane to give the title compound (590 mg).
$^1$H NMR (400 MHz, DMSO-d$_6$) δ 1.42 (9H, s), 1.74-1.77 (1H, m), 1.87-1.99 (1H, m), 2.88-2.97 (1H, m), 3.12-3.29 (2H, m), 4.06-4.20 (2H, m), 6.71 (2H, d, J=8.4 Hz), 7.07 (2H, d, J=8.0 Hz), 9.35 (1H, s).

G) tert-butyl 3,3-difluoro-4-(4-(((trifluoromethyl)sulfonyl)oxy)phenyl)piperidine-1-carboxylate To a mixture of tert-butyl 3,3-difluoro-4-(4-hydroxyphenyl)piperidine-1-carboxylate (540 mg) and DIEA (890 mg)

in dichloromethane (10 mL) was added trifluoromethanesulfonic anhydride (973 mg) under ice-cooling. The reaction mixture was stirred for 2 hr under ice-cooling, and diluted with dichloromethane. The organic layer was washed with water, dried over anhydrous sodium sulfate, and concentrated under reduced pressure. The residue was purified by silica gel chromatography (ethyl acetate/petroleum ether) to give the title compound (486 mg).

$^1$H NMR (400 MHz, DMSO-$d_6$) δ 1.49 (9H, s), 1.86-1.90 (1H, d, J 13.6 Hz), 2.10-2.21 (1H, m), 2.85 (1H, brs), 3.02-3.13 (2H, m), 4.34-4.40 (2H, m), 7.26 (2H, d, J=8.4 Hz), 7.39 (2H, d, J=8.8 Hz).

H) tert-butyl 3,3-difluoro-4-(4-(4,4,5,5-tetramethyl-1,3,2-dioxaborolan-2-yl)phenyl)piperidine-1-carboxylate To a mixture of tert-butyl 3,3-difluoro-4-(4-(((trifluoromethyl)sulfonyl)oxy)phenyl)piperidine-1-carboxylate (272 mg), bis(pinacolato)diboron (186 mg) and potassium acetate (179 mg) in 1,4-dioxane (5 mL) was added dichloro(1,1'-bis(diphenylphosphino)ferrocene)palladium(II) (45 mg) under nitrogen atmosphere. The reaction mixture was stirred at 90° C. for 3 hr. The insoluble substance was removed by the filtration, and the filtrate was concentrated under reduced pressure. The residue was purified by thin layer silica gel chromatography (ethyl acetate/petroleum ether) to give the title compound (155 mg).

MS(ESI+): [M-$C_4H_9$+H]$^+$ 368.2.
MS(ESI+). found: 368.3.

I) 1-(2,6-difluorophenyl)-3-(4-(3,3-difluoropiperidin-4-yl)phenyl)-4-methoxy-1H-pyrazolo[4,3-c]pyridine The title compound (186 mg) was obtained using 7-chloro-1-(2,6-difluorophenyl)-4-methoxy-1H-pyrazolo[4,3-c]pyridin-3-yl trifluoromethanesulfonate obtained in Step A of Example 152 (125 mg) and tert-butyl 3,3-difluoro-4-(4-(4,4,5,5-tetramethyl-1,3,2-dioxaborolan-2-yl)phenyl)piperidine-1-carboxylate (122 mg), in the same manner as in Step B of Example 152 and Step D of Example 311.

MS(ESI+): [M+H]$^+$ 457.2.
MS(ESI+). found: 457.2.

J) 1-(4-(4-(1-(2,6-difluorophenyl)-4-methoxy-1H-pyrazolo[4,3-c]pyridin-3-yl)phenyl)-3,3-difluoropiperidin-1-yl)ethanone To a mixture of 1-(2,6-difluorophenyl)-3-(4-(3,3-difluoropiperidin-4-yl)phenyl)-4-methoxy-1H-pyrazolo[4,3-c]pyridine (186 mg) and triethylamine (91.0 mg) in dichloromethane (4 mL) was added acetic anhydride (67.0 mg) under ice-cooling. The reaction mixture was stirred at room temperature for 2 hr, and diluted with dichloromethane. The organic layer was washed with water, dried over anhydrous sodium sulfate, and concentrated under reduced pressure to give the title compound (200 mg).

MS(ESI+): [M+H]$^+$ 499.2.
MS(ESI+). found: 499.2.

K) 3-(4-(1-acetyl-3,3-difluoropiperidin-4-yl)phenyl)-1-(2,6-difluorophenyl)-1,5-dihydro-4H-pyrazolo[4,3-c]pyridin-4-one The title compound (108 mg) was obtained using 1-(4-(4-(1-(2,6-difluorophenyl)-4-methoxy-1H-pyrazolo[4,3-c]pyridin-3-yl)phenyl)-3,3-difluoropiperidin-1-yl)ethanone (196 mg), in the same manner as in Step C of Example 152.

MS(ESI+): [M+H]$^+$ 485.2.
MS(ESI+). found: 485.1.

Example 317

1-(2,2-difluorocyclohexyl)-3-(4-(morpholin-4-yl)phenyl)-1,5-dihydro-4H-pyrazolo[4,3-c]pyridin-4-one A) 2-(4-methoxy-3-(4-(morpholin-4-yl)phenyl)-1H-pyrazolo[4,3-c]pyridin-1-yl)cyclohexanol To a solution of 4-methoxy-3-(4-(morpholin-4-yl)phenyl)-1H-pyrazolo[4,3-c]pyridine (500 mg) obtained in Step G of Example 305 in anhydrous DMF (5 mL) was added sodium hydride (60% dispersion in mineral oil, 72.0 mg), and the mixture was stirred for 30 min. To the reaction mixture was added 7-oxabicyclo[4.1.0]heptane (1.60 g) at room temperature, and the mixture was stirred at 80° C. for 5 hr. The reaction mixture was added to ice-water, and the mixture was extracted with ethyl acetate. The organic layer was washed with saturated brine, dried over anhydrous sodium sulfate, and concentrated under reduced pressure. The residue was purified by silica gel chromatography (ethyl acetate/petroleum ether) to give the title compound (400 mg).

MS(ESI+): [M+H]$^+$ 409.2.
MS(ESI+). found: 409.3.

B) 2-(4-methoxy-3-(4-(morpholin-4-yl)phenyl)-1H-pyrazolo[4,3-c]pyridin-1-yl)cyclohexanone To a solution of oxalyl chloride (910 mg) in dichloromethane (3 mL) was added DMSO (670 mg) under nitrogen atmosphere at –78° C. The reaction mixture was stirred for 30 min, and a solution of 2-(4-methoxy-3-(4-(morpholin-4-yl)phenyl)-1H-pyrazolo[4,3-c]pyridin-1-yl)cyclohexanol (350 mg) in dichloromethane (2 mL) was added thereto. The reaction mixture was stirred at –78° C. for 1 hr, and triethylamine (1.2 g) was added thereto. The reaction mixture was stirred at –78° C. for 1.5 hr, and added to ice-water, and the mixture was extracted with ethyl acetate. The organic layer was washed with saturated aqueous sodium carbonate solution, dried over anhydrous sodium sulfate, and concentrated under reduced pressure. The residue was purified by silica gel chromatography (ethyl acetate/petroleum ether) to give the title compound (190 mg).

MS(ESI+): [M+H]$^+$ 407.2.
MS(ESI+). found: 407.2.

C) 1-(2,2-difluorocyclohexyl)-4-methoxy-3-(4-(morpholin-4-yl)phenyl)-1H-pyrazolo[4,3-c]pyridine To a solution of 2-(4-methoxy-3-(4-(morpholin-4-yl)phenyl)-1H-pyrazolo[4,3-c]pyridin-1-yl)cyclohexanone (170 mg) in anhydrous dichloromethane (2 mL) was added N,N-diethylaminosulfur trifluoride (200 mg) under ice-cooling. The reaction mixture was stirred at room temperature for 5 hr, and added to ice-water, and the mixture was extracted with dichloromethane. The organic layer was washed with saturated brine, dried over anhydrous sodium sulfate, and concentrated under reduced pressure. The residue was purified by thin layer silica gel chromatography (ethyl acetate/petroleum ether) to give the title compound (30.0 mg).

MS(ESI+): [M+H]$^+$ 429.2.
MS(ESI+). found: 429.2.

D) 1-(2,2-difluorocyclohexyl)-3-(4-(morpholin-4-yl)phenyl)-1,5-dihydro-4H-pyrazolo[4,3-c]pyridin-4-one The title compound (14.5 mg) was obtained using 1-(2,2-difluorocyclohexyl)-4-methoxy-3-(4-(morpholin-4-yl)phenyl)-1H-pyrazolo[4,3-c]pyridine (30.0 mg), in the same manner as in Step C of Example 152.

MS(ESI+): [M+H]+415.2.

MS(ESI+). found: 415.2.

The structure formulas and compound names of the compounds obtained in Examples 181 to 317 are shown in Table 3.

TABLE 3-1

| Ex. | Structural Formula | Compound Name |
| --- | --- | --- |
| 181 | 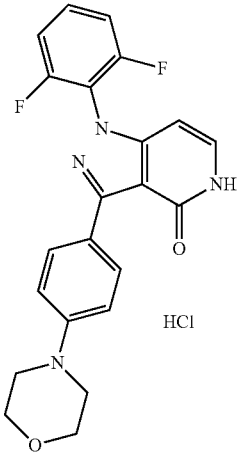 [SMILES: N=C(c1ccc(N2CCOCC2)cc1)c1c(Nc2c(F)cccc2F)cc[nH]c1=O ; Cl] | 1-(2,6-difluorophenyl)-3-(4-(morpholin-4-yl)phenyl)-1,5-dihydro-4H-pyrazolo[4,3-c]pyridin-4-one hydrochloride |
| 182 | 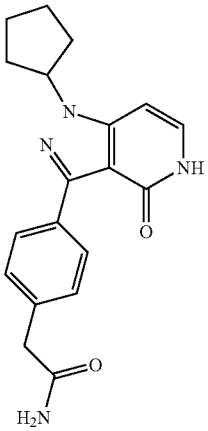 [SMILES: N=C(c1ccc(CC(N)=O)cc1)c1c(NC2CCCC2)cc[nH]c1=O] | 2-(4-(1-cyclopentyl-4-oxo-4,5-dihydro-1H-pyrazolo[4,3-c]pyridin-3-yl)phenyl)acetamide |
| 183 | 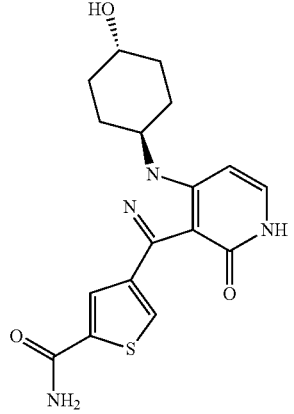 [SMILES: N=C(c1csc(C(N)=O)c1)c1c(N[C@H]2CC[C@H](O)CC2)cc[nH]c1=O] | 4-(1-(trans-4-hydroxycyclohexyl)-4-oxo-4,5-dihydro-1H-pyrazolo[4,3-c]pyridin-3-yl)thiophene-2-carboxamide |

TABLE 3-1-continued
| Ex. | Structural Formula | Compound Name |
|---|---|---|
| 184 | 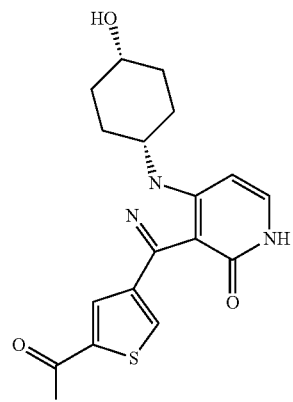 | 4-(1-(cis-4-hydroxycyclohexyl)-4-oxo-4,5-dihydro-1H-pyrazolo[4,3-c]pyridin-3-yl)thiophene-2-carboxamide |
| 185 | 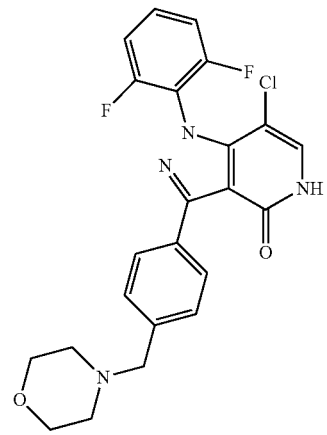 [SMILES: N=C(c1ccc(CN2CCOCC2)cc1)c1c(Nc2c(F)cccc2F)c(Cl)c[nH]c1=O] | 7-chloro-1-(2,6-difluorophenyl)-3-(4-(morpholin-4-ylmethyl)phenyl)-1,5-dihydro-4H-pyrazolo[4,3-c]pyridin-4-one |
| 186 | 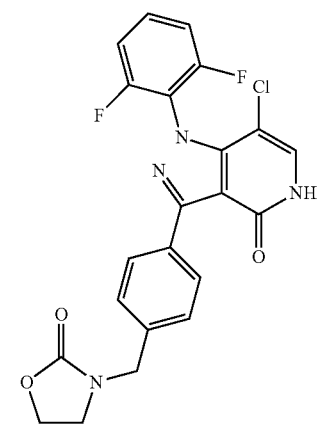 [SMILES: N=C(c1ccc(CN2CCOC2=O)cc1)c1c(Nc2c(F)cccc2F)c(Cl)c[nH]c1=O] | 7-chloro-1-(2,6-difluorophenyl)-3-(4-((2-oxo-1,3-oxazolidin-3-yl)methyl)phenyl)-1,5-dihydro-4H-pyrazolo[4,3-c]pyridin-4-one |

TABLE 3-1-continued
| Ex. | Structural Formula | Compound Name |
|---|---|---|
| 187 | 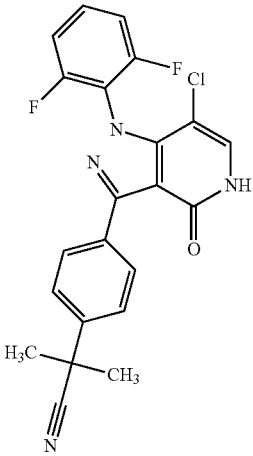 [SMILES: CC(C)(C#N)c1ccc(C(=N)c2c(Nc3c(F)cccc3F)c(Cl)c[nH]c2=O)cc1] | 2-(4-(7-chloro-1-(2,6-difluorophenyl)-4-oxo-4,5-dihydro-1H-pyrazolo[4,3-c]pyridin-3-yl)phenyl)-2-methylpropanenitrile |
| 188 | 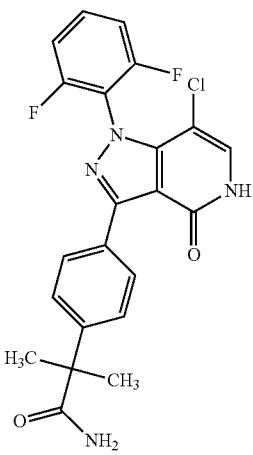 [SMILES: CC(C)(C(N)=O)c1ccc(-c2nn(-c3c(F)cccc3F)c3c(Cl)c[nH]c(=O)c23)cc1] | 2-(4-(7-chloro-1-(2,6-difluorophenyl)-4-oxo-4,5-dihydro-1H-pyrazolo[4,3-c]pyridin-3-yl)phenyl)-2-methylpropanamide |
| 189 | 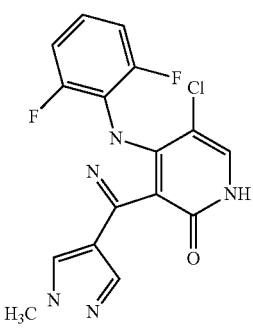 | 7-chloro-1-(2,6-difluorophenyl)-3-(1-methyl-1H-pyrazol-4-yl)-1,5-dihydro-4H-pyrazolo[4,3-c]pyridin-4-one |

TABLE 3-1-continued

| Ex. | Structural Formula | Compound Name |
|---|---|---|
| 190 | | 2-(4-(7-chloro-1-(2,6-difluorophenyl)-4-oxo-4,5-dihydro-1H-pyrazolo[4,3-c]pyridin-3-yl)-1H-pyrazol-1-yl)acetamide |
| 191 | | 4-(7-chloro-1-(2,6-difluorophenyl)-4-oxo-4,5-dihydro-1H-pyrazolo[4,3-c]pyridin-3-yl)-N-(cyanomethyl)thiophene-2-carboxamide |
| 192 | | 7-chloro-1-(2,6-difluorophenyl)-3-(5-(morpholin-4-ylcarbonyl)-3-thienyl)-1,5-dihydro-4H-pyrazolo[4,3-c]pyridin-4-one |

TABLE 3-1-continued

| Ex. | Structural Formula | Compound Name |
|---|---|---|
| 193 | | 4-(7-chloro-1-(2,6-difluorophenyl)-4-oxo-4,5-dihydro-1H-pyrazolo[4,3-c]pyridin-3-yl)-N-(morpholin-4-yl)thiophene-2-carboxamide |
| 194 | | 4-(7-chloro-1-(2,6-difluorophenyl)-4-oxo-4,5-dihydro-1H-pyrazolo[4,3-c]pyridin-3-yl)-N-methylbenzamide |
| 195 | | 7-chloro-1-(2,6-difluorophenyl)-3-(4-(2-oxopyrrolidin-1-yl)phenyl)-1,5-dihydro-4H-pyrazolo[4,3-c]pyridin-4-one |

TABLE 3-1-continued
| Ex. | Structural Formula | Compound Name |
|---|---|---|
| 196 | 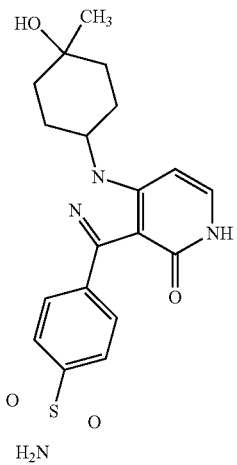 | 4-(1-(4-hydroxy-4-methylcyclohexyl)-4-oxo-4,5-dihydro-1H-pyrazolo[4,3-c]pyridin-3-yl)benzenesulfonamide |
| 197 | 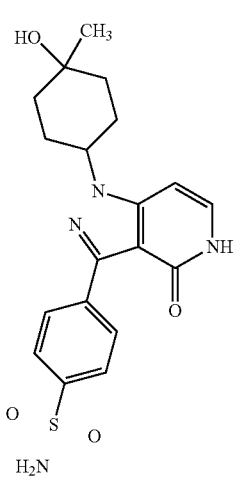 | 4-(1-(4-hydroxy-4-methylcyclohexyl)-4-oxo-4,5-dihydro-1H-pyrazolo[4,3-c]pyridin-3-yl)benzenesulfonamide |
| 198 | 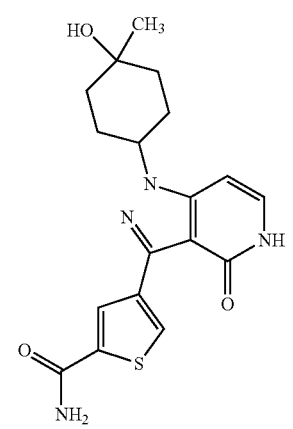 [SMILES: CC1(O)CCC(Nc2cc[nH]c(=O)c2C(=N)c2csc(C(N)=O)c2)CC1] | 4-(1-(4-hydroxy-4-methylcyclohexyl)-4-oxo-4,5-dihydro-1H-pyrazolo[4,3-c]pyridin-3-yl)thiophene-2-carboxamide |

TABLE 3-1-continued
| Ex. | Structural Formula | Compound Name |
|---|---|---|
| 199 | 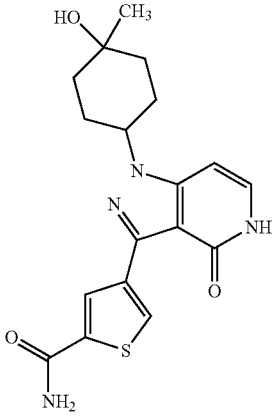 [SMILES: CC1(O)CCC(Nc2cc[nH]c(=O)c2C(=N)c2csc(C(N)=O)c2)CC1] | 4-(1-(4-hydroxy-4-methylcyclohexyl)-4-oxo-4,5-dihydro-1H-pyrazolo[4,3-c]pyridin-3-yl)thiophene-2-carboxamide |
| 200 | 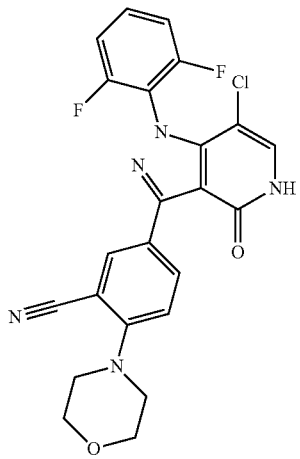 [SMILES: N#Cc1cc(C(=N)c2c(Nc3c(F)cccc3F)c(Cl)c[nH]c2=O)ccc1N1CCOCC1] | 5-(7-chloro-1-(2,6-difluorophenyl)-4-oxo-4,5-dihydro-1H-pyrazolo[4,3-c]pyridin-3-yl)-2-(morpholin-4-yl)benzonitrile |
| 201 | 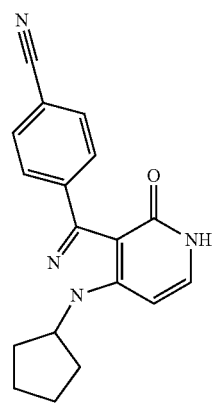 [SMILES: N#Cc1ccc(C(=N)c2c(NC3CCCC3)cc[nH]c2=O)cc1] | 4-(1-cyclopentyl-4-oxo-4,5-dihydro-1H-pyrazolo[4,3-c]pyridin-3-yl)benzonitrile |

TABLE 3-1-continued

| Ex. | Structural Formula | Compound Name |
|---|---|---|
| 202 | | 3-(1-cyclopentyl-4-oxo-4,5-dihydro-1H-pyrazolo[4,3-c]pyridin-3-yl)benzonitrile |
| 203 | | 7-chloro-1-(2,6-difluorophenyl)-3-(5-(morpholin-4-ylmethyl)-3-thienyl)-1,5-dihydro-4H-pyrazolo[4,3-c]pyridin-4-one |
| 204 | | 1-cyclopentyl-3-(1H-pyrazol-4-yl)-1,5-dihydro-4H-pyrazolo[4,3-c]pyridin-4-one |
| 205 | | 7-chloro-1-(2,6-difluorophenyl)-3-(1-(tetrahydro-2H-pyran-4-yl)-1H-pyrazol-4-yl)-1,5-dihydro-4H-pyrazolo[4,3-c]pyridin-4-one |

TABLE 3-1-continued
| Ex. | Structural Formula | Compound Name |
|---|---|---|
| 206 | 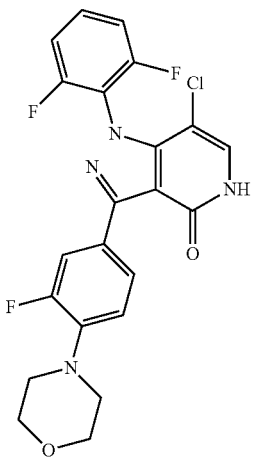 [SMILES: N=C(c1ccc(N2CCOCC2)c(F)c1)c1c(Nc2c(F)cccc2F)c(Cl)c[nH]c1=O] | 7-chloro-1-(2,6-difluorophenyl)-3-(3-fluoro-4-(morpholin-4-yl)phenyl)-1,5-dihydro-4H-pyrazolo[4,3-c]pyridin-4-one |
| 207 | 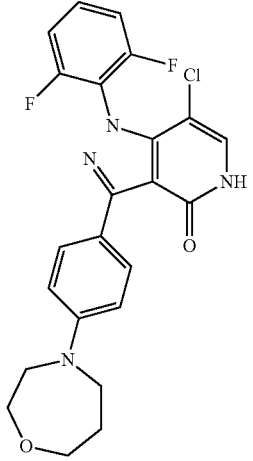 [SMILES: N=C(c1ccc(N2CCCOCC2)cc1)c1c(Nc2c(F)cccc2F)c(Cl)c[nH]c1=O] | 7-chloro-1-(2,6-difluorophenyl)-3-(4-(1,4-oxazepan-4-yl)phenyl)-1,5-dihydro-4H-pyrazolo[4,3-c]pyridin-4-one |
| 208 | 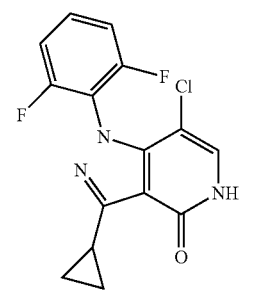 [SMILES: N=C(c1c(Nc2c(F)cccc2F)c(Cl)c[nH]c1=O)C1CC1] | 7-chloro-3-cyclopropyl-1-(2,6-difluorophenyl)-1,5-dihydro-4H-pyrazolo[4,3-c]pyridin-4-one |

TABLE 3-1-continued

| Ex. | Structural Formula | Compound Name |
|---|---|---|
| 209 | | 4-(1-(4-ethyl-4-hydroxycyclohexyl)-4-oxo-4,5-dihydro-1H-pyrazolo[4,3-c]pyridin-3-yl)benzenesulfonamide |
| 210 | | 4-(1-(4-ethyl-4-hydroxycyclohexyl)-4-oxo-4,5-dihydro-1H-pyrazolo[4,3-c]pyridin-3-yl)benzenesulfonamide |
| 211 | | 4-(1-(2-methylphenyl)-4-oxo-4,5-dihydro-1H-pyrazolo[4,3-c]pyridin-3-yl)benzenesulfonamide |

TABLE 3-1-continued

| Ex. | Structural Formula | Compound Name |
|---|---|---|
| 212 | | 4-(4-oxo-1-(2-(trifluoromethyl)phenyl)-4,5-dihydro-1H-pyrazolo[4,3-c]pyridin-3-yl)benzenesulfonamide |
| 213 | | 4-(1-(2-fluorophenyl)-4-oxo-4,5-dihydro-1H-pyrazolo[4,3-c]pyridin-3-yl)benzenesulfonamide |
| 214 | | 4-(1-(2-chlorophenyl)-4-oxo-4,5-dihydro-1H-pyrazolo[4,3-c]pyridin-3-yl)benzenesulfonamide |

TABLE 3-1-continued

| Ex. | Structural Formula | Compound Name |
|---|---|---|
| 215 | | 4-(7-chloro-1-(2,6-difluorophenyl)-4-oxo-4,5-dihydro-1H-pyrazolo[4,3-c]pyridin-3-yl)-2-fluorobenzamide |
| 216 | | 4-(7-chloro-1-(2,6-difluorophenyl)-4-oxo-4,5-dihydro-1H-pyrazolo[4,3-c]pyridin-3-yl)-2-fluoro-N-methylbenzamide |
| 217 | | 2-(4-(7-chloro-1-(2,6-difluorophenyl)-4-oxo-4,5-dihydro-1H-pyrazolo[4,3-c]pyridin-3-yl)phenoxy)-N-(2-methoxyethyl)acetamide |
| 218 | | 7-bromo-1-(2,6-difluorophenyl)-3-(4-(morpholin-4-yl)phenyl)-1,5-dihydro-4H-pyrazolo[4,3-c]pyridin-4-one |

TABLE 3-1-continued
| Ex. | Structural Formula | Compound Name |
|---|---|---|
| 219 | 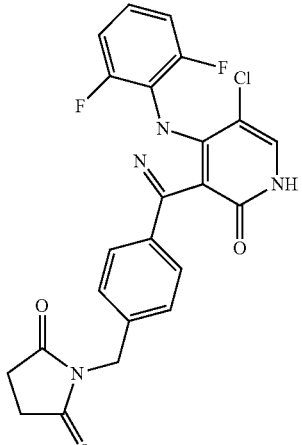 | 1-(4-(7-chloro-1-(2,6-difluorophenyl)-4-oxo-4,5-dihydro-1H-pyrazolo[4,3-c]pyridin-3-yl)benzyl)pyrrolidine-2,5-dione |
| 220 | 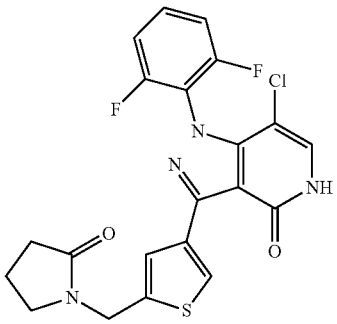 [SMILES: N=C(c1csc(CN2CCCC2=O)c1)c1c(Nc2c(F)cccc2F)c(Cl)c[nH]c1=O] | 7-chloro-1-(2,6-difluorophenyl)-3-(5-((2-oxopyrrolidin-1-yl)methyl)-3-thienyl)-1,5-dihydro-4H-pyrazolo[4,3-c]pyridin-4-one |
| 221 | 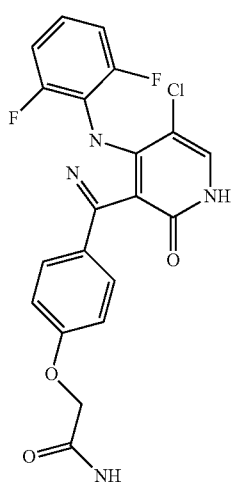 | 2-(4-(7-chloro-1-(2,6-difluorophenyl)-4-oxo-4,5-dihydro-1H-pyrazolo[4,3-c]pyridin-3-yl)phenoxy)-N-methylacetamide |

TABLE 3-1-continued
| Ex. | Structural Formula | Compound Name |
|---|---|---|
| 222 | 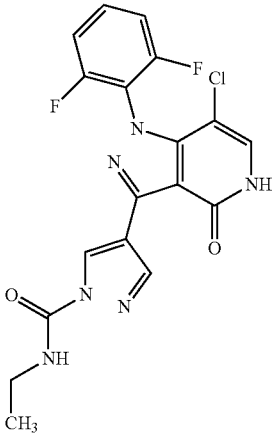 [SMILES: CCNC(=O)N/C=C(\C=N)C(=N)c1c(Nc2c(F)cccc2F)c(Cl)c[nH]c1=O] | 4-(7-chloro-1-(2,6-difluorophenyl)-4-oxo-4,5-dihydro-1H-pyrazolo[4,3-c]pyridin-3-yl)-N-ethyl-1H-pyrazole-1-carboxamide |
| 223 | 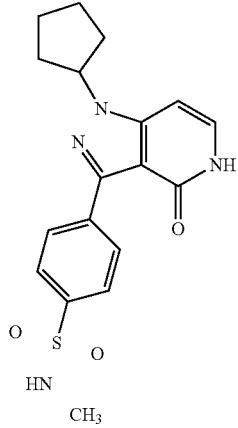 | 4-(1-cyclopentyl-4-oxo-4,5-dihydro-1H-pyrazolo[4,3-c]pyridin-3-yl)-N-methylbenzenesulfonamide |
| 224 | 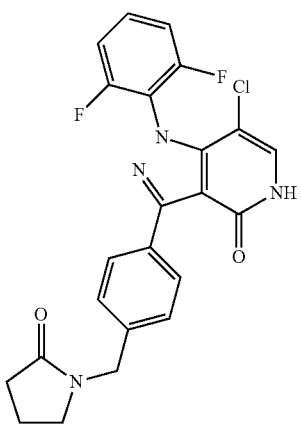 [SMILES: N=C(c1ccc(CN2CCCC2=O)cc1)c1c(Nc2c(F)cccc2F)c(Cl)c[nH]c1=O] | 7-chloro-1-(2,6-difluorophenyl)-3-(4-((2-oxopyrrolidin-1-yl)methyl)phenyl)-1,5-dihydro-4H-pyrazolo[4,3-c]pyridin-4-one |

TABLE 3-1-continued

| Ex. | Structural Formula | Compound Name |
|---|---|---|
| 225 | | 7-chloro-1-(2,6-difluorophenyl)-3-(4-(2-oxoimidazolidin-1-yl)phenyl)-1,5-dihydro-4H-pyrazolo[4,3-c]pyridin-4-one |
| 226 | | 7-chloro-1-(2,6-difluorophenyl)-3-(1-methyl-1H-benzimidazol-5-yl)-1,5-dihydro-4H-pyrazolo[4,3-c]pyridin-4-one |
| 227 | | 7-chloro-1-(2,6-difluorophenyl)-3-(2-oxo-2,3-dihydro-1H-indol-6-yl)-1,5-dihydro-4H-pyrazolo[4,3-c]pyridin-4-one |
| 228 | | 1-(2,6-difluorophenyl)-4-oxo-3-(1H-pyrazol-4-yl)-4,5-dihydro-1H-pyrazolo[4,3-c]pyridine-7-carbonitrile |

TABLE 3-1-continued

| Ex. | Structural Formula | Compound Name |
|---|---|---|
| 229 | | 1-(2,6-difluorophenyl)-3-(4-(morpholin-4-yl)phenyl)-4-oxo-4,5-dihydro-1H-pyrazolo[4,3-c]pyridine-7-carbonitrile |
| 230 | | 4-(1-(2,6-difluorophenyl)-4-oxo-4,5-dihydro-1H-pyrazolo[4,3-c]pyridin-3-yl)benzamide |
| 231 | | 4-(7-chloro-1-(2,6-difluorophenyl)-4-oxo-4,5-dihydro-1H-pyrazolo[4,3-c]pyridin-3-yl)-N-(2-methoxyethyl)benzamide |

TABLE 3-1-continued
| Ex. | Structural Formula | Compound Name |
| --- | --- | --- |
| 232 | 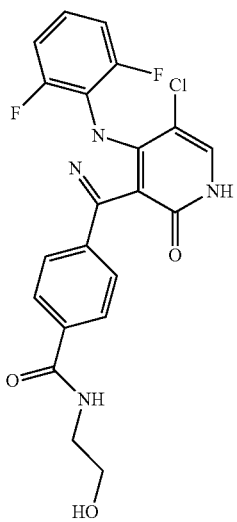 [SMILES: N=C(c1ccc(C(=O)NCCO)cc1)c1c(Nc2c(F)cccc2F)c(Cl)c[nH]c1=O] | 4-(7-chloro-1-(2,6-difluorophenyl)-4-oxo-4,5-dihydro-1H-pyrazolo[4,3-c]pyridin-3-yl)-N-(2-hydroxyethyl)benzamide |
| 233 | 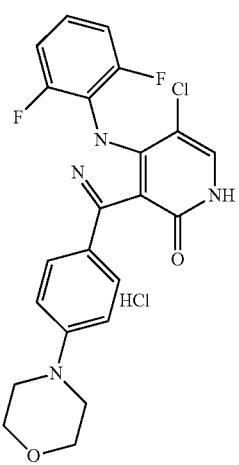 [SMILES: N=C(c1ccc(N2CCOCC2)cc1)c1c(Nc2c(F)cccc2F)c(Cl)c[nH]c1=O ; Cl] | 7-chloro-1-(2,6-difluorophenyl)-3-(4-(morpholin-4-yl)phenyl)-1,5-dihydro-4H-pyrazolo[4,3-c]pyridin-4-one hydrochloride |
| 234 | 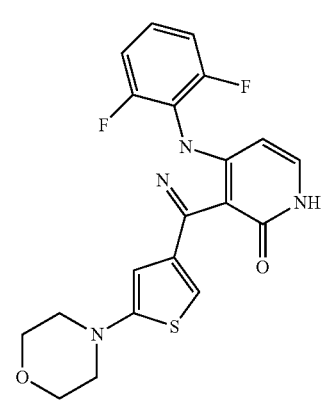 [SMILES: N=C(c1csc(N2CCOCC2)c1)c1c(Nc2c(F)cccc2F)cc[nH]c1=O] | 1-(2,6-difluorophenyl)-3-(5-(morpholin-4-yl)-3-thienyl)-1,5-dihydro-4H-pyrazolo[4,3-c]pyridin-4-one |

TABLE 3-1-continued

| Ex. | Structural Formula | Compound Name |
|---|---|---|
| 235 | | 1-(2,6-difluorophenyl)-7-methyl-3-(4-(morpholin-4-yl)phenyl)-1,5-dihydro-4H-pyrazolo[4,3-c]pyridin-4-one |
| 236 | | 7-chloro-1-(2,6-difluorophenyl)-3-(4-(thiomorpholin-4-yl)phenyl)-1,5-dihydro-4H-pyrazolo[4,3-c]pyridin-4-one |
| 237 | | 4-(1-(2,6-difluorophenyl)-4-oxo-4,5-dihydro-1H-pyrazolo[4,3-c]pyridin-3-yl)-N-(2-hydroxyethyl)benzamide |

TABLE 3-1-continued
| Ex. | Structural Formula | Compound Name |
|---|---|---|
| 238 | 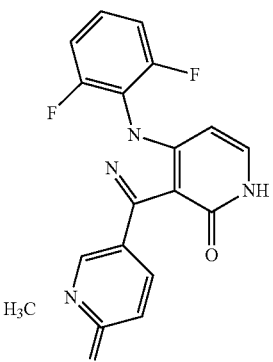 | 1-(2,6-difluorophenyl)-3-(1-methyl-6-oxo-1,6-dihydropyridin-3-yl)-1,5-dihydro-4H-pyrazolo[4,3-c]pyridin-4-one |
| 239 | 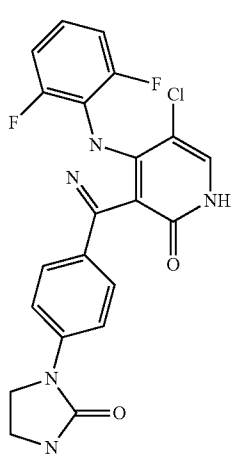 | 7-chloro-1-(2,6-difluorophenyl)-3-(4-(3-methyl-2-oxoimidazolidin-1-yl)phenyl)-1,5-dihydro-4H-pyrazolo[4,3-c]pyridin-4-one |
| 240 | 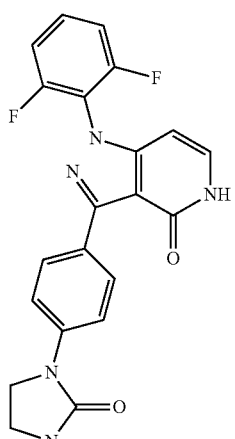 | 1-(2,6-difluorophenyl)-3-(4-(3-methyl-2-oxoimidazolidin-1-yl)phenyl)-1,5-dihydro-4H-pyrazolo[4,3-c]pyridin-4-one |

TABLE 3-1-continued
| Ex. | Structural Formula | Compound Name |
|---|---|---|
| 241 | 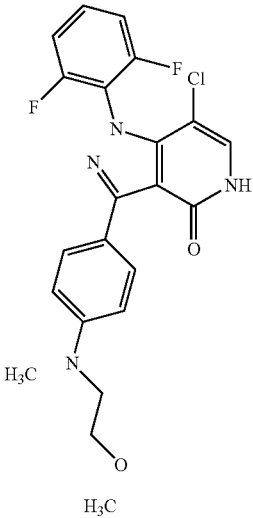 | 7-chloro-1-(2,6-difluorophenyl)-3-(4-((2-methoxyethyl)(methyl)amino)phenyl)-1,5-dihydro-4H-pyrazolo[4,3-c]pyridin-4-one |
| 242 | 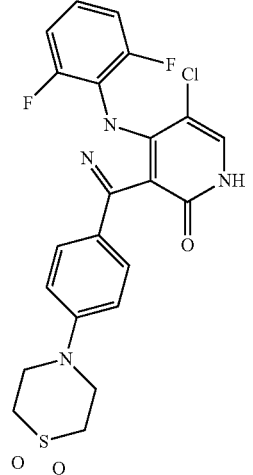 | 7-chloro-1-(2,6-difluorophenyl)-3-(4-(1,1-dioxidothiomorpholin-4-yl)phenyl)-1,5-dihydro-4H-pyrazolo[4,3-c]pyridin-4-one |
| 243 | 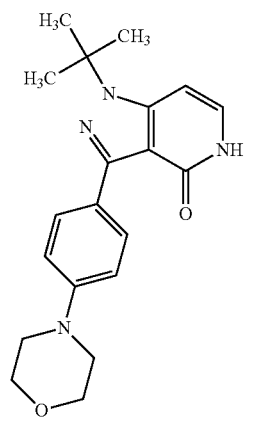 [SMILES: CC(C)(C)Nc1cc[nH]c(=O)c1C(=N)c1ccc(N2CCOCC2)cc1] | 1-tert-butyl-3-(4-(morpholin-4-yl)phenyl)-1,5-dihydro-4H-pyrazolo[4,3-c]pyridin-4-one |

TABLE 3-1-continued
| Ex. | Structural Formula | Compound Name |
|---|---|---|
| 244 | 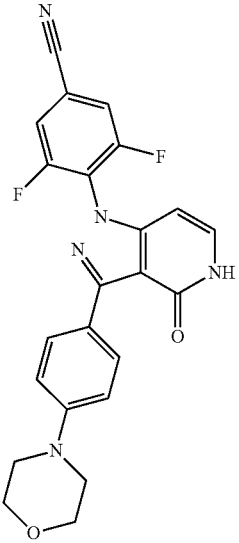 [SMILES: N#Cc1cc(F)c(Nc2cc[nH]c(=O)c2C(=N)c2ccc(N3CCOCC3)cc2)c(F)c1] | 3,5-difluoro-4-(3-(4-(morpholin-4-yl)phenyl)-4-oxo-4,5-dihydro-1H-pyrazolo[4,3-c]pyridin-1-yl)benzonitrile |
| 245 | 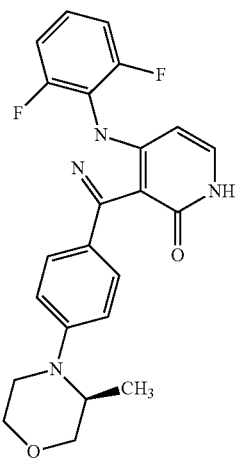 [SMILES: C[C@H]1COCCN1c1ccc(C(=N)c2c(Nc3c(F)cccc3F)cc[nH]c2=O)cc1] | 1-(2,6-difluorophenyl)-3-(4-((3S)-3-methylmorpholin-4-yl)phenyl)-1,5-dihydro-4H-pyrazolo[4,3-c]pyridin-4-one |
| 246 | 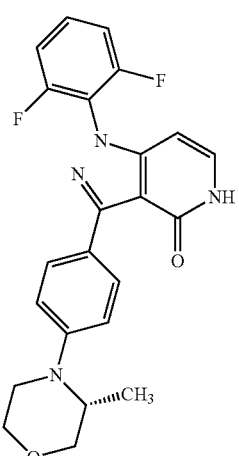 | 1-(2,6-difluorophenyl)-3-(4-((3R)-3-methylmorpholin-4-yl)phenyl)-1,5-dihydro-4H-pyrazolo[4,3-c]pyridin-4-one |

TABLE 3-1-continued

| Ex. | Structural Formula | Compound Name |
|---|---|---|
| 247 | | 4-(4-oxo-1-(pyridin-2-yl)-4,5-dihydro-1H-pyrazolo[4,3-c]pyridin-3-yl)thiophene-2-carboxamide |
| 248 | | 3-((1-tert-butyl-4-oxo-4,5-dihydro-1H-pyrazolo[4,3-c]pyridin-3-yl)amino)benzenesulfonamide |
| 249 | | 1-tert-butyl-3-((4-methoxybenzyl)amino)-1,5-dihydro-4H-pyrazolo[4,3-c]pyridin-4-one |
| 250 | | 3-anilino-1-tert-butyl-1,5-dihydro-4H-pyrazolo[4,3-c]pyridin-4-one |

TABLE 3-1-continued
| Ex. | Structural Formula | Compound Name |
|---|---|---|
| 251 | 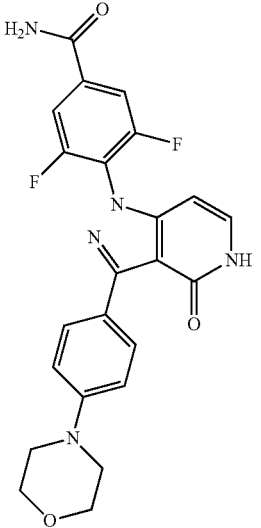 [SMILES: N=C(c1ccc(N2CCOCC2)cc1)c1c(Nc2c(F)cc(C(N)=O)cc2F)cc[nH]c1=O] | 3,5-difluoro-4-(3-(4-(morpholin-4-yl)phenyl)-4-oxo-4,5-dihydro-1H-pyrazolo[4,3-c]pyridin-1-yl)benzamide |
| 252 | 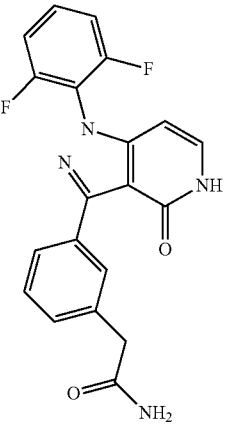 [SMILES: N=C(c1cccc(CC(N)=O)c1)c1c(Nc2c(F)cccc2F)cc[nH]c1=O] | 2-(3-(1-(2,6-difluorophenyl)-4-oxo-4,5-dihydro-1H-pyrazolo[4,3-c]pyridin-3-yl)phenyl)acetamide |
| 253 | 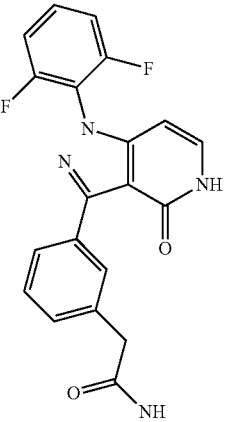 | 2-(3-(1-(2,6-difluorophenyl)-4-oxo-4,5-dihydro-1H-pyrazolo[4,3-c]pyridin-3-yl)phenyl)-N-methylacetamide |

TABLE 3-1-continued

| Ex. | Structural Formula | Compound Name |
|---|---|---|
| 254 | | 3-(7-chloro-1-(2,6-difluorophenyl)-4-oxo-4,5-dihydro-1H-pyrazolo[4,3-c]pyridin-3-yl)benzamide |
| 255 | | 3-(1-(2,6-difluorophenyl)-4-oxo-4,5-dihydro-1H-pyrazolo[4,3-c]pyridin-3-yl)benzamide |
| 256 | | 1-(2,6-difluorophenyl)-3-(4-(3,6-dihydro-2H-pyran-4-yl)phenyl)-1,5-dihydro-4H-pyrazolo[4,3-c]pyridin-4-one |

TABLE 3-1-continued
| Ex. | Structural Formula | Compound Name |
|---|---|---|
| 257 | 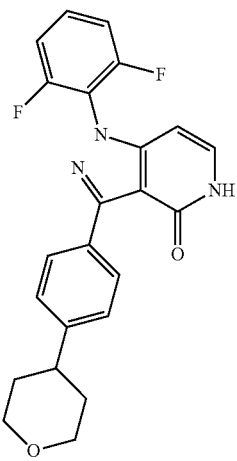 | 1-(2,6-difluorophenyl)-3-(4-(tetrahydro-2H-pyran-4-yl)phenyl)-1,5-dihydro-4H-pyrazolo[4,3-c]pyridin-4-one |
| 258 | 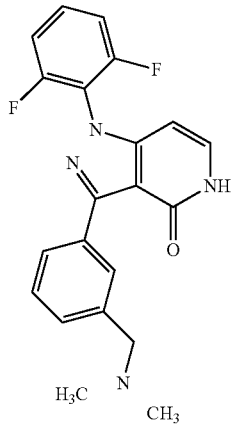 | 1-(2,6-difluorophenyl)-3-(3-((dimethylamino)methyl)phenyl)-1,5-dihydro-4H-pyrazolo[4,3-c]pyridin-4-one |
| 259 | 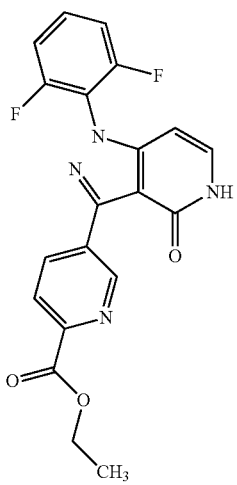 [SMILES: CCOC(=O)c1ccc(C(=N)c2c(Nc3c(F)cccc3F)cc[nH]c2=O)cn1] | ethyl 5-(1-(2,6-difluorophenyl)-4-oxo-4,5-dihydro-1H-pyrazolo[4,3-c]pyridin-3-yl)pyridine-2-carboxylate |

TABLE 3-1-continued

| Ex. | Structural Formula | Compound Name |
|---|---|---|
| 260 | 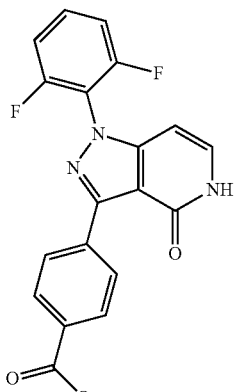 | methyl 4-(1-(2,6-difluorophenyl)-4-oxo-4,5-dihydro-1H-pyrazolo[4,3-c]pyridin-3-yl)benzoate |
| 261 | 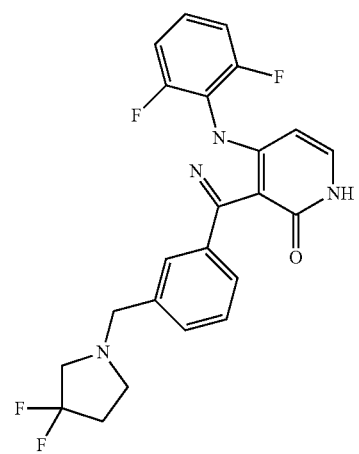 [SMILES: N=C(c1cccc(CN2CCC(F)(F)C2)c1)c1c(Nc2c(F)cccc2F)cc[nH]c1=O] | 1-(2,6-difluorophenyl)-3-(3-((3,3-difluoropyrrolidin-1-yl)methyl)phenyl)-1,5-dihydro-4H-pyrazolo[4,3-c]pyridin-4-one |
| 262 | 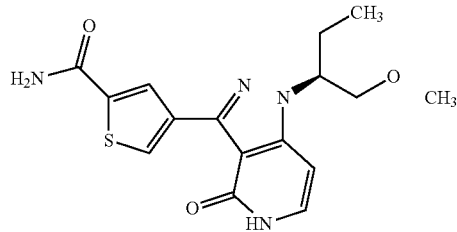 | 4-(1-((2S)-1-methoxybutan-2-yl)-4-oxo-4,5-dihydro-1H-pyrazolo[4,3-c]pyridin-3-yl)thiophene-2-carboxamide |
| 263 | 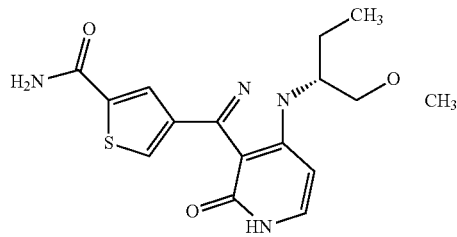 | 4-(1-((2R)-1-methoxybutan-2-yl)-4-oxo-4,5-dihydro-1H-pyrazolo[4,3-c]pyridin-3-yl)thiophene-2-carboxamide |
| 264 | 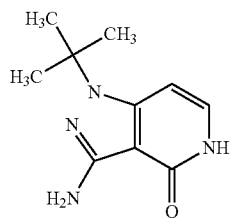 | 3-amino-1-tert-butyl-1,5-dihydro-4H-pyrazolo[4,3-c]pyridin-4-one |

TABLE 3-1-continued
| Ex. | Structural Formula | Compound Name |
|---|---|---|
| 265 | 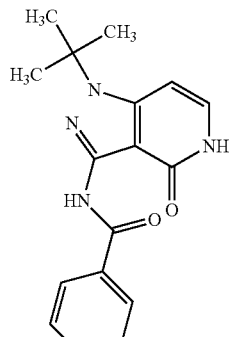 | N-(1-tert-butyl-4-oxo-4,5-dihydro-1H-pyrazolo[4,3-c]pyridin-3-yl)benzamide |
| 266 | 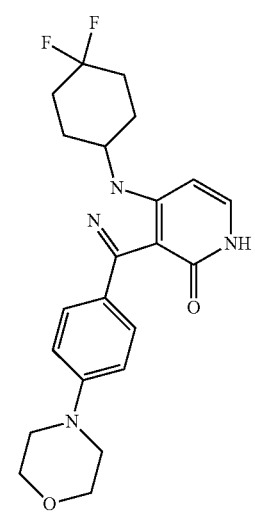 [SMILES: N=C(c1ccc(N2CCOCC2)cc1)c1c(NC2CCC(F)(F)CC2)cc[nH]c1=O] | 1-(4,4-difluorocyclohexyl)-3-(4-(morpholin-4-yl)phenyl)-1,5-dihydro-4H-pyrazolo[4,3-c]pyridin-4-one |
| 267 | 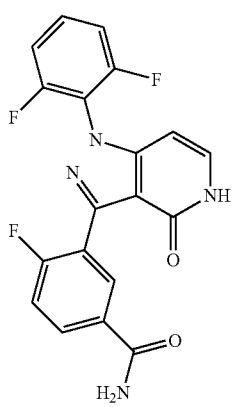 [SMILES: N=C(c1cc(C(N)=O)ccc1F)c1c(Nc2c(F)cccc2F)cc[nH]c1=O] | 3-(1-(2,6-difluorophenyl)-4-oxo-4,5-dihydro-1H-pyrazolo[4,3-c]pyridin-3-yl)-4-fluorobenzamide |

TABLE 3-1-continued
| Ex. | Structural Formula | Compound Name |
|---|---|---|
| 268 | 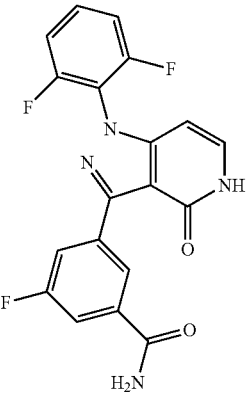 [SMILES: N=C(c1cc(F)cc(C(N)=O)c1)c1c(Nc2c(F)cccc2F)cc[nH]c1=O] | 3-(1-(2,6-difluorophenyl)-4-oxo-4,5-dihydro-1H-pyrazolo[4,3-c]pyridin-3-yl)-5-fluorobenzamide |
| 269 | 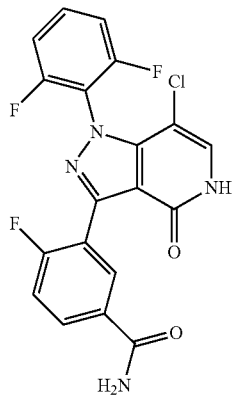 [SMILES: NC(=O)c1ccc(F)c(-c2nn(-c3c(F)cccc3F)c3c(Cl)c[nH]c(=O)c23)c1] | 3-(7-chloro-1-(2,6-difluorophenyl)-4-oxo-4,5-dihydro-1H-pyrazolo[4,3-c]pyridin-3-yl)-4-fluorobenzamide |
| 270 | 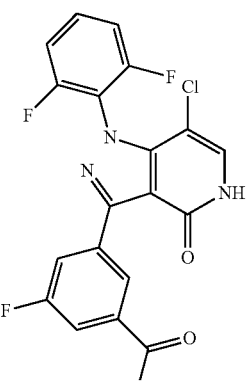 | 3-(7-chloro-1-(2,6-difluorophenyl)-4-oxo-4,5-dihydro-1H-pyrazolo[4,3-c]pyridin-3-yl)-5-fluorobenzamide |

TABLE 3-1-continued

| Ex. | Structural Formula | Compound Name |
|---|---|---|
| 271 | | 3-(7-chloro-1-(2,6-difluorophenyl)-4-oxo-4,5-dihydro-1H-pyrazolo[4,3-c]pyridin-3-yl)-4-fluoro-N-methylbenzamide |
| 272 | | 3-(1-(2,6-difluorophenyl)-4-oxo-4,5-dihydro-1H-pyrazolo[4,3-c]pyridin-3-yl)-4-fluoro-N-methylbenzamide |
| 273 | | 3-(7-chloro-1-(2,6-difluorophenyl)-4-oxo-4,5-dihydro-1H-pyrazolo[4,3-c]pyridin-3-yl)-5-fluoro-N-methylbenzamide |

TABLE 3-1-continued
| Ex. | Structural Formula | Compound Name |
|---|---|---|
| 274 | 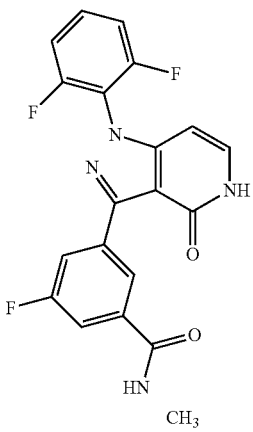 | 3-(1-(2,6-difluorophenyl)-4-oxo-4,5-dihydro-1H-pyrazolo[4,3-c]pyridin-3-yl)-5-fluoro-N-methylbenzamide |
| 275 | 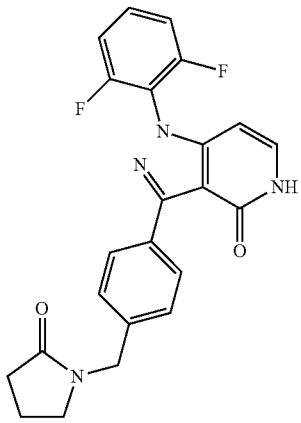 [SMILES: N=C(c1ccc(CN2CCCC2=O)cc1)c1c(Nc2c(F)cccc2F)cc[nH]c1=O] | 1-(2,6-difluorophenyl)-3-(4-((2-oxopyrrolidin-1-yl)methyl)phenyl)-1,5-dihydro-4H-pyrazolo[4,3-c]pyridin-4-one |
| 276 | 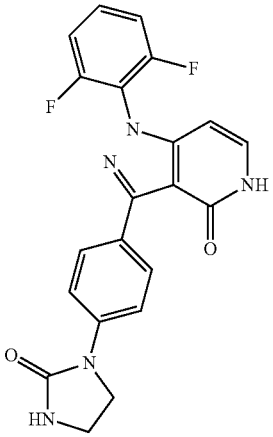 [SMILES: N=C(c1ccc(N2CCNC2=O)cc1)c1c(Nc2c(F)cccc2F)cc[nH]c1=O] | 1-(2,6-difluorophenyl)-3-(4-(2-oxoimidazolidin-1-yl)phenyl)-1,5-dihydro-4H-pyrazolo[4,3-c]pyridin-4-one |

TABLE 3-1-continued

| Ex. | Structural Formula | Compound Name |
|---|---|---|
| 277 | | N-(4-(1-(2,6-difluorophenyl)-4-oxo-4,5-dihydro-1H-pyrazolo[4,3-c]pyridin-3-yl)phenyl)acetamide |
| 278 | | 1-(2,6-difluorophenyl)-3-(3-(hydroxymethyl)phenyl)-1,5-dihydro-4H-pyrazolo[4,3-c]pyridin-4-one- |
| 279 | | 3-(4-(4-acetylpiperazin-1-yl)phenyl)-1-(2,6-difluorophenyl)-1,5-dihydro-4H-pyrazolo[4,3-c]pyridin-4-one |

TABLE 3-1-continued

| Ex. | Structural Formula | Compound Name |
|---|---|---|
| 280 | | 4-(7-bromo-1-cyclopentyl-4-oxo-4,5-dihydro-1H-pyrazolo[4,3-c]pyridin-3-yl)thiophene-2-carboxamide |
| 281 | | 4-(1-cyclopentyl-7-methyl-4-oxo-4,5-dihydro-1H-pyrazolo[4,3-c]pyridin-3-yl)thiophene-2-carboxamide |
| 282 | | 4-(1-cyclopentyl-7-cyclopropyl-4-oxo-4,5-dihydro-1H-pyrazolo[4,3-c]pyridin-3-yl)thiophene-2-carboxamide |
| 283 | | 3-anilino-1-cyclopentyl-1,5-dihydro-4H-pyrazolo[4,3-c]pyridin-4-one |

TABLE 3-1-continued

| Ex. | Structural Formula | Compound Name |
|---|---|---|
| 284 | | 3-((1-cyclopentyl-4-oxo-4,5-dihydro-1H-pyrazolo[4,3-c]pyridin-3-yl)amino)benzenesulfonamide |
| 285 | | 3-((7-bromo-1-cyclopentyl-4-oxo-4,5-dihydro-1H-pyrazolo[4,3-c]pyridin-3-yl)amino)benzenesulfonamide |
| 286 | | 4-(1-cyclopentyl-4-oxo-4,5-dihydro-1H-pyrazolo[4,3-c]pyridin-3-yl)-N,N-dimethylthiophene-2-carboxamide |
| 287 | | 1-(2,6-difluorophenyl)-3-(3-((3,3-difluoropyrrolidin-1-yl)methyl)phenyl)-1,5-dihydro-4H-pyrazolo[4,3-c]pyridin-4-one hydrochloride |

TABLE 3-1-continued
| Ex. | Structural Formula | Compound Name |
|---|---|---|
| 288 | 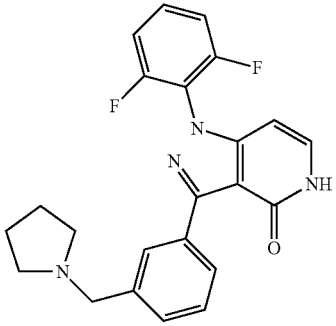 [SMILES: N=C(c1cccc(CN2CCCC2)c1)c1c(Nc2c(F)cccc2F)cc[nH]c1=O] | 1-(2,6-difluorophenyl)-3-(3-(pyrrolidin-1-ylmethyl)phenyl)-1,5-dihydro-4H-pyrazolo[4,3-c]pyridin-4-one |
| 289 | 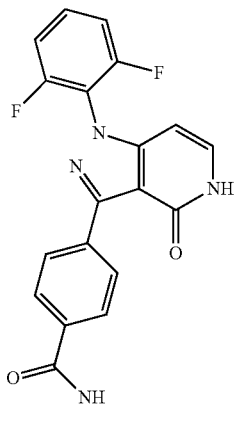 | 4-(1-(2,6-difluorophenyl)-4-oxo-4,5-dihydro-1H-pyrazolo[4,3-c]pyridin-3-yl)-N',N'-dimethylbenzhydrazide |
| 290 | 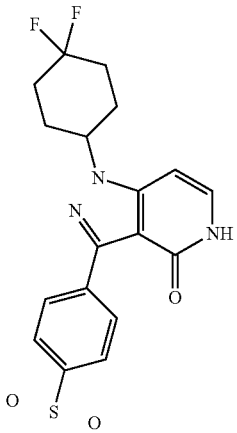 | 4-(1-(4,4-difluorocyclohexyl)-4-oxo-4,5-dihydro-1H-pyrazolo[4,3-c]pyridin-3-yl)benzenesulfonamide |

TABLE 3-1-continued
| Ex. | Structural Formula | Compound Name |
|---|---|---|
| 291 | 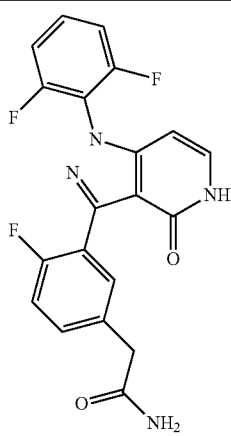 | 2-(3-(1-(2,6-difluorophenyl)-4-oxo-4,5-dihydro-1H-pyrazolo[4,3-c]pyridin-3-yl)-4-fluorophenyl)acetamide |
| 292 | 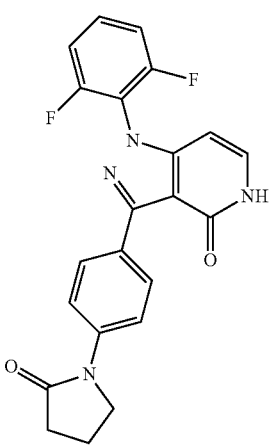 [SMILES: N=C(c1ccc(N2CCCC2=O)cc1)c1c(Nc2c(F)cccc2F)cc[nH]c1=O] | 1-(2,6-difluorophenyl)-3-(4-(2-oxopyrrolidin-1-yl)phenyl)-1,5-dihydro-4H-pyrazolo[4,3-c]pyridin-4-one |
| 293 | 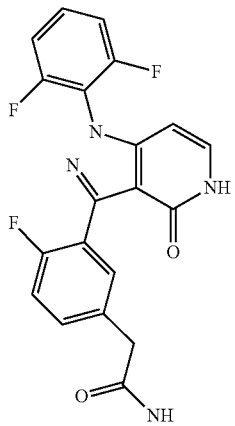 | 2-(3-(1-(2,6-difluorophenyl)-4-oxo-4,5-dihydro-1H-pyrazolo[4,3-c]pyridin-3-yl)-4-fluorophenyl)-N-methylacetamide |

| Ex. | Structural Formula | Compound Name |
|---|---|---|
| 294 | 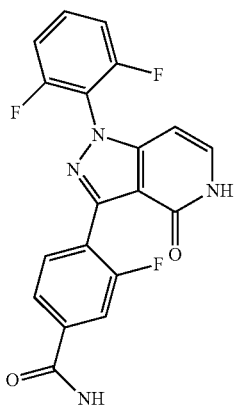 | 4-(1-(2,6-difluorophenyl)-4-oxo-4,5-dihydro-1H-pyrazolo[4,3-c]pyridin-3-yl)-3-fluoro-N-methylbenzamide |
| 295 | 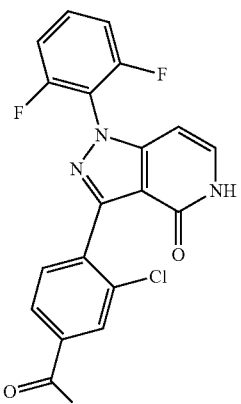 | 3-chloro-4-(1-(2,6-difluorophenyl)-4-oxo-4,5-dihydro-1H-pyrazolo[4,3-c]pyridin-3-yl)-N-methylbenzamide |
| 296 | 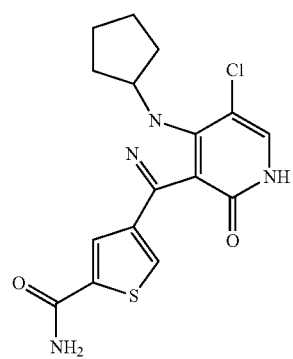 [SMILES: N=C(c1csc(C(N)=O)c1)c1c(NC2CCCC2)c(Cl)c[nH]c1=O] | 4-(7-chloro-1-cyclopentyl-4-oxo-4,5-dihydro-1H-pyrazolo[4,3-c]pyridin-3-yl)thiophene-2-carboxamide |

| Ex. | Structural Formula | Compound Name |
|---|---|---|
| 297 | | 4-((1-cyclopentyl-4-oxo-4,5-dihydro-1H-pyrazolo[4,3-c]pyridin-3-yl)amino)benzenesulfonamide |
| 298 | | 4-(1-(cis-4-aminocyclohexyl)-4-oxo-4,5-dihydro-1H-pyrazolo[4,3-c]pyridin-3-yl)thiophene-2-carboxamide |
| 299 | | 4-(1-(trans-4-aminocyclohexyl)-4-oxo-4,5-dihydro-1H-pyrazolo[4,3-c]pyridin-3-yl)thiophene-2-carboxamide |

TABLE 3-1-continued
| Ex. | Structural Formula | Compound Name |
|---|---|---|
| 300 | 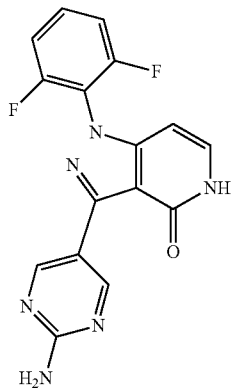 [SMILES: N=C(c1cnc(N)nc1)c1c(Nc2c(F)cccc2F)cc[nH]c1=O] | 3-(2-aminopyrimidin-5-yl)-1-(2,6-difluorophenyl)-1,5-dihydro-4H-pyrazolo[4,3-c]pyridin-4-one |
| 301 | 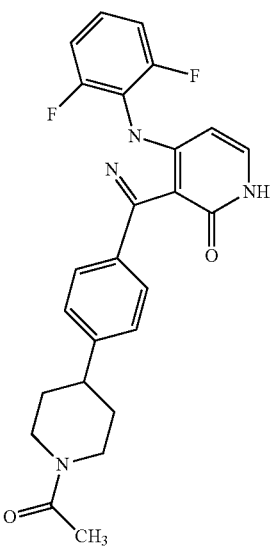 [SMILES: CC(=O)N1CCC(c2ccc(C(=N)c3c(Nc4c(F)cccc4F)cc[nH]c3=O)cc2)CC1] | 3-(4-(1-acetylpiperidin-4-yl)phenyl)-1-(2,6-difluorophenyl)-1,5-dihydro-4H-pyrazolo[4,3-c]pyridin-4-one |
| 302 | 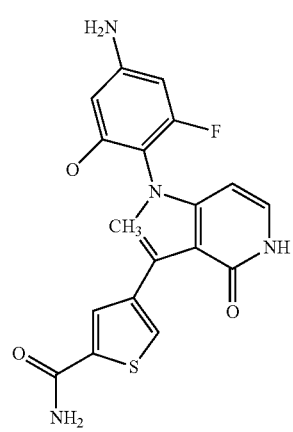 [SMILES: NC(=O)c1cc(-c2cn(-c3c(O)cc(N)cc3F)c3cc[nH]c(=O)c23)cs1] | 4-(1-(4-amino-2-fluoro-6-methoxyphenyl)-4-oxo-4,5-dihydro-1H-pyrrolo[3,2-c]pyridin-3-yl)thiophene-2-carboxamide |

TABLE 3-1-continued
| Ex. | Structural Formula | Compound Name |
|---|---|---|
| 303 | 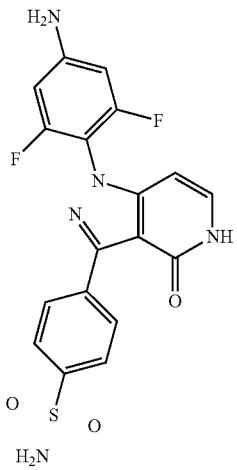 | 4-(1-(4-amino-2,6-difluorophenyl)-4-oxo-4,5-dihydro-1H-pyrazolo[4,3-c]pyridin-3-yl)benzenesulfonamide |
| 304 | 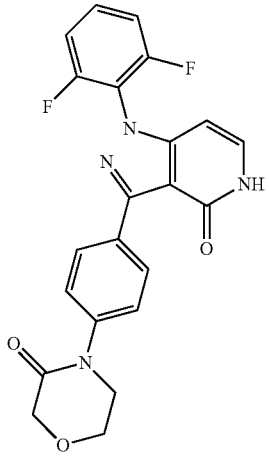 [SMILES: N=C(c1ccc(N2CCOCC2=O)cc1)c1c(Nc2c(F)cccc2F)cc[nH]c1=O] | 1-(2,6-difluorophenyl)-3-(4-(3-oxomorpholin-4-yl)phenyl)-1,5-dihydro-4H-pyrazolo[4,3-c]pyridin-4-one |
| 305 | 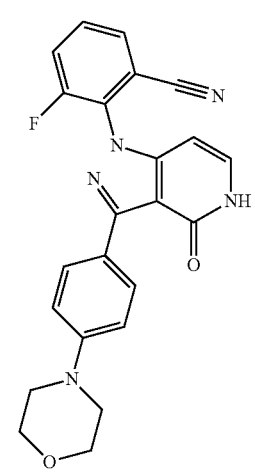 [SMILES: N#Cc1cccc(F)c1Nc1cc[nH]c(=O)c1C(=N)c1ccc(N2CCOCC2)cc1] | 3-fluoro-2-(3-(4-(morpholin-4-yl)phenyl)-4-oxo-4,5-dihydro-1H-pyrazolo[4,3-c]pyridin-1-yl)benzonitrile |

TABLE 3-1-continued
| Ex. | Structural Formula | Compound Name |
|---|---|---|
| 306 | 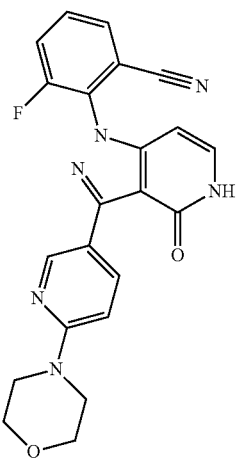 [SMILES: N#Cc1cccc(F)c1Nc1cc[nH]c(=O)c1C(=N)c1ccc(N2CCOCC2)nc1] | 3-fluoro-2-(3-(6-(morpholin-4-yl)pyridin-3-yl)-4-oxo-4,5-dihydro-1H-pyrazolo[4,3-c]pyridin-1-yl)benzonitrile |
| 307 | 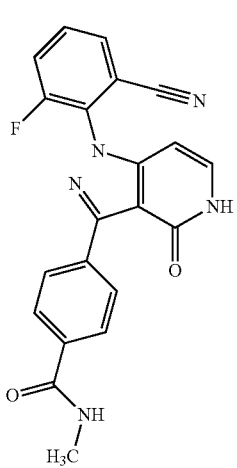 [SMILES: CNC(=O)c1ccc(C(=N)c2c(Nc3c(F)cccc3C#N)cc[nH]c2=O)cc1] | 4-(1-(2-cyano-6-fluorophenyl)-4-oxo-4,5-dihydro-1H-pyrazolo[4,3-c]pyridin-3-yl)-N-methylbenzamide |
| 308 | 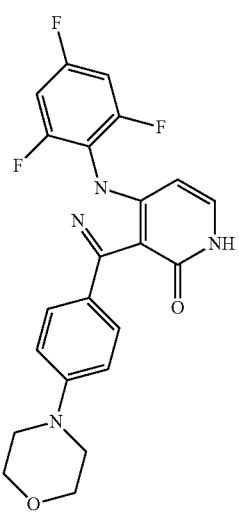 [SMILES: N=C(c1ccc(N2CCOCC2)cc1)c1c(Nc2c(F)cc(F)cc2F)cc[nH]c1=O] | 3-(4-(morpholin-4-yl)phenyl)-1-(2,4,6-trifluorophenyl)-1,5-dihydro-4H-pyrazolo[4,3-c]pyridin-4-one |

TABLE 3-1-continued
| Ex. | Structural Formula | Compound Name |
|---|---|---|
| 309 | 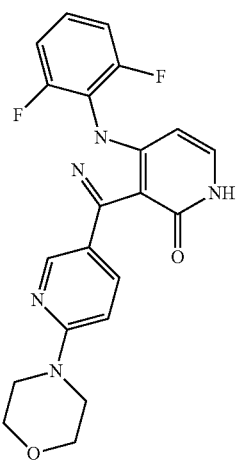 [SMILES: N=C(c1ccc(N2CCOCC2)nc1)c1c(Nc2c(F)cccc2F)cc[nH]c1=O] | 1-(2,6-difluorophenyl)-3-(6-(morpholin-4-yl)pyridin-3-yl)-1,5-dihydro-4H-pyrazolo[4,3-c]pyridin-4-one |
| 310 | 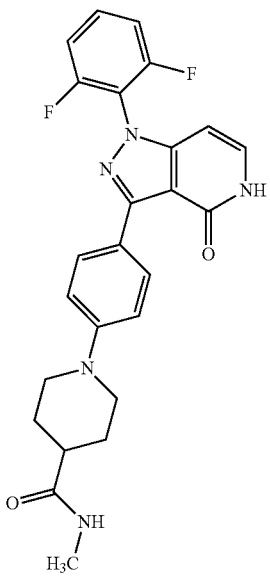 [SMILES: CNC(=O)C1CCN(c2ccc(-c3nn(-c4c(F)cccc4F)c4cc[nH]c(=O)c34)cc2)CC1] | 1-(4-(1-(2,6-difluorophenyl)-4-oxo-4,5-dihydro-1H-pyrazolo[4,3-c]pyridin-3-yl)phenyl)-N-methylpiperidine-4-carboxamide |
| 311 | 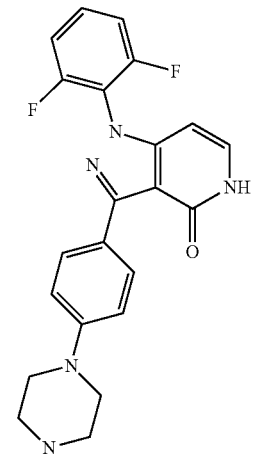 | 1-(2,6-difluorophenyl)-3-(4-(4-(methylsulfonyl)piperazin-1-yl)phenyl)-1,5-dihydro-4H-pyrazolo[4,3-c]pyridin-4-one |

TABLE 3-1-continued
| Ex. | Structural Formula | Compound Name |
|---|---|---|
| 312 | 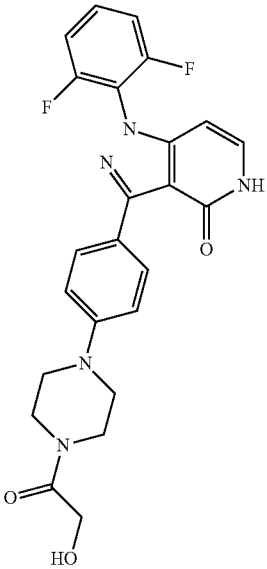 [SMILES: N=C(c1ccc(N2CCN(C(=O)CO)CC2)cc1)c1c(Nc2c(F)cccc2F)cc[nH]c1=O] | 1-(2,6-difluorophenyl)-3-(4-(4-glycoloylpiperazin-1-yl)phenyl)-1,5-dihydro-4H-pyrazolo[4,3-c]pyridin-4-one |
| 313 | 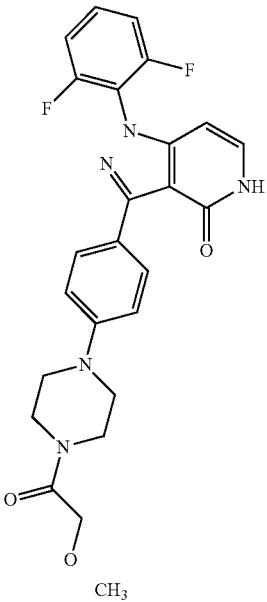 | 1-(2,6-difluorophenyl)-3-(4-(4-(methoxyacetyl)piperazin-1-yl)phenyl)-1,5-dihydro-4H-pyrazolo[4,3-c]pyridin-4-one |
| 314 | 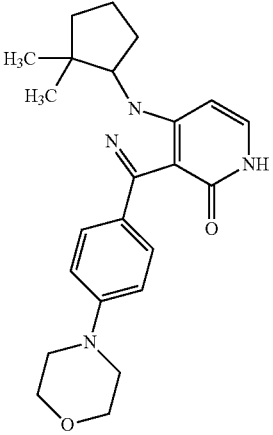 [SMILES: CC1(C)CCCC1Nc1cc[nH]c(=O)c1C(=N)c1ccc(N2CCOCC2)cc1] | 1-(2,2-dimethylcyclopentyl)-3-(4-(morpholin-4-yl)phenyl)-1,5-dihydro-4H-pyrazolo[4,3-c]pyridin-4-one |

TABLE 3-1-continued

| Ex. | Structural Formula | Compound Name |
|---|---|---|
| 315 | | 3-fluoro-2-(4-oxo-3-(1H-pyrazol-4-yl)-4,5-dihydro-1H-pyrazolo[4,3-c]pyridin-1-yl)benzonitrile |
| 316 | | 3-(4-(1-acetyl-3,3-difluoropiperidin-4-yl)phenyl)-1-(2,6-difluorophenyl)-1,5-dihydro-4H-pyrazolo[4,3-c]pyridin-4-one |
| 317 | | 1-(2,2-difluorocyclohexyl)-3-(4-(morpholin-4-yl)phenyl)-1,5-dihydro-4H-pyrazolo[4,3-c]pyridin-4-one |

Formulation Example 1

Production of Capsule

| 1) compound of Example 1 | 30 mg |
|---|---|
| 2) fine powder cellulose | 10 mg |
| 3) lactose | 19 mg |
| 4) magnesium stearate | 1 mg |
| Total | 60 mg |

1), 2), 3) and 4) are mixed and filled in a gelatin capsule.

Formulation Example 2

Production of Tablet

| 1) compound of Example 1 | 30 g |
|---|---|
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amounts of 1), 2) and 3) and 4) (30 g) are kneaded with water, and the mixture is vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

Experimental Example 1

JAK1 Enzyme Inhibition Test

JAK1 enzyme inhibitory activity of test compounds was measured by LANCE method (PerkinElmer). First, a test compound diluted with assay buffer (50 mM HEPES (pH=7.5), 10 mM $MgCl_2$, 1 mM EGTA, 2 mM DTT, 0.01% Tween20, 0.01% BSA) was added to 384-well plate at 2 μL each. Then, a JAK1 (Invitrogen) solution and a fluorescence-labeled peptide substrate (ULight-JAK1, PerkinElmer) solution diluted with assay buffer at 187.5 ng/mL and 300 nM, respectively were added at 2 μL each. Then, enzyme reaction was started by adding 2 μL each of ATP solution prepared with assay buffer at 150 μM. After the reaction at room temperature for 1 hr, Detection Buffer (PerkinElmer) prepared to be 20 mM EDTA, 4 nM europium-labeled anti-phosphotyrosine antibody (PerkinElmer) was added at 6 μL each. After standing at room temperature for 1 hr, fluorescence intensity (excitation wavelength 340 nm, fluorescence wavelength 665 nm, delay time 100 microsecond) was measured by a plate reader, Envision (PerkinElmer). The inhibitory activity of each compound was calculated as relative value where fluorescence intensity of a well without enzyme is considered as 100% inhibition. The results are shown in Table 4.

Experimental Example 2

Tyk2 Enzyme Inhibition Test

Tyk2 enzyme inhibitory activity of test compounds was measured by LANCE method (PerkinElmer). First, a test compound diluted with assay buffer (50 mM HEPES (pH=7.5), 10 mM $MgCl_2$, 1 mM EGTA, 2 mM DTT, 0.01% Tween20, 0.01% BSA) was added to 384-well plate at 2 μL each. Then, a Tyk2 (Invitrogen) solution and a fluorescence-labeled peptide substrate (ULight-JAK1, PerkinElmer) solution diluted with assay buffer at 375 ng/mL and 300 nM, respectively were added at 2 μL each. Then, enzyme reaction was started by adding 2 μL each of ATP solution prepared with assay buffer at 30 μM. After the reaction at room temperature for 1 hr, Detection Buffer (PerkinElmer) prepared to be 20 mM EDTA, 4 nM europium-labeled anti-phosphotyrosine antibody (PerkinElmer) was added at 6 μL each. After standing at room temperature for 1 hr, fluorescence intensity (excitation wavelength 340 nm, fluorescence wavelength 665 nm, delay time 100 microsecond) was measured by a plate reader, Envision (PerkinElmer). The inhibitory activity of each compound was calculated as relative value where fluorescence intensity of a well without enzyme is considered as 100% inhibition. The results are shown in Table 4.

TABLE 4

| | Inhibitory rate (%) | |
|---|---|---|
| Ex. No. | JAK1 10 μM | Tyk2 10 μM |
| 10 | | 38 |
| 19 | 44 | 27 |
| 41 | 38 | 49 |
| 53 | 10 | 28 |
| 90 | 38 | 22 |
| | Inhibitory rate (%) | |
| Ex. No. | JAK1 1 μM | Tyk2 1 μM |
| 1 | 40 | 51 |
| 2 | 99 | 97 |
| 3 | 97 | 96 |
| 4 | 99 | 99 |
| 5 | 97 | 96 |
| 6 | 98 | 99 |
| 7 | 95 | 90 |
| 8 | 98 | 98 |
| | Inhibitory rate (%) | |
| Ex. No. | JAK1 1 μM | Tyk2 1 μM |
| 9 | 97 | 93 |
| 11 | 55 | 66 |
| 12 | 98 | 98 |
| 13 | 99 | 99 |
| 14 | 99 | 98 |
| 15 | 99 | 97 |
| 16 | 93 | 88 |
| 17 | 87 | 69 |
| 18 | 93 | 80 |
| 20 | 59 | 35 |
| 21 | 97 | 95 |
| 22 | 77 | 53 |
| 23 | 98 | 98 |
| 24 | 35 | 33 |
| 25 | 77 | 71 |
| 26 | 20 | 41 |
| 27 | 98 | 98 |
| 28 | 99 | 97 |
| 29 | 14 | 83 |
| 30 | 94 | 92 |
| 31 | 95 | 90 |
| 32 | 98 | 95 |
| 33 | 99 | 99 |
| 34 | 92 | 99 |
| 35 | 99 | 97 |
| 36 | 97 | 98 |
| 37 | 99 | 99 |
| 38 | 100 | 99 |
| 39 | 99 | 98 |
| 40 | 78 | 78 |

TABLE 4-continued

| Ex. No. | JAK1 1 μM | Tyk2 1 μM |
|---|---|---|
| 42 | 53 | 51 |
| 43 | 87 | 91 |
| 44 | 94 | 91 |
| 45 | 90 | 74 |
| 46 | 91 | 95 |
| 47 | 62 | 71 |

Inhibitory rate (%)

| Ex. No. | JAK1 1 μM | Tyk2 1 μM |
|---|---|---|
| 48 | 3 | 7 |
| 49 | 85 | 89 |
| 50 | 92 | 92 |
| 51 | 90 | 84 |
| 52 | 43 | 46 |
| 54 | 91 | 91 |
| 55 | 78 | 85 |
| 56 | 13 | 31 |
| 57 | 88 | 81 |
| 58 | 86 | 91 |
| 59 | 66 | 56 |
| 60 | 50 | 89 |
| 61 | 8 | 41 |
| 62 | 69 | 81 |
| 63 | 59 | 51 |
| 65 | 27 | 76 |
| 66 | 66 | 92 |
| 67 | 55 | 91 |
| 68 | 4 | 67 |
| 69 | 28 | 92 |
| 70 | 41 | 88 |
| 71 | 99 | 97 |
| 72 | 97 | 99 |
| 73 | 45 | 83 |
| 74 | 44 | 85 |
| 75 | 93 | 84 |
| 76 | 92 | 99 |
| 77 | 96 | 99 |
| 78 | 23 | 75 |
| 79 | 44 | 93 |
| 80 | 82 | 97 |
| 81 | 62 | 97 |
| 82 | 95 | 78 |
| 83 | 97 | 89 |
| 84 | 84 | 58 |
| 85 | 90 | 100 |

Inhibitor rate (%)

| Ex. No. | JAK1 1 μM | Tyk2 1 μM |
|---|---|---|
| 86 | 94 | 85 |
| 87 | 99 | 96 |
| 88 | 96 | 91 |
| 89 | 64 | 94 |
| 91 | 19 | 92 |
| 92 | 100 | 99 |
| 93 | 98 | 99 |
| 94 | 80 | 78 |
| 95 | 86 | 98 |
| 96 | 94 | 99 |
| 97 | 97 | 99 |
| 98 | 78 | 97 |
| 99 | 97 | 99 |
| 100 | 96 | 77 |
| 101 | 80 | 91 |
| 102 | 67 | 94 |
| 103 | 48 | 91 |
| 104 | 94 | 99 |
| 105 | 88 | 66 |
| 106 | 91 | 98 |
| 107 | 96 | 98 |
| 108 | 99 | 100 |
| 109 | 61 | 94 |
| 110 | 46 | 91 |
| 111 | 96 | 99 |
| 112 | 89 | 98 |
| 115 | 87 | 66 |
| 116 | 89 | 99 |
| 117 | 99 | 98 |
| 118 | 94 | 99 |

TABLE 4-continued

| Ex. No. | JAK1 1 μM | Tyk2 1 μM |
|---|---|---|
| 119 | 100 | 99 |
| 120 | 88 | 98 |
| 121 | 87 | 97 |
| 122 | 99 | 100 |
| 123 | 99 | 99 |
| 124 | 89 | 98 |

Inhibitory rate (%)

| Ex. No. | JAK1 1 μM | Tyk2 1 μM |
|---|---|---|
| 125 | 80 | 96 |
| 126 | 99 | 98 |
| 127 | 99 | 97 |
| 128 | 93 | 93 |
| 129 | 98 | 97 |
| 130 | 76 | 96 |
| 131 | 97 | 99 |
| 132 | 27 | 74 |
| 133 | 47 | 90 |
| 134 | 78 | 97 |
| 135 | 56 | 97 |
| 136 | 59 | 93 |
| 137 | 77 | 98 |
| 138 | 94 | 99 |
| 139 | 96 | 98 |
| 140 | 17 | 91 |
| 141 | 99 | 92 |
| 142 | 96 | 97 |
| 143 | 93 | 92 |
| 144 | 99 | 95 |
| 145 | 99 | 100 |
| 146 | 69 | 98 |
| 147 | 74 | 99 |
| 148 | 99 | 98 |
| 149 | 100 | 99 |
| 150 | 99 | 98 |
| 151 | 98 | 98 |
| 152 | 97 | 99 |
| 153 | 89 | 100 |
| 154 | 90 | 99 |
| 155 | 100 | 99 |
| 156 | 100 | 100 |
| 157 | 100 | 99 |
| 158 | 91 | 91 |
| 159 | 91 | 87 |
| 160 | 98 | 98 |

Inhibitory rate (%)

| Ex. No. | JAK1 1 μM | Tyk2 1 μM |
|---|---|---|
| 161 | 79 | 99 |
| 162 | 99 | 99 |
| 163 | 98 | 100 |
| 164 | 66 | 99 |
| 165 | 96 | 98 |
| 166 | 98 | 100 |
| 167 | 53 | 97 |
| 168 | 46 | 97 |
| 169 | 79 | 99 |
| 170 | 99 | 98 |
| 171 | 100 | 100 |
| 172 | 99 | 97 |
| 173 | 99 | 96 |
| 174 | 99 | 98 |
| 175 | 86 | 100 |
| 176 | 95 | 100 |
| 177 | 91 | 100 |
| 178 | 93 | 99 |
| 179 | 94 | 100 |
| 180 | 92 | 101 |

Inhibitory rate (%)

| Ex. No. | JAK1 10 μM | Tyk2 10 μM |
|---|---|---|
| 208 | 28 | 83 |
| 249 | 30 | 25 |
| 264 | 44 | 12 |
| 265 | 21 | 24 |
| 267 | 17 | 31 |
| 269 | 24 | 29 |

TABLE 4-continued

| | Inhibitory rate (%) | |
|---|---|---|
| | JAK1 10 μM | Tyk2 1 μM |
| 271 | −1 | 26 |
| 272 | 12 | 25 |
| 293 | 0 | 22 |
| 295 | 24 | 80 |
| 298 | 81 | 58 |
| 182 | 98 | 98 |
| 183 | 100 | 100 |
| 184 | 100 | 99 |
| 185 | 72 | 99 |
| 186 | 82 | 99 |
| 187 | 83 | 98 |
| 188 | 84 | 100 |
| 189 | 92 | 100 |
| 190 | 81 | 99 |
| 191 | 98 | 100 |
| 192 | 94 | 99 |
| 193 | 99 | 100 |
| 194 | 67 | 100 |
| 195 | 79 | 100 |
| 196 | 100 | 100 |
| 197 | 99 | 98 |
| 198 | 100 | 100 |
| 199 | 99 | 100 |
| 200 | 22 | 98 |
| 201 | 96 | 97 |
| 202 | 80 | 87 |
| 203 | 81 | 100 |
| 204 | 98 | 98 |
| 205 | 34 | 97 |
| 206 | 45 | 100 |
| 207 | 73 | 100 |
| 209 | 99 | 99 |
| 210 | 99 | 97 |
| 211 | 99 | 98 |
| 212 | 99 | 96 |
| 213 | 98 | 99 |
| 214 | 99 | 99 |
| 215 | 22 | 94 |
| 216 | 27 | 97 |
| 217 | 74 | 99 |
| 218 | 85 | 99 |
| 219 | 82 | 98 |
| 220 | 98 | 100 |

| | Inhibitory rate (%) | |
|---|---|---|
| | JAK1 1 μM | Tyk2 1 μM |
| 221 | 80 | 99 |
| 222 | 69 | 98 |
| 223 | 99 | 97 |
| 224 | 78 | 99 |
| 225 | 58 | 99 |
| 226 | 40 | 98 |
| 227 | 54 | 97 |
| 228 | 85 | 99 |
| 229 | 81 | 98 |
| 230 | 92 | 99 |
| 231 | 51 | 99 |
| 232 | 60 | 100 |
| 233 | 79 | 99 |
| 234 | 99 | 99 |
| 235 | 92 | 99 |
| 236 | 65 | 99 |
| 237 | 87 | 99 |
| 238 | 72 | 91 |
| 239 | 46 | 99 |
| 240 | 88 | 99 |
| 241 | 53 | 98 |
| 242 | 27 | 97 |
| 243 | 52 | 76 |
| 244 | 89 | 97 |
| 245 | 96 | 100 |
| 246 | 94 | 99 |
| 247 | 86 | 88 |
| 248 | 96 | 70 |
| 250 | 93 | 69 |
| 251 | 96 | 99 |
| 252 | 91 | 98 |
| 253 | 87 | 98 |
| 254 | 65 | 98 |
| 255 | 93 | 98 |
| 256 | 92 | 98 |
| 257 | 96 | 98 |
| 258 | 43 | 88 |
| 259 | 59 | 81 |

| | Inhibitory rate (%) | |
|---|---|---|
| | JAK1 1 μM | Tyk2 1 μM |
| 260 | 77 | 94 |
| 261 | 41 | 94 |
| 262 | 97 | 92 |
| 263 | 97 | 90 |
| 266 | 85 | 91 |
| 268 | 4 | 33 |
| 270 | 0 | 69 |
| 273 | 1 | 71 |
| 274 | 34 | 77 |
| 275 | 96 | 98 |
| 276 | 91 | 99 |
| 277 | 95 | 99 |
| 278 | 92 | 98 |
| 279 | 96 | 99 |
| 280 | 94 | 97 |
| 281 | 96 | 96 |
| 282 | 76 | 85 |
| 283 | 98 | 93 |
| 284 | 99 | 96 |
| 285 | 70 | 82 |
| 286 | 98 | 97 |
| 288 | 55 | 94 |
| 289 | 92 | 99 |
| 290 | 98 | 95 |
| 292 | 97 | 99 |
| 294 | 35 | 92 |
| 296 | 90 | 96 |
| 297 | 98 | 99 |
| 299 | 99 | 99 |
| 300 | 68 | 83 |
| 301 | 97 | 99 |
| 302 | 97 | 95 |
| 303 | 99 | 100 |
| 304 | 97 | 99 |
| 305 | 93 | 99 |
| 306 | 90 | 98 |
| 307 | 92 | 99 |
| 308 | 91 | 98 |

| | Inhibitory rate (%) | |
|---|---|---|
| | JAK1 1 μM | Tyk2 1 μM |
| 309 | 93 | 99 |
| 310 | 93 | 100 |
| 311 | 95 | 99 |
| 312 | 94 | 99 |
| 313 | 95 | 100 |
| 314 | 95 | 99 |
| 315 | 97 | 98 |
| 316 | 99 | 99 |
| 317 | 96 | 99 |

INDUSTRIAL APPLICABILITY

The compound of the present invention has a superior JAK inhibitory action, and is useful as an agent for the treatment of autoimmune disease (rheumatoid arthritis, psoriasis, inflammatory bowel disease, Sjogren's syndrome, Behcet's disease, multiple sclerosis, systemic lupus erythematosus, etc.), cancer (leukemia, uterine leiomyosarcoma, prostate cancer, multiple myeloma, cachexia, myelofibrosis, etc.) and the like.

This application is based on patent application No. 2012-126462 filed in Japan, the contents of which are encompassed in full herein.

The invention claimed is:
1. A compound of formula (I):

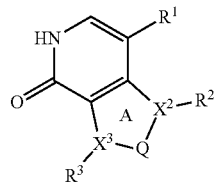

wherein
Ring A is a nitrogen-containing aromatic heterocycle wherein
Q is a nitrogen atom,
$X^2$ is a nitrogen atom, and
$X^3$ is a carbon atom;
$R^1$ is selected from the group consisting of
(1) a hydrogen atom,
(2) a halogen atom,
(3) a cyano group,
(4) a carboxy group,
(5) a $C_{1-6}$ alkyl-carbonyl group,
(6) a $C_{1-6}$ alkoxy-carbonyl group,
(7) a carbamoyl group optionally mono- or di-substituted by $C_{1-6}$ alkyl group(s),
(8) a $C_{1-6}$ alkyl group optionally substituted by 1 to 3 hydroxy groups, and
(9) a $C_{3-6}$ cycloalkyl group;
$R^2$ is selected from the group consisting of
(1) a $C_{1-2}$ alkyl group substituted by 1 to 3 substituents selected from the group consisting of
  (a) a $C_{6-14}$ aryl group optionally substituted by 1 to 3 $C_{1-6}$ alkoxy groups, and
  (b) a 3- to 8-membered monocyclic non-aromatic heterocyclic group optionally substituted by 1 to 3 $C_{1-6}$ alkyl groups,
(2) a $C_{3-6}$ alkyl group optionally substituted by 1 to 3 substituents selected from the group consisting of
  (a) a hydroxy group, and
  (b) a $C_{1-6}$ alkoxy group,
(3) a $C_{3-10}$ cycloalkyl group optionally substituted by 1 to 3 substituents selected from the group consisting of
  (a) a hydroxy group,
  (b) a $C_{1-6}$ alkyl group,
  (c) an oxo group,
  (d) a $C_{1-6}$ alkylenedioxy group,
  (e) a $C_{6-14}$ aryl group,
  (f) a halogen atom, and
  (g) an amino group,
(4) a $C_{6-14}$ aryl group optionally substituted by 1 to 3 substituents selected from the group consisting of
  (a) a halogen atom,
  (b) a $C_{1-6}$ alkyl group optionally substituted by 1 to 3 halogen atoms,
  (c) a cyano group,
  (d) a carbamoyl group,
  (e) an amino group, and
  (f) a $C_{1-6}$ alkoxy group,
(5) a 3- to 8-membered monocyclic non-aromatic heterocyclic group, and
(6) a 5- to 7-membered monocyclic aromatic heterocyclic group; and $R^3$ is selected from the group consisting of
(1) a $C_{3-10}$ cycloalkyl group,
(2) a $C_{3-10}$ cycloalkenyl group,
(3) a $C_{6-14}$ aryl group optionally substituted by 1 to 3 substituents selected from the group consisting of
  (a) a halogen atom,
  (b) a nitro group,
  (c) a cyano group,
  (d) a carbamoyl group optionally mono- or di-substituted by $C_{1-6}$ alkyl group(s) optionally substituted by 1 to 3 substituents selected from the group consisting of
    (i) a $C_{1-6}$ alkoxy group,
    (ii) a hydroxy group, and
    (iii) an amino group optionally mono- or di-substituted by $C_{1-6}$ alkyl group(s),
  (e) a sulfamoyl group optionally mono- or di-substituted by $C_{1-6}$ alkyl group(s),
  (f) a $C_{1-6}$ alkyl group optionally substituted by 1 to 3 substituents selected from the group consisting of
    (i) a halogen atom,
    (ii) a cyano group,
    (iii) a hydroxy group,
    (iv) a carbamoyl group optionally mono- or di-substituted by substituent(s) selected from the group consisting of a $C_{1-6}$ alkyl group and a $C_{3-10}$ cycloalkyl group,
    (v) an amino group optionally mono- or di-substituted by $C_{1-6}$ alkyl group(s), and
    (vi) a 3- to 8-membered monocyclic non-aromatic heterocyclic group optionally substituted by 1 to 3 substituents selected from the group consisting of an oxo group and a halogen atom,
  (g) a $C_{1-6}$ alkoxy group optionally substituted by 1 to 3 substituents selected from the group consisting of
    (i) a halogen atom,
    (ii) a cyano group,
    (iii) a hydroxy group, and
    (iv) a carbamoyl group optionally mono- or di-substituted by substituent(s) selected from a $C_{1-6}$ alkyl group optionally substituted by 1 to 3 $C_{1-6}$ alkoxy groups,
  (h) a $C_{1-6}$ alkoxy-carbonyl group,
  (i) an amino group optionally mono- or di-substituted by substituent(s) selected from the group consisting of
    (i) a $C_{1-6}$ alkyl-carbonyl group, and
    (ii) a $C_{1-6}$ alkyl group optionally substituted by 1 to 3 $C_{1-6}$ alkoxy groups,
  (j) a 3- to 8-membered monocyclic non-aromatic heterocyclic group optionally substituted by 1 to 3 substituents selected from the group consisting of
    (i) an oxo group,
    (ii) a $C_{1-6}$ alkyl group,
    (iii) a $C_{1-6}$ alkyl-carbonyl group optionally substituted by 1 to 3 substituents selected from the group consisting of a hydroxy group and a $C_{1-6}$ alkoxy group,
    (iv) a carbamoyl group optionally mono- or di-substituted by $C_{1-6}$ alkyl group(s),
    (v) a $C_{1-6}$ alkylsulfonyl group, and
    (vi) a halogen atom, and
  (k) a $C_{1-6}$ alkylenedioxy group,
(4) thienyl, pyridyl, pyrazolyl or pyrimidinyl, each optionally substituted by 1 to 3 substituents selected from the group consisting of (a) a carboxy group,
(b) a cyano group,
(c) a $C_{1-6}$ alkoxy-carbonyl group,
(d) a carbamoyl group optionally mono- or di-substituted by substituent(s) selected from the group consisting of
  (i) a $C_{1-6}$ alkyl group optionally substituted by 1 to 3 substituents selected from the group consisting of a hydroxy group and a cyano group,
  (ii) a $C_{3-10}$ cycloalkyl group optionally substituted by 1 to 3 cyano groups,
  (iii) a 5- to 7-membered monocyclic aromatic heterocyclic group optionally substituted by 1 to 3 $C_{1-6}$ alkyl groups, and
  (iv) a 3- to 8-membered monocyclic non-aromatic heterocyclic group,
(e) a 3- to 8-membered monocyclic non-aromatic heterocyclic group optionally substituted by 1 to 3 oxo groups,
(f) a $C_{1-6}$ alkyl group optionally substituted by 1 to 3 substituents selected from the group consisting of
  (i) a cyano group,
  (ii) a carbamoyl group, and
  (iii) a 3- to 8-membered monocyclic non-aromatic heterocyclic group optionally substituted by 1 to 3 oxo groups,
(g) a $C_{3-10}$ cycloalkyl group,
(h) a 3- to 8-membered monocyclic non-aromatic heterocyclylcarbonyl group, and
(i) an amino group,
(5) a 8- to 12-membered fused aromatic heterocyclic group optionally substituted by 1 to 3 $C_{1-6}$ alkyl groups,
(6) a 3- to 8-membered monocyclic non-aromatic heterocyclic group optionally substituted by 1 to 3 substituents selected from the group consisting of
  (a) an oxo group, and
  (b) a $C_{1-6}$ alkyl group,
(7) a 8- to 12-membered fused non-aromatic heterocyclic group optionally substituted by 1 to 3 oxo groups, and
(8) an amino group optionally mono- or di-substituted by substituent(s) selected from the group consisting of
  (a) a $C_{6-14}$ aryl group optionally substituted by 1 to 3 substituents selected from the group consisting of
    (i) a carbamoyl group, and
    (ii) a sulfamoyl group,
  (b) a $C_{1-6}$ alkyl group optionally substituted by 1 to 3 substituents selected from a $C_{6-14}$ aryl group optionally substituted by 1 to 3 $C_{1-6}$ alkoxy groups, and
  (c) a $C_{6-14}$ aryl-carbonyl group,
provided that 3-(3-fluorophenyl)-1-trityl-1,5-dihydro-4H-pyrazolo[4,3-c]pyridin-4-one is excluded,
or a salt thereof.

2. 4-(1-Cyclopentyl-4-oxo-4,5-dihydro-1H-pyrrolo[3,2-c]pyridin-3-yl)thiophene-2-carboxamide, or a salt thereof.

3. 2-(4-(1-(2,6-Difluorophenyl)-4-oxo-4,5-dihydro-1H-pyrazolo[4,3-c]pyridin-3-yl)phenyl)acetamide, or a salt thereof.

4. 3-((1-Cyclopentyl-4-oxo-4,5-dihydro-1H-pyrazolo[4,3-c]pyridin-3-yl)amino)benzenesulfonamide, or a salt thereof.

5. A pharmaceutical composition comprising the compound or salt of claim 1, and a pharmacologically acceptable carrier.

6. The pharmaceutical composition of claim 5, which is a janus kinase inhibitor.

7. A method of inhibiting janus kinase in a mammal, which comprises administering an effective amount of the compound or salt of claim 1 to the mammal.

8. A method for the treatment of an autoimmune disease, which comprises administering an effective amount of the compound or salt of claim 1 to a mammal.

* * * * *